US011530425B2

(12) United States Patent
Lu et al.

(10) Patent No.: US 11,530,425 B2
(45) Date of Patent: Dec. 20, 2022

(54) SYSTEMS, METHODS, AND COMPOSITIONS FOR CORRECTION OF FRAMESHIFT MUTATIONS

(71) Applicant: MASSACHUSETTS INSTITUTE OF TECHNOLOGY, Cambridge, MA (US)

(72) Inventors: Timothy Lu, Cambridge, MA (US); Shota Nakade, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 198 days.

(21) Appl. No.: 17/067,379

(22) Filed: Oct. 9, 2020

(65) Prior Publication Data

US 2021/0108229 A1 Apr. 15, 2021

Related U.S. Application Data

(60) Provisional application No. 62/984,422, filed on Mar. 3, 2020, provisional application No. 62/913,048, filed on Oct. 9, 2019.

(51) Int. Cl.
*C12N 15/90* (2006.01)
*A61K 48/00* (2006.01)
*C12N 9/22* (2006.01)
*C12N 15/11* (2006.01)
*C12N 9/12* (2006.01)
*C12N 15/10* (2006.01)

(52) U.S. Cl.
CPC ............ *C12N 15/907* (2013.01); *A61K 48/00* (2013.01); *C12N 9/22* (2013.01); *C12N 15/11* (2013.01); *C12N 2310/20* (2017.05); *C12N 2800/80* (2013.01)

(58) Field of Classification Search
None
See application file for complete search history.

(56) References Cited

U.S. PATENT DOCUMENTS 4,554,101 A  11/1985  Hopp

FOREIGN PATENT DOCUMENTS

| WO | WO2012118717 A2 | 9/2012 |
| WO | WO 2013163628 A2 | 10/2013 |
| WO | WO2017147056 A1 | 8/2017 |
| WO | WO2018165629 A1 | 9/2018 |
| WO | WO2019099943 A1 | 5/2019 |
| WO | WO2019118949 A1 | 6/2019 |
| WO | WO2019123014 A1 | 6/2019 |

OTHER PUBLICATIONS

Chu et al. (Increasing the efficiency of homology-directed repair for CRISPR-Cas9-induced precise gene editing in mammalian cells, Nature Biotechnology, vol. 33, No. 5, pp. 543-548, published Mar. 2015).*
Kyte et al., "A simple method for displaying the hydropathic character of a protein", J. Mol. Biol, 157: 105-132 (1982).
Perez-Pinera et al., "Gene targeting to the ROSA26 locus directed by engineered zinc finger nucleases", Nucl. Acids Res., 40(8):3741-3752 (2012).
Nakamura, Y., et al., "codon usage tabulated from the international DNA sequence databases: status for the year 2000" Nucl. Acids Res., 28:292 (2000).
Anderson, "Human gene therapy", Science, 256:808-8313 (1992).
Nabel and Feigner, "Direct gene transfer for immunotherapy and immunization", TIBTECH 11:211-217 (1993).
Mitani and Caskey, "Delivering therapeutic genes—matching approach and application", TIBTECH 11:162-166 (1993).
Dillon, "Regulating gene expression in gene therapy", TIBTECH 11:167-173 (1993).
Miller, "Human gene therapy comes of age", Nature 357:455-460 (1992).
Van Brunt, "Molecular Farming: Transgenic Animals as Bioreactors", Biotechnology 6(10): 1149-1154 (1988).
Vigne et al., "Third-generation adenovectors for gene therapy", Restorative Neurology and Neuroscience 8:35-36 (1995).
Kremer and Perricaudet, "Adenovirus and adeno-associated virus mediated gene transfer", British Medical Bulletin 51(1):31-44 (1995).
Haddada et al., "The Molecular Repertoire of Adenoviruses III", Current Topics in Microbiology and Immunology, Doerfler and Bohm (eds) (1995).
Yu et al., "Progress towards gene therapy for HIV infection", Gene Therapy 1:13-26 (1994).
Levy et al., "Cytosine and adenine base editing of the brain, liver, retina, heart and skeletal muscle of mice via adeno-associated viruses", Nature Biomedical Engineering vol. 4, pp. 97-110(2020).
Lai et al., "Efficient in vivo gene expression by trans-splicing adeno-associated viral vectors", Nat Biotechnol. 23(11):1435-9 (2005). doi: 10.1038/nbt1153.
Amirtaher-Ghahfarokhi et al., Decoding Non-Random Mutational Signatures at Cas9 Targeted Sites, Nucleic Acids Research, vol. 46, No. 16, Jul. 19, 2018.
Anob M. Chakrabarti et al., Target-Specific Precision of CRISPR-Mediated Genome Editing, Molecular Cell, vol. 73, No. 4, Dec. 13, 2018, pp. 699-713.
Jia Shou et al., Precise and Predictable CRISPR Chromosomal Rearrangements Reveal Principles of Cas9-Mediated Nucleotide Insertion, Molecular Cell, vol. 71, No. 4, Jul. 19, 2018, pp. 498-509.
PCT Application No. PCT/US2020/055131, International Search Report and Written Opinion, dated Jan. 25, 2021.

* cited by examiner

*Primary Examiner* — Suzanne M Noakes
*Assistant Examiner* — Jae W Lee
(74) *Attorney, Agent, or Firm* — Laura A. Labeots; Lathrop GPM LLP

(57) ABSTRACT

The disclosure provides systems, methods, and compositions for a target specific nuclease and a blunting enzyme to correct frameshift mutations for genome editing and treatment of diseases. In some embodiments, the target specific nuclease and the blunting enzyme are combined with a guide RNA and/or a microhomology-mediated end joining (MMEJ) inhibitor.

17 Claims, 23 Drawing Sheets
Specification includes a Sequence Listing.

```
[All types of frameshifts]
     Frameshifts              i.e.              In-frame correction
WT                       : AAA GGC GCT
+ 1 bp (3n+1(n≧0))       : AAA CGG CGC T    →   -1 frameshift SpCas9
+ 2 bp (3n+2(n≧0))       : AAA CCG GCG CT   →   +1 frameshift SpCas9
- 1 bp (-3n+2(n≧1))      : AAA -GCG CT      →   +1 frameshift SpCas9
- 2 bp (-3n+1(n≧1))      : AAA --CGC T      →   -1 frameshift SpCas9
+ 3 bp (3n(n≧1))         : In-frame
- 3 bp (-3n(n≧1))        : In-frame
```

SYSTEMS, METHODS, AND COMPOSITIONS FOR CORRECTION OF FRAMESHIFT MUTATIONS

RELATED APPLICATIONS

This application claims the benefit of U.S. Provisional Application No. 62/913,048 filed on Oct. 9, 2019 and U.S. Provisional Application No. 62/984,422, filed on Mar. 3, 2020, the entire disclosures of which are hereby incorporated herein by reference.

STATEMENT REGARDING FEDERALLY SPONSORED RESEARCH

The invention was made with government support under Grant No. U01CA250554 awarded by the U.S. National Institute of Health (NIT)/National Cancer Institute (NCI) Next Generation of Cancer Model (NGCM) program. The government has certain rights in the invention.

SEQUENCE LISTING

The instant application contains a Sequence Listing which has been submitted electronically in ASCII format and is hereby incorporated by reference in its entirety. Said ASCII copy, created on Aug. 8, 2022, is named 709874_083474-011US_ST25.txt and is 503 kilobytes in size.

FIELD

The subject matter disclosed herein is generally related to systems, methods, and compositions for correction frameshift mutations, accurate genome editing and treatment of diseases.

BACKGROUND

Frameshift mutations are genetic mutations that are caused by insertion or deletion (indels) of nucleotides in a coding region of a nucleic acid sequence that is not divisible by three. The indel results in mutated sequences that, due to the triplet nature of gene expression by codons, changes the reading frame of the codon and therefore change the translation of the nucleic acid sequence.

Frameshift mutations are present in number of diseases, but genetic treatments for these diseases are limited. They often involve removing large section from a genome sequence and lead to undesired side effects.

Therefore, there is need for more efficient tools to correct frameshift mutations.

SUMMARY

The present disclosure provides systems, methods, and compositions for correction frameshift mutations, accurate genome editing and treatment of diseases.

The present disclosure provides a composition, which comprises a target specific nuclease, wherein the target comprises a double stranded DNA (dsDNA), and a double strand break (DSB)-end blunting enzyme. The target specificity of the nuclease can be provided by a guide RNA (gRNA). The gRNA can be a single guide RNA (sgRNA). The sgRNA can comprise a nucleic acid sequence at least 75% identical to the nucleic acid sequence of SEQ ID NOs: 54-64. If desired, the composition can further comprise a MS2-binding protein, wherein the sgRNA can comprise one or more MS2 stem loops, and wherein the MS2-binding protein can be linked to the sgRNA by the one or more MS2 stem loops and can bind to the DSB-end blunting enzyme. If desired, the nuclease predominantly can induce staggered ends on the cleaved dsDNA. If desired, the nuclease can be an altered scissile variant. If desired, the altered scissile variant can be ΔF916, LZ3Cas9 (N690C, T769I, G915M, N980K), G915F, F916P, R918A, R919P or Q920P. If desired, the nuclease can be selected from the group consisting of SpCas9, LbCas12a, AsCas12a and FnCas12a.

In some embodiments, the nuclease can comprise an amino acid sequence at least 85% identical to an amino acid sequence selected from the group consisting of SEQ ID NOs: 95-106.

In some embodiments, the nuclease can comprise an amino acid sequence at least 90% identical to an amino acid sequence selected from the group consisting of SEQ ID NOs: 95-106.

In some embodiments, the nuclease can comprise an amino acid sequence at least 95% identical to an amino acid sequence selected from the group consisting of SEQ ID NOs: 95-106.

In some embodiments, the nuclease can comprise an amino acid sequence at least 99% identical to an amino acid sequence selected from the group consisting of SEQ ID NOs: 95-106.

In some embodiments, the nuclease can comprise an amino acid sequence selected from the group consisting of SEQ ID NOs: 95-106.

In some embodiments, the amino acid sequence can specifically bind to a protospacer-adjacent motif (PAM). The PAM can be selected from the group consisting of NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

In some embodiments, the DSB-end blunting enzyme can be a polymerase. The polymerase can be selected from the group consisting of DNA polymerase λ (POLL), DNA polymerase μ (POLM), DNA polymerase β (POLB), DNA polymerase γ (POLG), DNA polymerase ι (POLI), DNA polymerase η (POLH), TENT4A, DNA polymerase ν (POLN), DNA Ligase 4, DNTT, XRCC4, DNA Polymerase IV, fungi pol IV-like DNA polymerase, DNA polymerase/3'-5' exonuclease Pol X, and T4 DNA polymerase (T4pol).

In some embodiments, the DSB-end blunting enzyme can be a single-strand DNA specific nuclease. The single-strand DNA specific nuclease can be selected from the group consisting of MGME1, FEN1, DNA2, XRN2, EXOG, EXO5, AP endonuclease, RecJ exonuclease (RecJ), XseA, XseB, S1 nuclease (nucS), P1 nuclease, Artemis, T4 DNA polymerase (T4pol), and Csm1.

In some embodiments, the DSB-end blunting enzyme can be covalently bound to the nuclease by a linker. The linker can be a peptide.

In some embodiments, the dsDNA can be in a cell. The cell can be a eukaryotic cell. The eukaryotic cell can be a mammalian cell. The mammalian cell can be a human cell.

In some embodiments, the composition can further comprise an inhibitor of the microhomology-mediated end joining (MMEJ) pathway. The MMEJ pathway inhibitor can be a CtIP or MRN inhibitor. The CtIP inhibitor can be selected from KLHL15 and PIN1. The MRN inhibitor can be selected from E1b55K and E4orf6.

In some embodiments, a first nucleic acid molecule encoding the nuclease is disclosed.

In some embodiments, a second nucleic acid molecule encoding the DSB-end blunting enzyme is disclosed.

In some embodiments, a third nucleic acid molecule encoding the sgRNA is disclosed.

In some embodiments, one or more vectors comprising the nucleic acid molecule are disclosed.

In some embodiments, a cell comprising the composition, the nucleic acid molecule or the one or more vectors is disclosed. If desirable, the cell can be a prokaryotic cell. If desirable, the cell can be a eukaryotic cell. If desired, the eukaryotic cell can be a mammalian cell. If desired, the mammalian cell can be a human cell.

In some embodiments, a method of inserting or deleting one or more single base pairs in a double-stranded DNA (dsDNA) is disclosed, the method comprises cleaving the dsDNA at a target site with a target specific nuclease, wherein the cleavage results in overhangs on both dsDNA ends, inserting a nucleotide complementary to the overhanging nucleotide on both of the dsDNA ends using a double strand break (DSB)-end blunting enzyme, or removing the overhanging nucleotide on both of the dsDNA ends using the DSB-end blunting enzyme, and ligating the dsDNA ends together, thereby inserting or deleting a single base pair in the dsDNA. The target specificity of the nuclease can be provided by a guide RNA (gRNA). The gRNA can be a single guide RNA (sgRNA). The sgRNA can comprise a nucleic acid sequence at least 75% identical to the nucleic acid sequence of SEQ ID NOs: 54-64. The sgRNA can comprise one or more MS2 stem loops that link a MS2-binding protein to the sgRNA, and wherein the MS2-binding protein can bind to the DSB-blunting enzyme. The DSB-end blunting enzyme can be overexpressed. The nuclease can induce staggered ends on the cleaved dsDNA. The nuclease can be an altered scissile variant. The altered scissile variant can be ΔF916, G915F, F916P, R918A, R919P or Q920P. The nuclease can be selected from the group consisting of SpCas9, LZ3Cas9 (N690C, T769I, G915M, N980K), LbCas12a, AsCas12a and FnCas12a.

In some embodiments, the nuclease of the method can comprise an amino acid sequence at least 85% identical to an amino acid sequence selected from the group consisting of SEQ ID NOs: 95-106.

In some embodiments, the nuclease of the method can comprise an amino acid sequence at least 90% identical to an amino acid sequence selected from the group consisting of SEQ ID NOs: 95-106.

In some embodiments, the nuclease of the method can comprise an amino acid sequence at least 95% identical to an amino acid sequence selected from the group consisting of SEQ ID NOs: 95-106.

In some embodiments, the nuclease of the method can comprise an amino acid sequence at least 99% identical to an amino acid sequence selected from the group consisting of SEQ ID NOs: 95-106.

In some embodiments, the nuclease of the method can comprise an amino acid sequence selected from the group consisting of SEQ ID NOs: 95-106.

In some embodiments, the amino acid sequence of the method can specifically bind to a protospacer-adjacent motif (PAM). The PAM can be selected from the group consisting of NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

In some embodiments, the DSB-end blunting enzyme of the method can be a polymerase. The polymerase can be selected from the group consisting of DNA polymerase λ (POLL), DNA polymerase μ (POLM), DNA polymerase β, DNA polymerase γ (POLG), DNA polymerase ι (POLI), DNA polymerase η (POLH), TENT4A, DNA polymerase ν (POLN), DNA Ligase 4, DNTT, XRCC4, DNA Polymerase IV, fungi pol IV-like DNA polymerase, DNA polymerase/ 3'-5' exonuclease Pol X, and T4 DNA polymerase (T4pol).

In some embodiments, the DSB-end blunting enzyme of the method can be a single-strand DNA specific nuclease. The single-strand DNA specific nuclease can be selected from the group consisting of MGME1, FEN1, DNA2, XRN2, EXOG, EXO5, AP endonuclease, RecJ exonuclease, XseA, XseB, S1 nuclease (nucS), P1 nuclease, Artemis, T4 DNA polymerase (T4pol), and Csm1. The DSB-end blunting enzyme can be covalently bound to the nuclease by a linker. The linker can be a peptide.

In some embodiments, the dsDNA of the method can be a cell. The cell can be a eukaryotic cell. The eukaryotic cell can be a mammalian cell. The mammalian cell can be a human cell.

In some embodiments, the method can further comprise an inhibitor of the microhomology-mediated end joining (MMEJ) pathway. The MMEJ pathway inhibitor can be a CtIP or MRN inhibitor. The CtIP inhibitor can be selected from KLHL15 and PIN1. The MRN inhibitor can be selected from E1b55K and E4orf6.

In some embodiments, a method of treating a disease caused by a frameshift mutation in the dsDNA in a subject in need thereof comprising administering to the subject a therapeutically effective amount of the composition, the nucleic acid molecule, the vector or the cell is disclosed.

In some embodiments, a method of treating a disease caused by a frameshift mutation in the dsDNA in a subject in need thereof comprising inserting or deleting a single base pair in the dsDNA with the frameshift mutation according is disclosed.

In some embodiments, a method of enhancing out-frame mutation in the dsDNA in a subject in need thereof comprising administering to the subject a therapeutically effective amount of the composition, the nucleic acid molecule, the vector, or the cell is disclosed.

BRIEF DESCRIPTION OF THE DRAWINGS

Aspects, features, benefits, and advantages of the embodiments described herein will be apparent with regard to the following description, appended claims, and accompanying drawings where:

FIG. 1E is a diagram showing the probability distribution of indel mutations in PCSK9 exon 12 when induced by Cas9 and DNA polymerase λ (POLL) according to embodiments of the present teachings;

DETAILED DESCRIPTION

Figures 1, 2:
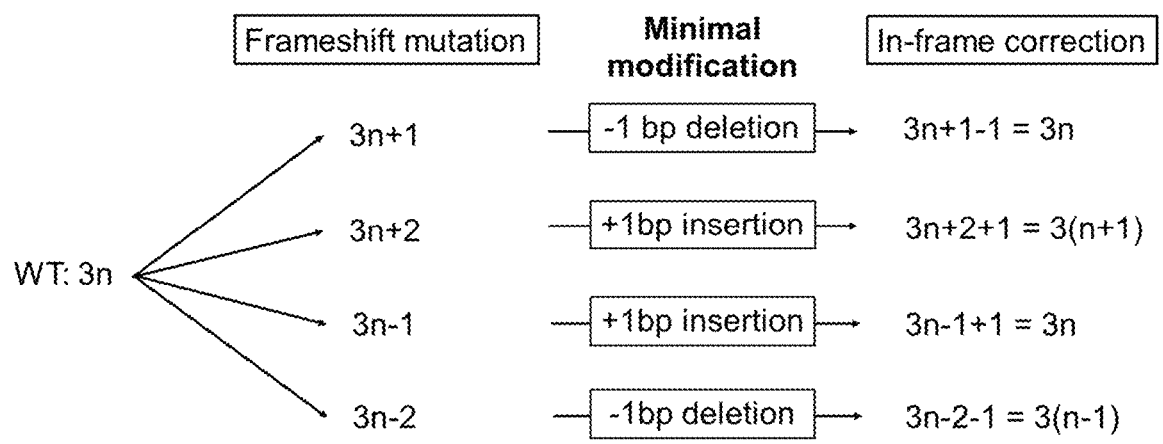
FIG. 1 is a schematic illustration of a variety of different frameshift mutations according to embodiments of the present teachings.
FIG. 2 is a schematic illustration of how frameshift mutations can be corrected according to embodiments of the present teachings.
Figure 3A:
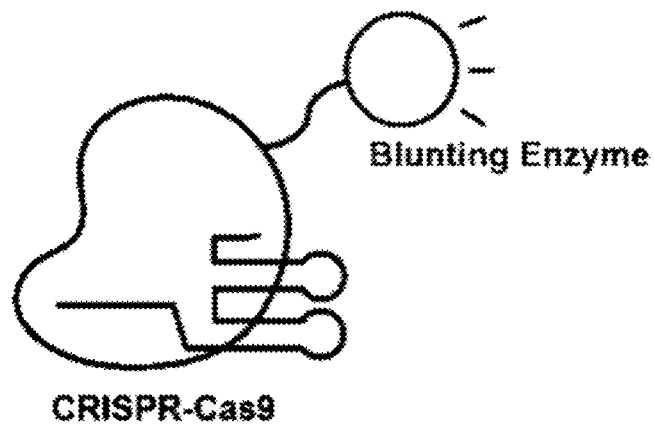
FIG. 3A is a schematic representation of a CRISPR-Cas9 and a blunting enzyme connected to the CRISPR-Cas9 by a linker, without the use of a donor template according to embodiments of the present teachings.
Figure 3B:
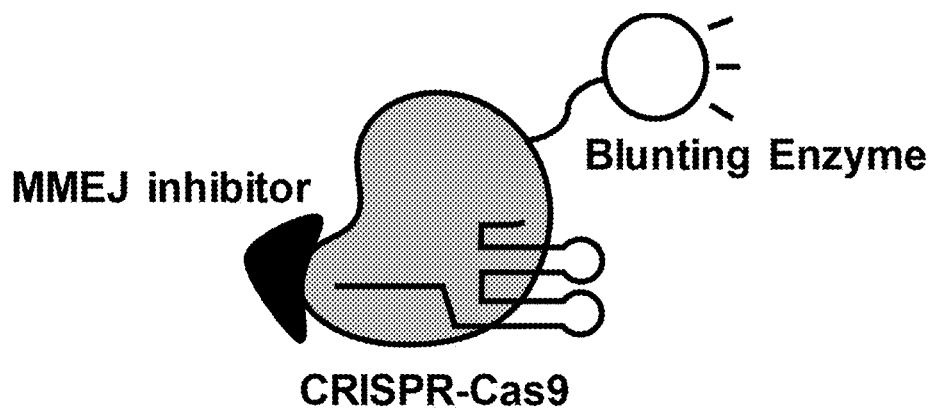
FIG. 3B is a schematic representation of a CRISPR-Cas9, a blunting enzyme and a microhomology-mediated end joining (MMEJ) inhibitor without the use of a donor template according to embodiments of the present teachings.
Figure 3C:
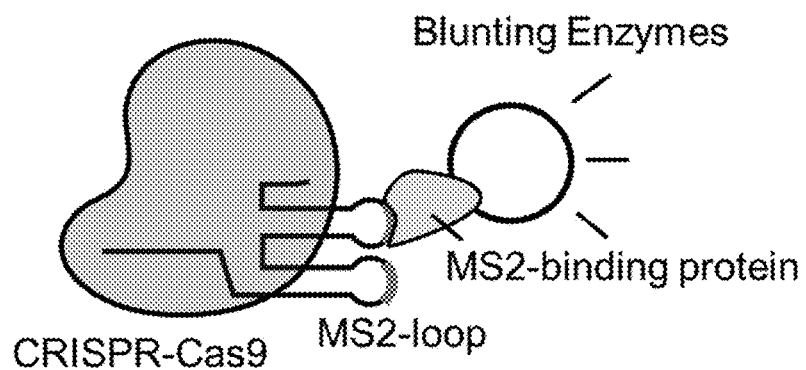
FIG. 3C is a schematic representation of a CRISPR-Cas9, a MS2-loop, MS2-binding protein, and a blunting enzyme according to embodiments of the present teachings.
Figure 3D:
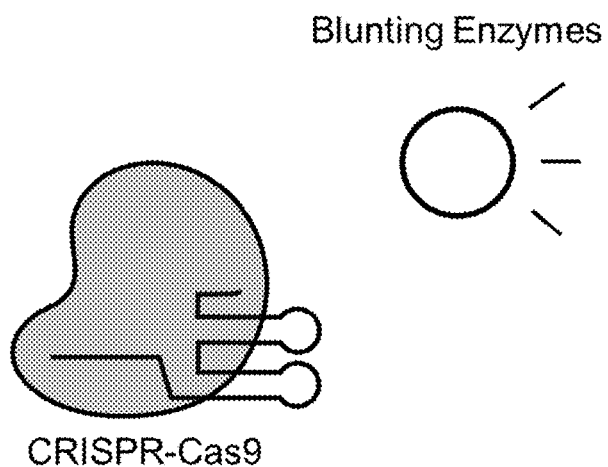
FIG. 3D is a schematic representation of a CRISPR-Cas9 and a blunting enzyme, without the use of a donor template according to embodiments of the present teachings.

It will be appreciated that for clarity, the following disclosure will describe various aspects of embodiments. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an," and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, +/−0.5% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

The term "staggered end" when it refers to a double stranded DNA (dsDNA) molecule refers to the 5' and or 3' ends of that molecule having at least one nucleotide that is not hybridized to the opposite strand of the dsDNA.

The term "blunt end" when it refers to a dsDNA molecule refers to the 5' and or 3' ends of that molecule having nucleotides that hybridize to the opposite strand of the dsDNA.

The term "variant" as used herein means a polypeptide or nucleotide sequence that differs from a given polypeptide or nucleotide sequence in amino acid or nucleic acid sequence by the addition (e.g., insertion), deletion, or conservative substitution of amino acids or nucleotides, but that retains the biological activity of the given polypeptide (e.g., a variant nucleic acid could still encode the same or a similar amino acid sequence). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al., J. Mol. Biol., 157: 105-132 (1982)). The hydropathic index of an amino acid is based on a consideration of its hydrophobicity and charge. It is known in the art that amino acids of similar hydropathic indexes can be substituted and still retain protein function. The present disclosure provides amino acids having hydropathic indexes of 2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. The present disclosure provides substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity. Use of "variant" herein is intended to encompass fragments of a variant unless otherwise contradicted by context. The term "protospacer-adjacent motif" as used herein refers to a DNA sequence immediately following a DNA sequence targeted by a nuclease. Examples of protospacer-adjacent motif include, without limitation, NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

The term "MS2 stem loop" as used herein refers to a pattern in a single stranded nucleotide strand originated from a bacterial virus when two regions of the same strand base-pair to form a double helix that ends in an unpaired loop.

Alternatively or additionally, a "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also, mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide.

However, also naturally occurring variants are to be understood to be encompassed by the term "variant" as used herein. Further, the variants usable in the present disclosure may also be derived from homologs, orthologs, or paralogs of the parent molecule or from artificially constructed variant, provided that the variant exhibits at least one biological activity of the parent molecule, i.e. is functionally active.

Alternatively, or additionally, a "variant" as used herein, can be characterized by a certain degree of sequence identity to the parent polypeptide or parent polynucleotide from which it is derived. More precisely, a protein variant in the context of the present disclosure exhibits at least 80% sequence identity to its parent polypeptide. A polynucleotide variant in the context of the present disclosure exhibits at least 70% sequence identity to its parent polynucleotide. The term "at least 70% sequence identity" is used throughout the specification with regard to polypeptide and polynucleotide sequence comparisons. This expression preferably refers to a sequence identity of at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90:5873-5877), with hmmalign (HMMER package, hmmer.wustl.edu/) or with the CLUSTAL algorithm (Thompson, J. D., Higgins, D. G. & Gibson, T. J. (1994) Nucleic Acids Res. 22, 4673-80) available e.g. on www.ebi.ac.uk/Tools/clustalw/or on www.ebi.ac.uk/Tools/clustalw2/index.html or on npsa-pbil.ibcp.fr/cgi-bin/npsa_automat.pl?page=/NPSA/npsa_clustalw.html. Preferred parameters used are the default parameters as they are set on www.ebi.ac.uk/Tools/clustalw/ or www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLAS TN and BLASTP programs of Altschul et al. (1990) J. Mol. Biol. 215:403-410. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

Overview

Some embodiments disclosed herein provide non-naturally occurring or engineered systems, methods, and compositions for target specific nucleases combined with blunting enzymes to correct frameshift mutations for genome editing and treatment of diseases. Frameshift mutations are genetic mutations that are caused by insertion and deletion (indels) of nucleotides in a DNA nucleic acid sequence that is not divisible by three. Due to the triplet nature of gene expression by codons, the indel can change the reading frame of the codon and therefore change the translation of the gene. Different types of frameshift mutations and examples of in-frame corrections of them are shown in FIGS. 1 and 2.

In some embodiments, the systems disclosed herein comprise a target specific nuclease, wherein the target comprises a double-stranded DNA (dsDNA) as well as a blunting enzyme. The systems disclosed herein can also comprise targeting moiety and/or a microhomology-mediated end joining (MMEJ) inhibitor.

In some embodiments, the target specific nuclease can be a CRISPR associated protein (Cas). In some embodiments, the targeted nuclease is a Cas9 protein as illustrated in FIGS. 3A-3D. In some embodiments, the blunting enzyme is joined to the targeted nuclease by a linker. In some embodiments, the blunting enzyme is separate from the targeted nuclease. In some embodiments, the composition further comprises a MMEJ inhibitor. In some embodiments, the composition further comprises a single guide RNA (sgRNA). In some embodiments, the composition further comprises a sgRNA and a MS2-binding protein, wherein the sgRNA comprises one or more MS2 stem loops. The MS2-binding protein is linked to the sgRNA by the one or more MS2 stem loops and binds to the blunting enzyme to form a blunting enzyme fused-MS2 binding protein.

Figure 4:
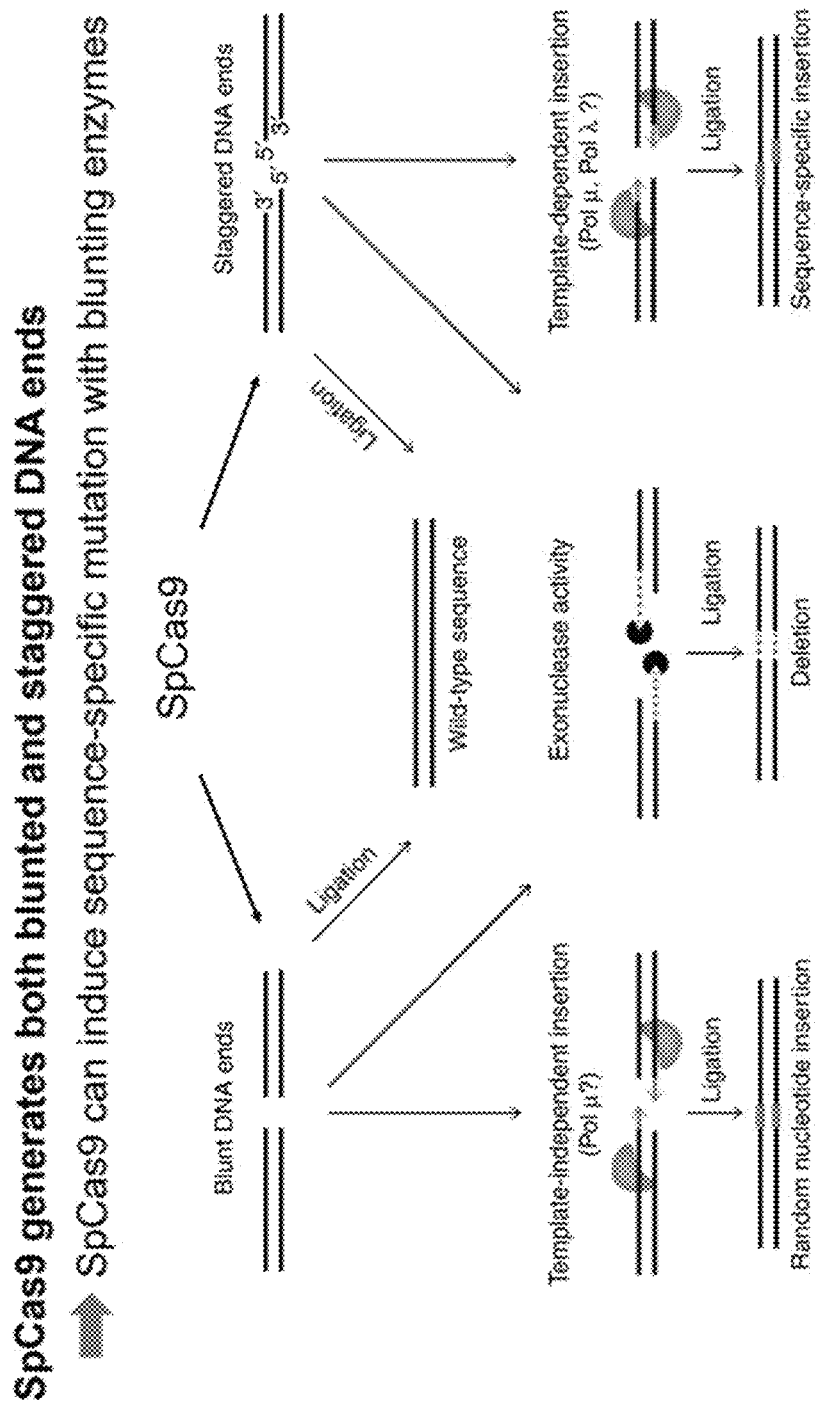
FIG. 4 is a schematic illustration of the process of using SpCas9 to generate both blunted and staggered DNA ends according to embodiments of the present teachings.
Figure 5:
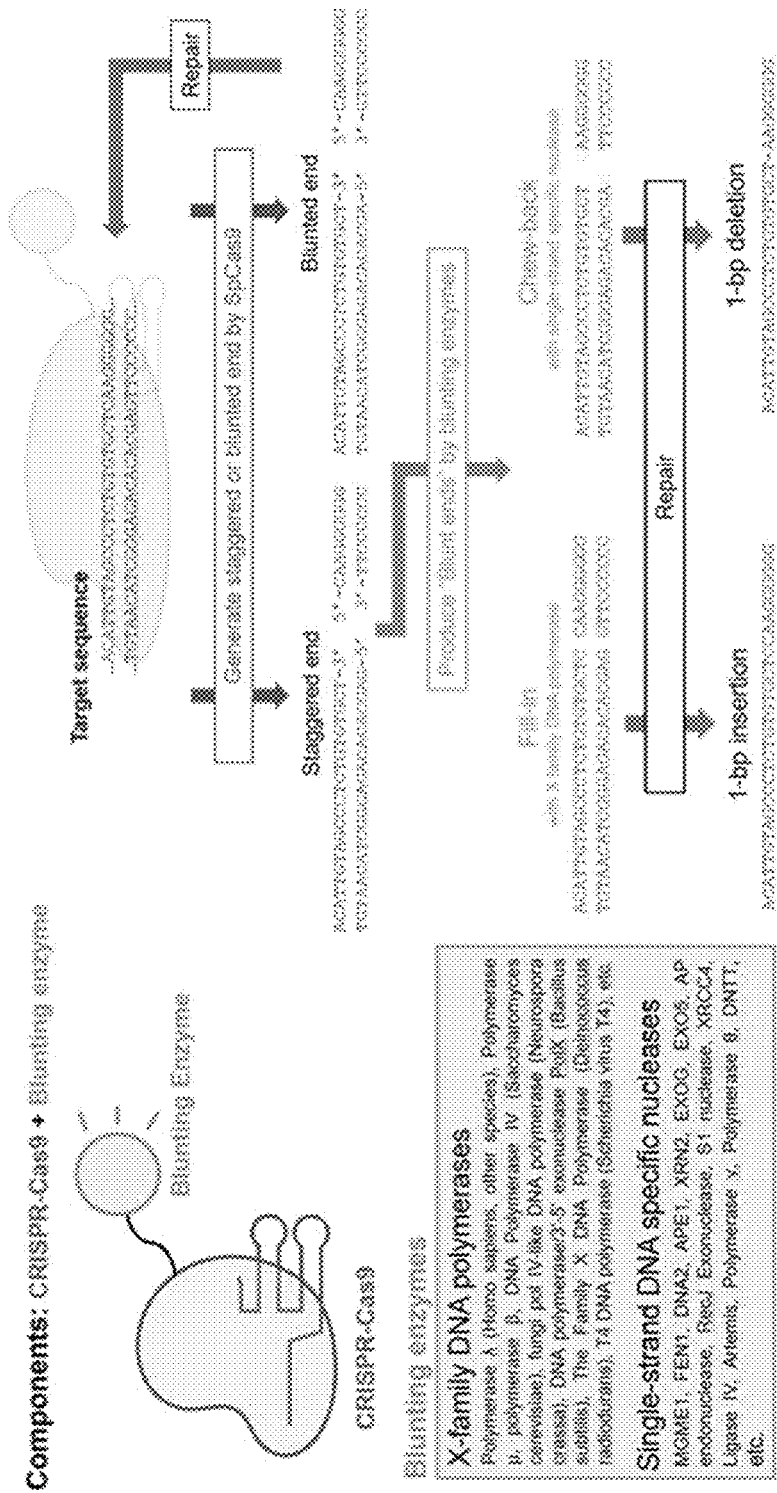
FIG. 5 is a schematic illustration of a Cas9 gene editing system resulting in an induction of a precise and predictable mutations without the use of a donor template according to embodiments of the present teachings. The Cas9 gene editing system comprises: a target sequence of the sequences of SEQ ID NO: 118 (acattgtagccctctgtgtgctcaagggggg) and SEQ ID NO: 119 (ccccccttgagcacacagagggctacaatgt); staggered end sequences of the sequences of SEQ ID NO: 120 (acattgtagccctctgtgtgct) and SEQ ID NO: 121 (gagcacacagagggctacaatgt), and SEQ ID NO: 122 (caagggggg) and SEQ ID NO: 123 (ccccccttt); blunted end sequences of the sequences of SEQ ID NO: 124 (acattgtagccctctgtgtgct) and SEQ ID NO: 125 (agcacacagagggctacaatgt), and SEQ ID NO: 126 (caagggggg) and SEQ ID NO: 127 (ccccccttg); produce "blunt ends" fill-in sequences of the sequences of SEQ ID NO: 128 (acattgtagccctctgtgtgctc) and SEQ ID NO: 129 (gagcacacagagggctacaatgt), and SEQ ID NO: 130 (caagggggg) and SEQ ID NO: 131 (ccccccttg); produce "blunt ends" chew-back sequences of the sequences of SEQ ID NO: 132 (acattgtagc cctctgtgtgct) and SEQ ID NO: 133 (agcacacagagggctacaatgt), and SEQ ID NO: 134 (aagggggg) and SEQ ID NO: 135 (cccccctt); a repair insertion sequence of the sequence of SEQ ID NO: 136 (acattgtagccctctgtgtgctccaagggggg); and a deletion sequence of the sequence of SEQ ID NO: 137 (acattgtagccctctgtgtgctaaggggggg)

The target specific nuclease combined with a blunting enzyme can correct frameshift mutations in genes in cells and tissues. In some embodiments, cells include eukaryotic cells, mammalian cells, and human cells. The target specific nuclease combined with a blunting enzyme can induce one or more single-base insertions and deletions (indels). In some embodiments, the targeted nuclease creates staggered ends when it cleaves the target dsDNA. When the staggered ends are created by the target specific nuclease, a blunting enzyme can be used to ether "fill in" the staggered end with a polymerase or "chew back" the staggered end with a nuclease. Filling in followed by ligation creates a one or more bp insertion and chewing back followed by ligation creates one or more bp deletion. (See FIGS. 4-5). In some embodiments, the target specific nuclease and a blunting enzyme induce a precise and predictable mutation in a dsDNA without the use of a donor template.

Microhomology-mediated end joining (MMEJ) is one of the pathways for repairing double-strand breaks in DNA. In MMEJ, microhomologous sequences are used to align broken ends often resulting in deletions flanking the original break. In some embodiments, if a target specific nuclease were used to cleave dsDNA, MMEJ could create an unintended deletion.

Figure 6:
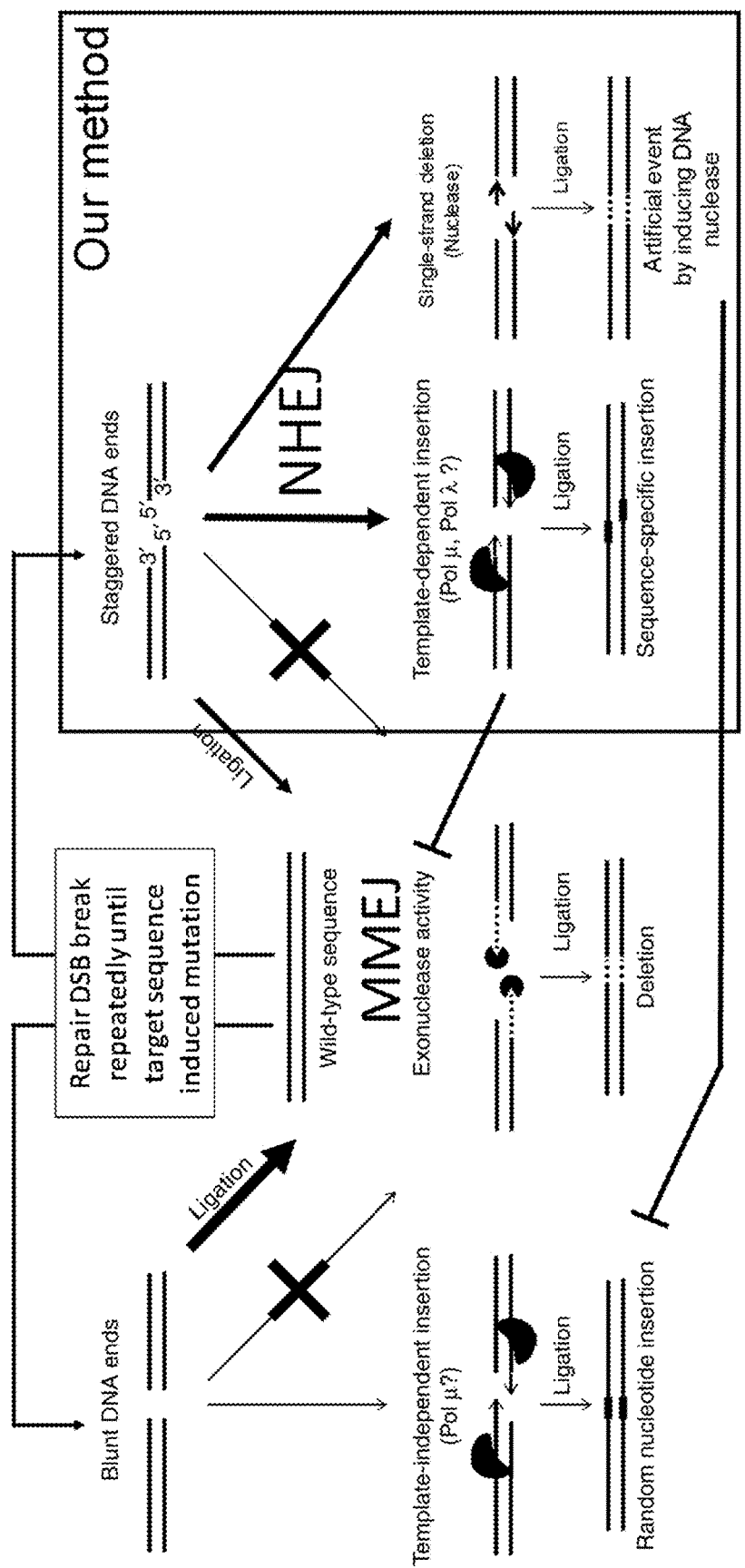
FIG. 6 is a schematic illustration of a variety of different frameshift mutations and how the composition in the instant disclosure corrects them according to embodiments of the present teachings.
Figure 7:
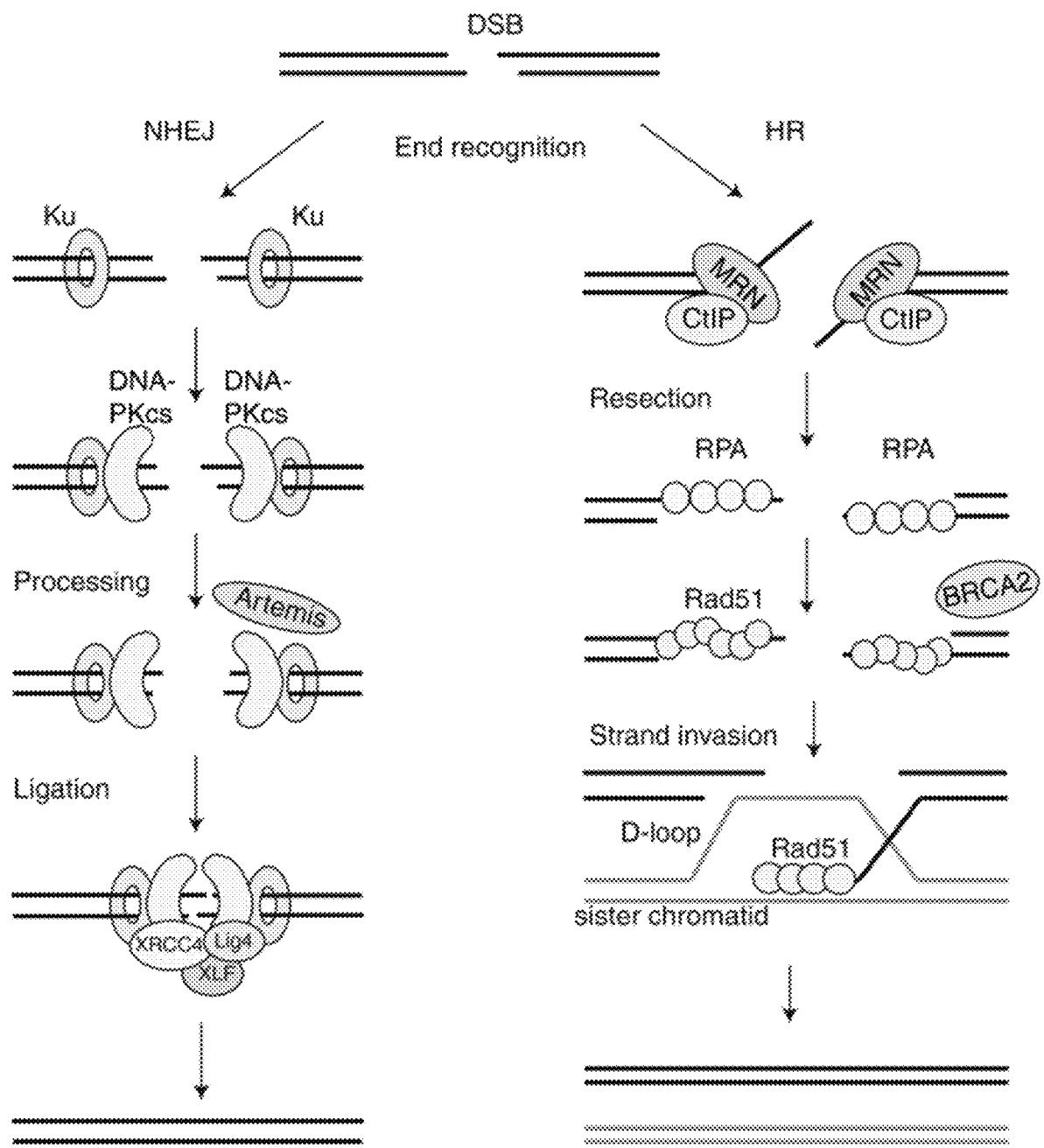
FIG. 7 is a schematic representation of two double-strand break repair pathways according to embodiments of the present teachings.

Non-homologous end joining (NHEJ) is another pathway for repairing double-strand breaks in DNA. In NHEJ, the broken ends are directly ligated together without use of a homologous template. In some embodiments, if a target specific nuclease were used to cleave dsDNA, NHEJ would directly ligate the cleaved dsDNA without deletions and therefore accurately edit the target sequence. (See FIGS. 6 and 7).

In some embodiments, an inhibitor of MMEJ is used to keep cleaved DNA from undergoing MMEJ and being subject to unintended deletion of the sequence of the dsDNA flanking the cleavage.

Target Specific Nucleases

In some embodiments, a target specific nuclease is a nuclease that cleaves a dsDNA and, at least in some cases, leaves a staggered end at the cleavage site. The target specific nuclease disclosed herein can be for example, without limitation, Cas12a, LbCas12a, FnCas12a, AsCas12a, Cas9, SpCas9, SaCas9, LZ3Cas9, Casφ, and the double combinations of Cas9 nickase, zinc finger nuclease (ZFN), and TAL Effector Nuclease (TALEN). The LZ3Cas9 disclosed here can be N690C, T769I, G915M, or N980K. In some embodiments, the target specific nuclease cleaves dsDNA in the genome of a cell providing staggered ends. In some embodiments, the target specific nuclease provides a dsDNA cleavage resulting in staggered ends more than 10% of the time. In some embodiments, the target specific nuclease provides a dsDNA cleavage resulting in staggered ends more than 20% of the time. In other embodiments, the target specific nuclease provides a dsDNA cleavage resulting in staggered ends more than 3, 40, 50, 60, 70, 80, 90, 95, or 99% of the time.

In some embodiments, the target specific nuclease is a CRISPR associated protein (Cas). In these embodiments, the Cas uses a guide RNA (gRNA) to provide specificity. In some embodiments, the gRNA is a single guide RNA (sgRNA) i.e., a fusion of two noncoding RNAs: a synthetic CRISPR RNA (crRNA) and a trans-activating CRISPR RNA (tracrRNA).

In general, a guide sequence is any polynucleotide sequence having sufficient complementarity with a target polynucleotide sequence to hybridize with the target sequence and direct sequence-specific binding of a Cas protein to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, ClustalX, BLAT, Novoalign (Novocraft Technologies, ELAND (Illunina, San Diego, Calif.), SOAP (available at soap.genoincs.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay.

In some embodiments, the sgRNA comprises a nucleic acid sequence selected from the group consisting of SEQ ID NOs: 54-64. For example, the sgRNA can comprise a nucleic acid sequence at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to a nucleic acid sequence selected from the group consisting of SEQ ID NOs: 54-64.

In some embodiments, the target specific nuclease is Cas9. In some embodiments, the target nuclease is a scissile variant. In some embodiments, the Cas9 is a scissile variant of Cas9. In some embodiments, the scissile is for example, without limitation, ΔF916, LZ3Cas9, G915F, F916P, R918A, R919P, Q920P, N690C, T769I, G915M and N980K. In some embodiments, the LZ3Cas9 is N690C, T769I, G915M, or N980K.

The target specific nuclease can comprise an amino acid sequence selected from the group consisting of SEQ ID NOs: 95-106. For example, the target specific nuclease comprises an amino acid sequence at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 95-106.

In some embodiments, the target specific nuclease is a zinc finger nuclease (ZFN). A single zinc finger contains approximately 30 amino acids and the domain functions by binding 3 consecutive base pairs of DNA via interactions of a single amino acid side chain per base pair. The modular structure of the zinc finger motif permits the conjunction of several domains in series, allowing for the recognition and targeting of extended sequences in multiples of 3 nucleotides. These targeted DNA-binding domains can be combined with a nuclease domain, such as FokI, to generate a site-specific nuclease, called a "zinc finger nuclease" (ZFNs) that can be used to introduce site-specific double strand breaks at targeted genomic loci. This DNA cleavage stimulates the natural DNA-repair machinery, leading to one of two possible repair pathways, NHEJ and HDR. For example, the ZFN can target the Rosa26 locus (Perez-Pinera et al. Nucleic Acids Research (2012) 40:3741-3752) or a dystrophin gene.

In some embodiments, the target specific nuclease is a TAL effector nuclease (TALEN). The TALEN can be used to introduce site-specific double strand breaks at targeted genomic loci. Site-specific double-strand breaks are created when two independent TALENs bind to nearby DNA sequences, thereby permitting dimerization of FokI and cleavage of the target DNA. TALENs have advanced genome editing due to their high rate of successful and efficient genetic modification. This DNA cleavage can stimulate the natural DNA-repair machinery, leading to one of two possible repair pathways: homology-directed repair (HDR) or the non-homologous end joining (NHEJ) pathway. The TALENs can be designed to target any gene involved in a genetic disease.

The TALENs can include a nuclease and a TALE DNA-binding domain that binds to the target gene in a TALEN target region. The target gene can have a mutation such as a frameshift mutation or a nonsense mutation. If the target gene has a mutation that causes a premature stop codon, the TALEN can be designed to recognize and bind a nucleotide sequence upstream or downstream from the premature stop codon. A "TALEN target region" includes the binding regions for two TALENs and the spacer region, which occurs between the binding regions. The two TALENs bind to different binding regions within the TALEN target region, after which the TALEN target region is cleaved. Examples of TALENs are described in International Patent Application No. PCT/US2013/038536, which is incorporated by reference in its entirety.

In some embodiments, the target specific nucleases include tags including for example, without limitation, 3×Flag, nuclear localization sequence (NLS), and the combination of 3×Flag and NLS.

Blunting Enzymes

In some embodiments, the blunting enzyme or double strand break-end blunting enzyme (both terms are used interchangeably herein), is an enzyme that is able either to remove or add nucleotides to a staggered end of a double stranded DNA molecule to produce a blunt end. In some embodiments, the blunting enzyme disclosed herein is a polymerase or a nuclease. In some embodiments, the DSB-blunting enzyme is a single-strand DNA specific nuclease.

In some embodiments, the blunting enzyme is a polymerase selected from polymerase λ (POLL), polymerase μ (POLM), polymerase ν (POLN), polymerase η (POLH), polymerase β (POLB), DNA polymerase θ (POLQ), DNA polymerase κ (POLK), DNA polymerase IV (*Saccharomyces cerevisiae*), DNA polymerase γ (POLG), DNA polymerase ι (POLI), DNA polymerase ξ, DNA polymerase ν (POLN), DNA nucleotidylexotransferase (DNTT), TENT4A, DNA ligase 4, fungi pol IV-like DNA polymerase (*Neurospora crassa*), DNA polymerase/3'-5' exonuclease PolX (*Bacillus subtilis*), Family X DNA Polymerase (*Deinococcus radiodurans*), and T4 DNA polymerase (Scherichia virus T4). In some embodiments, the blunting enzyme is a nuclease. In some embodiments, the nuclease is a single-strand DNA specific nuclease. In some embodiments, the nuclease is selected from MGME1, EXOG, APEX1, APEX2, FEN1, DNA2, APE1, XRN1, XRN2, EXOG, EXO5, AP endonuclease, RecJ Exonuclease (RecJ), XseA, XseB, S1 nuclease (nucS), P1 nuclease, XRCC4, Ligase IV, Artemis, and Csm1.

Except as specified above, the blunting enzymes can be from any organism. In some embodiments, the organism is a mammal. In other embodiments, the mammal is a human.

Figure 8:
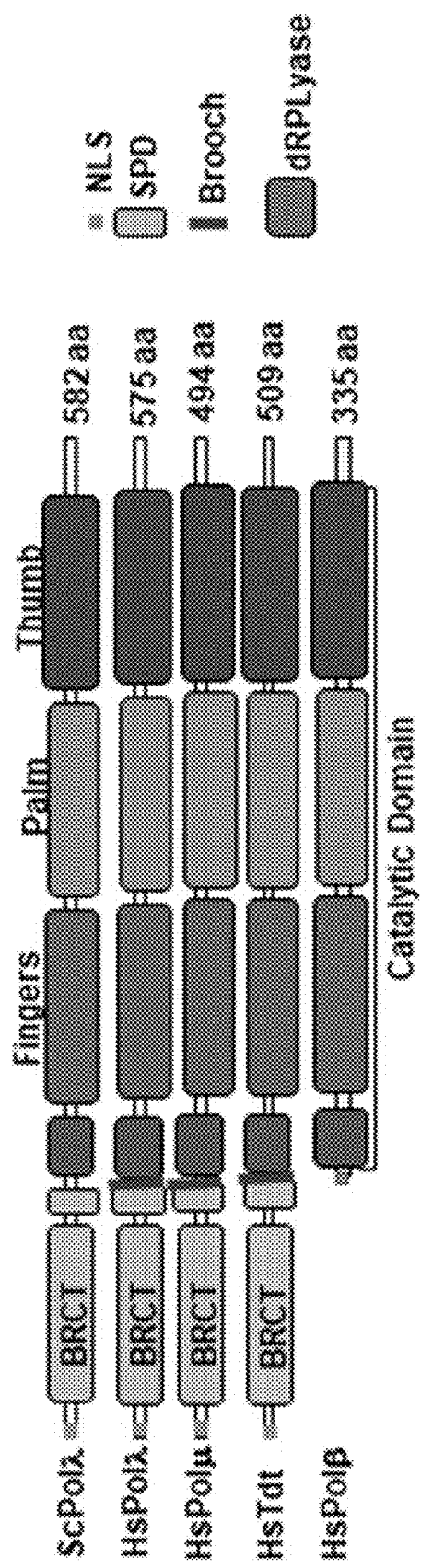
FIG. 8 is a schematic representation of the primary structures of family X polymerases according to embodiments of the present teachings.

Optimal enzymes can be selected that will enable the precision indel alleles to be stably increased in various cells and target sequences. In some embodiments, the blunting enzymes can be selected from variants such as mutants, truncations or chimeric variants of DNA polymerases and single-base specific DNA nucleases. Representative variants of DNA polymerases and single-base specific DNA nucleases, including but not limited to human POLM (H329G), human POLM (H329G, R389K), human BRCT(POLM)_POLL1, human BRCT(POLM)_POLL2, T4 DNA polymerase(Y320A), T4 DNA polymerase (A737V). Other variants include the family X polymerases ScPolλ, HsPolλ, HsPolμ, HsTdt and HsPolβ, shown schematically in FIG. 8. In some embodiments, the blunting enzymes or the variants thereof can be modified with protein tags such as Myc, Flag, VStag, nuclease localization sequence. For example, the blunting enzymes or the variants thereof can include but not limited to 3×Flag-NLS-EXOG, 3×Flag-NLS-T4 DNA polymerase, 3×Flag-NLS-T4 DNA polymerase(Y320A), VStag-APEX2-NLS-NLS, 3×Flag-NLS-XseA.

In some embodiments, the blunting enzyme is covalently bound to the target specific nuclease by a linker. In some embodiments, the linker is an amino acid, a peptide, or a polypeptide.

Microhomology-Mediated End Joining (MMEJ) Inhibitor

The target specific nuclease and blunting enzyme disclosed herein can be combined with a microhomology-mediated end joining (MMEJ) inhibitor. In some embodiments, the MMEJ inhibitor is a CtIP inhibitor (e.g., KLHL15, PIN1). In some embodiments, the MMEJ inhibitor is an MRN inhibitor (e.g., E1b55K+E40rf6).

Pathogenic Frameshift Mutations

Figure 9:
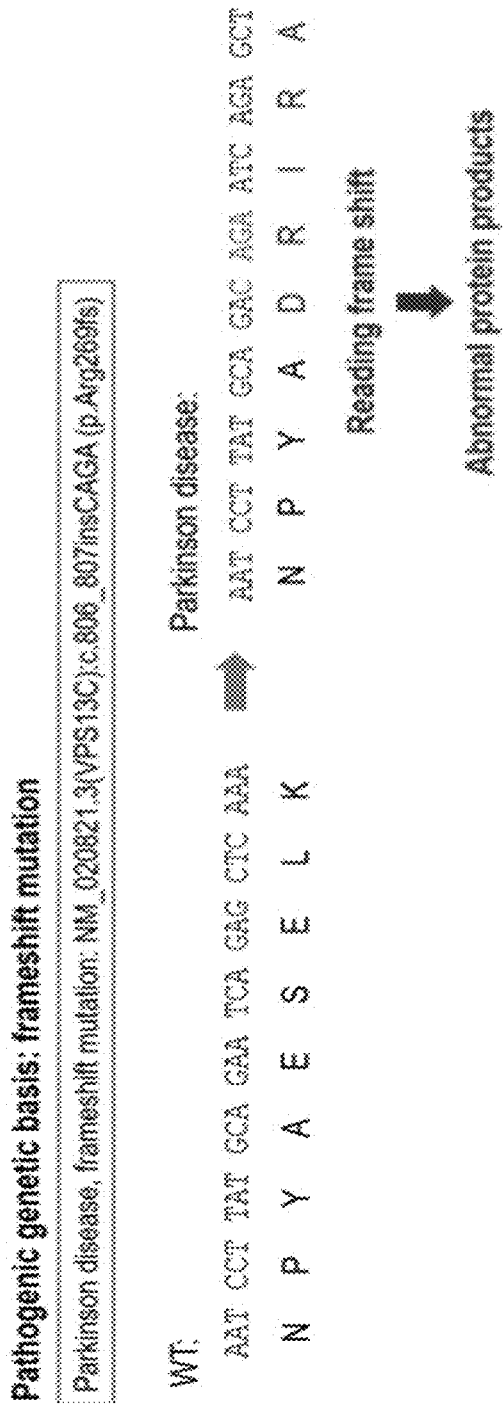
FIG. 9 is a schematic illustration of a frameshift mutation which is present in Parkinson's disease according to embodiments of the present teachings. The frameshift mutation comprises a WT sequence of the sequence of SEQ ID NO: 138 (aatccttatgcagaatcagagctcaaa) and a Parkinson disease sequence of the sequence of SEQ ID NO: 139 (aatccttatgcagacagaatcagagct)

The non-naturally occurring or engineered systems, methods, and compositions disclosed herein can be used to repair pathogenic genes in human cells and tissues, and can be used to correct the underlying genetic basis of many diseases, especially those conditions caused by a frameshift mutation. Pathogenic frameshifts can cause a wide variety of illnesses. One particular condition caused by a frameshift mutation is Parkinson's disease, caused by the frameshift mutation depicted in FIG. 9.

Figure 10:
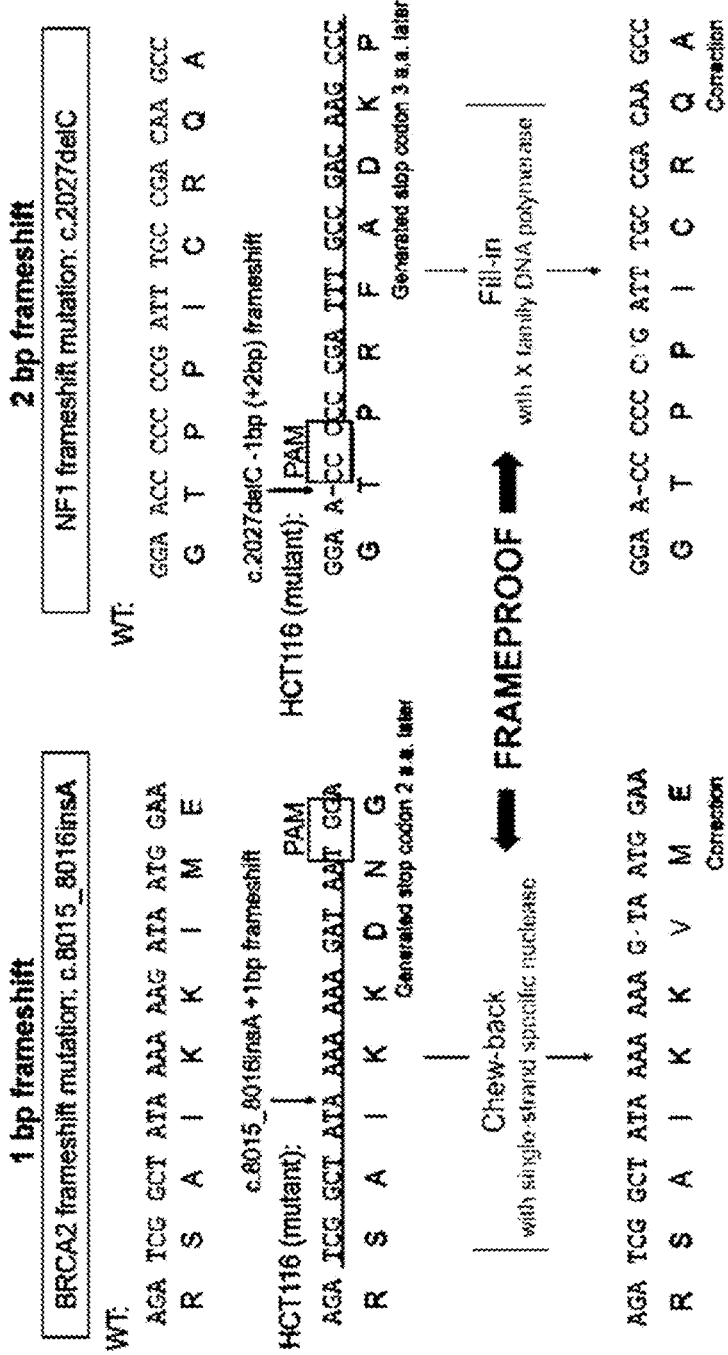
FIG. 10 is a schematic illustration of the use of the Cas9 gene editing system to correct a 1 bp BRCA2 frameshift mutation (c.8015_8016insA) and a 2 bp NF1 frameshift mutation (c.2027delC) according to embodiments of the present teachings. The 1 bp frameshift editing system comprises a WT sequence of the sequence of SEQ ID NO: 140 (agatcggctataaaaaagataatggaa), a HCT116 (mutant) sequence of the sequence of SEQ ID NO: 141 (agatcggctataaaaaagataatgga), and a chew-back sequence of the sequence of SEQ ID NO: 142 (agatcggctataaaaaaagtaatggaa). The 2 bp frameshift editing system comprises a WT sequence of the sequence of SEQ ID NO: 143 (ggaacccccccgatttgccgacaagcc), a HCT116 (mutant) sequence of the sequence of SEQ ID NO: 144 (ggaacccccgatttgccgacaagcc), and a fill-in sequence of the sequence of SEQ ID NO: 145 (ggaacccccccgatttgccgacaagcc)
Figure 11A:
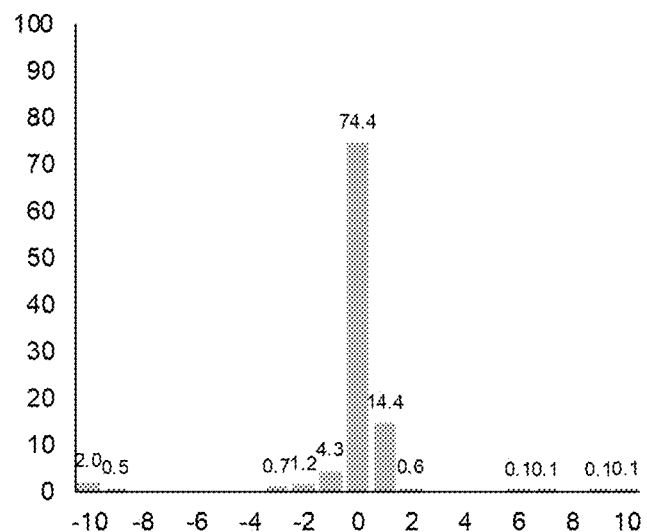
FIG. 11A is a diagram showing the probability distribution of indel mutations in PCSK9 exon 12 when induced by Cas9 only according to embodiments of the present teachings.
Figure 11B:
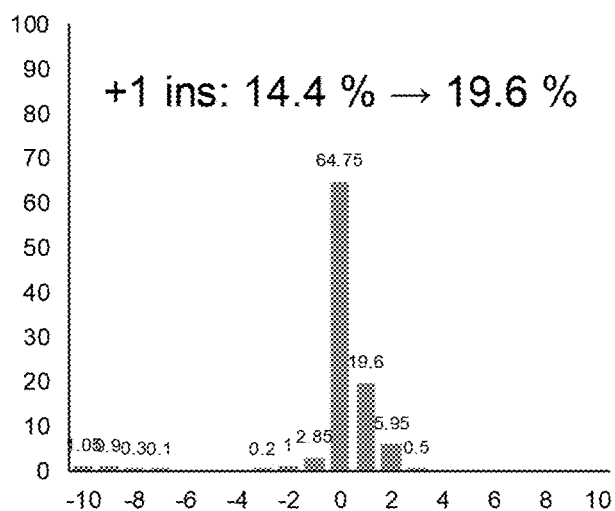
FIG. 11B is a diagram showing the probability distribution of indel mutations in PCSK9 exon 12 when induced by Cas9 and DNA polymerase µ (POLM) according to embodiments of the present teachings.
Figure 11C:
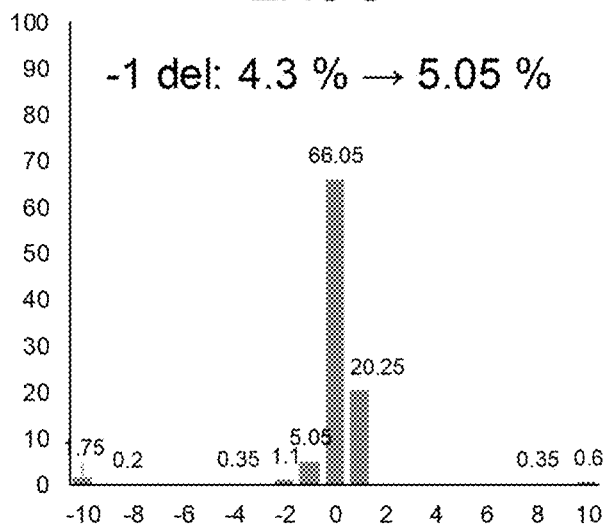
FIG. 11C is a diagram showing the probability distribution of indel mutations in PCSK9 exon 12 when induced by Cas9 and EXOG according to embodiments of the present teachings.
Figure 11D:
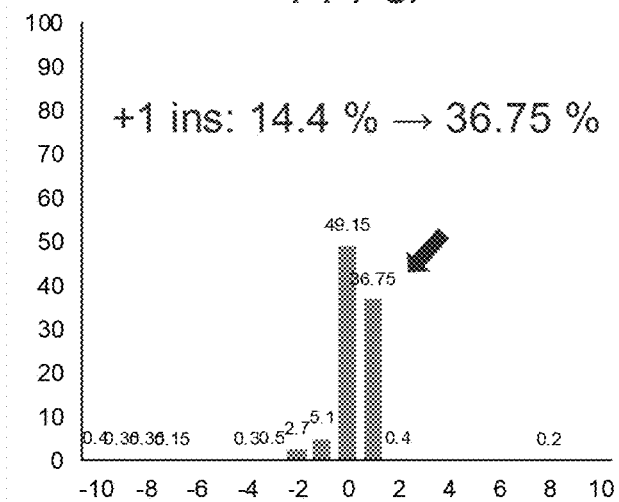
FIG. 11D is a diagram showing the probability distribution of indel mutations in PCSK9 exon 12 when induced by Cas9 and T4 DNA polymerase (T4pol) according to embodiments of the present teachings.
Figure 11E:
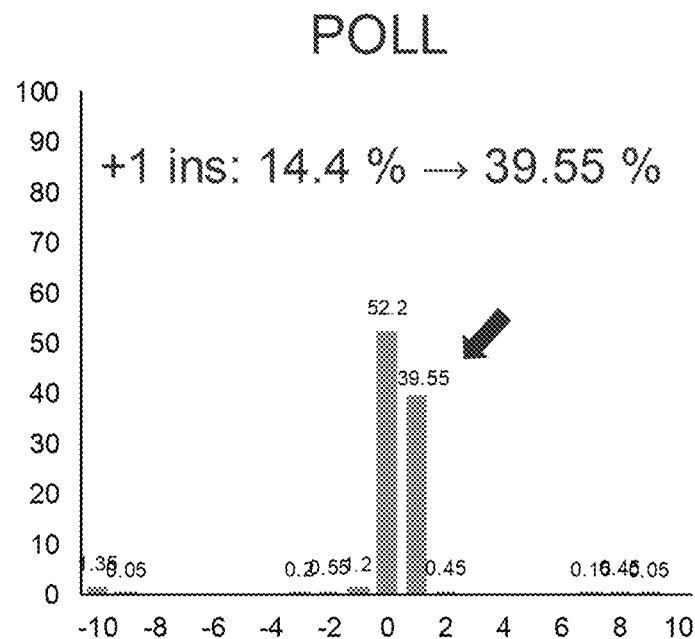
FIG. 11F is a diagram showing the probability distribution of indel mutations in PCSK9 exon 12 when induced by Cas9 and MGME1 according to embodiments of the present teachings.
FIG. 11G is a diagram showing the probability distribution of indel mutations in PCSK9 exon 12 when induced by Cas9 and RecJ exonuclease (RecJ) according to embodiments of the present teachings.
FIG. 11H is a diagram showing the probability distribution of indel mutations in PCSK9 exon 12 when induced by Cas9 and S1 Nuclease (nucS) according to embodiments of the present teachings.
Figure 11F:
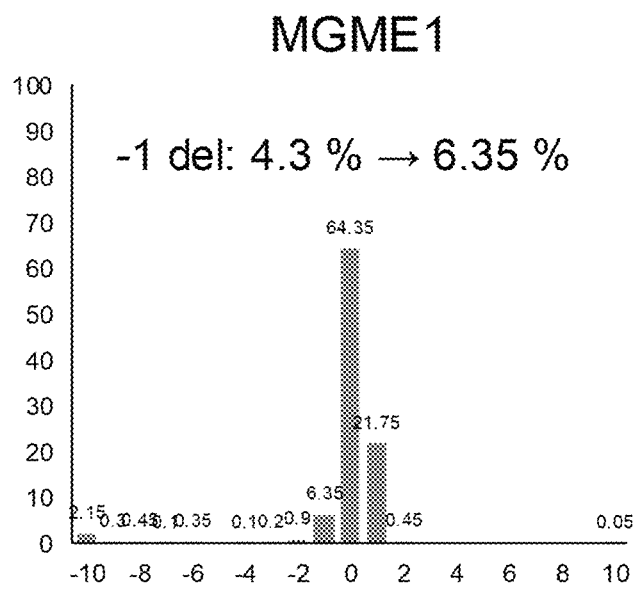
Figure 11G:
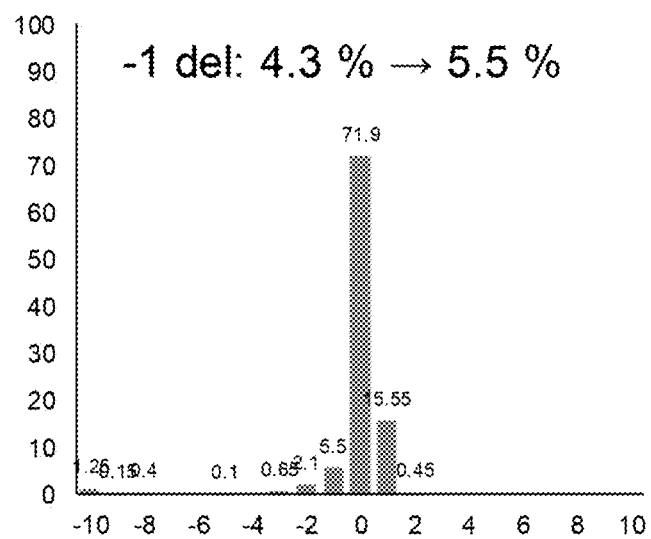
Figure 11H:
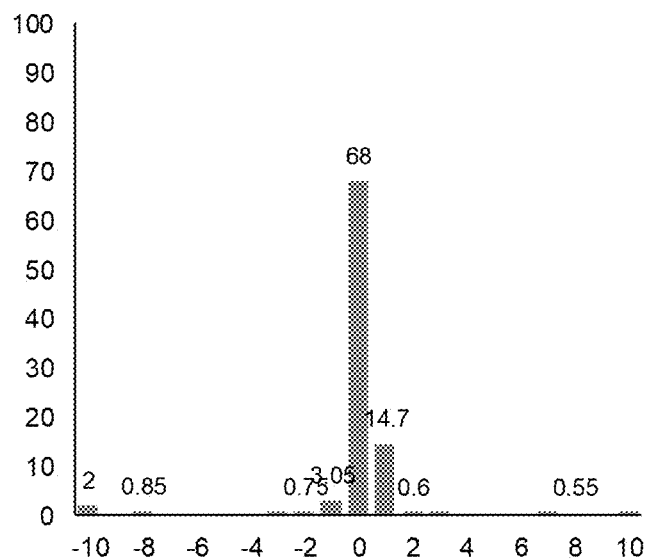

FIG. 10 illustrates the editing of a gene using CRISPR-Cas9 and a blunting enzyme without the use of a donor template. The Cas9 gene editing system corrects a 1 bp BRCA2 frameshift mutation (c.8015_8016insA) and a 2 bp NF1 frameshift mutation (c.2027delC). As the schematic in FIG. 10 demonstrates, a stop codon is prematurely generated due to the frameshift mutation. By using this technique, combining Cas9 and a blunting enzyme without the use of a donor template results in repair of the frameshift mutations.

Other conditions caused by frameshift mutations include, inter alia, the following: various cancers, Parkinson's disease, muscular dystrophy, cardiomyopathy, anemia, Crohn's disease, cystic fibrosis, tuberous sclerosis, Xia-Gibbs syndrome, dermatitis, atopic, ichthyosis vulgaris, Usher syndrome, hypothyroidism, ventricular tachycardia, hemochromatosis, retinitis pigmentosa, arthrogryposis, Robinow syndrome, peroxisome biogenesis disorders, Zellweger syndrome spectrum, cortisone reductase deficiency, deficiency of pyrroline-5-carboxylate reductase, Van der Woude syndrome, Neonatal hypotonia, MYH-associated polyposis, neutropenia, methylmalonic acidemia with homocystinuria, hypobetalipoproteinemia, medium-chain acyl-coenzyme A dehydrogenase deficiency, Sezary syndrome, Stargardt disease, glycogen storage disease, maple syrup urine disease, fibrochondrogenesis, Chudley-McCullough syndrome, spastic paraplegia, frontonasal dysplasia, monocarboxylate transporter 1 deficiency, urofacial syndrome, Hajdu-Cheney syndrome, radial aplasia-thrombocytopenia syndrome, Nager syndrome, White-Sutton syndrome, ichthyosis vulgaris, FLG-Related Disorders, Grange syndrome, Charcot-Marie-Tooth disease, achromatopsia, amelogenesis imperfecta, adult junctional epidermolysis bullosa, fumarase deficiency, and Senior-Loken syndrome.

The systems, methods, and compositions described herein can also be used to enhance out-frame mutations by avoiding indel in multiples of three by a predictable mutation. Out-frame mutation occurs when the reading frame of the target dsDNA is completely disrupted. Therefore, the systems, methods, and compositions described herein can produce knockout cell lines and organisms.

Delivery

In some embodiments, the target specific nuclease and blunting enzyme are introduced into a cell as a nucleic acid encoding each protein. The nucleic acid introduced into the eukaryotic cell is a plasmid DNA or viral vector. In some embodiments, the target specific nuclease and blunting enzyme are introduced into a cell via a ribonucleoprotein (RNP).

Preferably, delivery is in the form of a vector which may be a viral vector, such as a lenti- or baculo- or adeno-viral/adeno-associated viral vectors, but other means of delivery are known (such as yeast systems, microvesicles, gene guns/means of attaching vectors to gold nanoparticles) and are provided. The viral vector may be selected from a variety of families/genera of viruses, including, but not limited to Myoviridae, Siphoviridae, Podoviridae, Corticoviridae, Lipothrixviridae, Poxviridae, Iridoviridae, Adenoviridae, Polyomaviridae, Papillomaviridae, Mimiviridae, Pandoravirusa, Salterprovirusa, Inoviridae, Microviridae, Parvoviridae, Circoviridae, Hepadnaviridae, Caulimoviridae, Retroviridae, Cystoviridae, Reoviridae, Bimaviridae, Totiviridae, Partitiviridae, Filoviridae, Orthomyxoviridae, Deltavirusa, Leviviridae, Picomaviridae, Mamaviridae, Secoviridae, Potyviridae, Caliciviridae, Hepeviridae, Astroviridae, Nodaviridae, Tetraviridae, Luteoviridae, Tombusviridae, Coronaviridae, Arteriviridae, Flaviviridae, Togaviridae, Virgaviridae, Bromoviridae, Tymoviridae, Alphaflexiviridae, Sobemovirusa, or Idaeovirusa.

A vector may mean not only a viral or yeast system (for instance, where the nucleic acids of interest may be operably linked to and under the control of (in terms of expression, such as to ultimately provide a processed RNA) a promoter), but also direct delivery of nucleic acids into a host cell. For example, baculoviruses may be used for expression in insect cells. These insect cells may, in turn be useful for producing large quantities of further vectors, such as AAV or lentivirus adapted for delivery of the present invention. Also envisaged is a method of delivering the target specific nuclease and blunting enzyme comprising delivering to a cell mRNAs encoding each.

In some embodiments, expression of a nucleic acid sequence encoding the target specific nuclease and/or the blunting enzyme may be driven by a promoter. In some embodiments, the target specific nuclease is a Cas. In some embodiments, a single promoter drives expression of a nucleic acid sequence encoding a Cas and one or more of the guide sequences. In some embodiments, the Cas and guide sequence(s) are operably linked to and expressed from the same promoter. In some embodiments, the CRISPR enzyme and guide sequence(s) are expressed from different promoters. For example, the promoter(s) can be, but are not limited to, a UBC promoter, a PGK promoter, an EF1A promoter, a CMV promoter, an EFS promoter, a SV40 promoter, and a TRE promoter. The promoter may be a weak or a strong promoter. The promoter may be a constitutive promoter or an inducible promoter. In some embodiments, the promoter can also be an AAV ITR, and can be advantageous for eliminating the need for an additional promoter element, which can take up space in the vector. The additional space freed up by use of an AAV ITR can be used to drive the expression of additional elements, such as guide sequences. In some embodiments, the promoter may be a tissue specific promoter.

In some embodiments, an enzyme coding sequence encoding a target specific nuclease and/or a blunting enzyme is codon-optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database", and these tables can be adapted in a number of ways. See Nakamura, Y., et al. "codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a Cas protein correspond to the most frequently used codon for a particular amino acid.

In some embodiments, a vector encodes a target specific nuclease and/or a blunting enzyme comprising one or more nuclear localization sequences (NLSs), such as about or more than about 1, 2, 3, 4, 5, 6, 7, 8, 9, 10, or more NLSs. In some embodiments, the Cas protein comprises about or more than 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., one or more NLS at the amino-terminus and one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Typically, an NLS consists of one or more short sequences of positively charged lysines or arginines exposed on the protein surface, bur other types of NLS are known. In some embodiments, the NLS is between two domains, for example between the Cas13 protein and the viral protein. The NLS may also be between two functional domains separated or flanked by a glycine-serine linker.

In general, the one or more NLSs are of sufficient strength to drive accumulation of the target specific nuclease and/or the blunting enzyme in a detectable amount in the nucleus of a eukaryotic cell. In general, strength of nuclear localization activity may derive from the number of NLSs in the target specific nuclease and/or blunting enzyme, the particular NLS used, or a combination of these factors. Detection of accumulation in the nucleus may be performed by any suitable technique. For example, a detectable marker may be fused to the target specific nuclease and/or the blunting enzyme, such that location within a cell may be visualized, such as in combination with a means for detecting the location of the nucleus (e.g., a stain specific for the nucleus such as DAPI). Examples of detectable markers include fluorescent proteins (such as green fluorescent proteins, or GFP; RFP; CFP), and epitope tags (HA tag, FLAG tag, SNAP tag). Cell nuclei may also be isolated from cells, the contents of which may then be analyzed by any suitable process for detecting protein, such as immunohistochemistry, Western blot, or enzyme activity assay. Accumulation in the nucleus may also be determined indirectly.

In some aspects, the invention provides methods comprising delivering one or more polynucleotides, such as one or more vectors as described herein, one or more transcripts thereof, and/or one or proteins transcribed therefrom, to a host cell. In some aspects, the invention further provides cells produced by such methods, and organisms (such as animals, plants, or fungi) comprising or produced from such cells. In some embodiments, a Cas protein in combination with (and optionally complexed) with a guide sequence is delivered to a cell. Conventional viral and non-viral based gene transfer methods can be used to introduce nucleic acids in mammalian cells or target tissues. Such methods can be used to administer nucleic acids encoding a target specific nuclease and/or a blunting enzyme to cells in culture, or in a host organism. Non-viral vector delivery systems include DNA plasmids, RNA (e.g., a transcript of a vector described herein), naked nucleic acid, nucleic acid complexed with a delivery vehicle, such as a liposome, and ribonucleoprotein. Viral vector delivery systems include DNA and RNA viruses, which have either episomal or integrated genomes after delivery to the cell. For a review of gene therapy procedures, see Anderson, Science 256:808-8313 (1992); Navel and Felgner, TIBTECH 11:211-217 (1993); Mitani and Caskey, TIBTECH 11:162-166 (1993): Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer and Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

The target specific nuclease and/or the blunting enzyme can be delivered using adeno-associated virus (AAV), lentivirus, adenovirus, or other viral vector types, or combinations thereof. In some embodiments, Cas protein(s) and one or more guide RNAs can be packaged into one or more viral vectors. In some embodiments, the targeted trans-splicing system is delivered via AAV as a split intein system, similar to Levy et al. (Nature Biomedical Engineering, 2020, DOT: doi.org/10.1038/s41551-019-0501-5) in other embodiments, the target specific nuclease and/or the blunting enzyme can be delivered via AAV as a trans-splicing system, similar to Lai et al. (Nature Biotechnology, 2005, DOI: 10.1038/nbt1153). In some embodiments, the viral vector is delivered to the tissue of interest by, for example, an intramuscular injection, while other times the viral delivery is via intravenous, transdermal, intranasal, oral, mucosal, intrathecal, intracranial or other delivery methods. Such delivery may be either via a single dose, or multiple doses. One skilled in the art understands that the actual dosage to be delivered herein may vary greatly depending upon a variety of factors, such as the vector chosen, the target cell organism, or tissue, the general condition of the subject to be treated, the degree of transformation/modification sought, the administration route, the administration mode, the type of transformation/modification sought, etc.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues. Viral-mediated in vivo delivery of Cas13 and guide RNA provides a rapid and powerful technology for achieving precise mRNA perturbations within cells, especially in post-mitotic cells and tissues.

In certain embodiments, delivery of the target specific nuclease and/or the blunting enzyme to a cell is non-viral. In certain embodiments, the non-viral delivery system is selected from a ribonucleoprotein, cationic lipid vehicle, electroporation, nucleofection, calcium phosphate transfection, transfection through membrane disruption using mechanical shear forces, mechanical transfection, and nanoparticle delivery.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences.

Kits

The present disclosure provides kits for carrying out a method. The present disclosure provides the invention provides kits containing any one or more of the elements disclosed in the above methods and compositions. In some embodiments, the kit comprises a vector system and instructions for using the kit. In some embodiments, the kit comprises a vector system comprising regulatory elements and polynucleotides encoding the target specific nuclease and/or the blunting enzyme. In some embodiments, the kit comprises a viral delivery system of the target specific nuclease and/or the blunting enzyme. In some embodiments, the kit comprises a non-viral delivery system of the target specific nuclease and/or the blunting enzyme. Elements may be provided individually or in combinations, and may be provided in any suitable container, such as a vial, a bottle, or a tube. In some embodiments, the kit includes instruction in one or more languages, for examples, in more than one language.

In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10. In some embodiments, the kit comprises one or more oligonucleotides corresponding to a guide sequence for insertion into a vector so as to operably link the guide sequence and a regulatory element.

Sequences

Sequences of nucleases, enzymes, guides, and linkers can be found in Table 1 below.

TABLE 1

| SEQ ID NO | SEQUENCE |
|---|---|
| SEQ ID NO 1 POLL Homo sapiens | atggatcccagggtatcttgaaggcattcccaagcggcagaaattcatgctgatgcatcatcaaagtactgcaaagattcctaggagg gaagggagaagcagataagttcagcggcgccagtgcctgcccagggccatgtgtgccactggacgagccgggcagcagaactctt tgagagcagatgttcagcaggcgccagtgcctgcccagggcctcattcactcacattgtgtgatgaaggcatgactat gagcagccctctcagactcgagtgattagctggacagctccatgccagccgctgaggccgtgccttcaggaga ggaggctgtgatgtagctggacacccatgaggccctgcttcagcacatcttcacagagcgtcagccaagcaggatgcttc tattcctcctgcaccaaacacccagcccaagcaccaccctgttgatggcagcagtgaagcagtcacagcctgttgtgcagctcgatctgaagc cctcagtcagtgcgccactcctcacctcctgtgatgagaatgtcacagagagcttcctgataagcctctgtcacagc cctcaagcagcgggctatgccaaggcgcatcaatcacaaccctcatacagagatcttggaggctgtgaccaatccgtcggaagctggtcaccaagaaagt gaaggcccccggctgttgggaagcccatctgtgagaaatcatagagataccaagggctggaccaacaaccagtactcctggaacttccgaagacatcc gtcttgaagctcttccaacctctagagattgtcttcacctgaagtgctggaccaaggcatacactacagagccagaggactacac gcagccaggccgccccctgacaacccagcgcatgctcgaactgcttaactcggacgttcagaacatgtcgcaagacatgtcagactgtcaacccgc gagattgagcagacagtgccctgaactgcctttaactcggggtatttcagcgcgctcttcacgcgctctcacttcaccgcgc acctggttgctgacggtgctcagagatgtgatgtcaagcggcatgccccggtatctcagaacaatccggcccggcaa agggttcctcacagatgacttggtttgtcaaccacgagaagaatgtcagcagtgccaggagaacatgtgttacagaacaaatcaaccgc ggcgcaccggcctgccgagtgctgccactgcaaaccaaggcatgcttcaggcttcaggctcttaggctccctatggcgtcctcaccggcggc tccatgcgagccctgccgagtgctgcccaaccaaggcatgtgcccactgaggaagatgctcttcagaagatgctgtcagaacatgtgtcagaagatgctgtcaactgcactacccgagaacctgctgagcggac gtgggcgggcctgccgagtgctgcccaactggaggaagatgctctgcatgaggatgtctgaacattcgcggtcctgaactaccgagaacctgctgagcgggac tggtga |
| SEQ ID NO 2 POLM Homo sapiens | atggctctgccaaagaagaacgcgcacgggtggggtcccctcaggggaccgcagctcctcctctacaccttcggattccgggtgtt gcaatacccgtcgagcaccatcgtcgttatggatatctttggtgaccgaaatgcctgaggagtcttagagggttcctttacgggtgttggacgtttcggtgttggacgca tgttctagtgagcactgtcgttggatatatctttggtgaccgaaatgcctgaggagtcttgggcgtgcaagagtccgacactgagctggtgctcaccac cgctcagctcgctgcttgtgatatctttggtgaccgaaatgcctgaggagtcttgggcgtgcaagagtccgacaacagtcgacatcgattgg aagtagtggtccgaggaagcattggagatattggcgaaagccccctctgccgtctgatgctcatgtcgagagatctgaagtcatgagcagcatccgttc gggcttccaggctgccgagtcgccgagtcgccaactgcgaaggtctccaacttcggcgaacactgagcctgcgaacactccggcgaacactgcgaacactcggcgtacaagaactcc ttaaagcgctgccgggtctcgaggaagttgaggggtgagagggaaggaacgatgaacgatgaagtgtttacacaaatcttggagttga gtcaagacgggcggacatgtatcgagagggttcgaacgttcgaacgaagcagcaaagttaaacgcaaacgatgaacgatgaacctggagtaggtga gccctccgggcgcgagctgccagtaccgtcagcgctcacggaggattagacgcggacaacttcaaggtcgattcttgataactcatgttgcga gtcaccaccgccgccgctagccgtccatcttgaaggtgcgggtgttgaagtctctggagctggagcgccctgtgagaggatcattcagatcgaaaagaagaagccccagtcgggcacaccctttgtcactcacaccgtgagctg gatgggtccactaggccgtccatcttgaaggtgcgggtgttgaagtctctggagctggacagcatgcgagccctgtaattcagatcgacccggctgcgccctggcactcagttcccctgagccctgttctgaccccg gaccggcagtaaactttcttcaggctgccgagcaagccggttccaaagagagccgaggaacgatgaacaacgcaaaacgcctgactgacttagtacttcgcccccagcagccaacgcactga acaaaaaaacttcttcaggctgccgagcaagccggttccaaagagagccgaggaacgatgaacaacgcaaaacgcctgactgacttagtactttccccccagcagccaacgcactga |
| SEQ ID NO 3 POLM (H329G) Homo sapiens | atggctctgccaaagaagaacgcgcacgggtggggtcccctcaggggaccgcagctcctcctctacaccttcggattccgggtgtt gcaatacccgtcgagcaccgtgggacgtggaccgagcaggggttccttacgggcgctgcgaagagcctgcgagagctgcgagagctgtgctgaccac cgctcagctcgctgcttgtgatatctttggtgaccgaaatgcctgaggagtcttgggcgtgcaagagtccgacaacagtcgacatcgattgg aagtagtggtccgaggaagcattggagatattggcgaaagccccctctgccgtctgatgctcatgtcgagagatctgaagtcatgagcagcatccgttc gggcttccaggctgccgagtcgccgagtcgccaactgcgaaggtctccaacttcggcgaacactgagcctgcgaacactccggcgaacactgcgaacactcggcgtacaagaactcc ttaaagcgctgccgggtctcgaggaagttgaggggtgagagggaaggaacgatgaacgatgaagtgtttacacaaatcttggagttga gtcaagacgggcggacatgtatcgagagggttcgaacgttcgaacgaagcagcaaagttaaacgcaaacgatgaacgatgaacctggagtaggtga gccctccgggcgcgagctgccagtaccgtcagcgctcacggaggattagacgcggacaacttcaaggtcgattcttgataactcatgttgcgccaacgcctga |

TABLE 1-continued

| SEQ ID NO | SEQUENCE |
|---|---|
| | aggggcgagaggctggtttgctgccgcgcgagtaatgtgccgattgcaagaccaaggcttgatactgtaccaccaacaccaacattcatgttgcg |
| | agtcaccaccgcctcgcacagcagagccatcgatgacgcttcagagatcaaaatgcatattcagacttcctcagccccaggtgtggcg |
| | gtcggtgggtccactaggccgtgtccattcttggaagctgcttgtgcgggtggatttggcgtagccccgtcagccagttcccttcccttgcactcctggg |
| | gtgaccggcagtaaactgttccaaagagagctgcgaaggtcgcgaagatatctccacggaaagaaaggcctctgcttaactccacggcttcgacc |
| | ccgagccaaaactttcttccggctcgagcggaacgaagtacagatctcccgcactggagctgagctaccctcccccgagcgagcgaacgct |
| | ga |
| SEQ ID NO 4 POLM (H329G, R389K) Homo sapiens | atggctctgcaaagagaagacgcgcacggttggtgctgccgcgcaggttggggcgcacggcctcctctacacctccatctacgagatttccgggtgtt |
| | gcaatatacctgtcgagccccgatggacgtagcccgatgagacgggttccttacggcgtctcccgaagtaaaggcttcggtgttggacgca |
| | tgttctagtgaagcgaccatcgtcgttgattgatatctggctgaccgagtgcgaggagcttggggctgcaccaacagtgcctgaatgctgcgatcgattgg |
| | cggctgcactccgctgcttgttggataatatctggctgaccgaaagttcggggctgacatgcctgcatatgccctgatgccctctgaccgcaccacact |
| | gggcttccgaagctgcagatattgcggaagccgtattcctctaactgactctcaactgcgcaagttcgcactcagcatccgttc |
| | ttaaagcgtcgcgagtccgagaaacgtcgagaaggtgaggttgagaaggagcaaggaaaacatcggcgacaactccaaggcgggtcgtacaagaactcc |
| | tggacacggggtctgcgagaagaagttgagaggggcttcgaacgctcgacgctgcgcagaccaacgcgaaaagcggcaaaagctgaccccaacagtgaa |
| | gtccaagacgggcggcaagcacatcaccaagacctgctcttacgatcgtcttcgctgatgatcccaacaagtcgtcgaggagcagtaggccag |
| | ggcccgaacctccgggcgccctgtactgctccgcctcaagagacacggttagacgcggcaaactcaaggtgcgatgtcgattcttgataactcaccaacaag |
| | aggggcaggagctgttctgccgcctcgcacagcagagccatctgaagacgctttcagatcattgcatattcagactgtaccgtcagtgcgcggt |
| | cgtggtccactaggccgtccattcttggaagctgcggtttggcgtgtcgcgagttggtctgagcccggtcagcagttcccttgcactcctgggt |
| | ggaccgcagtaaactttccaagagagctgcgaaggttgcacagagaaggggccctctgcttaactccaccggctgttcgaccc |
| | gagcaaaaactttccttcaggctcgagcgaagaagtatcttccgccactggagtacttccccccgagcagcgcaacgcctga |
| SEQ ID NO 5 BRCT (POLM) POLL1 Homo sapiens | atggctctgcaaagagaagacgcgcacggttggtgctgccgcgcaggttggggcgcagcctctcctctacacctccatctacgagatttccgggtgtt |
| | gcaatatacctgtcgagccccgatggacgtagcccggtcagtagaacgggcttccttacggcgtctcccgaagtaaaggcttcggtgttggacgca |
| | tgttctagtgaagcgaccatcgtcgttgattgatatctggctgaccgagtgcgaggagcttggggctgcaccaacagtgcctgaatgctgcgatcgattgg |
| | cggctgcactccgctgcttgttggataatatctggctgaccgaaagttcggggctgacaatccagtagtgatccaaccacac |
| | agcccagcaagcaggcaggatgctctattcctcctgacccacctggcaccagtgaggcctgtcagacagccccatctcgaggagcagccagagg |
| | gcctcttctcccaaaaagctggatcagtcggatccaaccagcagccccatctcgaggagattgtgagccagccctgtcctgcaagcc |
| | caggtcaagtgggtcgtgcagcaaggttgcacaagaagggccctatgccaaggtgaccaatgcaaagccctggcaggtcctatcacagcctgcacctcgtaccag |
| | tacagtgttccagggagacaagtgaggggcccgtgctgccaaggctatggcccaagagagcttccataaagcctcacctgtaccag |
| | gaggccgcagtcctggatcctcagtagacgacagatcataagagccgagtggactggcgaagacctggagagctgagctgggcacctcg |
| | cagtgagacgtcctgtcttggagctcctcccaacatccggagcgtcatcgggacaggaccaagacgcccagatggtgaaacagggcttccagg |
| | gaaagggcagcaggctacagagattgagcagagacagtccaaagagagccccatctcaccgatcctcagcgtacgcgacactactggtgttgtggggaaaaacc |
| | caggtcaagtggggtcctcacagatgactggtgagccaagagaatggtcagcaacagaatgtctcaggtccgagttgctgcctgcaccttcaaacc |
| | ggcccatgcagccaccgcggcccgactgactgtggcccaaacccaaggcgccttgacccccactgccgaaaacccatggctgcag |
| | gtccctcgagccgctgccgagctgcgcccactcactgggccacccctgggcccagccccttcctcgcagccttcaaggctctacgaactcgctgggggactg |
| | gtga |
| SEQ ID NO 6 BRCT (POLM) POLL2 Homo sapiens | atggctctgcaaagagaagcgcacggttggtgctgccgcgcaggctcctcctacacctccatctacgagatttccgggtgtt |
| | gcaatatacctgtcgagccccgatggacgtagcccggtcagtagaacgggcttccttacgggtctccgaagtaaaggcttggttgaacgca |
| | tgttctagtgaagcgaccatcgtcgttgattgatatctggctgaccgagagtgcgaggagcttggggctgcaccaacagtgcctgaatgctgcgatcgattgg |
| | cggctgcactccgctgcttgttggataatatctggctgaccgaaagttcggggctgacatccagtagtgatgacatcctgcc |
| | aaagctgcggtccggaggaaggacagtccaggagggccctgctatgccagaggccggtatgccaggagcgcatcaagcctcatccctcgg |
| | taccagggccctgcagtatcccctggattggaaaggcgaatgggaaacatagagatgctcagaggagcgggcatttgcggaagctg |

TABLE 1-continued

| SEQ ID NO | SEQUENCE |
|---|---|
| | accatatcagtgagacgtgctgtcttcttctccaacatctgggagctcttctgcacaagactgccagatgtggtaccaacagggctt |
| | ccgaagtctgaagacatccagagattgagcagaccagcctccctgacaacccagcagccatcggctttaactctggctgtgttgacttcctgaacgtatgc |
| | caaggagggaggctacagagattgagcagacagtccagaagaaagcagaaggccagcccccagcagccggatcttcagcgcgttcacttgaca |
| | gtctctgcagcaaaggcgacctgtgatgtcgacgtgctcatcacagatgactggtgagccaagagaagatactgggggtgcgcgctccca |
| | ggccaggggcgcggcaccggcctggccgagtgctgccgagtgtgcctggaacatccagagctgagtcgtcagaaacatgcctcagcactgcttccactcggtccgtgcacac |
| | ttcaacgctccatgggccgagccctggccaaccaaggcatgagtgcgagtgtcagaaactgccccagcctcactttaggcctccacccaccggctgaagccctgtgacgg |
| | ctgcaaggtggggcctggcgagtgctgccactgagaaggatgtcttcaggcctcttaggcctccctaccggagcctgagcg |
| | ggactgtga |
| SEQ ID NO 7 | atggactataaggaccacgacgaagactacaaggatcatgatattgattacaaagacgatgacgataaggtcgatccccgcgg |
| 3xFlag-NLS- | ggtcggtatccacggagtcccagcagccgtatcagagatgctgtcgtccgaccgcagtcccctgagccgggtgcctgtcgaagctggg |
| EXOG | gctctggctggccgctccgaggggcctccccgaatccacaggaggctgctgtacacaatctgattcccctttaactggaacagagagcaagtgtacactcagtgtgctttatgate |
| Homo sapiens | atgggcaagacagggttgcctagatgggtcttctgaacctttcaaaggcaagatcatggttctccaaagcaagataatgagcagacacgaaagcattgtaaaataagcctgat |
| | cccaatatcccttccaactccagtgctctcagtgaaaccctgccctttgataacttcctctacaaccttgttgatcctccgcacgactctgaaaaactggtgggtcacgaggatggtggtcagagatgcgatcagaataacaaatt |
| | ttcaaggctgacagaaagttgaagatggacaacgtggcagtcccccacccatcggcttccagccatcggcttatatccggaatatctgatcccggaaatactgtggacacagccggaatattctgaatctgaatcagaatagaaatgtactgt |
| | ccagaggctgatgatgccgaggacaacgtggcagtccccccacccatcggcttccagccatcggcttatatccggaatatctgatcccggaaatacagggccgatgagaagtccagtatctaccgaccatggc |
| | ccagtggcctttgggtaccaatgaagccatcggttccagccaatgaatctaacgtaatcctggccgcagagagctccaggacctagaagaagtgtca |
| | ggactgtgttttctccattggataataacgggcagtgatatccggaatatctcggtgcagacctgacacctgtaagctcctgacttcctgggagtcaccttgt |
| | actgactacaagaaagattgaaggaccgccatgcagatcgagaactcaagctgaaaatatcaatcgaagaaactgaacactgaccagaagatagaagaagcagaactgaaccagatg |
| | attacttattatgtcgtatgagaagactacaagaactcaaagctaaggcagctagagactccga |
| SEQ ID NO 8 | atggactataaggaccacgacggagactacaaggatcatgatattgattacaaagacgatgacgataaggtcgatccccgcgg |
| 3xFlag-NLS- | ggtcggtatccacggagtcccagcagccgtatcagagatgctgcctgctgctatatccgcgcaacctccgctgctatatccgccaacctaactttatggggcaat |
| nucS | ctggccatgaaactgtcgctcactgtccaatcaactactcgatgcggggcagattgcaacctactccttaaaactcttggagaatctcatatgtgggcgactctactccat |
| Aspergillus | atttggccaacgtggcaatcggggtttgatctaccgtcaggtccgaatgacagctacagtgcatctctctatcccaaaactggcagtcaacaacatcacaccgaagataa |
| oryzae | ccccacccaatcatggggtgactatgacagggtccgttcacattgtgtccattataggataatcatcagcgccggttcatgacgaaaaattggag |
| | gaagtcctaatggacgaggcctcaggccggtgactggtcttatccgatattcccaagtccatgagtgatctgaaatccagtctcatccaacaaactagtgaagattggag |
| | gcagaagaaatagcctcaatggcatctgacggcatatgggcaaatgacattggctgccaccagagcagcatctgccttaagcatcactcagcctgaga |
| | aggtatagcactgtccgtggcaaatgctccagtcccagttggcaggttgcatgcagacggcagactcaaaaaaggatagcctgacc |
| | gatgaattgataattactaaagatcccagtaagcacgtcatgatcaccgagcaccacggatgacagagaaccactagtctgtcatgcagactgtg |
| | gctattattaatactccccgaccacggcccaagaccagcaagctcttcagagactcagagactttatagcaccagcggtgttatagacttgcg |
| | gcttggctggtgacctattgcgctccccagctga |
| SEQ ID NO 9 | atggactataaggaccacgacggagactacaaggatcatgatattgattacaaagacgatgacgataaggtcgatccccgcgg |
| 3xFlag-NLS- | ggtcggtatccacggagtcccagcagccgtatcagaagatgcgctatgccctcgccagcatgcggcaacatggtccaacgttcctgacccccgccaag |
| NucP1 | gtcctggcgcaaggcttcactttattatgccgaaagaagtcaactgctcttggggcgatgaaacccgcactgcttctggggtctcc |
| Penicillium | tggagtgctagttgcacttctatacacagcgagaagaagtgctacccaagctttctcccgacgagtgtgatctctgtacattcatcgg |
| citrinum | ataccagacatagctcgccaagatctctcaacaaaggactgctcattgattcatgccatatctcgtcaggaggcccgacagcagccgagtcgtcacagc |
| | gaccatggacaccttacacccgatatgccaagaagttgatcggccgtcagcccgtcagcaaaggccgacaaactccagacgcgctccttacgagtctgacaacctccacagc |
| | gattggaaattacccccgcaggcaattggttatgcctcacggagctgcggcactccaaaagcccgacaatcagacagttgaccttatccgactactcacggcagattatcgaat |
| | caatgtcttcaataggcagcggcttaatgcctcacggagctgcggcactccaaaagcccgacctacctactacgactctgatagatact |
| | attgaacttcaatattcagagacgtccaaagagggctaccgcgctcgaactggatataagcgagcataag |
| SEQ ID NO 10 | atggactataaggaccacgacgagactacaaggatcatgatattgattacaaagacgatgacgataaggtcgatccccgcgg |
| 3xFlag-NLS- | ggtcggtatccacggagtcccagcagccgcaagtgaagttatttcagaccattgcaggccagcgctcaaagtttctgtgaatcagctg |
| MGME1 | ccctgtggcttcctctcactccctatcatgtgcccgaccccggatgcggaagaaaagtgaccatagaagaagtgtgaccaagaaatactctaatttagtt |
| | cagtctctgtctcatccagaggcgtgcccagaccgcctttgctctgtggaagatgctttgctctgtggacccgtgaccaagcataagtg |

TABLE 1-continued

| SEQ ID NO | SEQUENCE |
|---|---|
| Homo sapiens | ccaaaccaaggtgaggacagacgagtgccacaaaactggttcctactctcaatccagagagaagtgataaccaaatgcaagtgatccttcag<br>ttcctttgaaatccccttgcaaaggaattgataccaagtgtgaccgagtccttcagcagacacattcagctttgatcatgttcttgttggaga<br>ggtggaaacagcggcgatgatctggaactgggagagatggcttaaagatacaactcaagttcatgttgtcatgtatgaagaacct<br>agccaggacgtcttttacaaggaaaacgttccacgaagcttgaaagatactttcaccccaggaacctaaaagagagatgaaa<br>tctcctaagtctggttacattgaagatgtccagaattcgagtatccaggcaagcctgtgtgattgaagcatcagagaacatagaactttaa<br>actatatagtctgctgctgacctgcaagttgtgctagtcaggcaagcctgtgtgattgattgaaccatcagagaacatagaacctttattcaa<br>gtacatttgacaaccactccaagttgtgccacccagctccatcatggtgccatgaaccatgactgaccaagtgcttcttcgactagaagat<br>atacggaaaagaaaagaaaccagaattcagaaacaacaagaattcagaatag |
| SEQ ID NO 11 3xFlag-NLS-RecJ Escherichia coli | atggactataaggaccacgacgacggagactacaaggatcatgatattgattacaaagacgatgacgataagatggcccaagaagaagcgaa<br>ggtcggtatccacgagtccccagcagccgaaccaggcagcagcagatccaacttagacgaagggaagtcagacagcggaaacacagggacttccggctga<br>gtgtccccccttcttagacgttcgagtgtccagcacgccgggtcgctcgtcgagaagaacctgagcctcgtccaggagactgacctgcctgcaac<br>agtgatggtgttgaaaaggccgttgagattctctataatgcattccaggagaactcggatcatagtgtagttgatttgcacgctgatgga<br>gcaactcaaccgcgttgacgtactccgcatcgcctgcctctcggttgctcaaacattgatcattgtcccccaatgcagttgaaaatggttatggac<br>tcagccccggaggttggtgaccaagcgcccggacgccagcctcatgcaatcgtcatgtcgatgtcatgtccatggaacctaaagg<br>cacgccgcagcctcggatcccgtgatttgaacgactcaatcacccgggatgaccacctccgggaatgcactgctgagccaataatcaatcctaacc<br>ttcgggatgtgtaactttccgacacatagtctatcctaattggccgaacttcggtcgccgccttgaacgttccttcgagatcaggggt<br>ggttcgacgagcggaacatagctaagtttgacatgcaggaatgctaggtctaggatgtgccggaaatgtctgacggcggtcgcacgttgaagctctttaagctctcaagtgtcctctgaaccgag<br>aacaatcgaatttgacatgcaggaatgctaggtctaggatggccggaaatgtctgagcccggaacctgcgtcaacgaacctcaggtggcaaacgag<br>atgcccaagctcgacatcgacaatatagttgaagcagagcgtcgcgttcaaggagccacgccgatgacgaattcggagacagcagggca<br>cactccctgcgacaatacccgttccgcgaccagcatgtacgagctctgatctctcggcagccctgcgaacgaactcgagacgcagcagcaccctgagcacgcgatccagccacc<br>tgcagataggagcgctaggcactccgcgtccgacaaagaaaggtccaccgcggcagttacgctattgctttgctctccgcagtgatgaacctaaagg<br>acctcggagatctatccaggggttccatatgggagctctgacgcttgacgtttttaccaggtatgatgtcaagttcggcggtcatgc<br>tatggctgcgccgccctcactggaggggatcaatttaaacctttcaacagaggtcgggaagcgtcgtcagtcgccgaatgacgtccttgc<br>ttcaaggcgaagtagtagcggagccgttggtgacgactcaagttgccgcacattcggggatgcgacagcgcctcaggagcgctcggcgccctgggg<br>ccagatgtccggagcgcgtgttcgacggcatcgctgcttaatgcagacgagcactggcagctgtgcgataatggcgtcaggtcagttgccataa<br>ccggtggcgcccccgtcgtcgatgcgagtgcgagcagctgccgcagccccgtgagcggcgaagcttagtggttcaatatccgcctata<br>gctgatattaacgagttcgagggaccgatcctgcaaattacctctgcaaatgacaatatctggcccatag |
| SEQ ID NO 12 3xFlag-NLS-T4 DNA polymerase Bacteriophage t4 | atggactataaggaccacgacgacggagactacaaggatcatgatattgattacaaagacgatgacgataagatggcccaagaagaagcgaa<br>ggtcggtatccacgagtccccagcagccgaaccaggaaattctattagtatccgagacagctggaaacaacactgtagagcggtatatgatgaaac<br>ggcaaacagagccacgtcgagagtgcgaatactccgagactgatcgaagcgcatagggacgatcgaagctcgaagcattggggataaccgatt<br>ttaaagtcgctgcctactctcgacactccgacccgatgaaggtgcagagaagtcatcatgcatggaagtcgttcgtcgctgcgaatgcgaatcggagttcactgagg<br>aattaagtcccgaccgatgaaggcgagtacgagtgacgctacaacacttgacgctaaacccgccgaaccactatgacgacggttcttatattgacctgctc<br>acaggtaatcacactacgccctttgacatgccttgacaatgaacgagatatgatggctagtatggctaagcatgcaaaagatcaaatattacaggct<br>ggaacatagaagaggtgcgatgtacaaaaactgtatgatggctcaaaaaagatcattatacctacaaagagaagtaggaagaaagatttcacctattggcaga<br>tgctttaccaaactcgttgcctgttctcccttgaacgtacacaatatattgatgtcggcccacaagatggctggtgccaagagagtgcctgtgtgcctagtctgccgattaataaacct<br>gcgcgaccaacccattccattaccgcaagataatatagccacaaagcgttccaggtgatctctgcaatgctgcaaggactgaagccatgtgcaagatctgcgatcattcttcaattcctcaaggaga<br>cctcaatgtcccgacccgttcccgaccgatgaaggtgcgatgcgataggaacgggggcgatgtcatcaaaaacggtggataggactgttgcgatcccgaaggtcgcagtcgaagaccggtctctatgtattgacctgctc<br>gcaaggtgtatcgacccttcagcgttaggtacgatcccggagcttttgtcttgcaagccgatcccgaaggtat<br>catgttcgaccttacgtcacttactcatcttcaattattgcaagttgacgaatactcgacccggcctcagttaaggtacaccccaatcc<br>atggtactacgagcgacaccccaaaacgtgctagcccacaatctgcgacgaacagtgatacctggagatgacacactactaagtgcacaacaccgaggggcata<br>acacagagtctgtatcgactgattgaggaatgaatgacaaagatgttgcggagaatgaacgccgaggcttaaaaa<br>atcattatgaagggagcgggtagcgttcaccgaatttccaagcacaggaatattttccaaagcacaggagagcgctacgcaatttccttaagctgtaataccaccttgctatatccaagtgatgactccttaatgagctgtaact<br>acaaagtctgacttgctaccggaacggtaactcatttcagattaccgaggatgaatgacaaagatgtgcggagaatgaaacgccgaggcttattaaaa<br>cactgtgtggcccttggcaacattcattcgagggaacgatctctgcaaattacctatcgcaaattacctatgacaatatctggcccagtgg |

TABLE 1-continued

| SEQ ID NO | SEQUENCE |
|---|---|
| | atcgcccgaaaatcaacgagtacctcaataaagtgtggtaccaatgacgaggattttatcgcagcaggcgatccgatagcgtgtatgtttg |
| | cgtgcacaaggtcattgaaaagtaggcgtggatcggtttatgagcagaatgatccttgtcgagtttatgaaccagttggtaaaaagatgg |
| | aacgatgatagatgagcgtaccagaaacttgtgactacatgaagaaatcgcggcactgatcgcacatgacaggaagcgatttcatgcc |
| | cccactcggttcaaaggcgtagggggtttctgaaagtaagaaacggtacgcctcaacgtctatgactgacatggacaagagagttcgcg |
| | aacctctttgaagatatatgggatgagaccaaagtcctcaactcaaagagctaccagaaggctctgaagaaagctacgacgcata |
| | ctccaggagggggaagagagtgttcaggagtattataaagatgataaaggatgcccggttcaaatgcccgttcaatatgcaaggtaag |
| | actgcgaatgatatgccaaatatgattctcgacggaaatattctcgacggagggtcccaagttcgttggtgacaaatgcatcgcc |
| | tggcgctggactgacgcctcccaagaatgccacgcagcgcggagtcccagtcgatcgacaactgtaaagagagctcttcagaagtcattcgttaaac |
| | ctctggccggatggtgtgaatccgcgggtatggaatcggaggagaaagcttcattggacttctcttcggttga |
| SEQ ID NO 13 3xFlag-NLS-T4 DNA polymerase (Y320A) Bacteriophage t4 | atggactataaggaccacgacggagactacaaggatcatgatattgattacaaagacgatgacgataaagacgatgacgataaagcggaa |
| | ggtcggtatccacggagtcccagcagcccaaggaatctctattatgactgaaacattgtagcgaggtctcatcgataagac |
| | ggcaaagaaagactcagaggtcgaaatactccgaatgcctcgagatgtcgagaaagcatgagagaaacattaagatatacggaagaatt |
| | gcgctcccccaaaaatttccctcccatgacacttccgacactcaggggtacgagaaagtcgttcgtcgtggaatgcgaatagagtcactggag |
| | ttaagttggcttacatctccgacacttcaagttgtacgaaggaagtcgttcgctgcggcaattgcgatagagtcactggag |
| | atagttcccgaccccgatgagccctggtagcaaggtacgaacgtgacgctaaactcgcaagagggatcgaacgaccgtcctattcattgacctgctc |
| | aattccatgtaagggctgtgtaagcaagtgggacgcgctaaactcgcggctaaacttgactgtgaagaggggatgaagtacccagaaatcttgg |
| | acaggagaaatgctactatgccctgatgtaccgatgaactagggtatcattatgagagtagaatatcacctggaataatataccaaaacattactaggcta |
| | ggaacatagaaggtcgatgtccaatgaacagtgccagtatgcttcaaagaagattctaatgaactgactactgatctgtgtaaaaagtt |
| | tgcttttaccaactgtctgcctagttcttccccctgaaagtgcccaacagagactgtgaatcgcctacgatgcgctacctgcccgattaaaaac |
| | gcgcgagaccaactcaaagtaattactagccaaaaattgatgttgcaagccattgatatagaagaatagaagacgctatcattcttcatttatcgacctgtgt |
| | ctgtcaatgctcccctattacgccaatacgtcaggtgaatgtaactccatagaagactggatgcgtcatctcacttcaattctctcaagggaga |
| | gcaaggtgatccccatagggtcccgctaaagcagtccttccccggagcttttgttcttggcaaaggcgatccgatcgcccgaaggtatat |
| | catgattcgacttagctcaacttcaccttcaatattcgacaagtgaatatactcccggcgcagttaaggtacgaaccatcc |
| | atgagtacatagccggtacagcctgttgacaataccagtgaaaggaaagactggaagaaaaaaccgttccgggagtacgacaaaaccaggagggcata |
| | atccaaaggaaatcgaaggaatatttttccaacgaaaagacttgaagcgagcagtctgttcgcgaagtcttcttaatgagctggctaaaa |
| | aacactttatgaagggtgggttagctgtcctacaagccagaggctgtgcaaccatgacacttggaacatctggagcagctaatcggaagatctgattaatt |
| | acacagctctactgagctctcttaactgattggaagattgaactcactacaccgaccaccacactttcgtcagtcggatcagtgtttg |
| | cactgtatgcgccttggcaacattcattcagatcgaccatcaagttgtgatcaggcggattttatcgcagcaggcgatccgatagcgtgtatgtttg |
| | atcgcccgaaaatcaacgagtacctcaataaaagtgacgaggatttatgggacaggcgatagcagaaccttgtgaaaaagatgg |
| | cgtgcacaaggtcattgaaaagtaggcgtggatcggtttatgagcagaatgatccttgtcgagtttatgaaccagttggtaaaaagatgg |
| | aacgatgatagatgagcgtaccagaaacttgtgactacatgaagaaatcgcggcactgatcgcacatgacaggaagcgatttcatgcc |
| | cccactcggttcaaaggcgtagggggtttctgaaagtaagaaacggtacgcctcaacgtctatgactgacatggacaagagagttcgcg |
| | aacctctttgaagatatatgggatgagaccaaagtcctcaactcaaagagctaccagaaggctctgaagaaagctacgacgcata |
| | ctccaggagggggaagagagtgttcaggagtattataaagatgataaaggatgcccggttcaaatgcccgttcaatatgcaaggtaag |
| | actgcgaatgatatgccaaatatgattctcgacggaaatattctcgacggagggtcccaagttcgttggtgacaaatgcatcgcc |
| | tggcgctggactgacgcctcccaagaatgccacgcagcgcggagtcccagtcgatcgacaactgtaaagagagctcttcagaagtcattcgttaaac |
| | ctctggccggatggtgtgaatccgcgggtatggaatcggaggagaaagcttcattggacttctcttcggttga |
| SEQ ID NO 14 3xFlag-NLS-T4 DNA polymerase (A737V) Bacteriophage t4 | atggactataaggaccacgacggagactacaaggatcatgatattgattacaaagacgatgacgataaagacgatgacgataaagcggaa |
| | ggtcggtatccacggagtcccagcagcccaaggaatctctattatgactgaaacattgtagcgaggtctcatcgataagac |
| | ggcaaagaaagactcagaggtcgaaatactccgaatgcctcgagatgtcgagaaagcatgagagaaacattaagatatacggaagaatt |
| | gcgctcccccaaaaatttccctcccatgacacttccgacactcaggggtacgagaaagtcgttcgtcgtggaatgcgaatagagtcactggag |
| | ttaagttggcttacatctccgacacttcaggtcagaaaatgtcagcttacgaaactccaaatctgactaatagagatacgcctctatttgacctgctc |
| | ataagttcccgaccccgatgagccctggtagcaaggtacgaacgtgacgctaaactcgcggctaaacttgactgtgaagaggggatgaagtacccagaaatcttgg |
| | acaggtaattcatgtacctgccctgtgacacagagctcgatgacaatgggtcaataatggtaaagagtgggacaataacaccaattcaaccagcca |
| | ggaacatagaaggtcgatgtgaccgtatattgaatcggtaagatcctcggagagagaagcattgtggagagaagcattcacccatggcaga |

TABLE 1-continued

| SEQ ID NO | SEQUENCE |
|---|---|
| SEQ ID NO 15 APEX1 Homo sapiens | gtgaaatctaagtgataaacatgtatgctcaaagagatctattcaatagatggagtagcatactcgactactcgatctgtataaaagtt tgctttaccaactgctagttctcccctgaagttctctagtatagctacacatagtcgcccaacagagaacaagaaagtagctccgtacgatggccgattaataaact gcgcagacaaccatccaagatattagtcacgcgttcatttgagtgcaatctgcaagctgcagccattgataagataaggggcttatcgaccttgt cctgtcaatgtcctattacgccaaatgccttcagtgactagacgtcttcaatgtaaatgcaacagtcgcatcaagaactgcgatcatcttcaaggaga gacaagatgaatcccccaacagggtccacactgacctcttccgggagctttgtcttgagccaagcgcatgccgaagtatat catgtcttttcgacctctacgtcacttcaccttccaattattcgacaagtgaatatatgcagcctattccggagctatctcggctaaccacccaatcc atgagtacatagccggtacagcccgaaagtatttttccaaccagtgacgaaagatgttcgcggaggaaagcgccgagtctgtaaaaa aatccttcaaggaaatcgcgaaagtatttccaagagcggtagcttctccaagcaggagttgcctcttccaactgcgaatgaagctgagcaact acacagtctgtactgaacttcagtgaggaatgtgaaaaagccgcacactctgctaatacccaatcaactttcgtcagtcgatcggatcagtgg cactgatgcctgggcaacatcattcagtactacgacctcagaagatgatgtggtaacaatgaggaaatcagctgaaccatttatcgccaggcaggcgatacgcaggttatctgtatgttg cgtcagaagtgcattgaaagtcgtaccggagtgcttacgacgtcctggtgcaaggtattctatgaaccaccagttgttgtaaaaaaagatgg aaccagatagatagtcgtaccggaaaaatttgtgactacatgaagaaactgttcgaaagctacgacgcctcaactaggcgacctcctgatgtcatgtgacccggttcaaggagacaagaggttcgtcgggg ccaactcattgaagatctgtaaggctagtgggaataatgggagacgcaaacagtccaactccaaggtgtgcaagaggctcggaaatgacagcctactgaggacggggaggaagcgggaagttaagaatgcccgcgaatcgcccgagcgaa ctccagagggggagcggtaccttccaacccaagaggaacaaaaagataaccttaaaagacttttgaaaacttaaaaaagttgaactaggtaataataaaagattg actgatatgatgatatcgcaaatgatgataaaggatattaaaaggatactcgaggactacgactcaagatacgcgaggttaag gtcgtctggggctgcacggagctcccaatcgccaaaaatacgcagaggtatctcgccttcaaatgggaatactgcttcaaatgtccactccggagggaatcccaactgttcagaagtcattcgttgcgcc tggcctctgctgacggcttagcacggcgggtgaacgacgacacgctggccttcaagacgactacgtaaggtgttctgcattatgatgatcgagtcgatcaagatggtctccaactgtgagtgctgattacgagaatg ttggttggcctctgattacttttgtgcccactctcgtacctgcattgtgacagatcgtcacggcagcaagatcgttcaaggcctcggcagtgatcactgtc ctatcaccctatacctagcactgtga |
| SEQ ID NO 16 VStag-APEX2-NLS-NLS Homo sapiens | atggtgggggtctgcaagccatcccaacccctgctggcctggacagcacggaatgcttaccaactgtgagtgctgattacag gacgccgttgagaagcgaagaagatccaagatccggaagatgccctcatcgcgagaagagaagagatgcgctcctcaatgtccgttgcacttcccactccctg gaacctttgactcaagggcaggagcccttgggaacctcaagacccaagatccggaactcactcaagaccctcagacaggccttgctcagcgctaacaacggcttgac atcgccttgaggcttaggacttggaccaacgcaagccaccatcttgagctacgcagccgatttctgaactggctggcgtcgccgttaggtcac gggtgacctaagatgttggggtccccgtagagaacctgagcccaccaagaaagtgcttagagaaggcttactgcctctgctacctcacctatggagtgcacacaagg accatttgaagatgttggggtcccctgactttgcctcaatcctcattcggacctctaatctcatttcgaccagacttatcacgagtgttgagtggagaggaagtctctt cagctcctgtgaaccagccttcggagcttggtgctcaaggtgtatcccgcctctgcgaattcagcaggccgaattcagcagctgcccgatcgacaaggttgcgatagattacgct gaggtggcaagcttctcgacaagagggtgaccgacgcgaatcagcgaggcgaccccaagagagaggaggaaggaagtgaccccaaga agaagggaaggtgacccccaagaggaagaggaagtgtga |
| SEQ ID NO 17 XRCC4 Homo sapiens | atggagagaaaaataagcagaatcacctgtttctgaaccagtataactcatttctacaagtatccttgggagaaaaactggaatctggttttgt tattaacttactgatgtcattcagcatggactgactggacagttgtcaggagcggaccagctgatgactgatgatactcagagattcctaagagcttaattttctaaagtcttgtttatttcttttga aatatgttggtgaactgaagatgttcttgaactgttgtaactggatttgtgtcaggaccagctgatgtatacagctgtgatgaagcagtaccagagaagaagtgatgaacatgaataggaaagggg gaaaacctgaaagatgtcccattcagaactgccttcattcagagtgtctcattcagagtgtcattcagatgctgagtgctgaagaaggccagctgagtcctctagacctatgacgaagatgttcaaggacgat ttgaaaaatgtgagctgaggctaaggaagcttttgattttataagccggttatcttttatgaccgttaatgctgaatgagagaaaacaagaaatcagaagtt |

TABLE 1-continued

| SEQ ID NO | SEQUENCE |
|---|---|
| | gcataataaattattaaatgcagctcaagacgacgagaacaaggacatcaaacaagaaggaaactcgaatctgttctgaatgactgctgacga |
| | gatccagtctgatgagagtactgatgagtactgatgatattgcaccaagtagagaacagagacgcgaatgcaagagaacagaacttggacagaacctaaatgctcctca |
| | atttcaagtcttgatgcatgatattgcaccaagtagagaacagagacgcgaatgcaagagaacagaacttggacagaacctaaatgctcctca |
| | ggagaatcagtctcaagaaagaaagcctgattcttcactactcgagacgtctaaaaggagcacatccagtctgaaacatgtcttagaa |
| | actctgagaaacagcagcccagaagaccctttgatcagagattaa |
| SEQ ID NO 18 V5tag-XRN1 Homo sapiens | atggacgcacaaacgacgacgtgagcgtcgcgtcgagaacaagctcaatggaaacagctgcaaacggtgatctcctccacatggctta |
| | ccatacgatgtccagattacgctcctccctccagatgaagaacaagctcgaattctgcaagtctgcagtcgacgtcagcatgggaagtcccaagttta |
| | cagatgatctcagacgcgtatccctccaatgatgaatgtccacttgagaattcacttcagatgtgaaattcagatgataaaatcttactgatatttcactacctggagtgttgttccg |
| | tatacatcagtcgctcccatccaaagtgttccttatggctgagatgtgctcgagatgtggctcctcgagcaaatgaaccagcagcagcagcaggcgttttagtcag |
| | cattattaaaccagaaagtcctttatggctgagatgtgctcgagatgtggctcctcgagcaaatgaaccagcagcagcagcaggcgttttagtcag |
| | caaggaggcagaagacaaattaaaaggcaatagaagaaggagaaactcttccacagaggcagatttgattccaactgtatcacaca |
| | ggaatcagtctatgccagtcacagtgaattcataaatcatgaagaacaagtcatggccacagtcatgccaaggagtcatcatgaacaatctactt |
| | ctcaggccatgagaccctcgagaaggagagacataaaatcatgaagaattactcagaatgcaaagcaagtcagatccaaacaca |
| | gacatgtctttatgttcagtgcgtgactcgtgatggctatgctggataaacaagtcatgaggcaatttctctctctaagagaagaagtcgattgggtgg |
| | caaaaaacaacctatgtgccagaactatgaagtatgaaagatacatttcacctgtcacatgtcttaatgagagaataatgactaggtaagttccagatt |
| | aaaagaaagatcacattaatatgaatatgaaggatcaacaatctgtaccatcctcgcaatggggttctcttggggttcttggcaatttatctcccatctacctc |
| | atttacattataatcatgatgcactccttcctttcatgagaaaatccttgatgctcggagcgttggctactcatagagaaccactcagtggacactacaagt |
| | tggtaacaagtacccccaatgaagcagcagcagtgtccgcagcagaagccaggaactacaaggaaaaaaagtaaaagggccagaa |
| | tctctgtgttggaactgtagacaaaaatgaagcaaaactgttagaaacttctaaggatattaaggagatagaactttaaggtaattagatgaatgactatttgaaa |
| | ctgagttagacaatacagtggatttgcactgatctcatggaaactgacgaagatggggtgacgtgtatgtgctgagtgattcgctgcatcaagcgcatttatgtt |
| | caggcaataacagtggatttgcactgatctcatggaaactgacgaagatggggtgacgtgtatgtgctgagtgattcgctgcatcaagcgcatttatgtt |
| | acatcagtacactcaaatcatttgaactaggaaactatgaaatcatccatttaaatgcatggctcttcctgcttcatctgcagcagcagcaaatttactc |
| | ctgcatctaccagccttgatgaccaagttatgatccacctattgatggaagactcaccatatattgagaaataccacctgattttaaaactgccactaaatggaaaacacagg |
| | aatggaagcctggttgttaatccattgatgatggccttaatgctgttaatctctccatgtgatagagacacagagtttatctcctctccagaaagttccctgccata |
| | gaacagtgtgtacaaggtataaatatgaatatgaaggatcacacaaattttttgaagaaacacagttcagctattccagaagcgtcggagaaaa |
| | atattctgtggattcctactcgaaaaaatagggatgcagaatcatagtgagaagtgctgagtgatctaccagtcatcagtgctggaaaatcgtcttgtaatggc |
| | acatcagtacactcaaatcatttgaactaggaaactatgaaatcatccatttaaatgcatggctcttcctgcttcatctgcagcagcagcaaatttactc |
| | ctcacctgagaaagctagagtcgtgctgtcatcagtggagatgagataagaacaagttaactggaagaactcaaggaatctcagaacactacctga |
| | agaatgcccccacctcaaagtggtcatctgagcagtgttgtatgatcgcagttgtcttcaaacttgtcagacatctgcgactccgttcctccaatatccaaaa |
| | gtctagaaacaactgttcctttcttgtgattccttcctttgttcaacaatctggtcgtgcctatgctgaaccatctgtctgggaactcctattatgctgcactagaaccagcataaatattctataaagtacaaccca |
| | cagaaggtaggattcgtgtgatttcagcatctcagtgaaccattcatgtgaaccatctgatgcttaatcagaaccagcataaatattctataaagtacaaccca |
| | ggatatgtgttggccagtcgcctggagtggtgtcggagtggataccttgttcaaggttacaggaagtattttattggaagaggatcctaggagaagccctc |
| | atgaggaccatcaagcaactcttaactcaacatcaacaagaacaaatgaccctgaatatctcaacaagtaagaacaagtgaagtgaatg |
| | gatgtattcatctgcagcagaacaactctggcagagaatctgggagaagagctccagaacttcaaagaagttctagtatattagccaagatgt |
| | gttcatgaagatgacattggcctgagaaattggcactgagctattgttcctttgttatcaaactgttgtgaagaagtgcagaaacatcctgtcagtact |
| | gaagttcgcgttcctctgtgattttacaaattctggatgcagtatgtcagagaaattgtggagaaactcgaaaggcaagccaagaaagaataataa |
| | gacctgatgatttgttcctcgagaatggtcttattcagcattccatgtgaaccaatctgaacctttatgctgcactacagaaccagcattcctgatcggatccagagattgtctcttttt |
| | cagaggtaggattcgtgtgatttcagcatctcagtgaaccattcatgtgaaccatctgatgcttaatcagaaccagcataaatattctataaagtacaaccca |
| | gacgctgtgtaatgtaatattattgatgaagaatttcctggagggttaacatcagaaactgctgcctcgaacatgaagatgtcactgactgtcatcaacactgctcaagttc |
| | taccttctcatggagctcgtcctcggagctggatctgcgcaggaaactgcgatctcgaaaagcacttttgtgaccactactaaaggatgattcgcaac |
| | atcagtccctccaccttgtccccaatggatgcgcctgaacagctgcagcatatctgcgcaccatcgtactcacccactactcagaaatttaaaagagttaaga |
| | attggcagtccttcacggatctggaaatgacaaccttgttcaaaaatgcagcaataacagtgttaatatcagcagcactagtgaccagcacaagacagtagt |
| | gcctaaagctgagtgttgctcccaaaaatctggagcccttaatgacacagtggaagccctcgacacaaggtgcagctgtactcacagaaaatttaaaagagttaaga |
| | aaaattgatgctctaacactggactggaccatacgaaagaatcaacacagatctgcaatgaaacaaacagattgctaatgaaatcctgctcctcaacagaagaatatgg |

TABLE 1-continued

| SEQ ID NO | SEQUENCE |
|---|---|
| | attaccctctcagcctaaacaaataagaattagcatcttatatgaacaagcctcacagtgctaatgagtctacataatgttcagtctatgacaata |
| | tgtgttggctgcctgccccagctcagatccctcgtatccacacagtaactgactttctgaatttgttcccttgtcatgtccacaacctgattct |
| | ccttcttaggatgccacagaccggttgccaagtaaaatatctaagcttatggtacatggtactggtacatgggccacgtgcactctgaaatgaag |
| | ccaagagaaagctgactttgcttacaacagttgggctctagatgcatgaattcccttgccttcacaagtgattgcaaattatccttcagctgt |
| | accacctggaacaattcctgccgcttccccccaccactgtgaccactgtggaccagctgctggatcactatgaagcaacactatgaatccttc |
| | gtcgtctcatcctttggctcaatgccatgggaccagtttataccctccagttcttaccctcagttccgaagccctccatcactacttatattctggaccatgccatg |
| | gctggggaataccagggggtgtgacaactccagttcagacttcaagtgcagcctactaaaaaagggtgcaaacaaaagactttgaagataagg |
| | aagcccagagttccaagccactccagtctcctccattcaagtcaagtcctgaaaccttgcccatgtcaaagtaagcccacggagagctcatcagcttct |
| | ttgaagcctccgatgctcaacctctttcattcaagctgaaaacctgaccatacctcaccatatctccaccatatctccaccatatcaacacaatcctt |
| | ctccaagaagaaaatcaagaaaacgctgttgttaattttggtgttcaaacctcgagtaa |
| SEQ ID NO 19 DNA2 Homo sapiens | atggagcagctgacgaactgaactgagctgctgatgagaagagtttgggaggaggaggtgggagctgcggcggagctatttcagagaagaagtgg |
| | tagctcctttccaacagctctgagcacgaggtgatcaccgtagcggttgtgcagtcaatacgtacgagacagaggaaactgt |
| | gaaaagcgcctgtcatcactgctctcacagtcctggaatgacatcctttaggaatgactggtgttctgttccagtagagccagg |
| | agatcattcattggaggagaatgcacatctgaactggaatagataagaattgaattctgattctgtatccagacatgtcagttctgg |
| | caccagctgtcccatgagctagtatcgcagtagagaagagccctgagtgaacctttaggagctctgaaactcctgacacgcacacgcaaatgcaatg |
| | gtacgtgctccatgagtgttcaaaagcgcataaaaagaaactcaagaactgcttcaaaacaattcaagaaataag |
| | acattgaaggaaatgaccgctaaatctaagtcaagatgaaataaaaacaagaagactactctctcgtttgtaaatgggcaggaga |
| | ttcatgcataaaaacctgactgctcccctagagattggtccccctcaggttcggattcgccccagaaaaaaaaaaaaaaaaaaaaaaaagcccgg |
| | tgaaccaatggatattgaagaaagcatttggtcctccagaatcagcattgtctaaaaacgtggaatcaacttctattgtcagactcttctact |
| | aaaaacaaaatacaagatatgccctggaaaaacgttgtcagcaagaaaccgtcagcagaatcaaatctcctaggacaaactaatgtctatcactcttact |
| | agcagcagagaagactgatccagaggctgctccaggtgccttgcttctcctactcagcaatctgtactgcaacactgtaagacaacagtactt |
| | acaataattaggagaggaaaactgtaaatatgaagaaactttaggagctcctttatagacgagcagtgaacaacagtgattgtagtt |
| | cagtcccaattgtgatgctgccaaaagtaataaaaagagaaccactcgatattctggctacatggtcttggtcttaatgctaa |
| | ccctggagtcaatgtgaagcttggccgtaaccactactagctctctcggaaatgtccaaataaacatactcagatcagcttggtgcagtgcattgg |
| | aaacctgattagaagagtatttgtaaggtgaacatgtaaagtcactgtttgcttgctagaggatgtgaagagatgtaacatgacaacagtactt |
| | gcaggtgacagagttattgaagtgaacaaagtcactgttaagtggaggaaagtcacatggctcagaatcaactttgctcagatagacaatccccattaggaaat |
| | gtttattagacagaaactgcgtcgcctgtcagaatcaacctaaaacctggtctctgagaactctagaacaagttaattatagataccccattaggaaat |
| | cttccaattgatggaaaccgttttgcttcagcaagatgcgcatctcattaagagcacccacctatatcgtgtcttttatatccctcagttctgttctt |
| | ccacatgatgcaaagatacagtgcctgcggacagaaaaaccaacctgatatgccttctctacgcctggttttttttttagcgtttgtttgtgttgacca |
| | gctaatcatcacacactcgctgtgacaatatttcttgaagtagccaagttaaaataggattttttcgtttggctcagatctcagaaggttcatccagctat |
| | ccagcatctacagcaagaaatcgatcaagtccatatctacaaaatactatgaaaaactgggacagaaacctcacacagtctacacatatagtgcaaca |
| | catgtatgggaataacatcattccaatttgatttttgtattgtgatgaaggcctccaaattagcaacaattgctccgtgagtgaa |
| | ccttttttcacggagattgtgtttagtggggcagaaagagtgctgttgtacagtttaaccgtgcagatcaaaatctcagtctgcagaaactg |
| | ctgacctattcaggagggcaaagctggaggagcaatgccaatgcagcaaagtgcctaaccaagtcaccttaaagatgtgaagctgaactg |
| | gaatttttagtcgatcatttcgataatcctggttgatgggagtattgaaccaacaatcctgttttttccttaatacagacaagttccagcgccag |
| | aacaagttgaaaaagtggtgtgaccaatttaacagagcccaaatcaatgatttattggccacgtctcatggcacgtcgaattacacagagacaat |
| | tattggtattattgcaccgcagcagcaaatctaagagatctattctttgtaggatgaatgatgaatgacactttgaagattggcgactcttaa |
| | accaagagagtcagttctctgggagtcagcaacataaactgattcttctgggtgtgcctcaccaatgtctatcctcttggaggaagctgctgacttttaa |
| | tgtgcataccagacaacataattaatcattgatcttctgtgctaagagagaacataactacctccagagtcgtttcaggaaatcaagttcaggaagagctgtaatcattttaaa |
| | ctcagaaaattaatcattgatcttctgaaagaatgaaaaagttctgttggggtgacttctcaaagagtaa |
| SEQ ID NO 20 Myc-POLQ-Flag Homo sapiens | atggaacaaaagttgattctgaagagattgtaagaagaagaaggtttctccttcctgcgtccgagcgggaacccgggcgttcagaat |
| | caggtcagattcgtcctgaaggcgtctgcctgaaggccgagctgccaggagccgtcgaggagcggcgtcctctctccgggccgtcgacgccccgacct |
| | ggtccgctgccgaaggcctgaaatacccacagttggtgaaaaatgatgttgaatgcaggcaggagaattgcacctatggccttgcttgggaattg |
| | cctaaagcagtccgaaaataccacagttggtgaaaaatgatgttgaatgcaggcaggagaattgcacctatggccttgcttgggaattg |
| | aaagaattagtttatcagctctcagaagtgctgaagaggacttatttgaagggttttgaaatgcgaacaagcctgaaggctt |
| | tgtttattcctcccttgtctgttgctaagagagagaacataactacctccagagtcgtttcaggaagtagaagaaaaaaaaaaaaaaaaaaaaaaaaaaaaatcaggaagaaatagacggttatatgggca |

TABLE 1-continued

| SEQ ID NO | SEQUENCE |
|---|---|
| | gcacctctccatcaaggcattctcttcattggatattgcagtctgcacaattgagagagccaatgtctgatcaatgcctcatagaggaaataa |
| | gatgatcgttaggaatggttggttggatgaattacatatgctaggcagagactctcaccgaggtatctctgctggaacttttgctgaccaagattgc |
| | tatattactcggaaatcagactgctcaggcagctagccagttcctgtctccaatcgtgcaaatcgtggcatgatgctaccctcctaattg |
| | gagctgtggcttcctggttgaatgctgaactctaccatacccgactttcgcctgacccgttttggagtcagtaaagtggaattccatatga |
| | ctcttcatgaaactgtgagggaattgagccgctagttcagtgaggagatggaggaccatgtgttagctgtgttgagacgattgtgata |
| | accatcagtattactttttgtccatcaaagaaatggtgtgaagaagctgagaagtgcagatatcattgctcgagagtttataatcatcaagctgagg |
| | gattggtgaacccctcgaatgccccaccagtaatctgaaccacaaagaactcctgaagtgatggatcagttaagacggtgcctcaggactg |
| | gactcctgtattacagagaaactgtaccatgggagtagcattccatcatgcagttctactttgaggaggagatcatgaagagctttcgtc |
| | aaggtcccattgcctattggcgcaactcctcctctcggtgggtgaattaccctgcgctgtgatttgcaaccccatttttggtgtcg |
| | acctctcagatattccttacttataagcacagatggtgcgtcgtgcgtggagagtgaacagtaggcacagtaggagagtatcttaattgtaagaacctct |
| | gagaaatcaaaggctatcccttcaggttctcgaagataatagttggtgggagtggcaaagtacatcacaagatatgcataatctgctgcacattatggctgcaagtat |
| | gaaagaaggagcaaggaatcagaagccagatgctcagtcaggcagatggctgtgatgtgctaccagaaaatgaattc |
| | atccagagtacagaagccagtcagtgatgaacagaagaagtgtatcatccaacacatcggttcgtcaccattcttcttcttcacttctccagctg |
| | atgactactagtatttgctgacctgcagatttctgttcagaaatgatcttcagaaatgatcttcatctctgttacccatgtttgaggatt |
| | gactactatgatggtatcgattttctgtttctgggaagttgccaacttcaatgaaaaggtggcagagtagtggaagggaggggtt |
| | ctgcccgtgtgtaaagaaagtagcagcaagaccaaatgctgacatatgaacagaatgcaatgtccccaaatcaatcttcaacaaaagtctttcaccagtctgtgc |
| | tattagtttaatcaggaagttccctaaggaaatcagaaatgatgtgggcagatcaatcttcgaacagcatccactgggcagcagtgaatgcagagtgcctttacgttggcatcca |
| | tatgcagggatgatttgactgctgtgtgactatctgggtgactggcagaagggttctgaaaagttaactgacgagcagcgcctctcatgactggcagacctgtgct |
| | agagcaaatattgtgaggtgaagtgacaaatcagtctgccttcaaaagtgccggaacagtcagcagtatggaaggaggaagcagtt |
| | gaagaagctcgcaatacgcttagtggagacttagtgaaatggagtgcaatggaactccagtgccctgttacattgactcattggactgtgctc |
| | aatgattctcagcaggacttagtgaaatggagtggtcaatgaacatctagatgttcttaaaatttaacatcagtaatgcagactactagacaaaagtaacacaatttagtgattcttatt |
| | gaagtaaagaacacacatcatagtgcaagctaaataaagttcctggtgatatatccaaactaaaaataagtacagctcttaattgaattaataagagaccaagtaactccaaagaaataaa |
| | tgtgaaagctaagcttaatacagagaatacaaccaagctaataacctgagccatatgatgtgggaaatcagtagctgaacacagtgtcagtatacccagtaagt |
| | actccatcaagctggacattagcacaataatcatgtttcgacttagttgccctctgtgtttagccctgtttagcctggttagccccaacagaactcaat |
| | aacaaactaaaaatacatagaaggaacaccaaccaaccggcagcaggcaaagagaaactagctgtttccatgagctcttacactcatcagaaatactacaac |
| | gaactctttccagactaaatgccaaactaggacagaagaacaccatcctgactccagtttcaggttcacatggaaagacagacagaactcaat |
| | gaacatgaaacaaagcagtgatccacatgggttgatcatccaatttgactcctccagaagccgattccatcatcttcaataccattggaaccagttactcttgattc |
| | tttaaaaggatagaactccaccggtgtagaagaagaatgtctccagtctccagaggtctctccgtcccagttgaatatgatgtgtggatagttgaccaaagactgctcataagttgaatggtcatt |
| | gatgcatatctggtccacagaacaatactcctgtatctcaagtcaagatcaagatatcaagataggttatagttcagaataacatcaaacctcttcaggttgatgaagtgcta |
| | caagagacctaattaaaaatcaaatgaatgaagatgaagatcagatacccaccagcagtgacctgttgactgtcaatgatgaatcattatatttcagaaat |
| | ggatcgtcaagatgttgaagcttggacaatggaatattcctgtccaagagaatcatactgtagtatcctcagacattagaactaa |
| | gtgatcctacttgatgagcaccaccagatgatcaaggtgagagatcaagtggaggaccaagatgaaaatcaaattactggaccagg |
| | caaaatcattcattcattggtcagggcatcattgattcaagtcaagtcgagactgcaaggatttagataagaaagatctcaagaaaatgaaaa |
| | gctaaatcatgacctataaacttttccagtgtgattaatggtttacaacctggtgaacaagttcaaccatgcaatgcgaatgaaaacacaa |
| | gtgcagggaattcattttcttctaataagtgatgataatggtcttcatcctccaccacactctgcttcaagctgactttaaaaacaccagttcttgaaac |
| | acctgaagaaagtaatatagtgatatatgttttacaaccctgtgtgaacaagtttcacttcagttactcagccttgacattccaggattcttaaagtccagg |
| | gagtagaaatgggtcaagaacaacagcccttagtgacacaagcccttatcagttcacttcagttactcagtctcagccttgacattccaggattcttaagtccagg |

TABLE 1-continued

| SEQ ID NO | SEQUENCE |
|---|---|
| | cagttcagaaagttgtccataattgatgtagcaaggtgaccaaaatcattccaacattcattaaggagtggcggtgcaaaaagcgatttccatct |
| | cactgcttgtgaaaagatagaagtttgacatcttctaaaactggtcagtaggttaagcaagtcagtaggtagctcacctcaggaaattccatt |
| | agagatgatggattcccattaaaggtgtgatgacacctggtgtgactggcagtagtgctgggtggatgcctatattttcactgc |
| | agaaggaacaaaagcattctgaaattgtcactagtgccagttggttccacctccttagatccagcctgactttgaaagacagatggtaccttcatc |
| | ttgcttgcgaaaggaatctgataaagagactcgtgtgtgtcatagtccagattccagatctcatccagagctataaaattctcttcttgtgcatctccttggagc |
| | aaagttatgaagatccaaggtggcatgctggtactagatccaggatccagggcgactcttcatagcacatagttctcttcctcatgag |
| | cttccactcctagaaggatggaagaccaagcaagggatccaaaaggctcaaactcttgttgcagaagaaacctcaagatgttccgcaaggtggaaatgccctct |
| | cagtaggtccattctcatcttcaacctcatgaatcagtcaacctttgtgcagatgctttagtagtccaagatggaaacctcaacgcctgatgc |
| | aattgaaccaggccatcaactagtgcacagtgtttcttccaccagtcagatcgctggaggttattttggaattgaagtgccccc |
| | aaatagagatgcactagtcaagcagcaagaaaactcctggttcaacctttaaaggcatgatttcatcctggatcatatttccggcaagcatgaatcactaatgctatta |
| | ccaagtgtctcccctcaggaaaactgccttgctcaagatattccccatgatcgtagtcctcaaggatatgtcaagtttcaagttctgatgcagcagcacagagagtggaa |
| | acgaataaccttacagaaccaaatattcagaatgtgccaagagattttgaaatcaaaatgccacactagtgaactcaaacgatgctttggaacaaaaacataaatatgcgacatgcttgttcccagtggtctcaaatactgctgtcactccagcttg |
| | cgtaggcaaaggctactcccatggcagagaaaattaaggaggttcaccgtgatccgaatccagccagcacagtgaggagaga |
| | gcagcagaggaggatgcacttcaattacggcgacatgcttttgcctttcccagtggttcaatactgctgtgactactccagcttg |
| | aactgagatctggcttatccccatgatcagcagctcagcagtagtaaccatggatctagttcaaattgtcacactagtgaagcaattagaa |
| | acgaataaccttacagaccaaatattcagaatgtgccaagagatttgccaagattgtataattgccaaataagttgtcaaattgtcaaatatgtccaaaatagcaacagtaagtgatgcgaacttcaaacgtgcaa |
| | gatgattgagcagtctgttgggatctgtgaggcatgctcgaccatttggggacatacagaggatgaatgcatttcaattcaattcatgacagacagacagtaatggggagcacacagtggagaga |
| | gagagacagagtggcattaagaagagacggattgtcagactcgaggaagctcagcaatttcgacattgccaaattttttcaagttgggaagaggcttgatcctatatttcacgttgaacgggaatcaacaacctctatcgaaagc |
| | gtgaagaataccttgtaaaagaggccgtatccaacatcagtcagcagagcagccacagtagtgcaacagttgtaaaatagcccacagtcacgaaagagaaacgtcaagga |
| | cctctcctcacctttcaaatcccaggttgaaagtgctgtaaaactgtctgtaaaactggtgtgaaagcgaacagtgtgaaagtgaaatagcccatatgaaggtcagtgaaaaatagggagctcagtt |
| | tgttcgcccaatcagaggaggctccttcctcaaaacatcagaggagctgaccatgtaagtagctgtaaaactggggtctaaaggactttt |
| | gcaagaatgaaatggaaagctaccaaagcgatgacgacaagtaa |
| SEQ ID NO 21 POLB Homo sapiens | atggactaaggaccacgacggagactacaaggatcatgtatattgattacaaagacgatgacgataagtggcccaaagaagaagcgaa |
| | ggtcggtatccacggagtcccagcgcctagcacgccgtagcacgaaggcgccgcaggagactctccaacggagggatcaccgacgcatgctcacag |
| | aactgccaaacttgaaagagagctgagcaaggcatatcccaaagtgctaccaagaaagcacgcttcatgagttttagcaacgtgaaaatgctattacgta |
| | aataagagttggagctcaagaaaattgcctggagtaggaaacaaaaattgctcgactcgagttggcactatggcatggccatctgcctgcgaaattgcaaggaagtttgag |
| | actgaaaagattcgcaggatgatacgcaggatctcagaaaaacacagaagactctcagaacactgaaccatcagcgaatgaaccatcagcgaatggaccatcagcgaatgaccatcatcagcgaatggcatggtccatctgaaatacattggggactttgaa |
| | atgaagaatctcctcgtgaagagatgtggacatgctaaaatgcaagatattgtaccaaaatgaagtttaaaaaagtggattctgaatacatgtctacagtctgtggca |
| | gttccagaagagtccagtggtgactgtcacaaaaggttcatttatcacagaattgtccccgaacatcaataaatgatctcacagaaaaagtgaacaagccaaaactgtta |
| | catcagttggcagaaaagaatatccacacagaagaattgatatcagttgatccagaagtgatgcacagtttaagtcaaccaaggcctcacagctactgaaagccactggagtg |
| | atatttcaataagtaaggtttggagcaatatgaggcctcatgacgctcaagaaaagacactcttgattacatccaagtacatcaggagaaataccggaccaagacccgagcgaatga |
| SEQ ID NO 22 POLH Homo sapiens | atggcctactgacaggatgcagtggtgctcctgagcatcgaaggactgttattgtcaagtggacacagcagcggcaaaatccccattgaggaataaa |
| | cctgtcgcagtgtacaagtcaaatcatggaggtggtggaataattggggaatgtcgtcgtgagctcactggaagctactcactgaagccaaatttgaccctggaaagtcgacttcactgaagcgcacagctgagtcgatagggaa |
| | gcagatgctatgtgctgaatatgtctctgttttgctgtgtgatgaactgccagcacttacatcagagctgccaaggtctatgagagcagagctttggcgcattactcatctaccaacagagctgtttgggaggaagccacacacactgaaaagcggagaag |
| | gactacaaagctacaaggtcagcctatctgggatctattcaatgctaccttgtgccaagactcatgacaaaggtcatctacagagacactgacagaag |
| | cgttcagaagaggtgattgtggaagaatgcagagcagcaaggagagacctcagtttcagttttcagttgtaatacctgcaattgcacaaactagtcaaactgtagctgaagccta |
| | ggcaaaactggtgctgaactaaaacagcccaaccgccaacctgttcactggtgtcagtccacacgcctgtttcacactgggtctgaattcacacaatgccattcg |
| | caaaatccgcagtgcttggagaaatgtagggcgaaacacctgtgtcattgagatccaagtaatcttgccgaggatcagatctctagaattcagcgaggacagtaatcctgagatccagtttacccaggattggactagaagcggggttgagcataagcaggaagaggagaga |
| | ccaaaaccatggctgcttgggagaagaaatctcccaggagaagaaacgagcctcttggctaatgcagagctctgaatctctcattgaaactaccaggaagccatccaggagcaactac |
| | actagagagagactgctaagaaccgaaatgatgatgagaccagggtagctgaagggaagcaccgagctagagctagctagccaa |

TABLE 1-continued

| SEQ ID NO | SEQUENCE |
|---|---|
| | tcagcagcctgcgctgctgcctaccgctgtgctcaagatgagcgatgcattactgtcatcaagaactgtaatacttctg |
| | gaatcagacagaaatgtcctcctccacaagtctttcctctgtcacagtgagccatgatgcattactgtcatcaagaactgtaatacttctg  |
| | cttgagcagtgaccagtctctgcaagttgccagttgccagttgccaatttctgcctctgccaaggaagtggccagcggtgacagccata |
| | agaaagcaaccacgtctctgaatcattcttccaaaaagtgcagaaagtcaaagtacaggaacaagttaaggagcttgcttcatcttactgtccactc |
| | aggctcccatgagcaatcaccaagccctcattcaccagcccttaaaccagtcaaagtacaggaacaagcagcaaactgccttcttaagcagaaagctgc |
| | ttctaagcaggaaacagcttaataattcttcagttcttcccccaaacagtagaagaatcctctaaagcaactcctgcagagtcaactgtaaagcattaccaaactcttaccaacagcc |
| | tatccagggtgtgtccctgttgtgaagggtgtgaagtgaggtgctgaagcagccaatctgtctcagtcttcagctgctgaggaccaagt |
| | aagcatgcagccctcttcagcttccaaatctgtcgtgaggtgactcagaacacatgactacattttgactgcagaaatcdttttgca |
| | gccctgagagttgtgcctccctggtgtccccagttgttccgcatctcatcaaggcaaaatcccaagagcccttggctgctgcactaataaacgcccca |
| | ggcctgaggcatgcaaacattggaatcatttttaagcattaacacattag |
| SEQ ID NO 23 POLG Homo sapiens | atggctagccgcctgctctgaggaaggtgccggccgcggccgcggtccagctccggggcctcgggtctccactcc |
| | gtccccgtccgacccccagccgtatcctcggaggggccagccagcgcagccagccagcagcagcaacagccagcag |
| | cgcaagtgtatctccaggtgtcagccggcactgggcacaaccatggacatcctcgagagggctcccacgagcaatcttcg |
| | ggcaaggagggagtgcctgccggcgagcccgaggcctgcgtcagaagctcgagaacgaccgcctggggtcagccagcg |
| | tgccctgccccgacgtgacgacactgctgcccgggccaactgcttgcgaggaccacttccactctgcccaagcagagcct |
| | gccctacctggagggcgccaactgcttgcgtgcaggcaggcgtgaggcatccggcgagagcccagccagctcggccctggactgtcgaggggacttg |
| | cggccccgagggggaggcctaccgccatcccccgaagcccctggtatccggccagcgtggcaaccagccttctggcacccactcttggaccacagccagct |
| | ccccaccattgccggtgccctcatccccgtgactgctggtcctatcccggctgcgcaggcctgcccacgagcagcgtcagccagcag |
| | gtgccgggctgacctatccccggagcctgcccactactagggggcactcccctagagtgctgccccagaagaactgaagactgctagtggtgggcac |
| | aatgttccttgaccagctttccagcgcttggatagcagcccaaggagagcccccatgactagatctcctgacaccatgacatgccat |
| | ctcagggtaagcagtctccaagccagtctgaggatcccatctggaacctgggactgtgtgagaagtcagcagtgcaagatctggcaagagcaagtgcacag |
| | gtccagagaaagcagagaagggccagagctgtcagatccatctggaaggaagacctgctttgtgaaggacaccgaggaactggtttgaaggtcaccaggaccg |
| | gtaccaccgctgcctcccttgcactacttggaggcctcatggtggggcgctgcccctgagctcctgacacacgctgtcacaacctggccaagctgccacag |
| | gctgatccggctgccgcgcgggagctgtgccggagagttcctgctcactgacaataagtccaaacgtagaagaactggattacttag |
| | aagtgaggctgagcccagatgctgaggcaatgcaaatgacaaccgacgtgcagtgcaaccctagcctgcctagtagtagccctggaagtgctggcccaaggacac |
| | gtaatgtggagacccccttccaacagccctcctgccaacagacgggaagaactgtcacccgaaactgtcaccactagcagcccgttttcaaggatggttaatagct |
| | tgctctggaaatcaacaaatgattctttcggaggaaccgtcagcctctctggccccaaagttggggtgctgcctccaggcagccagcctgc |
| | ccggtgctgtggagccctgatcggaacctcaaccgcacggcgaagtaggcagtgagaccatgctgccggcccacctt |
| | cgggttcgtggagccctagctgatgatgaggactcactactgctgggcccagcggtgagtcctgagagccccactgtgccagcatgacatcagcc |
| | gctaccgcttggtgatgatgaccagtcaggcaaggtcagcgatgcactggtgcagcatttgcagttgagacttgagacattgcagttgacactgctact |
| | agccctcgggtggatgcacacggcccgcggcctcatgtgggccagcctttgctgagcgttactaagtcgaagagtcaacaactggtcacacagc |
| | gcatgccaaaatctcaactatacggccatatgtacgctcaccaagggctctgcggatgcgagttcatcagaagagttcaatgcagagaaagtc |
| | gggagttgaacctgcaagaagatggctgctatgctctgaggtgtctgctggagagaggagtcactgctcagaagaacaactgctgca |
| | acagtgaagatggaggtgttgctgacaccagcacagttgcaaggcacgagactgagcatcaatgaaggtgaagagcttgaagcttgacatactgct |
| | ctgacataccatcggtaccccgtgctgtgcccgagccctgatcagcggccctgagccctgctgtgcccatgaaggtgcctacgccacagaggccagctgtga |
| | atgggtggtacagagcctgtcgttgactacttcaccatgtgccatgtgttgaaaagtttgaagagttttgcatagatgggcgcttctg |
| | catcagcatcatgacgacgaggctcgctacccgtgcgggaaggaccgctggatgcccggcgatattgacgtcagtcaggcctcaggaagatccagcaaccacttgacca |
| | ggtcgtgcgtccgcaagcgggtctgaatgactgcatttcagtgacgtcgcctccgatttcagtgacgtcgcctcttttcagtgacgtcgatattgacgtcaggcctgaggaagaggaagaag |

TABLE 1-continued

| SEQ ID NO | SEQUENCE |
|---|---|
| | tgaccatggattgtaaaccccttccaacccaactggatgaaagagatacggatccccaggtgaagcgctggatattaccagataat |
| | tgaactcaccaaaggtccttggaaaaaacaagcagcctggaccatag |
| SEQ ID NO 24 POLN Homo sapiens | atggaaaattatgaggcttgtaggctttgatctctgatccttgctctccagtgtgctcgaagattatgtctgtcatgatcaggtgattca |
| | gtggattctaagacttgggaagagtacacaggtacaggtacatatggaagtgatcagacagtccagttctaagtattcagtacaaggaaga |
| | ctcaatcaccacagacaaaaggatcttaaatcttaagaagtcagacatcaagagagttctgccaagtctctccagtctcctgtcaggctca |
| | cagatcagctgctgtcgaccaaaacagaggagcatctcaatggagcatcgacttctcaagttgtttaattccacagtataatcaagaggcttcagttcta |
| | cagaaaagggcataaaagaaagcattcctaaatgggatgtccaatgggaacgagcatccattacaatagaagagacatttaaaagaaactattacata |
| | taatttgtcagagaaagacaataaaattggcatttgatgatttggcagaagtctgaagaactctggaaactcaggagca |
| | ttgaaaaacattttgtgatattagcattggatggtccaccagtcctgtgatgatggcagaaccccgttctctcgtcgagagaattggtggttagtaaacgcaagcaga |
| | gtgatgtatactgatggttccaccagtcccggctgccctgttcctgtcggctgtgttgtctgcattcaataggcaagagactc |
| | gggtggccatggctgctgccagatgccccggccctgtccttctggagggcttgtgctcaaacaatgaacatttcaaaatgtcctgtattgttttaatg |
| | ctaaggatttttgagaatagtgctgcagttttggcaatgatggcagttgaagcatgtctgattttatagggctagatcccagaattgctgcat |
| | ggctatagatctcagtgatgcacccctttgaagtttacgggagaacctgaagacactcacagacttcacagcttgctctaaactgaaggatat |
| | ggttttcgcaactcttcgtacttggagcctctcctgatcaccccatttgcagtgatgaagagcagtcattttgtcgcagaagtctcagcatacaa |
| | agaagactcagcacttcctgggctcgtctccaaggaatttggacaagaacattttgtgcagaacaacagtctccagaaataccagtcta |
| | cagcttcgagagatctctgccaagcttaaagctcgagacctgtaaatgctctccgagactccccattaccccaagatcaagctcaacctttgt |
| | catcagaagcagtgttaaatgctctgcgagactccccattccctccctacagtgcatgaaatcaaggctccaaggactgactgaagactttcagcaagcacctaa |
| | agatggttactagctgcatgaaaagggctcatgaaaaaggctccattccctctacatgatcagctgaactcgtgactgaagactttcagcaagcatcctaa |
| | tatccagtgatctccagcaccccaattcagattactctcagcagctctctctaagaatttaaagaagcaagatttctcacgatctccccgagggccat |
| | gttgtttcatccaaaggccacacttctcagcacgacagattctactctagattctcactctgaagaatttcatctcagatgcattgcattctacacattctcggagatccgaacttctgaa |
| | gttatttccaggaattgaaagagagatgatgatttctcactctgatttcacagtggaaggttgccgctgggtgaacaggtggacacggacagacagag |
| | agcaaccaagaaaggtggtacgcgtggtggtataggaggcaggagaaggagtgcctgtcgcccgagcacacgcgcaggagcagctgcctgtgtgagagctgcc |
| | cagtttttggaagcttgcctggacagaaaataaggacctcgcccgagcacacgcgcaggcatgcgcaggaccaactggtcgtgtgtc |
| | catcatgggcagaagggagaccccctgcaaggattcacgctgccatgatccatgtctcactgcagtggctgctccccacacctgacggccaggctggtg |
| | ggtgcaaggctccgctgcgatgagctgctgtttgaagtgaagtaagaacgtccatgatccccaaggtgcagctccgagtgcagatcgcagtccgaggaggctgcagtcccttgaa |
| | gcccagatccatcctgtgagcctggaccccccaaggtgagcctgagccctagtgggaacaacctggtcacctgacagg |
| | aggcctgggcctttttcgcctcatttctcattttgtctgtag |
| SEQ ID NO 25 TENT4A Homo sapiens | atggctcccctgtcctgaagaagcagtcatgagaagaggtgtgaaactgctgcgcttgtgcgaccgctgat |
| | gtacagatatttggcagcttagtacaggctttatctcctgagctggctgacatagaccctggtagtggaaataggtgctctcttcacagct |
| | gctgagcaagcctcgcggaagcaacctgctgagctgtcccctcaagttccatcaaggttgggcagccaagccggtatacgtaccaaataaaagctcacag |
| | atcaggagagctgaagttgaaaagtgacatcagcttaacaagtaacatcagaagcagcctcaagaagcctgaattgtaacagggtcatcaaggaaaatattc |
| | atggccattagcttctgattttagtactagaacagagctgcagggaagcctgatgaaaaacctgaagtcttacaggtgaatgctctcatacagctcaatttta |
| | agaatttaattaattactgaaaaaccggtattgaaaacctggattatagaaccccctgcctcaaaggagagcctatcgccaaaggagagcatgaccagcagggt |
| | ttcgattactgtgatcctgtgcgtgcattggaacgatctgaagaccccctgtgccaggcatctgccagcctgtcaagcgccaaagtactttaggaagaatcat |
| | caaagtaactcaggaggtgattgactaccaggtgatcaaagaggaagtgggcagcaagaccagagaccaaccgcgcagcggacagcag |
| | gatcaagatcaaagagcgaatagcagaccccctcaggcctctggcctctcctgctctcactttctggagtgacgttgattcagacacacgccctgcag |
| | cgctgccagcccagcaggtcttaccagtttcctcctgctctctgctctggcctggcctggagtgcatcaagagaattacatggacacacgcccaaacctcag |
| | aacgccagtgttacggactgaacaactgatcatgacaacaacatcagacaccaggttactacctccaccgaccacagggtcctgtccttgcag |
| | acaagctggtgagaaggaacgtgcttttgaagtagccctcgagaagctcttccccggccattccctccagcgccgcgtacgctcctcgagc |
| | cctcatctgtatcataagcacaacggcacacagggacaccaccaggttactctcatgaaggctcatcataccccaaggcggcacagctctgggtagc |
| | ggaggtgtgcgcccctgggcaacaggggacaccaccaggtattaaccgaccggctggaggagaaaaacacacacacaagga |
| | acagtctgccctgagctcagcagataa |

TABLE 1-continued

| SEQ ID NO | SEQUENCE |
|---|---|
| SEQ ID NO 26<br>DNA Ligase 4<br>Homo sapiens | atggctgcctcacaaacttcacaaactgtgttgcattcacgttcctttgcagatttgtgttcaacttagaacgaatacagaaagtaaaggacgtgc<br>agaaaaaatcagacactcagggaattttagatcttggagagaaattcatgatgctcatagaagaaccacacaaagatgcacagactcttttatcc<br>agcaatgagactaattccttcctcagctagaaagaatgccctatggaagaaatatgctgtcaagctttatatgcttaattgcttaattt<br>acctagagatgaaaagatgccctcaaacttttaaactacagaaacctgaacttagactcagttgcctggaagactgtaagctgcatattt<br>tgtgttgaagccaagatgttaacagaaaagagccttctcaactataaacacagagtcagcacttagagtcgcttgagtgcactagatgctaggcaactgc<br>aaagacctaataacaaagagacctctctcaactatctttcgtttctcataatgatgctgcactacagattgcttactacagagttctaactaatctgctaaaga<br>ctggtgttagtcagcaaactatctttctgttttcataatgatgctgcactacagattgcttactacagagatggcttaggcaactgc<br>atgatcctctgtaggactcagtgatcttcatcttatttctgctaagtgatgcctgagtctgagtgatattgagcacattgagaaggat<br>atgaaaatcagagttctaacatagaaaccaagctagtgtgtgaacgtatgcaaatgcacaagatggagatatatataactttcctcgaaat<br>ggatataacactgatcagttggctctaatactacaaaacttcatgcaaaaggaactaagtttgtatataaaagatgagaagattcgatctg<br>tgatgtgagatgatggcttttcatgtttagatctgtcatactccgtcgtgggtctgcgcaccatgaaaagaactgtatgatctgggttgaat<br>caaactgttatgtgtttgagcctgcagagctatctctcatactccgtcgtgggtctgcgcaccatgaaaagaactgtatgatctgggttgaat<br>tggccaagtattggaagccttcatagaaaagctccacaagcagcatttatgtggaacagaagcagaagtacattgaaccttgtaatt<br>ctgtcattgtcagattaaaggcagcagagatcgtaccagagatgtatgtataaaatggctgcacctgcttttcccagaattgaaaagataagag<br>gaagaggaattatgctgaatgaaaacaacctctattcagtcgatgacctggagaccatgaagtcgtcttaagtgaactatccatctaaacatcataac<br>gactaatggacatttaagtgttggagatggatggaggtggaatgacacgggtggaatgatgtcttattctgtgcagcaga<br>gaagccccctgcaagtgaagccatcgtttcatactctcgtgtgggtctgctatctagactatcagagggagtccaagagaatctgattgaaat<br>tggccaagtattggaagccttcatagaaagctccacaagcagcatttatgtggaacagaagcagaagtacattgaaccttgtaatt<br>ctgtcattgtcagattaaaggcagcagagatcgtaccagagatgtatgtataaaatggctgcacctgcttttcccagaattgaaaagataagag<br>agtggtgatgatgaaccacaagaaaaaagcgaaagtgcccaagaaagtattgaattattgagcacttaaaagcactaa<br>cctactaacgtaacaaaatctctatatattgaagatggaacattccagggcccagcatggtttagaagttagagatggtttaccacatggacgccctcgcttatgatgattcat<br>agaattgtcaataaacatgtgttgttatataqtacaaatccaggccatgagctttagaagttgaacaaaagtttgtacacatggaagccctcgcttatgattcat<br>agtgccatcaacatggcacatttgccctgataatgattgctgatagatattcattgatactatccggattgctccctccctcdcag<br>ctcaggaattaaaattcacgacgagaccactttagaaatgctctcgatctgattaggggacatcagtgagctatagaaagcttgg<br>agctccggttcatggagcaaagtagttctgttagtgagggagtgdcatgtaagtaatggagaagtgttgcagatttaaag<br>cttaagaagaactttaagaagaagttaaatccaaagaagttgggaactggtgaactgaataaataaataccagagaaccagta<br>tttgattaa |
| SEQ ID NO 27<br>XRN<br>Homo sapiens | atgggctccgccgcctgccccgccccccggagcctgcggagcctgcgctgcagcctcgcggagcagtcgcagcgcccacgcgatgg<br>gacgcgggctggggattcagcacgcgagcctggagcaattcaggaccgcgggcaggagccctataggtccgaactcgcagga<br>gggtcctcctccactccgctcttccgcaaccccggaagccccgcattttggtctccgaaga<br>ggtcagaggctgtgtaatgctgtgtgagcaatgcagccacaatgaatgcaagattcaatgcagtgtaagcatcaactaatccaatgatg<br>tggagtttgataatctgtattgatgatgatgacagacttctcagtattgtgaagaaccaagcaccaaaaatgaagatgaacagtgaaatgat<br>ggtgcaattttgagtacatattgaggaggttcaggacgaagcagcagcagtccagaccacagagcagcaacagccagaatcatgaggaagaaaatattg<br>atgaaaagtggtgctttctcccccagaaaaatatgacagaacaacttgacagcaactgaaggaaccatggacagaaaatatcatggacaatcttgctaaa<br>tgcctctcgctattacatgatgatgatgctttaaataatgacctggttggagaaatttgacagtattcgatgctccttgcgatcttgcttcatt<br>cataaatcatgatgacagcctaccattagaagcaaagaccctggcagcaccatgcctaaccatgtcatcatttgtgtatgtgagagatgctgtcatta<br>tgctagctccggttgcagaggattgaagttcaccatttaccattatggacagaattcaaaccaaccaaccaacgccaaccatctgtgtcttgtactaatcagttgg<br>acatgagttcaagatgtgaatgtcttctagtaataatcagctcagccatccctagagttggaagaatggcatcaagccaaccattggtcagtgtgaagtt<br>atctcccttcgctttcaatgtcttcgtgggaaatgactcctccatcgcaaaatggggtttacctacagatggttatgtcaatgtgagattttgaatcatttg<br>aaaaaatggtacatcaaaactggggttacctacagacactgtatgaagaacatcttgcaatcttagtctagcaagttggtggagattgtgaagtt<br>gaggatagcattttaaaagagaagatgaaggcagatgacacatctctgataccctagaagataagaagaagagtgaaggaagagatcaac<br>cagcttcactccagtgaaaatcaacttctagtccttggatatctcctaatacgagttaatgctccctaagggtccaagtgccgtcccattaggagaattaagcga<br>tgaatgcagaagatgcagaactgacagtgaacctgaccagagaagtatgtcaggttatgagaagtccgctgaagcacgcggttactacaagaacaat<br>aagcagaagcagctgatgacaagtgaacctgaagctgacaatccgcgtgagaaatccgcgtgaagctgatcctgagattattaccaggaccgtt<br>ttgatggatcagcgatgacgagaaatccgcgtgagaaatccgcgtgaagctgatcctgagattattaccaggaccgtt |

TABLE 1-continued

| SEQ ID NO | SEQUENCE |
|---|---|
| SEQ ID NO 28 3xFlag_NLS_ PolIV Escherichia coli | gcttcctggaagtggtattatccattcattatgaccattgcttcagacttgaaggcattgagacatgccatctgatttgagaaggtacgaaa cgtttaaaccactagaacaactatgcttccagctgcaagtggtaattttctacctccatgcgaagctcatgagtgatcctgattc tagtaatgacttctatctgagatttgctattgatttgaatgggaagaaagagaatatgcatgcaagtgttgctcttcgccatcgtggagacgagtcg aaggctacgagctgcctgccatgagagaggtataccagactccactccaagagaacagcaagaaaacagcctgagtgatctttattgtggg gaaacatcaccgctgcctcatgactcttctcagtgtaccagacaggtccacagacaggtccagaggtaccccgaacatgtagggattc aaggaagttctcttggatgaagaagccattcttcagattacatttctaaagctgtaatgttcctgttcctatgttaaggatctgacacagaacactgtagtca gtattaattttaagaccaccagtttgcccagaatcagcatggcggtgaagcagttgctagaagccttacacgtgctttcctcagcgagaacttata tgactggaaaaatccagcaatggagggcagtgatgccaagagccgaagccaatccagctggctttaaccgtgaccgaggcctgcacctggatcagcagct tcaggactttggccatgatggtcaagagccagccgcaatgactgagccatgaaccaggcgactacaccaccagtggaacttata caggccgccttgacagagggttgggctggctggtggatacaattggaattaa taccagatgctagctggccttgggcctggtgggatgtgggagactgcgtgagagccaggcgtcaaaccagaatgtcccagacaagacgactaccc ctttgccaccctccagagagatacaattgaattaa |
| SEQ ID NO 29 3xFlag_NLS_ XseA Escherichia coli | atggactataaggaccacgacgacgacgatgataaggcccaaagaagaagcggaa ggtcggtatccacggagtcccagcagcctgccagcggggataaagcgataagatgacgataagatgcccaaagaagaagcggaa ggtcggtatccacggagtcccagcagcctgccagcctgagccgggtaaccaaaccgtcgactgtctc gagcagtgcaagtcggcaagtctgcgtcgcagcctggaattaccagccagagtacgtagcgtaccttaagcaccttaagatgaca cggcgcaagtagctgcgcatgttcggaacagcaagcaagtgtccaccagagtacgtccgccacacatggacacaactgacacaagtactctcagggccaat atcatctttatgagccgccggcagaagcccggtgactactacaataatttgtcgactgcagtataaaaacgctccgtccacccttcagcaaaagatgagcaact caaggcaagtccaggcagaaggcctcttcgacgagtccgacagacccagccctcattgtgtggccctcattgtggcctcataacctaa acgctcctgggcagagatgtaagagcataggcgcacggcgaataagcgcaacgacttcaacagctgggatatcgttgatcgtggtggccagggcgatg ggaagatcttggtcttcaacagaggcgtcacgcaggaccaccagcaacctcttcaccagccagcttgtgtgatcctggacttttcaggccttatgagacgga cgtccaccaatgccgccgattttgagccgaccggagagccaacgaccagaccgatgggatgatgacgacgatcttgccatccgcaatcactccaccg agcaggtccgaactgtcaaccaacatcccccaacctcggctgccgcacagacgagttgtcttgtctgaaatca gttgcagcgaactgctcagaccgcccaaagatgctcggtgaaacaagcgcctcaatcagcaaatcccaactaagatccatcggcacaaacccgca ttcaacaactggagtatagacactgctggagaccttgcgcgccgcacaactcccgcaatctgcgagagtcggaaatcgcttaacgcgttcggagg |

TABLE 1-continued

| SEQ ID NO | SEQUENCE |
|---|---|
| SEQ ID NO 30<br>3xFlag_NLS_XseB<br>*Escherichia coli* | ccgtgagcccactgtcaacctcgctgcgtgacgctgccacggaccaatgtgctcaaaaggtaaaacaagtcaaagct<br>ggagaaatgcttactactcggctcgaagacggatggtgatccgaaagtgaagtcaaaatataccaacctgtcaagaagtcgaaaaggtgcat<br>tga |
| SEQ ID NO 31<br>3xFlag-NLS-SpCas9-NLS (Addgene #100000055)<br>*Streptococcus pyogenes* | atggactataaggaccacgacgactacaaggatcatgatattgattacaaagacgatgacgatgacaaagaagaggaa<br>ggtcggtatccacggagtcccagcagccgacaagaagtacagcattggagaaaacactagtgagctgagcagatcgtg<br>acgcttgaatcaggaagtgccaacaagcgagcccagagctccctttgaagcggagtctgactgagcaggagtcagctcgtcctagacaagccagccaaactt<br>caacaggcggacagcgagtccagattctccttagtgataatgagatgcctcctgacaccgtcacgcagacaacgatgt<br>tga<br>atggactataaggaccacgacgactacaaggatcatgatattgattacaaagacgatgacgatgacaaagaagaggaa<br>ggtcgtatccacggagtcccagcagccgacaagaagtacagcattggagaaacacagtgagctgagcagatcgtgacc<br>gacgagtaccaaggtgccaacagcgagaaaatccaaggtgctgggcaacaccggccacagcatcaagaagaacctgatcggagccctgctg<br>ttccagcggcgaaacagcgagccggatccaccttggagctggtgggaggacaagctctcttccacagcgaagatacaaccagacggaaccgatctgtatct<br>cagaagatctcagccaacgagatgcccaagtggacaagtgcttccttccacagcggaagtccttccggtggaagataagaagc<br>acgagcgaccccatcttcggcaatatcgtggacgaggtggacctgaggagcacaccatctaccacaggcgaagaaactggt<br>ggacagaccgacaagcgactcgctgatctatctggcctggcacaagctgcggggacattctgaggcactcctgatcgaggccgac<br>tgaacccgacaacagcgagttgacaagtgttcatccagctggttgcagaccctacaacagcagcctgcgggaaaaccccatcaaccagagc<br>ggcggagcgccaagcacctcatcctgtctgccagactgagcaagagacgctgaaaatctgatgcccagccagtgaag<br>aatggccgtgttcggaaactgattgcctggcggcttcgagaacctgatcgcacaacttcaagagcaacttggccgatgccaaactgcag<br>ctgagcaaggacacctacgacgacgatctggacaacctgctggcccagattggagatcggtacgacgtgttctgcgccaagaacc<br>tgtccgacgccatcctgctgagcgacatcctgagagtgaacacaagagaaaccccagccagccgtctatgatcaagagatacgac<br>gagcaccaccaggacctgacgctgccgctgctgaaagctctgtgcggagcagcgctgagaagtaaagattttctgaccagagacaa<br>cggtacggccgtcacatttgacgtggacgtggaagagttcacaagccatcaagcccatctgaaagatggacgcaccgga<br>gaactgctgtaagctgatcaacgcggagacctgctgcggaagcagctcatcaagcaccgcatcccaccagatcaccgtggga<br>gagctgcaccgcatccggggcgaggaagatttaccattctgaaggacaaccgggaaagatcagaagatcctgacctccgatc<br>ccctactacgtcggcccttggccaggggaaacagccagctcatcgagcgggatgaccaacctcgataagaacctgcccaaagtgtctgc<br>aaggtggtgacaaggcgcttccgccagagtctgtacgagtacctgacaaagtgaacaactactgaccgaggaatagaaggccccgctcct<br>caagccgagcgaagcctgatacttcaccgtggaccctgctgttcaaaagaccaaccgggaatacgacgtgaagcagtcttcaa<br>gagcggcgagccagatcggtgctgcccgagctgccatcgtgaatcgttcgacctgctgaagatcaagcccctcctgggcacataccactgttgtgaaatctgtgctgaaaattatc<br>aaggacaagcagactcctggacaatggaaaacgagggacattctgaaagatatcgtctgacactgttgaggacagagatgatc<br>gaggacaagcttcaaaactctgacccaatgtgacgacaaagtgctgaccaagcagcgaagctgaacagctgggggcaggctg<br>agccggaagctcaacgcatccggacaacagcatcccggacatcctgaattcctgaagtccgcgcttcgcacgagcagcac<br>catgcagctgatccacgacgacagcctgaccttaaagaggacatccagagaaagcccagggtccggccaggcgatagcctgcacgagcac<br>ttgccaatctggccggcagccccgcattgaaggggcatccgcagagactggccgagctcgtgaagttgatgggccggc<br>acaagccgacaatcgtgatcgagatggcccgagagcagaatctccagtaactagccagctgcgcacgagccgagaatgaagcg<br>gatcgaagagggccatcaagatgggcgaacccagcctcaaagcacagccagctgcccgaggaacctgtacct<br>gtactacctccagatgggggatatgtacgtgcagcccactaggtggaacaccagcagtcgccagttggccactacgtgcctca<br>ggactttctgaaggacgactcccatcgacaacaagtgctgacagaagcctgatgaaagcccgggcaacagacgctgcctccgaaga<br>ggtcgtgaagaagaactactggcgccagctgttgaagcagctgattaccaagacggagaacaacgcgcagatcacaaagagctggcacagatc<br>agaggcggctcagcgaactgatagccgctgatcatcacagagaagctgcctgatgcagccggaagattatcccagacgacgatcc<br>ctgatcaaaatgcgccttccagtttacaaagtcgcgagatcaacaactacccacgcgcctacctgaacgctgctggagacagagccgc<br>caggaatcggcaaggtacccaagctggaatgtacctgtactcttccagagcaacatcatgaactttcaagaccgatttcgcgctgagatcc<br>gaagcggcctgatctgagacaacggtggagatcgtgtgggataaagggccgttttgccacccgcaagccatctatcctgccacatctacctgatcagggaaccagcagta<br>gcatgcccaagctgaatatgaaagaagactggagcccaaaggtcgcaggggtgcagccacctggagcaaagagctgcaaaagtgcggggcttcaccagggctgagtatga<br>gctgatcgccaagggactgggacccttgaagaaactgaaactgcttgcagggccctcaaggcccaccgtggcctatattctgtgtctggtgctgccaaag<br>tggaaaggcagcagtgctgatatcaatgagcctgagatcgagattcgagcccttccccattctgtgtgcaccgagaagcccat |

TABLE 1-continued

| SEQ ID NO | SEQUENCE |
|---|---|
| | cgactttctggaagccaagggctacaaaggagtcatgatattgattacaaagacgatgacgataaggtgcccaaagaagaagcggaa |
| | gaagagaatgtctgcctctgcctgcctgcctcgcggcgaactgcagaaggtgaacttctgagcactactggacgagatcatcag |
| | actatgagaagctgaagggtcccccgaggataatgagcagaagcagctgtttgtggaacgacaagcactactggacgagatcatcag |
| | cagatcagcaggcgagttctccaagaggatatcatccccatcttacctgaccagctgccacctgaccaatctggacaagctgtccgcctacaacaaggacgggatagccat |
| | cagaagcaggccggagatatctcccctggaagttgctggacgccacctgatccacctgaccaatctggacaaactggaagcattgacgaaggcatcatggacaccatcgaccgg |
| | aagaggtaccaccagcacaaaggccggggcgaaaaggccggcaaaagagcatcaccgagcatcaccgctacgacgacaacggatcgacctgtctc |
| | agctggaggcgacaaaaggccggggcgacaaaagagcggcaggcaacaaaagagaa agtaa |
| SEQ ID NO 32 3xFlag-NLS-SpCas9(ΔP916)-NLS Streptococcus pyogenes | atggactataaggaccacgacgacgagactacaaggatcatgatattgattacaaagacgatgacgataaggtgcccaaagaagaagcggaa ggtcggtatccaagggagtcccagcgccaagaagaagcggaaggtgcccaagaagaagaggaagcaccctgatcac gacgagtacaaggtgcccagcaagaattcaagtgctgggcaacaccgaccggcaacgacagtatatacgagaagttctttctcgaccagcaagaa ttcgacagcggcggcgaaaacggcggccggccgagtactcagagatacagcggccggccaaggtgaagcggaagaagaagaacaaag gcaacagcggcagcagcaagaagcagcagcagaaggacgagagtcctcccacgagccggcgactacatccggtgcaactctcgcacctctcgaaaacgcaggtaaaactggt ggacagcaagccgacaacgacaagaggccctcgctgctgatatctctgaaggacggtcgagaccgtttccggccactttctctgatcagggcaacgacgc gcccgtaccaagccgagaaagcctgctgaaccaccgagcgcctgtgcgcagacacatgaacactcaagagcaactcgagccggccaaactgacg aatggctgtctggaaaccctgatcctgcctgcctgcccgaccctgtccaagccctgaccgctgccggactgtttcgccgccgccaaatcgaag ctgacaaggacaacctacgacgacgacagaatccctgctgaagcagcctctgacgacctgatgaagccagcgcctctgatcaagagagatacga tgccgacgccatccctacgtcgactgccgcgacttgcagagctgcggcgagaccacccagcgctcacaaagagcttggtacaacaacatccggaagatacgaaga aggccccagcagggtctgcctgatcgaaggctgcagcaggtccgcgacacattcgagggctgaccgtgtacctcgtacaccgttgagggatgatcc cggtcacgccgcgctacattgacgggaagcagcgcagcaggacctctgaaagcggctctctgtgcgtcctgtggaagacaaggcgtgccatcccatccgatcac gaactgtcgtgaagctgaacagaggaccctgcgtcggaggagcagcgagttcaccatcttacccattcctgaaggcagcacatttggagaagtcgaccttccagca gagctcacgccatctgctcggcgctctcaggagaatttaccatctgaaggacaacggagcagatctggctagtccgctgcgataaagcaccggaaacct ccctactacgtgggccctctggacaccgtgaaatgtacgtggacaccgtgaccgcaggaagcatctggccagttccggccaggcgatagcgcagac agaagacaggcagtgtccgagcttcgtgaagacagagctagcacagcgttctttcagcacgtacgtcgcaggactcgtagcaatgcgtgaagtgaacgg cgcctactacgagcagctgaaggaagctactggcctcgatgcccaatccctccagatccatccgtgccggacgccctctatgcgcgggctaccg gccttaccaggactgtcgaaaagcgagagaagcagccgcgcagcgagagaagcagctgcgcagcgaagaagtgtggtggcgcagatcacag aagaagcgggaaggcatcaagaagtcggaggacaatgcaagtgatgccggaaatcttacagacgcttcgtgggagaaaccctgcctgagaag tgtaatcctaccgagaggcgcatatgcggaacactcaagacagaaatcagacggcaatactcaatcaccaccccgtgaaaacggcggcgaaca tcatgaacttcttcaaggcgattctgatcgacccgagaagtgaggactggctaggctatatgccggccagcgtacttccagggggcagagcgatcggggaaatcggggatatgaaaaagggtaaactgctggatgaactg caaaagggcagcgaaaggccgagaccgaaggtagctgtgacgagatcctcgagcagatctcacctgaacgaagcgggattt gccctccagatcaccacagccggatccctcgtgacgagtactccacccgaaaggtcatcctcgaagaactgcctcaaggtgctgcaggcctgaactctatgtcttca cagcctcgctgtgaaacggattgtaccatcgactccaatcagcaggatggactcaacttaactgaccagaccgacctcctgaagga gccgctccgatcaaaagcgcctggcgacaaatcatcggcagcagacggacaacgctgctggacaacgtggggccaagtaccgcacaagtcgaga agcgcctgtccgaccagaagggcaaagaactggatcaaggagtctcttctaacgacaactccacaagaaccacgtgtcgctgatcatgaaacgggtcgagcggccaaaagctcca ggaaatcggcaagcggttaagggagttacgggaaacgtggacttttctcaaggaccaacatcatggaacgagtctgggcaacttccgcaatcgctcgagg aagcccctccgggatattaattgaacgtggcaaaggcagtgatgctctctgctgtacatacctggagctatccttccttcgacgccaaagtg atgaagcagctgaagcggcggcgctacaccggctggggacgctgtctcgaaagggcaacagcgatctaaactgaaagcatcatcgaaattcgatagctgc gagaatggcagcaagcagtacgtgtacggatttctacaggaagctggccagtggctgaaggaagagagttctatccagcagctgcagaataagac gaaaatcggcaagcagaaccagttctacaaaggtaaccctaggaggagtcgtccgaggaatgcgagagcctctggcctcaagctgtccgattt ccgagcttctgacagttccagttttaaaagtacagacgctggaaactgacgactgtcgacatcaaggaccgctcgaaaaccgtcggaaacgcgccatccctatacccaagaagac gagcttcctgacagttccagttttaaaagtacagacgctggaaactgacgactgtcgacatcaaggaccgctcgaaaaccgtcggaaacgcgccatccctatacccaagaagac tgatcaaaagttggccagctggatggaactacctacgcggactgtacgaggatctgataaaggccggaagagctgccaagagcgagatcag gaaatcggccaagttcaccaagtactcaagaattctctcagacaacatgacccaaggcttcaagaggcggagatctacccggcaacgcgagatccgg agcggctgtctccgctcgatgcaaatagcgatcgatcctaagtacgactccgtgccaatgaaggtgctcctccctaaagtggtgggtgcgcagtgtg aagcccccaaatcttcttaccatgcgcagacaatcgcgaacgggaagcgatcagtcgccctgggcgcttcagcagcccacccaccgctgatgatagc tgatcaagtaatatcgtgaagaactgtacggcgaggtgaaagaactgcgatgtcgtgcgcaccagcccccgggggatccttcagatgatccc gaaaagggcagcagtttgaaaagaacaccactcgaagaaaggtgaaaaggctggtaaagcttccgaggggtaccctgggagaacccatcag tgatcagtaagcaggtctgaatgagcgggaactggcggcgctcattcagagctgagagcgagtgtgggtggggcaaaagtc acttctgaaggtctgccccggtgaactggacaagcgtgaaaggtgggaatcatcaaggaccgtaagtatcgcagtactctcgagcggaaatg acgaatgtccgcctcccccgagataatgagcgagaactgcgagaaacagcgttgttgaacgcaaagcacgagctaactggagatcatgaca atgagaagctgagggagctagaatgagccgagaactgcgtttgtgaacagcagaaacgctactggagatcatgaca |

TABLE 1-continued

| SEQ ID NO | SEQUENCE |
|---|---|
| | gatcagcgagttctccaagagagtgatcctggcgacgctaatctgacaaagtgtgtcgcctacaacaagcacgatgagcatca |
| | gagagcaggccgagatatcatccacctgttacctgaccaattgggagtccctgccgccttcaagtactttgacaccaccatcgaccggaa |
| | gaggtaccagcaccagcaaaaggcggccagcaagaaattcaaggtgctgggcaacaccggcatcagccggcctgcaccggctcaccgg |
| | ctgggaggcgacaaaaggcggcggcacgaaaaggccggcagcaaggaagaaaagtaa |
| SEQ ID NO | atggactataaggaccacgacggagactacaaggatcatgatattgattacaaagacgatgacgataaggactgccccaagaagaagcggaa |
| 33 | ggtcggtatccacggagtcccagcagccaagaagccgacaagccatcggctggacctacaagatctgtggctggcgtgatcacc |
| 3xFlag-NLS- | gacgagtacaaggtgcccagcaagaaattcaaggtgctgggcaacaccggcgacagatacacaagaagaccggatcgtatct |
| SpCas9(G915F)- | tcgacgcgggcaacacagccgtaccaaggtgctgggcaagctgtgatcaggctggagagtcaccaaggaagacggtccagagagtaagaagc |
| NLS | gcaagatcttcagcaacgagatggccaagctcgactgctgttgggccggagctgagcagcaaggcatgatcggctacactcccacctgtaccaactgt |
| Streptococcus | acgagcggcacccatcttcggcaacatcgtggacgaggtggccatctaccatctgcggaggcagctctatctgaagatggtccactcctgaggcgac |
| pyogenes | ggacaggccgacaaggccgactctgatcatctggcctgccctgaacatgataccaagcttccgggccactcctgatcggaggcgac |
| | tgaaccaggacagcgaccaacgagcactctcgcagacctgatcaaccagctgttgaggaaaaccccatcaaccgccagc |
| | ggcgtcgagcgcaaggccatcctgtctgcgcagaccttgagcaagcagaccgctgagcaaagcagaaactgatcgaacagctgcccggggagaagaag |
| | aatggcctgttcgaaacctgatgcctgcagctcaccaggaacccaccaagtacagcgacgtttgaacctgatcgccgaggacgcagaactgcc |
| | ctgcaagaacacctacgacgagctggactgacagaaaccatcttccagctgatcaagctcgggatcctcaaggatacgacaagataagaccggag |
| | tgtccgccctctccggccgtgtgatgagccccgagataccatccagcctgcctatgatcatgatcaagatacgac |
| | gagcaccaccagaccgaccctgctgaaagctgctctgtgcggcagcagctccacaagaagatttcttcgacagagcaaagaa |
| | cggctacgcgggcctacattgacggggagcagcaggaagagttctacaagttccatcacaacgacctgaccctgcaaaggaatgacagaccactggga |
| | gaactgctcgtgaagtgaacagaagagaccctgctgcggaagcagcggaccttcgataacggcagcatcccccaccagatccttgacggggacttctgcgat |
| | gagctgccgcattctgggggccctgcaggggaagatttaccatgatctgaccaaggtgcctggcaagagatacagccatgatccagtgcgcagagatacgac |
| | cctactacgtggcctctggcagggaaacagcagatcgcccacagagttcatcaagcgcagaatatgcgaccaatcccaacctgccagaaagtcaaccctggaacttcg |
| | aggagtggtggacaaggcgcttccgccaagtacttcaccgtgtactaacgagtgaccacaagttgaataacgtgaccgagggaatgaagaactgcggaatgaagaaccgcctctgcc |
| | caagcaccgctgtgaacagtctgaccctgctgtataacgagctgaccaaagtgaaatacgtgaccgagggaatgagaaaggcccgccaacatcgatgaatgcaagaaagagaggactactcaa |
| | gaaaatcgagtgcttcgactcggtgaaatcccggtggaatctgctcaaccctgcatcaccaccgtgttgaggacagagagtgtgaaaattatc |
| | aaggacaagacctccgacaatgaggacaatctgacgacaagcagcctgtctgacagaagatcagaaaacactgtgaggacagacgcagagagagatgatc |
| | gaggaacggctgaaacctatgagcactctcgaggaaaccgggcacaagcagctcctgattctcgaagtccgaagcgtttgcaaacgaaactt |
| | agccaagtgatccaccagacctccggaacactcaaggaacagcagaagtccacgggccaggtccgcagcgatcagtcacgacac |
| | catgcagctgatccatgatgattcgctaagaaggggcatccgagacatgtacgttgatcaaggctggagcagaggcagtgagaaaaggaagcgaaaactt |
| | attgcaatctggcggcagccccaccattgcccagatcgtgatcaaatgccagagcggacagcaggagaacgagttcatcagacagaggaaccaagagcagcccgcgaagtgatggccggc |
| | acaagcccgagaacatcgtcatcgaaatgcgaagaggtccagcgtgctgcaaagagctactgcacaaaaccatgacgcaagaagaactga |
| | gatccagaagggccatcaaaagactggctgactactgcagtggacactctgccggagaacaccacctgtgaagaacggtggatccagactgcggaagaagagctgacct |
| | gtactactgcgatggcggatatgcgggatactgcagacaaggacagaagaccggtgagacagcgatgaagaacgacatatctgcctcca |
| | gagcttctgaagagacctgacctcatcgacacaaaagttgctgctactgggcagcaccgagatactgacgaacgacgttcaaaccgtcccctccaaga |
| | ggtcgtgaagaagatgaagaactactggcggcagctgctgaacgcgaagctgatcacacagagaaagtttcgacaatctgaccaaggcagaaggcagaagatcct |
| | gaaagggcatcaagagaagtgactacgagacaacagtgcctcagagcttcctgaaagacgacagcatcgacacaaagtactatctcgaccatggatatccag |
| | gacttccgcttctcaagcatgccaaccgagagtacagagaagcagctcgagcagctggaacagcagaacatcaagaagagaagcctggcggaacctcatcaccagcag |
| | acttctgaagcaagtgctacaaagaggtgaaaggtggaccacatagaggaaaagttccggacagccagctgcatacatcagcgccact |
| | agagatccggcgccgcgacagaggaacctgagcgatagcagaagagcctcagaagaaaaatatgcggccctgatacttcaaagctgtacctggcagccct |
| | atgagaagctgaaggacatgaggcgtgaacggcgaaaacgtttgtggagcgaaacgtcaagcccctgcgtgtcgcgaatacatcaccgagatcatctgacca |
| | gatcagcgagttctccaagagagtgatcctggcgacgctaatctgacaaagtgtgtcgcctacaacaagcacgatgagcatca |
| | gagaggcaggccgagaatatcatccacctgttacctgaccaattgggagtccctgccgccttcaagtactttgacaccaccatcgaccggaa |
| | gaggtaccagcaccagcaaaaggcggccagcaagaaattcaaggtgctgggcaacaccggcatcagccggcctgcaccggctcaccgg |

TABLE 1-continued

| SEQ ID NO | SEQUENCE |
|---|---|
| SEQ ID NO 34 3xFlag-NLS-SpCas9(Q920P)-NLS Streptococcus pyogenes | atggactataaggaccaccacgacgactactacaaggatcatgatattgattacaaagacgatgacgataagatgacgatgggccccaaagaagaagcggaa ggtcgtatccacggagtccagcagcgacaagaagtacagcattggcctggacatcggcaccaactctgtggctggcgtgatcacc gacgagcaaggtgccagcagaaattcaaggtgctgggcaacaccgaccgccagcagcatcaagagaacctgatcggagccctgctg ttcgacagcggcgaaacagcagagcgagcgccggcaagggcgacaacgcggctcctcccacagacgagagtctttcgtcgaggaacacg...（以下略） |

TABLE 1-continued

| SEQ ID NO | SEQUENCE |
|---|---|
| SEQ ID NO 35 3xFlag-NLS-SpCas9(F916P)-NLS: *Streptococcus pyogenes* | atggactataaggaccacgacggagactacaaggatcatgatattgattacaaagacgatgacgataaggatggcccaaagaagaagcggaa ggtcgtgatcacggagtcccagcagcaagaaattcaaggtgccaacctgttggtcgatcgga ggtcgtgatcacggagtcccagcagcaagaaattcaaggtgtgggccaacaccgacagcatcgggctggcaaccctgaagaacctgatcggagcctgctg ttcgacagcggcgaaacagcgaggcctgcaacatcggcaacatcttcggcaactgctttcacagcgacgcgaagaatacacagcgaagaaccgatctgctatct gcaagatcttcagcaacgagatggccaaggtggacgacagctgttccaccgagactgcctaccaccatctccacctgaaagaactgtt acgagcggcacccatcttcggcaacctcgggctgatctatctggacgagtgttcatccagctggtgcagacctacaaccagctgtccgagagaccatcaaccagctgtccgagagaccatcaaccagctgt ggcgtgacgcccaaggaccgcatcctgtccgagagtgcagaagagaacagcgatctgatcgcccagcgactgcccggcagcgaag tgaacccgacaacaggcctctgtccgacaagcgacgctgtgtcagacctacaaccagcggctgtccgacaaggaactcgacctaacatcaccatccaagagaacctgatcgccca ggcctgaccccggatgccgatcacgccgtcctggagaacctgatcctgctgcccgaaacctactctcggcctgatcggaccacttcatcgccctgattcccaccgcaaactgttgctggaggatg gtgtctgacctcctgcgtgtcacctctccgagctgcagaagacacaccatccaggatgccaaatgctgcccgggtcctatgtcaagagatacgac gagcacccaccgctcgactctcagcgacatcctgcaaagacctgctctcgagaagaggaacaaagattctctccgaccagcaagaa cggctagcgcgctacattgacggcgggtcagcgagagagaactgcctcacaagctgtcaccagcgttcatcaaggccatctgtgcc gaactgctcgtgaagctgacagagaagaacatccaacccatcggtgaaagattcctaccgatgaacggcctgagcggaacagctg cctactacggctacccgcgtctgactctctgtcggagatggtcaaagtacagcgaggatctgctgatcctgaagctggaagatagaagtaaacatcaagcgctgccatctcgaggatc gagcgcgaaggatttattcaggatcctgtgacgatttcaaagatcaccaagatcctgaccttcgaatcccgtgccaagaatcctggaagagtc catgctctgagcagttcaggatccatcgagctgcggtgaacctggagaaactctgcgatcaaggaaccctacgaggattgacagcgatcaacaccacgacggcgatcctgaagcaagctgggaagcggaaggtatatgaagctgcggcggcgtcaggtgaaatcgtga ccgagtcgtcggctaccgcggcggtcaggtcctacagcggtccacctcgggaagatctgctctgaagatctgcaaggaagatatcgccaag cgcgagcggcggctgaccggacaagaacaaggacaccatccgcggagcagctgctgaacgccaagctgatcaccgctggtgaaagcggatccaagatt gaaaggagcctgcaggcctgcaacgacatcctggaccgggatcatcgatagacagctggcagttcaaagggccgggatattgcaagatctcttaacggattggaccccaagaagtgctg agctgccgcagaaggccaagatctgaatatcgtgaagaaagaccagaagggcgcctggaaggacccaagcgggcaagggcgagctgaaaggtaccagctcatcctgacgaggaacagcga cactgaccccgaccctgctctctctccaggcgggtgcgtgcggtcgatcatatgtcaggatctagagaatctacctgcctatgaccaggaagctgg acagctgctgcaccccacagcggagtcgactccagtgaagaactggtgttgaagtggtggaacagcacgcctcagagatgaaggagctggaaacaggcca cactgaccccagatgggcaaaggcgaacctctgtccggcatctgagagcagccagaaaatcgaagagcaggagcaggagcaatgaagcgcggacttcgctt tcagagagcggcagcctggacggcctccacctgccaaagagaagcccatcgagcctctgtaagagcaaagctcgagagagacagaacatcagccg gaagaggccacctggtaccagagatgtgttgtacatgttcgctgccaagtgtgccatcaagatcgagaagccggaagaaattccacctgacaagacctgtacacc gagggcgagagatcgcagcggaaaatgattgccaaagagcgagagaaggtcaactcgcaagaaatctgtgtctgcaaactgcaagaggc ccactgatcgagactgtccactacggcactgggcagcgcagatcaaagttgaacagcattggcgactggagatatccggacaacttgaaccaccgctcaacaattg gggcccctgaagcctgaattccacgatgagcttgtggggaagctggaactgcacatgaagaggctctctgagtggagagagaacacagagactggcgtggctgccgggagcaggaagctgg acagcaagacagccgcagcacaagacagcttcaatcacagaccgctgatcgaaacgcttggtctggtcaaaaataaaaagtaa |
| SEQ ID NO 36 3xFlag-NLS- | atggactataaggaccacgacggagactacaaggatcatgatattgattacaaagacgatgacgataaggatggcccaaagaagaagcggaa ggtcgtgatcacggagtcccagcagcaagaaattcaaggtgccaacctgttggcggtgatcacggagtcccagcagcaagaaattcaaggtgtggccaacactgttggtcgatcggagccctgctg |

TABLE 1-continued

| SEQ ID NO | SEQUENCE |
|---|---|
| SpCas9(R918A)-NLS *Streptococcus pyogenes* | ttcgcagcggcgaaacagccgaggcaccggcaggtaccggctgaagagaaccgccagaagaagatacaccagacggaagaacggatctgtatct<br>gcaagagatcttcagcaacgacagatgccaagtggacgacagcttcttccacgacggaagagtcttcctgtggaagaggataagaagc<br>acgagccggccccccatcttcgcaacgagaggtggctccgtcctgctggccctacactaccctgaagaaactggt<br>ggacagcaccgacaaggccgactcggctgatctatctgccagactgagcagcgtcgatctgcgggccacttcctgatcgaggcgac<br>tgaaccgacacagcagcgtgacaagtccatcctgcgactcaacagcagcgtgttcgagaaaccccatcaacgccagc<br>gcgtgacgccaaggccatcctgtcgcagactgagcaagagagacggctgaaaaatcgatgccagctgcccagcgagaag<br>aatggcctgtctcggaaacctgattgccctgagctggtgcctgagcaacctgtcgaccagtcggcagcaactcgacctggccgacaaactgaac<br>ctgagcaaggacacctacgacgacgacctgacaacctgtctggccagaaatcggcctgcgagacctgtttctggccgacaaacc<br>tgtccgccgcctccgtgcgccaagagatttacctatcctgaggacatccttcgagacatcgagaagatcctgacctcgaagatg<br>agccaccaggaccggaccctgcgaaagtctcgtgcgcagcagcgtctaaggtctacaaactgcaagtctatcaagtccatgaccagaagaa<br>cggctacgccgggctacattgacggcgagcagcaggaagtctacaagtctatcaagtgccccatccgaaagatggacggcaccgag<br>gaactgctcgtcgaaagtgaacagagagacctgctgcgaaagtccatcgtggaggaccatcaacaacgcacgcatcccccaacagtgctgcc<br>gagctcgacgcccatcgcgcgcaggagatttttaccatcctgacggatcctgaggacaatcctgagaagatcctgacctcctactcccgcatcg<br>ccctactagaccctgcccagcggaaacagcagattcgcctgatgacagacaagagagagggaaaaccatcaccccctgaacttcg<br>aggaagtggtggacaaggccctgctgtacagtacttcaccgtgtataacgagctgaccaaagtgaatacgtgaccgagggaatgagaaagccccgctcctct<br>gagcgcgagcgccatgctgacaagaaagccatcgtgaccctgaagtcacaagagctgcagctgaagctacttcaa<br>gaaaatcgagtgcttcgactcctggtggaaatcccgggtggaagaccatttcgaacctctcaacgcctcccctggcacatacccgatcgtctgaaattatc<br>aaggacaagaccttcctggacaatgaggaaaaccgaggacattctggaagatatctgtgaaacctgaccctgtgaggcaagataccaccagtgttgaggacagagatgatc<br>gaggaaccggcctgaaacctatgccacctgtcgagacgaagtgatgaagcagctgaagcagcgtgaagcacacccccacgagatctgggcgtgggcaggctg<br>agccggaaggctgatcaacgacctgcggaaggcaccgacaataccggatcgtcggcagcatatcggattctgaagtccggcaacatcgacaaactt<br>catgccgatgcccgacgagctgacctttaagaggggacatcctcagaacagcaagaagcccaggtcccgcaggcgatacgccagcgcacgac<br>attgccaattggcccggcagccccccccattgaagaagggcatccctgaaagcccagaagaaccagaaggcaagagtgtgacgagctcgtgaaagtgatggccggc<br>acaagcccagaacatcgtcgatgccagaccggaacatcgtgaaagatccagagaggccatggccaacctcccaagagatcgagaacgctgaccagcg<br>gtactacctgtactacctgcagaatggccgggatatgtacgtgcgaggaaccttgtgtctttccaagacagcaaggaccatcgtcaagacactcagttt<br>gagcttctgaaggacgactccatgacaatattggccggaccccaagcgtggagacagcgggagtttgcacgcggcaaactggcacattgcacgcaaccctgcacccaaagatctatctcaagaagaaaatcggc<br>gatcgtgaagaagatgaagaactatatcggcaagagctgcaggtgaacatctgaccagagaagtctgaaagagatctactctgccccaagagaacagcgatac<br>agggcggcttcgacagcctgaaaaccccagtaagcaagcagtcgacacacaggccagacagcggcttcgggatcagcagctcctgttcgacttcgaagtgcgaaaaaccgccg<br>ctgaaaagggcaagtcgccctcgcgaactgcctggcagccgaactgcaagctctgcaagtcatcgagtcatcatgatctgattctcctccaaatatgaaagcactacagcgatcccagc<br>gaagagaatgcggccgtctgcgcctgcgccagaagtacccagatgagcgaactgaatgagcaaaggaatcacagaagagacagagagagagcaaagtgcttgggaaacgactgatcaatgggaagagctacgctctggaccatgatcagcagc<br>cagatcagcagcgtccacgagatccatcatccatccaccccttaccgtgaccgccccacccgtgaccgccagcatcaccgccctgccactatctggtgaccgccttcaagactttgacaccaagtctgaccgg<br>aagaggcaccaccagaaaaagcccgggccaccatcaagaggtctggacgcccgaaaaagcccgcaaaaagaggcaaaagcgaaaaagaa<br>agctgggaggcgacaaaaagccgggcgggcgggagcggcgcagagaggtgccacctctaccacccgaagaaactggt |
| SEQ ID NO 37<br>3xFlag-NLS-SpCas9(R919P)-NLS *Streptococcus* | atggactataaggaccacgacggagactacaaggactacgatgatcatgatattgattacaaagacgatgacgataagatggccccaaagaagaagcggaa<br>ggtcggtcatccacggagtccccagcagcgacaagaagtacagcatcggcctggacatcggcaccaactctgtgggctgggccgtgatcacc<br>gacgagtacaaggtgccaagcaaaattcaaggtgctggcaacaccgaccgccacagcatcaagaagaacctgatcggagcctgctg<br>ttcgacagcggcgaaacagccgaggccactcggggaaacctgcgcgttgtgtgtgaggagaagctcttccacgactggaagaccaaacggcaccgagagagacagcagcagccaagatctgtatct<br>acgagcggcacccctcttcggcaacatcgtggacgaggtggccagcaacggcagatcaaggatacatcagccagagcaccagccggaaac<br>tgcacgagaggagaccacccggaatgggcgaactgtacgaggaagatctggagacgagc |

TABLE 1-continued

| SEQ ID NO | SEQUENCE |
|---|---|
| *pyogenes* | ggacagcaccgacaagccgacctggcctgatctatctggcctgccacatgatcaagttcgggcacttcctgatcgagggcgac<br>tgaacccgacaaacagcgacgttgacaagttcatccagctgtgtcagaccgagcaggacgagacccccaagaaacccatcaacgacgagc<br>ggcgtggacgccaagccatcctgtctgcagactgagcaggagagcgctggaaatgatcgacctccagcctgccccagcgagaacgaag<br>aatggcctgttcggaaacctgattgccctgagcctgggcctggcctagacttcaagagacaactcaagatcgacctggcgatgccaaactgcag<br>ctgagcaaggacacctacgacgacgatctggacaacctgctggcccagatcggcgaccagtacgccgatctgttcctggccgcacaagc<br>tgtccgacgcatcctgctgagcgacatcctgagagtgaacactgagagctctcgtgcggcacagcgctgcctatagatcaagagatacgac<br>agccaccaggactgctacagcggctacattgacggcggcgcagagatccggttgcaggcaggagcgctgcctacgccacatcaagagattagc<br>cggctacgccggctacatgacggcgaagacgaagaccctgcctgaggcgcagcctctacaagttcatcaagcccatcctgaagaaaatggacggaaccgag<br>gaactgctcgtgcgactgaacagagacgaagagctaccgagaggcagaccaggagcagcgcaacctggaggagctgctgaacacctcccgagaccaacctggga<br>gagctgcaggcatctgggcggcaggaagatttaccatttcctgaaggacaacgggaagatcagaagatcgaagatcctgacctcggaacttcg<br>ccctactacgtggtgacctgcctgccccaggacgcttccagcacagctcatcgaggtatgaccaacttcgatagaacaaagcggaaacagttcg<br>cagccgacggtgcgaggggtcaccgtgtacagcgaaataccgaccggaaatacgtgaccgaaggaatggaaagcccggcctctct<br>gagcggcgagcagaaaaggcatcgtggacctgctcaagacccaagcaccgacccaagcagcaggggcgtgaaaggtgaccgtgaagaggactacttcaa<br>gaaaatcgatgctgctgactcctgtgaaatctccggcaatgggaaaacgaggacatctcggaaatagtctgtgaccggaatgtcaagagagagagagatgatc<br>gaggacaaggactctgtcaaccatctgctgaccgacgtgacgagccagtgaaaggagacgaccacactgttgaggcagagagcaggctg<br>agcgggaagctgataccgagcagcatccggacacgcctgtttcctgaagccttgagaccagagcctgagcttccgacgcagagcac<br>catgcagctgatccactgcctgagcagcccgaccgaccttaagaggacatctccagaacatcgcagacgtgaaaggccagacagagagagagaccggaagctgacct<br>attgccattcaaggccggctgtgatcgaacagaattgatgaatgcagaaacaaggaacagcccaaggaatgatggacggccg<br>acaagccggaacactgtgatcaagaacggcccagtctgcctgaaaaaccccgtgaaaacctgagaagtcaaaacccagtgaagctg<br>gatcgagaggcatcaaatggccggaatatgtccagaagctgggcaagatatgacaaccaagctgagcatccagcacgaccaaggaaacgagaagctgacct<br>gtactacctcgaagatgggcggatatgtccagaagctggcagaacaaaaaggcgtcaactacaaccggcagaaggaacacctgagagaggaagctgcctca<br>gagcttctgaaggacgacctccatgacgacaaagtgctgacaacagcgggcagaaggacccacgggcagaagaacgcaaggaacggaccgaaccaagagcgcag<br>ggtcgtgaaggatatgaaacctactagcggcagctccgaaggcctgattaccaactgtagcaagctggtgaacctcgacaattgcacaaagcacgtgaagcagatc<br>agaggcgcctgaacgtgatactagaagcgcttcatcaagcccaagcggttgaaccggaatcaccgacaacactcacaagaggaacacccactgttggaagtagagagccggaatcaccgac<br>ctggaccccgatgaacactaagtattaacaaagtccagtgtttcaaccgagaggacatacgcaaggaccgaaggatgtaggagccacgaggagcagcagc<br>ttccggaagtatttccaggctctcgtcccgaaacccgaacccccgggaactgcgagaacaaagaagaaactccagcgagcagatagaagaccacctgcaaaacgaatatccggagagagactggagggatccgtcaacaatgggaccgaagaacagccacatagccaagcgggggactggataagcccatcaagagccgc<br>caggaatcggcctgcccaaggccagcgaaaaaagtaccccccagaacttccttccaagaacaatcatgaagttccagcgagactagtgagggagatcctgcagacaggtcgtgggagagtcttacaaggtcagcagtactacagaagggatcctgcaagaagaggggatagcaggaagcgagatcctgcaagctgaagagcgatcc<br>gaagcggcctgatcgaacaaaccggaggtcagacaggtgcgagacaggtgcgagacaggtacggcgtcaagcaaagtctatctggtcaaagaaggtgctcatccctgccaagagaaacacgctga<br>gctgcggatcgccaagggagaatctggactgacaggaaagagactgaaagagagggagtgtacgagcgggttcgcagagagagagaagagaggcagagttcgagtgctggctggccaaag<br>tggaagggccaagtccaagaagactggagaagctgaacagagagagagttcgaagaagtctgtcaccatccaagaggagaacacttgtggaaagaacccat<br>cgacttcctgaagctctgaagcagcgaaggagtacaaagaagttcgtcagagtcaagagaaggaggaagaactgtcaatcatcaaagctgcctaagtactactccagccaagcgg<br>acagaatgagaatgctgtgcctctccgcagactcgcagctgcaggttgacgcaggtacgaaaaaataggcagaagaggaagaactgtgtttgtggtgaaacacacactgaaaagatcctacctggccagc<br>actatgagaagctgaaggtccccccaaggtgaaagtagagcaggaacaataagagcaaggcgaggaagagtagatcatcag<br>cagatcgaagtccttccaggatgtctggaagactctccctgaatctgacaagtgctccgccaatcaagcagggagcaggtgatgcggatgagggtacatgagcggatgagggtacctgccttcaagtactacctggcaggataaccgacaagcagggataagaggcccatcatcag<br>cagaaggcggagtaccagccggtgtatgaccgcaaacggatcagagcagcatcaaccgacccggcagaagcaggtagcagtaccggaggaagtaccggcatagaccgaggaagagcaag<br>aagaggtccggagcggaccgcagaccggatatcactccccttacctcgagcaggcccttaccgcaagacacccggtaccagagatccgacaagacccgatgcacaagagaccgcgtc<br>agctcgtggaggcggccggacttactgaaagggccagcaaaaggcggcacagaagctgcatcgatccggcaaaaagtaa |

| SEQ ID NO | |
|---|---|
| 38<br>3xFlag-NLS-<br>SpCas9-<br>NLS(N690C/<br>T769I/G915M/<br>N980K): | atggactataaggaccacgacggcgagactacaaggatcatgataattgattacaaagacgatgacgataaagtggcccaagaagcggaa<br>ggtcggtatccacggatccccagcagcccaagaatccagcagcaagagcatccgtggacactggtggccgtgatcaac<br>gacgagtacaaggtgccaagccgacgaattcaaggtgctgggcaacaccgacaggcatcggcgcattggtggaggaaccctgctg<br>ttcgacagcggcgagacagcggaacaagctgacaagcctgaagaacgtctccgcagatacacaccggatgaaaaggaagattcgtctatctct<br>gcaagatcttcagcaacgagatggccaaggtggacgacagcttcttccacagactgaagaagtctttcctggtggaagaagataagaagc<br>acgagcggcaccccatctttcggcaacatcgtcgacgaggtggcctacaacatgaggataccccaccatctaccacctgagaaagaaactggt<br>ggacagcaccgacaaggccgacctgcggctgatctatctggcctgccacatgatcaagttccgggcacttcctgatcgagggcgacc |

TABLE 1-continued

| SEQ ID NO | SEQUENCE |
|---|---|
| SEQ ID NO<br>LZ3Cas9Addgene<br>#140561<br>*Streptococcus*<br>*pyogenes* | tgaacccgacaacgacgactggacaagctgttcatccagtcggtgcagacctacaaccagctgttcgaggaaaacccatcaacgcagc<br>ggcgtggaccgccaaggccatcctgtcgccagactgagcaagacagagcggctgaaaacctgatcgccagctgccgaggatgccaaactgag<br>aatggcctgtctggaaacctgattgcctgactgactgacccaacttcaagagcaactcgactggccgaggatgccaaactgag<br>ctgagcaaggacacctacgacgacctggacaacctgctggccagcctgctgcgtgctgatcgaagcgacgtttctggccgaacc<br>tgtccgcgcgctacctctgacgactcggagcttggagaccgactggacaccagcgccccctgagcgcctctatgatcaagagatacgac<br>gagcaccaaggactgacctgctgaaagctcctgtgcgcgacggcagcgtctacagtctacaagccatcctgagaagattcttcgacaagcaagaa<br>cggctacgccggctacattgacggcggcgcagcagccaggagagtctacaagttcatcaagccatcctgacaagtggacgaccgag<br>gaactgctcgtgaagctgaacagagaggacctgctgcggaagcagcggacctcgacaacgatcccaccagatctaacctggga<br>gagctgcagaaaatcctccgcggccaggcaagtttttaccccattcctgaagacaacgggaaaaatctgagaagatcctgaccttccgcatc<br>cctactacggtgtggaccaggcgcttccgccaagactcgccagcttcatcgagcggatgaccactcgataagaactcgtgaatacgaagaagactcg<br>aggaagtggtggacagctgcctgtgaccagtacttcaccgtgtataacgagctgaccaaagtgaatacgtgaccggaatgagaagccgcctcct<br>gagccggagcgagccaggccatgcgacctgcgaatctccggtgaaatcctgggtgaagatcggttcaacgctgaccctgagcactctgaaaaattatc<br>gaaatcgagtgctctgactcgtggaatctccggtgaaatcctgggtgaagatcggttcaacgctgaccctgtgaagatctggcacataccacgatctgtgaagatgatc<br>aggacaagactctcgacaataggaaaaacgaggacattctgaagatctctgaaagtatgtgacgacctgaggacagatacaccggtagggcagtg<br>gaggaacgggcgtgaaaactatgccaccttgtcgacgacaagctgtcgacgaagcagtgatgaagcagtctgaagccggcagcacggatacaccggtgagggcaggctg<br>agccggaagctgtatcaacggcgcaggaagcatccgcaagcaatctccggatttcctgaactccggaagtgtcggctctgcgcctgcagaaactt<br>catgcagctgatccacgacgacagccgcccccatgaagaagggcatcctcagagcggtaggtgtgcgccagggcgagtcgcagcagccggc<br>attgccaattggccgcggcagccctgatcgaatggccaagcctaaaggatgagcaagacgacaccagatctaacctggga<br>gatcgaagagggcatcaaagactggatggccagcagatctgaaaaagaccaatccgtgaaaacctgcagaacgatctgcacctactcta<br>gtactactcgcgaatggcggcgatatgtatgtggacgaggaactgacatcaaccggctcgtgaccatatctgcctca<br>gagcttctgaaggacgactccatgcaacaagtgctgaccagagaacgcaaggctgatcaccgcagcgagaagtctgaccatctgaccaaggccgaggaagccgag<br>ggtcgtgaagaagatgaagaactatgggcggcaagtaaggcatgtcatcaagagatgaagcacgacggcagtcatctgaccaaggcagcactgtgaaggaaga<br>gaggcggcctggaaagcctgatgaacaattaagtacgagaaggacaagctgcatgtgatcatccaagagcagctggtggttcatcaagacccagacacgatggccagcatcgacaagttccga<br>cctgatcaaaagtaccctaaatggcaaatgaccctgaaacgtgaaactcttctctacagcaaaccatgaacttttcaagacccaaagctggccaacgcggcgatcc<br>ggaagccccttgtgataagacaatcggcaaaacgggagagaccccttccaccatggcgcggatttgccaccgcggaaggctctga<br>gcatgcccaagtgaatcgaatatcgggaaagaagactggggacctcaagaagtgcagctaccggggctccacagatgaatgcgcctgatgggtggttgctccaagag<br>gctgatcgccagaagagaagaactgggactcgaagagtgtgaaaagactgaaagctgaagaacgagactgtcgaagaagacgaataaaagtgctcgaagaagaacagagatcccat<br>tggaaaagttcaagctccaaagaccgaaaactcggggatgacccaagagtatactcgcaagctgcagcgcaagtgccccgttgagagtcagagcgccg<br>gctctctgaagcaatgcctgaactggtctactctcaggcgacctgactcaagctgccctcagctactactcctgtctgaccaagcagtcatcctgccagc<br>gaagagaatcgggcaggctgcgctctgacgtcgacggccgggggatatgagccagaaacgaactgacagcagctgtgaactactccaaatatgtgacacaagcactacacaagcaccgggatcatcgag<br>actatgagaagctgaaggggctccccgagagttgtctcaaagagctgactgagcagatggcagcgcgcttagctaccagcaccgggataagccat<br>cagatcagccagcggcagtctgacaagactatcatccaccctgttaccctgaccgccaataatcggaccaaaggtcaaagcagcaggtttcgccgcttgacactcttgacactcatgcgcgaccaggctgtgacccacttgagacaccgcatcctaccgacgacgatcgaccctgtctc<br>aagaggtggaggcgtgacacaagagccggcgccaccgaaaaagccggcacgaaaggttctaactgctgggcaagagaaatgagga<br>agctggaggcgacgaagcgtcaagtacgccttataacgcagatcgaagagtgtagaacgccctgattgacacgacacgggatgaaa |
| SEQ ID NO<br>39<br>3xFlag-NLS-<br>SaCas9-P2A-<br>EGFP<br>*Staphylococcus*<br>*aureus* | atggactataaggaccacgacggagactacaaggatcatgatattgattacaaagacgatgacgataaagtggcccgaagaaagcgcaa<br>ggtcgagcgtccatgaaaagcgtcatgaaagcgtcagactacactctcaaggaagtccaagctgacatcgggctgacatcgggatacaagtgtgggtatggatattgactatgaaacaaggga<br>cgtgatcgacgacgaaggcgtcagactgtccaaggagccaagaaatcaaagggaggaacaatgaaggagaaggagaaggcaaggcgcctg<br>aaacgacgagaaggcacacaagatccaggggttgaagaagtccaagaaatctgcttcgattacaacctgctgaccgaccatgagcgtgaattaat<br>ccttatgaacagcacgagggcctgagtcgagtgtcagaagtttccgaccattcgagctgagtgagtgagtgagtgagga<br>gcataacgtcaatgaggtggaaggacaccgacaacggtcagagaagaggccttcacgcaatgcaaagcctggaagaga<br>gtatgtcgcagagcagtctgaaagtgcagaaggcatgcgaggtgagttgcaattaatggttcaagacaagactacgtcaaag<br>aagccaagcagctgctgaaggtcgctcgatcgtgatgcagcagatcacagcgctatatccagcggaatacaatcaaggaatatcaaggaatcaggatacgtcgatcgtgatgcagcaggtgagcaggtgtgagactcaagccggaattgttgtggaatagcatgttatgcaaagagagtctggagactgaccaccaccaccatcggagggagac<br>cctactatgaggctgaagacgtcaagtaccttataacgcagatcgaagagtgtacaacgccctgattgacacgacacgggatgaaa<br>cagaagagctgaaagcgtcaagtaccttataacgcagatcgaagagtgtacaacgccctgattgacacgacacgggatgaaa |

TABLE 1-continued

| SEQ ID NO | SEQUENCE |
|---|---|
| | acgagaaactgaatactatgagaagttccagatcatcgaaaacgtgtttaagcagaagaaaagcctacactgaaacagattgctcaaggaga |
| | tcctgtcaacgagcacgaagaggactcaaggctaccgggctgacaagcactggatgaacacagagttcaccaatctgactatctaccagagttcaccgagacatcca |
| | acatcacgacgcggaagaaatcattgaacagcgcgaacctgctggatcagattgctaagatcctgactatctaccagagttccgaggacatcca |
| | ggaagagctgactaacctgacacgtgagctgactacccaggaagagatcgaacagaattagtaactgaacagagttcctgaaagggtacaaccggaacacaacctg |
| | tccctgaaagctcatcaatctgattctgatgatctgcatgtgatggcataacaacgacatcagattgcaatctttaaccggctgaactggaccaaaaa |
| | gtggacctgagtcagcagaagagatcccaaccactgtgacctgccaaccactgtgcgtgatcattgctgagctgcttcaccggttcatccagagcat |
| | caaagtgatcaatgagtgcagaactgagatgcgaaaacgaaacggcagcgagcagtaccgccaatgaagacgcattatccgaactcgaaagagacgcaagta |
| | cctgattgaaaaatcaagctgacgagtctgcacgtatgcagaagaaagtgctctgtgattctgtgatttctgaggactgtcaagaccctgaacaatcca |
| | ttcaactacgagtcgatcattatccagactgctgctagtcagatctcagatcggggaagagcgtgtccctcgacaattccttaacaacaggctggtgtcaagcaggaagaactcctaaa |
| | aaggccgcatcagcaagaccaaaaaggagtacctgctggaagaggggaacatcaacagattctccgtccagaagatctcgtcattattaaccggat |
| | ctgaacgcaacagatagcgtctcgcgtctgatcatccggatctgattccagatctgcatggtggatctggtagtcagtcctatcaa |
| | cggcgggttcaatcttctgaggcgcaaatgaagttaaaagagcgcaaacaaagggtacaagcaccatgccgaagtcctgtgattatc |
| | gcaaatgccgactcatcttaaggagtggaaaagctggaaaatgatgagaccaagagaccaagagagatcatcaagacattaagaaacccgggccg |
| | aatctatgccgcaaactgagacagaacaaggagttcatcactcctcaccgagatcaagcatctcaacgagactaccaaggaatttcaaggactacaa |
| | gtactctcaccggtggaatagcaacgagacgagtgttcaagctgtcactgaagccagattccgtgatagtacaagaaagaccgataaaggaatacctgctat |
| | tgtgaacaatcgaacggactgtacgacaagatatgacaagctgatcaacagctgaaaaagaaccactgtataagctcgatgtaccaccac |
| | tgatctcagacatatcagaaactcaagctgattggaccccgtaagaactacaaagaactcacctcaaagatcaagaagatcaagctgataaatctgacactac |
| | gtactctcaccggtggatcaacaaagtgctgcaagtgtcactgaagccagattccgtgatagtacaagaaagaccgataaaggatcctatt |
| | agacgattacctcacctaacgactgccaggagaactacgtggcgaaagctgccactcaaagaggtctcacgacaagaccgcaccctg |
| | gactgtcaagatctgatgtcatcaaaaggagagaactactcaagtgccgaactgtgatgataagcccccgaattatcaaaacaatc |
| | caaccaggcagagttcatcgctgaagtgaatatgattgacatcaccaccggaccactctaccggaggaacatgaaaacatgatggtcatcggtgaacaatgactgc |
| | tgaaccgcattgaagtgaataatgtacaaagtactcaagccaggttcttcacatctcggaaaacctgatgagttggagagacaaccctggaccggaa |
| | gcctcaagactcagatatccaagatcaggagcgatatgacacgagttctcaactgacaacgacatcggatgtacagaccttcagattatcagaaa |
| | aggcagtccggcgggagggcagaggaagtcttcaactcaaagtcgagctcgagcgcgacgtgaaactcaagtcagctgagcaaggc |
| | gaggagtgttcacgggtggtgccatcgcacgctggtgcctgaagctcatctgaccaccggcaagtcagcgtccgggtccgaccccgag |
| | gcgatgccacctacggcaagctgcaagctgcagccgctcagcccgccaagcagactcttcaagtccgccatgccgaaggctacgtccaggag |
| | ctacgcgtgcagtctcagtgttcaagaagacgcgcaacagcccgcgaggtgaagttcgagaccgacacccctgtgaccgctgaa |
| | gcaccttctcaagagacgccgaacatcctgggacaactcggcaacatcatcagcaacaagctctatcatgccgacaaag |
| | gggcatcgacttcaaggaggacgaacttcaagttcaaggcgggacgagctgaccgagactgactgatgacaagagcgagcgcgaccgccaagctctatcatgccgacaaag |
| | cagaagaacggcatcaaggtgaacttcaagctgcgggtccatcccgtcgagctcagccgacccggcaagtcagccgctgaccaccagccgcag |
| | gcgatgccacctacggcaagctgcaagctgcagccgctcagcccgccaagcagactcttcaagtccgccatgccgaaggctacgtccaggag |
| | ctacgcgtgcagtgtcagtgttcaagaagacgcgcaacagcccgcgaggtgaagttcgagaccgacaccctgtgaccgctgaa |
| | gcaccttctcaagagacgccgaacatcctgggacaactcggcaacatcatcagcaacaagctctatcatgccgacaaagccccaagagccccaacgacccaacgagagcgat |
| | cacatgtcctgcggtctcgtgaccgccgcggagctgcacctccggcacaagtgtacaagtgt |
| SEQ ID NO 40 FnCas12a-NLS-3xHA(addgene #64709) Francisella novicida | atgagcatctaccaggagttcgtcaacaagtattcactgagtaagacactgcggttcgacctcgaccgagaactgaac |
| | aaggccgaggcctgattctgacgaagaagcgggcaaagacagatcattgataaatacccaccagttcttatc |
| | gagaaattctgcaagctgtgacagtgagctgcagaattctcaagaagaccaagagcgaagacgatgacaacc |
| | tgcagaaggaggactcaagtccgccaagtactagcagagccagaagactcatcaagaaatctgcaacc |
| | agaatctgatcgatcactgattctgaggagacccgatcaagaagcttgatgcgaaacaatgggattgaactgtcaaggctaa |
| | ctccgtactctctgataatctaccatggagaggagcttccatatccacgaaccatttcaaggcttcacagaaccagaag |
| | atctctgaaggacaaagcccgaggcaattaattacgaacagatcaagatcggcaattcaacaattaccgaactgacactataagact |
| | agcgagtgaaccagcagggctctttcctgacgaggtttgaatcgacactatgacaactccagctccattactactcaattcat |
| | aaaactctgaagaaatacaagtgtctgacgtactccaaacagatcctgagtgatcctgtcaaagagatcctgaggaagatgact |
| | cagacggtcactacctgcagagcttatgagcccgtcagagtgctggctaacaagatctgacagctgcgctgactgtctgcctg |
| | ttcgatgacctgaagctcaagtgacctgaagcctagctacctcaaaaacgataagtgacagcctgcacagcctgtcacgcaggtttgatg |
| | atattccgattgggacccgcctcctgagtacattacacagcagatcgctcaagaaccctgataatcctcaagcacagggaact |
| | gatcgtcaagaaccgagaagctcgagctgacctgagctctgaaacattaagctgcactgaggagttcaacaagcagggatattgaca |
| | aacagtccgcttgaggaaatcctgccaacttcgcaacctcgcaactctcgaatcctgaatgatcccccagattttgatgagatcgccaagaacaatcagctgctgcagatc |

TABLE 1-continued

| SEQ ID NO | SEQUENCE |
|---|---|
| | agtattaagtaccagaaccagggcaagaaagacctgctgcaggcttcagcagagaagatgactgaagccatcaagatctctggaccaga |
| | ccaacaatctgtcgcacagtcgcaaagtctccattagtcagtcagaggatatggctaatcctgataagacgaacacttctacctggtgtt |
| | cgaggaatgttactcgagtggcaaacatgtccccctgtataagaacaagaggaactcatcacacagactatcctgtcatcaaggatgacaagta |
| | actgaactcgaaaatagtacccctggccacgctgcaggttggaataagaacaagagctgacaacactgtaccctgttcatcaggatgacaagta |
| | ctatctggagtgatgaataaaaacaattaagatcttcgatgacaagcaattaaggagaagaaatacaggaagaaatcgtgta |
| | taagctgctgccggcaataagagtgctgctaagtgttcttcagcgccaagtgagaaattgagtcaactgaggattgcaggaagttattg |
| | attagaaatcactcaacactcaagaacgggagccccaagaaggattttgagcatcctgaaagtcaggaaagctgtacctgt |
| | acttctacaagcagagcatccaaaacactcccaaacacacatacaagaacacacagggatcgaatgatcagaagtcattcaggaaagctgtacctgt |
| | ccggaggtgaaatcgagcatgtttaaaagctgactttgaagagtcacctgaaacatgggaaagctgtaccgtt |
| | tccagatctataacaaagattttcagcatgaacgagaggccgaactgttgtaccggaagcagcagtaaacctgaaatcactccaccagctaaggaggcc |
| | catgcgatgatgtctataaacgaacggagaacaatcctaagaaaagagagcggttcgaataccaaggacgaagatcagtgaaacgatcatgcacagctaacgatcatgaagacaaacgatgtg |
| | cccttgccaatcaccattcaacttcaagtgccgcttaacaattctgctgacgagatcaatctgctgaaggacaaaatcaatcgatgtg |
| | cacatcctgagcattgacctgagcagcggcatcgttaagaagaggtcgaagaggtatcgagagccggcgccacgcgaagagagggaatatcattcaac |
| | atcattggcaatgaccggatgaaaaccaaactaaccggatcaaccgctaaactgctgaatcagaaggataagaagatcagcgaggacgtggaagaa |
| | aatcaacacaactcaaggagtggaaggctatctgagccaggtgtcatcagactgtcaaagatgcaagtggttcatgctgagcgtgcgatgcattgggtg |
| | ttcgaggatctgaacttcggcttaagaggggcgcttaagtggcaaatgaaagatctgaaaacaaagatgtgaaaaagctga |
| | attaccggtgttaagataacgagtcgaagacaccggcatcgtcgcaagaccggatcaacttccaagagagccaccacagttgg |
| | ggaaacagacaggcatcattctactgtgccaggtaactgtttcagcaggaaggtttgaatgaatcgagttttctcttcgattacaaga |
| | tgagtcagtgagcaagtccaggaattttcagcaagttcgatcagtcgtttataatcgacaagggtacttccgagttctctactgccctaaata |
| | actcggcgacagcgcgaggggaaatgaacaattcagccggctcccagccggattgatatacaaatctcgaaatctcatctcgattaaaaccaattgg |
| | gacactaggaggtgtaccacaaggagccaggagtcggaaaagctggaagctgctgacctcagtggacactccatggacgtgatcggagacagcgc |
| | catcgtggcgagagtgataagccgtgctgatgtagcagagaagctctcacaagactatctatcagtcaatcgaatgatcaaggagcgcgc |
| | actgactatctgattagcgcccgtgctgaagcccggctgctgaaggggactgatgctgcgtggcgagatctcttcgacagacaggaacaataccaggagcacgaagaagaagctgaacctgtcatt |
| | aagaacaggagatactcagttgtccagataaccagataaacgcacccacgagaggcgcagcaggaaggaacaaaagaaaaaag |
| | ggatcctaccatagctgtccagattacgcttatctcagacgtggctgattatgcatcaccatatgatgtcccgactgatgcctaa |
| SEQ ID NO 41 AsCas12a-NLS-3xHA(addgene #69982) Acidaminococcus spec | atgacacagttcgagggttcttaccaacctgtatcagtcagtgagcgaagcacactgcggtttgagctgtcatccacaaggcagacctgaagcacatc caggacaggggcttcatcgaggacgaagccaaggccgcatgacacacaaggcgaagccattcatcgatcggatctacagactatg ccgaccagtccctgctcgatcgaggagacccgtggcggaatgggagaacatgcgccgcatactcatcggccggacagacaacctgaccgatgccatcaat ggagacagccctctgccgatcagcagcggaccagaggcctcaaggcgctgtacaccctactctatccgcggaggacagcaggggcaccgccgagg agcagagaccagcgtcgtgctgagcgaacgatctccacacaacagcagcgggcgtaaacgcacctaccactcttcacgcctgatcacgcgt atcgacagcccggggacaccatcgagaacgtgaaggaagaggcagcgccagagacgtgaaggcgcagcctgcggaggtcgtgcacccgttgttcctccctttttataa gccccagtctgcgggagcactctgagaacgtgaccgatccgaagaaggtgataaccagctgcgatgatccgagaggtcctccggaggcaggatcggagtctgccacatctcacaagactgccgcactctttccttcccgaaggctg aacgaggctgaactggtcatccagaagaagatagaagagatcatctggaggagttaagagcgacgagtatcttcatcctcgaagtacaacgaacactgtag tcctgtccagataggaacgtgctgagcagccgaggccctgttaagagctgaggaattaagactgagagagcagcggtatcagcagcccctctgttaagcaga agaaacagaacgtcaagcagcgctgtcaagcagaaaccagcaagagccgagctgagatgagcgagaatgcctgatgagaaagatccggaagaagctg agcaatctgccgaccaggatcttctggcgaccacctgagagatactgctaaagctgggtaagacacctggaagataccaacacctgaagcacaaggctg accaaggcctcaagcagcagaatcgcagcccctgctcaagactgttcagcctgagcttctgacaatgccaagcaactgcggaagctgacaaggacaa gagcctactcgttgaagcagacgctactatctggcatcatgccaaagcagagggctcgagtcacgagaaggacgctgaattaaggcctcaacgctgagatcgacctggaggttcggatgcgccacagagaga ccagccagagccgaggtcacagctgaggtcgtctgcatggagcccctgactgcccaaagtgcgccaagtgatgcccagccacagcgtgaccgagcctgag gaccgctgccatctcacacgaaggattcagagcctgccaggctgagccccagcctatggaagagaaaacagaccctgagctgaagccccagctcggagacaatgccagcatctccggaacagcgggtatcagcatgcggtatagctccaggctcgggagcctcccaagtatggccaagcgcttgatcggcctgaatgatcggcctgctgg cctgaagaagccaagaagccaaagttgctgacgataaccaagaactctatcgacattcgtagatgggacaccgggaggctcagtgatcttaagcagaaggcctcaagcaacctctgtgctaccagaagaccaaagcccacgaaccgaaggcgtgtgtcgtctagccctgcgaggcaagctgacgaccctgctgacctgtag gacttccaagggatttctgtccagatacgtgttgtcagataacgctctactctctatcgatatcgtcaagcctggctgtaaggacctgggagctggggcgag |

TABLE 1-continued

| SEQ ID NO | SEQUENCE |
|---|---|
| | tactatgccgagctgaatccctgctgtaccacatcagcttccagagaatgccgagaagagatcatggatgcctggaacaggcaagct |
| | gtacctgttccagatctataacaaggacttgccaaggcaccacggcaagctaattgcacactgtattgaccggcctgttttctccag |
| | agaacctggccaaggacaagatcaagctgaatgctgaaggctgaaggatcagaaaaccccaatcccgaccctgtacgagctgagagagatggcacaccggct |
| | gggagaagatgctgaacaagaagtgaaggctgaagatcagaagatcagaaaacccaatcccgaccctgtaccgagagctgagactatgtaatcac |
| | agactgccacgaccgtctgatgaggcaggcctgcctgaacgtatcacaacggaggtctcacgagatcatcaaggataggcg |
| | ctttaccagcgacaagtctttctcacgtgctcatcggcctatcacactgagccgccaattcccatcacaagtcaacagagagtgaatgcctac |
| | ctgaaggagcagcggggagcctgaacaccatccagcagttgattaccgagagctgaacaacggagaagagaaggtggcagcaggc |
| | aggcctgtctgctgtggcacaatcaaggatctgagcaggtgcatctgagccagtgatccgatgatccactacc |
| | aggccggtgatgcataagctgaattcgctgtgcttaaggagactatccagcagaggacaagacgcgccgagaagcgtgtcaaccatacagctgacagacc |
| | gatgtgcaactccctgccaagatgggcaccagctggctcctgtttacggctgccatacatcaagatcgatccctgaccgcttcgt |
| | ggaccccccgtcggtggaaaaccatcagtacgaccctgaagagtgactttgcactacgacgtgaaaacgg |
| | cgacttcatccgtcaagatgaacagaaatctgtcctccagagggcctgcccgggtttatgccccgagtacacagattcaccggacatacc |
| | cgagacacagtttgaccgccaaggagcaccctttcatcgcgtggagagaaggggcatcgtgttcaggagtggctccaacatccctgccaagctgtg |
| | gagaactgacgatctccacgccacatgagtgcccacctgatccgcagcagtgatgcgacatctgccaatccgccacaggcgagg |
| | actacatcaacagcccgtgcgcatctgaaatggcgtgctcgatgggccagtctgatccaccggaagacctgaagaccaggagccaatg |
| | gcgctaccacatccgccctcaagggccagctgccgatcgcgtctgaataccagcggaggcctgaaaaggcggccaagcaaaggataaggat |
| | ggactgctgccctactcagattggtctatccctacgacgtcgtgattacgatccccgactgcctaa |
| | taccctagcagtgttccagattacgcttatccctacgacgtcgtgattatgatccccgactgcctaa |
| SEQ ID NO 42 HLbCas12a-NLS-3xHA (addgene #69988) Lachnospiraceae bacterium | atgagccaagctggaagtgaaagttacaaactgctactccctgtcctaagaacctgagagttcaaggtcaagcatccctgtgggcaagaccgagaaatc |
| | gacaataagcgctgctgtggaggacgaagaggcgcaggatttataagggcctgaagaagctgctgatcgtcgtactatctgtcttat |
| | aacgactggctgcacgcatcaagtctgaacaattacatcagcctgttccggaaagaaacacagaacgaaccggaagctgatgaagatagat |
| | agctggaactggatcaattctgcggaaggagatctcggcagagctcaagagcctcaagagccggaagcaagctcaaggcttcaatggcttcaccgcttctt |
| | atcgagacaatcctgccagagttcctggacgataaggacagagacatccatcggcttcaggttgaacagtcgcgctgtcaacgacttcaccggcttcaccgcttctt |
| | tgataacagagaatatgtttccgagggcaaggctggacatctttgataagcacgaggtgcaggagtcaaggagaagtcgaacagcaagctcatgatgtgaag |
| | gattcttgaggcggctgtcttacttgctgaccagcttctcacaagggcgtgtataacgcatcagaagcggcgcctcgtgaccgagagcgg |
| | cgagaagatcaaggctcggactgagagtacaatcaacctgtataatcagaaaaccaagcagaggctgctgaggagttaagcacctgtataagcaggt |
| | gctgagcgatcgggagctctcgagctctcaagccagggctatacatccgcaggagctgtatgcggctacggcgacgagtgtaagaagcc |
| | cagcagatcttcagctccatccaagctggagaagctgattgacgatagtcaagctttgacggagagcgccgaacaagtaaaccccagaacgccgaaga |
| | gccatccgaccaatctccaagaacttccagagatcgacgacgatatcccaagaaagatcggctcctttctctggagcagcgagtacg |
| | gaaggccgtggtgaccgatctgtctgtgtggagaagcgaatcgagagactcaagagctgatagatcaccaaggtgatagatcagctcctgaacgctg |
| | tgttgacgggcgatttgtgctgagaagctctgtttacagagagagttgctcatcagaagacgcgtggtggccatcaaggatatggatgcttctgtgaagagctt |
| | cagaattacatcctacgacttacactactcaaggaagttcagcaagctacgcctgtgcgatagtcagtgtgtggaaagaaccaaccactctacccctgcagaaga |
| | ctgaaggtggaacacactctacggcatcccaattatgttgacccagacctgagaagcctcaaggatacgctcaggtatctgccatcatgatgaag |
| | ttcatgggcgccaaggtgctggacaaggataagcaacagagcatatggggacaactctgagagatacgattgaagagatcaactacgagcaatcatgttaagagc |
| | aagtacgccaaggtgctgaagatgttctttactgatcaagcagatgctggcctactataaccccgaggacatcaaccgcgaagaaatgcacatcaagaag |
| | gatgctgcaaagttcttctttgagactgctgatggatccaagctgtcacaagtcgctcaagctcgatatgtgcaagaatcgtcccggtatcgaatgcctcacgatt |
| | aagggcatatgttctgagaacagaaagttaagactgatatgactacagagactcaggcttctcagaggagtggagcaggcatgaagaatgatgatgccatgcctccacgatt |
| | tcaacttctctctgagagacagaaagtataaggacatccggcggcttctcagagaggatggagcaggctataaggtgagttcgagtctgcca |
| | ccaatgactacaccatgtacttcaagctgtttgacgagaacaatcaggcctgagctcctaccagagctttccatcacagcgacc |
| | gcgcctccgaagaagggagcgtggtgctgccaacagcaactccatcgccaacctccctgctctcaatcagaatcgcatcgaccaaaaaccacac |
| | cctgtcctacgacgtgtataaggaagtagaggctttctgagactgtgaagcaccagacgatcctccccgacgtgatccggccaatctgtgtata |
| | tgtggtggtgacggcaaggccagcgcagcatccggagcagtattccccgagcccgcgaactgtcggccgcatcaagaatccatcaaggagctcaagaaggagcatcaagatcaagaagactgtgtata |
| | accactctctgtgaccagaaaggagaaggttccgagcccgcgaactgtcgaacccatcagcgcgatcaatcggcaaggagctcaaggagctcaagaaggaatcaagaggctcaagaggttcgagtctgcca |

TABLE 1-continued

| SEQ ID NO | SEQUENCE |
|---|---|
| | gctatatctctcaggtggtgcacaagatctgcgagctggtggagaagtacgatgccgtgatcgcctgaactctggcttaagaa |
| | tagccgtgaagtgggagaagcaggtgtatcagaggttcgagaagatgctgatcgataagctgaactacatgtggacaagtctaatcc |
| | ttgtgcaacaggcggcgcctgaaggctatcaccaataagttcaggagtttcatgtctaccagaacgcttcatctttacat |
| | ccctgcctggtgacatccaagatgcgatcctatcctaccggctttgtgaacctgctgaaaccaagtataccagatcgccattccaagaagttca |
| | tcagaagtggaagctgtactcctacgcaaccgatcagaatcttccgaatctcaagaagaacaacgttcgactggagaggtgtgcc |
| | tgaccagcgcctataaggagctgttcaacaggactgcatcagcatcaataccagggcgatatcaccaggcggaacagcatcaacagc |
| | gcctctacttctagcttatgccctgatgagccctgatgtgcagatcgcggaaacatgtgcgaaacagctgccatcctgcaaagaacgcgaccatgc |
| | tgtgaagaactcgacggatctcttctacgatgcggcgcatcgacggagtgagaggacacatcctgcaaagaacgcgacgccaatgg |
| | gcctataacatcgccagaaaagtgctctgggcatccggccagttcaagaaggccgaggagaagcccacgacaaaaggtgataagtgaagatcgccatct |
| | ctaacaaggagtggtggatacgcccagacaagttgaagcacaaagatcctcaagaaagcgccggcgcgctgctgattatgccagcaggaaa |
| | aagggatcctactccagctgtttccagttaccgtcccaggacgcggctgattatgcataccatatgatgtccccgactatgctaa |
| SEQ ID NO 43 3xGS | ggcggcggaggggggtggcagcggcggggtcg |
| SEQ ID NO 44 (SGGS)2-XTEN-(SGGS)2 | tctggaggatctagcggaggatcctctggcagcggagacaccagagagcagtcagcaacacagagagcagtggcggcagcagcgg cggctcg |
| SEQ ID NO 45 A(EAAAK)4 A | gctgaggcggcggcggcaaaagaagcagcggcaaaagaagctgccgcaaaggaagcagcagcaaaagccttgaagccgaagtgctgcta aggaggctgccgcaaaagaggctgccgcaaaagaagcagccgctaaagcg |
| SEQ ID NO 46 3xFlag-NLS | ggatccgactataaggaccacgacggagactacaaggatcatgatattgattacaaagacgatgatgtgccccaaagaagaagcg gaaggtcggtatccacggagtcccagagcg |
| SEQ ID NO 47 3xFlag | ggatccgactataaggaccacgacggagactacaaggatcatgatattgattacaaagacgatgatgtggattacaaagacgatgataaggtgatcagcaccagtgatgaggtatccccacggagtcccagc agcg |
| SEQ ID NO 48 (H4)3: | GGTTCTCGAAGTGAGGCAGCTCGCGAAGGAGCTGCGCGAAAAAGAACTCAGCAAA GGAAGCAGCCAAAGCACTGAGGCGCCTGCTGCTAAAGACGACTGCCGCCAAAG AAGCTGGGCCAAAGGAAGCTGCGCGCTCAAAGAAGAAGCAGCAGCCAGCCGCCAAAGAG GCAGCGGCCAAGGAGCTGCTCAAAGAAGAAGCAGCAGCTAAAGGAGGAGCGGATCG |
| SEQ ID NO 49 GPcPc | GCCGAAGCGGTGGTTCAGGGGATCCGAGGAAGTCCTGTTCCCCCTCTACCCACCA ACTAATAGCAGTCAACTCATCAACTCCGCTCACTCCGCTCCGTGCCGAGTGCCCCGC CAACCAATAGCTCATCAACTCCGCTCCGCTCCCTAGTCCAGTCCAGTACCTAGCACCCC TCCAACAAATCTAGCAGTACACCACCCACCCACCAAGCCCTAGCGCGTCG |
| SEQ ID NO 50 GPGcP | GCTGGTTCTGGTGGCTCAGGGGGTTCCGGTGTTCCGGTGTTCCCAGTACCAAGTACTCCTCCCA CTCCCTCTCCAAGTACGCCGCTACACCTCCACCCACCCAGCGGCGGCTCTGGCAATTCCAG TGGTTCAGGCGTAGTCCCGTGCCAAGTACGGCCACCAACTCCAAGTCCATCAACACC ACCGACCCCTTCTCCGTCTGCATCG |

TABLE 1-continued

| SEQ ID NO | SEQUENCE |
|---|---|
| SEQ ID NO 51 GPbGbP | GCGGGTTCTGGAGGTTCAGGCGGAGCGGAGCGTGGCAGTCCAGTCCAGTGCCGAGCACACCGCCA ACACCGAGCCCAAGTACGCCACCCGACTCCAAGTCCAGCATACAGCCGAGCAACCGAAG ATTCAGTCTACTCACGACATCCAGCGGAAAACGGCAAATCTAATTTCTGAATTGCT ATGTTTCCGGTTTTCACCCCTCAGACATCCAGACCTGAGACAGCTGAACTGAAAG GATTGAAAGGTTGAACACTCCGACTTGAGCTTGATAAGGACTGGTCATTCTATTTG CTGTATTACCCGAGTTCACTCCGACCCAAAGATGAATACCATGTCAGTGAAT CATGTCACGCTGAGCCAACCCAAGATCTGAAATGGACCACTCCAAAAATTCAAGTCTACTC GGGTAGCCGGAGAAGCGGCGGTCTATCCAACGACTCCAAAAATTCAAGTCTACTC AAGACACCCTGCCAGAATGAAAATCAAACTTTTGAAATTGCTACGTCTCTGGATC CATCCGTCAGACATCGAAGTTGATCTGTTGAAAACGGTGAGCGAATTGAGAAGTG GAGCATTCAGATCTTAGCTTCAGTAAGACTGGTCTTTTATCTCTGTATTACACGG AGTTCACTCCGACAAAGATGAATACGCCTGTCAGTTAACCACGTCACGCTGT CACAGCCAAAGATAGTGAAATGGGATCGACCAGTGCCCTCAACACCCCTACTC CTAGTCCGAGCACTCCTCCAACGCCTTCACCATCTGCCTCG |
| SEQ ID NO 52 GPZP | GCTGGTTCCGGCGGATCTGGTGGATCGGTGGCAGCCCCGTCCTCCCTTCTACTCCACCCA CACCGTCCCCGTCAACTCCGTCCGTCCGTCCAGTGAAGGTACTCTCTCAC GTACATTCTACACTGGGTTGTCAAAGCATGTGGAAGACGTGCCAGCCTTCCAGGCGCTT GGAAGCCTCAATGACCTTCAGTTTTTCGCTACAATAGCACAAGGATCGAAAGTCACAA CCTATGGGTCTCTGGAGACAGTCGAAGGGATGGAGGACTGGAAACAGGATAGCCA ATTGCAAAAAGCGAGAGGAGATATCTTTATGGAGACGCTTAAAGACATTGTTGAGTA TTACAACGACTCTAACGTAGTCACGTATTCCAGGGCGTATTGGGTGTGAGATAGA GAATAACCGGAGTTCCGGCGCTTTTGGAAATATTATTACGATGCCAAGACTACATC GAGTTAACAAGAAAATTCAGCCTGGTGCCTTTGACCCAGCTGCACAAATTACA AAACAGAAGTGGGAGGCGAGCCAGTGTACCTTCAAAGGGCAAAAGCATACTGGA GGAGAGTGTCCCGCAACTCTCAGTAGTCGACTTCTGAAAGTCTAACCTCCCCAGGCGTGAGAAGAA TCGAACAGGATCCCCCTTGCTTACAGCTTCCAAGGCCCAAGATTGATGTTCACTGGACA AGGGCTGGAGGTCCAAGAGCCCAGTGTACCTTCAAAGGGATGTGTTGCATAACGGTAAT GGGACGTATCAGTCATGGTCGTGGTGGCAGCTCACTGGAGCTCCCTCCAAGATACGGCCACCATAC TCTTGCCATGTGCAACACAACTCCCCCAACTCCATCCGGCCAGCCACTCCAGTACCCCCCTACTCCGTCAGC GCCCCGTGCCATCAACAACTCCCCCAACTCCATCCGGCCAGCCACTCCAGTACCCCCCTACTCCGTCAGC CTCG |
| SEQ ID NO 53 GGZGZP | GCTGGTTCCGGGGGTCAGGAGGAGTGGAGGGTCTCGGAGGCTCAGGA GGTAGCCGGTGGTAGTGACGGCCAGGTACGTCTCACCTATATCTATACAGGATTGTCTA AGCATGTTGAAGACGTGCCCGCCTTTGCAGGCACTGGGTTCTTTGAACGACCTCCAGTT TTTCCGCTACACAGTAAGACCCGAAAAATCTCAGCCCATGGGCTCTGGAGCAAGT TGAAGGTATGGAGGAGGACTGGAAACAGGACAGTCAATTCAAAAGGCCAGAGAAGATA TTTTTATGGAAACCTTGAAGGATATTGTCGAGATAGAAAATAATCGGTGTGCCTTT CGTGCTGCAGGGCGATTCGGTTGCGAGAATAGAAATATAATCGATTCTAGTGTGCCTTT TGGAAGTATTACTACGACGGAAAAGATTATATCGAATTTAATAAGAGATTCCTGCG TGGGTGCCGTTTGACCCGGCCGCCACACAATTACTAAACAAAAGTGGGAACCG GTGTATGTTCAGAGGGCTAAGGCGTACCTTGAAGAGAGTGCCCCGCTACGTGGTTG TTACTTCACACCAAGCACCAGTGAAAAAAAAATTGAAGCTGTCCTTGCATATGACT TCTATCCTGGGAAGATCACGTACACTGGAACACGGAGCCGGAGGTACAAGAACCTG AACTGCGAGGGGACGTCCTCCATAACGGAACGTACCTCTACTCTCCCGGGCTCAGCGTCAGCATTCCTCTCCTC TGCCGGTTCCACCTCAGGACACTGCCGCCTTACTCCTGTCACGTGCAGCATTCCTCTCCTC GCTCAACCCCTTGTCGCCCGGCAGGACACTGCCGCCTTACTCCTGTCACGTGCAGCATTCCTCTCCTC GCTCAACCCCTTGTCGCCCGGCAGCTCTGGGGGTTCGGCGAAGCGGAGGA TCTGGTGGGTCCGATGTAGGTACTCACTTACTACTTACATATACACGGGTCTTAGTAAAC |

TABLE 1-continued

| SEQ ID NO | SEQUENCE |
|---|---|
| | ACGTCGAGGATGTCCCGCGTTCCAAGCTCTGGGTAGTTTGAATGATCTCCAATTTTT |
| | TAGATACAATAGCAAAGATCGAAAAGATCCAACCAATGGGACTCTGAGACAGGTGG |
| | AGGGAATGGAAGATTGAAACAAGATTCTCAACTCCAGAAGGCTAGGAAGACATTT |
| | TCATGGAAACGCTCAAAGATATTGTAGAGTATTATAATGATTCTAACGGCAGCCACG |
| | TCCTTCAGGGGCATTGGGTGTGAGATTGAAAACAATCGATCTAGCGGTGCATTTTG |
| | GAAATATTACTATGATGGCAAAGACTATATCGAATTCAACAAGGAAATTCCAGCATG |
| | GGTCCCATTCGACCCCGCGGCTCAATTACCAATGCAAAATGGAAGCCGAACCTGT |
| | CTACGTACAACGGGCGAAGGCATATCTTGAGGAGGAATGCCCCGCGACCCTTCCGAAA |
| | GTACCTTAAGTACTCCAAGAACATTCTCGATCGGCCAGGACCCCCCTTCTGTGGTAGTC |
| | ACCAGCCATGCAGGCACCTGGGGAGAAGAAGAAACTCAAGTGCCTGGCCTACGATTTC |
| | TACCCTGGGAAATCGATGTCCTTCATAACGGCAATGCACCTATCAGTCAGTGGTCGTG |
| | ATTGAGAGGTGATGTCTTCAAGACACCGACCTATAGCTTGTCATGTCCAACACTCTCCCTCG |
| | GCTGTTCCCCCTCAAGACACCGACCTATAGCTTGTCATGTCCAACACTCTCCCTCG |
| | CTCAACCACTCCGTGTCCCATGGGAGGCTAGCCCAGTGCCCAGCACACCCCTACTCC |
| | CTCTCCTTCTACTCCACCGACCCCTTCACCGTCCGCTTCG |
| SEQ ID NO 54 GGGCTGAG AGAGGGAC AAGT | GGGCTGAGAGAGGGACAAGTgtttagagctagaaatagcaagtaaaataaggctagtccgttatcaacttgaaaaagtgg caccgagtcggtgc |
| SEQ ID NO 55 AGTGTGCA TTGCCACC TCAG | AGTGTGCATTGCCACCTCAGgtttagagctagaaatagcaagttaaaataaggctagtccgttatcaacttgaaaaagtggc accgagtcggtgc |
| SEQ ID NO 56 GCAGGACT CCTTTCCT CCAT | GCAGGACTCCTTTCCTCCATgtttagagctagaaatagcaagttaaaataaggctagtccgttatcaacttgaaaaagtggca ccgagtcggtgc |
| SEQ ID NO 57 ATAGGAGA AGATGATG TATA | ATAGGAGAAGATGATGTATAgtttagagctagaaatagcaagttaaaataaggctagtccgttatcaacttgaaaaagtgg caccgagtcggtgc |
| SEQ ID NO 58 AAAACGTT TCCAAGAC ATGA | AAAACGTTCCAAGACATGAgtttagagctagaaatagcaagttaaaataaggctagtccgttatcaacttgaaaaagtggc accgagtcggtgc |
| SEQ ID NO 59 CCGCCGTC CAAGACCT ACCG | CCGCCGTCCAAGACCTACCGgtttagagctagaaatagcaagttaaaataaggctagtccgttatcaacttgaaaaagtggc accgagtcggtgc |

TABLE 1-continued

| SEQ ID NO | SEQUENCE |
|---|---|
| SEQ ID NO 60 CCAAGAAG CGCACCAC CTCC | CCAAGAAGCGCACCACCTCCgttttagagctagaaatagcaagttaaaataaggctagtccgttatcaacttgaaaaagtggc accgagtcggtgc |
| SEQ ID NO 61 AGCCTGGA AGCACGA ATGGT | AGCCTGAAGCACGAATGGTgttttagagctagaaatagcaagttaaaataaggctagtccgttatcaacttgaaaaagtg gcaccgagtcggtgc |
| SEQ ID NO 62 ACATACCA AGAGAATC ACCC | ACATACCAAGAGAATCACCCgttttagagctagaaatagcaagttaaaataaggctagtccgttatcaacttgaaaaagtg gcaccgagtcggtgc |
| SEQ ID NO 63 GAAGGAG GAGGCCTA AGGA | GAAGGAGGAGGCCTAAGGAgttttagagctagaaatagcaagttaaaataaggctagtccgttatcaacttgaaaaagtg gcaccgagtcggtgc |
| SEQ ID NO 64 AAGAAGA CTAGCTGA GCTCT: | AAGAAGACTAGCTGAGCTCTgttttagagctagaaatagcaagttaaaataaggctagtccgttatcaacttgaaaaagtg gcaccgagtcggtgc |
| SEQ ID NO 65 POLL: | MDPRGILKAFPKRQKIHADASSKVLAKIPRREEGEEAEEWLSSLRAHVVRTGIGRARAE LFEKQIVQHGGQLCPAQGPGVTHIVVDEGMDYERALRLLRLPQLPPGAQLVKSAWLSL CLQERRLVDVAGFSIFIPSRYLDHPQPSKAEQDASIPPGTHEALLQTALSPPPPTRPVSPP QKAKEAPNTQAQPISDDEASDGEETQVSAADLEALLISGHYPTSLEGDCEPSPAPAVLDK WVCAQPSSQKATNHNLHITEKLEVLAKAYSVQGDKWRALGVAKAINALKSPHKPVTS YQEACSIPGIGKRMAEKIIEILESGHLRKLDHISESVPVLELFSNIWGAGIKTAQMWYQQ GFRSLEDIRSQASLTTQQAIGLKHYSDFLERMPREFATEIEQTVQKAAQAFNSGLLCVAC GSYRRGKATCGDVDVLITHPDCRSHRCIFSRLLDSLRQEGFLTDDLVSQEENGQQQKYL GVCRLPGPGRRHRRLDIIVVPYSEFACALLYFTGSAHFNRSMRALAKTKGMSLSEHALS TAVVRNTHGCKVGPGRVLPTPTEKDVFRLLGLPYREPAERDW |
| SEQ ID NO 66 POLM: | MALPKRRRARVGSPSGDAASSTPPSTRFPGVAIYLVEPRMGRSRRAFLITGLARSKGFRV LDACSSEATHVMEETSAERAVSWQERRMAAAPPGCTPPALLDISWLTESLGAGQPVP VECRHRLEVAGPRKGPLSPAWMPAYACQRPTPLTHHNTGLSSEALEITLAEAAGFEGSEGR LLTFCRAASVLKALPSPVTTLSQLQGLPHFGEHSSRVVQELLEHGVCEEVERVRSERY QTMKLFTQIFGVGVKTADRWYREGLRTLDDLREQPOQKLTQQQKAGLQHHQDLSTPVL RSDVDALQQVVEEAVGQALPGATVTLTGGPFRRGKLQGHDVDFLITHPKEGQEAGLLPR VMCRLQDQGLLIYHQHQSCCESPTRLAQQSHMDAFERSFCIFRLLPQPPGAAVGGSTRP CPSWKAVRVDLLVVAPVSQFPFALLGWTGSKLFQRELRRFSRKEKGLWLNSHGLFDPEQ KTFFQAASEEDIFRHLGLEYLPPEQRNA |

TABLE 1-continued

| SEQ ID NO | SEQUENCE |
|---|---|
| SEQ ID NO 67 POLM(H329G): | MALPKRRRARVGSPSGDAASSTPPSTRFPGVAIYLVEPRMGRSRRAFLTGLARSKGFRV LDACSSEATHVVMEETSAEEAVSWQERRMAAAPPGCTPPALLDISWLTESLGAGQPVP VECRHRLEVAGPRKGPLSPAWMPAYACQRPTPLTHHNTGLSEALEILAEAAGFEGSEGR LLTFCRAASVLKALPSSPVTTLSQLQGLPHFGEHSSRVVQELLEHGVCEEVERVRRSERY QTMKLFTQIFGVGVKTADRWYREGLRTLDDLREQPQKLTQQQKAGLQHHQDLSTPVL RSDVDALQQVVEEAVGQALPGATVTLTGGFRRGKLQGGDVDFLITHPKEGQEAGLLPR VMCRLQDQGLIIYHQHQSCCESPTRLAQQSHMDAFERSKCIFRLPQPPGAAVGGSTRP CPSWKAVRVDLVVAPVSQFPFALLGWTGSKLFQRELRRFSRKEKGLMLNSHGLFDPEQ KTFFQAASEEDIFRHLGLEYLPPEQRNA |
| SEQ ID NO 68 POLM(H329G, R389K): | MALPKRRRARVGSPSGDAASSTPPSTRFPGVAIYLVEPRMGRSRRAFLTGLARSKGFRV LDACSSEATHVVMEETSAEEAVSWQERRMAAAPPGCTPPALLDISWLTESLGAGQPVP VECRHRLEVAGPRKGPLSPAWMPAYACQRPTPLTHHNTGLSEALEILAEAAGFEGSEGR LLTFCRAASVLKALPSSPVTTLSQLQGLPHFGEHSRVVQELLEHGVCEEVERVRRSERY QTMKLFTQIFGVGVKTADRWYREGLRTLDDLREQPQKLTQQQKAGLQHHQDLSTPVL RSDVDALQQVVEEAVGQALPGATVTLTGGFRRGKLQGGDVDFLITHPKEGQEAGLLPR VMCRLQDQGLIIYHQHQSCCESPTRLAQQSHMDAFERSFCIFRLPQPPGAAVGGSTRP CPSWKAVRVDLVVAPVSQFPFALLGWTGSKLFQRELRRFSRKEKGLMLNSHGLFDPEQ KTFFQAASEEDIFRHLGLEYLPPEQRNA |
| SEQ ID NO 69 BRCT(POLM) POLL1: | MALPKRRRARVGSPSGDAASSTPPSTRFPGVAIYLVEPRMGRSRRAFLTGLARSKGFRV LDACSSEATHVVMEETSAEEAVSWQERRMAAAPPGCTPPALLDISWLTESLGAGQPIPS RYLDHPQPSKAEQDASIPPGTHEALLQTALSPPPPTRPVSPPQKAKEAPNTQAQPISDDE ASDGEETQVSAADLEALISGHYPTSLEGDCEPSPAPAVLDKWVCAQPSSQKATNHLHI TEKLEVLAKAYSVQGDKWRALGYAKAINALKSFHKPVTSYQEACSIPGIGKRMAEKIIEI LESGHLRKLDHISESVPVLELFSNIWGAGTKTAQMVYQQGFRRSLEDIRSQASLTTQOAIG LKHYSDFLERMPREEATEIEQTVQKAAQAFNSGLLCVACGSYRRGKATCGDVDVLITHP DGRSHRGIFSRLLDSLRQEGFLTDDLVSQEENGQOOKYLGVCRLPGPGRRHRRLDIIVVP YSEFACALLYFTGSAHFNRSMRALAKTKGMSLSEHALSTAVVRNTHGCKVGPGRVLPT PTEKDVFRLLGLPYREPAERDW |
| SEQ ID NO 70 BRCT(POLM) POLL2: | MALPKRRRARVGSPSGDAASSTPPSTRFPGVAIYLVEPRMGRSRRAFLTGLARSKGFRV LDACSSEATHVVMEETSAEEAVSWQERRMAAAPPGCTPPALLDISWLTESLGAGQPVP VECRHRLEVAGPRKGPLSSSQKATNHNLHITEKLEVLAKAYSVQGDKWRALGYAKAIN ALKSFHKPVTSYQEACSIPGIGKRMAEKIIRILESGHLRKLDHISESVPVLELFSNIWGAGT KTAQMVYQOGFRSLEDIRSQASLTTQQAIGLKHYSDFLERMPREEATEIEQTVQKAAQA FNSGLLCVACGSYRRGKATCGDVDVLITHPDGRSHRGIFSRLLDSLRQEGFLTDDLVSQ EENGQOOKYLGVCRLPCPGRRHRRLDIIVVPYSEFACALLYFTGSAHFNRSMRALAKTK GMSLSEHALSTAVVRNTHGCKVGPGRVLPTPTEKDVFRLLGLPYREPAERDW |
| SEQ ID NO 71 3xFlag-NLS-EXOG: | MDYKDHDGDYKDHDIDYKDDDDKMAPKKKRKVGIHGVPAAAIKSIASRLRGSRRFLS GFVAGAVVGAAGAGLAALQFRSQGABGALTGKQPDGSABKAVLEQFGFPLTGTEARC YTNHALSYDQAKRVPRWVLEHISKSKSIMGDADRKHCKFKPDNIPTFSAFNEDVVGSG WSRGHMAPAGNNKFSSKKAMAETFYLSNIVPQDFDNNSGYWNRIEMYCRELTERFEDV WVVSGPLTLPQTRGDGKKIVSYQVIGEDNVAVPSHLYKVILARRSSVSTEPLALGAFVV PNEAIGFQPQLTEFQVSLQDLEKLSGLVFPFPHLDRTSDIRNICSVDTCKLLDFQEFTLYLS TRKIEGARSVLRLEKIMENLKNAEIEPDDYFMSRYEKKLEELKAKEQSGTQIRKPS |
| SEQ ID NO 72 | MDYKDHDGDYKDHDIDYKDDDDKMAPKKKRKVGIHGVPAAPRLLPISAATLALAQLT YGWGNLGHETVAYIAQFVASSTESFCQNILGDDSTYLANVATWADTYKYTDAGEFS |

TABLE 1-continued

| SEQ ID NO | SEQUENCE |
|---|---|
| SEQ ID NO 3xFlag-NLS-nucS: | KPYHFIDAQDNPPQSCCVDYDRDCGSAGCSISAIQNVTNILLESPNGSEALNALKFVVHII GDIHQPLHDENLEAGGNGIDVTYDGETTNLHHIWDTNMPEEAAGGYSLSVAKTYADLL TERIKTGTYSSKKDSWTDGIDIKDPVSTSMIWAADANTYVCSTVLDDGLAYINSTDLSGE YYDKSQPVFEELIAKAGYRLAAWLDLIASQPS |
| SEQ ID NO 73 3xFlag-NLS-NucP1: | MDYKDHDGDYKDHDIDYKDDDDKMAPKKKRKVGIHGVPAAWGALGHATVAVVAQH YVSPEAASWAQGILGSSSSYLASIASWADEYRLTSAGKWSASLHFIDAEDNPPTNCNV DYERDCGSSGCSISAIANYTQRVSDSSLSSENHAEALRFLVHFIGDMTQPLHDEAYAVG GNKINVTFDGYHDNLHSDWDTYMPQKLIGGHALSDAESWAKTLVQNIESGNYTAQAIG WIKGDNISEPITTATRWASDANALVCTVMPHGAAALQTGDLYPTYYDSVIDTIELQIA KGGYRLANWINEI |
| SEQ ID NO 74 3xFlag-NLS-MGME1: | MDYKDHDGDYKDHDIDYKDDDDKMAPKKKRKVGIHGVPAAKMLFQTICRQLRSSK FSVESAALVAFSTSSYSCGRKKKVNPYEEVDQEKYSNLVQSVLSSRGVAQTPGSVEEDA LLCGPVSKHKLPNQGEDRRVPQNWFPIFNPERSDKPNASDPSVPLKIPLQRNVIPSVTRV LQQTMTKQQVFLLERWKQRMILELGEDGFKEYTSSPHVCDHVYMKNLARDVFLQGKR FHEALESILSPQETLKERDENLLKSGYIESVQHILKDVSGVRALESAVQHETLNYIGLLDC VAEYQGKLJCVIDWKTSEKPKPPIQSTFDNPLQVVAYMGAMNHDTNYSFQVQCGLIVVA YKDGSPAHPHFMDAELCSQYWIKWLLRLEEYTEKKNQNIQKPEYSE |
| SEQ ID NO 75 3xFlag-NLS-recj: | MDYKDHDGDYKDHDIDYKDDDDKMAPKKKRKVGIHGVPAAVKQQIQLRRREVDETA DLPAELPPLLRRLYASRGVRSAQELERSVKGMLPWQQLSGVEKAVEILYNAFREGTRIIV VGDFDADGATSALVLAMRSLGCSNIDYLVPNRFEDGYGLSPEVVDQAHARGAQLIV TVDNGISSHAGVEHARSLGIPVIVTDHHLPGDTLPAAEAIINPNLRDCNFPSKSLAGVGV AFYLMALRTFLRDQGWFDERNIAIPNLAELLDLVALGTVADVPLDANNRILTWQGM SRIRAGKCRPGIKALLEVANRDAQKLAASDLGFALGPRLNAAGRLDDMSVGVALLLCD NIGEARVLANELDALNQTRKEIEQGMQIEALTLCEKLERSRDTLPGGLAMYHPEWHQG VVGILASRIKERFHRPVIAFAPAGDGTLKGSGRSIQGLHMRDALERLDTLYPGMMLKFG GHAMAAGLSLEEDKFKLFQQRFGELVTEWLDPSLLQGEVVSDGPLSPAEMTMEVAQLL RDAGPWGQMFPEPLFDGHFRLLQQRLVGERHLKVMVEPVGGGPLLDGIAFNVDTALM PDNGVREVQLAYKLDINEFRGNRSLQIIIDNIWPI |
| SEQ ID NO 76 3xFlag-NLS-T4 DNA polymerase: | MDYKDHDGDYKDHDIDYKDDDDKMAPKKKRKVGIHGKNCAPQKFPSMKDARDWMKRMED YIDENGKERTREVEYLPTMFRHCKEESKYKDIYGKNCAPQKFPSMKDARDWMKRMED IGLEALGMNDFKLAYISDTYGSEIVTDRKFVRVANCDIEVTGDKFPDPMKAEYEIDAITH YDSIDDRFYVFDLLNSMYGSVSKWDAKLAAKLDCEGGDEVPQEILDRVIYMPFDNERD MLMEYINLWEQKRPAIFTGWNIEGFDVPYIMNRVKMILGERSMKRSPIGRVKSKLIQN MYGSKEIYSIDGVSILDYLDLYKKFAFTNLPSFSLESVAQHETKKGKLPYDGPINKLRET NHQRYISYNIIDVESVQAIDKIRGFIDLVLSMSYYAKMPFSGVMSPIKTWDAIIFNSLKGE HKVIPQQGSHVKQSFPGAFVFEPKPIARRYIMSFDLTSLYPSIIRQVNISPETIRGQFKVHPI HEYIAGTAPKPSDEYSCSPNGWMYDKHQEGIIPKEIAKVFFQRKDWKKKMPAEEMNAE AIKKIIMKGAGSCSTKPEVERYVKFSDDFLNELSNYTESVLNSLIEECEKAATLANTNQL NRKILINSLYGALGNIHFRYDLRNATAITIFGQVGIQWIARKINEYLNKVCGTNDEDFIA AGDTDSVYYCVDKVIEKVGLDRFKEQNDLVEFMNQFGKKKMEPMIDVAYRELCDYM NNREHLMHDREAISCPPLGSKGVGGFWKAKKRYALNVYDMEDKRFAEPHLKIMGM ETQQSSTPKAVQEALEESIRRILQEGEESVQEYYKNFEKEYRQLDYKVIAEVKTANDIAK YDDKGWPGFKCPFHIRGVLTYRRAVSLGVAPILDGNKVMVLPLREGNPFGDKCIAMP SGTELPKEIRSDVLSWIDHSTLFQKSFVKPLAGMCESAGMDYEEKASLDFLFG |
| SEQ ID NO 77 | MDYKDHDGDYKDHDIDYKDDDDKMAPKKKRKVGIHGVPAAKEFYISIETVGNNIVER YIDENGKERTREVEYLPTMFRHCKEESKYKDIYGKNCAPQKFPSMKDARDWMKRMED |

TABLE 1-continued

| SEQ ID NO | SEQUENCE |
|---|---|
| SEQ ID NO 77 3xFlag-NLS-T4 DNA polymerase (Y320A): | IGLEALGMNDFKLAYISDTYGSEIVDRKFVRVANCDIEVTGDKFPDPMKAEYEIDAITH YDSIDDRFYVFDLLNSMYGSVSKWDAKLAAKLDCEGGDEVPQEILDRVIYMPFDNERD MLMEYINLWEQKRPAIFTGWNIEGFDVPYIMNRVKMILGERSMKRFSPIGRVKSKLIQN MYGSKEIYSIDGVSILDLYKKFAFTNLPSFSLESVAQHETKKGKLPDGPINKLRET NHQRYISANIIDVESVQAIDKIRGFIDLVLSMSYYAKMPFSGVMSPIKTWDAIIFNSLKGE HKVIPQQGSHVKQSPPGAFVFEPKPIARRYIMSFDLTSLYPSIIRQVNISPETIRGQFKVHPI HEYIAGTAPKPSDEYSCSPNGWMYDKHQEGIIPKEIAKVFFQRKDWKKKMFAEEMNAE AIKKIIMKGAGSCSTKPEVERYVKFSDDFLNELSNYTESVLNSLIEECEKAATLANTNQL NRKILINSLYGALGNIHFRYDLRNATAITIPGQVGIQWIARKINEYLNKVCGTNDEDFIA AGDTDSVYVCVDKVIEKVGLLDRFKEQNDLVEFMNQFGKKKMEPMIDVAYRELCDYM NNREHLMHDREAISCPPLGSKGVGGFWKAKKRYALNVYDMEKRFAEPHLKIMGM ETQQSSTPKAVQEALEESIRRILQEGEESVQEYYKNFEKEYRQLDYKVIAEVKTANDIAK YDDKGWNPGFKCPFHIRGVLTYRRAVSGLGVAPILDGNKVMVLPLREGNPFGDKCIAWP SGTELPKEIRSDVLSWIDHSTLFQKSFVKPLAGMCESAGMDYEEKASLDFLFG |
| SEQ ID NO 78 3xFlag-NLS-T4 DNA polymerase (A737V): | MDYKDHDGDYKDHDIDYKDDDDKMAPKKKRKVGIHGVPAAKEFYISIETVGNNIVER YIDENGKERTREVEYLPTMFRHCKEESKYDIYGKNCAPQKFPSMKDARDWMKRMED IGLEALGMNDFKLAYISDTYGSEIVDRKFVRVANCDIEVTGDKFPDPMKAEYEIDAITH YDSIDDRFYVFDLLNSMYGSVSKWDAKLAAKLDCEGGDEVPQEILDRVIYMPFDNERD MLMEYINLWEQKRPAIFTGWNIEGFDVPYIMNRVKMILGERSMKRFSPIGRVKSKLIQN MYGSKEIYSIDGVSILDLYKKFAFTNLPSFSLESVAQHETKKGKLPDGPINKLRET NHQRYISYNIIDVESVQAIDKIRGFIDLVLSMSYYAKMPFSGVMSPIKTWDAIIFNSLKGE HKVIPQQGSHVKQSPPGAFVFEPKPIARRYIMSFDLTSLYPSIIRQVNISPETIRGQFKVHPI HEYIAGTAPKPSDEYSCSPNGWMYDKHQEGIIPKEIAKVFFQRKDWKKKMFAEEMNAE AIKKIIMKGAGSCSTKPEVERYVKFSDDFLNELSNYTESVLNSLIEECEKAATLANTNQL NRKILINSLYGALGNIHFRYDLRNATAITIPGQVGIQWIARKINEYLNKVCGTNDEDFIA AGDTDSVYVCVDKVIEKVGLLDRFKEQNDLVEFMNQFGKKKMEPMIDVAYRELCDYM NNREHLMHDREAISCPPLGSKGVGGFWKAKKRYALNVYDMEKRFAEPHLKIMGM ETQQSSTPKVVQEALEESIRRILQEGEESVQEYYKNFEKEYRQLDYKVIAEVKTANDIAK YDDKGWNPGFKCPFHIRGVLTYRRAVSGLGVAPILDGNKVMVLPLREGNPFGDKCIAWP SGTELPKEIRSDVLSWIDHSTLFQKSFVKPLAGMCESAGMDYEEKASLDFLFG |
| SEQ ID NO 79 APEX1: | MAPKRGKKGAVAEDGDELRTEPEAKKSKTAAKKNDKEAAGEGPALYEDPPDQKTSPS GKPATLKICSWNVDGLRAWIKKKGLDWVKEEAPDILCLQETKCSENKLPAELQELPGLS HQYWSAPSDKEGYSGVGLLSRQCPLKVSYGIGDEEHDQEGRVIVAEFDSFVLVTAVVP NAGRGLVRLEYRQRWDEAFRKFLKGLASRKPLVLCGDLNVAHEEIDLRNPKGNKKNA GFTPQERQGFGELLQAVPLADSFRHLYPNTPYAYTFWTYMIVINARSKNVGWRLDYFLL SHSLLPALCDSKIRSKALGSDHCPITLYLAL |
| SEQ ID NO 80 VStag-APEX2-NLS-NLS (Addgene #124617): | MVRGSGKPIPNPLLGLDSTGKSYPTVSADYQDAVEKAKKKLRGFIAEKRCAPLMLRLAF HSAGTFDKGTKTGGPPGTIKHPAELAHSANNGLDIAVRLLEPLKAEFPILSYADFYQLAG VVAVEVTGGPKVFHPGREDKPEPPPEGRLPDPIKGSDHLRDVFGKAMGLTDQDIVALS GGHTIGAAHKERSGFEGPWTSNPLIFDNSYFTELLSGEKEGLLQLPSDKALLSDPVFRPL VDKYAADEDAFFADYAEAHQKLSELGFADAEFSRADPKKKRKVDPKKKRKV KV |

TABLE 1-continued

| SEQ ID NO | SEQUENCE |
|---|---|
| SEQ ID NO 81 XRCC4: | MERKISRIHLVSEPSITHFLQVSWEKTLESGFVITLTDGHSAWTGTVSESEISQEADDMA MEKGKVVGELRKALLSGAGPADVYTFNFSKESCYFFEEKNLKDVSFRLGSFNLEKVENP AEVIRELICYCLDTIAENQAKNEHLQKENERLLRDMNDVQGRFEKCVSAKEALETDLYK RPILVLNEKKTKIRSLHNKLLNAAQEREKDIKQEGETAICSEMTADRDPVVDESTDEESE NQTDLSLASAAVSKDDSIISSLDVTDIAPSRKRQRMQRNLGTEPKMAPQENQLQEKE KPDSSLPETSKKEHISAENMSLETLRNSSPEDLFDEI |
| SEQ ID NO 82 V5tag-XRN1 (Addgene #66596): | MDAQTRRRERRAEKQAQWKAANGGSPPHMAYPYDVPDYAPPSRAQASNSAVDGTAG MGVPKFYRWISERYPCLSEVVKEHQIPEFDNLYLDMNGIIHQCSHPNDDVHFRISDDKI FTDIFHYLEVLFRIIKPRKVFFMAVDGVAPRAKMNQQRGRRFRSAKEAEDKIKKAIEKG ETLPTEARFDSNCITPGTEFMARLHEHLKYFVNMKISTDKSWQGVTIYFSGHETPGEGEH KIMEFIRSEKAKPDHDPNTRHCLYGLDADLIMLGLTSHEAHFSLLREEVRPGGKKTQRV CAPEETTFHLLHLSLMREYIDYEFSVLKEKITFKYDIERIIDDWILMGFLVGNDFIPHLPHL HINHDALPLLYGTYVTILPELGGYINESGHLNLPRFEKYLVKLSDFDREHFSEVFVDLKW FESKVGNKYLNEAAGVAAEEARNYKEKKKLKGQENSLCWTALDKNEGEMITSKDNLE DETEDDDLFETEFRQYKRTYMTKMGVDVVSDDFLADQAACVQAIQWILHYYHGV QSWSWYYPYHYAPFLSDIHNISTLKIHEELGKPKFPEQLLAVLPAASKNLLPACYQHLM TNEDSPIIEYYPPDFKTDLNGKQQEWEAVLIPFIDEKRLLEAMETCNHSLKKEERKRNQ HSECLMCWYDRDTEFIYPSPWPEKFPAIERCCTRYKIISLDAWRVDINKNKITRIDQKAL YFCGFPTLKHIRHKFPLKKSGVQVFQQSSRGENMMLEILVDAESDELTVENVASSVLGK SVFVNWPHLEEARVAVSDGETKFYLEEPPGTQKLYSGRTAPPSKVVHLGDKEQSNWA KEVQGISEHYLRRKGIINETSAVVYAQLLTGRKYQINQNGEVRLEKQWSKQVVPPVYQ TIVKDIRAFDSRFSNIKTLDDLFPLRSMVFMLGTPYYGCTGEVQDSGDVITEGRIRVIFSIP CEPNLDALIQNQHKYSIKYNPGYVLASRLGVSGYILVSRFTGSIFIGRGSRRNPHGDHKAN VGLNLKFNKNEEVPGYTKKVGSEMMYSSAAEQLLAEYLERAPELFSYIAKNSQEDVF YEDDIWPGENENGAEKVQEIITWLKGHPSVTLSLSRSSCDLQIIDAAIVEKIEEVEKCKQR KNNKKVRTVTVKPHLLYRPLEQGHGVIPDRDAEFCLFDRVVNVRENFSVPVGLRGTIIGI KGANREADVLEEVLFDEEFPGGLTIRCSPGRGYRLPTSALVNLSHGSRSETGNQKLTAIV KPQPAVHQHSSSSVSSGHLGALNHSPQSLFVPTQVPTKDDDEFCNIWQSLQGSGKMQY FQPTIQEKGAVLPEQISVNPLLFGLGSLGMNFPLPSQVFANYPSAVPPGTIPAFPPPTGWD QKMSNKQPNSGIENFLASLNIISKENEVQSSHHGEPPSEEHLSPQSFAMGTRMLKEILKID GSNTVDHKNEIKQIANEIPVSSNRRDEYGLPSQPKQNKKLASYMNKPHSANEYHNVQS MDNMCWPAPSQIPPVSTPVTELSRICSLVGMPQPDFSFLRMPQTMTVCQVKLSNGLLVH GPQCHSENEAKEKAALFALQQLGSLGMNFPLPSQVFANYPSAVPPGTIPAFPPPTGWD HYGSNYALGAANIMPSSSHLFGSMPWGPSVPVPGKPFHHTLYSGTMPMAGGIPGGVHN QFIPLQVIKKRVANKKNEENKEAQSSQATPVQTSQPDSSNIVKVSPRESSSASLKSSPIAQ PASSFQVETASQGHSISHHKSTPISSSRRKSRKLAVNFGVSKPSE |
| SEQ ID NO 83 DNA2: | MEQLNELELLMEKSFWEEAELPAELFQKKVVASFPRTVLSTGMDNRYLVLAVNTVQNK EGNCEKRLVITASQSLENKELCILRNDWCSVPVEPGDIIHLEGDCTSDTWIIDKDPGYLIL YPDMLISGTSIASSIRCMRRAVLSETFRSSDPATRQMLIGTVLHEVFQKAINNSFAPEKLQ ELAFQTIQEIRHLKEMYRLNLSQDEIKQEVEDYLPSFCKWAGDFMHKNTSTDFPQMQLS LPSDNSKDNSTCNIEVVKPMDIEESIWSPRFGLKGKIDVTVGVKIHRGYKTYKYIMPLEL KTGKESNSIEHRSQVVLYTLLSQERRADPREAGLLLYLKTGQMYPVPANHLDKRELLKLR NQMAFSLFHRISKSATRQKTQLASLPLQIIEEEKTCKYCSQIGNCALYSRAVEBQQMDCSSV PIVMLPKIEEETQHLKQTHLEYFSLWCLMLTLESQSKDNKKNHQNIWLMPASEMEKSGS CIGNLIRMEHVKIVCDGQYLHNFQCKHGAIPVTNLMAGDRVIVSGEERSLFALSRGYVK EINMTTVTCLLDRNLSVLPESTLFRLDQEEKNCDIDTPLGNLSKLMENTFVSKKLRDLIID FREPQFISYLSSVLPHDAKDTVACILKGLNKPQRQAMKKVLLSKDYTLIVGMPGTGKTT TICTLVRILYACGFSVLLTSYTHSAVDNILLKLAKFKIGFLRLGQIQKVHPAIQQFTEQEIC RSKSIKSLALLEELYNSQLIVATTCMGINHPIFSRKIFDFCIVDEASQISQPICLGPLFFSRRF |

TABLE 1-continued

| SEQ ID NO | SEQUENCE |
|---|---|
| | VLVGDHQQLPPIVLNREARALGMSESLFKRLEQNKSAVVQLTVQYRMNSKIMSLSNKL<br>TYEGKLECGSDKVANAVINLRHFKDVKLELEFYADYSDNPWLMGVFEPNNPVCFLNTD<br>KVPAPEQVEKGGVSNVTEAKLIVFLTSIFVKAGCSPSDIGIIAPYRQQLKIINDLLARSIGM<br>VEVNTVDKYQGRDKSIVLVSFVRSNKDGTVGELLKDWRRLNVAITRAKHKLILLGCVP<br>SLNCYPPLEKLLNHLNSEKLIIDLPSREHESLCHILGDFQRE |
| SEQ ID NO<br>84<br>Myc-POLQ-<br>Flag (Addgene<br>#73132): | MEQKLISEEDLLRKRGILNLLRRSGKRRRSESGSDFSGSGDSSASPQFLSGSVLSPPPG<br>LGRCLKAAAAGECKPTVPDYEIDKLLLANWGLPKAVLEKYHSFGVKKMFEWQAECLL<br>LGQVLEGKNLVYSAPTSAGKTVAELILLKRVLEMRKKALFILPFVSVAKEKKYYLQSL<br>FQEVGIKVDGYMGSTSPSRRHFSSLLDIAVCTIERANGLINRLIEENKMDLLGMVVDELH<br>MLGDSHRGYLLELLLTKICYITRKSASCQADLASSLSNAVQIVGMSATLPNLELVASWL<br>NAELYHTDFRPVPLLESVKVGNSIYDSSMKLVREFEPMLQVKGDEDHVVSLCYETICDN<br>HSVLLFCPSKKWCEKLADIIAREFYNLHHQAEGLVKPSECPPVILEQKELLEVMDQLRRL<br>PSGLDSVLQKTVPWGVAFHHAGLTFEERDIIEGAFRQGLIRVLAATSTLSSGVNLPARRV<br>IIRTPIFPGGRPLDILTYKQMVGRAGRKGVDTVGESILICKNSEKSKGIALLQGSLKPVRSC<br>LQRREGEVTGSMIRAILEIIVGGVASTSQDMHTYAACTFLAASMKEGKQGIQRNQESV<br>QLGAIEACVMWLLENEPIQSTEASDGTEGKYYHPTHLGSATLSSSLSPADTLDIFADLQR<br>AMKGFVLENDLHILYLVTPMFEDWTTIDWYRPFCLWEKLPTSMKRVAELVGVEEGFLA<br>RCVKGKVVARTERQHRQMAIHKRFFTSLVLLDLISEVPLREINQKYGCNRGQIQSLQQS<br>AAVYAGMITVFSNRLGWHNMELLLSFQKRLTFGIQRELCDLVRVSLLNAQRARVLIYA<br>SGFHTVADLARANIVEVEVILKNAVPFKSARKAVDEEEAVEERRNMRTIWVTGRKGL<br>TEREAAALIVEEARMILQQDLVEMGVQWNPCALLHSSTCSLTHSESEVKEHTFISQTKSS<br>YKKLTSKNKSNTIFSDSYIKHSPNIVQDLNKSREHTSSFNCNFQNGNQEHQRCSIFRARK<br>RASLDINKEKPGASQNEGKTSDKKVVQTFSQKTKKAPLNFNSEKMSRSFRSWKRKHL<br>KRSRDSSPLKDSGACRIHLQGQTLSNPSLCEDPFTLDEKKTEFRNSGPFAKNVSLSGKEK<br>DNKTSFPLQIKQNCSWNITLTNDNFVEHIVTGSQSKNVTCQATSVVSEKGRGVAVEAEK<br>INEVLIQNGSKNQNVTVMKHHDIHPINQYLRKQSHEQTSTITKQKNIIERQMPCEAVSSYIN<br>RDSNVTINCERIKLNTEENKPSHFQALGDDISRTVIPSEVLPSAGAFSKSBGQHENFLNISR<br>LQEKTGTYTTNKTKNNHVSDLGLVLCDFEDSFYLDTQSEKIIQQMATENAKLGAKDTN<br>LAAGIMQKSLVQQNSMNSFQKECHIPFPAEQHPLGATKIHDHLDLKTVGTMKQSSDSHG<br>VDILTPESPIFHSPILLEENGLFLKKNEVSVTDSQLNSFLQGYQTQETVKPVILLIPQKRTPT<br>GVEGECLPVPETSLNMSDSLLFDSFSDDYLVKEQLPDMQMEPLPSEVTSNHFSDSLCL<br>QEDLIKKSNVNENQDTHQQLITCSNDESIIFSEMDSVQMVEALDNVDIFPVQEKNHTVVS<br>PRALELSDPVLDEHHQGDGDQDERAEKSKLTGTRQNHSFIWSGASFDLSPGLQRIL<br>DKVSSPLENEKLKSMTINFSSLNRKNTELNEEQEVISNLETKQVQGISFSSNNEVKSKIEM<br>LENNANHDETSSLLPRKESNIVDDNGLIPPTPIPTSASKLTFPGILETPVNPWKTNNVLQP<br>GESYLFGSPSDIKNHDLSPGSRNGFKDNSPISDTSFSLQLSQDGLQLTPASSSESLSIIDVA<br>SDQNLFQTFIKEWRCKKRFSISLACEKIRSLTSSKTATIGSRFKQASSPQEPIPIRDDGFPIKG<br>CDDTLVVGLAVCWGGRDAYYFSLQKEQKHSEISASLVPPSLLDPSLTLKDRMWYLQSCL<br>RKESDKECSVVIYDFIQSYKILLLSCGISLEQSYEDPKVACWLLDPDSQEPTLHSIVTSFLP<br>HELPLLEGMETSQGIQSLGLNAGSEHSGRYRASVESILIFNSMNQLNSLLQKENLQDVFR<br>KVEMPSOYCLALLELNGIGFSTAECESQKHIMQAKLDAIETQAYQLAGHSFSFTSSDDIA<br>EVLFLEIKLLPNREMKNQGSKKTLGSTRRGIDNGRKLRLGRQFSTSKDVLNKLKALHPL<br>PGLILEWRRITNAITKVVFPLQREKCLNPPLGMERLYPVSQSHTATGRIFFTEPNIQNVPR<br>DFEIKMPTLVGESPPSQAVGKGLLPMGRGKYKKGFSVNPRCQAQMEERAADRGMPFSI<br>SMRHAFVPFPGGSILAADYSQLELRIIAHLSHDRRLIQVLNTGADVFRSIAAEWKMIEPE<br>SVGDDLRQQAKQICYGIIYGMGAKSLGEQMGIKENDAACYIDSFKSRYTGINQFMTETV<br>KNCKRDGFVQTILGRRRYLPGIKDNNPYRKAHAERQAINTIVQGSAADIVKIATVNIQKQ<br>LETFHSTFKSHGHREGMLQSDRTGLSRKRKLQGMFCPIRGGFFILQHDELLYEVAEED<br>VVQVAQIVKNEMESAVKLSVKLKVKIGASWGELKDFDVPGMDYKDDDDK |

TABLE 1-continued

| SEQ ID NO | SEQUENCE |
|---|---|
| SEQ ID NO 85 POLB: | MDYKDHDGDYKDHDIDYKDDDDKMAPKKKRKVGIHGVPAAASKRKAPQETLNGGIT DMLTELANFEKNVSQAIHKYNAYRKAASVIAKYPHKIKSGAEAKKLPGVGTKIAEKIDE FLATGKLRKLEKIRQDDTSSSINFLTRVSGIGPSAARKFVDEGIKTLEDLRKNEDKLNHH QRIGLKYFGDFEKRIPREEMLQMQDIVLNEVKKVDSEYIATVCGSFRRGAESSGDMDVL LTHPSFTSESTKQPKLLHQVVEQLQKVHFITDTLSKGETKFMGVCQLPSKNDEKEYPHR RIDIRLIPKDQYYCGVLYFTGSDIFNKMRAHALEKGFTINEYTIRPLGVTGVAGEPLPVD SEKDIFDYIQWKYREPKDRSE |
| SEQ ID NO 86 POLH: | MATGQDRVALVDMDCFFVQVEQRQNPHLRNKPCAVVQYKSWKGGGIIAVSYEARAF GVTRSMWADDAKKLCPDLLLAQVRESRGKANLTKYREASVEVMEIMSRFAVIERASID EAYVDLTSAVQERLQKLQGQPISADLLPSTYIEGLPQGPTTAEETVQKEGMRKQGLFQW LDSLQIDNLTSPDLQLTVGAVIVEEMRAAIERETGQCSAGISHNKVLAKLACGLNKPNR QTLVSHGSVPQLFSQMPIRKIRSLGGASVIEILGIEYMGELTQFTESQLQSHFGEKNG SWLYAMCRGIEHDPVKPRQLPKTIGCSKNFPCKTALATREQVQWLLQLAQELEERLT KDRNDNDRVATQLVVSIRVQGDKRLSSLRRCCALTRYDAHKMSHDAFTVIKNCNTSGI QTEWSPPLTMLFLCATKFSASAPSSTDITSFLSSDPSSLPKVPVTSSEAKTQGSGPAVTA TKKATTSLESFFQKAEABKQVKEASLSSLTAPTQAPMSNPSKPSLPFQTSQSTGTEPFFK QKSLLLKQKQLNNSSVSSPQQNPWSNCKALPNSLPTEYPGCVPVCEGVSKLEESSKATP AEMDLAHNSQSMHASSASKSVLEVTQKATPNPSLLAAEDQVPCEKCGSLVPVWDMPE HMDYHFALELQKSFLQPHSSNPQVVSAVSHQGKRNPKSPLACTNKRPREGMQTLESFF KPLTH |
| SEQ ID NO 87 POLG: | MASRLLWRKVAGATVGPGPVPAPGRWVSSSVPASDPSDGQRRRQQQQQQQQQ PQQPQVLSSEGGQLRHNPLDIQMLSRGLHEQIFGQQGEMPGEAAVRRSVEHLQKHGLM GQPAVPLPDVELRLPLYGDNLDQHFRLLAQKQSLPEYLEAANLLQAQLPPKPPAWAW AEGWTRYGPEGEAVPVAIPEERALVFDVEVCLAEGTCPTLAVAISPSAWYSWCSQRLVE ERYSWTSQLSPADLIPLEVPTGASSPTQRDWQEQLVVGHNVSFDRAHIREQYLIQGSRM RFLDTMSMHMAISGLSSFQRSLWIAAKQGKHKVQPPTKQGQKSQRKARRGPAISSWDW LDISSVNSLAEVHRLYVGGPPLEKEPRELFVKGTMCDIRENFQDLMQYCAQDVWATHE VFQQQLPLFLERCPRHPVTLAGMLEMGVSYLPVNQNWERYLAEAQGTYEELQREMKKS LMDLANDACQLLSGERYKEDDPWLWDLEWDLQEFKQKKAKKVKKEPATASKLLPIEGAG APGDPMDQEDLGPCSEEEEFQQDVMARACLQKLKGTTELLPKRPQHLPGHPGWYRKL CPRLDDPAWTPGPSLLSLQMRVTPKLMALITWDGFPLHYSERHGWGYLIVPGRRDNLAK LPTGTTLESAGVVCPYRAIESLYRKHCLEOQGKQQLMPQEAGLAEEFLLTDNSAIWQTVE ELDYLEVEAEAKMENLRAAVPGQPLALITARGGPKDTQPSYHHGNGPYNDVDIPGCWFF KLPHKDGNSCNVGSPFAKDFLPKMEDGTLQAGPGASGPRALEINKMISFWRNAHKRIS SQMVVWLPRSALPRAVIRHPDYDEEGLYGAILPQVVTAGTITRRAVEPTWLTASNARPD RVGSELKAMVQAPPGYTLVGADVDSQELWIRAVLGDAHFAGMHGCTAFGWMTLQGR KSRGTDLHSKTATTVGISREHAKIFNYGRIYGAGQPPAERLLMQFNHRLTQQEAABKAQ QMYAATKGLRWNYRLSDEGEWLVRELNLPVDRTEGGWISLQDLRKVQRETARKSQWK KWEVVAERAWKGGTESEMFNKLESIATSDIPRTPVLGCCISRALEPSAVQEFMTSRVN WVVQSSAVDYLHLMLVAMKWLFEEFAIDGRFCISIHDEVRYLVREEDRYRAALALQIT NLLTRCMFAYKLGLNDLPQSVAFFSAVDIDRCLRKEVTMDCKTPSNPTGMERRYGIPQG EALDIYQIIELTKGSLEKRSQPGP |
| SEQ ID NO 88 POLN: | MENYEALVGFDLCNTPLSSVAQKIMSAMHSGDLVDSKTWGKSTETMEVINKSSVKYSV QLEDRKTQSPEKKDLKSLRSQTSRGSAKLLSPQSFSVRLTDQLSADQKQKSISSLTLSSCLI PQYNQEASVLQKKGHRCKHFLMENINNENKGSINLKRKHITYNNLSEKTSKQMALEED TDDAEGYLNSGNSGALKKKHFCDIRHLDDWAKSQLIEMLKQAAALVITVMYTDGSTQLG ADQTPVSSVRGIVVLVKRQARGGHGCPDAPACGPVLEGFVSDDPCIYIQIEHSAIWDQEQ EAHQQFARNVLFQTMKCKCPVICFNAKDFVRIVLQFFGNDGSWKHVADFIGLDPRIAA |

TABLE 1-continued

| SEQ ID NO | SEQUENCE |
|---|---|
| | WLIDPSDATPSFEDLVEKYCEKSITVKVNSTYGNSSRNIVNQNVRENLKTLYRLTMDLC<br>SKLKDYGLWQLFRTLELPLIPILAVMESHAIQVNKEEMEKTSALLGARLKELEQEAHFV<br>AGERFLITSNNQLREILFGKLKLHLLSQRNSLPRTGLQKYPSTSEAVLNALRDLHPLPKIL<br>EYRQVHKIKSTFVDGLLACMKKGSISSTWNQTGTVTGRLSAKHPNIQGISKHPIQITTPK<br>NFKGKEDKILTLTISPRAMFVSSKGHTFLAADFSQIELRLITHLSGDPELLKLFQESERDDVF<br>STLTSQMKDVPEQVTHADREQTKKVVYAVVYGAGKERLAACLGVPIQEAAQFLESFL<br>QKYKKIKDFARAAIAQCHQTGCVVSIMGRRRPLPRIHAHDQQLRAQAERQAVNFVVQG<br>SAADLCKLAMIHVFTAVAASHTLTARLVAQIHDELLFEVEDPQIPECAALVRRTMESLE<br>QVQALELQLQVPLKVSLSAGRSWGHLVPLQEAWGPPGPCRTESPSNSLAAPGSPASTQ<br>PPPLHFSPSFCL |
| SEQ ID NO 89 TENT4A: | MASPCPEEAAMRREVVKRIETVVKDLWPTADVQIFGSFSTGLYLPTSDIDLVFGKWER<br>PPLQLLEQALRKHNVAEPCSIKVLDKATVPIIKLTDQETEVKDISFNMETGVRAAEFIK<br>NYMKKYISLLPYLILVLKQFLLQRDLNEVFTGCISSYSLILMAISFLQLHPRIDARRADENL<br>GMLLVEFFELYGRNFNYLKTGIRIKEGGAYIAKEEIMKAMTSGYRPSMLCIEDPLLPGND<br>VGRSSYGAMQVKQVFDYAYIVLSHAVSPLARSYPNRDAESTLIGRIIKVTQEVIDYRRWI<br>KEKWGSKAHPSPGMDSRIKIKERIATCNGEQTQNREPESPYGQRLTLSLSSPQLLSSGSSA<br>SSVSSLSGSDVDSDTPCTTPSVYQFSLQAPAPLMAGLPTALPMPSGKPQTTSRTLIMTT<br>NNQTRFTIPPPTLGVAPVPCRQAGVEGTASLKAVHHMSSPAIPSASPNPLSSPHLYHKHN<br>GMKLSMKGSHGHTQGGGYSSVSVGSGGVRPPVGNRGHQYNRTGWRRKKHTHTRDSLP<br>VSLSR |
| SEQ ID NO 90 DNA Ligase 4: | MAASQTSQTVASHVPFADLCSTLERIQKSKGRAEKIRHFREFLDSWRKFHDALHKNHK<br>DVTDSFYPAMRLILPQLERERMAYGIKETMLAKLYIELLNLPRDGKDALKLLNYRTPTG<br>THGDAGDFAMIAYFVLKPRCLQKGSLTIQQVNDLLDSIASNNSAKRKDLIKKSLLQLITQ<br>SSALEQKMLIRMIIKDLKLGVSQQTIPSVFHNDAAELHNVTDLEKVCRQLHDPSVGLSD<br>ISITLRFSAFKPMLAAIADIEHIEKDMKHQSFYIETKLDGERMQMHKGDVYKFYSRNGY<br>NYTDQFGASPTEGSLTPFIHNAFKADIQICILDGEMMAYNPNTQTFMQKGTKFDIKRMV<br>EDSDLQTCYCVFDVLMVNNKKLGHETLRKRYEILSSIFTPIPGRIEIVQKTQAHTKNEVID<br>ALNEAIDKREEGIMVLPLSIYKPDKRGEGWLKIKPEYVSGLMDELDLILIVGGYWGKGS<br>RGGMMSHFLCAVAEKPPPGEKPSVFHTLSRVGSGCTMKELYDLGLKLAKYWKPFHRK<br>APPSSILCGTEKPEVVIEPCNSVIVQIKAAEIVPSDMYKTGCTLRFPRIEKIRDDKEWHEC<br>MTLDDLEQLRGKASGKLASKHLYIGGDDEPQEKKRKAAPKMKKVIGIIEHLKAPNLTN<br>VNKISNIFEDVEFCVMSGTDSQPKPDLENRIAEFGGYIVQNPGPDTYCVIAGSENIRVKNII<br>LSNKHDVVKPAWLLECFKTKSFVPWQPRFMIHMCPSTKEHFAREYDCYGDSYFIDTDL<br>NQLKEVRSGIKNSNEQTPEEMASLIADLEYRYSWDCSPLSMFRRHTVYLDSYAVINDLS<br>TKNEGTRLAIKALELRFPHGAKVVSCLAEGVSHVIIGEDHSRVADFKAFRRTFKRKFKILK<br>ESWVTDSIDKCELQEENQYLI |
| SEQ ID NO 91 XRN: | MGSAACPRGALPELAPCCQPREQSQPHTRWDAGCGIQHPGEEFRTLGGARAYRVPNS<br>QEGRSSPTRFFPAPEGPAHCFVSSPDRAFWVSEEVQRLLLSNACQPKECNGVKIPVDASK<br>PNPNDVEFDNLYLDMNGIIHPCTHPEDKPAPKNEDEMMVAIFEYIDRLFSIVRPRLLYM<br>AIDGVAPRAKMNQQRSRFRASKEGMEAAVEKQRVRBEILAKGGFLPPEEIKERFDSNC<br>ITPGTEFMDNLAKCLRYYIADRLNNDPGWKNLTVILSDASAPGEGEHKIMDYIRRQRAQ<br>PNHDPNTHHCLCGADADLIMLGLATHEPNFTIREEFKPNKPKPCCGLCNQPFGHEVDCE<br>GLPREKKGKHDELADSLPCAEGEFIFLRLNVLREYLERELTMASLPFTFDVERSIDDWVF<br>MCFFVGNDFLPHLPSLEIRENAIDRLVNIYKNVHKTGGYLTESGVNLQRVQMIMLAV<br>GEVEDSIFKKRKDDEDSFRRRQKEKRKMRKDQPAFTPSGLITPHALGSRNSPGSQVAS<br>NPRQAAYEMRMQNNSSPSISPNTSFTSDGSPSPLGGGIKRKAEDSDSEPEPEDNVRLMEAG<br>WKQRYYKNKFDVDAADEKFRRKVQSYVEGLCWLRYYYQGCASWKWYYPPHYAP<br>FASDFEGIADMPSDFEKGTKPFKPLEQLMGVFPAASGNFLPPSWRKLMSDPDSSIIDFYPE |

TABLE 1-continued

| SEQ ID NO | SEQUENCE |
|---|---|
| | DFAIDLNGKKYAWQGVALLPFVDERRLRAALEEVYPDLTPEETRRNSLGGDVLFVGKH<br>HPLHDRFILELYQTGSTEPVEVPPELCHGIQKFSLDEEAALPDQIVCSPVPMLRDLTQNTV<br>VSINFKDPQFAEDYIFPKAVMLPGARKPAAVLKPSDMEKSSNGRQWKPQLGFNRDRRPV<br>HLDQAAPRTLGHVMPRGSGTGIYSNAAPPPVTYQGNLYRPLLRGQAQIPKLMSNMRPQ<br>DSWRGPPLFQQQRFDRGVGAEPLLPWNRMLQTQNAAFQPNQYQMLAGPGGYPPRRD<br>DRGGRQGYPREGRKYPLPPSGRYNWN |
| SEQ ID NO 92<br>3xFlag_NLS_<br>PolIV: | MDYKDHDGDYKDHDIDYKDDDDKMAPKKKRKVGIHGVPAASLKGKFFAFLPNTSS<br>NKFFKSILEKKGATIVSSIQNCLQSSRKEVILIEDSFVDSDMHLTQKDIFQREAGLNDVDE<br>FLGKIEQSGIQCVKTSCITKWVQNDKPAFQKDDLIKFQPSIIVISDNADDGQSSTDKESEIS<br>TDVESERNDDSNNKDMIQASKPLKRLLQEDKGRASLVTDKTKYKNNELIIGALKRLTKK<br>YEIEGEKFRARSYRLAKQSMENCDFNVRSGEEAHTKLRNIGPSIAKKIQVILDTGVLPGL<br>NDSVGLEDKLKYFKNCYGIGSEIAKRWNLLNFESFCVAAKKDPEEFVSDWTILFGWSYY<br>DDWLCKMSRNECFAHLKKVQKALRGIDPECQVELQGSYNRGYSKCGIDLLFFKPFCN<br>DTTELAKIMETLCIKLYKDGYIHCFLQLTPNLEKLFLKRIVERFRTAKIVGYGERKRWYS<br>SEIIKFFMGVKLSPRELEELKEMKNDEGTLLIEEEEEETKLKPIDQYMSLNAKDGNYCR<br>RLDFFCCKWDELGAGRIHYTGSKEYNRWIRILAAQKGFKLTQHGLFRNNILLESFNERRI<br>FELLNLKYAEPEHRNIEWEKKTG |
| SEQ ID NO 93<br>3xFlag_NLS_<br>XseA: | MDYKDHDGDYKDHDIDYKDDDDKMAPKKKRKVGIHGVPAALPSQSPAIFTVSRLNQT<br>VRLLLEHEMGQVWISGEISNFTQPASGHWYFTLKDDTAQVRCAMFRNSNRRVTFRPQH<br>GQQVLVRANITLYEPRGDYQIIVESMQPAGEGLLQQKYEQLKAKLQAEGLFPDQQYKKP<br>LPSPAHCVGVITSKTGAALHDILHVLKRRDPSLPVIIYPAAVQGDDAPGQIVRAIELANQ<br>RNECDVLIVGRGGGSLEDLWSFNDERVARAIFTSRIPVVSAVGHETDVTIADFVADLRAP<br>TPSAAAEVVSRNQQELLRQVQSTRQRLEMAMDYLANRTRRFTQIHHRLQQOHPQLRL<br>ARQQTMERLQRKMSFALENQKRTGQQQQRLTQRLNQQPKIHRAQTRIQQLEYR<br>LAETLRAQLSATRERRPGNAVTHLEAVSPLSTLARGYSVTTATDGNVLKKVKQVKAGEM<br>LTTRLEDGWIESEVKNIQPVKKSRKKVH |
| SEQ ID NO 94<br>3xFlag_NLS_<br>XseB: | MDYKDHDGDYKDHDIDYKDDDDKMAPKKKRKVGIHGVPAAPKKNEAPASFEKALSE<br>LEQIVTRLESGDLPLEEALNEFERGVQLARQGQAKLQQAEQRVQILLSDNEDASLTPFTP<br>DNE |
| SEQ ID NO 95<br>3xFlag-NLS-<br>SpCas9-NLS<br>(Addgene<br>#100000055) | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEAATLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVNELTKVKYVTEGMRKPAFLSGEQKKAIVDLLFK<br>TNRKVTVKQLKEDYFKKIECFDSVEISGVEDRFNASLGTYHDLLKIIKDFLDNEENED<br>ILEDIVLTLTLFEDREMIEERLKTYAHLFDDKVMKQLKRRRYTGWGRLSRKLINGIRDK<br>QSGKTILDFLKSDGFANRNFMQLIHDDSLTFKEDIQKAQVSGQDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIKRQLVETRQITKHVAQILDSRMNTKYDENDKLIREVKVITLKSKLVSDF |

TABLE 1-continued

| SEQ ID NO | SEQUENCE |
|---|---|
| | RKDFQFYKVREINNYHHAHDAYLNAVVGTALIKKYPKLESEFVYGDYKVDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO 96<br>3xFlag-NLS-SpCas9(delta F916)-NLS: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVNELTKVKVYTEGMRKPAFLSGEQKKAIVDLLFK<br>TNRKVTVKQLKEDYFKKIECFDSVEISGVEDRFNASLGTYHDLLKIIKDFLDNEENED<br>ILEDIVLTLTLFEDREMIEERLKTYAHLFDDKVMKQLKRRYTGWGRLSRKLINGIRDK<br>QSGKTILDFLKSDGFANRNFMQLIHDDSLTFKEDIQKAQVSGQDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGIKRQLVETRQITHVAQILDSRMNTKYDENDKLIREVKVITLKSKLVSDFR<br>KDFQFYKVREINNYHHAHDAYLNAVVGTALIKKYPKLESEFVYGDYKVDVRKMIAK<br>SEQEIGKATAKYFFYSNIMNFKTEITLANGEIRKRPLIETNGETGEIVWDKGRDFATVRK<br>VLSMPQVNIVKKTEVQTGGFSKESILPKRNSDKLIARKKDWDPKKYGGFDSPTVAYSVL<br>VVAKVEKGKSKKLKSVKELLGITIMERSSFEKNPIDFLEAKGYKEVKKDLIIKLPKYSLFE<br>LENGRKRMLASAGELQKGNELALPSKYVNFLYLASHYEKLKGSPEDNEQKQLFVEQHK<br>HYLDEIIEQISEFSKRVILADANLDKVLSAYNKHRDKPIREQAENIIHLFTLTNLGAPAAF<br>KYFDTTIDRKRYTSTKEVLDATLIHQSITGLYETRIDLSQLGGDKRPAATKKAGQAKKK<br>K |
| SEQ ID NO 97<br>3xFlag-NLS-SpCas9(G915F)-NLS: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVNELTKVKVYTEGMRKPAFLSGEQKKAIVDLLFK<br>TNRKVTVKQLKEDYFKKIECFDSVEISGVEDRFNASLGTYHDLLKIIKDFLDNEENED<br>ILEDIVLTLTLFEDREMIEERLKTYAHLFDDKVMKQLKRRYTGWGRLSRKLINGIRDK<br>QSGKTILDFLKSDGFANRNFMQLIHDDSLTFKEDIQKAQVSGQDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG |

TABLE 1-continued

| SEQ ID NO | SEQUENCE |
|---|---|
| | GLSELDKAFFIKRQLVETRQITKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO 98<br>3xFlag-NLS-SpCas9(Q920P)-NLS: | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFPHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRYTGWGRLSRKLINGIRDK<br>QSGKTILDFLKSDGFANRFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIKRQLVETRQVIKHVAQILDSRMNTKYDENDKLIREVKVITLKSKLVSDF<br>RKDFQFYKVREINNYHHAHDAYLNAVVGTALIKKYPKLESEFVYGDYKVYDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO 99<br>3xFlag-NLS-SpCas9(F916P)-NLS | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFPHRLEESFLVEEDKKHERHPIFGNIVDEVAYHEKYPTIY<br>HLRKKLVDSTDKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVYNELTKVKYVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRYTGWGRLSRKLINGIRDK<br>QSGKTILDFLKSDGFANRFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMVDQELDINRLSDYDVDHIVPQSFLKD |

TABLE 1-continued

| SEQ ID NO | SEQUENCE |
|---|---|
| | DSIDNKVLTRSDKNRGKSDNVPSEEVVKKMKNYWRQLLNAKLITQRKFDNLTKAERG<br>GLSELDKAGFIKRQLVETRQVIKHVAQILDSRMNTKYDENDKLIREVKVITLKSKLVSDF<br>RKDFQFYKVREINNYHHAHDAYLNAVVGTALIKKYPKLESEFVYGDYKVDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>100<br>3xFlag-NLS-<br>SpCas9(R918A)-<br>NLS | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVNELTKVKVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL<br>GSQILKEHPVENTQLQNEKLYLYYLQNGRDMYVDQELDINRLSDYDVDHIVPQSFLKD<br>DSIDNKVLTRSDKNRGKSDNVPSEEVVKKMKNYWRQLLNAKLITQRKFDNLTKAERG<br>GLSELDKAGFIARQLVETRQVIKHVAQILDSRMNTKYDENDKLIREVKVITLKSKLVSDF<br>RKDFQFYKVREINNYHHAHDAYLNAVVGTALIKKYPKLESEFVYGDYKVDVRKMIA<br>KSEQEIGKATAKYFFYSNIMNFFKTEITLANGEIRKRPLIETNGETGEIVWDKGRDFATVR<br>KVLSMPQVNIVKKTEVQTGGFSKESILPKRNSDKLIARKKDWDPKKYGGFDSPTVAYSV<br>LVVAKVEKGKSKKLKSVKELLGITIMERSSFEKNPIDFLEAKGYKEVKKDLIIKLPKYSLF<br>ELENGRKRMLASAGELQKGNELALPSKYVNFLYLASHYEKLKGSPEDNEQKQLFVEQH<br>KHYLDEIIEQISEFSKRVILADANLDKVLSAYNKHRDKPIREQAENIIHLFTLTNLGAPAA<br>FKYFDTTIDRKRYTSTKEVLDATLIHQSITGLYETRIDLSQLGGDKRPAATKKAGQAKKK<br>K |
| SEQ ID NO<br>101<br>3xFlag-NLS-<br>SpCas9(R919P)-<br>NLS | MDYKDHDGDYKDHDIDYKDDDDKMAPKKKRKVGIHGVPAADKKYSIGLDIGTNSVG<br>WAVITDEYKVPSKKFKVLGNTDRHSIKKNLIGALLFDSGETAEATRLKRTARRRYTRRK<br>NRICYLQEIFSNEMAKVDDSFFHRLEESFLVEEDKKHERHPIFGNIVDEVAYHEKYPTIY<br>HLRKKLVDSTKADLRLIYLALAHMIKFRGHFLIEGDLNPDNSDVDKLFIQLVQTYNQL<br>FEENPINASGVDAKAILSARLSKSRRLENLIAQLPGEKKNGLFGNLIALSLGLTPNFKSNF<br>DLAEDAKLQLSKDTYDDDLDNLLAQIGDQYADLFLAAKNLSDAILLSDILRVNTEITKA<br>PLSASMIKRYDEHHQDLTLLKALVRQQLPEKYKEIFFDQSKNGYAGYIDGGASQEEFYK<br>FIKPILEKMDGTEELLVKLNREDLLRKQRTFDNGSIPHQIHLGELHAILRRQEDFYPFLKD<br>NREKIEKILTFRIPYYVGPLARGNSRFAWMTRKSEETITPWNFEEVVDKGASAQSFIERM<br>TNFDKNLPNEKVLPKHSLLYEYFTVNELTKVKVTEGMRKPAFLSGEQKKAIVDLLFK<br>TNRKVTVKQLKEDYFKKIECFDSVEISGVEDRFNASLGTYHDLLKIIKDKDFLDNEENED<br>ILEDIVLTLTLFEDREMIEERLKTYAHLFDDKVMKQLKRRYTGWGRLSRKLINGIRDK<br>QSGKTILDFLKSDGFANRNFMQLIHDDSLTFKEDIQKAQVSGQGDSLHEHIANLAGSPAI<br>KKGILQTVKVVDELVKVMGRHKPENIVIEMARENQTTQKGQKNSRERMKRIEEGIKEL |

TABLE 1-continued

| SEQ ID NO | SEQUENCE |
|---|---|
| | GSQILKEHPVENTQLQNEKLYLYYLQNGRDMVDQELDINRLSDYDVDHIVPQSFLKD |
| | DSIDNKVLTRSDKNRGKSDNVPSEEVVKKMKNYWRQLLNAKLITQRKFDNLTKAERG |
| | GLSELDKAGFIKPQLVETRQITKHVAQILDSRMNTKYDENDKLIREVKVITLKSKLVSDF |
| | RKDFQFYKVREINNYHHAHDAYLNAVVGTALIKKYPKLESEFVYGDYKVYDVRKMIA |
| | KSEQEIGKATAKYFFYSNIMNFFKTEITLANGEIRKRPLIETNGETGEIVWDKGRDFATVR |
| | KVLSMPQVNIVKKTEVQTGGFSKESILPKRNSDKLIARKKDWDPKKYGGFDSPTVAYSV |
| | LVVAKVEKGKSKKLKSVKELLGITIMERSSFEKNPIDFLEAKGYKEVKKDLIIKLPKYSLF |
| | ELENGRKRMLASAGELQKGNELALPSKYVNFLYLASHYEKLKGSPEDNEQKQLFVEQH |
| | KHYLDEIIEQISEFSKRVILADANLDKVLSAYNKHRDKPIREQAENIIHLFTLTNLGAPAA |
| | FKYFDTTIDRKRYTSTKEVLDATLIHQSITGLYETRIDLSQLGGDKRPAATKKAGQAKKK |
| | K |
| SEQ ID NO 102 3xFlag-NLS-SpCas9-NLS(N690C T769I G915M N980K): LZ3Cas9Addgene #140561: | MDYKDHDGDYKDHDIDYKDDDDKMAPKKKRKVGIHGVPAADKKYSIGLDIGTNSVG WAVITDEYKVPSKKFKVLGNTDRHSIKKNLIGALLFDSGETAEATRLKRTARRRYTRRK NRICYLQEIFSNEMAKVDDSFFHRLEESFLVEEDKKHERHPIFGNIVDEVAYHEKYPTIY HLRKKLVDSTDKADLRLIYLALAHMIKFRGHFLIEGDLNPDNSDVDKLFIQLVQTYNQL FEENPINASGVDAKAILSARLSKSRRLENLIAQLPGEKKNGLFGNLIALSLGLTPNFKSNF DLAEDAKLQLSKDTYDDDLDNLLAQIGDQYADLFLAAKNSDAILLSDILRVNTEITKA PLSASMIKRYDEHHQDLTLLKALVRQQLPEKYKEIFFDQSKNGYAGYIDGGASQEEFYK FIKPILEKMDGTEELLVKLNREDLLRKQRTFDNGSIPHQIHLGELHAILRRQEDFYPFLKD NREKIEKILTFRIPYYVGPLARGNSRFAWMTRKSEETITPWNFEEVVDKGASAQSFIERM TNFDKNLPNEKVLPKHSLLYEYFTVNELTKVKYVTEGMRKPAFLSGEQKKAIVDLLFK TNRKVTVKQLKEDYFKKIECFDSVEISGVEDRFNASLGTYHDLLKIIKDKDFLDNEENED ILEDIVLTLTLFEDREMIEERLKTYAHLFDDKVMKQLKRRRYTGWGRLSRKLINGIRDK QSGKTILDFLKSDGFACRNFMQLIHDDSLTFKEDIQKAQVSGQGDSLHEHIANLAGSPAI KKGILQTVKVVDELVKVMGRHKPENIVIEMARENQTTQKGQKNSRERMKRIEEGIKELG SQILKEHPVENTQLQNEKLYLYYLQNGRDMVDQELDINRLSDYDVDHIVPQSFLKDDS IDNKVLTRSDKNRGKSDNVPSEEVVKKMKNYWRQLLNAKLITQRKFDNLTKAERGGLS ELDKAMFIKRQLVETRQITKHVAQILDSRMNTKYDENDKLIREVKVITLKSKLVSDFRK DFQFYKVREINKYHHAHDAYLNAVVGTALIKKYPKLESEFVYGDYKVYDVRKMIAKSE QEIGKATAKYFFYSNIMNFFKTEITLANGEIRKRPLIETNGETGEIVWDKGRDFATVRKV LSMPQVNIVKKTEVQTGGFSKESILPKRNSDKLIARKKDWDPKKYGGFDSPTVAYSVLV VAKVEKGKSKKLKSVKELLGITIMERSSFEKNPIDFLEAKGYKEVKKDLIIKLPKYSLFEL ENGRKRMLASAGELQKGNELALPSKYVNFLYLASHYEKLKGSPEDNEQKQLFVEQHKH YLDEIIEQISEFSKRVILADANLDKVLSAYNKHRDKPIREQAENIIHLFTLTNLGAPAAFK YFDTTIDRKRYTSTKEVLDATLIHQSITGLYETRIDLSQLGGDKRPAATKKAGQAKKKK |
| SEQ ID NO 103 3xFlag-NLS-SaCas9-P2A-EGFP: | MDYKDHDGDYKDHDIDYKDDDDKMAPKKKRKVEASMKRNYILGLDIGITSVGYGIID YETRDVIDAGVRLFKEANVENNEGRRSKRGARRLKRRRRHRIQRVKKLLFDYNLLTDH SELSGINPYEARVKGLSQKLSEEEFSAALLHLAKRRGVHNVNEVEEDTGNELSTKEQISR NSKALEEKYVAELQLERLKKDGEVRGSINRFKTSDYVKEAKQLLKVQKAYHQLDQSFI DTYIDLLETRRTYYEGPGEGSPFGWKDIKEWYEMLMGHCTYFPEELRSVKYAYNADLY NALNDLNNLVITRDENEKLEYYEKFQIIENVFKQKKKPTLKQIAKEILVNEEDIKGYRVT STGKPEFTNLKVYHDIKDITARKEIIENAELLDQIAKILTIYQSSEDIQEELTNLNSELTQEE IEQISNLKGYTGTHNLSLKAINLILDELWHTNDNQIAIFNRLKLVPKKVDLSQQKEIPTTL VDDFILSPVVKRSFIQSIKVINAIIKKYGLPNDIIIELAREKNSDAQKMINEMQKRNRQTN ERIEEIIRTTGKENAKYLIEKIKLHDMQEGKCLYSLEAIPLEDLLNNPFNYEVDHIIPRSVS FDNSFNNKVLVKQEENSKKGNRTPFQYLSSSDSKISYETFKKHILNLAKGKGRISKTKKE YLLEERDINRFSVQKDFINRNLVDTRYATRGLMNLLRSYFRVNNLDVKVKSINGGFTSF LRRKWKFKKERNKGYKHHAEDALIIANADFIFKEWKKLDKAKKVMENQMFEEKQAES MPEIETEQEYKEIFITPHQIKHIKDFKDYKYSHRVDKKPNRELINDTLYSTRKDDKGNTLI |

TABLE 1-continued

| SEQ ID NO | SEQUENCE |
|---|---|
| | VNNLNGLYDKNDKLKKLINKSPEKLLMYHHDPQTYQKLKLIMEQYGDEKNPLYKYY |
| | EETGNVLTKYSKKDNGPVIKKIKYYGNKLNAHLDITDDYPNSRNKVVKLSLKPYRFDV |
| | YLDNGVYKFVTVKNLDVIKKENYYEVNSKCYEEAAKLKKISNQAEFIASFYNNDLIKIN |
| | GELYRVIGVNNDLLNRIEVNMIDITYREYLENMDKRPPRIIKTIASKTQSIKKYSTDILG |
| | NLYEVKSKKHPQIIKKGRSGGEGRGSLLTCGDVEENPGPMVSKGEELFTGVPIVEL |
| | DGDVNGHKFSVSGEGEGDATYGKLTLKFICTTGKLFVPWPTLVTTLJTYGVQCFSRYPDH |
| | MKQHDFFKSAMPEGYVQERTIFFKDDGNYKTRAEVKFEGDTLVNRIELKGIDFKEDGNI |
| | LGHKLEYNYNSHNVYIMADKQKNGIKVNFKIRHNIEDGSVQLADHYQQNTPIGDGPVL |
| | LPDNHYLSTQSALSKDPNEKRDHMVLLEFVTAAGITLGMDELYK |
| SEQ ID NO 104 FnCas12a-NLS-3xHA (addgene #64709): | MSIYQEFVNKYSLSKTLREELIPQGKTLENIKARGLILDDEKRAKDYKKAKQIIDKYHQF FIEEILSSVCISEDLLQNYSDVYFKLKKSDDDNLQKDFKSAKDTIKKQISEYIKDSEKFKN LFNQNLIDAKKGQESDLILWLKQSKDNGIELFKANSDITDIDEALEIIKSPKGWTTYFKGF HENRKNVYSSNDIPTSIIYRIVDDNLPKFLENKAKYESLKDKAPEAINYEQIKKDLAEELT FDIDYKTSEVNQRVFSLDEVFEIANFNNYLMQSGITKFNTIIGGKFVNGENTKRGINEYI NLYSQQINDKTLKKYRMSVLFKQILSDTESKSFVIDKLEDDSDVVTTMQSFYEQIAAFKT VEEKSIKETLSLLFDDLKAQKLDLSKIYFKNDKSLTDLSQQVFDDYSVIGTAVLEYITQQI APKNLDNPSKKEQELIAKKTEKAKYLSLETIKLALEEFNKHRDIDKQCRFEEILANFAAIP MIFDEIAQNKDNLAQISIKYQNQGKKDLLQASAEDDVKAIKDLLQTNNLLHKLKIFHIS QSEDKANILDDKEHFYLIVFEECYFELANIVPLIYNKIRNYITQKPYSDEKFKLNFENSTLA NGWDKNKEPDNTAILFIKDDKYYLGVMNKKNNKIFDDKAIKENKGEGYKKIVYKLLPG ANKMLPKVFFSAKSIKFYNPSEDILRIRNHSTHTKNGSPQKGYEKFEFNIEDCRKFIDFYK QSISKHPEWKDFGFRRSDTQRYNSIDEFYREVENQGYKLIFENISESYIDSVVNQGKLYL FQIYNKDFSAYSKGRPNLHTLYWKALFDERNLQDVVVKLNGEAELFYRKQSIPKKITHP AKEAIANKNKDNPKKESVFEYDLIKDKRFTEDKFFHCPITINFKSSGANKFNDEINLLLK EKANDVHILSIDRGERHLAYTLVDGKGNIIKQDTFNIIGNDRMKTNYHDKLAAIEKDR DSARKDWKKINNIKEMKEGYLSQVVHEIAKLVIEYNAIVVFEDLNFGFKRGRFKVEKQV YQKLEKMLIEKLNYLVFKDNEFDKTGVLRAYQLTAPEETFKKMGKQTGITYYVPAGFT SKICPVTGFVNQLYPKYESVSKSQEFFSKFDKICYNLDKGYFEFSFDYKNFGDKAAKGK WTIASFGSRLINFRNSDKNHWDTREVYPTKELEKLLKDYSIEYGHGECIKAAICGESDK KFFAKLTSVLNTILQMRNSKTGTELDYLISPVADVNGNFFDSRQAPKNMPQDADANGA YHIGLKGLMLLGRIKNNQEGKKLNLVIKNEEYFEFVQNRNNKRPAATKKAGQAKKKK GSYPYDVPDYAYPYDVPDYA |
| SEQ ID NO 105 AsCas12a-NLS-3xHA (addgene #69982): | MTQFEGFTNLYQVSKTLRFELIPQGKTLKHIQEQGFIEEDKARNDHYKELKPIIDRIYKTY ADQCLQLVQLDWENLSAAIDSYRKEKTEETRNALIEEQATYRNAIHDYFIGRTDNLTDAI NKRHAEIYKGLFKAELFNGKVLKQLGTVTTTEHENALLRSFDKFTYFSGFYENRKNVF SAEDISTAIPHRIVQDNFPKFKENCHIFTRLITAVPSLREHFENVKKAIGIFVSTSIEEVSFP FYNQLLTQTQIDLYNQLLGGISREAGTEKIKGLNEVLNLAIQKNDETAHIIASLPHRFIPLF KQILSDRNTLSPILEEFKSDEEVIQSFCKYKTLLRNENVLETAEALFNELNSIDLTHIFISHK KLETTSSALCDHWDTLRNALYERRISELITGKITKSAKEKVQRSLKHEDINLQEIISAAGKE LSEAFKQKTSEILSHAHAALDQPLPTTLKKQEEKEILKSQLDSLLGLYHLLDWFAVDESN EVDPEFSARLTGIKLEMEPSLSFYNKARNYATKKPYSVEKFKLNFQMPTLASGWDVNK EKNNGAILFVKNGLYYLGIMPKQKGRYKALSFEPTEKTSEGFDKMYYDYFPDAAKMIP KCSTQLKAVTAHFQTHTTPILLSNNFIEPLEITKEIYDLNNPEKEPKKFQTAYAKKTGDQK GYREALCKWIDFTRDFLSKYTKTTSIDLSSLRPSSQYKDLGEYYAELNPLLYHISFQRIAE KEIMDAVETGKLYLFQIYNKDFAKGHGKPNLHTLYWTGLFSPENLAKTSIKLNGQAEL FYRPKSRMKRMAHRLGEKMLNKKLKDQKTFIPDTLYQELYDYVNHRLSHDLSDEARA LLPNVITKEVSHEIIKDRRFTSDKFFHVPITLNYQAANSPSKFNQRVNAYLKEHPETPIIG IDRGERNLIYITVIDSTGKILEQRSLNTIQQPDYQKKLDNREKERVAARQAWSVVGTIKD LKQGYLSQVIHEIVDLMIHYQAVVVLENLNFGFKSKRTGIAEKAVYQQFEKMLIDKLNC |

TABLE 1-continued

| SEQ ID NO | SEQUENCE |
|---|---|
| | LVLKDYPAEKVGGVLNPYQLTDQFTSFAKMGTQSGFLFYVPAPYTSKIDPLTGFVDPFV<br>WKTIKNHESRKHFLEGPDFLHYDVKTGDFLHFKMNRNLSFQRGLPGFMPAWDIVFEK<br>NETQFDAKGTPFIAGKRIVPVIENHRFTGRYRDLYPANELIALLEEKGIVFRDGSNILPKL<br>LENDDSHAIDTMVALIRSVLQMRNSNAATGEDYINSPVRDLNGVCFDSRFQNPEWPMD<br>ADANGAYHIALKGQLLLNHLKESKDLKLQNGISNQDWLAYIQELRNKRPAATKKAGQ<br>AKKKKGSYPYDVPDYAYPYDVPDYA |
| SEQ ID NO 106 HLbCas12a-NLS-3xHA(addgene #69988): | MSKLEKFTNCYSLSKTLRFKAIPVGKTQENIDNKRLLVEDEKRAEDYKGVKKLLDRYYL<br>SFINDVLHSIKLKNLNNYISLFRKKTRTEKENKELENLEINLRKEIAKAFKGNEGYKSLFK<br>KDIIETILPEFLDDKDEIALVNSFNGFTTAFTGFFDNRENMFSEEAKSTSIAFRCINENLTR<br>YISNMDIFEKVDAIFDKHEVQEIKEKILNSDYDVEDFFEGEFFNFVLTQEGIDVYNAIIGGF<br>VTESGEKIKGLNEYINLYNQKTKQKLPFKFPLYKQVLSDRESLSFYGEGYTSDEEVLEVF<br>RNTLNKNSEIFSSIKKLEKLFKNFDEYSSAGIFVKNGPAISTISKDIFGEWNVIRDKWNAE<br>YDDIHLKKKAVVTEKYEDDRRKSFKKIGSFSLEQLQEYADADLSVVEKLKEIIIQKVDEI<br>YKVYGSSEKLFDADFVLEKSLKKNDAVVAIMKDLLDSVKSFENYIKAFFGEGKETNRD<br>ESFYGDFVLAYDILLKVDHIYDAIRNVVTQKPYSDKFKLYFQNPQFMGGWDKDKETD<br>YRATILRYGSKYYLAIMDKKYAKCLQKIDKDDVNGNYEKINYKLLPGPNKMLPKVFFS<br>KKWMAYYNPSEDIQKIYKNGTPFKKGDMFNLNDCHKLIDFFKDSISRYPKWSNAYDFNF<br>SETEKYKDIAGFYREVEEQGYKVSFESASKKEVDKLVEEGKLYMPQIYNKDFSDKSHGT<br>PNLHTMYFKLLFDENNHGQIRLSGGAELFMRRASLKKEELVVHPANSPIANKNPDNPKK<br>TTTLSYDVYKDKRFSEDQYELHIPIAINKCPKNIFKINTEVRVLLKHDDNPYVIGIDRGER<br>NLLYIVVVDGKGNIVEQYSLNEIINNFNGIRIKTDYHSLLDKKEKERFEARQNWTSIENIK<br>ELKAGYISQVHKICELVEKYDAVIALEDLNSGFKNSRVKVEKQVYQKFEKMLIDKLNY<br>MVDKKSNPCATGGALKGYQITNKFESFKSMSTQNGFIFYFIPAWLTSKIDPSTGFVNLLKT<br>KYTSIADSKKFISSFDRIMYVPEEDLEEFALDYIKKWKLYSYGNRIRIFRN<br>PKKNNVFDWEEVCLTSAYKELFNKYGINYQQQDIRALLCEQSDKAFYSSFMALMSLML<br>QMRNSITGRTDVDFLISPVKNSDGIFYDSRNYEAQENAILPKNADANGAYNIARKVLWA<br>IGQFKKAEDEKLDKVKIAISNKEWLEYAQTSVKHKRPAATKKAGQAKKKKGSYPYDVP<br>DYAYPYDVPDYAYPYDVPDYA |
| SEQ ID NO 107 3xGS: | GGGSGGGSGGGS |
| SEQ ID NO 108 (SGGS)2-XTEN-(SGGS)2 | SGGSSGGSSGSETPGTSESATPESSGGSSGGS |
| SEQ ID NO 109 (H4)2 | AEAAAKEAAAKEAAAKALEAEAAAKEAAAKEAAAKA |
| SEQ ID NO 110 3xFlag-NLS | GSDYKDHDGDYKDHDIDYKDDDDKMAPKKKRKVGIHGVPAA |
| SEQ ID NO 111 3xFlag: | GSDYKDHDGDYKDHDIDYKDDDDKGIHGVPAA |

TABLE 1-continued

| SEQ ID NO | SEQUENCE |
|---|---|
| SEQ ID NO 112 (H4)3: | GSGSEAAAKEAAAKEAAAKEAAAKALEAAAAKEAAAKEAAAKEAAAKGSGSAAAKE AAAKEAAAKEAAAKGSGS |
| SEQ ID NO 113 GPcPcPc: | AGSGGGSGGGGSPVPSTPPTNSSSTPPTPSPSPVPSTPPTNSSSTPPTPSPSPVPSTPPTNSSS TPPTPSPSAS |
| SEQ ID NO 114 GPGcP: | AGSGGGSGGGGSPVPSTPPTPSPSTPPTPSPSGGSGNSSGSGGGSPVPSTPPTPSPSTPPTPSPS AS |
| SEQ ID NO 115 GPbGbP: | AGSGGGSGGGGSPVPSTPPTPSPSTPPTPSPSIQRTPKIQVYSRHPAENGKSNFLNCYVSGF HPSDIEVDLLKNGERIEKVEHSDLSFSKDWSFYLLYYTEFTPTEKDEYACRVNHVTLSQP KIVKWDRDGGSGGSGGSGGSIQRTPKIQVYSRHPAENGKSNFLNCYVSGFHPSDIEVDL LKNGERIEKVEHSDLSFSKDWSFYLLYYTEFTPTEKDEYACRVNHVTLSQPKIVKWDRD PVPSTPPTPSPSTPPTPSPSAS |
| SEQ ID NO 116 GPZP: | AGSGGGSGGGGSPVPSTPPTPSPSTPPTPSPSDGRYSLTYIYTGLSKHVEDVPAFQALGSL NDLQFFRYNSKDRKSQPMGLWRQVEGMEDWKQDSQLQKAREDIFMETLKDIVEYYND SNGSHVLQGRFGCEIENNRSSGAFWKYYDGKDYIEFNKEIPAWVPFDPAAQITKQKW EAEPVVVQRAKAYLEEECPATLRKYLKYSKNILDRQDPPSVVVTSHQAPGEKKKLKCL AYDFYPGKIDVHWTRAGEVQEPELRGDVLHNGNGTYQSWVVAVPPQDTAPYSCHVQ HSSLAQPLVVPWEASPVPSTPPTPSPSTPPTPSAS |
| SEQ ID NO 117 GGZGZP: | AGSGGGSGGGGSGGGSGGGSGGGSDGRYSLTYIYTGLSKHVEDVPAFQALGSLNDLQFF RYNSKDRKSQPMGLWRQVEGMEDWKQDSQLQKAREDIFMETLKDIVEYYNDSNGSHV LQGRFGCEIENNRSSGAFWKYYYDGKDYIEFNKEIPAWVPFDPAAQITKQKWEAEPVY VQRAKAYLEEECPATLRKYLKYSKNILDRQDPPSVVVTSHQAPGEKKKLKCLAYDFYP GKIDVHWTRAGEVQEPELRGDVLHNGNGTYQSWVVAVPPQDTAPYSCHVQHSSLAQ PLVVPWEASGGSGGSGGSGGSGGSDGRYSLTYIYTGLSKHVEDVPAFQALGSLNDLQFFRYN SKDRKSQPMGLWRQVEGMEDWKQDSQLQKAREDIFMETLKDIVEYYNDSNGSHVLQG RFGCEIENNRSSGAFWKYYYDGKDYIEFNKEIPAWVPFDPAAQITKQKWEAEPVVVQR AKAYLEEECPATLRKYLKYSKNILDRQDPPSVVVTSHQAPGEKKKLKCLAYDFYPGKID VHWTRAGEVQEPELRGDVLHNGNGTYQSWVVAVPPQDTAPYSCHVQHSSLAQPLVV PWEASPVPSTPPTPSPSTPPTPSPSAS |

The skilled person in the art would appreciate that the amino acid sequences, peptides, polypeptides, nucleases, polymerases, blunting enzymes, guide RNAs, and single guide RNAs disclosed herein can be encoded by nucleic acid molecules. The skilled person in the art would also appreciate that vectors comprising these nucleic acid molecules could be used as vehicles to carry the genetic materials into cells. The vector can be a plasmid and is generally made of a DNA sequence that consists of an insert and a larger sequence that serves as the "backbone" of the vector.

EXAMPLES

While several experimental Examples are contemplated, these Examples are intended non-limiting.

Example 1

Indels Editing in PCSK9 Gene Using Cas9 and Blunting Enzymes

Figure 12A:
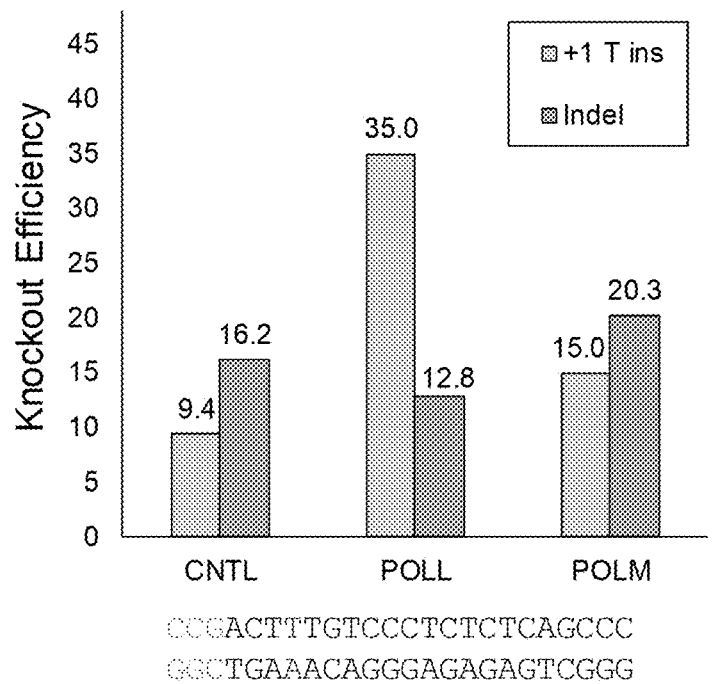
FIG. 12A is a diagram showing probability distribution of +1 T insertion and indel mutations in PCSK9 exon 12 when induced by Cas9 and POLL, and Cas9 and POLM for a target sequence of the sequences of SEQ ID NO: 146 (ccgactttgtccctctctcagccc) and SEQ ID NO: 147 (gggctgagagagggacaaagtcgg) according to embodiments of the present teachings.
Figure 12B:
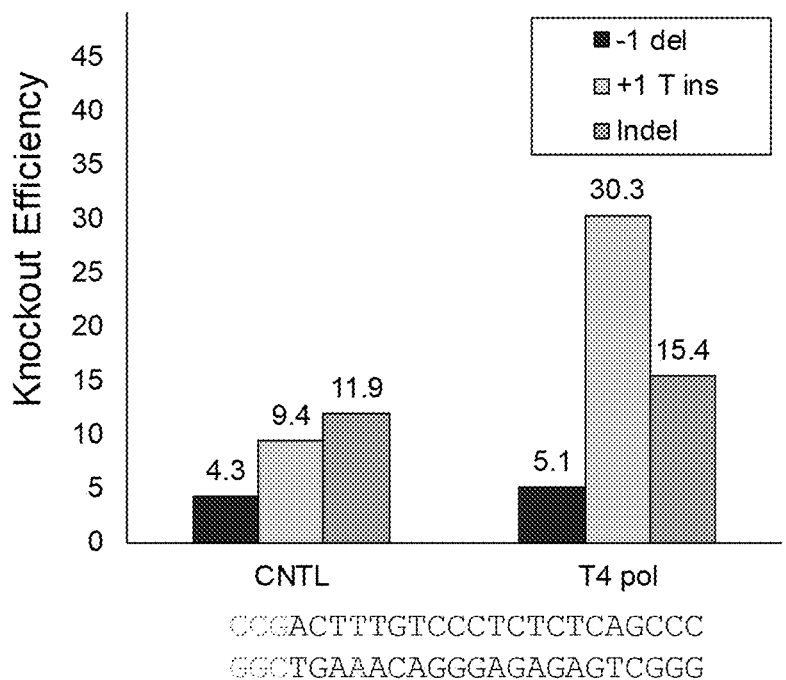
FIG. 12B is a diagram showing probability distribution of −1 deletion, +1T insertion and indel mutations in PCSK9 exon 12 when induced by Cas9 and T4 polymerase for a target sequence of the sequences of SEQ ID NO: 148 (ccgactttgtccctctctcagccc) and SEQ ID NO: 149 (gggctgagagagggacaaagtcgg) according to embodiments of the present teachings.
Figure 13A:
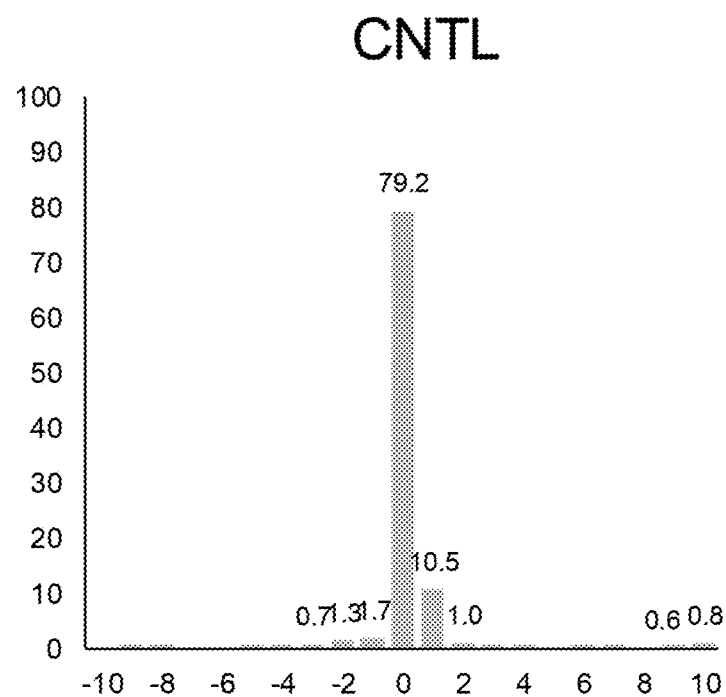
FIG. 13A is a diagram showing probability distribution of indel mutations in GYPB gene when induced by Cas9 only according to embodiments of the present teachings.
Figure 13B:
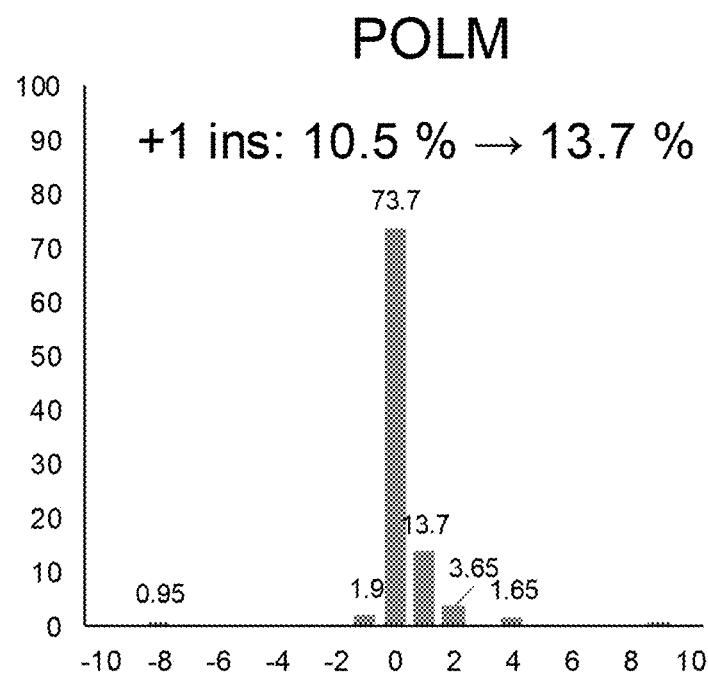
FIG. 13B is a diagram showing the probability distribution of indel mutations in GYPB when induced by Cas9 and POLM according to embodiments of the present teachings.
Figure 13C:
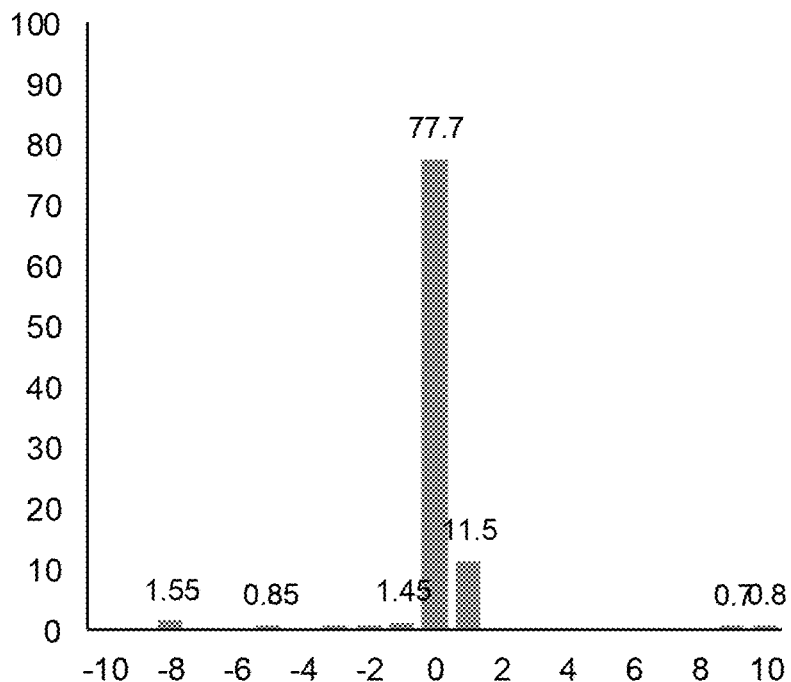
FIG. 13C is a diagram showing the probability distribution of indel mutations in GYPB when induced by Cas9 and EXOG according to embodiments of the present teachings.
Figure 13D:
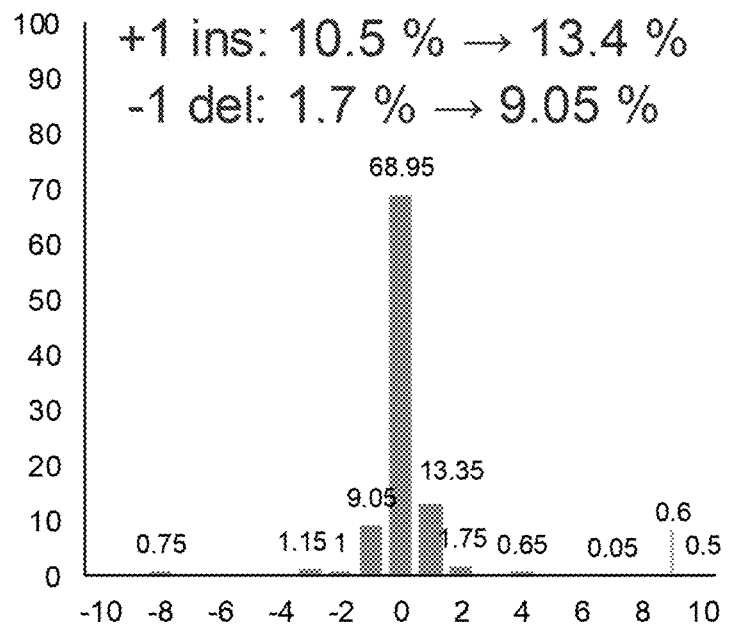
FIG. 13D is a diagram showing the probability distribution of indel mutations in GYPB when induced by Cas9 and T4pol according to embodiments of the present teachings.
Figure 13E:
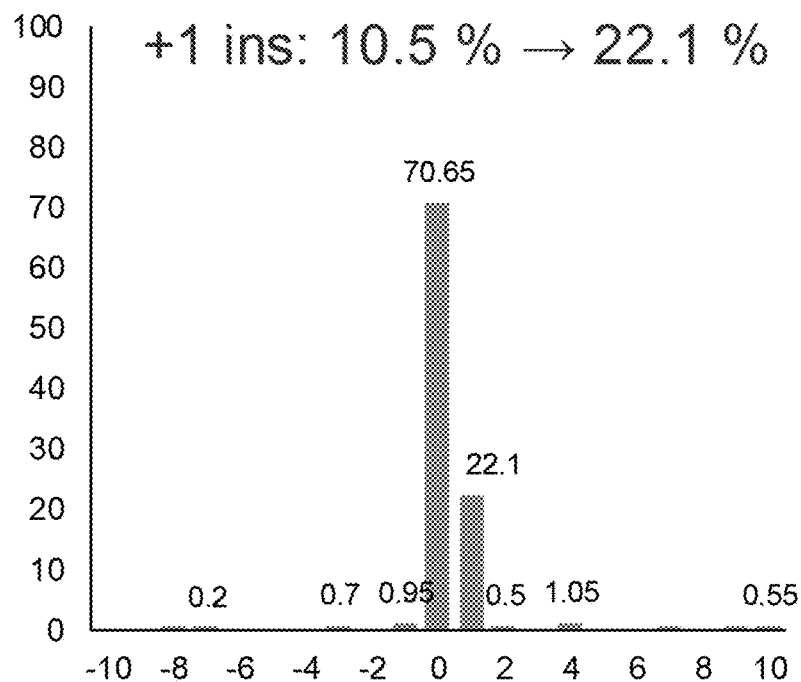
FIG. 13E is a diagram showing the probability distribution of indel mutations in GYPB when induced by Cas9 and POLL according to embodiments of the present teachings.
Figure 13F:
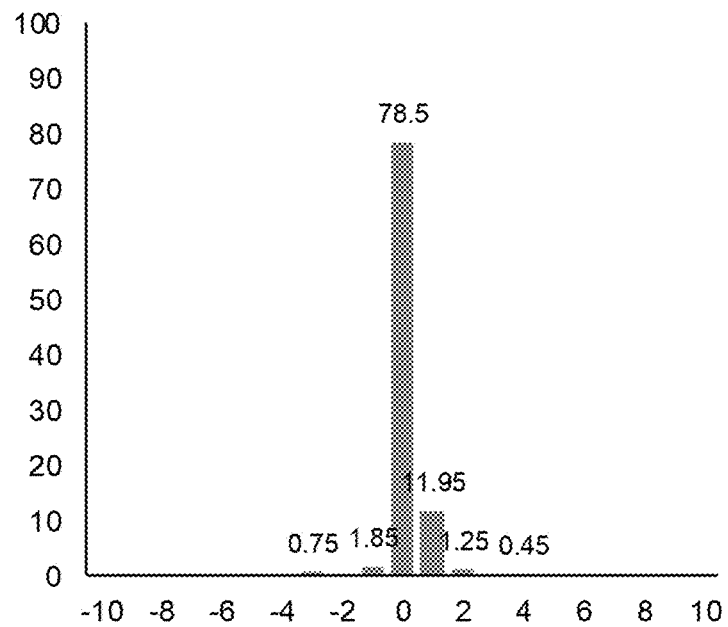
FIG. 13F is a diagram showing the probability distribution of indel mutations in GYPB when induced by Cas9 and MGME according to embodiments of the present teachings.
Figure 13G:
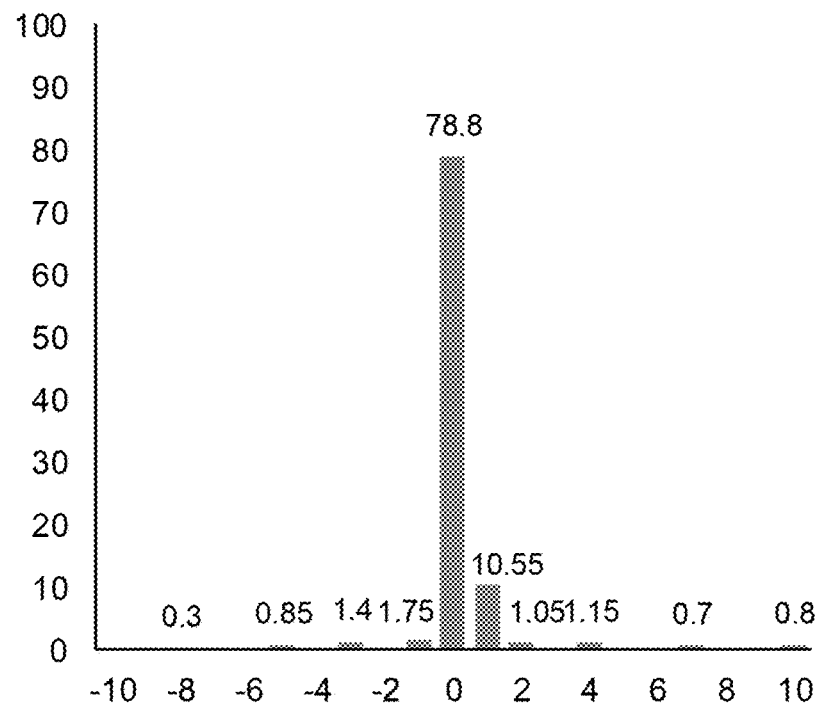
FIG. 13G is a diagram showing the probability distribution of indel mutations in GYPB when induced by Cas9 and RecJ according to embodiments of the present teachings.
Figure 13H:
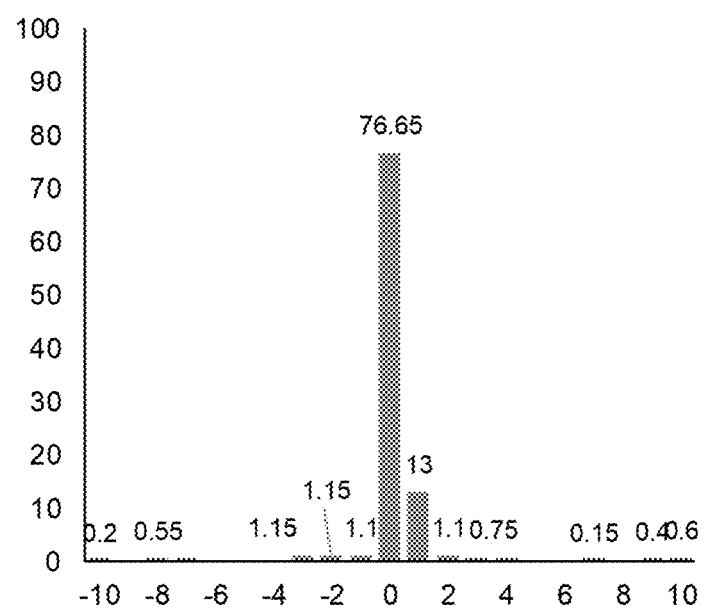
FIG. 13H is a diagram showing the probability distribution of indel mutations in GYPB when induced by Cas9 and nucS according to embodiments of the present teachings.
Figure 14A:
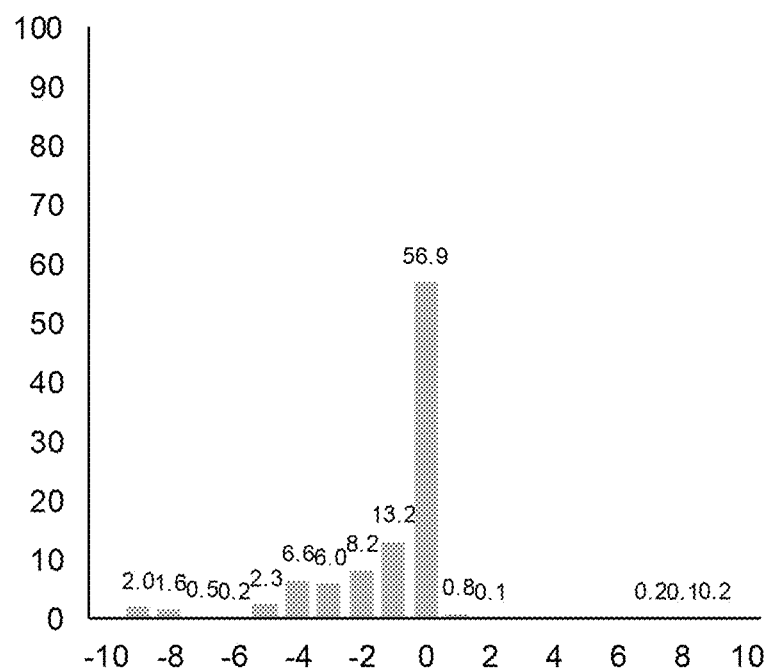
FIG. 14A is a diagram showing the probability distribution of indel mutations in TPH2 exon 9 when induced by Cas9 alone according to embodiments of the present teachings.
Figure 14B:
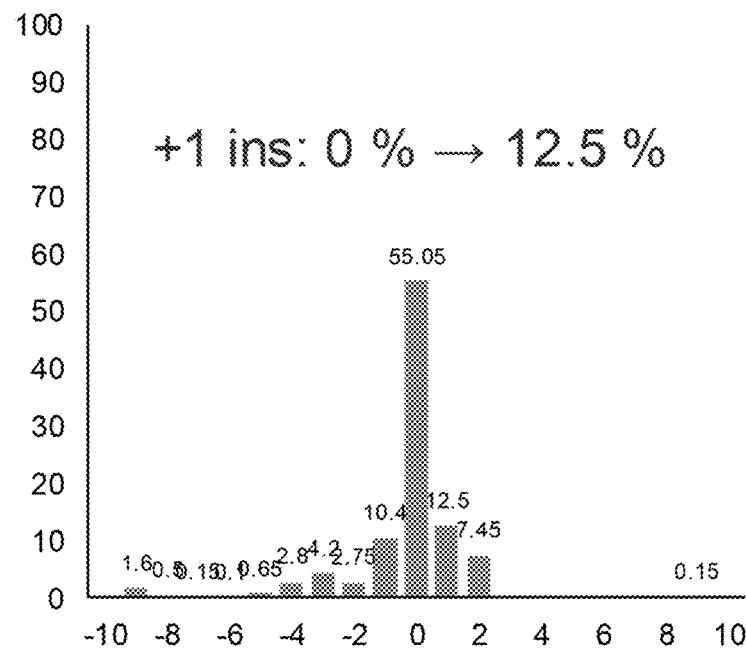
FIG. 14B is a diagram showing the probability distribution of indel mutations in TPH2 exon 9 when induced by Cas9 and POLM according to embodiments of the present teachings.
Figure 14C:
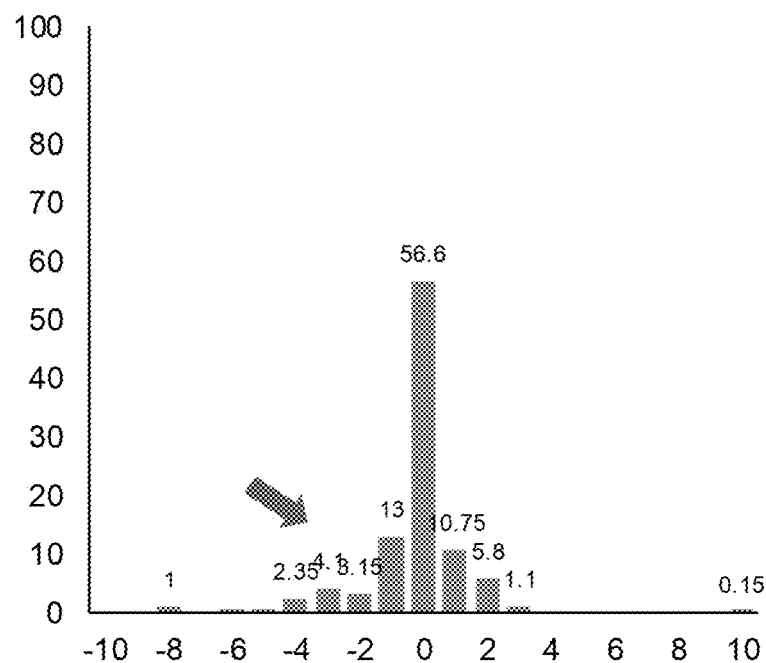
FIG. 14C is a diagram showing the probability distribution of indel mutations in TPH2 exon 9 when induced by Cas9 and EXOG according to embodiments of the present teachings.
Figure 14D:
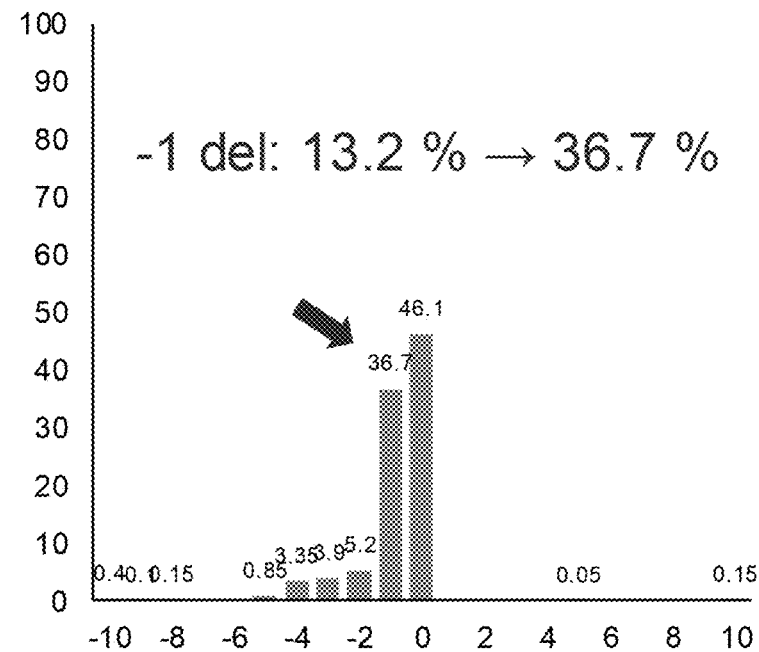
FIG. 14D is a diagram showing the probability distribution of indel mutations in TPH2 exon 9 when induced by Cas9 and T4pol according to embodiments of the present teachings.
Figure 14E:
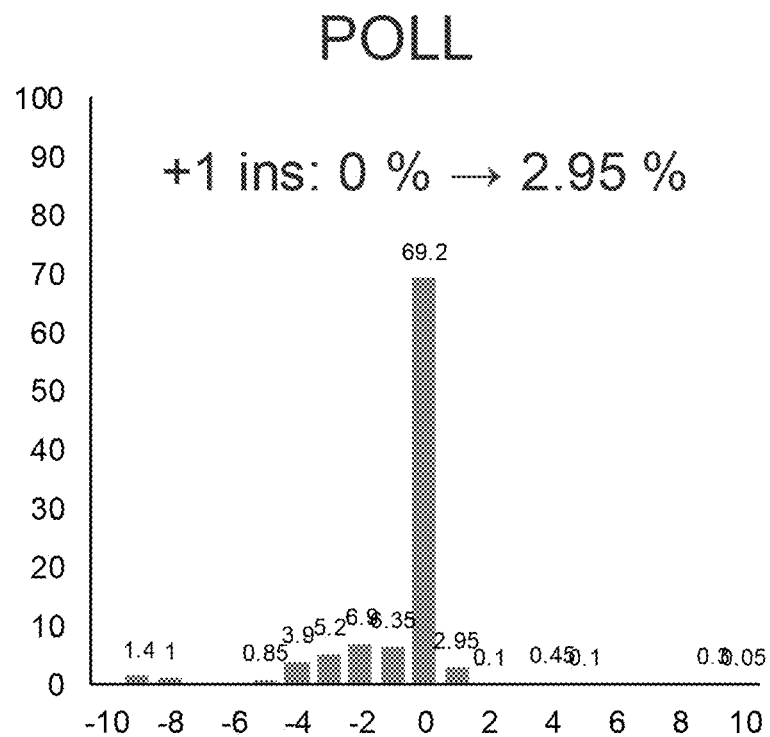
FIG. 14E is a diagram showing the probability distribution of indel mutations in TPH2 exon 9 when induced by Cas9 and POLL according to embodiments of the present teachings.
Figure 14F:
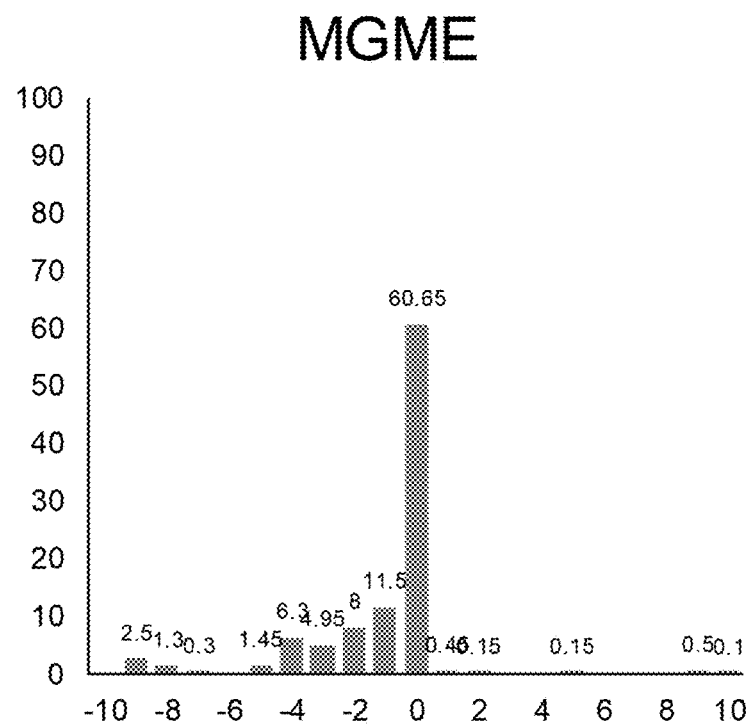
FIG. 14F is a diagram showing the probability distribution of indel mutations in TPH2 exon 9 when induced by Cas9 and MGME according to embodiments of the present teachings.
Figure 14G:
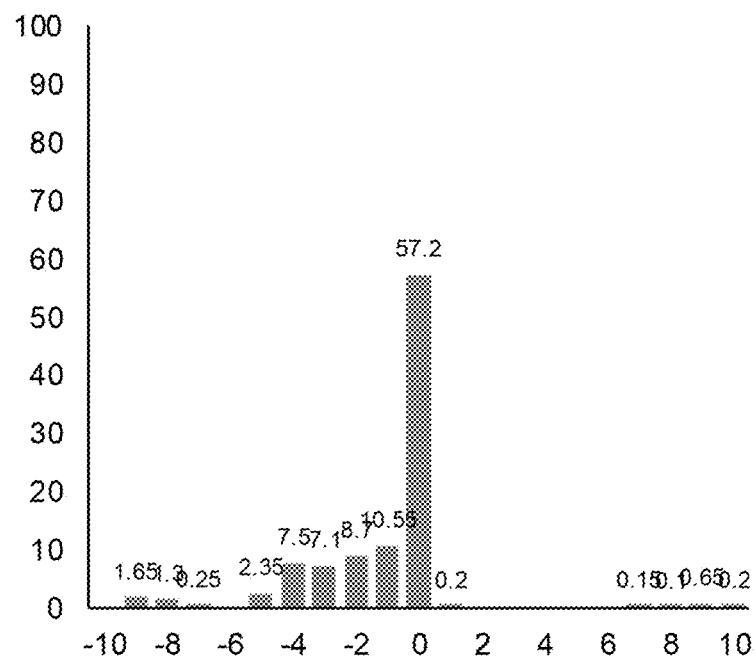
FIG. 14G is a diagram showing the probability distribution of indel mutations in TPH2 exon 9 when induced by Cas9 and RecJ according to embodiments of the present teachings.
Figure 14H:
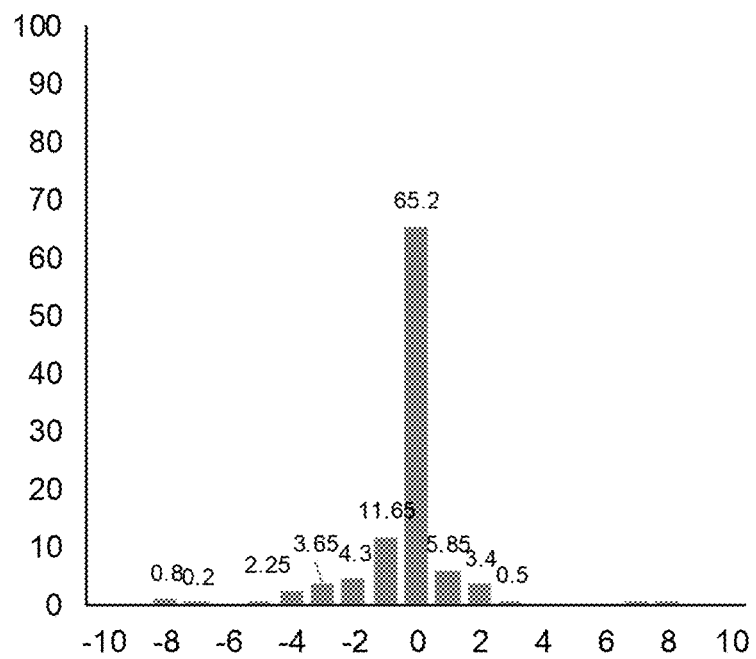
FIG. 14H is a diagram showing the probability distribution of indel mutations in TPH2 exon 9 when induced by Cas9 and nucS according to embodiments of the present teachings.

To test for the efficiency of inducing indels in a target gene using Cas9 and blunting enzymes, Cas9 and PCSK9 exon 12 targeting sgRNA were co-transferred into cultured mammalian cells in combination with DNA polymerase µ (POLM), EXOG, T4 DNA polymerase (T4pol), DNA polymerase λ (POLL), MGME1, RecJ exonuclease (RecJ) or Nuclease S1 (nucS). Cas9 and sgRNA alone served as the negative control. The occurrence of indels for the control and each of the combinations was measured. HEK293T cells were used. Results for each of the combinations are presented in FIGS. 11A-11H and comparisons between the control and blunting enzymes are presented in FIGS. 12A-12B.

POLM (FIG. 11B), T4pol (FIG. 11D) and POLL (FIG. 11E) were found to increase the percentage of +1 insertion from 14.4% to 19.6%, 14.4% to 36.75%, and 14.4% to 39.55%, respectively. EXOG (FIG. 11C), MGME1 (FIG. 11F) and RecJ (FIG. 11G) were found to increase the percentage of −1 deletion from 4.3% to 5.05%, 4.3% to 6.35%, and 4.3% to 5.5% respectively.

POLL (FIG. 12A) and T4pol (FIG. 12B) were found to increase the +1 insertion frequency from 9.4% to 35.0% and 9.4% to 30.3% respectively.

Example 2

Indels Editing in GYPB Gene Using Cas9 and Blunting Enzymes

To test for the efficiency of inducing indels in a target gene using Cas9 and blunting enzymes, Cas9 and GYPB targeting sgRNA were co-transferred into cultured mammalian cells in combination with DNA polymerase µ (POLM), EXOG, T4 DNA polymerase (T4pol), DNA polymerase λ (POLL), MGME, RecJ exonuclease (RecJ) or Nuclease S1 (nucS). Cas9 and sgRNA alone served as the negative control. The occurrence of indels for the control and each of the combinations was measured. Results for each of the combinations are presented in FIGS. 13A-13H.

POLM (FIG. 13B), T4pol (FIG. 13D) and POLL (FIG. 13E) were found to increase the percentage of +1 insertion mutations from 10.5% to 13.7%, 10.5% to 13.4%, and 10.5% to 22.1% respectively. T4 polymerase (FIG. 13D) was found to increase the percentage of −1 deletion mutations from 1.7% to 9.05%

Example 3

Indels Editing in TPH2 Gene Using Cas9 and Blunting Enzymes

To test for the efficiency of inducing indels in a target gene using Cas9 and blunting enzymes, Cas9 and TPH2 targeting sgRNA were co-transferred into cultured mammalian cells in combination with POLM, EXOG, T4 polymerase, DNA polymerase λ (POLL), MGME1, RecJ exonuclease (RecJ) or Nuclease S1 (nucS). Cas9 and sgRNA alone served as the negative control. The occurrence of indels for the control and each of the combinations was measured. Results for each of the combinations are presented in FIGS. 14A-14H.

DNA polymerase µ (POLM) (FIG. 14B) and DNA polymerase λ (POLL) (FIG. 14E) were found to increase the percentage of +1 insertion mutations from 0% to 12.5% and 0% to 2.95 respectively. T4 DNA polymerase (T4pol) (FIG. 14D) were found to increase the percentage of −1 deletion mutations from 13.2% to 36.7%.

One skilled in the art will appreciate further features and advantages of the invention based on the above-described embodiments. Accordingly, the invention is not to be limited by what has been particularly shown and described, except as indicated by the appended claims.

What is claimed is:

1. A composition comprising:
   (a) a target specific nuclease, wherein a target comprises a double-stranded DNA (dsDNA); and
   (b) a double strand break (DSB)-end blunting enzyme;
   wherein the target specific nuclease is selected from the group consisting of Cas12a, LbCas12a, FnCas12a, AsCas12a, Cas9, SpCas9, SaCas9, LZ3Cas9, Casccφ, and the double combinations of Cas9 nickase, zinc finger nuclease (ZFN), and TAL Effector Nuclease (TALEN),
   wherein the composition further comprises an inhibitor of the microhomology-mediated end joining (MMEJ) pathway, and
   wherein the MMEJ pathway inhibitor is a CtIP inhibitor selected from KLHL15 and PIN1.

2. The composition of claim 1 further comprising a guide RNA (gRNA).

3. The composition of claim 2, wherein the gRNA is a single guide RNA (sgRNA) comprising one or more stem loops.

4. The composition of claim 3, wherein the sgRNA comprises a nucleic acid sequence that is at least 75% identical to a nucleic acid sequence transcribed from a nucleic acid sequence selected from the group consisting of SEQ ID NOS 54-64.

5. The composition of claim 3, further comprising a MS2-binding protein, and wherein the MS2-binding protein is linked to the sgRNA by the one or more MS2 stem loops of the sgRNA.

6. The composition of claim 1, wherein the nuclease induces staggered ends upon cleaving the dsDNA, optionally wherein the nuclease is an altered scissile variant.

7. The composition of claim 1, wherein the nuclease comprises an amino acid sequence at least 85% identical to an amino acid sequence selected from the group consisting of SEQ ID NOs: 95-106.

8. The composition of claim 7, wherein the nuclease specifically binds to a protospacer-adjacent motif (PAM).

9. The composition of claim 8, wherein the PAM is selected from the group consisting of NNNNGATT, NNNNGNNN, NNG, NG, NGAN, NGNG, NGAG, NGCG, NAAG, NGN, NRN, NNGRRN, NNNRRT, TTTN, TTTV, TYCV, TATV, TYCV, TATV, TTN, KYTV, TYCV, TATV, and TBN.

10. The composition of claim 1, wherein the DSB-end blunting enzyme is a polymerase.

11. The composition of claim 10, wherein the polymerase is selected from the group consisting of DNA polymerase λ (lambda) (POLL), DNA polymerase µ (mu) (POLM), DNA polymerase β (beta) (POLB), DNA polymerase γ (gamma) (POLG), DNA polymerase τ (iota) (POLI), DNA polymerase η (eta) (POLH), TENT4A, DNA polymerase ν (nu) (POLN), DNA Ligase 4, DNTT, XRCC4, DNA Polymerase IV, fungi pol IV-like DNA polymerase, DNA polymerase/3'-5' exonuclease Pol X, and T4 DNA polymerase (T4pol).

12. The composition of claim 1, wherein the DSB-end blunting enzyme is a single-strand DNA specific nuclease.

13. The composition of claim 12, wherein the single-strand DNA specific nuclease is selected from the group consisting of MGME1, FEN1, DNA2, XRN2, EXOG, EXO1, AP endonuclease, RecJ exonuclease (RecJ), XseA, XseB, nuclease S1 (nucS), P1 nuclease, Artemis, T4 DNA polymerase (T4pol), and Csm1, optionally wherein the DSB-end blunting enzyme is modified with a protein tag comprising Myc, Flag or VStag.

14. The composition of claim 1, wherein the DSB-end blunting enzyme is covalently bound to the nuclease by a linker.

15. The composition of claim 14, wherein the linker is a peptide.

16. The composition of claim 1, further comprising an inhibitor of the MMEJ pathway, wherein the MMEJ pathway inhibitor is an MRN inhibitor selected from E1b55K and E4orf6.

17. A method of treating a disease caused by a frameshift mutation in a dsDNA in a subject comprising:
   administering to the subject a therapeutically effective amount of the composition of claim 1,
   wherein at least one base pair in the dsDNA is inserted or deleted within the frameshift mutation and optionally wherein the composition further comprises a guide RNA (gRNA).

* * * * *

SEQUENCE LISTING

```
<160> NUMBER OF SEQ ID NOS: 149

<210> SEQ ID NO 1
<211> LENGTH: 1728
<212> TYPE: DNA
<213> ORGANISM: Homo sapiens

<400> SEQUENCE: 1
atggatccca ggggtatctt gaaggcattt cccaagcggc agaaaattca tgctgatgca      60
tcatcaaaag tacttgcaaa gattcctagg agggaagagg gagaagaagc agaagagtgg     120
ctgagctccc ttcgggccca tgttgtgcgc actggcattg gacgagcccg ggcagaactc     180
tttgagaagc agattgttca gcatggcggc cagctatgcc ctgcccaggg cccaggtgtc     240
actcacattg tggtggatga aggcatggac tatgagcgag ccctccgcct tctcagacta     300
ccccagctgc ccccgggtgc tcagctggtg aagtcagcct ggctgagctt gtgccttcag     360
```

| | | |
|---|---|---|
| gagaggaggc tggtggatgt agctggattc agcatcttca tccccagtag gtacttggac | 420 | |
| catccacagc ccagcaaggc agagcaggat gcttctattc ctcctggcac ccatgaggcc | 480 | |
| ctgcttcaga cagcccttc tcctcctcct cctcccacca ggcctgtgtc tcctcccaa | 540 | |
| aaggcaaaag aggcaccaaa cacccaagcc cagcccatct ctgatgatga agccagtgat | 600 | |
| ggggaagaaa cccaggttag tgcagctgat ctggaagccc tcatcagtgg ccactacccc | 660 | |
| acctcccttg agggagattg tgagcctagc ccagcccctg ctgtcctgga taagtgggtc | 720 | |
| tgtgcacagc cctcaagcca aaggcgacc aatcacaacc tccatatcac agagaagctg | 780 | |
| gaagttctgg ccaaagccta cagtgttcag ggagacaagt ggagggccct gggctatgcc | 840 | |
| aaggccatca atgccctcaa gagcttccat aagcctgtca cctcgtacca ggaggcctgc | 900 | |
| agtatccctg ggattgggaa gcggatggct gagaaaatca tagagatcct ggagagcggg | 960 | |
| catttgcgga agctggacca tatcagtgag agcgtgcctg tcttggagct cttctccaac | 1020 | |
| atctggggag ctggaccaa gactgcccag atgtggtacc aacagggctt ccgaagtctg | 1080 | |
| gaagacatcc gcagccaggc ctccctgaca acccagcagg ccatcggcct gaagcattac | 1140 | |
| agtgacttcc tggaacgtat gcccagggag gaggctacag agattgagca gacagtccag | 1200 | |
| aaagcagccc aggcctttaa ctctgggctg ctgtgtgtgg catgtggttc ataccgacgg | 1260 | |
| ggaaaggcga cctgtggtga tgtcgacgtg ctcatcactc acccagatgg ccggtcccac | 1320 | |
| cggggtatct tcagccgcct ccttgacagt cttcggcagg aagggttcct cacagatgac | 1380 | |
| ttggtgagcc aagaggagaa tggtcagcaa cagaagtact tggggtgtg ccggctccca | 1440 | |
| gggccagggc ggcggcaccg gcgcctggac atcatcgtgg tgccctatag cgagtttgcc | 1500 | |
| tgtgccctgc tctacttcac cggctctgca cacttcaacc gctccatgcg agccctggcc | 1560 | |
| aaaaccaagg gcatgagtct gtcagaacat gccctcagca ctgctgtggt ccggaacacc | 1620 | |
| catggctgca aggtggggcc tggccgagtg ctgcccactc ccactgagaa ggatgtcttc | 1680 | |
| aggctcttag gcctccccta ccgagaacct gctgagcggg actggtga | 1728 | |

<210> SEQ ID NO 2
<211> LENGTH: 1488
<212> TYPE: DNA
<213> ORGANISM: Homo sapiens

<400> SEQUENCE: 2

| | | |
|---|---|---|
| atggctctgc caaagagaag acgcgcacgg gttgggtccc cttcagggga cgcagcctcc | 60 | |
| tctacacctc catctacgag atttccgggt gttgcaatat acctcgtcga gccccggatg | 120 | |
| ggacgcagta cgggctttt ccttacgggt ctcgcccgaa gtaaaggctt tcgggtgttg | 180 | |
| gacgcatgtt ctagtgaagc gacccatgtc gttatggagg agacgagtgc tgaggaggct | 240 | |
| gtaagctggc aagagcgccg aatggctgct gcaccacccg gctgcactcc gcctgctttg | 300 | |
| ttggatatat cttggctgac cgaaagtctt gggctggac aaccagtacc ggttgagtgc | 360 | |
| cgacatcgat tggaagtagc tggtccgagg aaaggccccc tctcaccggc ctggatgcct | 420 | |
| gcatatgcct gccaacggcc caccctctg acgcaccaca acactgggct tccgaggca | 480 | |
| ttggagatat tggcggaagc tgcgggcttt gaagggtccg aagggagatt gctcacgttc | 540 | |
| tgtagagcag catccgttct taaagcgctg ccgagtcccg taactacact gtctcaactg | 600 | |
| cagggcctgc cacacttcgg cgaacactca agccgggtcg tacaagaact cctggagcac | 660 | |
| ggggtctgcg aggaagttga gagggtgagg cgaagcgaac gataccaaac gatgaagctg | 720 | |
| tttacacaaa tctttggagt tggagtcaag acggcggaca gatggtatcg agaggggctt | 780 | |

| | | |
|---|---|---|
| cgaacgctcg acgatctgcg cgagcaaccg caaaagctga cccaacagca aaaggccgga | 840 |
| ctgcagcatc accaggacct ttcaacacct gttcttcggt ctgacgttga tgctctccaa | 900 |
| caagtcgtcg aggaggcagt aggccaggcc cttccgggcg ctactgttac gctcacggga | 960 |
| ggatttagac gcggcaaact tcaaggtcac gatgtcgatt tcttgataac tcacccaaaa | 1020 |
| gaggggcagg aggctggttt gctgccgcgg gtaatgtgcc gattgcaaga ccaaggcttg | 1080 |
| atactgtacc accaacacca acattcatgt tgcgagtcac ccacgcgcct cgcacagcag | 1140 |
| agccatatgg acgctttcga gagatcattt tgcatattca gacttcctca gcccccaggt | 1200 |
| gcggcggtcg gtgggtccac taggccgtgt ccatcttgga aggctgtgcg ggtggatttg | 1260 |
| gtcgtagcgc ccgtcagcca gtttcccttt gcactcctgg ggtggaccgg cagtaaactg | 1320 |
| ttccaaagag agctgcgaag gttctcacga aaagagaagg gcctctggct taactcccac | 1380 |
| ggcctgttcg accccgagca aaaaactttc tttcaggctg cgagcgaaga agatatcttc | 1440 |
| cgccacctgg gacttgagta ccttcccccc gagcagcgca acgcctga | 1488 |

<210> SEQ ID NO 3
<211> LENGTH: 1488
<212> TYPE: DNA
<213> ORGANISM: Homo sapiens

<400> SEQUENCE: 3

| | | |
|---|---|---|
| atggctctgc caaagagaag acgcgcacgg gttgggtccc cttcagggga cgcagcctcc | 60 |
| tctacacctc catctacgag atttccgggt gttgcaatat acctcgtcga gccccggatg | 120 |
| ggacgcagta gacgggcttt ccttacgggt ctcgcccgaa gtaaaggctt tcgggtgttg | 180 |
| gacgcatgtt ctagtgaagc gacccatgtc gttatggagg agacgagtgc tgaggaggct | 240 |
| gtaagctggc aagagcgccg aatggctgct gcaccacccg gctgcactcc gcctgctttg | 300 |
| ttggatatat cttggctgac cgaaagtctt ggggctggac aaccagtacc ggttgagtgc | 360 |
| cgacatcgat tggaagtagc tggtccgagg aaaggccccc tctcaccggc ctggatgcct | 420 |
| gcatatgcct gccaacggcc caccccctctg acgcaccaca acactgggct ttccgaggca | 480 |
| ttggagatat tggcggaagc tgcgggcttt gaagggtccg aagggagatt gctcacgttc | 540 |
| tgtagagcag catccgttct taaagcgctg ccgagtcccg taactacact gtctcaactg | 600 |
| cagggcctgc cacacttcgg cgaacactca agccgggtcg tacaagaact cctgagcac | 660 |
| ggggtctgcg aggaagttga gagggtgagg cgaagcgaac gataccaaac gatgaagctg | 720 |
| tttacacaaa tctttggagt tggagtcaag acggcggaca gatggtatcg agagggcttt | 780 |
| cgaacgctcg acgatctgcg cgagcaaccg caaaagctga cccaacagca aaaggccgga | 840 |
| ctgcagcatc accaggacct ttcaacacct gttcttcggt ctgacgttga tgctctccaa | 900 |
| caagtcgtcg aggaggcagt aggccaggcc cttccgggcg ctactgttac gctcacggga | 960 |
| ggatttagac gcggcaaact tcaaggtggc gatgtcgatt tcttgataac tcacccaaaa | 1020 |
| gaggggcagg aggctggttt gctgccgcgg gtaatgtgcc gattgcaaga ccaaggcttg | 1080 |
| atactgtacc accaacacca acattcatgt tgcgagtcac ccacgcgcct cgcacagcag | 1140 |
| agccatatgg acgctttcga gagatcaaaa tgcatattca gacttcctca gcccccaggt | 1200 |
| gcggcggtcg gtgggtccac taggccgtgt ccatcttgga aggctgtgcg ggtggatttg | 1260 |
| gtcgtagcgc ccgtcagcca gtttcccttt gcactcctgg ggtggaccgg cagtaaactg | 1320 |
| ttccaaagag agctgcgaag gttctcacga aaagagaagg gcctctggct taactcccac | 1380 |

| | |
|---|---|
| ggcctgttcg accccgagca aaaaactttc tttcaggctg cgagcgaaga agatatcttc | 1440 |
| cgccacctgg gacttgagta ccttcccccc gagcagcgca acgcctga | 1488 |

<210> SEQ ID NO 4
<211> LENGTH: 1488
<212> TYPE: DNA
<213> ORGANISM: Homo sapiens

<400> SEQUENCE: 4

| | |
|---|---|
| atggctctgc caaagagaag acgcgcacgg gttgggtccc cttcagggga cgcagcctcc | 60 |
| tctacacctc catctacgag atttccgggt gttgcaatat acctcgtcga gccccggatg | 120 |
| ggacgcagta gacgggcttt ccttacgggt ctcgcccgaa gtaaaggctt tcgggtgttg | 180 |
| gacgcatgtt ctagtgaagc gacccatgtc gttatggagg agacgagtgc tgaggaggct | 240 |
| gtaagctggc aagagcgccg aatggctgct gcaccacccg gctgcactcc gcctgctttg | 300 |
| ttggatatat cttggctgac cgaaagtctt ggggctggac aaccagtacc ggttgagtgc | 360 |
| cgacatcgat tggaagtagc tggtccgagg aaaggccccc tctcaccggc tggatgcct | 420 |
| gcatatgcct gccaacggcc cacccctctg acgcaccaca acactgggct ttccgaggca | 480 |
| ttggagatat tggcggaagc tgcgggcttt gaagggtccg aagggagatt gctcacgttc | 540 |
| tgtagagcag catccgttct taaagcgctg ccgagtcccg taactacact gtctcaactg | 600 |
| cagggcctgc cacacttcgg cgaacactca agcgggtcg tacaagaact cctggagcac | 660 |
| ggggtctgcg aggaagttga gagggtgagg cgaagcgaac gataccaaac gatgaagctg | 720 |
| tttacacaaa tctttggagt tggagtcaag acggcggaca gatggtatcg agaggggctt | 780 |
| cgaacgctcg acgatctgcg cgagcaaccg caaaagctga cccaacagca aaaggccgga | 840 |
| ctgcagcatc accaggacct ttcaacacct gttcttcggt ctgacgttga tgctctccaa | 900 |
| caagtcgtcg aggaggcagt aggccaggcc cttccgggcg ctactgttac gctcacggga | 960 |
| ggatttagac gcggcaaact tcaaggtggc gatgtcgatt tcttgataac tcacccaaaa | 1020 |
| gaggggcagg aggctggttt gctgccgcgg gtaatgtgcc gattgcaaga ccaaggcttg | 1080 |
| atactgtacc accaacacca acattcatgt tgcgagtcac ccacgcgcct cgcacagcag | 1140 |
| agccatatgg acgctttcga gagatcattt tgcatattca gacttcctca gccccaggt | 1200 |
| gcggcggtcg gtgggtccac taggccgtgt ccatcttgga aggctgtgcg ggtgatttg | 1260 |
| gtcgtagcgc ccgtcagcca gtttcccttt gcactcctgg ggtggaccgg cagtaaactg | 1320 |
| ttccaaagag agctgcgaag gttctcacga aaagagaagg gcctctggct taactcccac | 1380 |
| ggcctgttcg accccgagca aaaaactttc tttcaggctg cgagcgaaga agatatcttc | 1440 |
| cgccacctgg gacttgagta ccttcccccc gagcagcgca acgcctga | 1488 |

<210> SEQ ID NO 5
<211> LENGTH: 1674
<212> TYPE: DNA
<213> ORGANISM: Homo sapiens

<400> SEQUENCE: 5

| | |
|---|---|
| atggctctgc caaagagaag acgcgcacgg gttgggtccc cttcagggga cgcagcctcc | 60 |
| tctacacctc catctacgag atttccgggt gttgcaatat acctcgtcga gccccggatg | 120 |
| ggacgcagta gacgggcttt ccttacgggt ctcgcccgaa gtaaaggctt tcgggtgttg | 180 |
| gacgcatgtt ctagtgaagc gacccatgtc gttatggagg agacgagtgc tgaggaggct | 240 |
| gtaagctggc aagagcgccg aatggctgct gcaccacccg gctgcactcc gcctgctttg | 300 |

| | |
|---|---|
| ttggatatat cttggctgac cgaaagtctt ggggctggac aaccaatccc cagtaggtac | 360 |
| ttggaccatc cacagcccag caaggcagag caggatgctt ctattcctcc tggcacccat | 420 |
| gaggccctgc ttcagacagc cctttctcct cctcctcctc ccaccaggcc tgtgtctcct | 480 |
| ccccaaaagg caaagagggc accaaacacc caagcccagc ccatctctga tgatgaagcc | 540 |
| agtgatgggg aagaaaccca ggttagtgca gctgatctgg aagccctcat cagtggccac | 600 |
| tacccccacct cccttgaggg agattgtgag cctagcccag ccctgctgt cctggataag | 660 |
| tgggtctgtg cacagccctc aagccagaag gcgaccaatc acaacctcca tatcacagag | 720 |
| aagctggaag ttctggccaa agcctacagt gttcagggag acaagtggag ggccctgggc | 780 |
| tatgccaagg ccatcaatgc cctcaagagc ttccataagc ctgtcacctc gtaccaggag | 840 |
| gcctgcagta tccctgggat tgggaagcgg atggctgaga aaatcataga gatcctggag | 900 |
| agcgggcatt tgcggaagct ggaccatatc agtgagagcg tgcctgtctt ggagctcttc | 960 |
| tccaacatct ggggagctgg gaccaagact gcccagatgt ggtaccaaca gggcttccga | 1020 |
| agtctggaag acatccgcag ccaggcctcc ctgacaaccc agcaggccat cggcctgaag | 1080 |
| cattacagtg acttcctgga acgtatgccc agggaggagg ctacagagat tgagcagaca | 1140 |
| gtccagaaag cagcccaggc cttaactct gggctgctgt gtgtggcatg tggttcatac | 1200 |
| cgacggggaa aggcgacctg tggtgatgtc gacgtgctca tcactcaccc agatggccgg | 1260 |
| tcccaccggg gtatcttcag ccgcctcctt gacagtcttc ggcaggaagg gttcctcaca | 1320 |
| gatgacttgg tgagccaaga ggagaatggt cagcaacaga agtacttggg ggtgtgccgg | 1380 |
| ctcccagggc cagggcggcg gcaccggcgc ctggacatca tcgtggtgcc ctatagcgag | 1440 |
| tttgcctgtg ccctgctcta cttcaccggc tctgcacact tcaaccgctc catgcgagcc | 1500 |
| ctggccaaaa ccaagggcat gagtctgtca gaacatgccc tcagcactgc tgtggtccgg | 1560 |
| aacacccatg ctgcaaggt ggggcctggc cgagtgctgc ccactcccac tgagaaggat | 1620 |
| gtcttcaggc tcttaggcct cccctaccga gaacctgctg agcgggactg gtga | 1674 |

<210> SEQ ID NO 6
<211> LENGTH: 1401
<212> TYPE: DNA
<213> ORGANISM: Homo sapiens

<400> SEQUENCE: 6

| | |
|---|---|
| atggctctgc caaagagaag acgcgcacgg gttgggtccc cttcaggga cgcagcctcc | 60 |
| tctacacctc catctacgag atttccgggt gttgcaatat acctcgtcga gccccggatg | 120 |
| ggacgcagta gacgggcttt ccttacgggt ctcgcccgaa gtaaaggctt tcgggtgttg | 180 |
| gacgcatgtt ctagtgaagc gacccatgtc gttatggagg agacgagtgc tgaggaggct | 240 |
| gtaagctggc aagagcgccg aatggctgct gcaccaccg gctgcactcc gcctgctttg | 300 |
| ttggatatat cttggctgac cgaaagtctt ggggctggac aaccagtacc ggttgagtgc | 360 |
| cgacatcgat tggaagtagc tggtccgagg aaaggccccc tctcatcaag ccagaaggcg | 420 |
| accaatcaca acctccatat cacagagaag ctggaagttc tggccaaagc ctacagtgtt | 480 |
| cagggagaca gtggagggc ctgggctat gccaaggcca tcaatgccct caagagcttc | 540 |
| cataagcctg tcacctcgta ccaggaggcc tgcagtatcc ctgggattgg aagcggatg | 600 |
| gctgagaaaa tcatagagat cctggagagc gggcatttgc ggaagctgga ccatatcagt | 660 |
| gagagcgtgc ctgtcttgga gctcttctcc aacatctggg gagctgggac caagactgcc | 720 |

```
cagatgtggt accaacaggg cttccgaagt ctggaagaca tccgcagcca ggcctccctg    780
acaacccagc aggccatcgg cctgaagcat tacagtgact tcctggaacg tatgcccagg    840
gaggaggcta cagagattga gcagacagtc cagaaagcag cccaggcctt taactctggg    900
ctgctgtgtg tggcatgtgg ttcataccga cggggaaagg cgacctgtgg tgatgtcgac    960
gtgctcatca ctcacccaga tggccggtcc caccggggta tcttcagccg cctccttgac   1020
agtcttcggc aggaagggtt cctcacagat gacttggtga ccaagagga gaatggtcag   1080 caacagaagt acttgggggt gtgccggctc ccagggccag ggcggcggca ccggcgcctg   1140
gacatcatcg tggtgcccta tagcgagttt gcctgtgccc tgctctactt caccggctct   1200
gcacacttca accgctccat gcgagccctg gccaaaacca agggcatgag tctgtcagaa   1260
catgccctca gcactgctgt ggtccggaac acccatggct gcaaggtggg gcctggccga   1320
gtgctgccca ctcccactga aaggatgtc ttcaggctct taggcctccc ctaccgagaa   1380
cctgctgagc gggactggtg a                                             1401

<210> SEQ ID NO 7
<211> LENGTH: 1224
<212> TYPE: DNA
<213> ORGANISM: Homo sapiens

<400> SEQUENCE: 7
atggactata aggaccacga cggagactac aaggatcatg atattgatta caaagacgat     60
gacgataaga tggccccaaa gaagaagcgg aaggtcggta tccacggagt cccagcagcc    120
gctatcaaga gtatcgcttc ccgcctccgg ggttcccgtc gttttctgag cggcttcgtg    180
gctggggctg tagtgggcgc tgcgggagct gggctcgcgg ccctgcagtt cttccggagt    240
cagggcgctg agggagcgtt gacagggaag cagccggatg gatctgcaga aaaggctgtc    300
ttggaacaat ttggattccc tttaactgga acagaggcaa ggtgttacac taatcacgct    360
ttgtcttatg atcaggcaaa gcgggtgcct agatgggttc ttgaacatat ttccaaaagc    420
aagataatgg gtgatgcaga cagaaagcat tgtaaattta gcctgatcc caatatccct    480 ccaaccttca gtgccttcaa tgaagattat gttggaagtg ggtggtcacg aggacacatg    540
gctccagcag gaaataacaa attttcaagt aaagccatgg ctgaaacctt ttacctttct    600
aacattgtgc tcaggatttt gataataat tctggatatt ggaacagaat agaaatgtac    660
tgtcgagagc tgacagaaag gtttgaagat gtttgggtgg tatctgggcc tttgacctta    720
cctcagacta gaggcgatgg aaagaaaata gttagttacc aggtgattgg cgaggacaac    780
gtggcagtcc cctcacacct ttataaggta atcctggccc gcagaagctc agtatctacc    840
gaaccactgg cgctaggggc ctttgtggta cccaatgaag ccatcggctt ccagccccag    900
ttaactgaat tccaagtgag cctccaggac ctagagaagt tgtcaggact ggtgtttttt    960
cctcatttgg atagaactag tgatatccgg aatatctgct ctgtggacac ctgtaagctc   1020
ctggatttcc aggagttcac cttgtacttg agtacaagaa agattgaagg agcccgatca   1080
gtgctcagac tggaaaagat catggaaaac ttgaagaatg cagagattga accagatgat   1140
tactttatga gtcgctatga agaagctga gaagaactca agctaagga gcagtcagga   1200 acccagataa gaaagccatc ctag                                          1224

<210> SEQ ID NO 8
<211> LENGTH: 981
<212> TYPE: DNA
<213> ORGANISM: Aspergillus oryzae
```

<400> SEQUENCE: 8

```
atggactata aggaccacga cggagactac aaggatcatg atattgatta caaagacgat    60
gacgataaga tggccccaaa gaagaagcgg aaggtcggta tccacggagt cccagcagcc   120
cccaggctcc tgcctatatc cgccgcaacc ctcgctctgg cccaacttac ttatggctgg   180
ggcaatctgg gccatgaaac tgtcgcttac attgctcaat ctttcgtcgc gtcaagtacc   240
gagagcttct gccaaaacat attgggggac gactctactt catatttggc caacgtggca   300
acatgggcgg atacttacaa atatacggat gcgggcgaat ttagcaaacc ctatcacttt   360
atagacgcac aggataaccc accccaatca tgcggggttg actatgacag ggattgtggg   420
tccgccgggt gctctatctc agcaattcaa aactacacga acatactgct ggaaagtcct   480
aatgggagcg aggctctgaa cgcactgaaa tttgttgtcc atattatagg agatattcat   540
cagccgttgc atgacgaaaa tttggaggca ggaggaaatg gcatcgatgt gacatatgac   600
ggggagacta cgaaccttca tcacatttgg gatactaaca tgccggaaga agccgcggga   660
gggtatagct tgtccgtggc aaagacttat gcagatttgc tcaccgagag gataaaaaca   720
ggtacttact cctcaaaaaa ggatagctgg accgatggaa ttgatataaa agatccagta   780
agcacgtcta tgatttgggc ggcggatgca aacacctacg tctgtagtac ggtacttgat   840
gacggtcttg cttatattaa ttccactgac ctctccggcg aatactacga caagtcacaa   900
ccagtcttcg aagaacttat agccaaagcg ggttatagac ttgcggcttg gctggacctt   960
attgcgtccc agcccagctg a                                             981
```

<210> SEQ ID NO 9
<211> LENGTH: 912
<212> TYPE: DNA
<213> ORGANISM: Penicillium citrinum

<400> SEQUENCE: 9

```
atggactata aggaccacga cggagactac aaggatcatg atattgatta caaagacgat    60
gacgataaga tggccccaaa gaagaagcgg aaggtcggta tccacggagt cccagcagcc   120
tggggtgccc tcggccatgc gacagtagcc tatgtagctc aacattatgt aagtcccgaa   180
gccgcgtctt gggcgcaagg catttttggt tcctcaagtt catcatattt ggcttcaata   240
gcttcttggg ccgatgaata ccggctgacc tccgccggca gtggagtgc tagtttgcac   300
tttattgatg ccgaagataa tccacccacg aactgcaacg tcgactatga acgggattgt   360
ggatcttccg ggtgctccat atcagctata gctaattata cacagcgagt aagtgactca   420
agtctttctt ccgaaaatca tgcggaagca ctgcgattct tggtacactt catcggggac   480
atgacacagc ctttgcacga tgaagcctac gcggtgggcg gtaataaaat aaacgttaca   540
tttgatggtt atcatgacaa cctgcacagc gattgggaca cgtatatgcc acagaaattg   600
atcggcggtc atgcgctttc agacgcagag tcctgggcaa agacgctggt tcaaaatatc   660
gaatctggaa attacaccgc gcaggccatt ggttggatca aaggcgacaa catctcagaa   720
ccaatcacaa ccgcaacgcg atgggcgtca gacgccaatg ctcttgtatg tacggtggtt   780
atgcctcacg gagctgcggc acttcagaca ggtgaccttt atccgactta ctacgactct   840
gtgatagata ctattgaact tcaaatagct aaaggaggct accggctcgc gaactggata   900
aacgagatat ag                                                       912
```

<210> SEQ ID NO 10

<211> LENGTH: 1197
<212> TYPE: DNA
<213> ORGANISM: Homo sapiens

<400> SEQUENCE: 10

| | | | | | |
|---|---|---|---|---|---|
| atggactata | aggaccacga | cggagactac | aaggatcatg | atattgatta | caaagacgat | 60 |
| gacgataaga | tggccccaaa | gaagaagcgg | aaggtcggta | tccacggagt | cccagcagcc | 120 |
| aagatgaagt | tatttcagac | catttgcagg | cagctcagga | gttcaaagtt | ttctgtggaa | 180 |
| tcagctgccc | ttgtggcttt | ctctacttcc | tcttactcat | gtggccggaa | gaaaaaagtg | 240 |
| aacccatatg | aagaagtgga | ccaagaaaaa | tactctaatt | tagttcagtc | tgtcttgtca | 300 |
| tccagaggcg | tcgcccagac | cccgggatcg | gtggaggaag | atgctttgct | ctgtggaccc | 360 |
| gtgagcaagc | ataagctgcc | aaaccaaggt | gaggacagac | gagtgccaca | aaactggttt | 420 |
| cctatcttca | atccagagag | aagtgataaa | ccaaatgcaa | gtgatccttc | agttcctttg | 480 |
| aaaatcccct | tgcaaaggaa | tgtgatacca | agtgtgaccc | gagtccttca | gcagaccatg | 540 |
| acaaaacaac | aggttttctt | gttggagagg | tggaaacagc | ggatgattct | ggaactggga | 600 |
| gaagatggct | ttaaagaata | cacttcaagt | tttcatgttt | gtgatcatgt | gtatatgaag | 660 |
| aacctagcca | gggacgtctt | tttacaaggg | aaacggttcc | acgaagcctt | ggaaagcata | 720 |
| ctttcacccc | aggaaacctt | aaaagagaga | tgaaaaatc | tcctcaagtc | tggttacatt | 780 |
| gaaagtgtcc | agcatattct | gaaagatgtc | agtggagtgc | gagctcttga | agtgctgtt | 840 |
| caacatgaaa | ccttaaacta | tataggtctg | ctggactgtg | tggctgagta | tcagggcaag | 900 |
| ctctgtgtga | ttgattggaa | gacatcagag | aaaccaaagc | cttttattca | aagtacattt | 960 |
| gacaacccac | tgcaagttgt | ggcatacatg | ggtgccatga | accatgatac | caactacagc | 1020 |
| tttcaggttc | aatgtggctt | aattgtggtg | gcctacaaag | atggatcacc | tgcccaccca | 1080 |
| catttcatgg | atgcagagct | ctgttcccag | tactggacca | agtggcttct | tcgactagaa | 1140 |
| gaatatacgg | aaaagaaaaa | gaaccagaat | attcagaaac | cagaatattc | agaatag | 1197 |

<210> SEQ ID NO 11
<211> LENGTH: 1854
<212> TYPE: DNA
<213> ORGANISM: Escherichia coli

<400> SEQUENCE: 11

| | | | | | |
|---|---|---|---|---|---|
| atggactata | aggaccacga | cggagactac | aaggatcatg | atattgatta | caaagacgat | 60 |
| gacgataaga | tggccccaaa | gaagaagcgg | aaggtcggta | tccacggagt | cccagcagcc | 120 |
| gtgaagcagc | agatccaact | tagacgaagg | gaagtcgacg | aaacagcgga | ccttccggct | 180 |
| gagttgcctc | cccttcttag | acgattgtat | gcaagtcgcg | gggttcgctc | tgcacaggaa | 240 |
| cttgagcgct | ctgtcaaggg | aatgctgccc | tggcaacagt | tgagtggtgt | tgaaaaggcc | 300 |
| gttgagattc | tctataatgc | attcagggaa | ggaactcgga | tcatagtggt | aggtgatttc | 360 |
| gacgctgatg | gagcaacttc | aaccgcgttg | agcgtactcg | ccatgcgctc | tctcgggtgc | 420 |
| tcaaacattg | actatttggt | ccccaatcga | tttgaagatg | gttatggact | cagcccggag | 480 |
| gtggttgacc | aagcgcatgc | ccggggcgcc | cagctcatcg | tcactgtcga | taacgggata | 540 |
| agctctcacg | ccggtgtcga | acacgctcgc | agcctcggga | ttcccgtgat | tgtgactgac | 600 |
| caccaccttc | cggagatac | actccccgct | gctgaggcaa | taatcaatcc | taaccttcgg | 660 |
| gattgtaact | ttccgagcaa | atcactcgca | ggggtagggg | tcgcattcta | tctcatgctg | 720 |
| gcgctcagaa | cgttccttcg | agatcagggg | tggttcgacg | agcggaacat | agctatacct | 780 |

```
aatttggccg aacttttgga tctcgtggcg cttggcacgg ttgcagacgt tgtccctctg      840
gacgcgaaca atcgaatttt gacatggcag ggaatgtcta ggattagagc cgggaaatgt      900
aggcctggta ttaaagctct cttggaggtg gcaaaccgag atgcccagaa gctcgcagct      960
agtgacttgg gttttgcttt gggaccccgc ctgaacgctg cagggcgcct ggatgacatg     1020
agcgtaggcg tagcacttct cttgtgcgac aatataggtg aagcgagagt acttgcaaac     1080
gaactggatg cgcttaacca gacaagaaag gaaattgagc agggcatgca gatagaggcg     1140
cttaccctgt gtgaaaagct cgaacgatct cgagacaccc ttccaggcgg actcgcgatg     1200
tatcaccctg aatggcacca gggtgtcgta ggcatcctcg cgtcccgcat aaaagaaagg     1260
ttccaccggc cagttatagc ttttgctccc gcaggtgatg aacccttaa aggatctggg      1320 agatctatcc aggggcttca tatgcgggat gctttggagc ggcttgacac tctttaccca     1380
ggtatgatgc tcaagttcgg cggtcatgct atggctgccg gcctctcact ggaggaggat     1440
aaatttaaac tctttcaaca gaggttcggg gagcttgtga cggaatggct ggatccgtcc     1500
ttgcttcaag gcgaagtagt tagcgacgga cctctcagtc ctgcggagat gacgatggag     1560
gtagcgcaac tgctcaggga cgctgggccg tggggccaga tgttcccgga gccgttgttc     1620
gacggccatt tcaggttgct tcaacagcgc ctcgtcggag aacggcatct caaagtaatg     1680
gttgagccag tcggtggcgg cccctgctt gatggcatcg ctttcaatgt agacactgca      1740
ctgtggcccg ataatggcgt tcgagaggtt cagcttgcct ataagctgga tattaacgag     1800
tttcgaggga accgatctct gcaaattata atagacaata tctggcccat atag           1854
```

<210> SEQ ID NO 12
<211> LENGTH: 2814
<212> TYPE: DNA
<213> ORGANISM: Bacteriophage T4

<400> SEQUENCE: 12

```
atggactata aggaccacga cggagactac aaggatcatg atattgatta caaagacgat       60
gacgataaga tggccccaaa gaagaagcgg aaggtcggta tccacggagt cccagcagcc      120
aaggaattct atattagtat cgagacagtg gaaacaaca ttgtagagcg gtatatcgat       180
gaaaacggca agaaaggac tcgagaggtc gaataccttc cgaccatgtt tcgccactgt       240
aaagaagaat ctaagtacaa agatatttac gggaagaatt gcgctcccca aaaatttccc      300
tccatgaagg atgctcgaga ctggatgaag cgcatggagg acataggtct cgaagcattg      360
gggatgaacg attttaagtt ggcttacatc tccgacactt acgggtcaga aatagtgtac      420
gataggaagt tcgttcgcgt ggcaaattgc gatatagagg tcactggaga taagttcccg      480
gacccgatga aggcggagta cgaaattgac gctataacac actatgactc aatcgacgac      540
cggttctatg tatttgacct gctcaattcc atgtacgggt ctgtaagcaa gtgggacgct      600
aaactcgcgg ctaaacttga ctgtgaagga ggggatgaag tacctcagga atcttggac      660 agggtaatct acatgcccctt tgacaatgaa cgagatatgc ttatggagta cattaatttg     720
tgggagcaaa agcgccccgc aatatttaca ggctggaaca tagaagggtt cgatgtaccg     780
tatattatga atcgggtaaa gatgatcctc ggagagagaa gcatgaaaag atttccacct     840
attggcagag tgaaatctaa gttgatacaa acatgtatg gctcaaaaga gatctattca      900
atagatggag ttagcatact cgactacctg gatctgtata aaaagtttgc ttttaccaac     960
ttgcctagct tctcccttga aagtgtcgcc caacacgaga ccaagaaagg taagctgccg    1020
```

```
tacgatggcc cgattaataa actgcgcgag accaaccatc aaagatatat tagctacaac   1080
ataattgatg tcgaatctgt gcaagccatt gataagataa ggggctttat cgaccttgtc   1140
ctgtcaatgt cctattacgc caaaatgccg ttctcaggtg taatgtcacc cataaagacg   1200
tgggatgcga tcatcttcaa ttctctcaag ggagagcaca aggtgatccc caacagggg    1260 tcccacgtaa agcagtcctt cccgggagct tttgtctttg agccaaagcc gatcgcccga   1320
aggtatatca tgtctttcga ccttacgtca ctttaccctt caattattcg acaagtgaat   1380
atatcacccg agactatccg gggccagttt aaggtacacc caatccatga gtacatagcc   1440
ggtacagccc caaacccag tgacgaatac tcttgcagcc ctaatgggtg gatgtacgac    1500
aaacaccagg agggcataat cccaaaggaa atcgcgaaag tatttttcca acggaaagac   1560
tggaagaaaa agatgttcgc ggaggaaatg aacgccgagg ctattaaaaa aatcattatg   1620
aagggagcgg gtagctgttc taccaagcca gaggtagagc gctacgtcaa attcagtgat   1680
gacttcctta atgagctgag taactacaca gagtctgtac tgaactcact gattgaggaa   1740
tgtgaaaaag ccgcaacact tgctaatacc aatcaactga atcggaagat cctgattaat   1800
tcactgtatg gcgccttggg caacattcat ttcagatact acgacctcag gaatgccacg   1860
gccattacaa ttttcggtca ggtcgggatc cagtggatcg cccgaaaaat caacgagtac   1920
ctcaataaag tgtgtggtac caatgacgag gattttatcg cagcaggcga taccgatagc   1980
gtgtatgttt gcgtcgacaa ggtcattgaa aaggtagggc tggatcggtt taaggagcag   2040
aatgatcttg tcgagtttat gaaccagttt ggtaaaaaaa agatggaacc gatgatagat   2100
gtagcgtacc gagaactttg tgactacatg aataatcgcg agcacttgat gcacatggac   2160
agggaagcga tttcatgccc cccactcggt tcaagggcg tagggggttt ctggaaagct    2220
aagaaacggt acgccctcaa cgtctatgac atggaagaca gaggttcgc ggaacctcat    2280 ttgaagataa tggggatgga gacgcaacag tcctcaactc caaaggctgt gcaagaggct   2340
ctggaagaaa gcatacgacg catactccag gaggggaag agagtgttca ggagtattat    2400
aaaaactttg aaaaggagta ccgccagctt gactacaagg taatcgcgga ggttaagact   2460
gcgaatgata tcgccaaata tgatgataaa ggatggcccg gtttcaaatg ccctttccat   2520
atacgagggg tcctcaccta ccgccgcgcc gtgtctggtc tgggggtcgc accaattctc   2580
gacgaaaata aggttatggt actcccactc cgcgagggga atccgtttgg tgacaaatgc   2640
atcgcctggc cgtctggtac ggagctcccc aaggaaatac gcagcgacgt cctcagttgg   2700
atcgaccact ccacactgtt tcagaagtca ttcgttaaac ctctggccgg gatgtgtgaa   2760
tccgcgggta tggactacga ggagaaagct tcattggact ttcttttcgg ttga         2814

<210> SEQ ID NO 13
<211> LENGTH: 2814
<212> TYPE: DNA
<213> ORGANISM: Bacteriophage T4

<400> SEQUENCE: 13
atggactata aggaccacga cggagactac aaggatcatg atattgatta caaagacgat     60
gacgataaga tggcccccaaa gaagaagcgg aaggtcggta tccacggagt cccagcagcc   120
aaggaattct atattagtat cgagacagtg ggaaacaaca ttgtagagcg gtatatcgat   180
gaaaacggca agaaaggac tcgagaggtc gaataccttc cgaccatgtt tcgccactgt   240
aaagaagaat ctaagtacaa agatatttac gggaagaatt gcgctcccca aaaatttccc   300
tccatgaagg atgctcgaga ctggatgaag cgcatggagg acataggtct cgaagcattg   360
```

```
gggatgaacg attttaagtt ggcttacatc tccgacactt acgggtcaga aatagtgtac    420
gataggaagt tcgttcgcgt ggcaaattgc gatatagagg tcactggaga taagttcccg    480
gacccgatga aggcggagta cgaaattgac gctataacac actatgactc aatcgacgac    540
cggttctatg tatttgacct gctcaattcc atgtacgggt ctgtaagcaa gtgggacgct    600
aaactcgcgg ctaaacttga ctgtgaagga ggggatgaag tacctcagga atcttggac    660 agggtaatct acatgcccctt tgacaatgaa cgagatatgc ttatgagta cattaatttg    720 tgggagcaaa agcgccccgc aatatttaca ggctggaaca tagaagggtt cgatgtaccg    780
tatattatga atcgggtaaa gatgatcctc ggagagagaa gcatgaaaag attttcacct    840
attggcagag tgaaatctaa gttgatacaa aacatgtatg gctcaaaaga gatctattca    900
atagatggag ttagcatact cgactacctg gatctgtata aaaagtttgc ttttaccaac    960
ttgcctagct tctcccttga aagtgtcgcc caacacgaga ccaagaaagg taagctgccg   1020
tacgatggcc cgattaataa actgcgcgag accaaccatc aaagatatat tagcgccaac   1080
ataattgatg tcgaatctgt gcaagccatt gataagataa ggggctttat cgaccttgtc   1140
ctgtcaatgt cctattacgc caaaatgccg ttctcaggtg taatgtcacc cataaagacg   1200
tgggatgcga tcatcttcaa ttctctcaag ggagagcaca aggtgatccc ccaacagggg   1260
tcccacgtaa agcagtcctt cccgggagct tttgtctttg agccaaagcc gatcgcccga   1320
aggtatatca tgtctttcga ccttacgtca ctttacccctt caattattcg acaagtgaat   1380
atatcacccg agactatccg gggccagttt aaggtacacc caatccatga gtacatagcc   1440
ggtacagccc caaacccag tgacgaatac tcttgcagcc ctaatgggtg gatgtacgac   1500
aaacaccagg agggcataat cccaaaggaa atcgcgaaag tattttttcca acggaaagac   1560 tggaagaaaa agatgttcgc ggaggaaatg aacgccgagg ctattaaaaa aatcattatg   1620
aagggagcgg gtagctgttc taccaagcca gaggtagagc gctacgtcaa attcagtgat   1680
gacttcctta atgagctgag taactacaca gagtctgtac tgaactcact gattgaggaa   1740
tgtgaaaaag ccgcaacact tgctaatacc aatcaactga atcggaagat cctgattaat   1800
tcactgtatg gcgccttggg caacattcat ttcagatact acgacctcag gaatgccacg   1860
gccattacaa ttttcggtca ggtcgggatc cagtggatcg cccgaaaaat caacgagtac   1920
ctcaataaag tgtgtggtac caatgacgag gattttatcg cagcaggcga taccgatagc   1980
gtgtatgttt gcgtcgacaa ggtcattgaa aaggtagggc tggatcggtt taaggagcag   2040
aatgatcttg tcgagtttat gaaccagttt ggtaaaaaaa agatgaaacc gatgatagat   2100
gtagcgtacc gagaactttg tgactacatg aataatcgcg agcacttgat gcacatggac   2160
agggaagcga tttcatgccc cccactcggt tcaaagggcg tagggggttt ctggaaagct   2220
aagaaacggt acgccctcaa cgtctatgac atggaagaca gaggttcgc ggaacctcat   2280 ttgaagataa tggggatgga gacgcaacag tcctcaactc caaaggctgt gcaagaggct   2340
ctggaagaaa gcatacgacg catactccag gaggggaag agagtgttca ggagtattat   2400
aaaaactttg aaaaggagta ccgccagctt gactacaagg taatcgcgga ggttaagact   2460
gcgaatgata tcgccaaata tgatgataaa ggatggcccg gtttcaaatg cccttttccat   2520 atacgagggg tcctcaccta ccgccgcgcc gtgtctggtc tggggtcgc accaattctc   2580 gacgaaaata aggttatggt actcccactc cgcgagggga atccgtttgg tgacaaatgc   2640
atcgcctggc cgtctggtac ggagctcccc aaggaaatac gcagcgacgt cctcagttgg   2700
```

```
atcgaccact ccacactgtt tcagaagtca ttcgttaaac ctctggccgg gatgtgtgaa    2760
tccgcgggta tggactacga ggagaaagct tcattggact ttcttttcgg ttga          2814

<210> SEQ ID NO 14
<211> LENGTH: 2814
<212> TYPE: DNA
<213> ORGANISM: Bacteriophage T4

<400> SEQUENCE: 14
atggactata aggaccacga cggagactac aaggatcatg atattgatta caaagacgat     60
gacgataaga tggccccaaa gaagaagcgg aaggtcggta tccacggagt cccagcagcc    120
aaggaattct atattagtat cgagacagtg ggaaacaaca ttgtagagcg gtatatcgat    180
gaaaacggca agaaaggac tcgagaggtc gaataccttc cgaccatgtt tcgccactgt     240
aaagaagaat ctaagtacaa agatatttac gggaagaatt gcgctcccca aaaatttccc    300
tccatgaagg atgctcgaga ctggatgaag cgcatggagg acataggtct cgaagcattg    360
gggatgaacg attttaagtt ggcttacatc tccgacactt acgggtcaga aatagtgtac    420
gataggaagt tcgttcgcgt ggcaaattgc gatatagagg tcactggaga taagttcccg    480
gacccgatga aggcggagta cgaaattgac gctataacac actatgactc aatcgacgac    540
cggttctatg tatttgacct gctcaattcc atgtacgggt ctgtaagcaa gtgggacgct    600
aaactcgcgg ctaaacttga ctgtgaagga ggggatgaag tacctcagga atcttggac    660 agggtaatct acatgcccct tgacaatgaa cgagatatgc ttatggagta cattaatttg    720
tgggagcaaa agcgccccgc aatatttaca ggctggaaca tagaagggtt cgatgtaccg    780
tatattatga atcgggtaaa gatgatcctc ggagagagaa gcatgaaaag attttcacct    840
attggcagag tgaaatctaa gttgatacaa aacatgtatg gctcaaaaga gatctattca    900
atagatggag ttagcatact cgactacctg gatctgtata aaaagtttgc ttttaccaac    960
ttgcctagct tctcccttga aagtgtcgcc aacacgaga ccaagaaagg taagctgccg    1020
tacgatggcc cgattaataa actgcgcgag accaaccatc aaagatatat tagctacaac    1080
ataattgatg tcgaatctgt gcaagccatt gataagataa ggggctttat cgaccttgtc    1140
ctgtcaatgt cctattacgc caaaatgccg ttctcaggtg taatgtcacc cataaagacg    1200
tgggatgcga tcatcttcaa ttctctcaag ggagagcaca aggtgatccc caacaggggg    1260
tcccacgtaa agcagtcctt cccgggagct tttgtctttg agccaaagcc gatcgcccga    1320
aggtatatca tgtctttcga ccttacgtca ctttacccctt caattattcg acaagtgaat    1380
atatcacccg agactatccg gggccagttt aaggtacacc caatccatga gtacatagcc    1440
ggtacagccc caaacccag tgacgaatac tcttgcagcc ctaatgggtg gatgtacgac    1500
aaacaccagg agggcataat cccaaaggaa atcgcgaaag tatttttcca acggaaagac    1560
tggaagaaaa agatgttcgc ggaggaaatg aacgccgagg ctattaaaaa aatcattatg    1620
aagggagcgg gtagctgttc taccaagcca gaggtagagc gctacgtcaa attcagtgat    1680
gacttcctta atgagctgag taactacaca gagtctgtac tgaactcact gattgaggaa    1740
tgtgaaaaag ccgcaacact tgctaatacc aatcaactga atcggaagat cctgattaat    1800
tcactgtatg gcgccttggg caacattcat ttcagatact acgacctcag gaatgccacg    1860
gccattacaa ttttcggtca ggtcgggatc cagtggatcg cccgaaaaat caacgagtac    1920
ctcaataaag tgtgtggtac caatgacgag gattttatcg cagcaggcga taccgatagc    1980
gtgtatgttt gcgtcgacaa ggtcattgaa aaggtagggc tggatcggtt taaggagcag    2040
```

```
aatgatcttg tcgagtttat gaaccagttt ggtaaaaaaa agatggaacc gatgatagat    2100
gtagcgtacc gagaactttg tgactacatg aataatcgcg agcacttgat gcacatggac    2160
agggaagcga tttcatgccc cccactcggt tcaaagggcg tagggggttt ctggaaagct    2220
aagaaacggt acgccctcaa cgtctatgac atggaagaca agaggttcgc ggaacctcat    2280
ttgaagataa tggggatgga gacgcaacag tcctcaactc caaaggtggt gcaagaggct    2340
ctggaagaaa gcatacgacg catactccag gaggggaag agagtgttca ggagtattat     2400
aaaaactttg aaaaggagta ccgccagctt gactacaagg taatcgcgga ggttaagact    2460
gcgaatgata tcgccaaata tgatgataaa ggatggcccg gtttcaaatg ccctttccat    2520
atacgagggg tcctcaccta ccgccgcgcc gtgtctggtc tgggggtcgc accaattctc    2580
gacgaaaata aggttatggt actcccactc cgcgagggga atccgtttgg tgacaaatgc    2640
atcgcctggc cgtctggtac ggagctcccc aaggaaatac gcagcgacgt cctcagttgg    2700
atcgaccact ccacactgtt tcagaagtca ttcgttaaac ctctggccgg gatgtgtgaa    2760
tccgcgggta tggactacga ggagaaagct tcattggact ttcttttcgg ttga          2814
```

<210> SEQ ID NO 15  
<211> LENGTH: 960  
<212> TYPE: DNA  
<213> ORGANISM: Homo sapiens

<400> SEQUENCE: 15

```
atggctccga agcgtgggaa aaagggagcg gtggcggaag acggggatga gctcaggaca     60
gagccagagg ccaagaagag taagacggcc gcaaagaaaa atgacaaaga ggcagcagga    120
gagggcccag ccctgtatga ggaccccca gatcagaaaa cctcacccag tggcaaacct     180
gccacactca agatctgctc ttggaatgtg gatgggcttc gagcctggat taagaagaaa    240
ggattagatt gggtaaagga agaagcccca gatatactgt gccttcaaga gaccaaatgt    300
tcagagaaca aactaccagc tgaacttcag gagctgcctg actctctca tcaatactgg     360 tcagctcctt cggacaagga agggtacagt ggcgtgggcc tgctttcccg ccagtgccca    420
ctcaaagttt cttacggcat aggcgatgag gagcatgatc aggaaggccg ggtgattgtg    480
gctgaatttg actcgtttgt gctggtaaca gcatatgtac ctaatgcagg ccgaggtctg    540
gtacgactgg agtaccggca gcgctgggat gaagcctttc gcaagttcct gaagggcctg    600
gcttcccgaa agccccttgt gctgtgtgga gacctcaatg tggcacatga agaaattgac    660
cttcgcaacc ccaaggggaa caaaaagaat gctggcttca cgccacaaga gcgccaaggc    720 ttcgggaat tactgcaggc tgtgccactg gctgacagct ttaggcacct ctaccccaac     780
acaccctatg cctacacctt ttggacttat atgatgaatg ctcgatccaa gaatgttggt    840
tggcgccttg attactttt gttgtcccac tctctgttac ctgcattgtg tgacagcaag    900
atccgttcca aggccctcgg cagtgatcac tgtcctatca ccctatacct agcactgtga    960
```

<210> SEQ ID NO 16  
<211> LENGTH: 894  
<212> TYPE: DNA  
<213> ORGANISM: Homo sapiens

<400> SEQUENCE: 16

```
atggtgcggg ttctggcaa gcccatcccc aaccccctgc tgggcctgga cagcaccgga     60
aagtcttacc caactgtgag tgctgattac caggacgccg ttgagaaggc gaagaagaag    120
```

| | |
|---|---|
| ctcagaggct tcatcgctga aagagatgc gctcctctaa tgctccgttt ggcattccac | 180 |
| tctgctggaa cctttgacaa gggcacgaag accggtggac ccttcggaac catcaagcac | 240 |
| cctgccgaac tggctcacag cgctaacaac ggtcttgaca tcgctgttag gcttttggag | 300 |
| ccactcaagg cggagttccc tattttgagc tacgccgatt tctaccagtt ggctggcgtt | 360 |
| gttgccgttg aggtcacggg tggacctaag gttccattcc accctggaag agaggacaag | 420 |
| cctgagccac caccagaggg tcgcttgcct gatcccacta agggtctga ccatttgaga | 480 |
| gatgtgtttg gcaaagctat ggggcttact gaccaagata tcgttgctct atctgggggt | 540 |
| cacactattg gagctgcaca caaggagcgt tctggatttg agggtccctg gacctctaat | 600 |
| cctcttattt tcgacaactc atacttcacg gagttgttga gtggtgagaa ggaaggtctc | 660 |
| cttcagctac cttctgacaa ggctcttttg tctgaccctg tattccgccc tctcgttgat | 720 |
| aaatatgcag cggacgaaga tgccttcttt gctgattacg ctgaggctca ccaaaagctt | 780 |
| tccgagcttg ggtttgctga tgccgaattc agcagggccg accccaagaa gaagaggaag | 840 |
| gtggacccca agaagaagag gaaggtggac cccaagaaga gaggaaggt gtga | 894 |

<210> SEQ ID NO 17
<211> LENGTH: 1005
<212> TYPE: DNA
<213> ORGANISM: Homo sapiens

<400> SEQUENCE: 17

| | |
|---|---|
| atggagagaa aaataagcag aatccacctt gtttctgaac ccagtataac tcattttcta | 60 |
| caagtatctt gggagaaaac actggaatct ggttttgtta ttacacttac tgatggtcat | 120 |
| tcagcatgga ctgggacagt ttctgaatca gagatttccc aagaagctga tgacatggca | 180 |
| atggaaaaag ggaaatatgt tggtgaactg agaaaagcat tgttgtcagg agcaggacca | 240 |
| gctgatgtat acacgtttaa ttttttctaaa gagtcttgtt atttcttctt tgagaaaaac | 300 |
| ctgaaagatg tctcattcag acttggttcc ttcaacctag agaaagttga aacccagct | 360 |
| gaagtcatta gagaacttat ttgttattgc ttggacacca ttgcagaaaa tcaagccaaa | 420 |
| aatgagcacc tgcagaaaga aaatgaaagg cttctgagag attggaatga tgttcaagga | 480 |
| cgatttgaaa aatgtgtgag tgctaaggaa gctttggaga ctgatcttta taagcggttt | 540 |
| attctggtgt tgaatgagaa gaaaacaaaa atcagaagtt tgcataataa attattaaat | 600 |
| gcagctcaag aacgagaaaa ggacatcaaa caagaagggg aaactgcaat ctgttctgaa | 660 |
| atgactgctg accgagatcc agtctatgat gagagtactg atgaggaaag tgaaaaccaa | 720 |
| actgatctct ctgggttggc ttcagctgct gtaagtaaag atgattccat tatttcaagt | 780 |
| cttgatgtca ctgatattgc accaagtaga aaaaggagac agcgaatgca agaaatcttt | 840 |
| gggacagaac ctaaaatggc tcctcaggag aatcagcttc aagaaaagga aaagcctgat | 900 |
| tcttcactac ctgagacgtc taaaaaggag cacatctcag ctgaaaacat gtctttagaa | 960 |
| actctgagaa acagcagccc agaagacctc tttgatgaga tttaa | 1005 |

<210> SEQ ID NO 18
<211> LENGTH: 5289
<212> TYPE: DNA
<213> ORGANISM: Homo sapiens

<400> SEQUENCE: 18

| | |
|---|---|
| atggacgcac aaacacgacg acgtgagcgt cgcgctgaga acaagctca atggaaagct | 60 |
| gcaaacggtg gatctcctcc acatatggct tacccatacg atgttccaga ttacgctcct | 120 |

| | |
|---|---|
| ccatctcgag ctcaagcttc gaattctgca gtcgacggta ccgcgggcat gggagtcccc | 180 |
| aagtttttaca gatggatctc agagcggtat ccctgtctca gcgaagtggt gaaagagcat | 240 |
| cagattcctg aatttgacaa cttgtacctg gatatgaatg gaattataca tcagtgctcc | 300 |
| catcctaatg atgatgatgt tcactttaga atttcagatg ataaaatctt tactgatatt | 360 |
| tttcactacc tggaggtgtt gtttcgcatt attaaaccca ggaaagtgtt ctttatggct | 420 |
| gtagatggtg tggctcctcg agcaaaaatg aaccagcagc gtgggaggcg ttttaggtca | 480 |
| gcaaaggagg cagaagacaa aattaaaaag gcaatagaga agggagaaac tcttcctaca | 540 |
| gaggccagat ttgattccaa ctgtatcaca ccaggaactg aatttatggc caggttacat | 600 |
| gaacatctga agtattttgt aaatatgaaa atttccacag acaagtcatg gcaaggagtt | 660 |
| accatctact tctcaggcca tgagactcct ggagaaggag agcataaaat catgaaattt | 720 |
| atcagatccg agaaagcaaa gccagatcat gatccaaaca ccagacactg tctttatggt | 780 |
| ttagatgctg acttgattat gcttggatta acaagtcatg aggcacattt ttctctctta | 840 |
| agagaagaag ttcgatttgg tggcaaaaaa acacaacggg tatgtgctcc agaagaaact | 900 |
| acatttcacc ttctacactt gtctttaatg agagagtata ttgactatga gttttcagta | 960 |
| ttaaaagaaa agatcacatt taaatatgat attgaaagga atagatga ttggattttg | 1020 |
| atggggtttc ttgttggtaa tgattttatc cctcatctac ctcatttaca tattaatcat | 1080 |
| gatgcactgc ctcttcttta tggaacatat gttaccatcc tgccagaact tgggggttat | 1140 |
| attaatgaaa gtgggcacct caacttacct cgatttgaga ataccttgt gaaactatca | 1200 |
| gattttgatc gggagcactt cagtgaagtt tttgtggacc taaaatggtt tgaaagcaaa | 1260 |
| gttggtaaca agtacctcaa tgaagcagca ggtgtcgcag cagaagaagc caggaactac | 1320 |
| aaggaaaaga aaagttaaa gggccaggaa aattctctgt gttggactgc tttagacaaa | 1380 |
| aatgaaggcg aaatgataac ttctaaggat aatttagaag atgagactga agatgatgac | 1440 |
| ctatttgaaa ctgagtttag acaatataaa agaacatatt acatgacgaa gatgggggtt | 1500 |
| gacgtagtat ctgatgactt tctggctgat caagctgcat gttatgttca ggcaatacag | 1560 |
| tggattttgc actattacta tcatggagtt cagtcctgga gctggtatta tccttatcat | 1620 |
| tatgcgcctt tcctgtctga tatacacaac atcagtacac tcaaaatcca ttttgaacta | 1680 |
| ggaaaacctt ttaagccatt tgaacagctt cttgctgtac ttccagcagc cagcaaaaat | 1740 |
| ttacttcctg catgctacca gcatttgatg accaatgaag actcaccaat tatagaatat | 1800 |
| tacccacctg attttaaaac tgacctaaat gggaaacaac aggaatggga agctgtggtg | 1860 |
| ttaatcccctt ttattgatga gaagcgatta ttggaagcca tggagacatg taaccactcc | 1920 |
| ctcaaaaagg aagagaggaa aagaaaccaa catagtgagt gcctaatgtg ctggtatgat | 1980 |
| agagacacag agtttatcta tccttctcca tggccagaaa agttccctgc catagaacga | 2040 |
| tgttgtacaa ggtataaaat aatatcctta gatgcttggc gtgtagacat aaacaaaaac | 2100 |
| aaaataacca gaattgacca gaaagcatta tatttctgtg gatttcctac tctgaaacac | 2160 |
| atcagacaca aatttttttt gaagaaaagt ggtgttcaag tattccagca aagcagtcgt | 2220 |
| ggagaaaaca tgatgttgga aatcttagtg gatgcagaat cagatgaact taccgtagaa | 2280 |
| aatgtagctt catcagtgct tggaaaatct gtctttgtta attggcctca ccttgaggaa | 2340 |
| gctagagtcg tggctgtatc agatggagaa actaagtttt acttggaaga acctccagga | 2400 |
| acacagaagc tttattcagg aagaactgcc ccaccatcta aagtggttca tcttggagat | 2460 |

```
aaagaacaat ctaactgggc aaaagaagta caaggaattt cagaacacta cctgagaaga   2520
aaaggaataa taataaatga aacatctgca gttgtgtatg ctcagttact cacaggtcgt   2580
aaatatcaaa taaatcaaaa tggtgaagtt cgtctagaga aacagtggtc aaaacaagtt   2640 gttcctttg tttatcaaac tattgtcaag gacatccgag ctttcgactc ccgtttctcc    2700
aatatcaaaa cattggatga tttgtttcct ctgagaagta tggtctttat gctgggaact   2760
ccctattatg gctgcactgg agaagttcag gattcaggtg atgtgattac agaaggtagg   2820
attcgtgtga ttttcagcat tccatgtgaa cccaatcttg atgctttaat acagaaccag   2880
cataaatatt ctataaagta caacccagga tatgtgttgg ccagtcgcct tggagtgagt   2940
ggataccttg tttcaaggtt tacaggaagt attttttattg gaagaggatc taggagaaac   3000
cctcatggag accataaagc aaatgtgggt ttaaatctca aattcaacaa gaaaaatgag   3060
gaggtacctg gatatactaa gaaagttgga agtgaatgga tgtattcatc tgcagcagaa   3120
caacttctgg cagagtactt agagagagct ccagaactat ttagttatat agccaaaaat   3180
agccaagagg atgtgttcta tgaagatgac atttggcctg agaaaatgga aatggtgct    3240 gaaaaagttc aagaaattat tacttggcta aaaggacatc ctgtcagtac tttatctcgt   3300
tcttcttgtg atttacaaat tctggatgca gctattgttg agaaaattga ggaagaagtc   3360
gaaaagtgca agcaaagaaa gaataataag aaggtgcgag taacagtgaa accccatttg   3420
ctatacagac ctttagaaca gcaacatgga gtcattcctg atcgggatgc agaattttgt   3480 cttttttgacc gtgttgtaaa tgtgagagaa aacttctcag ttccagttgg ccttcgaggc   3540
accatcatag aataaaagg agctaataga gaagccgatg tactatttga agtattattt    3600
gatgaagaat ttcctggagg gttaacaata agatgctcac ctggtagagg ttatcgactg   3660
ccaacaagtg ccttggtgaa cctttctcat gggagtcgct ctgaaactgg aaatcagaag   3720
ttgacagcca tcgtaaaacc acaaccagct gtacatcaac atagctcaag ttcatcagtt   3780
tcctctgggc atttgggagc cctcaaccat tcccctcaat cacttttgt tcctactcaa    3840 gtacctacta aagatgatga tgaattctgc aacatttggc agtccttaca gggatctgga   3900
aagatgcaat actttcagcc aactatacaa gagaagggtg cagttctacc tcaagaaata   3960
agccaagtaa atcaacatca taaatctggc tttaatgaca acagtgttaa atatcagcaa   4020
agaaaacatg accctcacag aaaatttaaa gaagagtgta agagtcctaa agctgagtgt   4080
tggtcccaaa aaatgtccaa taagcagcct aactctggaa ttgagaactt tttagcatct   4140
ttgaatatct ccaaagaaaa tgaagtacag tcatctcatc atggggagcc tccaagtgaa   4200
gagcatttgt caccacagtc atttgccatg ggaacacgga tgcttaaaga aattctaaaa   4260
attgatggct ctaacactgt ggaccataag aatgaaatca aacagattgc taatgaaatc   4320
cctgtttcct ctaacagaag agatgaatat ggattaccct ctcagcctaa acaaaataag   4380
aaattagcat cttatatgaa caagcctcac agtgctaatg agtaccataa tgttcagtct   4440
atggacaata tgtgttggcc tgcccccagc cagatccctc ctgtatccac accagtaact   4500
gaactttctc gaatttgttc ccttgttgga atgccacaac ctgatttctc ctttcttagg   4560
atgccacaga caatgaccgt ttgccaagta aaattatcta atggcttact ggtacatggg   4620
ccacagtgcc actctgaaaa tgaagccaaa gagaaagctg cacttttgc tttacaacag   4680 ttgggctcct taggcatgaa tttccctttg ccttcacaag tatttgcaaa ttatccttca   4740
gctgtaccac ctggaaccat tcctccagcc tttcccccac ctactggctg ggatcactat   4800
ggaagcaact atgcattggg ggcagctaat ataatgcctt cgtcgtctca tctctttggc   4860
```

```
tcaatgccat ggggaccatc ggtgccagtt cctgggaagc ccttccatca tactttatat    4920
tctgggacca tgcccatggc tgggggaata ccagggggtg tgcacaatca gtttataccg    4980
ctgcaggtta ctaaaaaaag ggttgcaaac aaaagaact ttgagaataa ggaagcccag    5040
agttctcaag ccactccagt tcagactagc cagccagatt cttccaacat tgtcaaagta    5100
agtccacggg agagctcatc agcttctttg aagtcctctc cgattgctca acctgcatct    5160
tcttttcaag ttgaaactgc ctctcaaggc catagtatat ctcaccataa gtcaacacca    5220
atctcttctt caagaagaaa atcaagaaaa ctggctgtta attttggtgt ttctaaacct    5280
tctgagtaa                                                            5289

<210> SEQ ID NO 19
<211> LENGTH: 3183
<212> TYPE: DNA
<213> ORGANISM: Homo sapiens

<400> SEQUENCE: 19
atggagcagc tgaacgaact ggagctgctg atggagaaga ttttggga ggaggcggag      60 ctgccggcgg agctatttca gaagaaagtg gtagcttcct ttccaagaac agttctgagc    120
acaggaatgg ataaccggta cctggtgttg gcagtcaata ctgtacagaa caaagaggga    180
aactgtgaaa agcgcctggt catcactgct tcacagtcac tagaaaataa agaactatgc    240
atccttagga atgactggtg ttctgttcca gtagagccag agatatcat tcatttggag    300 ggagactgca catctgacac ttggataata gataaagatt ttggatattt gattctgtat    360
ccagacatgc tgatttctgg caccagcata gccagtagta ttcgatgtat gagaagagct    420
gtcctgagtg aaacttttag gagctctgat ccagccacac gccaaatgct aattggtacg    480
gttctccatg aggtgtttca aaaagccata ataatagct ttgccccaga aaagctacaa    540
gaacttgctt ttcaaacaat tcaagaaata agacatttga ggaaatgta ccgcttaaat    600 ctaagtcaag atgaaataaa acaagaagta gaggactatc ttccttcgtt ttgtaaatgg    660
gcaggagatt tcatgcataa aaacacttcg actgacttcc ctcagatgca gctctctctg    720
ccaagtgata atagtaagga taattcaaca tgtaacattg aagtcgtgaa accaatggat    780
attgaagaaa gcatttggtc ccctagggtt tggattgaaag gcaaaataga tgttacagtt    840
ggtgtgaaaa tacatcgagg gtaaaaaca aaatacaaga taatgccgct ggaacttaaa    900
actggcaaag aatcaaattc tattgaacac cgtagtcagg ttgttctgta cactctacta    960
agccaagaga gaagagctga tccagaggct ggcttgcttc tctacctcaa gactggtcag   1020
atgtaccctg tgcctgccaa ccatctagat aaaagagaat tattaaagct aagaaaccag   1080
atggcattct cattgtttca ccgtattagc aaatctgcta ctagacagaa gacacagctt   1140
gcttctttgc cacaaataat tgaggaagag aaaacttgta atattgttc acaaattggc   1200 aattgtgctc tttatagcag agcagttgaa caacagatgg attgtagttc agtcccaatt   1260
gtgatgctgc ccaaaataga agaagaaacc cagcatctga agcaaacaca cttagaatat   1320
ttcagccttt ggtgtctaat gttaaccctg gagtcacaat cgaaggataa taaaaagaat   1380
caccaaaata tctggctaat gcctgcttcg gaaatggaga agagtggcag ttgcattgga   1440
aacctgatta gaatggaaca tgtaaagata gtttgtgatg ggcaatatt acataatttc   1500 caatgtaaac atggtgccat acctgtcaca aatctaatgg caggtgacag agttattgta   1560
agtggagaag aaaggtcact gtttgctttg tctagaggat atgtgaagga gattaacatg   1620
```

-continued

```
acaacagtaa cttgtttatt agacagaaac ttgtcggtcc ttccagaatc aactttgttc    1680
agattagacc aagaagaaaa aaattgtgat atagatacc cattaggaaa tctttccaaa     1740
ttgatggaaa acacgtttgt cagcaaaaaa cttcgagatt taattattga ctttcgtgaa    1800
cctcagttta tatcctacct tagttctgtt cttccacatg atgcaaagga tacagttgcc    1860
tgcattctaa agggtttgaa taagcctcag aggcaagcga tgaaaaggt acttctttca     1920 aaagactaca cactcatcgt gggtatgcct gggacaggaa aaacaactac gatatgtact    1980
ctcgtaagaa ttctctacgc ctgtggtttt agcgttttgt tgaccagcta tacacactct    2040
gctgttgaca atattctttt gaagttagcc aagtttaaaa taggattttt gcgtttgggt    2100
cagattcaga aggttcatcc agctatccag caatttacag agcaagaaat ttgcagatca    2160
aagtccatta aatccttagc tcttctagaa gaactctaca atagtcaact tatagttgca    2220
acaacatgta tgggaataaa ccatccaata tttttcccgta aaatttttga ttttttgtatt   2280 gtggatgaag cctctcaaat tagccaacca atttgtctgg gcccccttttt tttttcacgg   2340 agatttgtgt tagtggggga ccatcagcag cttcctcccc tggtgctaaa ccgtgaagca    2400
agagctcttg gcatgagtga aagcttattc aagaggctgg agcagaataa gagtgctgtt    2460
gtacagttaa ccgtgcagta cagaatgaac agtaaaatta tgtccttaag taataagctg    2520
acctatgagg gcaagctgga gtgtggatca gacaaagtgg ccaatgcagt gataaaccta    2580
cgtcacttta aagatgtgaa gctggaactg gaatttatg ctgactattc tgataatcct     2640
tggttgatgg gagtatttga acccaacaat cctgtttgtt tccttaatac agacaaggtt    2700
ccagcgccag aacaagttga aaaggtggt gtgagcaatg taacagaagc caaactcata    2760
gttttcctaa cctccatttt tgttaaggct ggatgcagtc cctctgatat tggtattatt    2820
gcaccgtaca gcagcaatt aaagatcatc aatgatttat tggcacgttc tattgggatg    2880
gtcgaagtta atacagtaga caaataccaa ggaagggaca aaagtattgt cctagtatct    2940
tttgttagaa gtaataagga tggaactgtt ggtgaactct tgaaagattg gcgacgtctt    3000
aatgttgcta taaccagagc caaacataaa ctgattcttc tggggtgtgt gccctcacta    3060
aattgctatc ctcctttgga gaagctgctt aatcatttaa actcagaaaa attaatcatt    3120
gatcttccat caagagaaca tgaaagtctt tgccacatat tgggtgactt tcaaagagaa    3180
taa                                                                   3183
```

<210> SEQ ID NO 20
<211> LENGTH: 7857
<212> TYPE: DNA
<213> ORGANISM: Homo sapiens

<400> SEQUENCE: 20

```
atggaacaaa agttgatttc tgaagaagat ttgttaagaa agagagggat cctgaatctt     60
ctgcgtcgga gtgggaaacg gcggcgttca gaatcaggct cagattcgtt ctcgggaagc    120
ggcggtgaca gcagtgccag cccccagttc ctctccgggt ccgtgctgag cccgccgccc    180
ggccttggtc gctgcctgaa ggccgcagct gcaggagaat gcaagcctac agttcctgac    240
tacgaaatag acaagctact attggcaaac tggggacttc ctaaagcagt tctgaaaaaa    300
taccacagtt ttggtgtaaa aaagatgttt gaatggcagg cagagtgcct tttgcttgga    360
caagtcctgg aaggaaagaa tttagtttat tcagctccta caagtgctgg gaagactctt    420
gtggcagaat tacttatttt gaagcgggtt ttggaaatgc ggaagaaagc tttgtttatt    480
cttccctttg tttctgtggc taaagagaag aaatactacc tccagagtct gtttcaggaa    540
```

```
gtaggaataa aagtagacgg ttatatgggc agcacctctc catcaaggca tttctcttca    600
ttggatattg cagtctgcac aattgagaga gccaatggtc tgatcaatcg cctcatagag    660
gaaaataaga tggatctgtt aggaatggtg gttgtggatg aattacatat gctgggagac    720
tctcaccgag ggtatctgct ggaacttttg ctgaccaaga tttgctatat tactcggaaa    780
tcagcatctt gtcaggcaga tctagccagt tctctgtcta atgctgtgca atcgttggc     840 atgagtgcta cccttcctaa tttgagcttg tggcttcct ggttgaatgc tgaactctac     900
cataccgact ttcgccctgt accgcttttg gagtcagtaa agttggaaa ttccatatat     960 gactcttcaa tgaaacttgt gagggaattt gagcccatgc ttcaagtgaa gggagatgag   1020
gaccatgttg ttagcttatg ttatgagacg atttgtgata accattcagt attactttt    1080 tgtccatcaa agaaatggtg tgagaagctg gcagatatca ttgctcgaga gttttataat   1140
ctacatcatc aagctgaggg attggtgaaa ccctctgaat gcccaccagt aattctggaa   1200
caaaaagaac tcctggaagt gatggatcag ttaagacggt tgccttcagg actggactct   1260
gtattacaga aaactgtacc atggggagta gcatttcatc atgcaggtct acttttgag    1320 gagagggata tcattgaagg agcctttcgt caaggtctca ttcgagtctt ggcggcaact   1380
tctactcttt cttctggggt gaatttacct gcacgtcgtg tgattattcg aaccccctatt  1440 tttggtggtc gacctctaga tattcttact tataagcaga tggttggtcg tgctggcagg   1500
aaaggagtgg acacagtagg cgagagtatc ttaatttgta agaactctga gaaatcaaaa   1560
ggcatagctc tccttcaggg ttctctaaag cctgttcgca gctgtctgca aagacgagaa   1620
ggagaagaag taactggcag catgatacga gctattctgg agataatagt tggtggagtg   1680
gcaagtacat cacaagatat gcatacttat gctgcctgca catttttggc tgcaagtatg   1740
aaagaaggga agcaaggaat tcagagaaat caagagtctg ttcagcttgg agcgattgag   1800
gcctgtgtga tgtggctact agaaaatgaa ttcatccaga gtacagaagc cagtgatgga   1860
acagaaggaa aggtgtatca tccaacacat cttggttcgg ccactctttc ttcttcactt   1920
tctccagctg atactttaga tattttgct gacctgcaaa gagcaatgaa gggctttgtt    1980
ttagagaatg atcttcatat tctctatctg gttacaccta tgtttgagga ttggactact   2040
attgattggt atcgattttt ctgtttatgg gagaagttgc caacttcaat gaaaagggtg   2100
gcagagctag tgggagttga agaggggttc ttggcccgtt gtgtgaaagg aaaagtagta   2160
gccagaactg agagacagca tcgacaaatg gccatccata aaaggttttt caccagtctt   2220
gtgctattag atttaatcag tgaagttccc ttaagggaaa taaatcagaa atatggatgc   2280
aatcgtgggc agattcaatc tttgcaacag tcagctgctg tttatgcagg gatgattaca   2340
gtattttcca accgtctggg ctggcacaac atggaactac tactttccca atttcagaag   2400
cgtcttacgt ttggcatcca gagggagctg tgtgacctgg ttcgggtatc cttactaaat   2460
gctcagagag ccaggttct ctatgcttct ggctttcata ctgtggcaga ccttgctaga    2520
gcaaatattg tggaggtgga ggtgattctg aaaaatgctg tgccttttcaa agtgcccgg   2580 aaggcagtgg atgaggaaga ggaagcagtt gaagaacgtc gcaatatgcg aactatctgg   2640
gtgactggca gaaaaggttt aactgaaagg gaagcagcag cccttatagt ggaagaagcc   2700
agaatgattc tgcagcagga cttagttgaa atgggagtgc aatggaatcc atgtgccctg   2760
ttacattcta gtcatgctc attgactcat agtgagtccg aagtaaagga acacacattt    2820
atatcccaaa ctaagagttc ttataaaaaa ttaacatcaa agaacaaaag taacacaata   2880
```

```
tttagtgatt cttatattaa gcattcacca aatatagtgc aagacttaaa taaaagtaga    2940
gagcatacaa gttcctttaa ttgtaatttc cagaatggga atcaagaaca tcagagatgt    3000
tccattttca gagcaagaaa acgggcctct ttagatataa ataaagagaa gccaggagcc    3060
tctcagaatg aggggaaaac aagtgataag aaagttgttc agacttttc acagaaaaca    3120 aaaaaggcac ctttgaattt caattcagaa aagatgagca gaagttttcg atcttggaaa    3180
cgtagaaagc atctaaagcg atctagggac agcagccccc tgaaagactc tggagcgtgt    3240
agaatccatt tacaaggaca gactctgtct aatcctagtc tttgtgaaga cccgtttacc    3300
ttagatgaga agaaaacgga atttagaaat tcaggccat ttgctaaaaa tgtatctttg    3360
agtggtaagg aaaaagataa taaaacatca ttcccattac aaataaagca aaattgttca    3420
tggaacataa cactaactaa tgataatttt gtggagcata ttgtcacagg atctcagagt    3480
aaaaatgtga cttgtcaggc cactagtgtg gttagtgaaa agggcagagg agtagctgtt    3540
gaggcagaaa aataaatga agtgctgata caaaatggtt caaaaaacca gaatgtttat    3600
atgaaacacc atgacatcca tccaattaac cagtacctgc gaaagcaatc tcatgaacag    3660
acaagcacta ttaccaaaca gaaaatata atagagagac aaatgccctg tgaagcagtc    3720
agtagttaca taaatagaga ctcaaatgtt actatcaatt gtgaaaggat aaagcttaat    3780
acagaggaaa ataaaccaag tcattttcag gcattaggag atgatataag cagaactgtg    3840
atacccagtg aagtacttcc atcagctgga gcatttagca aatcagaagg ccagcatgag    3900
aattttctaa atatttctag actacaagaa aaaacaggta cttatacaac aaacaaaact    3960
aaaaataatc atgtttctga cttaggttta gtcctctgtg atttgaaga tagttttctat    4020 ctggatactc agtcagagaa aataatacaa cagatggcaa ctgaaaatgc caaactagga    4080
gcaaaggaca ccaacctggc agcagggata atgcagaaga gcttagtcca acagaactca    4140
atgaactctt ttcagaagga gtgtcacatt ccttttcctg ctgaacagca ccctctagga    4200
gcgactaaga tagatcattt ggaccttaag actgtaggta ctatgaaaca aagcagtgat    4260
tcacatgggg ttgatatcct gactccagaa agcccgattt tccattctcc aatactattg    4320
gaggaaaatg gtctttttt aaaaaagaat gaagtttctg ttactgattc acaattaaat    4380
agttttcttc aaggttatca aacacaagaa actgtgaaac cagttatact tctgattcct    4440
caaaagagaa ctcccactgg tgtagaagga gaatgtcttc cagttcctga acaagtttg    4500 aatatgagtg atagtttact atttgatagc ttcagtgatg actatctagt aaaagaacaa    4560
ttacctgata tgcaaatgaa agaacccctt ccttcagaag taacatcaaa ccatttagt    4620 gattctctgt gtctacaaga agacctaatt aaaaaatcaa atgtaaatga gaatcaagat    4680
acccaccagc agttgacttg ttccaatgat gaatctatta tattttcaga aatggattct    4740
gttcagatgg ttgaagcttt ggacaatgtg atatatttc ctgtccaaga gaagaatcat    4800
actgtagtat ctcctagagc attagaacta agtgatccag tacttgatga gcaccaccaa    4860
ggtgatcaag atggaggaga tcaagatgaa agggctgaaa aatcaaaatt aactgggacc    4920
aggcaaaatc attcattcat ttggtcaggg gcatcatttg atctaagtcc aggactgcaa    4980
aggattttag ataaagtatc cagtcctcta gaaaatgaaa agctaaaatc aatgactata    5040
aacttttcca gtttgaatag aaaaaataca gagttaaatg aagaacaaga agttatttca    5100
aacttggaga caaacaagt gcagggaatt tcattttctt ctaataatga agtaaaaagc    5160
aagattgaga tgctagaaaa caatgccaat catgatgaaa cctcatccct cttacctcgt    5220
aaagaaagta atatagttga tgataatggt ctcattcctc ctacacccat tccaacatct    5280
```

```
gcttctaagc tgacatttcc agggattctt gaaacacctg taaacccttg gaaaactaat     5340
aatgttttac aacctggtga aagttattta tttggctcac cttcagatat taaaaaccac     5400
gatttaagtc cagggagtag aaatgggttc aaagacaaca gccctattag tgacacaagc     5460
ttttcacttc agttatcaca ggatggatta cagttaactc cagcctcaag cagttcagaa     5520
agtttgtcca taattgatgt agcaagtgac caaaatcttt tccaaacatt cattaaggag     5580
tggcggtgca aaaagcgatt ttccatctca ctggcttgtg aaaagattag aagtttgaca     5640
tcttctaaaa ctgctactat tggcagtagg tttaagcaag ctagctcacc tcaggaaatt     5700
cctattagag atgatggatt tcccattaaa ggttgtgatg acaccttggt ggttggactg     5760
gcagtatgct ggggtggaag ggatgcctat tattttcac tgcagaagga acaaaagcat      5820
tctgaaatta gtgccagttt ggttccacct tctttagatc caagcctgac tttgaaagac     5880
aggatgtggt accttcaatc ttgcttgcga aaggaatctg ataaagaatg ttctgttgtc     5940
atctatgact tcatccagag ctataaaatt cttcttcttt cttgtggcat ctccttggag     6000
caaagttatg aagatcctaa ggtggcatgc tggttactag atccagattc tcaggagccg     6060
actcttcata gcatagttac cagttttctt cctcatgagc ttccactcct agaagggatg     6120
gagaccagcc aagggattca aagcctgggg ctaaatgctg gcagtgagca ttctgggcga     6180
tacagagcat ctgtggagtc cattctcatc ttcaactcta tgaatcagct caactctttg     6240
ttgcagaagg aaaaccttca agatgttttc cgtaaggtgg aaatgccctc tcagtactgc     6300
ttggccttgc tagaactaaa tggaattggc tttagtactg cagaatgtga aagtcagaaa     6360
catataatgc aagccaagct ggatgcaatt gagacccagg cctatcaact agctggccac     6420
agttttctt tcaccagttc agatgacatc gctgaggttt tatttttgga attgaagttg      6480
cccccaaata gagagatgaa aaaccaaggc agcaagaaaa ctctgggttc taccagaaga     6540
gggattgaca atggacgcaa gctaaggctg gaagacagt tcagcactag taaggacgtt      6600
ttaaataaat taaaggcatt acatccttta ccaggcttga tattagaatg gagaagaatc     6660
actaatgcta ttaccaaagt ggtctttccc cttcagcggg aaaagtgtct taatcctttt     6720
cttggaatgg aaagaatcta tcctgtatca cagtcgcaca ctgctacagg acgaataacc     6780
tttacagaac caaatattca gaatgtgcca agagattttg aaatcaaaat gccaacacta     6840
gtaggagaaa gcccaccttc tcaagctgta ggcaaaggcc tacttcccat gggcagagga     6900
aaatataaga agggtttcag cgtgaatcct agatgccagg cacagatgga ggagagagct     6960
gcagacagag gaatgccatt ttcaattagc atgcgacatg cctttgtgcc tttcccaggt     7020
ggttcaatac tggctgctga ctactctcag cttgaactga ggatcttggc tcatttatcc     7080
catgatcgtc gtctcattca agtgttaaac actggagctg atgttttcag gagcattgca     7140
gcagagtgga agatgattga gccagagtct gttggggatg atctgaggca gcaggcaaaa     7200
cagatttgct atgggatcat ttatggaatg ggagctaaat cttttgggaga gcagatgggc     7260
attaaagaaa atgatgctgc atgctatatt gactccttca atccagata cacagggatt      7320
aatcaattca tgacagagac agtgaagaat tgtaaaagag acggatttgt tcagaccatt     7380
ttgggaaggc gtagatattt gccaggaatc aaagacaaca accctatcg taaagctcac      7440
gctgagcgtc aagctatcaa cacaatagtc caaggatcag cagctgatat tgtcaaaata     7500
gccacagtta acattcagaa gcaattagag accttccact caaccttcaa atcccatggt     7560
catcgagagg gtatgctcca aagtgaccga acaggattgt cacgaaagag aaaactgcaa     7620
```

| | |
|---|---:|
| gggatgttct gcccaatcag aggaggcttc ttcatccttc aactccatga tgaactccta | 7680 |
| tatgaagtgg cagaagaaga tgttgttcag gtagctcaga ttgtcaagaa tgaaatggaa | 7740 |
| agtgctgtaa aactgtctgt gaaattgaaa gtgaaagtga aaataggcgc cagctgggga | 7800 |
| gagctaaagg actttgatgt gcccgggatg gactacaaag acgatgacga caagtaa | 7857 |

<210> SEQ ID NO 21
<211> LENGTH: 1128
<212> TYPE: DNA
<213> ORGANISM: Homo sapiens

<400> SEQUENCE: 21

| | |
|---|---:|
| atggactata aggaccacga cggagactac aaggatcatg atattgatta caaagacgat | 60 |
| gacgataaga tggcccccaaa gaagaagcgg aaggtcggta tccacggagt cccagcagcc | 120 |
| gctagcaaac ggaaggcgcc gcaggagact ctcaacgggg aatcaccga catgctcaca | 180 |
| gaactcgcaa actttgagaa gaacgtgagc caagctatcc acaagtacaa tgcttacaga | 240 |
| aaagcagcat ctgttatagc aaaatacccca cacaaaataa agagtggagc tgaagctaag | 300 |
| aaattgcctg gagtaggaac aaaaattgct gaaaagattg atgagttttt agcaactgga | 360 |
| aaattacgta aactggaaaa gattcggcag gatgatacga gttcatccat caatttcctg | 420 |
| actcgagtta gtggcattgg tccatctgct gcaaggaagt ttgtagatga aggaattaaa | 480 |
| acactagaag atctcagaaa aaatgaagat aaattgaacc atcatcagcg aattgggctg | 540 |
| aaatattttg gggactttga aaaagaatt cctcgtgaag atgttaca aatgcaagat | 600 |
| attgtactaa atgaagttaa aaaagtggat tctgaataca ttgctacagt ctgtggcagt | 660 |
| ttcagaagag gtgcagagtc cagtggtgac atggatgttc tcctgacca tcccagcttc | 720 |
| acttcagaat caaccaaaca gccaaaactg ttacatcagg ttgtggagca gttacaaaag | 780 |
| gttcattta tcacagatac cctgtcaaag ggtgagacaa agttcatggg tgtttgccag | 840 |
| cttcccagta aaaatgatga aaagaatat ccacacagaa gaattgatat caggttgata | 900 |
| cccaaagatc agtattactg tggtgttctc tatttcactg ggagtgatat tttcaataag | 960 |
| aatatgaggg ctcatgccct agaaaagggt ttcacaatca atgagtacac catccgtccc | 1020 |
| tgggagtca ctggagttgc aggagaaccc ctgccagtgg atagtgaaaa agacatcttt | 1080 |
| gattacatcc agtggaaata ccgggaaccc aaggaccgga gcgaatga | 1128 |

<210> SEQ ID NO 22
<211> LENGTH: 2142
<212> TYPE: DNA
<213> ORGANISM: Homo sapiens

<400> SEQUENCE: 22

| | |
|---|---:|
| atggctactg gacaggatcg agtggttgct ctcgtggaca tggactgttt ttttgttcaa | 60 |
| gtggagcagc ggcaaaatcc tcatttgagg aataaacctt gtgcagttgt acagtacaaa | 120 |
| tcatggaagt gtggtggaat aattgcagtg agttatgaag ctcgtgcatt ggagtcact | 180 |
| agaagtatgt gggcagatga tgctaagaag ttatgtccag atcttctact ggcacaagtt | 240 |
| cgtgagtccc gtgggaaagc taacctcacc aagtaccggg aagccagtgt tgaagtgatg | 300 |
| gagataatgt ctcgttttgc tgtgattgaa cgtgccagca ttgatgaggc ttacgtagat | 360 |
| ctgaccagtg ctgtacaaga gagactacaa aagctacaag gtcagcctat ctcggcagac | 420 |
| ttgttgccaa gcacttacat tgaagggttg ccccaaggcc ctacaacggc agaagagact | 480 |
| gttcagaaag aggggatgcg aaaacaaggc ttatttcaat ggctcgattc tcttcagatt | 540 |

-continued

```
gataacctca cctctccaga cctgcagctc accgtgggag cagtgattgt ggaggaaatg      600
agagcagcca tagagaggga gactggtttt cagtgttcag ctggaatttc acacaataag      660
gtcctggcaa aactggcctg tggactaaac aagcccaacc gccaaaccct ggtttcacat      720
gggtcagtcc cacagctctt cagccaaatg cccattcgca aaatccgtag tcttggagga      780
aagctagggg cctctgtcat tgagatccta gggatagaat acatgggtga actgacccag      840
ttcactgaat cccagctcca gagtcatttt ggggagaaga atgggtcttg gctatatgcc      900
atgtgccgag ggattgaaca tgatccagtt aaacccaggc aactacccaa aaccattggc      960
tgtagtaaga acttcccagg aaaaacagct cttgctactc gggaacaggt acaatggtgg     1020
ctgttgcaat tagcccagga actagaggag agactgacta aagaccgaaa tgataatgac     1080
agggtagcca cccagctggt tgtgagcatt cgtgtacaag gagacaaacg cctcagcagc     1140
ctgcgccgct gctgtgccct tacccgctat gatgctcaca agatgagcca tgatgcattt     1200
actgtcatca agaactgtaa tacttctgga atccagacag aatggtctcc tcctctcaca     1260
atgcttttcc tctgtgctac aaaatttttct gcctctgccc cttcatcttc tacagacatc     1320
accagcttct tgagcagtga cccaagttct ctgccaaagg tgccagttac cagctcagaa     1380
gctaagaccc agggaagtgg cccagcggtg acagccacta gaaagcaac cacgtctctg     1440 gaatcattct tccaaaaagc tgcagaaagg cagaaagtta agaagcttc gcttcatct     1500 cttactgctc ccactcaggc tcccatgagc aattcaccat ccaagccctc attacctttt     1560
caaaccagtc aaagtacagg aactgagccc ttctttaagc agaaaagtct gcttctaaag     1620
cagaaacagc ttaataattc ttcagtttct tccccccaac aaaacccatg gtccaactgt     1680
aaagcattac caaactcttt accaacagag tatccagggt gtgtccctgt ttgtgaaggg     1740
gtgtcgaagc tagaagaatc ctctaaagca actcctgcag agatggattt ggcccacaac     1800
agccaaagca tgcacgcctc ttcagcttcc aaatctgtgc tggaggtgac tcagaaagca     1860
accccaaatc caagtcttct agctgctgag gaccaagtgc cctgtgagaa gtgtggctcc     1920
ctggtaccgg tatgggatat gccagaacac atggactatc attttgcatt ggagttgcag     1980 aaatccttt tgcagcccca ctcttcaaac ccccaggttg tttctgccgt atctcatcaa     2040
ggcaaaagaa atcccaagag ccctttggcc tgcactaata aacgccccag gcctgagggc     2100
atgcaaacat tggaatcatt ttttaagcca ttaacacatt ag                        2142
```

<210> SEQ ID NO 23
<211> LENGTH: 3723
<212> TYPE: DNA
<213> ORGANISM: Homo sapiens

<400> SEQUENCE: 23

```
atggctagcc gcctgctctg gaggaaggtg gccggcgcca ccgtcgggcc agggccggtt       60
ccagctccgg ggcgctgggt ctccagctcc gtccccgcgt ccgaccccag cgacgggcag      120
cggcggcggc agcagcagca gcagcagcag cagcagcagc aacagcagcc tcagcagccg      180
caagtgctat cctcggaggg cgggcagctg cggcacaacc cattggacat ccagatgctc      240
tcgagagggc tgcacgagca aatcttcggg caaggagggg agatgcctgg cgaggccgcg      300
gtgcgccgca cgtcgagca cctgcagaag cacgggctct gggggcagcc agccgtgccc      360
ttgcccgacg tggagctgcg cctgccgccc ctctacgggg acaacctgga ccagcacttc      420
cgcctcctgg cccagaagca gagcctgccc tacctggagg cggccaactt gctgttgcag      480
```

```
gcccagctgc ccccgaagcc cccggcttgg gcctgggcgg agggctggac ccggtacggc    540
cccgaggggg aggccgtacc cgtggccatc cccgaggagc gggccctggt gttcgacgtg    600
gaggtctgct tggcagaggg aacttgcccc acattggcgg tggccatatc cccctcggcc    660
tggtattcct ggtgcagcca gcggctggtg gaagagcgtt actcttggac cagccagctg    720
tcgccggctg acctcatccc cctggaggtc cctactggtg ccagcagccc cacccagaga    780
gactggcagg agcagttagt ggtggggcac aatgtttcct ttgaccgagc tcatatcagg    840
gagcagtacc tgatccaggg ttcccgcatg cgtttcctgg acaccatgag catgcacatg    900
gccatctcag ggctaagcag cttccagcgc agtctgtgga tagcagccaa gcagggcaaa    960
cacaaggtcc agcccccac aaagcaaggc cagaagtccc agaggaaagc cagaagaggc   1020
ccagcgatct catcctggga ctggctggac atcagcagtg tcaacagtct ggcagaggtg   1080
cacagacttt atgtaggggg gcctccctta gagaaggagc ctcgagaact gtttgtgaag   1140
ggcaccatga aggacattcg tgagaacttc caggacctga tgcagtactg tgcccaggac   1200
gtgtgggcca cccatgaggt tttccagcag cagctaccgc tcttcttgga gaggtgtccc   1260
cacccagtga ctctggccgg catgctggag atgggtgtct cctacctgcc tgtcaaccag   1320
aactgggagc gttacctggc agaggcacag ggcacttatg aggagctcca gcgggagatg   1380
aagaagtcgt tgatggatct ggccaatgat gcctgccagc tgctctcagg agagaggtac   1440
aaagaagacc cctggctctg ggacctggag tgggacctgc aagaatttaa gcagaagaaa   1500
gctaagaagg tgaagaagga accagccaca gccagcaagt tgcccatcga ggggctggg   1560 gcccctggtg atcccatgga tcaggaagac ctcggcccct gcagtgagga ggaggagttt   1620
caacaagatg tcatggcccg cgcctgcttg cagaagctga gggaccac agagctcctg   1680 cccagcggc cccagcacct tcctggacac cctggatggt accggaagct ctgccccgg   1740 ctagacgacc ctgcatggac cccgggcccc agcctcctca gcctgcagat gcgggtcaca   1800
cctaaactca tggcacttac ctgggatggc ttccctctgc actactcaga gcgtcatggc   1860
tggggctact tggtgcctgg gcggcgggac aacctggcca agctgccgac aggtaccacc   1920
ctggagtcag ctggggtggt ctgccccctac agagccatcg agtccctgta caggaagcac   1980
tgtctcgaac agggggaagca gcagctgatg ccccaggagg ccggcctggc ggaggagttc   2040
ctgctcactg acaatagtgc catatggcaa acggtagaag aactggatta cttagaagtg   2100
gaggctgagg ccaagatgga gaacttgcga gctgcagtgc caggtcaacc cctagctctg   2160
actgcccgtg gtggccccaa ggacacccag cccagctatc accatggcaa tggaccttac   2220
aacgacgtgg acatccctgg ctgctggttt ttcaagctgc ctcacaagga tggtaatagc   2280
tgtaatgtgg gaagcccctt tgccaaggac ttcctgccca agatggagga tggcacccctg   2340 caggctggcc caggaggtgc cagtgggccc cgtgctctgg aaatcaacaa aatgattcct   2400
ttctggagga acgcccataa acgtatcagc tcccagatgg tggtgtggct gcccaggtca   2460
gctctgcccc gtgctgtgat caggcacccc gactatgatg aggaaggcct ctatgggcc   2520 atcctgcccc aagtggtgac tgccggcacc atcactcgcc gggctgtgga gcccacatgg   2580
ctcaccgcca gcaatgcccg gcctgaccga gtaggcagtg agttgaaagc catggtgcag   2640 gcccccacctg gctacacccct tgtgggtgct gatgtggact cccaagagct gtggattgca   2700
gctgtgcttg gagacgccca ctttgccggc atgcatggct gcacagcctt gggtggatg   2760 acactgcagg gcaggaagag caggggcact gatctacaca gtaagacagc cactactgtg   2820
ggcatcagcc gtgagcatgc caaaatcttc aactacggcc gcatctatgg tgctgggcag   2880
```

```
cccctttgctg agcgcttact aatgcagttt aaccaccggc tcacacagca ggaggcagct    2940
gagaaggccc agcagatgta cgctgccacc aagggcctcc gctggtatcg gctgtcggat    3000
gagggcgagt ggctggtgag ggagttgaac ctcccagtgg acaggactga gggtggctgg    3060
atttccctgc aggatctgcg caaggtccag agagaaactg caaggaagtc acagtggaag    3120
aagtgggagg tggttgctga cgggcatgg aaggggggca cagagtcaga aatgttcaat     3180
aagcttgaga gcattgctac gtctgacata ccacgtaccc cggtgctggg ctgctgcatc    3240
agccgagccc tggagccctc ggctgtccag gaagagttta tgaccagccg tgtgaattgg    3300
gtggtacaga gctctgctgt tgactactta cacctcatgc ttgtggccat gaagtggctg    3360
tttgaagagt ttgccataga tgggcgcttc tgcatcagca tccatgacga ggttcgctac    3420
ctggtgcggg aggaggaccg ctaccgcgct gccctggcct tgcagatcac caacctcttg    3480
accaggtgca tgtttgccta caagctgggt ctgaatgact tgccccagtc agtcgccttt    3540
ttcagtgcag tcgatattga ccggtgcctc aggaaggaag tgaccatgga ttgtaaaacc    3600
ccttccaacc caactgggat ggaaaggaga tacgggattc cccagggtga agcgctggat    3660
atttaccaga taattgaact caccaaaggc tccttggaaa aacgaagcca gcctggacca    3720
tag                                                                  3723

<210> SEQ ID NO 24
<211> LENGTH: 2703
<212> TYPE: DNA
<213> ORGANISM: Homo sapiens

<400> SEQUENCE: 24
atggaaaatt atgaggcatt ggtaggcttt gatctctgta atacaccgct ctccagtgtt     60
gctcagaaga ttatgtctgc tatgcattca ggtgatttag tggattctaa gacttgggga   120
aagagtacag agactatgga agtgataaac aagtccagtg ttaagtattc agtacaactt   180
gaagacagga agactcaatc accagaaaaa aaggatctta atctttaag aagtcagaca    240 tcaagaggtt ctgccaagct gtctcctcag tccttcagtg tcaggctcac agatcagctg   300
tctgctgacc aaaaacagaa gagcatcagc tcattgactc tttcaagttg tttaattcca   360
cagtataatc aagaggcttc agttctacag aaaaagggc ataaaagaaa gcatttccta    420
atggagaata taaataatga aaataaagga agcattaatc ttaaaagaaa acatattaca   480
tataataatt tgtcagagaa acaagtaaa caaatggcat tggaagaaga tactgatgac    540
gccgaaggct acctaaattc tgggaactca ggagcattga aaaacatttt ttgtgatatt   600
aggcatttgg atgattgggc aaaaagccag ctgattgaaa tgctcaaaca ggcagcagcc   660
ctggtgataa ctgtgatgta tactgatggt tccacccagc taggagctga ccagaccccc   720
gtttcttctg ttagaggaat tgtggtgtta gtaaaacgcc aagcagaggg tggccatggc   780
tgtccagatg ccccggcctg tggtcctgtt ctggagggct tgtgtcaga tgatccatgc    840 atctacattc aaatagagca ctctgctatc tgggaccaag aacaggaggc acatcaacaa   900
tttgcccgga acgtgctatt tcaaacaatg aaatgtaaat gtcctgttat ttgttttaat   960
gctaaggatt ttgtgagaat agtgctgcag tttttttggca atgatggcag ttggaagcat  1020
gttgctgatt ttatagggct agatcccaga attgctgcat ggcttataga tcctagtgat  1080
gccacaccct cttttgaaga tttagtagaa aaatactgtg aaaaatccat tacagttaaa  1140
gtgaacagca catatggaa ttcctcaaga aatattgtga atcagaatgt acgtgagaac   1200
```

| | |
|---|---:|
| ctgaagacac tctacagact acaatggac ctttgctcta aactgaagga ttatggttta | 1260 |
| tggcaactat ttcgtacttt ggagcttcct ctgataccaa ttttggcagt gatggaaagc | 1320 |
| catgccattc aggtgaacaa agaggagatg gagaagacgt cagcacttct tggggctcgt | 1380 |
| ctcaaggaat tggagcaaga agctcatttt gttgcaggag aacggtttct tataacgagc | 1440 |
| aataaccagc ttcgagagat cctctttggc aagttaaagc tgcacctgct gagtcaaagg | 1500 |
| aacagtctcc ccagaacggg gttgcagaaa tacccgtcta catcagaagc agtgttaaat | 1560 |
| gctctgcgag accttcatcc attacccaag ataattttgg aatacaggca ggttcacaag | 1620 |
| atcaagtcaa cctttgtaga tggattacta gcttgcatga aaaagggctc catttcctct | 1680 |
| acatggaatc agactggaac tgtgactgga agactttcag ccaagcatcc taatatccaa | 1740 |
| ggtatctcca agcacccaat tcagattact acacctaaga attttaaagg taaagaagac | 1800 |
| aagattctca cgatctcccc gagggccatg tttgtttcat ccaaaggcca cacctttcta | 1860 |
| gcagcagact tttcacagat tgaattgcgc attcttacac atttatctgg agatccggaa | 1920 |
| cttctgaagt tattccagga atctgaaaga gatgatgtat tttctactct gacttcacag | 1980 |
| tggaaggatg tgcccgtgga acaggtgaca cacgcagaca gagagcaaac caagaaggtg | 2040 |
| gtgtacgcgg tggtctatgg agcagggaag gagcggctgg ctgcttgcct tggagttcct | 2100 |
| attcaggaag ctgcccagtt tttggagagt tttttgcaga agtacaagaa aatcaaggac | 2160 |
| ttcgcccgag cagctattgc ccagtgtcac cagacaggct gtgtggtgtc catcatgggc | 2220 |
| agaaggagac ccctgccaag gattcacgct catgaccagc aactccgggc acaagcagag | 2280 |
| cgacaggcag tgaacttcgt ggtgcaaggc tccgctgctg acctctgcaa gctggccatg | 2340 |
| atccatgtct tcactgcagt ggctgcttcc cacaccttga cggccaggct ggtggcccag | 2400 |
| atccatgatg agctgctgtt tgaagtggaa gatccgcaga tcccggagtg tgcagctctc | 2460 |
| gtcaggagga ccatggagtc cttggaacag gtgcaggcat tggagctgca gcttcaggta | 2520 |
| cccctcaagg tgagcctgag tgccggccgc tcatggggac acctggtgcc actgcaggag | 2580 |
| gcctggggcc ctccgccagg cccatgtcgc actgagtctc ccagcaacag cctggctgcc | 2640 |
| cctgggtccc ctgccagcac ccagcccca cccctgcatt tttcgccttc attttgtctg | 2700 |
| tag | 2703 |

<210> SEQ ID NO 25
<211> LENGTH: 1629
<212> TYPE: DNA
<213> ORGANISM: Homo sapiens

<400> SEQUENCE: 25

| | |
|---|---:|
| atggcttccc cttgtcctga agaagcagct atgagaagag aggtggtgaa acggatcgaa | 60 |
| actgtggtga aagacctttg gccgacggct gatgtacaga tatttggcag ctttagtaca | 120 |
| ggtctttatc ttccaactag cgacatagac ctggtggtct tcgggaaatg ggagcgtcct | 180 |
| cctttacagc tgctggagca agccctgcgg aagcacaacg tggctgagcc gtgttccatc | 240 |
| aaagtccttg acaaggctac ggtaccaata ataaagctca cagatcagga gactgaagtg | 300 |
| aaagttgaca tcagctttaa catggagacg ggcgtccggg cagcggagtt catcaagaat | 360 |
| tacatgaaga atattcatt gctgccttac ttgattttag tattgaaaca gttccttctg | 420 |
| cagagggacc tgaatgaagt ttttacaggt ggaattagct catacagcct aatttttaatg | 480 |
| gccattagct ttctacagtt gcatccaaga attgatgccc ggagagctga tgaaaacctt | 540 |
| ggaatgcttc ttgtagaatt ttttgaactc tatgggagaa attttaatta cttgaaaacc | 600 |

```
ggtattagaa tcaaagaagg aggtgcctat atcgccaaag aggagatcat gaaagccatg      660
accagcgggt acagaccgtc gatgctgtgc attgaggacc ccctgctgcc agggaatgac      720
gttggccgga gctcctatgg cgccatgcag gtgaagcagg tcttcgatta tgcctacata      780
gtgctcagcc atgctgtgtc accgctggcc aggtcctatc aaacagaga cgccgaaagt       840 actttaggaa gaatcatcaa agtaactcag gaggtgattg actaccggag gtggatcaaa      900
gagaagtggg gcagcaaagc ccacccgtcg ccaggcatgg acagcaggat caagatcaaa      960
gagcgaatag ccacatgcaa tggggagcag acgcagaacc gagagcccga gtctccctat     1020
ggccagcgct tgactttgtc gctgtccagc ccccagctcc tgtcttcagg ctcctcggcc     1080
tcttctgtgt cttcactttc tgggagtgac gttgattcag acacaccgcc ctgcacaacg     1140
cccagtgttt accagttcag tctgcaagcg ccagctcctc tcatggccgg cttacccacc     1200
gccttgccaa tgcccagtgg caaacctcag cccaccactt ccagaacact gatcatgaca     1260
accaacaatc agaccaggtt tactatacct ccaccgaccc taggggttgc tcctgttcct     1320
tgcagacaag ctggtgtaga aggaactgcg tctttgaaag ccgtccacca catgtcttcc     1380
ccggccattc cctcagcgtc ccccaacccg ctctcgagcc ctcatctgta tcataagcac     1440
aacggcatga aactgtccat gaagggctct cacggccaca cccaaggcgg cggctacagc     1500
tctgtgggta gcggaggtgt gcggccccct gtgggcaaca ggggacacca ccagtataac     1560
cgcaccggct ggaggaggaa aaaacacaca cacacgggga cagtctgcc cgtgagcctc     1620 agcagataa                                                             1629

<210> SEQ ID NO 26
<211> LENGTH: 2736
<212> TYPE: DNA
<213> ORGANISM: Homo sapiens

<400> SEQUENCE: 26
atggctgcct cacaaacttc acaaactgtt gcatctcacg ttcctttttgc agatttgtgt      60 tcaactttag aacgaataca gaaaagtaaa ggacgtgcag aaaaaatcag acacttcagg     120 gaattttttag attcttggag aaaatttcat gatgctcttc ataagaacca caaagatgtc     180
acagactctt tttatccagc aatgagacta attcttcctc agctagaaag agagagaatg     240
gcctatggaa ttaaagaaac tatgcttgct aagctttata ttgagttgct taatttacct     300
agagatggaa agatgccct caaacttta aactacagaa cacccactgg aactcatgga      360
gatgctggag actttgcaat gattgcatat tttgtgttga agccaagatg tttacagaaa     420
ggaagtttaa ccatacagca agtaaacgac cttttagact caattgccag caataattct     480
gctaaaagaa aagacctaat aaaaaagagc cttcttcaac ttataactca gagttcagca     540
cttgagcaaa agtggcttat acggatgatc ataaaggatt taaagcttgg tgttagtcag    600
caaactatct tttctgttттt tcataatgat gctgctgagt tgcataatgt cactacagat     660
ctggaaaaag tctgtaggca actgcatgat ccttctgtag gactcagtga tatttctatc    720
actttatttt ctgcatttaa accaatgcta gctgctattg cagatattga gcacattgag   780
aaggatatga acatcagag tttctacata gaaaccaagc tagatggtga acgtatgcaa      840
atgcacaaag atggagatgt atataaatac ttctctcgaa atggatataa ctacactgat   900
cagtttggtg cttctcctac tgaaggttct cттacccccaт tcattcataa tgcattcaaa    960
gcagatatac aaatctgtat tcttgatggt gagatgatgg cctataatcc taatacacaa     1020
```

```
actttcatgc aaaagggaac taagtttgat attaaaagaa tggtagagga ttctgatctg    1080
caaacttgtt attgtgtttt tgatgtattg atggttaata ataaaaagct agggcatgag    1140
actctgagaa agaggtatga gattcttagt agtattttta caccaattcc aggtagaata    1200
gaaatagtgc agaaaacaca agctcatact aagaatgaag taattgatgc attgaatgaa    1260
gcaatagata aagagaaga gggaattatg gtaaacaac ctctatccat ctacaagcca     1320
gacaaaagag gtgaagggtg gttaaaaatt aaaccagagt atgtcagtgg actaatggat    1380
gaattggaca ttttaattgt tggaggatat tggggtaaag gatcacgggg tggaatgatg    1440
tctcattttc tgtgtgcagt agcagagaag ccccctcctg gtgagaagcc atctgtgttt    1500
catactctct ctcgtgttgg gtctggctgc accatgaaag aactgtatga tctgggtttg    1560
aaattggcca agtattggaa gccttttcat agaaaagctc caccaagcag cattttatgt    1620
ggaacagaga agccagaagt atacattgaa ccttgtaatt ctgtcattgt tcagattaaa    1680
gcagcagaga tcgtacccag tgatatgtat aaaactggct gcaccttgcg ttttccacga    1740
attgaaaaga taagagatga caaggagtgg catgagtgca tgaccctgga cgacctagaa    1800
caacttaggg ggaaggcatc tggtaagctc gcatctaaac accttatat aggtggtgat    1860 gatgaaccac aagaaaaaaa gcggaaagct gccccaaaga tgaagaaagt tattggaatt    1920
attgagcact aaaagcacc taaccttact aacgttaaca aaatttctaa tatatttgaa    1980
gatgtagagt tttgtgttat gagtggaaca gatagccagc caaagcctga cctggagaac    2040
agaattgcag aatttggtgg ttatatagta caaaatccag gcccagacac gtactgtgta    2100
attgcagggt ctgagaacat cagagtgaaa aacataattt tgtcaaataa acatgatgtt    2160
gtcaagcctg catggctttt agaatgtttt aagaccaaaa gctttgtacc atggcagcct    2220
cgctttatga ttcatatgtg cccatcaacc aaagaacatt tgcccgtga atatgattgc     2280 tatggtgata gttatttcat tgatacagac ttgaaccaac tgaaggaagt attctcagga    2340
attaaaaatt ctaacgagca gactcctgaa gaaatggctt ctctgattgc tgatttagaa    2400
tatcggtatt cctgggattg ctctcctctc agtatgtttc gacgccacac cgtttatttg    2460
gactcgtatg ctgttattaa tgacctgagt accaaaaatg aggggacaag gttagctatt    2520
aaagccttgg agcttcggtt tcatggagca aaagtagttt cttgtttagc tgagggagtg    2580
tctcatgtaa taattgggga agatcatagt cgtgttgcag attttaaagc ttttagaaga    2640
acttttaaga gaaagtttaa aatcctaaaa gaaagttggg taactgattc aatagacaag    2700
tgtgaattac aagaagaaaa ccagtatttg atttaa                             2736
```

<210> SEQ ID NO 27
<211> LENGTH: 3087
<212> TYPE: DNA
<213> ORGANISM: Homo sapiens

<400> SEQUENCE: 27

```
atgggctccg ccgcctgccc ccggggagcc ttgccggagc tcgcgccctg ctgccagcct     60
cgcgagcagt cgcagcccca cacgcgatgg gacgcgggct gtgggattca gcaccccggg    120
ggcgaggaat tcaggaccct cggcggggca agggcctata gggttccgaa ctcgcaggag    180
ggtcgctcct cccctactcg cttttttccg gcaccggaag gccccgccca ctgctttgtt    240
tcctctccag accgcgcatt tgggtctcg gaagaggttc agaggctgtt gttgagcaat     300
gcatgccagc caaagaatg caatggtgta agattccag ttgatgccag taaacctaat     360
ccaaatgatg tggagtttga taatctgtat ttggatatga atggaatcat ccatccctgt    420
```

```
actcatcctg aagacaaacc agcaccaaaa aatgaagatg aaatgatggt tgcaattttt    480
gagtacattg acagactttt cagtattgta agaccaagaa gacttctcta catggcaata    540
gatggagtgg caccacgtgc taaaatgaac cagcagcgtt caaggaggtt cagggcatca    600
aaagaaggaa tggaagcagc agtcgagaag cagcgagtca gggaagaaat attggcaaaa    660
ggtggctttc ttcctccaga agaaataaaa gaaagatttg acagcaactg tattacacca    720
ggaactgaat tcatggacaa tcttgctaaa tgccttcgct attacatagc tgatcgttta    780
aataatgacc ctgggtggaa aaatttgaca gttattttat ctgatgctag tgctcctggt    840
gaaggagaac ataaaatcat ggattacatt agaaggcaaa gagcccagcc taaccatgac    900
ccaaatactc atcattgttt atgtggagca gatgctgatc tcattatgct tggccttgcc    960
acacatgaac cgaactttac cattattaga gaagaattca aaccaaacaa gcccaaacca   1020
tgtggtcttt gtaatcagtt tggacatgag gtcaaagatt gtgaaggttt gccaagagaa   1080
aagaagggaa agcatgatga acttgccgat agtcttcctt gtgcagaagg agagtttatc   1140
ttccttcggc ttaatgttct tcgtgagtat ttggaaagag aactcacaat ggccagccta   1200
ccattcacat ttgatgttga gaggagcatt gatgactggg ttttcatgtg cttcttgtg    1260 ggaaatgact tcctccctca tttgccatcg ttagagatta gggaaaatgc aattgaccgt   1320
ttggttaaca tatacaaaaa tgtggtacac aaaactgggg gttaccttac agaaagtggt   1380
tatgtcaatc tgcaaagagt acagatgatc atgttagcag ttggtgaagt tgaggatagc   1440 attttttaaaa agagaaagga tgatgaggac agtttttagaa gacgacagaa agaaaaaaga   1500
aagagaatga agagagatca accagctttc actcctagtg gaatattaac tcctcatgcc   1560
ttgggttcaa gaaattcacc aggttctcaa gtagccagta atccgagaca agcagcctat   1620
gaaatgagga tgcagaataa ctctagtcct tcgatatctc ctaatacgag tttcacatct   1680
gatggctccc cgtctccatt aggaggaatt aagcgaaaag cagaagacag tgacagtgaa   1740
cctgagccag aggataatgt caggttatgg gaagctggct ggaagcagcg gtactacaag   1800
aacaaatttg atgtggatgc agctgatgag aaattccgtc ggaaagttgt gcagtcgtac   1860
gttgaaggac tttgctgggt tcttagatat tattaccagg gctgtgcttc ctggaagtgg   1920
tattatccat tcattatgc accatttgct tcagactttg aaggcattgc agacatgcca   1980
tctgattttg agaagggtac gaaaccgttt aaaccactag aacaacttat ggggtatttt   2040
ccagctgcaa gtggtaattt tctacctcca tcatggcgga agctcatgag tgatcctgat   2100
tctagtataa ttgacttcta tcctgaagat tttgctattg atttgaatgg aagaaatat    2160 gcatggcaag gtgttgctct cttgccattc gtggatgagc gaaggctacg agctgcccta   2220
gaagaggtat acccagacct cactccagaa gagaccagaa gaaacagcct tggaggtgat   2280
gtcttatttg tggggaaaca tcacccactc catgacttca ttttagagct gtaccagaca   2340
ggttccacag agccagtgga ggtacccct gaactatgtc atgggattca aggaaagttt   2400
tctttggatg aagaagccat tcttccagat caaatagtat gttctcctgt tcctatgtta   2460
agggatctga cacagaacac tgtagtcagt attaatttta aagacccaca gtttgctgaa   2520
gattacattt ttaaagctgt aatgcttcca ggagcaagaa agccagcagc agtactgaaa   2580
cctagtgact gggaaaaatc cagcaatgga cggcagtgga agcctcagct tggctttaac   2640
cgtgaccgga ggcctgtgca cctggatcag gcagccttca ggactttggg ccatgtgatg   2700
ccaagaggct caggaactgg catttacagc aatgctgcac caccacctgt gacttaccag   2760
```

```
ggaaacttat acaggccgct tttgagagga caagcccaga ttccaaaact tatgtcaaat      2820
atgaggcccc aggattcctg gcgaggtcct cctcccyttt tccagcagca aaggtttgac      2880
agaggcgttg gggctgaacc tctgctccca tggaaccgga tgctgcaaac ccagaatgca      2940
gccttccagc caaaccagta ccagatgcta gctgggcctg gtgggtatcc acccagacga      3000
gatgatcgtg gagggagaca gggatatccc agagaaggaa ggaaataccc tttgccacca      3060
ccctcaggaa gatacaattg gaattaa                                          3087
```

<210> SEQ ID NO 28
<211> LENGTH: 1863
<212> TYPE: DNA
<213> ORGANISM: Escherichia coli

<400> SEQUENCE: 28

```
atggactata aggaccacga cggagactac aaggatcatg atattgatta caaagacgat        60
gacgataaga tggcccccaaa gaagaagcgg aaggtcggta tccacggagt cccagcagcc      120
tcattgaagg gaaaattttt tgcatttctc ccgaacccta cacctcatc  caataagttt      180 tttaagtcaa ttcttgagaa gaaggagct acaattgtat catctattca aaattgcctc       240
cagagttcta ggaagagagt cattatcctt atagaggaca gtttcgtcga cagtgacatg      300
cacctgacac agaaggacat ttttcaacgc gaggctggct tgaacgacgt agacgagttt      360
ttgggtaaaa ttgaacaatc cggcatccag tgcgttaaga ctagctgcat taccaagtgg      420
gttcaaaacg acaaattcgc ttttcaaaag gacgatttga ttaagttcca accgagtatc      480
atagtcatta gtgacaatgc cgatgatgga cagagtagca ctgacaaaga aagcgaaatc      540
tcaactgacg tagaatcaga gcgaaacgat gactcaaaca caaagacat  gattcaggcc      600 tccaaaccgc tcaaacggtt gcttcaggag gataaaggtc gcgcttccct tgttaccgat      660
aaaaccaagt ataaaaataa tgaacttata ataggcgcgc ttaaacgact taccaagaag      720
tacgagattg agggtgaaaa attccgagct cggtcctacc ggctcgctaa caatctatg       780 gaaaattgtg atttcaatgt tagaagcgga gaggaagcac atacaaagtt gagaaacatc      840
ggtcctagta ttgctaaaaa aattcaggtc attcttgata cggagttct  cccgggtctc      900 aacgattccg ttggccttga agacaagctg aaatatttta agaactgcta tggaatcggg      960
tcagagatag caaacggtg gaatctcctt aactttgagt catttgcgt  ggctgctaag      1020 aaagaccccg aggaatttgt gtccgattgg acgatattgt tcgggtggag  ttattatgat      1080
gattggcttt gcaaaatgtc caggaatgaa tgcttcgccc atcttaagaa ggtccaaaag      1140
gctttgcgcg gaatcgaccc cgaatgtcag gtcgagcttc aagggtcata caatcggggt      1200
tactcaaaat gcgggggatat agatctcctc tttttaagc cattctgcaa cgataccact      1260
gaactcgcta agatcatgga gacactctgc ataaagcttt ataaagatgg gtatatacat      1320
tgcttcttgc aattgacgcc caacttggag aagctttttc ttaaaagaat tgttgaacgg      1380
ttccggacag ccaagattgt tggctatgga gaacgaaaac gctggtattc atcagaaatt      1440
atcaagaaat tctttatggg agtgaagttg tccccccgcg agctcgaaga attgaaggag      1500
atgaaaaacg acgagggaac cctgttgatc gaggaagaag aagaggaaac gaagctgaag      1560
cccattgacc agtacatgag cctgaacgct aaagacggaa actactgccg aaggttggat      1620
tttttctgtt gtaagtggga cgagctgggg gcggggagga tacactatac gggtagcaaa      1680
gagtataata ggtggataag gatactcgcc gcgcaaaaag ggttcaaact gacccagcat      1740
ggacttttcc ggaacaacat actcctggag tctttcaacg aaaggcgaat cttcgaactc      1800
```

| | |
|---|---|
| ctgaacctta agtatgccga gccggagcac cgcaatatag agtgggaaaa aaagacggga | 1860 |
| tga | 1863 |

<210> SEQ ID NO 29
<211> LENGTH: 1488
<212> TYPE: DNA
<213> ORGANISM: Escherichia coli

<400> SEQUENCE: 29

| | |
|---|---|
| atggactata aggaccacga cggagactac aaggatcatg atattgatta caaagacgat | 60 |
| gacgataaga tggccccaaa gaagaagcgg aaggtcggta tccacggagt cccagcagcc | 120 |
| ctgcctagtc agagccccgc aatatttaca gtgagtcgcc ttaaccaaac cgttcgactg | 180 |
| ttgctcgagc acgaaatggg gcaagtctgg atctccgggg aaatatcaaa ttttacgcag | 240 |
| ccagcctccg gtcactggta cttcactctt aaagatgaca cggcgcaagt acgctgcgcc | 300 |
| atgtttcgga acagcaatag acgagtgacg ttccggccac aacatggaca gcaagtactc | 360 |
| gtcagggcca atatcactct ttatgagccg cgcggtgact atcaaataat tgtcgaatct | 420 |
| atgcaacccg cgggggaggg tttgctccag caaaagtatg agcaactcaa agcgaagctc | 480 |
| caggcagaag gcctgttcga ccagcagtat aaaaaaccgc tcccgtcacc cgctcattgt | 540 |
| gttggcgtca taacctctaa gacgggtgct gcgttgcacg acattcttca gtgcttaag | 600 |
| cgccgagacc catctctgcc tgttatcatc tacccagcgg ccgttcaagg cgatgacgct | 660 |
| cctgggcaga tagtaagagc aatagaactg gcgaatcagc ggaacgaatg tgatgtgctg | 720 |
| atcgttgggc gcggcggagg gagcttggaa gatctttggt ccttcaacga tgagcgcgtc | 780 |
| gcacgggcaa tcttcaccag ccggataccg tagtttcag cggtggggca tgagacggac | 840 |
| gtcacaatcg ccgattttgt agccgacctg agagcaccga cgccatcagc ggcagcagaa | 900 |
| gtcgtcagcc gcaatcagca ggagctgctc aggcaggtcc agagcacccg caacgcctc | 960 |
| gagatggcga tggattacta tcttgccaat cgaacacgac gattcaccca gattcaccac | 1020 |
| cggttgcagc agcaacatcc ccaacttcgg ctggcccgac agcaaacaat gctggaacgc | 1080 |
| ctccagaaac ggatgagttt tgctctggaa aatcagttga agcgaactgg tcaacagcag | 1140 |
| caaagactga ctcagcgcct caatcagcaa aatccccaac ctaagatcca tcgggcacaa | 1200 |
| acccgcattc aacaactgga gtatagactg gctgagacct tgcgcgccca gctctccgca | 1260 |
| actcgcgaga ggttcggaaa tgccgtaacg catttggagg ccgtgagccc actgtcaacc | 1320 |
| ctcgctcggg gctactccgt gacgactgcc acggacggca atgtgctcaa aaaggtaaaa | 1380 |
| caagtcaaag ctggagaaat gcttactact cggctcgaag acggatggat cgaaagtgaa | 1440 |
| gtcaaaaata tacaacctgt caagaagagt cggaaaaagg tgcattga | 1488 |

<210> SEQ ID NO 30
<211> LENGTH: 360
<212> TYPE: DNA
<213> ORGANISM: Escherichia coli

<400> SEQUENCE: 30

| | |
|---|---|
| atggactata aggaccacga cggagactac aaggatcatg atattgatta caaagacgat | 60 |
| gacgataaga tggccccaaa gaagaagcgg aaggtcggta tccacggagt cccagcagcc | 120 |
| ccgaaaaaaa acgaagcccc cgcctccttt gagaaagcac ttagcgagct ggagcagatc | 180 |
| gtgacgcgct tggaatcagg ggatctccct ttggaagagg cattgaatga gtttgagcga | 240 |

-continued

| | |
|---|---|
| ggagttcagc tcgctagaca aggccaggcc aaacttcaac aggcggaaca gcgagtccag | 300 |
| attctcctta gtgataatga ggatgcctct ctgacaccgt tcacgccaga caacgagtga | 360 |

<210> SEQ ID NO 31
<211> LENGTH: 4272
<212> TYPE: DNA
<213> ORGANISM: Streptococcus pyogenes

<400> SEQUENCE: 31

| | |
|---|---|
| atggactata aggaccacga cggagactac aaggatcatg atattgatta caaagacgat | 60 |
| gacgataaga tggccccaaa gaagaagcgg aaggtcggta tccacggagt cccagcagcc | 120 |
| gacaagaagt acagcatcgg cctggacatc ggcaccaact ctgtgggctg ggccgtgatc | 180 |
| accgacgagt acaaggtgcc cagcaagaaa ttcaaggtgc tgggcaacac cgaccggcac | 240 |
| agcatcaaga gaacctgat cggagccctg ctgttcgaca cggcgaaac agccgaggcc | 300 |
| acccggctga gagaaccgc cagaagaaga tacaccagac ggaagaaccg gatctgctat | 360 |
| ctgcaagaga tcttcagcaa cgagatggcc aaggtggacg acagcttctt ccacagactg | 420 |
| gaagagtcct tcctggtgga agaggataag aagcacgagc ggcaccccat cttcggcaac | 480 |
| atcgtggaca aggtggccta ccacgagaag taccccacca tctaccacct gagaaagaaa | 540 |
| ctggtggaca gcaccgacaa ggccgacctg cggctgatct atctggccct ggcccacatg | 600 |
| atcaagttcc ggggccactt cctgatcgag ggcgacctga accccgacaa cagcgacgtt | 660 |
| gacaagctgt tcatccagct ggtgcagacc tacaaccagc tgttcgagga aaaccccatc | 720 |
| aacgccagcg gcgtggacgc caaggccatc ctgtctgcca gactgagcaa gagcagacgg | 780 |
| ctggaaaatc tgatcgccca gctgcccggc gagaagaaga tggcctgttt cggaaacctg | 840 |
| attgccctga gcctgggcct gacccccaac ttcaagagca cttcgacct ggccgaggat | 900 |
| gccaaactgc agctgagcaa ggacacctac gacgacgacc tggacaacct gctggcccag | 960 |
| atcggcgacc agtacgccga cctgtttctg gccgccaaga acctgtccga cgccatcctg | 1020 |
| ctgagcgaca tcctgagagt gaacaccgag atcaccaagg ccccctgag cgcctctatg | 1080 |
| atcaagagat acgacgagca ccaccaggac ctgaccctgc tgaaagctct cgtgcggcag | 1140 |
| cagctgcctg agaagtacaa agagattttc ttcgaccaga gcaagaacgg ctacgccggc | 1200 |
| tacattgacg gcggagccag ccaggaagag ttctacaagt tcatcaagcc catcctggaa | 1260 |
| aagatggacg gcaccgagga actgctcgtg aagctgaaca gagaggacct gctgcggaag | 1320 |
| cagcggacct tcgacaacgg cagcatcccc caccagatcc acctgggaga gctgcacgcc | 1380 |
| attctgcggc ggcaggaaga tttttaccca ttcctgaagg acaaccggga aaagatcgag | 1440 |
| aagatcctga ccttccgcat ccctactac gtgggccctc tggccagggg aaacagcaga | 1500 |
| ttcgcctgga tgaccagaaa gagcgaggaa accatcaccc cctggaactt cgaggaagtg | 1560 |
| gtggacaagg gcgcttccgc ccagagcttc atcgagcgga tgaccaactt cgataagaac | 1620 |
| ctgcccaacg agaaggtgct gcccaagcac agcctgctgt acgagtactt caccgtgtat | 1680 |
| aacgagctga ccaaagtgaa atacgtgacc gagggaatga gaaagcccgc cttcctgagc | 1740 |
| ggcgagcaga aaaaggccat cgtggacctg ctgttcaaga ccaaccggaa agtgaccgtg | 1800 |
| aagcagctga aggagacta cttcaagaaa atcgagtgct tcgactccgt ggaaatctcc | 1860 |
| ggcgtggaag atcggttcaa cgcctccctg ggcacatacc acgatctgct gaaaattatc | 1920 |
| aaggacaagg acttcctgga caatgaggaa aacgaggaca ttctggaaga tatcgtgctg | 1980 |
| accctgacac tgtttgagga cagagagatg atcgaggaac ggctgaaaac ctatgcccac | 2040 |

```
ctgttcgacg acaaagtgat gaagcagctg aagcggcgga gatacaccgg ctggggcagg    2100
ctgagccgga agctgatcaa cggcatccgg acaagcagt ccggcaagac aatcctggat     2160
ttcctgaagt ccgacggctt cgccaacaga aacttcatgc agctgatcca cgacgacagc    2220 ctgacccttta aagaggacat ccagaaagcc caggtgtccg ccagggcga tagcctgcac    2280 gagcacattg ccaatctggc cggcagcccc gccattaaga agggcatcct gcagacagtg    2340
aaggtggtgg acgagctcgt gaaagtgatg ggccggcaca agcccgagaa catcgtgatc    2400
gaaatggcca gagagaacca gaccacccag aagggacaga gaacagccg cgagagaatg     2460 aagcggatcg aagagggcat caaagagctg ggcagccaga tcctgaaaga cacccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc     3480 agaaagaagg actgggaccc taagaagtac ggcggcttcg acagcccac cgtggcctat     3540 tctgtgctgg tggtggccaa agtggaaaag ggcaagtcca agaaactgaa gagtgtgaaa    3600
gagctgctgg gatcaccat catggaaaga agcagcttcg agaagaatcc catcgacttt    3660
ctggaagcca gggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccacccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaagt aa                                                       4272

<210> SEQ ID NO 32
```

<211> LENGTH: 4269
<212> TYPE: DNA
<213> ORGANISM: Streptococcus pyogenes

<400> SEQUENCE: 32

| | | | | | |
|---|---|---|---|---|---|
| atggactata | aggaccacga | cggagactac | aaggatcatg | atattgatta | caaagacgat | 60 |
| gacgataaga | tggccccaaa | gaagaagcgg | aaggtcggta | tccacggagt | cccagcagcc | 120 |
| gacaagaagt | acagcatcgg | cctggacatc | ggcaccaact | ctgtgggctg | ggccgtgatc | 180 |
| accgacgagt | acaaggtgcc | cagcaagaaa | ttcaaggtgc | tgggcaacac | cgaccggcac | 240 |
| agcatcaaga | agaacctgat | cggagccctg | ctgttcgaca | gcggcgaaac | agccgaggcc | 300 |
| acccggctga | agagaaccgc | cagaagaaga | tacaccagac | ggaagaaccg | gatctgctat | 360 |
| ctgcaagaga | tcttcagcaa | cgagatggcc | aaggtggacg | acagcttctt | ccacagactg | 420 |
| gaagagtcct | tcctggtgga | agaggataag | aagcacgagc | ggcaccccat | cttcggcaac | 480 |
| atcgtggacg | aggtggccta | ccacgagaag | tacccaccca | tctaccaccct | gagaaagaaa | 540 |
| ctggtggaca | gcaccgacaa | ggccgacctg | cggctgatct | atctggccct | ggcccacatg | 600 |
| atcaagttcc | ggggccactt | cctgatcgag | ggcgacctga | accccgacaa | cagcgacgtt | 660 |
| gacaagctgt | tcatccagct | ggtgcagacc | tacaaccagc | tgttcgagga | aaaccccatc | 720 |
| aacgccagcg | gcgtggacgc | caaggccatc | ctgtctgcca | gactgagcaa | gagcagacgg | 780 |
| ctggaaaatc | tgatcgccca | gctgcccggc | gagaagaaga | atggcctgtt | cggaaacctg | 840 |
| attgccctga | gcctgggcct | gacccccaac | ttcaagagca | acttcgacct | ggccgaggat | 900 |
| gccaaactgc | agctgagcaa | ggacacctac | gacgacgacc | tggacaacct | gctggcccag | 960 |
| atcggcgacc | agtacgccga | cctgtttctg | gccgccaaga | acctgtccga | cgccatcctg | 1020 |
| ctgagcgaca | tcctgagagt | gaacaccgag | atcaccaagg | cccccctgag | cgcctctatg | 1080 |
| atcaagagat | acgacgagca | ccaccaggac | ctgaccctgc | tgaaagctct | cgtgcggcag | 1140 |
| cagctgcctg | agaagtacaa | agagattttc | ttcgaccaga | gcaagaacgg | ctacgccggc | 1200 |
| tacattgacg | gcggagccag | ccaggaagag | ttctacaagt | tcatcaagcc | catcctggaa | 1260 |
| aagatggacg | gcaccgagga | actgctcgtg | aagctgaaca | gagaggacct | gctgcggaag | 1320 |
| cagcggacct | tcgacaacgg | cagcatcccc | caccagatcc | acctgggaga | gctgcacgcc | 1380 |
| attctgcggc | ggcaggaaga | tttttaccca | ttcctgaagg | acaaccggga | aaagatcgag | 1440 |
| aagatcctga | ccttccgcat | cccctactac | gtgggccctc | tggccagggg | aaacagcaga | 1500 |
| ttcgcctgga | tgaccagaaa | gagcgaggaa | accatcaccc | cctggaactt | cgaggaagtg | 1560 |
| gtggacaagg | gcgcttccgc | ccagagcttc | atcgagcgga | tgaccaactt | cgataagaac | 1620 |
| ctgcccaacg | agaaggtgct | gcccaagcac | agcctgctgt | acgagtactt | caccgtgtat | 1680 |
| aacgagctga | ccaaagtgaa | atacgtgacc | gagggaatga | gaaagcccgc | cttcctgagc | 1740 |
| ggcgagcaga | aaaaggccat | cgtggacctg | ctgttcaaga | ccaaccggaa | agtgaccgtg | 1800 |
| aagcagctga | agaggactac | cttcaagaaa | atcgagtgct | tcgactccgt | ggaaatctcc | 1860 |
| ggcgtggaag | atcggttcaa | cgcctccctg | ggcacatacc | acgatctgct | gaaaattatc | 1920 |
| aaggacaagg | acttcctgga | caatgaggaa | aacgaggaca | ttctggaaga | tatcgtgctg | 1980 |
| accctgacac | tgtttgagga | cagagagatg | atcgaggaac | ggctgaaaac | ctatgcccac | 2040 |
| ctgttcgacg | acaaagtgat | gaagcagctg | aagcggcgga | gatacaccgg | ctggggcagg | 2100 |
| ctgagccgga | agctgatcaa | cggcatccgg | gacaagcagt | ccggcaagac | aatcctggat | 2160 |
| ttcctgaagt | ccgacggctt | cgccaacaga | aacttcatgc | agctgatcca | cgacgacagc | 2220 |

```
ctgacctttA aagaggacat ccagaaagcc caggtgtccg gccagggcga tagcctgcac    2280
gagcacattg ccaatctggc cggcagcccc gccattaaga agggcatcct gcagacagtg    2340
aaggtggtgg acgagctcgt gaaagtgatg ggccggcaca agcccgagaa catcgtgatc    2400
gaaatggcca gagagaacca gaccacccag aagggacaga gaacagccg cgagagaatg     2460 aagcggatcg aagagggcat caaagagctg gcagccaga tcctgaaaga acaccccgtg     2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga aaagttcga caatctgacc     2820 aaggccgaga gaggcggcct gagcgaactg gataaggccg gcatcaagag acagctggtg    2880
gaaacccggc agatcacaaa gcacgtggca cagatcctgg actcccggat gaacactaag    2940
tacgacgaga atgacaagct gatccgggaa gtgaaagtga tcacccctgaa gtccaagctg    3000 gtgtccgatt tccggaagga tttccagttt tacaaagtgc gcgagatcaa caactaccac    3060
cacgcccacg acgcctacct gaacgccgtc gtgggaaccg ccctgatcaa aaagtaccct   3120
aagctggaaa gcgagttcgt gtacggcgac tacaaggtgt acgacgtgcg gaagatgatc   3180
gccaagagcg agcaggaaat cggcaaggct accgccaagt acttcttcta cagcaacatc   3240
atgaactttt tcaagaccga gattacccctg ccaacggcg agatccggaa gcggcctctg    3300
atcgagacaa acggcgaaac cggggagatc gtgtgggata agggccggga ttttgccacc   3360
gtgcggaaag tgctgagcat gccccaagtg aatatcgtga aaaagaccga ggtgcagaca   3420
ggcggcttca gcaaagagtc tatcctgccc aagaggaaca gcgataagct gatcgccaga   3480
aagaaggact gggacccctaa gaagtacggc ggcttcgaca ccccaccgt ggcctattct    3540 gtgctggtgg tggccaaagt ggaaaagggc aagtccaaga aactgaagag tgtgaaagag   3600
ctgctgggga tcaccatcat ggaagaagc agcttcgaga agaatcccat cgactttctg    3660
gaagccaagg gctacaaaga agtgaaaaag gacctgatca tcaagctgcc taagtactcc    3720
ctgttcgagc tggaaaacgg ccggaagaga atgctggcct ctgccggcga actgcagaag   3780
ggaaacgaac tggccctgcc ctccaaatat gtgaacttcc tgtacctggc cagccactat    3840
gagaagctga aggctcccc cgaggataat gagcagaaac agctgtttgt ggaacagcac    3900
aagcactacc tggacgagat catcgagcag atcagcgagt ctccaagag agtgatcctg    3960 gccgacgcta atctggacaa agtgctgtcc gcctacaaca agcaccggga taagcccatc   4020
agagagcagg ccgagaatat catccacctg tttacccctga ccaatctggg agcccctgcc    4080
gccttcaagt actttgacac caccatcgac cggaagaggt acaccagcac caaagaggtg    4140
ctggacgcca ccctgatcca ccagagcatc accggcctgt acgagacacg gatcgacctg    4200
tctcagctgg gaggcgacaa aaggccggcg gccacgaaaa aggccggcca ggcaaaaaag    4260
aaaaagtaa                                                            4269

<210> SEQ ID NO 33
<211> LENGTH: 4272
<212> TYPE: DNA
<213> ORGANISM: Streptococcus pyogenes

<400> SEQUENCE: 33
```

```
atggactata aggaccacga cggagactac aaggatcatg atattgatta caaagacgat     60
gacgataaga tggccccaaa gaagaagcgg aaggtcggta tccacggagt cccagcagcc    120
gacaagaagt acagcatcgg cctggacatc ggcaccaact ctgtgggctg ggccgtgatc    180
accgacgagt acaaggtgcc cagcaagaaa ttcaaggtgc tgggcaacac cgaccggcac    240
agcatcaaga gaacctgat cggagccctg ctgttcgaca gcggcgaaac agccgaggcc    300
acccggctga agaaccgc cagaagaaga taccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcacccat cttcggcaac    480
atcgtggacg aggtggccta ccacgagaag taccccacca tctaccacct gagaaagaaa    540
ctggtgaca gcaccgacaa ggccgacctg cggctgatct atctggccct ggcccacatg    600
atcaagttcc ggggccactt cctgatcgag ggcgacctga accccgacaa cagcgacgtt    660
gacaagctgt tcatccagct ggtgcagacc tacaaccagc tgttcgagga aaacccatc    720
aacgccagcg gcgtggacgc caaggccatc ctgtctgcca gactgagcaa gagcagacgg    780
ctggaaaatc tgatcgccca gctgcccggc gagaagaaga tggcctgtt cggaaacctg    840
attgccctga gcctgggcct gacccccaac ttcaagagca cttcgacct ggccgaggat    900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg cccccctgag cgcctctatg   1080
atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga ttttttaccca ttcctgaagg acaaccggga aaagatcgag   1440
aagatcctga ccttccgcat ccctactac gtgggccctc tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aggaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa acgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta agaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca agcccgagaa catcgtgatc   2400
```

```
gaaatggcca gagagaacca gaccacccag aagggacaga agaacagccg cgagagaatg    2460
aagcggatcg aagagggcat caaagagctg ggcagccaga tcctgaaaga acaccccgtg    2520
gaaaacaccc agctgcagaa cgagaagctg tacctgtact acctgcagaa tgggcgggat    2580
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggcct ttttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcacccT gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttTcaagac cgagattacc ctggccaacg gcgagatccg gaagcggcct    3300
ctgatcgaga caaacggcga aaccgggGAG atcgtgtggg ataagggccg gattttgcc    3360 accgtgcgga aagtgctgag catgccccaa gtgaatatcg tgaaaaagac cgaggtgcag    3420
acaggcggct tcagcaaaga gtctatcctg cccaagagga cagcgataaa gctgatcgcc    3480
agaaagaagg actgggaccc taagaagtac ggcggcttcg acagccccac cgtggcctat    3540
tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gcccTccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg cggccacga aaaaggccgg ccaggcaaaa    4260
aagaaaaagt aa                                                       4272
```

<210> SEQ ID NO 34
<211> LENGTH: 4272
<212> TYPE: DNA
<213> ORGANISM: Streptococcus pyogenes

<400> SEQUENCE: 34

```
atggactata aggaccacga cggagactac aaggatcatg atattgatta caaagacgat     60
gacgataaga tggcccccaa gaagaagcgg aaggtcggta tccacggagt cccagcagcc    120
gacaagaagt acagcatcgg cctggacatc ggcaccaact ctgtgggctg ggccgtgatc    180
```

```
accgacgagt acaaggtgcc cagcaagaaa ttcaaggtgc tgggcaacac cgaccggcac    240
agcatcaaga agaacctgat cggagccctg ctgttcgaca cgggcgaaac agccgaggcc    300 accccggctga agagaaccgc cagaagaaga tacaccgac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag tacccccacca tctaccacct gagaaagaaa    540
ctggtggaca gcaccgacaa ggccgacctg cggctgatct atctggccct ggcccacatg    600
atcaagttcc ggggccactt cctgatcgag ggcgacctga cccccgacaa cagcgacgtt    660
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga tggcctgtt cggaaacctg    840 attgccctga gcctgggcct gacccccaac ttcaagagca cttcgacct ggccgaggat    900 gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg   1080 atcaagagat acgacgagca ccaccaggac ctgaccctgc tgaaagctct cgtgcggcag   1140
cagctgcctg agaagtacaa agagatttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga ttttatccca ttcctgaagg acaaccggga aaagatcgag   1440
aagatcctga ccttccgcat ccctactac gtgggccctc tggccagggg aaacagcaga   1500
ttcgcctgga tgaccagaaa gagcgaggaa accatcaccc cctggaactt cgaggaagtg   1560
gtggacaagg cgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctcccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgaccttta agaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca agcccgagaa catcgtgatc   2400
gaaatggcca gagagaacca gaccacccag aagggacaga gaacagccg cgagagaatg   2460 aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
```

```
atgtacgtgg accaggaact ggacatcaac cggctgtccg actacgatgt ggaccatatc    2640
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacccctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggatttttgcc    3360 accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagccccac cgtggcctat    3540
tctgtgctgg tggtggccaa agtggaaaag ggcaagtcca gaaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaggccgg ccaggcaaaa    4260 aagaaaaagt aa                                                        4272

<210> SEQ ID NO 35
<211> LENGTH: 4272
<212> TYPE: DNA
<213> ORGANISM: Streptococcus pyogenes

<400> SEQUENCE: 35
atggactata aggaccacga cggagactac aaggatcatg atattgatta caaagacgat      60
gacgataaga tggcccccaa gaagaagcgg aaggtcggta ccacggagt cccagcagcc     120 gacaagaagt acagcatcgg cctggacatc ggcaccaact ctgtgggctg gccgtgatc     180 accgacgagt acaaggtgcc cagcaagaaa ttcaaggtgc tgggcaacac cgaccggcac     240
agcatcaaga agaacctgat cggagcccctg ctgttcgaca cggcgaaac agccgaggcc     300 acccggctga agagaaccgc cagaagaaga taccaccgac ggaagaaccg gatctgctat     360
```

```
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag taccccacca tctaccacct gagaaagaaa    540
ctggtggaca gcaccgacaa ggccgacctg cggctgatct atctggccct ggcccacatg    600
atcaagttcc ggggccactt cctgatcgag ggcgacctga ccccgacaa cagcgacgtg    660
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga tggcctgtt cggaaacctg    840
attgccctga gcctgggcct gacccccaac ttcaagagca cttcgacct ggccgaggat    900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg    1080
atcaagagat cgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct cgacaacgg cagcatcccc caccagatcc acctgggaga gctgcacgcc    1380
attctgcggc ggcaggaaga ttttacccca ttcctgaagg acaaccggga aaagatcgag   1440
aagatcctga ccttccgcat ccctactac gtgggccctc tggccagggg aaacagcaga    1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga aaagcccgc cttcctgagc    1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa acgaggaca ttctggaaga tatcgtgctg    1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgacctta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400
gaaatggcca gagaaaacca gaccacccag aagggacaga agaacagccg cgagagaatg   2460
aagcggatcg aagagggcat caaagagctg ggcagccaga tcctgaaaga caccccgtg    2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagagcgac    2700
aagaaccggg gcaagagcga caacgtgccc tccgaagagg tcgtgaagaa gatgaagaac   2760
```

```
tactggcggc agctgctgaa cgccaagctg attacccaga gaaagttcga caatctgacc    2820
aaggccgaga gaggcggcct gagcgaactg gataaggccg gccccatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataaa gctgatcgcc    3480
agaaagaagg actgggaccc taagaagtac ggcggcttcg acagccccac cgtggcctat    3540
tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgttt tgtggaacag    3900
cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttgga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg cggccacga aaaaggccgg ccaggcaaaa    4260
aagaaaaagt aa                                                       4272
```

<210> SEQ ID NO 36
<211> LENGTH: 4272
<212> TYPE: DNA
<213> ORGANISM: Streptococcus pyogenes

<400> SEQUENCE: 36

```
atggactata aggaccacga cggagactac aaggatcatg atattgatta caaagacgat     60
gacgataaga tggcccccaa gaagaagcgg aaggtcggta tccacggagt cccagcagcc    120
gacaagaagt acagcatcgg cctggacatc ggcaccaact ctgtgggctg gccgtgatc    180
accgacgagt acaaggtgcc cagcaagaaa ttcaaggtgc tgggcaacac cgaccggcac    240
agcatcaaga agaacctgat cggagccctg ctgttcgaca gcggcgaaac agccgaggcc    300
acccggctga agagaaccgc cagaagaaga taccaccgac ggaagaaccg gatctgctat    360
ctgcaagaga tctttcagca acgagatggc caaggtggacg acagcttctt ccacagactg    420
gaagagtcct tcctggtgga agaggataag aagcacgagc ggcacccccat cttcggcaac    480
atcgtggacg aggtggccta ccacgagaag tacccccacca tctaccacct gagaaagaaa    540
```

```
ctggtggaca gcaccgacaa ggccgacctg cggctgatct atctggccct ggcccacatg      600
atcaagttcc ggggccactt cctgatcgag ggcgacctga accccgacaa cagcgacgtt      660
gacaagctgt tcatccagct ggtgcagacc tacaaccagc tgttcgagga aaaccccatc      720
aacgccagcg gcgtggacgc caaggccatc ctgtctgcca gactgagcaa gagcagacgg      780
ctggaaaatc tgatcgccca gctgcccggc gagaagaaga atggcctgtt cggaaacctg      840
attgccctga gcctgggcct gacccccaac ttcaagagca cttcgacct ggccgaggat       900
gccaaactgc agctgagcaa ggacacctac gacgacgacc tggacaacct gctggcccag      960
atcggcgacc agtacgccga cctgtttctg gccgccaaga acctgtccga cgccatcctg     1020
ctgagcgaca tcctgagagt gaacaccgag atcaccaagg ccccctgag cgcctctatg      1080
atcaagagat acgacgagca ccaccaggac ctgaccctgc tgaaagctct cgtgcggcag     1140
cagctgcctg agaagtacaa agagattttc ttcgaccaga gcaagaacgg ctacgccggc     1200
tacattgacg gcggagccag ccaggaagag ttctacaagt tcatcaagcc catcctggaa     1260
aagatggacg gcaccgagga actgctcgtg aagctgaaca gagaggacct gctgcggaag     1320
cagcggacct tcgacaacgg cagcatcccc caccagatcc acctgggaga gctgcacgcc     1380
attctgcggc ggcaggaaga tttttaccca ttcctgaagg acaaccggga aaagatcgag     1440
aagatcctga ccttccgcat cccctactac gtgggccctc tggccagggg aaacagcaga     1500
ttcgcctgga tgaccagaaa gagcgaggaa accatcaccc cctggaactt cgaggaagtg     1560
gtggacaagg gcgcttccgc ccagagcttc atcgagcgga tgaccaactt cgataagaac     1620
ctgcccaacg agaaggtgct gcccaagcac agcctgctgt acgagtactt caccgtgtat     1680
aacgagctga ccaaagtgaa atacgtgacc gagggaatga aaagcccgc cttcctgagc      1740
ggcgagcaga aaaaggccat cgtggacctg ctgttcaaga ccaaccggaa agtgaccgtg     1800
aagcagctga aagaggacta cttcaagaaa atcgagtgct tcgactccgt ggaaatctcc     1860
ggcgtggaag atcggttcaa cgcctccctg ggcacatacc acgatctgct gaaaattatc     1920
aaggacaagg acttcctgga caatgaggaa aacgaggaca ttctggaaga tatcgtgctg     1980
accctgacac tgtttgagga cagagagatg atcgaggaac ggctgaaaac ctatgcccac     2040
ctgttcgacg acaaagtgat gaagcagctg aagcggcgga gatacaccgg ctggggcagg     2100
ctgagccgga agctgatcaa cggcatccgg gacaagcagt ccggcaagac aatcctggat     2160
ttcctgaagt ccgacggctt cgccaacaga aacttcatgc agctgatcca cgacgacagc     2220
ctgacctttta agaggacat ccagaaagcc caggtgtccg gccagggcga tagcctgcac      2280
gagcacattg ccaatctggc cggcagcccc gccattaaga agggcatcct gcagacagtg     2340
aaggtggtgg acgagctcgt gaaagtgatg ggccggcaca gcccgagaa catcgtgatc      2400
gaaatggcca gagagaacca gaccacccag aagggacaga agaacagccg cgagagaatg     2460
aagcggatcg aagagggcat caaagagctg ggcagccaga tcctgaaaga acaccccgtg     2520
gaaaacaccc agctgcagaa cgagaagctg tacctgtact acctgcagaa tgggcgggat     2580
atgtacgtgg accaggaact ggacatcaac cggctgtccg actacgatgt ggaccatatc     2640
gtgcctcaga gctttctgaa ggacgactcc atcgacaaca aggtgctgac cagaagcgac     2700
aagaaccggg gcaagagcga caacgtgccc tccgaagagg tcgtgaagaa gatgaagaac     2760
tactggcggc agctgctgaa cgccaagctg attacccaga gaaagttcga caatctgacc     2820
aaggccgaga gaggcggcct gagcgaactg gataaggccg gcttcatcgc cagacagctg     2880
gtggaaaccc ggcagatcac aaagcacgtg gcacagatcc tggactcccg gatgaacact     2940
```

```
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga atcggcaag gctaccgcca agtacttctt ctacagcaac     3240
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc     3480 agaaagaagg actgggaccc taagaagtac ggcggcttcg acagccccac cgtggcctat    3540
tctgtgctgg tggtggccaa agtggaaaag ggcaagtcca agaaactgaa gagtgtgaaa    3600
gagctgctgg ggatcaccat catggaaga agcagcttcg agaagaatcc catcgacttt     3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtgaacag      3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag     4140
gtgctggacg ccaccctgat ccaccagagc atcaccggcc tgtacgagac acggatcgac    4200
ctgtctcagc tgggaggcga caaaaggccg gcggccacga aaaggccgg ccaggcaaaa     4260 aagaaaaagt aa                                                        4272

<210> SEQ ID NO 37
<211> LENGTH: 4272
<212> TYPE: DNA
<213> ORGANISM: Streptococcus pyogenes

<400> SEQUENCE: 37
atggactata aggaccacga cggagactac aaggatcatg atattgatta caaagacgat      60
gacgataaga tggcccccaa gaagaagcgg aaggtcggta tccacggagt cccagcagcc     120
gacaagaagt acagcatcgg cctggacatc ggcaccaact ctgtgggctg ggccgtgatc     180
accgacgagt acaaggtgcc cagcaagaaa ttcaaggtgc tgggcaacac cgaccggcac    240
agcatcaaga agaacctgat cggagccctg ctgttcgaca gcggcgaaac agccgaggcc     300
acccggctga agagaaccgc cagaagaaga taccagac ggaagaaccg gatctgctat       360
ctgcaagaga tcttcagcaa cgagatggcc aaggtggacg acagcttctt ccacagactg    420
gaagagtcct tcctggtgga agaggataag aagcacgagc ggcacccat cttcggcaac     480 atcgtggaca aggtggccta ccacgagaag taccccacca tctaccacct gagaaagaaa    540
ctggtggaca gcaccgacaa ggccgacctg cggctgatct atctggccct ggcccacatg    600
atcaagttcc ggggccactt cctgatcgag ggcgacctga accccgacaa cagcgacgtt    660
gacaagctgt tcatccagct ggtgcagacc tacaaccagc tgttcgagga aaaccccatc    720
```

```
aacgccagcg gcgtggacgc caaggccatc ctgtctgcca gactgagcaa gagcagacgg    780
ctggaaaatc tgatcgccca gctgcccggc gagaagaaga atggcctgtt cggaaacctg    840
attgccctga gcctgggcct gaccccaac ttcaagagca acttcgacct ggccgaggat     900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg cccccctgag cgcctctatg   1080
atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga tttttaccca ttcctgaagg acaaccggga aaagatcgag   1440
aagatcctga ccttccgcat cccctactac gtgggccctc tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttctggaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgacctta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400
gaaatggcca gagagaacca gaccacccag aagggacaga gaacagccg cgagagaatg   2460
aagcggatcg aagagggcat caaagagctg ggcagccaga tcctgaaaga acaccccgtg   2520
gaaacacccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attacccaga gaaagttcga caatctgacc   2820
aaggccgaga gaggcggcct gagcgaactg gataaggccg gcttcatcaa gccccagctg   2880
gtggaaaccc ggcagatcac aaagcacgtg gcacagatcc tggactcccg gatgaacact   2940
aagtacgacg agaatgacaa gctgatccgg gaagtgaaag tgatcaccct gaagtccaag   3000
ctggtgtccg atttccggaa ggatttccag ttttacaaag tgcgcgagat caacaactac   3060
caccacgccc acgacgccta cctgaacgcc gtcgtgggaa ccgccctgat caaaaagtac   3120
```

-continued

```
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact ttttcaagac cgagattacc ctggccaacg gcgagatccg aagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc     3480
agaaagaagg actgggaccc taagaagtac ggcggcttcg acagccccac cgtggcctat    3540
tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900
cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaagt aa                                                       4272
```

<210> SEQ ID NO 38
<211> LENGTH: 4272
<212> TYPE: DNA
<213> ORGANISM: Streptococcus pyogenes

<400> SEQUENCE: 38

```
atggactata aggaccacga cggagactac aaggatcatg atattgatta caaagacgat     60
gacgataaga tggcccccaa gaagaagcgg aaggtcggta tccacggagt cccagcagcc    120
gacaagaagt acagcatcgg cctggacatc ggcaccaact ctgtgggctg gccgtgatc     180
accgacgagt acaaggtgcc cagcaagaaa ttcaaggtgc tgggcaacac cgaccggcac    240
agcatcaaga gaacctgat cggagccctg ctgttcgaca cggcgaaac agccgaggcc      300
acccggctga gagaaccgc cagaagaaga taccagac ggaagaaccg gatctgctat        360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag taccccacca tctaccacct gagaaagaaa    540
ctggtggaca gcaccgacaa ggcgacctg cggctgatct atctggccct ggcccacatg     600
atcaagttcc ggggccactt cctgatcgag ggcgacctga accccgacaa cagcgacgtg    660
gacaagctgt tcatccagct ggtgcagacc tacaaccagc tgttcgagga aaaccccatc    720
aacgccagcg gcgtggacgc caaggccatc ctgtctgcca gactgagcaa gagcagacgg    780
ctggaaaatc tgatcgccca gctgcccggc gagaagaaga atggcctgtt cggaaacctg    840
attgccctga gcctgggcct gacccccaac ttcaagagca acttcgacct ggccgaggat    900
```

```
gccaaactgc agctgagcaa ggacacctac gacgacgacc tggacaacct gctggcccag   960
atcggcgacc agtacgccga cctgtttctg gccgccaaga acctgtccga cgccatcctg  1020
ctgagcgaca tcctgagagt gaacaccgag atcaccaagg ccccctgag cgcctctatg   1080
atcaagagat acgacgagca ccaccaggac ctgaccctgc tgaaagctct cgtgcggcag  1140
cagctgcctg agaagtacaa agagattttc ttcgaccaga gcaagaacgg ctacgccggc  1200
tacattgacg gcggagccag ccaggaagag ttctacaagt tcatcaagcc catcctggaa  1260
aagatggacg gcaccgagga actgctcgtg aagctgaaca gagaggacct gctgcggaag  1320
cagcggacct tcgacaacgg cagcatcccc caccagatcc acctgggaga gctgcacgcc  1380
attctgcggc ggcaggaaga tttttaccca ttcctgaagg acaaccggga aaagatcgag  1440
aagatcctga ccttccgcat cccctactac gtgggccctc tggccagggg aaacagcaga  1500
ttcgcctgga tgaccagaaa gagcgaggaa accatcaccc cctggaactt cgaggaagtg  1560
gtggacaagg gcgcttccgc ccagagcttc atcgagcgga tgaccaactt cgataagaac  1620
ctgcccaacg agaaggtgct gcccaagcac agcctgctgt acgagtactt caccgtgtat  1680
aacgagctga ccaaagtgaa atacgtgacc gagggaatga gaaagcccgc cttcctgagc  1740
ggcgagcaga aaaaggccat cgtggacctg ctgttcaaga ccaaccggaa agtgaccgtg  1800
aagcagctga agaggactac cttcaagaaa atcgagtgct tcgactccgt ggaaatctcc  1860
ggcgtggaag atcggttcaa cgcctccctg ggcacatacc acgatctgct gaaaattatc  1920
aaggacaagg acttcctgga caatgaggaa aacgaggaca ttctggaaga tatcgtgctg  1980
accctgacac tgtttgagga cagagagatg atcgaggaac ggctgaaaac ctatgcccac  2040
ctgttcgacg acaaagtgat gaagcagctg aagcggcgga gatacaccgg ctggggcagg  2100
ctgagccgga agctgatcaa cggcatccgg gacaagcagt ccggcaagac aatcctggat  2160
ttcctgaagt ccgacggctt cgcctgcaga aacttcatgc agctgatcca cgacgacagc  2220
ctgacctttc aagaggacat ccagaaagcc caggtgtccg gccagggcga tagcctgcac  2280
gagcacattg ccaatctggc cggcagcccc gccattaaga agggcatcct gcagacagtg  2340
aaggtggtgg acgagctcgt gaaagtgatg ggccggcaca gcccgagaa catcgtgatc  2400
gaaatggcca gagagaacca gatcacccag aagggacaga gaacagccg cgagagaatg  2460
aagcggatcg aagagggcat caaagagctg ggcagccaga tcctgaaaga acaccccgtg  2520
gaaacacccc agctgcagaa cgagaagctg tacctgtact acctgcagaa tgggcgggat  2580
atgtacgtgg accaggaact ggacatcaac cggctgtccg actacgatgt ggaccatatc  2640
gtgcctcaga gctttctgaa ggacgactcc atcgacaaca aggtgctgac cagaagcgac  2700
aagaaccggg gcaagagcga caacgtgccc tccgaagagg tcgtgaagaa gatgaagaac  2760
tactggcggc agctgctgaa cgccaagctg attacccaga gaaagttcga caatctgacc  2820
aaggccgaga gcggcct gagcgaactg gataaggcca tgttcatcaa gagacagctg  2880
gtggaaaccc ggcagatcac aaagcacgtg gcacagatcc tggactcccg gatgaacact  2940
aagtacgacg agaatgacaa gctgatccgg gaagtgaaag tgatcacct gaagtccaag  3000
ctggtgtccg atttccggaa ggatttccag ttttacaaag tgcgcgagat caacaaatac  3060
caccacgccc acgacgccta cctgaacgcc gtcgtgggaa ccgccctgat caaaaagtac  3120
cctaagctgg aaagcgagtt cgtgtacggc gactacaagg tgtacgacgt gcggaagatg  3180
atcgccaaga gcgagcagga aatcggcaag gctaccgcca gtacttctt ctacagcaac  3240
atcatgaact tttttcaagac cgagattacc ctggccaacg gcgagatccg gaagcggcct  3300
```

| | |
|---|---|
| ctgatcgaga caaacggcga aaccggggag atcgtgtggg ataagggccg ggattttgcc | 3360 |
| accgtgcgga aagtgctgag catgccccaa gtgaatatcg tgaaaaagac cgaggtgcag | 3420 |
| acaggcggct tcagcaaaga gtctatcctg cccaagagga acagcgataa gctgatcgcc | 3480 |
| agaaagaagg actgggaccc taagaagtac ggcggcttcg acagccccac cgtggcctat | 3540 |
| tctgtgctgg tggtggccaa agtggaaaag gcaagtcca agaaactgaa gagtgtgaaa | 3600 |
| gagctgctgg ggatcaccat catggaaaga agcagcttcg agaagaatcc catcgacttt | 3660 |
| ctggaagcca agggctacaa agaagtgaaa aaggacctga tcatcaagct gcctaagtac | 3720 |
| tccctgttcg agctggaaaa cggccggaag agaatgctgg cctctgccgg cgaactgcag | 3780 |
| aagggaaacg aactggccct gccctccaaa tatgtgaact tcctgtacct ggccagccac | 3840 |
| tatgagaagc tgaagggctc ccccgaggat aatgagcaga acagctgtt tgtggaacag | 3900 |
| cacaagcact acctggacga gatcatcgag cagatcagcg agttctccaa gagagtgatc | 3960 |
| ctggccgacg ctaatctgga caaagtgctg tccgcctaca caagcaccg gataagccc | 4020 |
| atcagagagc aggccgagaa tatcatccac ctgtttaccc tgaccaatct gggagcccct | 4080 |
| gccgccttca gtactttga caccaccatc gaccggaaga ggtacaccag caccaaagag | 4140 |
| gtgctggacg ccaccctgat ccaccagagc atcaccggcc tgtacgagac acggatcgac | 4200 |
| ctgtctcagc tgggaggcga caaaaggccg gcggccacga aaaaggccgg ccaggcaaaa | 4260 |
| aagaaaaagt aa | 4272 |

<210> SEQ ID NO 39
<211> LENGTH: 4053
<212> TYPE: DNA
<213> ORGANISM: Staphylococcus aureus

<400> SEQUENCE: 39

| | |
|---|---|
| atggactata aggaccacga cggagactac aaggatcatg atattgatta caaagacgat | 60 |
| gacgataaga tggccccgaa gaaaaagcgc aaggtcgaag cgtccatgaa aaggaactac | 120 |
| attctggggc tggacatcgg gattacaagc gtggggtatg ggattattga ctatgaaaca | 180 |
| agggacgtga tcgacgcagg cgtcagactg ttcaaggagg ccaacgtgga aaacaatgag | 240 |
| ggacggagaa gcaagagggg agccaggcgc ctgaaacgac ggagaaggca cagaatccag | 300 |
| agggtgaaga aactgctgtt cgattacaac ctgctgaccg accattctga gctgagtgga | 360 |
| attaatcctt atgaagccag ggtgaaaggc ctgagtcaga agctgtcaga ggaagagttt | 420 |
| tccgcagctc tgctgcacct ggctaagcgc cgaggagtgc ataacgtcaa tgaggtggaa | 480 |
| gaggacaccg gcaacgagct gtctacaaag gaacagatct cacgcaatag caaagctctg | 540 |
| gaagagaagt atgtcgcaga gctacagctg gaacggctga aaaagatgg cgaggtgaga | 600 |
| gggtcaatta ataggttcaa gacaagcgac tacgtcaaag aagccaagca gctgctgaaa | 660 |
| gtgcagaagg cttaccacca gctggatcag agcttcatcg atacttatat cgacctgctg | 720 |
| gagactcgga gaacctacta tgagggacca ggagaaggga ccccttcgg atggaaagac | 780 |
| atcaaggaat ggtacgagat gctgatggga cattgcacct attttccaga agagctgaga | 840 |
| agcgtcaagt acgcttataa cgcagatctg tacaacgccc tgaatgacct gaacaacctg | 900 |
| gtcatcacca gggatgaaaa cgagaaactg gaatactatg agaagttcca gatcatcgaa | 960 |
| aacgtgttta agcagaagaa aaagcctaca ctgaaacaga ttgctaagga gatcctggtc | 1020 |
| aacgaagagg acatcaaggg ctaccggtg acaagcactg gaaaaccaga gttcaccaat | 1080 |

```
ctgaaagtgt atcacgatat taaggacatc acagcacgga aagaaatcat tgagaacgcc    1140
gaactgctgg atcagattgc taagatcctg actatctacc agagttccga ggacatccag    1200
gaagagctga ctaacctgaa cagcgagctg acccaggaag agatcgaaca gattagtaat    1260
ctgaaggggt acaccggaac acacaacctg tccctgaaag ctatcaatct gattctggat    1320
gagctgtggc atacaaacga caatcagatt gcaatcttta accggctgaa gctggtacca    1380
aaaaaggtgg acctgagtca gcagaaagag atcccaacca cactggtgga cgatttcatt    1440
ctgtcacccg tggtcaagcg gagcttcatc cagagcatca agtgatcaa cgccatcatc    1500 aagaagtacg gcctgcccaa tgatatcatt atcgagctgg ctagggagaa aacagcaag    1560 gacgcacaga agatgatcaa tgagatgcag aaacgaaacc ggcagaccaa tgaacgcatt    1620
gaagagatta tccgaactac cgggaaagag aacgcaaagt acctgattga aaaaatcaag    1680
ctgcacgata tgcaggaggg aaagtgtctg tattctctgg aggccatccc cctggaggac    1740
ctgctgaaca atccattcaa ctacgaggtc gatcatatta tccccagaag cgtgtccttc    1800
gacaattcct ttaacaacaa ggtgctggtc aagcaggaag agaactctaa aaagggcaat    1860
aggactcctt tccagtacct gtctagttca gattccaaga tctcttacga aacctttaaa    1920
aagcacattc tgaatctggc caaaggaaag ggccgcatca gcaagaccaa aaaggagtac    1980
ctgctggaag agcgggacat caacagattc tccgtccaga aggattttat taaccggaat    2040
ctggtggaca agatacgc tactcgcggc ctgatgaatc tgctgcgatc ctatttccgg    2100
gtgaacaatc tggatgtgaa agtcaagtcc atcaacggcg ggttcacatc ttttctgagg    2160
cgcaaatgga agtttaaaaa ggagcgcaac aaagggtaca agcaccatgc cgaagatgct    2220
ctgattatcg caaatgccga cttcatcttt aaggagtgga aaaagctgga caaagccaag    2280
aaagtgatgg agaaccagat gttcgaagag aagcaggccg aatctatgcc cgaaatcgag    2340
acagaacagg agtacaagga gattttcatc actcctcacc agatcaagca tatcaaggat    2400
ttcaaggact acaagtactc tcaccgggtg gataaaaagc ccaacagaga gctgatcaat    2460
gacacccgtt atagtacaag aaaagacgat aaggggaata cctgattgt gaacaatctg    2520 aacggactgt acgacaaaga taatgacaag ctgaaaaagc tgatcaacaa agtcccgag    2580 aagctgctga tgtaccacca tgatcctcag acatatcaga actgaagct gattatggag    2640 cagtacggcg acgagaagaa cccactgtat aagtactatg aagagactgg gaactacctg    2700
accaagtata gcaaaaagga taatggcccc gtgatcaaga gatcaagta ctatgggaac    2760 aagctgaatg cccatctgga catcacagac gattaccct acagtcgcaa caaggtggtc    2820
aagctgtcac tgaagccata cagattcgat gtctatctgg acaacggcgt gtataaattt    2880
gtgactgtca agaatctgga tgtcatcaaa aaggagaact actatgaagt gaatagcaag    2940
tgctacgaag aggctaaaaa gctgaaaaag attagcaacc aggcagagtt catcgcctcc    3000
ttttacaaca cgacctgat taagatcaat ggcgaactgt ataggtcat cggggtgaac    3060 aatgatctgc tgaaccgcat tgaagtgaat atgattgaca tcacttaccg agagtatctg    3120
gaaaacatga atgataagcg ccccctcga attatcaaaa caatcgcctc taagactcag    3180
agtatcaaaa agtactcaac cgacattctg ggaaacctgt atgaggtgaa gagcaaaaag    3240
caccctcaga ttatcaaaaa gggcaggtcc ggcggcggag agggcagagg aagtcttcta    3300
acatgcggtg acgtggagga gaatcccggc ccaatggtga gcaagggcga ggagctgttc    3360
accggggtgg tgcccatcct ggtcgagctg gacggcgacg taaacggcca aagttcagc    3420 gtgtccggcg agggcgaggg cgatgccacc tacggcaagc tgaccctgaa gttcatctgc    3480
```

```
accaccggca agctgcccgt gccctggccc accctcgtga ccaccctgac ctacggcgtg    3540
cagtgcttca gccgctaccc cgaccacatg aagcagcacg acttcttcaa gtccgccatg    3600
cccgaaggct acgtccagga gcgcaccatc ttcttcaagg acgacggcaa ctacaagacc    3660
cgcgccgagg tgaagttcga gggcgacacc ctggtgaacc gcatcgagct gaagggcatc    3720
gacttcaagg aggacggcaa catcctgggg cacaagctgg agtacaacta caacagccac    3780
aacgtctata tcatggccga caagcagaag aacggcatca aggtgaactt caagatccgc    3840
cacaacatcg aggacggcag cgtgcagctc gccgaccact accagcagaa cacccccatc    3900
ggcgacggcc ccgtgctgct gcccgacaac cactacctga gcacccagtc cgccctgagc    3960
aaagacccca acgagaagcg cgatcacatg gtcctgctgg agttcgtgac cgccgccggg    4020
atcactctcg gcatggacga gctgtacaag taa                                 4053

<210> SEQ ID NO 40
<211> LENGTH: 4038
<212> TYPE: DNA
<213> ORGANISM: Francisella novicida

<400> SEQUENCE: 40
atgagcatct accaggagtt cgtcaacaag tattcactga gtaagacact gcggttcgag      60
ctgatcccac agggcaagac actggagaac atcaaggccc gaggcctgat tctgacgat     120 gagaagcggg caaaagacta taagaaagcc aagcagatca ttgataaata ccaccagttc     180
tttatcgagg aaattctgag ctccgtgtgc atcagtgagg atctgctgca gaattactca     240
gacgtgtact tcaagctgaa gaagagcgac gatgacaacc tgcagaagga cttcaagtcc     300
gccaaggaca ccatcaagaa acagattagc gagtacatca aggactccga aaagtttaaa     360
aatctgttca ccagaatctc gatcgatgct aagaaaggcc aggagtccga cctgatcctg     420
tggctgaaac agtctaagga caatgggatt gaactgttca aggctaactc cgatatcact     480
gatattgacg aggcactgga aatcatcaag agcttcaagg gatggaccac atacttaaa     540 ggcttccacg agaaccgcaa gaacgtgtac tccagcaacg acattcctac ctccatcatc     600
taccgaatcg tcgatgacaa tctgccaaag ttcctggaga caaggccaa atatgaatct     660 ctgaaggaca agctcccga ggcaattaat tacgaacaga tcaagaaaga tctggctgag     720
gaactgacat tcgatatcga ctataagact agcgaggtga ccagagggt cttttccctg     780 gacgaggtgt ttgaaatcgc caatttcaac aattacctga ccagtccgg cattactaaa     840 ttcaatacca tcattggcgg gaagtttgtg acggggaga taccaagcg caagggaatt     900 aacgaataca tcaatctgta tagccagcag atcaacgaca aaactctgaa gaaatacaag     960
atgtctgtgc tgttcaaaca gatcctgagt gataccgagt ccagtctttt tgtcattgat    1020
aaactggaag atgactcaga cgtggtcact accatgcaga gcttttatga gcagatcgcc    1080
gctttcaaga cagtggagga aaaatctatt aaggaaactc tgagtctgct gttcgatgac    1140
ctgaaagccc agaagctgga cctgagtaag atctacttca aaaacgataa gagtctgaca    1200
gacctgtcac agcaggtgtt tgatgactat tccgtgattg ggaccgccgt cctggagtac    1260
attacacagc agatcgctcc aaagaacctg gataatccct ctaagaaaga gcaggaactg    1320
atcgctaaga aaccgagaa ggcaaaatat ctgagtctgg aaacaattaa gctggcactg    1380
gaggagttca acaagcacag ggatattgac aaacagtgcc gctttgagga atcctggcc    1440 aacttcgcag ccatccccat gattttgat gagatcgccc agaacaaaga caatctggct    1500
```

```
cagatcagta ttaagtacca gaaccagggc aagaaagacc tgctgcaggc ttcagcagaa    1560
gatgacgtga aagccatcaa ggatctgctg gaccagacca acaatctgct gcacaagctg    1620
aaaatcttcc atattagtca gtcagaggat aaggctaata tcctggataa agacgaacac    1680
ttctacctgg tgttcgagga atgttacttc gagctggcaa acattgtccc cctgtataac    1740
aagattagga actacatcac acagaagcct tactctgacg agaagtttaa actgaacttc    1800
gaaaatagta ccctggccaa cgggtgggat aagaacaagg agcctgacaa cacagctatc    1860
ctgttcatca aggatgacaa gtactatctg ggagtgatga ataagaaaaa caataagatc    1920
ttcgatgaca agccattaa ggagaacaaa ggggaaggat acaagaaaat cgtgtataag     1980
ctgctgcccg gcgcaaataa gatgctgcct aaggtgttct tcagcgccaa gagtatcaaa    2040
ttctacaacc catccgagga catcctgcgg attagaaatc actcaacaca tactaagaac    2100
gggagccccc agaagggata tgagaaattt gagttcaaca tcgaggattg caggaagttt    2160
attgacttct acaagcagag catctccaaa caccctgaat ggaaggattt tggcttccgg    2220
tttttccgaca cacagagata taactctatc gacgagttct accgcgaggt ggaaaatcag    2280
gggtataagc tgacttttga gaacatttct gaaagttaca tcgacagcgt ggtcaatcag    2340
ggaaagctgt acctgttcca gatctataac aaagattttt cagcatacag caagggcaga    2400
ccaaacctgc atacactgta ctggaaggcc ctgttcgatg agaggaatct gcaggacgtg    2460
gtctataaac tgaacggaga ggccgaactg ttttaccgga agcagtctat tcctaagaaa    2520
atcactcacc cagctaagga ggccatcgct aacaagaaca aggacaatcc taagaaagag    2580
agcgtgttcg aatacgatct gattaaggac aagcggttca ccgaagataa gttctttttc    2640
cattgtccaa tcaccattaa cttcaagtca gcggcgcta caagttcaa cgacgagatc     2700
aatctgctgc tgaaggaaaa agcaaacgat gtgcacatcc tgagcattga ccgaggagag    2760
cggcatctgg cctactatac cctggtggat ggcaaaggga atatcattaa gcaggataca    2820
ttcaacatca ttggcaatga ccggatgaaa accaactacc acgataaact ggctgcaatc    2880
gagaaggata gagactcagc taggaaggac tggaagaaaa tcaacaacat taaggagatg    2940
aaggaaggct atctgagcca ggtggtccat gagattgcaa agctggtcat cgaatacaat    3000
gccattgtgg tgttcgagga tctgaacttc ggctttaaga gggggcgctt taaggtggaa    3060
aaacaggtct atcagaagct ggagaaaatg ctgatcgaaa agctgaatta cctggtgttt    3120
aaagataacg agttcgacaa gaccggaggc gtcctgagag cctaccagct gacagctccc    3180
tttgaaactt tcaagaaaat gggaaaacag acaggcatca tctactatgt gccagccgga    3240
ttcacttcca gatctgcccc cgtgaccggc tttgtcaacc agctgtaccc taaatatgag    3300
tcagtgagca gtcccagga ttttttcagc aagttcgata agatctgtta taatctggac     3360
aaggggtact tcgagttttc cttcgattac aagaacttcg gcgacaaggc cgctaagggg    3420
aaatggacca ttgcctcctt cggatctcgc ctgatcaact ttcgaaattc cgataaaaac    3480
cacaattggg acactaggga ggtgtaccca accaaggagc tggaaaagct gctgaaagac    3540
tactctatcg agtatggaca tggcgaatgc atcaaggcag ccatctgtgg cgagagtgat    3600
aagaaatttt tcgccaagct gacctcagtg ctgaatacaa tcctgcagat gcggaactca    3660
aagaccggga cagaactgga ctatctgatt agccccgtgg ctgatgtcaa cggaaacttc    3720
ttcgacagca gacaggcacc caaaaatatg cctcaggatg cagacgccaa cggggcctac    3780
cacatcgggc tgaagggact gatgctgctg ggccggatca gaacaatca ggaggggaag     3840
aagctgaacc tggtcattaa gaacgaggaa tacttcgagt ttgtccagaa tagaaataac    3900
```

-continued

| | |
|---|---|
| aaaaggccgg cggccacgaa aaaggccggc caggcaaaaa agaaaaaggg atcctaccca | 3960 |
| tacgatgttc cagattacgc ttatccctac gacgtgcctg attatgcata cccatatgat | 4020 |
| gtccccgact atgcctaa | 4038 |

<210> SEQ ID NO 41
<211> LENGTH: 4059
<212> TYPE: DNA
<213> ORGANISM: Acidaminococcus spec

<400> SEQUENCE: 41

| | |
|---|---|
| atgacacagt tcgagggctt taccaacctg tatcaggtga gcaagacact gcggtttgag | 60 |
| ctgatcccac agggcaagac cctgaagcac atccaggagc agggcttcat cgaggaggac | 120 |
| aaggcccgca atgatcacta caaggagctg aagcccatca tcgatcggat ctacaagacc | 180 |
| tatgccgacc agtgcctgca gctggtgcag ctggattggg agaacctgag cgccgccatc | 240 |
| gactcctata gaaaggagaa aaccgaggag acaaggaacg ccctgatcga ggagcaggcc | 300 |
| acatatcgca atgccatcca cgactacttc atcggccgga cagacaacct gaccgatgcc | 360 |
| atcaataaga gacacgccga gatctacaag ggcctgttca aggccgagct gtttaatggc | 420 |
| aaggtgctga agcagctggg caccgtgacc acaaccgagc acgagaacgc cctgctgcgg | 480 |
| agcttcgaca gtttacaac ctacttctcc ggcttttatg agaacaggaa gaacgtgttc | 540 |
| agcgccgagg atatcagcac agccatccca caccgcatcg tgcaggacaa cttccccaag | 600 |
| tttaaggaga attgtcacat cttcacacgc ctgatcaccg ccgtgcccag cctgcgggag | 660 |
| cactttgaga cgtgaagaa ggccatcggc atcttcgtga gcacctccat cgaggaggtg | 720 |
| ttttccttcc cttttataa ccagctgctg acacagaccc agatcgacct gtataaccag | 780 |
| ctgctgggag gaatctctcg ggaggcaggc accgagaaga tcaagggcct gaacgaggtg | 840 |
| ctgaatctgg ccatccagaa gaatgatgag acagcccaca tcatcgcctc cctgccacac | 900 |
| agattcatcc ccctgtttaa gcagatcctg tccgatagga cacccctgtc tttcatcctg | 960 |
| gaggagttta gagcgacga ggaagtgatc cagtccttct gcaagtacaa gacactgctg | 1020 |
| agaaacgaga cgtgctgga cagccgag gccctgttta cgagctgaa cagcatcgac | 1080 |
| ctgacacaca tcttcatcag ccacaagaag ctggagacaa tcagcagcgc cctgtgcgac | 1140 |
| cactgggata cactgaggaa tgccctgtat gagcggaga tctccgagct gacaggcaag | 1200 |
| atcaccaagt ctgccaagga aaggtgcag cgcagcctga gcacgagga tatcaacctg | 1260 |
| caggagatca tctctgccgc aggcaaggag ctgagcgagg ccttcaagca gaaaaccagc | 1320 |
| gagatcctgt cccacgcaca cgccgccctg gatcagccac tgcctacaac cctgaagaag | 1380 |
| caggaggaga aggagatcct gaagtctcag ctggacagcc tgctgggcct gtaccacctg | 1440 |
| ctggactggt ttgccgtgga tgagtccaac gaggtggacc ccgagttctc tgcccggctg | 1500 |
| accggcatca gctggagat ggagccttct ctgagcttct acaacaaggc cagaaattat | 1560 |
| gccaccaaga gccctactc cgtggagaag ttcaagctga ctttcagat gcctacactg | 1620 |
| gcctctggct gggacgtgaa taaggagaag aacaatggcg ccatcctgtt tgtgaagaac | 1680 |
| ggcctgtact atctgggcat catgccaaag cagaagggca ggtataaggc cctgagcttc | 1740 |
| gagcccacag agaaaaccag cgagggcttt gataagatgt actatgacta cttccctgat | 1800 |
| gccgccaaga tgatcccaaa gtgcagcacc cagctgaagg ccgtgacagc ccactttcag | 1860 |
| acccacacaa cccccatcct gctgtccaac aatttcatcg agcctctgga gatcacaaag | 1920 |

```
gagatctacg acctgaacaa tcctgagaag gagccaaaga agtttcagac agcctacgcc    1980
aagaaaaccg gcgaccagaa gggctacaga gaggccctgt gcaagtggat cgacttcaca    2040
agggattttc tgtccaagta taccaagaca acctctatcg atctgtctag cctgcggcca    2100
tcctctcagt ataaggacct gggcgagtac tatgccgagc tgaatcccct gctgtaccac    2160
atcagcttcc agagaatcgc cgagaaggag atcatggatg ccgtggagac aggcaagctg    2220
tacctgttcc agatctataa caaggacttt gccaagggcc accacggcaa gcctaatctg    2280
cacacactgt attggaccgg cctgttttct ccagagaacc tggccaagac aagcatcaag    2340
ctgaatggcc aggccgagct gttctaccgc cctaagtcca ggatgaagag gatggcacac    2400
cggctgggag agaagatgct gaacaagaag ctgaaggatc agaaaacccc aatccccgac    2460
accctgtacc aggagctgta cgactatgtg aatcacagac tgtcccacga cctgtctgat    2520
gaggccaggg ccctgctgcc caacgtgatc accaaggagg tgtctcacga gatcatcaag    2580
gataggcgct ttaccagcga caagttcttt ttccacgtgc ctatcacact gaactatcag    2640
gccgccaatt ccccatctaa gttcaaccag agggtgaatg cctacctgaa ggagcacccc    2700
gagacaccta tcatcggcat cgatcggggc gagagaaacc tgatctatat cacagtgatc    2760
gactccaccg gcaagatcct ggagcagcgg agcctgaaca ccatccagca gtttgattac    2820
cagaagaagc tggacaacag ggagaaggag agggtggcag caaggcaggc ctggtctgtg    2880
gtgggcacaa tcaaggatct gaagcagggc tatctgagcc aggtcatcca cgagatcgtg    2940
gacctgatga tccactacca ggccgtggtg gtgctggaga acctgaattt cggctttaag    3000
agcaagagga ccggcatcgc cgagaaggcc gtgtaccagc agttcgagaa gatgctgatc    3060
gataagctga attgcctggt gctgaaggac tatccagcag agaaagtggg aggcgtgctg    3120
aacccatacc agctgacaga ccagttcacc tcctttgcca agatgggcac ccagtctggc    3180
ttcctgtttt acgtgcctgc cccatataca tctaagatcg atcccctgac cggcttcgtg    3240
gacccccttcg tgtggaaaac catcaagaat cacgagagcc gcaagcactt cctggagggc    3300
ttcgactttc tgcactacga cgtgaaaacc ggcgacttca tcctgcactt taagatgaac    3360
agaaatctgt ccttccagag gggcctgccc ggctttatgc ctgcatggga tatcgtgttc    3420
gagaagaacg agacacagtt tgacgccaag ggcacccctt catcgccgg caagagaatc    3480
gtgccagtga tcgagaatca cagattcacc ggcagatacc gggacctgta tcctgccaac    3540
gagctgatcg ccctgctgga ggagaagggc atcgtgttca gggatggctc caacatcctg    3600
ccaaagctgc tggagaatga cgattctcac gccatcgaca ccatggtggc cctgatccgc    3660
agcgtgctgc agatgcggaa ctccaatgcc gccacaggcg aggactatat caacagcccc    3720
gtgcgcgatc tgaatggcgt gtgcttcgac tcccggtttc agaacccaga gtggcccatg    3780
gacgccgatg ccaatggcgc ctaccacatc gccctgaagg ccagctgct gctgaatcac    3840
ctgaaggaga gcaaggatct gaagctgcag aacggcatct ccaatcagga ctggctggcc    3900
tacatccagg agctgcgcaa caaaaggccg gcggccacga aaaaggccgg ccaggcaaaa    3960
aagaaaaagg gatcctaccc atacgatgtt ccagattacg cttatcccta cgacgtgcct    4020
gattatgcat acccatatga tgtccccgac tatgcctaa                           4059
```

<210> SEQ ID NO 42
<211> LENGTH: 3822
<212> TYPE: DNA
<213> ORGANISM: Lachnospiraceae bacterium

<400> SEQUENCE: 42

```
atgagcaagc tggagaagtt tacaaactgc tactccctgt ctaagaccct gaggttcaag      60
gccatccctg tgggcaagac ccaggagaac atcgacaata gcggctgct ggtggaggac      120 gagaagagag ccgaggatta aagggcgtg aagaagctgc tggatcgcta ctatctgtct      180
tttatcaacg acgtgctgca cagcatcaag ctgaagaatc tgaacaatta catcagcctg      240
ttccggaaga aaccagaac cgagaaggag aataaggagc tggagaaccct ggagatcaat      300 ctgcggaagg agatcgccaa ggccttcaag ggcaacgagg ctacaagtc cctgtttaag      360 aaggatatca tcgagacaat cctgccagag ttcctggacg ataaggacga gatcgccctg      420
gtgaacagct tcaatggctt taccacagcc ttcaccggct tctttgataa cagagagaat      480
atgttttccg aggaggccaa gagcacatcc atcgccttca ggtgtatcaa cgagaatctg      540
acccgctaca tctctaatat ggacatcttc gagaaggtgg acgccatctt tgataagcac      600
gaggtgcagg agatcaagga aagatcctg aacagcgact atgatgtgga ggatttcttt      660
gagggcgagt tctttaactt tgtgctgaca caggagggca tcgacgtgta taacgccatc      720
atcggcggct tcgtgaccga gagcggcgag aagatcaagg gcctgaacga gtacatcaac      780
ctgtataatc agaaaaccaa gcagaagctg cctaagtta gccactgta taagcaggtg      840 ctgagcgatc gggagtctct gagcttctac ggcgagggct atacatccga tgaggaggtg      900
ctggaggtgt ttagaaacac cctgaacaag aacagcgaga tcttcagctc catcaagaag      960
ctggagaagc tgttcaagaa ttttgacgag tactctagcg ccggcatctt tgtgaagaac     1020 ggcccccgcca tcagcacaat ctccaaggat atcttcggcg agtggaacgt gatccgggac     1080
aagtggaatg ccgagtatga cgatatccac ctgaagaaga aggccgtggt gaccgagaag     1140
tacgaggacg atcggagaaa gtccttcaag aagatcggct ccttttctct ggagcagctg     1200
caggagtacg ccgacgccga tctgtctgtg gtggagaagc tgaaggagat catcatccag     1260
aaggtggatg agatctacaa ggtgtatggc tcctctgaga gctgttcga cgccgatttt     1320 gtgctggaga gagcctgaa gaagaacgac gccgtggtgg ccatcatgaa ggacctgctg     1380
gattctgtga agagcttcga gaattacatc aaggccttct ttggcgaggg caaggagaca     1440
aacagggacg agtccttcta tggcgatttt gtgctggcct acgacatcct gctgaaggtg     1500
gaccacatct acgatgccat ccgcaattat gtgacccaga gccctactc taaggataag     1560 ttcaagctgt attttcagaa ccctcagttc atgggcggct gggacaagga taaggagaca     1620
gactatcggg ccaccatcct gagatacggc tccaagtact atctggccat catggataag     1680
aagtacgcca agtgcctgca gaagatcgac aaggacgatg tgaacggcaa ttacgagaag     1740
atcaactata gctgctgcc cggccctaat aagatgctgc caaaggtgtt cttttctaag     1800
aagtggatgg cctactataa ccccagcgag gacatccaga gatctacaa gaatggcaca     1860 ttcaagaagg gcgatatgtt taacctgaat gactgtcaca agctgatcga cttctttaag     1920
gatagcatct cccggtatcc aaagtggtcc aatgcctacg atttcaactt ttctgagaca     1980
gagaagtata aggacatcgc cggcttttac agagaggtgg aggagcaggg ctataaggtg     2040
agcttcgagt ctgccagcaa gaaggaggtg gataagctgg tggaggaggg caagctgtat     2100
atgttccaga tctataacaa ggactttttcc gataagtctc acggcacacc caatctgcac     2160
accatgtact tcaagctgct gtttgacgag aacaatcacg acagatcag gctgagcgga     2220 ggagcagagc tgttcatgag gcgcgcctcc ctgaagaagg aggagctggt ggtgcaccca     2280
gccaactccc ctatcgccaa caagaatcca gataatccca gaaaaccac aaccctgtcc     2340
```

```
tacgacgtgt ataaggataa gaggttttct gaggaccagt acgagctgca catcccaatc    2400
gccatcaata agtgcccaa gaacatcttc aagatcaata cagaggtgcg cgtgctgctg    2460
aagcacgacg ataaccccta tgtgatcggc atcgataggg gcgagcgcaa tctgctgtat    2520
atcgtggtgg tggacggcaa gggcaacatc gtggagcagt attccctgaa cgagatcatc    2580
aacaacttca acggcatcag gatcaagaca gattaccact ctctgctgga caagaaggag    2640
aaggagaggt cgaggcccg ccagaactgg acctccatcg agaatatcaa ggagctgaag    2700
gccggctata tctctcaggt ggtgcacaag atctgcgagc tggtggagaa gtacgatgcc    2760
gtgatcgccc tggaggacct gaactctggc tttaagaata gccgcgtgaa ggtggagaag    2820
caggtgtatc agaagttcga gaagatgctg atcgataagc tgaactacat ggtggacaag    2880
aagtctaatc cttgtgcaac aggcggcgcc ctgaagggct atcagatcac caataagttc    2940
gagagcttta agtccatgtc tacccagaac ggcttcatct tttacatccc tgcctggctg    3000
acatccaaga tcgatccatc taccggcttt gtgaacctgc tgaaaaccaa gtataccagc    3060
atcgccgatt ccaagaagtt catcagctcc tttgacagga tcatgtacgt gcccgaggag    3120
gatctgttcg agtttgccct ggactataag aacttctctc gcacagacgc cgattacatc    3180
aagaagtgga agctgtactc ctacggcaac cggatcagaa tcttccggaa tcctaagaag    3240
aacaacgtgt cgactgggag ggaggtgtgc ctgaccagcg cctataagga gctgttcaac    3300
aagtacggca tcaattatca gcagggcgat atcagagccc tgctgtgcga gcagtccgac    3360
aaggccttct actctagctt tatggccctg atgagcctga tgctgcagat gcggaacagc    3420
atcacaggcc gcaccgacgt ggatttctg atcagccctg tgaagaactc cgacggcatc    3480
ttctacgata gccggaacta tgaggcccag gagaatgcca tcctgccaaa gaacgccgac    3540
gccaatggcg cctataacat cgccagaaag gtgctgtggg ccatcggcca gttcaagaag    3600
gccgaggacg agaagctgga taaggtgaag atcgccatct ctaacaagga gtggctggag    3660
tacgcccaga ccagcgtgaa gcacaaaagg cggcggcca cgaaaaaggc cggccaggca    3720
aaaaagaaaa agggatccta cccatacgat gttccagatt acgcttatcc ctacgacgtg    3780
cctgattatg catacccata tgatgtcccc gactatgcct aa    3822
```

<210> SEQ ID NO 43
<211> LENGTH: 36
<212> TYPE: DNA
<213> ORGANISM: Artificial Sequence
<220> FEATURE:
<223> OTHER INFORMATION: 3xGS tag

<400> SEQUENCE: 43

```
ggcggcggga gcggggtgg cagcggcggc gggtcg                                36
```

<210> SEQ ID NO 44
<211> LENGTH: 96
<212> TYPE: DNA
<213> ORGANISM: Artificial Sequence
<220> FEATURE:
<223> OTHER INFORMATION: Linker

<400> SEQUENCE: 44

```
tctggaggat ctagcggagg atcctctggc agcgagacac caggaacaag cgagtcagca    60
acaccagaga gcagtggcgg cagcagcggc ggctcg                               96
```

<210> SEQ ID NO 45
<211> LENGTH: 138

```
<212> TYPE: DNA
<213> ORGANISM: Artificial Sequence
<220> FEATURE:
<223> OTHER INFORMATION: Linker

<400> SEQUENCE: 45
gctgaggcgg cggcaaaaga agcagcggca aaagaagctg ccgcaaagga agcagcagca      60
aaagcccttg aagccgaagc tgctgctaag gaggctgccg caaaagaggc tgccgccaaa     120
gaagcagccg ctaaagcg                                                  138

<210> SEQ ID NO 46
<211> LENGTH: 123
<212> TYPE: DNA
<213> ORGANISM: Artificial Sequence
<220> FEATURE:
<223> OTHER INFORMATION: Linker

<400> SEQUENCE: 46
ggatccgact ataaggacca cgacggagac tacaaggatc atgatattga ttacaaagac      60
gatgacgata agatggcccc aaagaagaag cggaaggtcg gtatccacgg agtcccagca     120
gcg                                                                  123

<210> SEQ ID NO 47
<211> LENGTH: 96
<212> TYPE: DNA
<213> ORGANISM: Artificial Sequence
<220> FEATURE:
<223> OTHER INFORMATION: Linker

<400> SEQUENCE: 47
ggatccgact ataaggacca cgacggagac tacaaggatc atgatattga ttacaaagac      60
gatgacgata agggtatcca cggagtccca gcagcg                               96

<210> SEQ ID NO 48
<211> LENGTH: 222
<212> TYPE: DNA
<213> ORGANISM: Artificial Sequence
<220> FEATURE:
<223> OTHER INFORMATION: Linker

<400> SEQUENCE: 48
ggttctggaa gtgaggcagc tgcgaaggag gctgcggcga aagaagctgc agcaaaggaa      60
gcagcagcaa aggcactgga ggccgctgct gctaaagagg ctgccgccaa agaagctgcg     120
gcaaaggaag ctgcggctaa gggaagtggg agcagcgcgg ccaaagaggc agcggccaag     180
gaagctgctg caaaagaagc agcagctaaa gggagcggat cg                        222

<210> SEQ ID NO 49
<211> LENGTH: 222
<212> TYPE: DNA
<213> ORGANISM: Artificial Sequence
<220> FEATURE:
<223> OTHER INFORMATION: Artificial sequence

<400> SEQUENCE: 49
gccggaagcg gtggttcagg gggatccgga ggaagtcctg ttccctctac cccaccaact      60
aatagcagct caacccctcc gaccccctct ccgtcaccgg tgccgagtac cccgccaacc     120
aatagctcat caactccgcc tacgccgtcc cctagtccag tacctagcac ccctccaaca     180
aattctagca gtacaccacc cacaccaagc cctagcgcgt cg                        222
```

<210> SEQ ID NO 50
<211> LENGTH: 198
<212> TYPE: DNA
<213> ORGANISM: Artificial Sequence
<220> FEATURE:
<223> OTHER INFORMATION: Artificial sequence

<400> SEQUENCE: 50

```
gctggttctg gtggctcagg gggttccggt ggttccccag taccaagtac tcctcccact      60
ccctctccaa gtacgccgcc tacaccctca cccagcggcg gctctggcaa ttccagtggt     120
tcaggcggta gtcccgtgcc aagtacgcca ccaactccaa gtccatcaac accaccgacc     180
ccttctccgt ctgcatcg                                                   198
```

<210> SEQ ID NO 51
<211> LENGTH: 786
<212> TYPE: DNA
<213> ORGANISM: Artificial Sequence
<220> FEATURE:
<223> OTHER INFORMATION: Artificial sequence

<400> SEQUENCE: 51

```
gcgggttctg gaggttcagg cgggagcggt ggcagtccag tgccgagcac accgccaaca      60
ccgagcccaa gtacgccacc gactccaagt cccagcatac agcgaacacc gaagattcag     120
gtctactcac gacacccagc ggaaaacggc aaatctaatt ttctgaattg ctatgtttcc     180
ggttttcacc cctcagacat cgaggtcgac ctgctgaaga acggtgaaag gattgaaaag     240
gttgaacact ccgacttgag ctttagtaag gactggtcat tctatttgct gtattacacc     300
gagttcactc cgaccgaaaa ggatgaatac gcatgtcgag tgaatcatgt cacgctgagc     360
caacccaaga tcgtgaaatg ggacagggac gggggggtctg ggggtagcgg aggaagcggc     420
gggtctatcc aacgcactcc aaaaattcaa gtctactcaa gacaccctgc cgagaatgga     480
aaatcaaact ttttgaattg ctacgtctct ggattccatc cgtcagacat cgaagttgat     540
ctgttgaaaa acggtgagcg aattgagaaa gtggagcatt cagatcttag cttcagtaaa     600
gactggtcct tttatctctt gtattacacg gagttcactc ccacagaaaa agatgaatac     660
gcctgtcgag ttaaccacgt cacgctgtca cagccaaaga tagtgaaatg ggatcgcgac     720
ccagtgccct caacacccc tactcctagt ccgagcactc ctccaacgcc ttcaccatct     780
gcctcg                                                                786
```

<210> SEQ ID NO 52
<211> LENGTH: 978
<212> TYPE: DNA
<213> ORGANISM: Artificial Sequence
<220> FEATURE:
<223> OTHER INFORMATION: Artificial sequence

<400> SEQUENCE: 52

```
gctggttccg gcggatctgg tggatctggt ggcagccccg tcccttctac tccacccaca      60
ccgtccccgt caactcctcc cacccccgtct ccgtccgatg aaggtactc tctcacgtac     120 atctacactg ggttgtcaaa gcatgtggaa gacgtgccag ccttccaggc gcttggaagc     180
ctcaatgacc ttcagttttt tcgctacaat agcaaggatc gaaagtcaca acctatgggt     240
ctctggagac aggtcgaagg gatggaggac tggaaacagg atagccaatt gcaaaaagcg     300
agagaggata tctttatgga gacgcttaaa gacattgttg agtattacaa cgactctaac     360
ggtagtcacg tattgcaggg ccgatttggg tgtgagatag agaataaccg gagttccggc     420
```

```
gcttttttgga aatattatta cgatggcaag gactacatcg agtttaacaa agaaattcca    480
gcctgggtgc cttttgaccc agctgcacaa attacaaaac agaagtggga ggcggagcca    540
gtgtacgttc aaagggcaaa agcatacttg gaggaagagt gtcccgcaac tctccgaaag    600
tacttgaagt attctaaaaa catactggat cgacaggatc cccttcagt agtcgtaacc     660 tcccaccagg ccccaggtga aagaagaag ttgaaatgcc ttgcttacga cttctaccca     720
ggcaagattg atgttcactg acaagggct ggtgaggtcc aagagcccga acttagaggg     780
gatgtgttgc ataacggtaa tgggacgtat cagtcatggg tcgtggtggc agtccctcct    840
caagatacgg caccatactc ttgccatgtg caacacagct cactggcgca gccactcgta    900
gtgccttggg aggccagccc cgtgccatca actcccccaa ctccatcacc tagtaccccc    960
cctactccgt cagcctcg                                                   978

<210> SEQ ID NO 53
<211> LENGTH: 1818
<212> TYPE: DNA
<213> ORGANISM: Artificial Sequence
<220> FEATURE:
<223> OTHER INFORMATION: Artificial sequence

<400> SEQUENCE: 53
gctggttctg gggggtcagg agggagtgga gggtctggag gttctggagg ctcaggaggt     60
agcggtggta gtgacggcag gtacagtctc acctatatct atacaggatt gtctaagcat    120
gttgaagacg tgcccgcctt tcaggcactg ggttctttga cgacctcca gttttttccgc   180 tacaacagta aagaccgaaa atctcagccc atggggctct ggagacaagt tgaaggtatg    240
gaggactgga acaggacag tcaattgcaa aaggccagag aagatatttt tatggaaacc      300
ttgaaggata ttgtcgagta ctacaacgat tcaaacgggt cccacgtgct gcagggccga    360
ttcggttgcg agatagaaaa taatcgatct agtggtgcct tttggaagta ttactacgac    420
ggaaaagatt atatcgaatt taataaagag attcctgcgt gggtgccgtt tgacccggcg    480
gcacaaatta ctaaacaaaa gtgggaagcg gaaccggtgt atgttcagag ggctaaggcg    540
taccttgaag aagagtgccc cgctacgttg aggaaatacc tcaaatattc caaaaatatc    600
ttggatcgac aagatccacc tagcgtggtt gttacttcac accaagcacc aggtgaaaaa    660
aaaaaattga gtgtcttgc atatgacttc tatcctggga gatcgacgt acactggaca      720 cgagccggag aggtacaaga acctgaactg cgaggggacg tcctccataa cgggaacggt    780
acctatcaaa gttgggtggt ggttgcggtt ccacctcagg acactgcgcc ttactcctgt    840
cacgtgcagc attcctctct cgctcaaccc cttgtcgtgc cgtgggaggc ctccggaggg    900
tctggcggaa gcgaggatc tggtgggtcc gatggtaggt actcacttac ttacatatac    960
acgggtctta gtaaacacgt cgaggatgtc ccggcgttcc aagctctggg tagtttgaat   1020
gatctccaat tttttagata caatagcaaa gatcgaaaaa gccaaccaat gggactctgg   1080
agacaggtgg agggaatgga agattggaaa caagattctc aactccagaa ggctagggaa   1140
gacattttca tggaaacgct caaagatatt gtagagtatt ataatgattc taacggcagc   1200
cacgtccttc aggggcgatt tggtgtgag attgaaaaca atcgatctag cggtgcattt    1260
tggaaatatt actatgatgg caaagactat atcgaattca acaaggaaat tccagcatgg   1320
gtcccattcg accccgcggc tcaaattacc aagcaaaaat gggaagccga acctgtctac   1380
gtacaacggg cgaaggcata tcttgaggag gaatgccccg cgaccctccg aaagtacctt   1440
```

```
aagtactcca agaacattct cgatcggcag gaccccccett ctgtggtagt caccagccat    1500
caggcacctg gggagaagaa gaaactcaag tgcctggcct acgatttcta ccctgggaaa    1560
atcgatgtcc actggacgag agcgggtgag gtgcaagagc cagaattgag aggtgatgtc    1620
cttcataacg gcaatggcac ctatcagtca tgggtggtcg tggctgttcc ccctcaagac    1680
acggcaccgt atagctgtca tgtccaacac tcctccctcg ctcaaccact cgtggtccca    1740
tgggaggcta gcccagtgcc cagcacaccc cctactccct ctccttctac tccaccgacc    1800
ccttcaccgt ccgcttcg                                                  1818

<210> SEQ ID NO 54
<211> LENGTH: 96
<212> TYPE: DNA
<213> ORGANISM: Artificial Sequence
<220> FEATURE:
<223> OTHER INFORMATION: Artificial sequence

<400> SEQUENCE: 54
gggctgagag agggacaagt gttttagagc tagaaatagc aagttaaaat aaggctagtc    60
cgttatcaac ttgaaaaagt ggcaccgagt cggtgc                              96

<210> SEQ ID NO 55
<211> LENGTH: 96
<212> TYPE: DNA
<213> ORGANISM: Artificial Sequence
<220> FEATURE:
<223> OTHER INFORMATION: Artificial sequence

<400> SEQUENCE: 55
agtgtgcatt gccacctcag gttttagagc tagaaatagc aagttaaaat aaggctagtc    60
cgttatcaac ttgaaaaagt ggcaccgagt cggtgc                              96

<210> SEQ ID NO 56
<211> LENGTH: 96
<212> TYPE: DNA
<213> ORGANISM: Artificial Sequence
<220> FEATURE:
<223> OTHER INFORMATION: Artificial sequence

<400> SEQUENCE: 56
gcaggactcc tttcctccat gttttagagc tagaaatagc aagttaaaat aaggctagtc    60
cgttatcaac ttgaaaaagt ggcaccgagt cggtgc                              96

<210> SEQ ID NO 57
<211> LENGTH: 96
<212> TYPE: DNA
<213> ORGANISM: Artificial Sequence
<220> FEATURE:
<223> OTHER INFORMATION: Artificial sequence

<400> SEQUENCE: 57
ataggagaag atgatgtata gttttagagc tagaaatagc aagttaaaat aaggctagtc    60
cgttatcaac ttgaaaaagt ggcaccgagt cggtgc                              96

<210> SEQ ID NO 58
<211> LENGTH: 96
<212> TYPE: DNA
<213> ORGANISM: Artificial Sequence
<220> FEATURE:
<223> OTHER INFORMATION: Artificial sequence

<400> SEQUENCE: 58
```

```
aaaacgtttc caagacatga gttttagagc tagaaatagc aagttaaaat aaggctagtc    60
cgttatcaac ttgaaaaagt ggcaccgagt cggtgc                              96
```

<210> SEQ ID NO 59
<211> LENGTH: 96
<212> TYPE: DNA
<213> ORGANISM: Artificial Sequence
<220> FEATURE:
<223> OTHER INFORMATION: Artificial sequence

<400> SEQUENCE: 59

```
ccgccgtcca agacctaccg gttttagagc tagaaatagc aagttaaaat aaggctagtc    60
cgttatcaac ttgaaaaagt ggcaccgagt cggtgc                              96
```

<210> SEQ ID NO 60
<211> LENGTH: 96
<212> TYPE: DNA
<213> ORGANISM: Artificial Sequence
<220> FEATURE:
<223> OTHER INFORMATION: Artificial sequence

<400> SEQUENCE: 60

```
ccaagaagcg caccacctcc gttttagagc tagaaatagc aagttaaaat aaggctagtc    60
cgttatcaac ttgaaaaagt ggcaccgagt cggtgc                              96
```

<210> SEQ ID NO 61
<211> LENGTH: 96
<212> TYPE: DNA
<213> ORGANISM: Artificial Sequence
<220> FEATURE:
<223> OTHER INFORMATION: Artificial sequence

<400> SEQUENCE: 61

```
agcctggaag cacgaatggt gttttagagc tagaaatagc aagttaaaat aaggctagtc    60
cgttatcaac ttgaaaaagt ggcaccgagt cggtgc                              96
```

<210> SEQ ID NO 62
<211> LENGTH: 96
<212> TYPE: DNA
<213> ORGANISM: Artificial Sequence
<220> FEATURE:
<223> OTHER INFORMATION: Artificial sequence

<400> SEQUENCE: 62

```
acataccaag agaatcaccc gttttagagc tagaaatagc aagttaaaat aaggctagtc    60
cgttatcaac ttgaaaaagt ggcaccgagt cggtgc                              96
```

<210> SEQ ID NO 63
<211> LENGTH: 95
<212> TYPE: DNA
<213> ORGANISM: Artificial Sequence
<220> FEATURE:
<223> OTHER INFORMATION: Artificial sequence

<400> SEQUENCE: 63

```
gaaggaggag gcctaaggag ttttagagct agaaatagca agttaaaata aggctagtcc    60
gttatcaact tgaaaaagtg caccgagtc ggtgc                                95
```

<210> SEQ ID NO 64
<211> LENGTH: 96
<212> TYPE: DNA

<213> ORGANISM: Artificial Sequence
<220> FEATURE:
<223> OTHER INFORMATION: Artificial sequence

<400> SEQUENCE: 64

```
aagaagacta gctgagctct gttttagagc tagaaatagc aagttaaaat aaggctagtc    60
cgttatcaac ttgaaaaagt ggcaccgagt cggtgc                              96
```

<210> SEQ ID NO 65
<211> LENGTH: 575
<212> TYPE: PRT
<213> ORGANISM: Homo sapiens

<400> SEQUENCE: 65

```
Met Asp Pro Arg Gly Ile Leu Lys Ala Phe Pro Lys Arg Gln Lys Ile
1               5                   10                  15

His Ala Asp Ala Ser Ser Lys Val Leu Ala Lys Ile Pro Arg Arg Glu
            20                  25                  30

Glu Gly Glu Glu Ala Glu Glu Trp Leu Ser Ser Leu Arg Ala His Val
        35                  40                  45

Val Arg Thr Gly Ile Gly Arg Ala Arg Ala Glu Leu Phe Glu Lys Gln
    50                  55                  60

Ile Val Gln His Gly Gly Gln Leu Cys Pro Ala Gln Gly Pro Gly Val
65                  70                  75                  80

Thr His Ile Val Val Asp Glu Gly Met Asp Tyr Glu Arg Ala Leu Arg
                85                  90                  95

Leu Leu Arg Leu Pro Gln Leu Pro Pro Gly Ala Gln Leu Val Lys Ser
            100                 105                 110

Ala Trp Leu Ser Leu Cys Leu Gln Glu Arg Arg Leu Val Asp Val Ala
        115                 120                 125

Gly Phe Ser Ile Phe Ile Pro Ser Arg Tyr Leu Asp His Pro Gln Pro
    130                 135                 140

Ser Lys Ala Glu Gln Asp Ala Ser Ile Pro Pro Gly Thr His Glu Ala
145                 150                 155                 160

Leu Leu Gln Thr Ala Leu Ser Pro Pro Pro Pro Thr Arg Pro Val
                165                 170                 175

Ser Pro Pro Gln Lys Ala Lys Glu Ala Pro Asn Thr Gln Ala Gln Pro
            180                 185                 190

Ile Ser Asp Asp Glu Ala Ser Asp Gly Glu Glu Thr Gln Val Ser Ala
        195                 200                 205

Ala Asp Leu Glu Ala Leu Ile Ser Gly His Tyr Pro Thr Ser Leu Glu
    210                 215                 220

Gly Asp Cys Glu Pro Ser Pro Ala Pro Ala Val Leu Asp Lys Trp Val
225                 230                 235                 240

Cys Ala Gln Pro Ser Ser Gln Lys Ala Thr Asn His Asn Leu His Ile
                245                 250                 255

Thr Glu Lys Leu Glu Val Leu Ala Lys Ala Tyr Ser Val Gln Gly Asp
            260                 265                 270

Lys Trp Arg Ala Leu Gly Tyr Ala Lys Ala Ile Asn Ala Leu Lys Ser
        275                 280                 285

Phe His Lys Pro Val Thr Ser Tyr Gln Glu Ala Cys Ser Ile Pro Gly
    290                 295                 300

Ile Gly Lys Arg Met Ala Glu Lys Ile Ile Glu Ile Leu Glu Ser Gly
305                 310                 315                 320

His Leu Arg Lys Leu Asp His Ile Ser Glu Ser Val Pro Val Leu Glu
```

|   |   |   | 325 |   |   |   | 330 |   |   |   | 335 |   |
|---|---|---|---|---|---|---|---|---|---|---|---|---|

Leu Phe Ser Asn Ile Trp Gly Ala Gly Thr Lys Thr Ala Gln Met Trp
            340                 345                 350

Tyr Gln Gln Gly Phe Arg Ser Leu Glu Asp Ile Arg Ser Gln Ala Ser
            355                 360                 365

Leu Thr Thr Gln Gln Ala Ile Gly Leu Lys His Tyr Ser Asp Phe Leu
            370                 375                 380

Glu Arg Met Pro Arg Glu Ala Thr Glu Ile Glu Gln Thr Val Gln
385                 390                 395                 400

Lys Ala Ala Gln Ala Phe Asn Ser Gly Leu Leu Cys Val Ala Cys Gly
                405                 410                 415

Ser Tyr Arg Arg Gly Lys Ala Thr Cys Gly Asp Val Asp Val Leu Ile
                420                 425                 430

Thr His Pro Asp Gly Arg Ser His Arg Gly Ile Phe Ser Arg Leu Leu
            435                 440                 445

Asp Ser Leu Arg Gln Glu Gly Phe Leu Thr Asp Asp Leu Val Ser Gln
            450                 455                 460

Glu Glu Asn Gly Gln Gln Gln Lys Tyr Leu Gly Val Cys Arg Leu Pro
465                 470                 475                 480

Gly Pro Gly Arg Arg His Arg Arg Leu Asp Ile Ile Val Val Pro Tyr
                485                 490                 495

Ser Glu Phe Ala Cys Ala Leu Leu Tyr Phe Thr Gly Ser Ala His Phe
            500                 505                 510

Asn Arg Ser Met Arg Ala Leu Ala Lys Thr Lys Gly Met Ser Leu Ser
            515                 520                 525

Glu His Ala Leu Ser Thr Ala Val Val Arg Asn Thr His Gly Cys Lys
            530                 535                 540

Val Gly Pro Gly Arg Val Leu Pro Thr Pro Thr Glu Lys Asp Val Phe
545                 550                 555                 560

Arg Leu Leu Gly Leu Pro Tyr Arg Glu Pro Ala Glu Arg Asp Trp
                565                 570                 575

<210> SEQ ID NO 66
<211> LENGTH: 495
<212> TYPE: PRT
<213> ORGANISM: Homo sapiens

<400> SEQUENCE: 66

Met Ala Leu Pro Lys Arg Arg Ala Arg Val Gly Ser Pro Ser Gly
1               5                   10                  15

Asp Ala Ala Ser Ser Thr Pro Pro Ser Thr Arg Phe Pro Gly Val Ala
                20                  25                  30

Ile Tyr Leu Val Glu Pro Arg Met Gly Arg Ser Arg Arg Ala Phe Leu
            35                  40                  45

Thr Gly Leu Ala Arg Ser Lys Gly Phe Arg Val Leu Asp Ala Cys Ser
            50                  55                  60

Ser Glu Ala Thr His Val Val Met Glu Glu Thr Ser Ala Glu Glu Ala
65                  70                  75                  80

Val Ser Trp Gln Glu Arg Arg Met Ala Ala Ala Pro Pro Gly Cys Thr
                85                  90                  95

Pro Pro Ala Leu Leu Asp Ile Ser Trp Leu Thr Glu Ser Leu Gly Ala
            100                 105                 110

Gly Gln Pro Val Pro Val Glu Cys Arg His Arg Leu Glu Val Ala Gly
            115                 120                 125

```
Pro Arg Lys Gly Pro Leu Ser Pro Ala Trp Met Pro Ala Tyr Ala Cys
    130                 135                 140

Gln Arg Pro Thr Pro Leu Thr His His Asn Thr Gly Leu Ser Glu Ala
145                 150                 155                 160

Leu Glu Ile Leu Ala Glu Ala Ala Gly Phe Glu Gly Ser Glu Gly Arg
                165                 170                 175

Leu Leu Thr Phe Cys Arg Ala Ala Ser Val Leu Lys Ala Leu Pro Ser
            180                 185                 190

Pro Val Thr Thr Leu Ser Gln Leu Gln Gly Leu Pro His Phe Gly Glu
        195                 200                 205

His Ser Ser Arg Val Val Gln Glu Leu Leu Glu His Gly Val Cys Glu
210                 215                 220

Glu Val Glu Arg Val Arg Arg Ser Glu Arg Tyr Gln Thr Met Lys Leu
225                 230                 235                 240

Phe Thr Gln Ile Phe Gly Val Gly Val Lys Thr Ala Asp Arg Trp Tyr
                245                 250                 255

Arg Glu Gly Leu Arg Thr Leu Asp Asp Leu Arg Glu Gln Pro Gln Lys
            260                 265                 270

Leu Thr Gln Gln Gln Lys Ala Gly Leu Gln His His Gln Asp Leu Ser
        275                 280                 285

Thr Pro Val Leu Arg Ser Asp Val Asp Ala Leu Gln Gln Val Val Glu
290                 295                 300

Glu Ala Val Gly Gln Ala Leu Pro Gly Ala Thr Val Thr Leu Thr Gly
305                 310                 315                 320

Gly Phe Arg Arg Gly Lys Leu Gln Gly His Asp Val Asp Phe Leu Ile
                325                 330                 335

Thr His Pro Lys Glu Gly Gln Glu Ala Gly Leu Leu Pro Arg Val Met
            340                 345                 350

Cys Arg Leu Gln Asp Gln Gly Leu Ile Leu Tyr His Gln His Gln His
        355                 360                 365

Ser Cys Cys Glu Ser Pro Thr Arg Leu Ala Gln Gln Ser His Met Asp
370                 375                 380

Ala Phe Glu Arg Ser Phe Cys Ile Phe Arg Leu Pro Gln Pro Pro Gly
385                 390                 395                 400

Ala Ala Val Gly Gly Ser Thr Arg Pro Cys Pro Ser Trp Lys Ala Val
                405                 410                 415

Arg Val Asp Leu Val Val Ala Pro Val Ser Gln Phe Pro Phe Ala Leu
            420                 425                 430

Leu Gly Trp Thr Gly Ser Lys Leu Phe Gln Arg Glu Leu Arg Arg Phe
        435                 440                 445

Ser Arg Lys Glu Lys Gly Leu Trp Leu Asn Ser His Gly Leu Phe Asp
450                 455                 460

Pro Glu Gln Lys Thr Phe Phe Gln Ala Ala Ser Glu Glu Asp Ile Phe
465                 470                 475                 480

Arg His Leu Gly Leu Glu Tyr Leu Pro Pro Glu Gln Arg Asn Ala
                485                 490                 495

<210> SEQ ID NO 67
<211> LENGTH: 495
<212> TYPE: PRT
<213> ORGANISM: Homo sapiens

<400> SEQUENCE: 67

Met Ala Leu Pro Lys Arg Arg Ala Arg Val Gly Ser Pro Ser Gly
1               5                   10                  15
```

```
Asp Ala Ala Ser Ser Thr Pro Pro Ser Thr Arg Phe Pro Gly Val Ala
             20                  25                  30

Ile Tyr Leu Val Glu Pro Arg Met Gly Arg Ser Arg Ala Phe Leu
         35                  40                  45

Thr Gly Leu Ala Arg Ser Lys Gly Phe Arg Val Leu Asp Ala Cys Ser
 50                  55                  60

Ser Glu Ala Thr His Val Val Met Glu Glu Thr Ser Ala Glu Glu Ala
 65                  70                  75                  80

Val Ser Trp Gln Glu Arg Arg Met Ala Ala Ala Pro Pro Gly Cys Thr
                 85                  90                  95

Pro Pro Ala Leu Leu Asp Ile Ser Trp Leu Thr Glu Ser Leu Gly Ala
            100                 105                 110

Gly Gln Pro Val Pro Val Glu Cys Arg His Arg Leu Glu Val Ala Gly
            115                 120                 125

Pro Arg Lys Gly Pro Leu Ser Pro Ala Trp Met Pro Ala Tyr Ala Cys
130                 135                 140

Gln Arg Pro Thr Pro Leu Thr His His Asn Thr Gly Leu Ser Glu Ala
145                 150                 155                 160

Leu Glu Ile Leu Ala Glu Ala Gly Phe Glu Gly Ser Glu Gly Arg
                165                 170                 175

Leu Leu Thr Phe Cys Arg Ala Ala Ser Val Leu Lys Ala Leu Pro Ser
            180                 185                 190

Pro Val Thr Thr Leu Ser Gln Leu Gln Gly Leu Pro His Phe Gly Glu
            195                 200                 205

His Ser Ser Arg Val Val Gln Glu Leu Leu Glu His Gly Val Cys Glu
            210                 215                 220

Glu Val Glu Arg Val Arg Arg Ser Glu Arg Tyr Gln Thr Met Lys Leu
225                 230                 235                 240

Phe Thr Gln Ile Phe Gly Val Gly Val Lys Thr Ala Asp Arg Trp Tyr
                245                 250                 255

Arg Glu Gly Leu Arg Thr Leu Asp Asp Leu Arg Glu Gln Pro Gln Lys
            260                 265                 270

Leu Thr Gln Gln Gln Lys Ala Gly Leu Gln His His Gln Asp Leu Ser
            275                 280                 285

Thr Pro Val Leu Arg Ser Asp Val Asp Ala Leu Gln Gln Val Val Glu
            290                 295                 300

Glu Ala Val Gly Gln Ala Leu Pro Gly Ala Thr Val Thr Leu Thr Gly
305                 310                 315                 320

Gly Phe Arg Arg Gly Lys Leu Gln Gly Gly Asp Val Asp Phe Leu Ile
                325                 330                 335

Thr His Pro Lys Glu Gly Gln Glu Ala Gly Leu Leu Pro Arg Val Met
            340                 345                 350

Cys Arg Leu Gln Asp Gln Gly Leu Ile Leu Tyr His Gln His Gln His
            355                 360                 365

Ser Cys Cys Glu Ser Pro Thr Arg Leu Ala Gln Gln Ser His Met Asp
            370                 375                 380

Ala Phe Glu Arg Ser Lys Cys Ile Phe Arg Leu Pro Gln Pro Pro Gly
385                 390                 395                 400

Ala Ala Val Gly Gly Ser Thr Arg Pro Cys Pro Ser Trp Lys Ala Val
                405                 410                 415

Arg Val Asp Leu Val Val Ala Pro Val Ser Gln Phe Pro Phe Ala Leu
            420                 425                 430
```

-continued

Leu Gly Trp Thr Gly Ser Lys Leu Phe Gln Arg Glu Leu Arg Arg Phe
         435                 440                 445

Ser Arg Lys Glu Lys Gly Leu Trp Leu Asn Ser His Gly Leu Phe Asp
450                 455                 460

Pro Glu Gln Lys Thr Phe Phe Gln Ala Ala Ser Glu Glu Asp Ile Phe
465                 470                 475                 480

Arg His Leu Gly Leu Glu Tyr Leu Pro Pro Glu Gln Arg Asn Ala
                485                 490                 495

<210> SEQ ID NO 68
<211> LENGTH: 495
<212> TYPE: PRT
<213> ORGANISM: Homo sapiens

<400> SEQUENCE: 68

Met Ala Leu Pro Lys Arg Arg Ala Arg Val Gly Ser Pro Ser Gly
1               5                   10                  15

Asp Ala Ser Ser Thr Pro Pro Ser Thr Arg Phe Pro Gly Val Ala
                20                  25                  30

Ile Tyr Leu Val Glu Pro Arg Met Gly Arg Ser Arg Arg Ala Phe Leu
             35                  40                  45

Thr Gly Leu Ala Arg Ser Lys Gly Phe Arg Val Leu Asp Ala Cys Ser
    50                  55                  60

Ser Glu Ala Thr His Val Val Met Glu Glu Thr Ser Ala Glu Glu Ala
65                  70                  75                  80

Val Ser Trp Gln Glu Arg Arg Met Ala Ala Pro Pro Gly Cys Thr
                85                  90                  95

Pro Pro Ala Leu Leu Asp Ile Ser Trp Leu Thr Glu Ser Leu Gly Ala
                100                 105                 110

Gly Gln Pro Val Pro Val Glu Cys Arg His Arg Leu Val Ala Gly
                115                 120                 125

Pro Arg Lys Gly Pro Leu Ser Pro Ala Trp Met Pro Ala Tyr Ala Cys
            130                 135                 140

Gln Arg Pro Thr Pro Leu Thr His His Asn Thr Gly Leu Ser Glu Ala
145                 150                 155                 160

Leu Glu Ile Leu Ala Glu Ala Ala Gly Phe Glu Gly Ser Glu Gly Arg
                165                 170                 175

Leu Leu Thr Phe Cys Arg Ala Ala Ser Val Leu Lys Ala Leu Pro Ser
                180                 185                 190

Pro Val Thr Thr Leu Ser Gln Leu Gln Gly Leu Pro His Phe Gly Glu
            195                 200                 205

His Ser Ser Arg Val Val Gln Glu Leu Leu Glu His Gly Val Cys Glu
            210                 215                 220

Glu Val Glu Arg Val Arg Arg Ser Glu Arg Tyr Gln Thr Met Lys Leu
225                 230                 235                 240

Phe Thr Gln Ile Phe Gly Val Gly Val Lys Thr Ala Asp Arg Trp Tyr
                245                 250                 255

Arg Glu Gly Leu Arg Thr Leu Asp Asp Leu Arg Glu Gln Pro Gln Lys
            260                 265                 270

Leu Thr Gln Gln Gln Lys Ala Gly Leu Gln His His Gln Asp Leu Ser
        275                 280                 285

Thr Pro Val Leu Arg Ser Asp Val Asp Ala Leu Gln Gln Val Val Glu
    290                 295                 300

Glu Ala Val Gly Gln Ala Leu Pro Gly Ala Thr Val Thr Leu Thr Gly
305                 310                 315                 320

-continued

Gly Phe Arg Arg Gly Lys Leu Gln Gly Gly Asp Val Asp Phe Leu Ile
                325                 330                 335

Thr His Pro Lys Glu Gly Gln Glu Ala Gly Leu Leu Pro Arg Val Met
            340                 345                 350

Cys Arg Leu Gln Asp Gln Gly Leu Ile Leu Tyr His Gln His Gln His
        355                 360                 365

Ser Cys Cys Glu Ser Pro Thr Arg Leu Ala Gln Gln Ser His Met Asp
370                 375                 380

Ala Phe Glu Arg Ser Phe Cys Ile Phe Arg Leu Pro Gln Pro Pro Gly
385                 390                 395                 400

Ala Ala Val Gly Gly Ser Thr Arg Pro Cys Pro Ser Trp Lys Ala Val
                405                 410                 415

Arg Val Asp Leu Val Val Ala Pro Val Ser Gln Phe Pro Phe Ala Leu
            420                 425                 430

Leu Gly Trp Thr Gly Ser Lys Leu Phe Gln Arg Glu Leu Arg Arg Phe
        435                 440                 445

Ser Arg Lys Glu Lys Gly Leu Trp Leu Asn Ser His Gly Leu Phe Asp
    450                 455                 460

Pro Glu Gln Lys Thr Phe Phe Gln Ala Ala Ser Glu Glu Asp Ile Phe
465                 470                 475                 480

Arg His Leu Gly Leu Glu Tyr Leu Pro Pro Glu Gln Arg Asn Ala
                485                 490                 495

<210> SEQ ID NO 69
<211> LENGTH: 557
<212> TYPE: PRT
<213> ORGANISM: Homo sapiens

<400> SEQUENCE: 69

Met Ala Leu Pro Lys Arg Arg Ala Arg Val Gly Ser Pro Ser Gly
1               5                   10                  15

Asp Ala Ala Ser Ser Thr Pro Pro Ser Thr Arg Phe Pro Gly Val Ala
                20                  25                  30

Ile Tyr Leu Val Glu Pro Arg Met Gly Arg Ser Arg Arg Ala Phe Leu
            35                  40                  45

Thr Gly Leu Ala Arg Ser Lys Gly Phe Arg Val Leu Asp Ala Cys Ser
        50                  55                  60

Ser Glu Ala Thr His Val Val Met Glu Glu Thr Ser Ala Glu Glu Ala
65                  70                  75                  80

Val Ser Trp Gln Glu Arg Arg Met Ala Ala Ala Pro Pro Gly Cys Thr
                85                  90                  95

Pro Pro Ala Leu Leu Asp Ile Ser Trp Leu Thr Glu Ser Leu Gly Ala
            100                 105                 110

Gly Gln Pro Ile Pro Ser Arg Tyr Leu Asp His Pro Gln Pro Ser Lys
        115                 120                 125

Ala Glu Gln Asp Ala Ser Ile Pro Pro Gly Thr His Glu Ala Leu Leu
    130                 135                 140

Gln Thr Ala Leu Ser Pro Pro Pro Thr Arg Pro Val Ser Pro
145                 150                 155                 160

Pro Gln Lys Ala Lys Glu Ala Pro Asn Thr Gln Ala Gln Pro Ile Ser
                165                 170                 175

Asp Asp Glu Ala Ser Asp Gly Glu Thr Gln Val Ser Ala Ala Asp
            180                 185                 190

Leu Glu Ala Leu Ile Ser Gly His Tyr Pro Thr Ser Leu Glu Gly Asp

```
            195                 200                 205
Cys Glu Pro Ser Pro Ala Pro Ala Val Leu Asp Lys Trp Val Cys Ala
    210                 215                 220
Gln Pro Ser Ser Gln Lys Ala Thr Asn His Asn Leu His Ile Thr Glu
225                 230                 235                 240
Lys Leu Glu Val Leu Ala Lys Ala Tyr Ser Val Gln Gly Asp Lys Trp
                245                 250                 255
Arg Ala Leu Gly Tyr Ala Lys Ala Ile Asn Ala Leu Lys Ser Phe His
            260                 265                 270
Lys Pro Val Thr Ser Tyr Gln Glu Ala Cys Ser Ile Pro Gly Ile Gly
        275                 280                 285
Lys Arg Met Ala Glu Lys Ile Ile Glu Ile Leu Glu Ser Gly His Leu
290                 295                 300
Arg Lys Leu Asp His Ile Ser Glu Ser Val Pro Val Leu Glu Leu Phe
305                 310                 315                 320
Ser Asn Ile Trp Gly Ala Gly Thr Lys Thr Ala Gln Met Trp Tyr Gln
                325                 330                 335
Gln Gly Phe Arg Ser Leu Glu Asp Ile Arg Ser Gln Ala Ser Leu Thr
            340                 345                 350
Thr Gln Gln Ala Ile Gly Leu Lys His Tyr Ser Asp Phe Leu Glu Arg
        355                 360                 365
Met Pro Arg Glu Glu Ala Thr Glu Ile Glu Gln Thr Val Gln Lys Ala
370                 375                 380
Ala Gln Ala Phe Asn Ser Gly Leu Leu Cys Val Ala Cys Gly Ser Tyr
385                 390                 395                 400
Arg Arg Gly Lys Ala Thr Cys Gly Asp Val Asp Val Leu Ile Thr His
                405                 410                 415
Pro Asp Gly Arg Ser His Arg Gly Ile Phe Ser Arg Leu Leu Asp Ser
            420                 425                 430
Leu Arg Gln Glu Gly Phe Leu Thr Asp Asp Leu Val Ser Gln Glu Glu
        435                 440                 445
Asn Gly Gln Gln Gln Lys Tyr Leu Gly Val Cys Arg Leu Pro Gly Pro
450                 455                 460
Gly Arg Arg His Arg Leu Asp Ile Ile Val Val Pro Tyr Ser Glu
465                 470                 475                 480
Phe Ala Cys Ala Leu Leu Tyr Phe Thr Gly Ser Ala His Phe Asn Arg
                485                 490                 495
Ser Met Arg Ala Leu Ala Lys Thr Lys Gly Met Ser Leu Ser Glu His
            500                 505                 510
Ala Leu Ser Thr Ala Val Val Arg Asn Thr His Gly Cys Lys Val Gly
        515                 520                 525
Pro Gly Arg Val Leu Pro Thr Pro Thr Glu Lys Asp Val Phe Arg Leu
530                 535                 540
Leu Gly Leu Pro Tyr Arg Glu Pro Ala Glu Arg Asp Trp
545                 550                 555

<210> SEQ ID NO 70
<211> LENGTH: 466
<212> TYPE: PRT
<213> ORGANISM: Homo sapiens

<400> SEQUENCE: 70

Met Ala Leu Pro Lys Arg Arg Ala Arg Val Gly Ser Pro Ser Gly
1               5                   10                  15
```

```
Asp Ala Ala Ser Ser Thr Pro Pro Ser Thr Arg Phe Pro Gly Val Ala
             20                  25                  30

Ile Tyr Leu Val Glu Pro Arg Met Gly Arg Ser Arg Arg Ala Phe Leu
         35                  40                  45

Thr Gly Leu Ala Arg Ser Lys Gly Phe Arg Val Leu Asp Ala Cys Ser
     50                  55                  60

Ser Glu Ala Thr His Val Val Met Glu Glu Thr Ser Ala Glu Glu Ala
65                  70                  75                  80

Val Ser Trp Gln Glu Arg Arg Met Ala Ala Pro Pro Gly Cys Thr
                 85                  90                  95

Pro Pro Ala Leu Leu Asp Ile Ser Trp Leu Thr Glu Ser Leu Gly Ala
             100                 105                 110

Gly Gln Pro Val Pro Val Glu Cys Arg His Arg Leu Glu Val Ala Gly
         115                 120                 125

Pro Arg Lys Gly Pro Leu Ser Ser Ser Gln Lys Ala Thr Asn His Asn
     130                 135                 140

Leu His Ile Thr Glu Lys Leu Glu Val Leu Ala Lys Ala Tyr Ser Val
145                 150                 155                 160

Gln Gly Asp Lys Trp Arg Ala Leu Gly Tyr Ala Lys Ala Ile Asn Ala
                 165                 170                 175

Leu Lys Ser Phe His Lys Pro Val Thr Ser Tyr Gln Glu Ala Cys Ser
             180                 185                 190

Ile Pro Gly Ile Gly Lys Arg Met Ala Glu Lys Ile Glu Ile Leu
         195                 200                 205

Glu Ser Gly His Leu Arg Lys Leu Asp His Ile Ser Glu Ser Val Pro
210                 215                 220

Val Leu Glu Leu Phe Ser Asn Ile Trp Gly Ala Gly Thr Lys Thr Ala
225                 230                 235                 240

Gln Met Trp Tyr Gln Gln Gly Phe Arg Ser Leu Glu Asp Ile Arg Ser
                 245                 250                 255

Gln Ala Ser Leu Thr Thr Gln Gln Ala Ile Gly Leu Lys His Tyr Ser
             260                 265                 270

Asp Phe Leu Glu Arg Met Pro Arg Glu Glu Ala Thr Glu Ile Glu Gln
         275                 280                 285

Thr Val Gln Lys Ala Ala Gln Ala Phe Asn Ser Gly Leu Leu Cys Val
     290                 295                 300

Ala Cys Gly Ser Tyr Arg Arg Gly Lys Ala Thr Cys Gly Asp Val Asp
305                 310                 315                 320

Val Leu Ile Thr His Pro Asp Gly Arg Ser His Arg Gly Ile Phe Ser
                 325                 330                 335

Arg Leu Leu Asp Ser Leu Arg Gln Glu Gly Phe Leu Thr Asp Asp Leu
             340                 345                 350

Val Ser Gln Glu Glu Asn Gly Gln Gln Gln Lys Tyr Leu Gly Val Cys
         355                 360                 365

Arg Leu Pro Gly Pro Gly Arg Arg His Arg Arg Leu Asp Ile Ile Val
     370                 375                 380

Val Pro Tyr Ser Glu Phe Ala Cys Ala Leu Leu Tyr Phe Thr Gly Ser
385                 390                 395                 400

Ala His Phe Asn Arg Ser Met Arg Ala Leu Ala Lys Thr Lys Gly Met
                 405                 410                 415

Ser Leu Ser Glu His Ala Leu Ser Thr Ala Val Val Arg Asn Thr His
             420                 425                 430

Gly Cys Lys Val Gly Pro Gly Arg Val Leu Pro Thr Pro Thr Glu Lys
```

```
                   435                 440                 445
Asp Val Phe Arg Leu Leu Gly Leu Pro Tyr Arg Glu Pro Ala Glu Arg
    450                 455                 460

Asp Trp
465

<210> SEQ ID NO 71
<211> LENGTH: 407
<212> TYPE: PRT
<213> ORGANISM: Homo sapiens

<400> SEQUENCE: 71

Met Asp Tyr Lys Asp His Asp Gly Asp Tyr Lys Asp His Asp Ile Asp
1               5                  10                  15

Tyr Lys Asp Asp Asp Asp Lys Met Ala Pro Lys Lys Lys Arg Lys Val
                20                  25                  30

Gly Ile His Gly Val Pro Ala Ala Ile Lys Ser Ile Ala Ser Arg
        35                  40                  45

Leu Arg Gly Ser Arg Arg Phe Leu Ser Gly Phe Val Ala Gly Ala Val
    50                  55                  60

Val Gly Ala Ala Gly Ala Gly Leu Ala Ala Leu Gln Phe Phe Arg Ser
65                  70                  75                  80

Gln Gly Ala Glu Gly Ala Leu Thr Gly Lys Gln Pro Asp Gly Ser Ala
                85                  90                  95

Glu Lys Ala Val Leu Glu Gln Phe Gly Phe Pro Leu Thr Gly Thr Glu
            100                 105                 110

Ala Arg Cys Tyr Thr Asn His Ala Leu Ser Tyr Asp Gln Ala Lys Arg
        115                 120                 125

Val Pro Arg Trp Val Leu Glu His Ile Ser Lys Ser Lys Ile Met Gly
    130                 135                 140

Asp Ala Asp Arg Lys His Cys Lys Phe Lys Pro Asp Pro Asn Ile Pro
145                 150                 155                 160

Pro Thr Phe Ser Ala Phe Asn Glu Asp Tyr Val Gly Ser Gly Trp Ser
                165                 170                 175

Arg Gly His Met Ala Pro Ala Gly Asn Asn Lys Phe Ser Ser Lys Ala
            180                 185                 190

Met Ala Glu Thr Phe Tyr Leu Ser Asn Ile Val Pro Gln Asp Phe Asp
        195                 200                 205

Asn Asn Ser Gly Tyr Trp Asn Arg Ile Glu Met Tyr Cys Arg Glu Leu
    210                 215                 220

Thr Glu Arg Phe Glu Asp Val Trp Val Val Ser Gly Pro Leu Thr Leu
225                 230                 235                 240

Pro Gln Thr Arg Gly Asp Gly Lys Lys Ile Val Ser Tyr Gln Val Ile
                245                 250                 255

Gly Glu Asp Asn Val Ala Val Pro Ser His Leu Tyr Lys Val Ile Leu
            260                 265                 270

Ala Arg Arg Ser Ser Val Ser Thr Glu Pro Leu Ala Leu Gly Ala Phe
        275                 280                 285

Val Val Pro Asn Glu Ala Ile Gly Phe Gln Pro Gln Leu Thr Glu Phe
    290                 295                 300

Gln Val Ser Leu Gln Asp Leu Glu Lys Leu Ser Gly Leu Val Phe Phe
305                 310                 315                 320

Pro His Leu Asp Arg Thr Ser Asp Ile Arg Asn Ile Cys Ser Val Asp
                325                 330                 335
```

```
Thr Cys Lys Leu Leu Asp Phe Gln Glu Phe Thr Leu Tyr Leu Ser Thr
            340                 345                 350

Arg Lys Ile Glu Gly Ala Arg Ser Val Leu Arg Leu Glu Lys Ile Met
355                 360                 365

Glu Asn Leu Lys Asn Ala Glu Ile Glu Pro Asp Asp Tyr Phe Met Ser
        370                 375                 380

Arg Tyr Glu Lys Lys Leu Glu Glu Leu Lys Ala Lys Glu Gln Ser Gly
385                 390                 395                 400

Thr Gln Ile Arg Lys Pro Ser
            405

<210> SEQ ID NO 72
<211> LENGTH: 326
<212> TYPE: PRT
<213> ORGANISM: Aspergillus oryzae

<400> SEQUENCE: 72

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Pro Arg Leu Leu Pro Ile Ser Ala
        35                  40                  45

Ala Thr Leu Ala Leu Ala Gln Leu Thr Tyr Gly Trp Gly Asn Leu Gly
50                  55                  60

His Glu Thr Val Ala Tyr Ile Ala Gln Ser Phe Val Ala Ser Ser Thr
65                  70                  75                  80

Glu Ser Phe Cys Gln Asn Ile Leu Gly Asp Asp Ser Thr Ser Tyr Leu
                85                  90                  95

Ala Asn Val Ala Thr Trp Ala Asp Thr Tyr Lys Tyr Thr Asp Ala Gly
            100                 105                 110

Glu Phe Ser Lys Pro Tyr His Phe Ile Asp Ala Gln Asp Asn Pro Pro
        115                 120                 125

Gln Ser Cys Gly Val Asp Tyr Asp Arg Asp Cys Gly Ser Ala Gly Cys
130                 135                 140

Ser Ile Ser Ala Ile Gln Asn Tyr Thr Asn Ile Leu Leu Glu Ser Pro
145                 150                 155                 160

Asn Gly Ser Glu Ala Leu Asn Ala Leu Lys Phe Val His Ile Ile
                165                 170                 175

Gly Asp Ile His Gln Pro Leu His Asp Glu Asn Leu Glu Ala Gly Gly
            180                 185                 190

Asn Gly Ile Asp Val Thr Tyr Asp Gly Glu Thr Thr Asn Leu His His
        195                 200                 205

Ile Trp Asp Thr Asn Met Pro Glu Glu Ala Ala Gly Gly Tyr Ser Leu
210                 215                 220

Ser Val Ala Lys Thr Tyr Ala Asp Leu Leu Thr Glu Arg Ile Lys Thr
225                 230                 235                 240

Gly Thr Tyr Ser Ser Lys Lys Asp Ser Trp Thr Asp Gly Ile Asp Ile
                245                 250                 255

Lys Asp Pro Val Ser Thr Ser Met Ile Trp Ala Ala Asp Ala Asn Thr
            260                 265                 270

Tyr Val Cys Ser Thr Val Leu Asp Asp Gly Leu Ala Tyr Ile Asn Ser
        275                 280                 285

Thr Asp Leu Ser Gly Glu Tyr Tyr Asp Lys Ser Gln Pro Val Phe Glu
290                 295                 300
```

```
Glu Leu Ile Ala Lys Ala Gly Tyr Arg Leu Ala Ala Trp Leu Asp Leu
305                 310                 315                 320

Ile Ala Ser Gln Pro Ser
                325

<210> SEQ ID NO 73
<211> LENGTH: 303
<212> TYPE: PRT
<213> ORGANISM: Penicillium citrinum

<400> SEQUENCE: 73

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Gly Val Pro Ala Ala Trp Gly Ala Leu Gly His Ala Thr
            35                  40                  45

Val Ala Tyr Val Ala Gln His Tyr Val Ser Pro Glu Ala Ala Ser Trp
    50                  55                  60

Ala Gln Gly Ile Leu Gly Ser Ser Ser Ser Tyr Leu Ala Ser Ile
65              70                  75                  80

Ala Ser Trp Ala Asp Glu Tyr Arg Leu Thr Ser Ala Gly Lys Trp Ser
                85                  90                  95

Ala Ser Leu His Phe Ile Asp Ala Glu Asp Asn Pro Pro Thr Asn Cys
            100                 105                 110

Asn Val Asp Tyr Glu Arg Asp Cys Gly Ser Ser Gly Cys Ser Ile Ser
        115                 120                 125

Ala Ile Ala Asn Tyr Thr Gln Arg Val Ser Asp Ser Ser Leu Ser Ser
    130                 135                 140

Glu Asn His Ala Glu Ala Leu Arg Phe Leu Val His Phe Ile Gly Asp
145                 150                 155                 160

Met Thr Gln Pro Leu His Asp Glu Ala Tyr Ala Val Gly Gly Asn Lys
                165                 170                 175

Ile Asn Val Thr Phe Asp Gly Tyr His Asp Asn Leu His Ser Asp Trp
            180                 185                 190

Asp Thr Tyr Met Pro Gln Lys Leu Ile Gly Gly His Ala Leu Ser Asp
        195                 200                 205

Ala Glu Ser Trp Ala Lys Thr Leu Val Gln Asn Ile Glu Ser Gly Asn
    210                 215                 220

Tyr Thr Ala Gln Ala Ile Gly Trp Ile Lys Gly Asp Asn Ile Ser Glu
225                 230                 235                 240

Pro Ile Thr Thr Ala Thr Arg Trp Ala Ser Asp Ala Asn Ala Leu Val
                245                 250                 255

Cys Thr Val Val Met Pro His Gly Ala Ala Ala Leu Gln Thr Gly Asp
            260                 265                 270

Leu Tyr Pro Thr Tyr Tyr Asp Ser Val Ile Asp Thr Ile Glu Leu Gln
        275                 280                 285

Ile Ala Lys Gly Gly Tyr Arg Leu Ala Asn Trp Ile Asn Glu Ile
    290                 295                 300

<210> SEQ ID NO 74
<211> LENGTH: 398
<212> TYPE: PRT
<213> ORGANISM: Homo sapiens

<400> SEQUENCE: 74
```

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20              25              30

Gly Ile His Gly Val Pro Ala Ala Lys Met Lys Leu Phe Gln Thr Ile
            35              40              45

Cys Arg Gln Leu Arg Ser Ser Lys Phe Ser Val Glu Ser Ala Ala Leu
    50              55              60

Val Ala Phe Ser Thr Ser Ser Tyr Ser Cys Gly Arg Lys Lys Lys Val
65              70              75              80

Asn Pro Tyr Glu Glu Val Asp Gln Glu Lys Tyr Ser Asn Leu Val Gln
                85              90              95

Ser Val Leu Ser Ser Arg Gly Val Ala Gln Thr Pro Gly Ser Val Glu
            100             105             110

Glu Asp Ala Leu Leu Cys Gly Pro Val Ser Lys His Lys Leu Pro Asn
            115             120             125

Gln Gly Glu Asp Arg Arg Val Pro Gln Asn Trp Phe Pro Ile Phe Asn
            130             135             140

Pro Glu Arg Ser Asp Lys Pro Asn Ala Ser Asp Pro Ser Val Pro Leu
145             150             155             160

Lys Ile Pro Leu Gln Arg Asn Val Ile Pro Ser Val Thr Arg Val Leu
            165             170             175

Gln Gln Thr Met Thr Lys Gln Val Phe Leu Leu Glu Arg Trp Lys
            180             185             190

Gln Arg Met Ile Leu Glu Leu Gly Glu Asp Gly Phe Lys Glu Tyr Thr
    195             200             205

Ser Ser Phe His Val Cys Asp His Val Tyr Met Lys Asn Leu Ala Arg
    210             215             220

Asp Val Phe Leu Gln Gly Lys Arg Phe His Glu Ala Leu Glu Ser Ile
225             230             235             240

Leu Ser Pro Gln Glu Thr Leu Lys Glu Arg Asp Glu Asn Leu Leu Lys
            245             250             255

Ser Gly Tyr Ile Glu Ser Val Gln His Ile Leu Lys Asp Val Ser Gly
            260             265             270

Val Arg Ala Leu Glu Ser Ala Val Gln His Glu Thr Leu Asn Tyr Ile
    275             280             285

Gly Leu Leu Asp Cys Val Ala Glu Tyr Gln Gly Lys Leu Cys Val Ile
    290             295             300

Asp Trp Lys Thr Ser Glu Lys Pro Lys Pro Phe Ile Gln Ser Thr Phe
305             310             315             320

Asp Asn Pro Leu Gln Val Val Ala Tyr Met Gly Ala Met Asn His Asp
            325             330             335

Thr Asn Tyr Ser Phe Gln Val Gln Cys Gly Leu Ile Val Val Ala Tyr
            340             345             350

Lys Asp Gly Ser Pro Ala His Pro His Phe Met Asp Ala Glu Leu Cys
            355             360             365

Ser Gln Tyr Trp Thr Lys Trp Leu Leu Arg Leu Glu Glu Tyr Thr Glu
    370             375             380

Lys Lys Lys Asn Gln Asn Ile Gln Lys Pro Glu Tyr Ser Glu
385             390             395

<210> SEQ ID NO 75
<211> LENGTH: 617

-continued

```
<212> TYPE: PRT
<213> ORGANISM: Escherichia coli

<400> SEQUENCE: 75

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Val Lys Gln Gln Ile Gln Leu Arg
        35                  40                  45

Arg Arg Glu Val Asp Glu Thr Ala Asp Leu Pro Ala Glu Leu Pro Pro
    50                  55                  60

Leu Leu Arg Arg Leu Tyr Ala Ser Arg Gly Val Arg Ser Ala Gln Glu
65                  70                  75                  80

Leu Glu Arg Ser Val Lys Gly Met Leu Pro Trp Gln Gln Leu Ser Gly
                85                  90                  95

Val Glu Lys Ala Val Glu Ile Leu Tyr Asn Ala Phe Arg Glu Gly Thr
            100                 105                 110

Arg Ile Ile Val Val Gly Asp Phe Asp Ala Asp Gly Ala Thr Ser Thr
        115                 120                 125

Ala Leu Ser Val Leu Ala Met Arg Ser Leu Gly Cys Ser Asn Ile Asp
    130                 135                 140

Tyr Leu Val Pro Asn Arg Phe Glu Asp Gly Tyr Gly Leu Ser Pro Glu
145                 150                 155                 160

Val Val Asp Gln Ala His Ala Arg Gly Ala Gln Leu Ile Val Thr Val
                165                 170                 175

Asp Asn Gly Ile Ser Ser His Ala Gly Val Glu His Ala Arg Ser Leu
            180                 185                 190

Gly Ile Pro Val Ile Val Thr Asp His His Leu Pro Gly Asp Thr Leu
        195                 200                 205

Pro Ala Ala Glu Ala Ile Ile Asn Pro Asn Leu Arg Asp Cys Asn Phe
    210                 215                 220

Pro Ser Lys Ser Leu Ala Gly Val Gly Val Ala Phe Tyr Leu Met Leu
225                 230                 235                 240

Ala Leu Arg Thr Phe Leu Arg Asp Gln Gly Trp Phe Asp Glu Arg Asn
                245                 250                 255

Ile Ala Ile Pro Asn Leu Ala Glu Leu Leu Asp Leu Val Ala Leu Gly
            260                 265                 270

Thr Val Ala Asp Val Val Pro Leu Asp Ala Asn Asn Arg Ile Leu Thr
        275                 280                 285

Trp Gln Gly Met Ser Arg Ile Arg Ala Gly Lys Cys Arg Pro Gly Ile
    290                 295                 300

Lys Ala Leu Leu Glu Val Ala Asn Arg Asp Ala Gln Lys Leu Ala Ala
305                 310                 315                 320

Ser Asp Leu Gly Phe Ala Leu Gly Pro Arg Leu Asn Ala Ala Gly Arg
                325                 330                 335

Leu Asp Asp Met Ser Val Gly Val Ala Leu Leu Leu Cys Asp Asn Ile
            340                 345                 350

Gly Glu Ala Arg Val Leu Ala Asn Glu Leu Asp Ala Leu Asn Gln Thr
        355                 360                 365

Arg Lys Glu Ile Glu Gln Gly Met Gln Ile Glu Ala Leu Thr Leu Cys
    370                 375                 380

Glu Lys Leu Glu Arg Ser Arg Asp Thr Leu Pro Gly Gly Leu Ala Met
385                 390                 395                 400
```

```
Tyr His Pro Glu Trp His Gln Gly Val Val Gly Ile Leu Ala Ser Arg
                405                 410                 415

Ile Lys Glu Arg Phe His Arg Pro Val Ile Ala Phe Ala Pro Ala Gly
            420                 425                 430

Asp Gly Thr Leu Lys Gly Ser Gly Arg Ser Ile Gln Gly Leu His Met
        435                 440                 445

Arg Asp Ala Leu Glu Arg Leu Asp Thr Leu Tyr Pro Gly Met Met Leu
    450                 455                 460

Lys Phe Gly Gly His Ala Met Ala Ala Gly Leu Ser Leu Glu Glu Asp
465                 470                 475                 480

Lys Phe Lys Leu Phe Gln Gln Arg Phe Gly Glu Leu Val Thr Glu Trp
                485                 490                 495

Leu Asp Pro Ser Leu Leu Gln Gly Glu Val Val Ser Asp Gly Pro Leu
            500                 505                 510

Ser Pro Ala Glu Met Thr Met Glu Val Ala Gln Leu Leu Arg Asp Ala
        515                 520                 525

Gly Pro Trp Gly Gln Met Phe Pro Glu Pro Leu Phe Asp Gly His Phe
    530                 535                 540

Arg Leu Leu Gln Gln Arg Leu Val Gly Glu Arg His Leu Lys Val Met
545                 550                 555                 560

Val Glu Pro Val Gly Gly Gly Pro Leu Leu Asp Gly Ile Ala Phe Asn
                565                 570                 575

Val Asp Thr Ala Leu Trp Pro Asp Asn Gly Val Arg Glu Val Gln Leu
            580                 585                 590

Ala Tyr Lys Leu Asp Ile Asn Glu Phe Arg Gly Asn Arg Ser Leu Gln
        595                 600                 605

Ile Ile Ile Asp Asn Ile Trp Pro Ile
    610                 615

<210> SEQ ID NO 76
<211> LENGTH: 937
<212> TYPE: PRT
<213> ORGANISM: Bacteriophage T4

<400> SEQUENCE: 76

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
                20                  25                  30

Gly Ile His Gly Val Pro Ala Ala Lys Glu Phe Tyr Ile Ser Ile Glu
            35                  40                  45

Thr Val Gly Asn Asn Ile Val Glu Arg Tyr Ile Asp Glu Asn Gly Lys
        50                  55                  60

Glu Arg Thr Arg Glu Val Glu Tyr Leu Pro Thr Met Phe Arg His Cys
65                  70                  75                  80

Lys Glu Glu Ser Lys Tyr Lys Asp Ile Tyr Gly Lys Asn Cys Ala Pro
                85                  90                  95

Gln Lys Phe Pro Ser Met Lys Asp Ala Arg Asp Trp Met Lys Arg Met
            100                 105                 110

Glu Asp Ile Gly Leu Glu Ala Leu Gly Met Asn Asp Phe Lys Leu Ala
        115                 120                 125

Tyr Ile Ser Asp Thr Tyr Gly Ser Glu Ile Val Tyr Asp Arg Lys Phe
    130                 135                 140

Val Arg Val Ala Asn Cys Asp Ile Glu Val Thr Gly Asp Lys Phe Pro
```

```
            145                 150                 155                 160
Asp Pro Met Lys Ala Glu Tyr Glu Ile Asp Ala Ile Thr His Tyr Asp
                165                 170                 175

Ser Ile Asp Asp Arg Phe Tyr Val Phe Asp Leu Leu Asn Ser Met Tyr
            180                 185                 190

Gly Ser Val Ser Lys Trp Asp Ala Lys Leu Ala Ala Lys Leu Asp Cys
            195                 200                 205

Glu Gly Gly Asp Glu Val Pro Gln Ile Leu Asp Arg Val Ile Tyr
        210                 215                 220

Met Pro Phe Asp Asn Glu Arg Asp Met Leu Met Glu Tyr Ile Asn Leu
225                 230                 235                 240

Trp Glu Gln Lys Arg Pro Ala Ile Phe Thr Gly Trp Asn Ile Glu Gly
                245                 250                 255

Phe Asp Val Pro Tyr Ile Met Asn Arg Val Lys Met Ile Leu Gly Glu
                260                 265                 270

Arg Ser Met Lys Arg Phe Ser Pro Ile Gly Arg Val Lys Ser Lys Leu
            275                 280                 285

Ile Gln Asn Met Tyr Gly Ser Lys Glu Ile Tyr Ser Ile Asp Gly Val
        290                 295                 300

Ser Ile Leu Asp Tyr Leu Asp Leu Tyr Lys Lys Phe Ala Phe Thr Asn
305                 310                 315                 320

Leu Pro Ser Phe Ser Leu Glu Ser Val Ala Gln His Glu Thr Lys Lys
                325                 330                 335

Gly Lys Leu Pro Tyr Asp Gly Pro Ile Asn Lys Leu Arg Glu Thr Asn
            340                 345                 350

His Gln Arg Tyr Ile Ser Tyr Asn Ile Ile Asp Val Glu Ser Val Gln
        355                 360                 365

Ala Ile Asp Lys Ile Arg Gly Phe Ile Asp Leu Val Leu Ser Met Ser
        370                 375                 380

Tyr Tyr Ala Lys Met Pro Phe Ser Gly Val Met Ser Pro Ile Lys Thr
385                 390                 395                 400

Trp Asp Ala Ile Ile Phe Asn Ser Leu Lys Gly Glu His Lys Val Ile
                405                 410                 415

Pro Gln Gln Gly Ser His Val Lys Gln Ser Phe Pro Gly Ala Phe Val
            420                 425                 430

Phe Glu Pro Lys Pro Ile Ala Arg Arg Tyr Ile Met Ser Phe Asp Leu
        435                 440                 445

Thr Ser Leu Tyr Pro Ser Ile Ile Arg Gln Val Asn Ile Ser Pro Glu
450                 455                 460

Thr Ile Arg Gly Gln Phe Lys Val His Pro Ile His Glu Tyr Ile Ala
465                 470                 475                 480

Gly Thr Ala Pro Lys Pro Ser Asp Glu Tyr Ser Cys Ser Pro Asn Gly
                485                 490                 495

Trp Met Tyr Asp Lys His Gln Glu Gly Ile Ile Pro Lys Glu Ile Ala
            500                 505                 510

Lys Val Phe Phe Gln Arg Lys Asp Trp Lys Lys Met Phe Ala Glu
        515                 520                 525

Glu Met Asn Ala Glu Ala Ile Lys Lys Ile Ile Met Lys Gly Ala Gly
        530                 535                 540

Ser Cys Ser Thr Lys Pro Glu Val Glu Arg Tyr Val Lys Phe Ser Asp
545                 550                 555                 560

Asp Phe Leu Asn Glu Leu Ser Asn Tyr Thr Glu Ser Val Leu Asn Ser
                565                 570                 575
```

Leu Ile Glu Glu Cys Glu Lys Ala Ala Thr Leu Ala Asn Thr Asn Gln
        580                 585                 590

Leu Asn Arg Lys Ile Leu Ile Asn Ser Leu Tyr Gly Ala Leu Gly Asn
            595                 600                 605

Ile His Phe Arg Tyr Tyr Asp Leu Arg Asn Ala Thr Ala Ile Thr Ile
        610                 615                 620

Phe Gly Gln Val Gly Ile Gln Trp Ile Ala Arg Lys Ile Asn Glu Tyr
625                 630                 635                 640

Leu Asn Lys Val Cys Gly Thr Asn Asp Glu Asp Phe Ile Ala Ala Gly
            645                 650                 655

Asp Thr Asp Ser Val Tyr Val Cys Val Asp Lys Val Ile Glu Lys Val
            660                 665                 670

Gly Leu Asp Arg Phe Lys Glu Gln Asn Asp Leu Val Glu Phe Met Asn
            675                 680                 685

Gln Phe Gly Lys Lys Lys Met Glu Pro Met Ile Asp Val Ala Tyr Arg
        690                 695                 700

Glu Leu Cys Asp Tyr Met Asn Asn Arg Glu His Leu Met His Met Asp
705                 710                 715                 720

Arg Glu Ala Ile Ser Cys Pro Pro Leu Gly Ser Lys Gly Val Gly Gly
            725                 730                 735

Phe Trp Lys Ala Lys Lys Arg Tyr Ala Leu Asn Val Tyr Asp Met Glu
            740                 745                 750

Asp Lys Arg Phe Ala Glu Pro His Leu Lys Ile Met Gly Met Glu Thr
            755                 760                 765

Gln Gln Ser Ser Thr Pro Lys Ala Val Gln Glu Ala Leu Glu Glu Ser
        770                 775                 780

Ile Arg Arg Ile Leu Gln Glu Gly Glu Glu Ser Val Gln Glu Tyr Tyr
785                 790                 795                 800

Lys Asn Phe Glu Lys Glu Tyr Arg Gln Leu Asp Tyr Lys Val Ile Ala
            805                 810                 815

Glu Val Lys Thr Ala Asn Asp Ile Ala Lys Tyr Asp Asp Lys Gly Trp
            820                 825                 830

Pro Gly Phe Lys Cys Pro Phe His Ile Arg Gly Val Leu Thr Tyr Arg
        835                 840                 845

Arg Ala Val Ser Gly Leu Gly Val Ala Pro Ile Leu Asp Gly Asn Lys
850                 855                 860

Val Met Val Leu Pro Leu Arg Glu Gly Asn Pro Phe Gly Asp Lys Cys
865                 870                 875                 880

Ile Ala Trp Pro Ser Gly Thr Glu Leu Pro Lys Glu Ile Arg Ser Asp
            885                 890                 895

Val Leu Ser Trp Ile Asp His Ser Thr Leu Phe Gln Lys Ser Phe Val
            900                 905                 910

Lys Pro Leu Ala Gly Met Cys Glu Ser Ala Gly Met Asp Tyr Glu Glu
        915                 920                 925

Lys Ala Ser Leu Asp Phe Leu Phe Gly
        930                 935

<210> SEQ ID NO 77
<211> LENGTH: 937
<212> TYPE: PRT
<213> ORGANISM: Bacteriophage T4

<400> SEQUENCE: 77

Met Asp Tyr Lys Asp His Asp Gly Asp Tyr Lys Asp His Asp Ile Asp

```
                1               5                  10                 15
            Tyr Lys Asp Asp Asp Lys Met Ala Pro Lys Lys Arg Lys Val
                         20                  25                  30
            Gly Ile His Gly Val Pro Ala Ala Lys Glu Phe Tyr Ile Ser Ile Glu
                         35                  40                  45
            Thr Val Gly Asn Asn Ile Val Glu Arg Tyr Ile Asp Glu Asn Gly Lys
            50                       55                  60
            Glu Arg Thr Arg Glu Val Glu Tyr Leu Pro Thr Met Phe Arg His Cys
            65                  70                  75                  80
            Lys Glu Glu Ser Lys Tyr Lys Asp Ile Tyr Gly Lys Asn Cys Ala Pro
                              85                  90                  95
            Gln Lys Phe Pro Ser Met Lys Asp Ala Arg Asp Trp Met Lys Arg Met
                             100                 105                 110
            Glu Asp Ile Gly Leu Glu Ala Leu Gly Met Asn Asp Phe Lys Leu Ala
                             115                 120                 125
            Tyr Ile Ser Asp Thr Tyr Gly Ser Glu Ile Val Tyr Asp Arg Lys Phe
                        130                 135                 140
            Val Arg Val Ala Asn Cys Asp Ile Glu Val Thr Gly Asp Lys Phe Pro
            145                 150                 155                 160
            Asp Pro Met Lys Ala Glu Tyr Glu Ile Asp Ala Ile Thr His Tyr Asp
                             165                 170                 175
            Ser Ile Asp Asp Arg Phe Tyr Val Phe Asp Leu Leu Asn Ser Met Tyr
                        180                 185                 190
            Gly Ser Val Ser Lys Trp Asp Ala Lys Leu Ala Ala Lys Leu Asp Cys
                        195                 200                 205
            Glu Gly Gly Asp Glu Val Pro Gln Glu Ile Leu Asp Arg Val Ile Tyr
            210                 215                 220
            Met Pro Phe Asp Asn Glu Arg Asp Met Leu Met Glu Tyr Ile Asn Leu
            225                 230                 235                 240
            Trp Glu Gln Lys Arg Pro Ala Ile Phe Thr Gly Trp Asn Ile Glu Gly
                             245                 250                 255
            Phe Asp Val Pro Tyr Ile Met Asn Arg Val Lys Met Ile Leu Gly Glu
                             260                 265                 270
            Arg Ser Met Lys Arg Phe Ser Pro Ile Gly Arg Val Lys Ser Lys Leu
                        275                 280                 285
            Ile Gln Asn Met Tyr Gly Ser Lys Glu Ile Tyr Ser Ile Asp Gly Val
                        290                 295                 300
            Ser Ile Leu Asp Tyr Leu Asp Leu Tyr Lys Lys Phe Ala Phe Thr Asn
            305                 310                 315                 320
            Leu Pro Ser Phe Ser Leu Glu Ser Val Ala Gln His Glu Thr Lys Lys
                             325                 330                 335
            Gly Lys Leu Pro Tyr Asp Gly Pro Ile Asn Lys Leu Arg Glu Thr Asn
                        340                 345                 350
            His Gln Arg Tyr Ile Ser Ala Asn Ile Asp Val Glu Ser Val Gln
                        355                 360                 365
            Ala Ile Asp Lys Ile Arg Gly Phe Ile Asp Leu Val Leu Ser Met Ser
                        370                 375                 380
            Tyr Tyr Ala Lys Met Pro Phe Ser Gly Val Met Ser Pro Ile Lys Thr
            385                 390                 395                 400
            Trp Asp Ala Ile Ile Phe Asn Ser Leu Lys Gly Glu His Lys Val Ile
                             405                 410                 415
            Pro Gln Gln Gly Ser His Val Lys Gln Ser Phe Pro Gly Ala Phe Val
                        420                 425                 430
```

```
Phe Glu Pro Lys Pro Ile Ala Arg Arg Tyr Ile Met Ser Phe Asp Leu
            435                 440                 445

Thr Ser Leu Tyr Pro Ser Ile Ile Arg Gln Val Asn Ile Ser Pro Glu
        450                 455                 460

Thr Ile Arg Gly Gln Phe Lys Val His Pro Ile His Glu Tyr Ile Ala
465                 470                 475                 480

Gly Thr Ala Pro Lys Pro Ser Asp Glu Tyr Ser Cys Ser Pro Asn Gly
                485                 490                 495

Trp Met Tyr Asp Lys His Gln Glu Gly Ile Ile Pro Lys Glu Ile Ala
                500                 505                 510

Lys Val Phe Phe Gln Arg Lys Asp Trp Lys Lys Met Phe Ala Glu
            515                 520                 525

Glu Met Asn Ala Glu Ala Ile Lys Lys Ile Ile Met Lys Gly Ala Gly
            530                 535                 540

Ser Cys Ser Thr Lys Pro Glu Val Glu Arg Tyr Val Lys Phe Ser Asp
545                 550                 555                 560

Asp Phe Leu Asn Glu Leu Ser Asn Tyr Thr Glu Ser Val Leu Asn Ser
                565                 570                 575

Leu Ile Glu Glu Cys Glu Lys Ala Ala Thr Leu Ala Asn Thr Asn Gln
            580                 585                 590

Leu Asn Arg Lys Ile Leu Ile Asn Ser Leu Tyr Gly Ala Leu Gly Asn
            595                 600                 605

Ile His Phe Arg Tyr Tyr Asp Leu Arg Asn Ala Thr Ala Ile Thr Ile
            610                 615                 620

Phe Gly Gln Val Gly Ile Gln Trp Ile Ala Arg Lys Ile Asn Glu Tyr
625                 630                 635                 640

Leu Asn Lys Val Cys Gly Thr Asn Asp Glu Asp Phe Ile Ala Ala Gly
                645                 650                 655

Asp Thr Asp Ser Val Tyr Val Cys Val Asp Lys Val Ile Glu Lys Val
                660                 665                 670

Gly Leu Asp Arg Phe Lys Glu Gln Asn Asp Leu Val Glu Phe Met Asn
            675                 680                 685

Gln Phe Gly Lys Lys Met Glu Pro Met Ile Asp Val Ala Tyr Arg
            690                 695                 700

Glu Leu Cys Asp Tyr Met Asn Asn Arg Glu His Leu Met His Met Asp
705                 710                 715                 720

Arg Glu Ala Ile Ser Cys Pro Pro Leu Gly Ser Lys Gly Val Gly Gly
                725                 730                 735

Phe Trp Lys Ala Lys Lys Arg Tyr Ala Leu Asn Val Tyr Asp Met Glu
            740                 745                 750

Asp Lys Arg Phe Ala Glu Pro His Leu Lys Ile Met Gly Met Glu Thr
            755                 760                 765

Gln Gln Ser Ser Thr Pro Lys Ala Val Gln Glu Ala Leu Glu Glu Ser
        770                 775                 780

Ile Arg Arg Ile Leu Gln Glu Gly Glu Glu Ser Val Gln Glu Tyr Tyr
785                 790                 795                 800

Lys Asn Phe Glu Lys Glu Tyr Arg Gln Leu Asp Tyr Lys Val Ile Ala
                805                 810                 815

Glu Val Lys Thr Ala Asn Asp Ile Ala Lys Tyr Asp Asp Lys Gly Trp
            820                 825                 830

Pro Gly Phe Lys Cys Pro Phe His Ile Arg Gly Val Leu Thr Tyr Arg
            835                 840                 845
```

```
Arg Ala Val Ser Gly Leu Gly Val Ala Pro Ile Leu Asp Gly Asn Lys
    850                 855                 860

Val Met Val Leu Pro Leu Arg Glu Gly Asn Pro Phe Gly Asp Lys Cys
865                 870                 875                 880

Ile Ala Trp Pro Ser Gly Thr Glu Leu Pro Lys Glu Ile Arg Ser Asp
                885                 890                 895

Val Leu Ser Trp Ile Asp His Ser Thr Leu Phe Gln Lys Ser Phe Val
            900                 905                 910

Lys Pro Leu Ala Gly Met Cys Glu Ser Ala Gly Met Asp Tyr Glu Glu
        915                 920                 925

Lys Ala Ser Leu Asp Phe Leu Phe Gly
    930                 935

<210> SEQ ID NO 78
<211> LENGTH: 937
<212> TYPE: PRT
<213> ORGANISM: Bacteriophage T4

<400> SEQUENCE: 78

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Lys Glu Phe Tyr Ile Ser Ile Glu
        35                  40                  45

Thr Val Gly Asn Asn Ile Val Glu Arg Tyr Ile Asp Glu Asn Gly Lys
    50                  55                  60

Glu Arg Thr Arg Glu Val Glu Tyr Leu Pro Thr Met Phe Arg His Cys
65                  70                  75                  80

Lys Glu Glu Ser Lys Tyr Lys Asp Ile Tyr Gly Lys Asn Cys Ala Pro
                85                  90                  95

Gln Lys Phe Pro Ser Met Lys Asp Ala Arg Asp Trp Met Lys Arg Met
            100                 105                 110

Glu Asp Ile Gly Leu Glu Ala Leu Gly Met Asn Asp Phe Lys Leu Ala
        115                 120                 125

Tyr Ile Ser Asp Thr Tyr Gly Ser Glu Ile Val Tyr Asp Arg Lys Phe
    130                 135                 140

Val Arg Val Ala Asn Cys Asp Ile Glu Val Thr Gly Asp Lys Phe Pro
145                 150                 155                 160

Asp Pro Met Lys Ala Glu Tyr Glu Ile Asp Ala Ile Thr His Tyr Asp
                165                 170                 175

Ser Ile Asp Asp Arg Phe Tyr Val Phe Asp Leu Leu Asn Ser Met Tyr
            180                 185                 190

Gly Ser Val Ser Lys Trp Asp Ala Lys Leu Ala Ala Lys Leu Asp Cys
        195                 200                 205

Glu Gly Gly Asp Glu Val Pro Gln Glu Ile Leu Asp Arg Val Ile Tyr
    210                 215                 220

Met Pro Phe Asp Asn Glu Arg Asp Met Leu Met Glu Tyr Ile Asn Leu
225                 230                 235                 240

Trp Glu Gln Lys Arg Pro Ala Ile Phe Thr Gly Trp Asn Ile Glu Gly
                245                 250                 255

Phe Asp Val Pro Tyr Ile Met Asn Arg Val Lys Met Ile Leu Gly Glu
            260                 265                 270

Arg Ser Met Lys Arg Phe Ser Pro Ile Gly Arg Val Lys Ser Lys Leu
        275                 280                 285
```

```
Ile Gln Asn Met Tyr Gly Ser Lys Glu Ile Tyr Ser Ile Asp Gly Val
    290                 295                 300

Ser Ile Leu Asp Tyr Leu Asp Leu Tyr Lys Lys Phe Ala Phe Thr Asn
305                 310                 315                 320

Leu Pro Ser Phe Ser Leu Glu Ser Val Ala Gln His Glu Thr Lys Lys
                    325                 330                 335

Gly Lys Leu Pro Tyr Asp Gly Pro Ile Asn Lys Leu Arg Glu Thr Asn
                340                 345                 350

His Gln Arg Tyr Ile Ser Tyr Asn Ile Ile Asp Val Glu Ser Val Gln
            355                 360                 365

Ala Ile Asp Lys Ile Arg Gly Phe Ile Asp Leu Val Leu Ser Met Ser
370                 375                 380

Tyr Tyr Ala Lys Met Pro Phe Ser Gly Val Met Ser Pro Ile Lys Thr
385                 390                 395                 400

Trp Asp Ala Ile Ile Phe Asn Ser Leu Lys Gly Glu His Lys Val Ile
                405                 410                 415

Pro Gln Gln Gly Ser His Val Lys Gln Ser Phe Pro Gly Ala Phe Val
                420                 425                 430

Phe Glu Pro Lys Pro Ile Ala Arg Arg Tyr Ile Met Ser Phe Asp Leu
            435                 440                 445

Thr Ser Leu Tyr Pro Ser Ile Ile Arg Gln Val Asn Ile Ser Pro Glu
450                 455                 460

Thr Ile Arg Gly Gln Phe Lys Val His Pro Ile His Glu Tyr Ile Ala
465                 470                 475                 480

Gly Thr Ala Pro Lys Pro Ser Asp Glu Tyr Ser Cys Ser Pro Asn Gly
                485                 490                 495

Trp Met Tyr Asp Lys His Gln Glu Gly Ile Ile Pro Lys Glu Ile Ala
                500                 505                 510

Lys Val Phe Phe Gln Arg Lys Asp Trp Lys Lys Met Phe Ala Glu
            515                 520                 525

Glu Met Asn Ala Glu Ala Ile Lys Lys Ile Ile Met Lys Gly Ala Gly
530                 535                 540

Ser Cys Ser Thr Lys Pro Glu Val Glu Arg Tyr Val Lys Phe Ser Asp
545                 550                 555                 560

Asp Phe Leu Asn Glu Leu Ser Asn Tyr Thr Glu Ser Val Leu Asn Ser
                565                 570                 575

Leu Ile Glu Glu Cys Glu Lys Ala Ala Thr Leu Ala Asn Thr Asn Gln
                580                 585                 590

Leu Asn Arg Lys Ile Leu Ile Asn Ser Leu Tyr Gly Ala Leu Gly Asn
            595                 600                 605

Ile His Phe Arg Tyr Tyr Asp Leu Arg Asn Ala Thr Ala Ile Thr Ile
610                 615                 620

Phe Gly Gln Val Gly Ile Gln Trp Ile Ala Arg Lys Ile Asn Glu Tyr
625                 630                 635                 640

Leu Asn Lys Val Cys Gly Thr Asn Asp Glu Asp Phe Ile Ala Ala Gly
                645                 650                 655

Asp Thr Asp Ser Val Tyr Val Cys Val Asp Lys Val Ile Glu Lys Val
                660                 665                 670

Gly Leu Asp Arg Phe Lys Glu Gln Asn Asp Leu Val Glu Phe Met Asn
            675                 680                 685

Gln Phe Gly Lys Lys Met Glu Pro Met Ile Asp Val Ala Tyr Arg
690                 695                 700
```

```
Glu Leu Cys Asp Tyr Met Asn Asn Arg Glu His Leu Met His Met Asp
705                 710                 715                 720

Arg Glu Ala Ile Ser Cys Pro Pro Leu Gly Ser Lys Gly Val Gly Gly
            725                 730                 735

Phe Trp Lys Ala Lys Lys Arg Tyr Ala Leu Asn Val Tyr Asp Met Glu
        740                 745                 750

Asp Lys Arg Phe Ala Glu Pro His Leu Lys Ile Met Gly Met Glu Thr
    755                 760                 765

Gln Gln Ser Ser Thr Pro Lys Val Val Gln Ala Leu Glu Glu Ser
770                 775                 780

Ile Arg Arg Ile Leu Gln Glu Gly Glu Ser Val Gln Glu Tyr Tyr
785                 790                 795                 800

Lys Asn Phe Glu Lys Glu Tyr Arg Gln Leu Asp Tyr Lys Val Ile Ala
            805                 810                 815

Glu Val Lys Thr Ala Asn Asp Ile Ala Lys Tyr Asp Asp Lys Gly Trp
            820                 825                 830

Pro Gly Phe Lys Cys Pro Phe His Ile Arg Gly Val Leu Thr Tyr Arg
            835                 840                 845

Arg Ala Val Ser Gly Leu Gly Val Ala Pro Ile Leu Asp Gly Asn Lys
850                 855                 860

Val Met Val Leu Pro Leu Arg Glu Gly Asn Pro Phe Gly Asp Lys Cys
865                 870                 875                 880

Ile Ala Trp Pro Ser Gly Thr Glu Leu Pro Lys Glu Ile Arg Ser Asp
                885                 890                 895

Val Leu Ser Trp Ile Asp His Ser Thr Leu Phe Gln Lys Ser Phe Val
                900                 905                 910

Lys Pro Leu Ala Gly Met Cys Glu Ser Ala Gly Met Asp Tyr Glu Glu
            915                 920                 925

Lys Ala Ser Leu Asp Phe Leu Phe Gly
            930                 935

<210> SEQ ID NO 79
<211> LENGTH: 319
<212> TYPE: PRT
<213> ORGANISM: Homo sapiens

<400> SEQUENCE: 79

Met Ala Pro Lys Arg Gly Lys Lys Gly Ala Val Ala Glu Asp Gly Asp
1               5                   10                  15

Glu Leu Arg Thr Glu Pro Glu Ala Lys Lys Ser Lys Thr Ala Ala Lys
            20                  25                  30

Lys Asn Asp Lys Glu Ala Ala Gly Glu Gly Pro Ala Leu Tyr Glu Asp
        35                  40                  45

Pro Pro Asp Gln Lys Thr Ser Pro Ser Gly Lys Pro Ala Thr Leu Lys
    50                  55                  60

Ile Cys Ser Trp Asn Val Asp Gly Leu Arg Ala Trp Ile Lys Lys Lys
65                  70                  75                  80

Gly Leu Asp Trp Val Lys Glu Glu Ala Pro Asp Ile Leu Cys Leu Gln
            85                  90                  95

Glu Thr Lys Cys Ser Glu Asn Lys Leu Pro Ala Glu Leu Gln Glu Leu
            100                 105                 110

Pro Gly Leu Ser His Gln Tyr Trp Ser Ala Pro Ser Asp Lys Glu Gly
        115                 120                 125

Tyr Ser Gly Val Gly Leu Leu Ser Arg Gln Cys Pro Leu Lys Val Ser
    130                 135                 140
```

```
Tyr Gly Ile Gly Asp Glu Glu His Asp Gln Glu Gly Arg Val Ile Val
145                 150                 155                 160

Ala Glu Phe Asp Ser Phe Val Leu Val Thr Ala Tyr Val Pro Asn Ala
                165                 170                 175

Gly Arg Gly Leu Val Arg Leu Glu Tyr Arg Gln Arg Trp Asp Glu Ala
            180                 185                 190

Phe Arg Lys Phe Leu Lys Gly Leu Ala Ser Arg Lys Pro Leu Val Leu
        195                 200                 205

Cys Gly Asp Leu Asn Val Ala His Glu Glu Ile Asp Leu Arg Asn Pro
    210                 215                 220

Lys Gly Asn Lys Lys Asn Ala Gly Phe Thr Pro Gln Glu Arg Gln Gly
225                 230                 235                 240

Phe Gly Glu Leu Leu Gln Ala Val Pro Leu Ala Asp Ser Phe Arg His
                245                 250                 255

Leu Tyr Pro Asn Thr Pro Tyr Ala Tyr Thr Phe Trp Thr Tyr Met Met
            260                 265                 270

Asn Ala Arg Ser Lys Asn Val Gly Trp Arg Leu Asp Tyr Phe Leu Leu
        275                 280                 285

Ser His Ser Leu Leu Pro Ala Leu Cys Asp Ser Lys Ile Arg Ser Lys
    290                 295                 300

Ala Leu Gly Ser Asp His Cys Pro Ile Thr Leu Tyr Leu Ala Leu
305                 310                 315

<210> SEQ ID NO 80
<211> LENGTH: 297
<212> TYPE: PRT
<213> ORGANISM: Artificial Sequence
<220> FEATURE:
<223> OTHER INFORMATION: Fusion protein

<400> SEQUENCE: 80

Met Val Arg Gly Ser Gly Lys Pro Ile Pro Asn Pro Leu Leu Gly Leu
1               5                   10                  15

Asp Ser Thr Gly Lys Ser Tyr Pro Thr Val Ser Ala Asp Tyr Gln Asp
                20                  25                  30

Ala Val Glu Lys Ala Lys Lys Lys Leu Arg Gly Phe Ile Ala Glu Lys
            35                  40                  45

Arg Cys Ala Pro Leu Met Leu Arg Leu Ala Phe His Ser Ala Gly Thr
        50                  55                  60

Phe Asp Lys Gly Thr Lys Thr Gly Gly Pro Phe Gly Thr Ile Lys His
65                  70                  75                  80

Pro Ala Glu Leu Ala His Ser Ala Asn Asn Gly Leu Asp Ile Ala Val
                85                  90                  95

Arg Leu Leu Glu Pro Leu Lys Ala Glu Phe Pro Ile Leu Ser Tyr Ala
            100                 105                 110

Asp Phe Tyr Gln Leu Ala Gly Val Val Ala Val Glu Val Thr Gly Gly
        115                 120                 125

Pro Lys Val Pro Phe His Pro Gly Arg Glu Asp Lys Pro Glu Pro Pro
    130                 135                 140

Pro Glu Gly Arg Leu Pro Asp Pro Thr Lys Gly Ser Asp His Leu Arg
145                 150                 155                 160

Asp Val Phe Gly Lys Ala Met Gly Leu Thr Asp Gln Asp Ile Val Ala
                165                 170                 175

Leu Ser Gly Gly His Thr Ile Gly Ala Ala His Lys Glu Arg Ser Gly
            180                 185                 190
```

```
Phe Glu Gly Pro Trp Thr Ser Asn Pro Leu Ile Phe Asp Asn Ser Tyr
            195                 200                 205

Phe Thr Glu Leu Leu Ser Gly Glu Lys Glu Gly Leu Leu Gln Leu Pro
    210                 215                 220

Ser Asp Lys Ala Leu Leu Ser Asp Pro Val Phe Arg Pro Leu Val Asp
225                 230                 235                 240

Lys Tyr Ala Ala Asp Glu Asp Ala Phe Phe Ala Asp Tyr Ala Glu Ala
                245                 250                 255

His Gln Lys Leu Ser Glu Leu Gly Phe Ala Asp Ala Glu Phe Ser Arg
            260                 265                 270

Ala Asp Pro Lys Lys Arg Lys Val Asp Pro Lys Lys Lys Arg Lys
                275                 280                 285

Val Asp Pro Lys Lys Lys Arg Lys Val
    290                 295

<210> SEQ ID NO 81
<211> LENGTH: 334
<212> TYPE: PRT
<213> ORGANISM: Homo sapiens

<400> SEQUENCE: 81

Met Glu Arg Lys Ile Ser Arg Ile His Leu Val Ser Glu Pro Ser Ile
1               5                   10                  15

Thr His Phe Leu Gln Val Ser Trp Glu Lys Thr Leu Glu Ser Gly Phe
            20                  25                  30

Val Ile Thr Leu Thr Asp Gly His Ser Ala Trp Thr Gly Thr Val Ser
        35                  40                  45

Glu Ser Glu Ile Ser Gln Glu Ala Asp Asp Met Ala Met Glu Lys Gly
    50                  55                  60

Lys Tyr Val Gly Glu Leu Arg Lys Ala Leu Leu Ser Gly Ala Gly Pro
65                  70                  75                  80

Ala Asp Val Tyr Thr Phe Asn Phe Ser Lys Glu Ser Cys Tyr Phe Phe
                85                  90                  95

Phe Glu Lys Asn Leu Lys Asp Val Ser Phe Arg Leu Gly Ser Phe Asn
            100                 105                 110

Leu Glu Lys Val Glu Asn Pro Ala Glu Val Ile Arg Glu Leu Ile Cys
        115                 120                 125

Tyr Cys Leu Asp Thr Ile Ala Glu Asn Gln Ala Lys Asn Glu His Leu
    130                 135                 140

Gln Lys Glu Asn Glu Arg Leu Leu Arg Asp Trp Asn Asp Val Gln Gly
145                 150                 155                 160

Arg Phe Glu Lys Cys Val Ser Ala Lys Glu Ala Leu Glu Thr Asp Leu
                165                 170                 175

Tyr Lys Arg Phe Ile Leu Val Leu Asn Glu Lys Lys Thr Lys Ile Arg
            180                 185                 190

Ser Leu His Asn Lys Leu Leu Asn Ala Ala Gln Glu Arg Glu Lys Asp
        195                 200                 205

Ile Lys Gln Glu Gly Glu Thr Ala Ile Cys Ser Glu Met Thr Ala Asp
    210                 215                 220

Arg Asp Pro Val Tyr Asp Glu Ser Thr Asp Glu Ser Glu Asn Gln
225                 230                 235                 240

Thr Asp Leu Ser Gly Leu Ala Ser Ala Ala Val Ser Lys Asp Asp Ser
                245                 250                 255

Ile Ile Ser Ser Leu Asp Val Thr Asp Ile Ala Pro Ser Arg Lys Arg
```

```
                260                 265                 270
Arg Gln Arg Met Gln Arg Asn Leu Gly Thr Glu Pro Lys Met Ala Pro
            275                 280                 285

Gln Glu Asn Gln Leu Gln Glu Lys Glu Lys Pro Asp Ser Ser Leu Pro
        290                 295                 300

Glu Thr Ser Lys Lys Glu His Ile Ser Ala Glu Asn Met Ser Leu Glu
305                 310                 315                 320

Thr Leu Arg Asn Ser Ser Pro Glu Asp Leu Phe Asp Glu Ile
                325                 330

<210> SEQ ID NO 82
<211> LENGTH: 1762
<212> TYPE: PRT
<213> ORGANISM: Artificial Sequence
<220> FEATURE:
<223> OTHER INFORMATION: Fusion protein

<400> SEQUENCE: 82

Met Asp Ala Gln Thr Arg Arg Arg Glu Arg Ala Glu Lys Gln Ala
1               5                   10                  15

Gln Trp Lys Ala Ala Asn Gly Gly Ser Pro Pro His Met Ala Tyr Pro
            20                  25                  30

Tyr Asp Val Pro Asp Tyr Ala Pro Pro Ser Arg Ala Gln Ala Ser Asn
        35                  40                  45

Ser Ala Val Asp Gly Thr Ala Gly Met Gly Val Pro Lys Phe Tyr Arg
    50                  55                  60

Trp Ile Ser Glu Arg Tyr Pro Cys Leu Ser Glu Val Val Lys Glu His
65                  70                  75                  80

Gln Ile Pro Glu Phe Asp Asn Leu Tyr Leu Asp Met Asn Gly Ile Ile
                85                  90                  95

His Gln Cys Ser His Pro Asn Asp Asp Asp Val His Phe Arg Ile Ser
            100                 105                 110

Asp Asp Lys Ile Phe Thr Asp Ile Phe His Tyr Leu Glu Val Leu Phe
        115                 120                 125

Arg Ile Ile Lys Pro Arg Lys Val Phe Phe Met Ala Val Asp Gly Val
    130                 135                 140

Ala Pro Arg Ala Lys Met Asn Gln Gln Arg Gly Arg Arg Phe Arg Ser
145                 150                 155                 160

Ala Lys Glu Ala Glu Asp Lys Ile Lys Lys Ala Ile Glu Lys Gly Glu
                165                 170                 175

Thr Leu Pro Thr Glu Ala Arg Phe Asp Ser Asn Cys Ile Thr Pro Gly
            180                 185                 190

Thr Glu Phe Met Ala Arg Leu His Glu His Leu Lys Tyr Phe Val Asn
        195                 200                 205

Met Lys Ile Ser Thr Asp Lys Ser Trp Gln Gly Val Thr Ile Tyr Phe
    210                 215                 220

Ser Gly His Glu Thr Pro Gly Glu Gly Glu His Lys Ile Met Glu Phe
225                 230                 235                 240

Ile Arg Ser Glu Lys Ala Lys Pro Asp His Asp Pro Asn Thr Arg His
                245                 250                 255

Cys Leu Tyr Gly Leu Asp Ala Asp Leu Ile Met Leu Gly Leu Thr Ser
            260                 265                 270

His Glu Ala His Phe Ser Leu Leu Arg Glu Glu Val Arg Phe Gly Gly
        275                 280                 285

Lys Lys Thr Gln Arg Val Cys Ala Pro Glu Glu Thr Thr Phe His Leu
```

```
                290                 295                 300
Leu His Leu Ser Leu Met Arg Glu Tyr Ile Asp Tyr Glu Phe Ser Val
305                 310                 315                 320

Leu Lys Glu Lys Ile Thr Phe Lys Tyr Asp Ile Glu Arg Ile Ile Asp
                325                 330                 335

Asp Trp Ile Leu Met Gly Phe Leu Val Gly Asn Asp Phe Ile Pro His
                340                 345                 350

Leu Pro His Leu His Ile Asn His Asp Ala Leu Pro Leu Leu Tyr Gly
            355                 360                 365

Thr Tyr Val Thr Ile Leu Pro Glu Leu Gly Gly Tyr Ile Asn Glu Ser
        370                 375                 380

Gly His Leu Asn Leu Pro Arg Phe Glu Lys Tyr Leu Val Lys Leu Ser
385                 390                 395                 400

Asp Phe Asp Arg Glu His Phe Ser Glu Val Phe Val Asp Leu Lys Trp
                405                 410                 415

Phe Glu Ser Lys Val Gly Asn Lys Tyr Leu Asn Glu Ala Ala Gly Val
                420                 425                 430

Ala Ala Glu Glu Ala Arg Asn Tyr Lys Glu Lys Lys Leu Lys Gly
            435                 440                 445

Gln Glu Asn Ser Leu Cys Trp Thr Ala Leu Asp Lys Asn Glu Gly Glu
    450                 455                 460

Met Ile Thr Ser Lys Asp Asn Leu Glu Asp Glu Thr Glu Asp Asp
465                 470                 475                 480

Leu Phe Glu Thr Glu Phe Arg Gln Tyr Lys Arg Thr Tyr Tyr Met Thr
                485                 490                 495

Lys Met Gly Val Asp Val Val Ser Asp Asp Phe Leu Ala Asp Gln Ala
                500                 505                 510

Ala Cys Tyr Val Gln Ala Ile Gln Trp Ile Leu His Tyr Tyr Tyr His
                515                 520                 525

Gly Val Gln Ser Trp Ser Trp Tyr Tyr Pro Tyr His Tyr Ala Pro Phe
            530                 535                 540

Leu Ser Asp Ile His Asn Ile Ser Thr Leu Lys Ile His Phe Glu Leu
545                 550                 555                 560

Gly Lys Pro Phe Lys Pro Phe Glu Gln Leu Leu Ala Val Leu Pro Ala
                565                 570                 575

Ala Ser Lys Asn Leu Leu Pro Ala Cys Tyr Gln His Leu Met Thr Asn
                580                 585                 590

Glu Asp Ser Pro Ile Ile Glu Tyr Tyr Pro Pro Asp Phe Lys Thr Asp
            595                 600                 605

Leu Asn Gly Lys Gln Gln Glu Trp Glu Ala Val Val Leu Ile Pro Phe
        610                 615                 620

Ile Asp Glu Lys Arg Leu Leu Glu Ala Met Glu Thr Cys Asn His Ser
625                 630                 635                 640

Leu Lys Lys Glu Glu Arg Lys Arg Asn Gln His Ser Glu Cys Leu Met
                645                 650                 655

Cys Trp Tyr Asp Arg Asp Thr Glu Phe Ile Tyr Pro Ser Pro Trp Pro
                660                 665                 670

Glu Lys Phe Pro Ala Ile Glu Arg Cys Cys Thr Arg Tyr Lys Ile Ile
            675                 680                 685

Ser Leu Asp Ala Trp Arg Val Asp Ile Asn Lys Asn Lys Ile Thr Arg
        690                 695                 700

Ile Asp Gln Lys Ala Leu Tyr Phe Cys Gly Phe Pro Thr Leu Lys His
705                 710                 715                 720
```

```
Ile Arg His Lys Phe Phe Leu Lys Lys Ser Gly Val Gln Val Phe Gln
            725                 730                 735

Gln Ser Ser Arg Gly Glu Asn Met Met Leu Glu Ile Leu Val Asp Ala
            740                 745                 750

Glu Ser Asp Glu Leu Thr Val Glu Asn Val Ala Ser Ser Val Leu Gly
            755                 760                 765

Lys Ser Val Phe Val Asn Trp Pro His Leu Glu Glu Ala Arg Val Val
770                 775                 780

Ala Val Ser Asp Gly Glu Thr Lys Phe Tyr Leu Glu Pro Pro Gly
785                 790                 795                 800

Thr Gln Lys Leu Tyr Ser Gly Arg Thr Ala Pro Pro Ser Lys Val Val
            805                 810                 815

His Leu Gly Asp Lys Glu Gln Ser Asn Trp Ala Lys Glu Val Gln Gly
            820                 825                 830

Ile Ser Glu His Tyr Leu Arg Arg Lys Gly Ile Ile Ile Asn Glu Thr
            835                 840                 845

Ser Ala Val Val Tyr Ala Gln Leu Leu Thr Gly Arg Lys Tyr Gln Ile
850                 855                 860

Asn Gln Asn Gly Glu Val Arg Leu Glu Lys Gln Trp Ser Lys Gln Val
865                 870                 875                 880

Val Pro Phe Val Tyr Gln Thr Ile Val Lys Asp Ile Arg Ala Phe Asp
            885                 890                 895

Ser Arg Phe Ser Asn Ile Lys Thr Leu Asp Asp Leu Phe Pro Leu Arg
            900                 905                 910

Ser Met Val Phe Met Leu Gly Thr Pro Tyr Tyr Gly Cys Thr Gly Glu
            915                 920                 925

Val Gln Asp Ser Gly Asp Val Ile Thr Glu Gly Arg Ile Arg Val Ile
            930                 935                 940

Phe Ser Ile Pro Cys Glu Pro Asn Leu Asp Ala Leu Ile Gln Asn Gln
945                 950                 955                 960

His Lys Tyr Ser Ile Lys Tyr Asn Pro Gly Tyr Val Leu Ala Ser Arg
            965                 970                 975

Leu Gly Val Ser Gly Tyr Leu Val Ser Arg Phe Thr Gly Ser Ile Phe
            980                 985                 990

Ile Gly Arg Gly Ser Arg Arg Asn  Pro His Gly Asp His  Lys Ala Asn
            995                 1000                1005

Val Gly  Leu Asn Leu Lys Phe  Asn Lys Lys Asn Glu  Glu Val Pro
    1010                1015                1020

Gly Tyr  Thr Lys Lys Val Gly  Ser Glu Trp Met Tyr  Ser Ser Ala
    1025                1030                1035

Ala Glu  Gln Leu Leu Ala Glu  Tyr Leu Glu Arg Ala  Pro Glu Leu
    1040                1045                1050

Phe Ser  Tyr Ile Ala Lys Asn  Ser Gln Glu Asp Val  Phe Tyr Glu
    1055                1060                1065

Asp Asp  Ile Trp Pro Gly Glu  Asn Glu Asn Gly Ala  Glu Lys Val
    1070                1075                1080

Gln Glu  Ile Ile Thr Trp Leu  Lys Gly His Pro Val  Ser Thr Leu
    1085                1090                1095

Ser Arg  Ser Ser Cys Asp Leu  Gln Ile Leu Asp Ala  Ala Ile Val
    1100                1105                1110

Glu Lys  Ile Glu Glu Glu Val  Glu Lys Cys Lys Gln  Arg Lys Asn
    1115                1120                1125
```

-continued

Asn Lys Lys Val Arg Val Thr Val Lys Pro His Leu Leu Tyr Arg
1130                1135                1140

Pro Leu Glu Gln Gln His Gly Val Ile Pro Asp Arg Asp Ala Glu
1145                1150                1155

Phe Cys Leu Phe Asp Arg Val Val Asn Val Arg Glu Asn Phe Ser
1160                1165                1170

Val Pro Val Gly Leu Arg Gly Thr Ile Ile Gly Ile Lys Gly Ala
1175                1180                1185

Asn Arg Glu Ala Asp Val Leu Phe Glu Val Leu Phe Asp Glu Glu
1190                1195                1200

Phe Pro Gly Gly Leu Thr Ile Arg Cys Ser Pro Gly Arg Gly Tyr
1205                1210                1215

Arg Leu Pro Thr Ser Ala Leu Val Asn Leu Ser His Gly Ser Arg
1220                1225                1230

Ser Glu Thr Gly Asn Gln Lys Leu Thr Ala Ile Val Lys Pro Gln
1235                1240                1245

Pro Ala Val His Gln His Ser Ser Ser Ser Val Ser Ser Gly
1250                1255                1260

His Leu Gly Ala Leu Asn His Ser Pro Gln Ser Leu Phe Val Pro
1265                1270                1275

Thr Gln Val Pro Thr Lys Asp Asp Glu Phe Cys Asn Ile Trp
1280                1285                1290

Gln Ser Leu Gln Gly Ser Gly Lys Met Gln Tyr Phe Gln Pro Thr
1295                1300                1305

Ile Gln Glu Lys Gly Ala Val Leu Pro Gln Glu Ile Ser Gln Val
1310                1315                1320

Asn Gln His His Lys Ser Gly Phe Asn Asp Asn Ser Val Lys Tyr
1325                1330                1335

Gln Gln Arg Lys His Asp Pro His Arg Lys Phe Lys Glu Glu Cys
1340                1345                1350

Lys Ser Pro Lys Ala Glu Cys Trp Ser Gln Lys Met Ser Asn Lys
1355                1360                1365

Gln Pro Asn Ser Gly Ile Glu Asn Phe Leu Ala Ser Leu Asn Ile
1370                1375                1380

Ser Lys Glu Asn Glu Val Gln Ser Ser His His Gly Glu Pro Pro
1385                1390                1395

Ser Glu Glu His Leu Ser Pro Gln Ser Phe Ala Met Gly Thr Arg
1400                1405                1410

Met Leu Lys Glu Ile Leu Lys Ile Asp Gly Ser Asn Thr Val Asp
1415                1420                1425

His Lys Asn Glu Ile Lys Gln Ile Ala Asn Glu Ile Pro Val Ser
1430                1435                1440

Ser Asn Arg Arg Asp Glu Tyr Gly Leu Pro Ser Gln Pro Lys Gln
1445                1450                1455

Asn Lys Lys Leu Ala Ser Tyr Met Asn Lys Pro His Ser Ala Asn
1460                1465                1470

Glu Tyr His Asn Val Gln Ser Met Asp Asn Met Cys Trp Pro Ala
1475                1480                1485

Pro Ser Gln Ile Pro Pro Val Ser Thr Pro Val Thr Glu Leu Ser
1490                1495                1500

Arg Ile Cys Ser Leu Val Gly Met Pro Gln Pro Asp Phe Ser Phe
1505                1510                1515

Leu Arg Met Pro Gln Thr Met Thr Val Cys Gln Val Lys Leu Ser

| | | | | 1520 | | | | 1525 | | | | 1530 | | |
|---|---|---|---|---|---|---|---|---|---|---|---|---|---|---|

Asn Gly Leu Leu Val His Gly Pro Gln Cys His Ser Glu Asn Glu
　　　1535　　　　　　　　　1540　　　　　　　　　1545

Ala Lys Glu Lys Ala Ala Leu Phe Ala Leu Gln Gln Leu Gly Ser
1550　　　　　　　　　1555　　　　　　　　　1560

Leu Gly Met Asn Phe Pro Leu Pro Ser Gln Val Phe Ala Asn Tyr
1565　　　　　　　　　1570　　　　　　　　　1575

Pro Ser Ala Val Pro Pro Gly Thr Ile Pro Pro Ala Phe Pro Pro
1580　　　　　　　　　1585　　　　　　　　　1590

Pro Thr Gly Trp Asp His Tyr Gly Ser Asn Tyr Ala Leu Gly Ala
1595　　　　　　　　　1600　　　　　　　　　1605

Ala Asn Ile Met Pro Ser Ser His Leu Phe Gly Ser Met Pro
1610　　　　　　　　　1615　　　　　　　　　1620

Trp Gly Pro Ser Val Pro Val Pro Gly Lys Pro Phe His His Thr
1625　　　　　　　　　1630　　　　　　　　　1635

Leu Tyr Ser Gly Thr Met Pro Met Ala Gly Gly Ile Pro Gly Gly
1640　　　　　　　　　1645　　　　　　　　　1650

Val His Asn Gln Phe Ile Pro Leu Gln Val Thr Lys Lys Arg Val
1655　　　　　　　　　1660　　　　　　　　　1665

Ala Asn Lys Lys Asn Phe Glu Asn Lys Glu Ala Gln Ser Ser Gln
1670　　　　　　　　　1675　　　　　　　　　1680

Ala Thr Pro Val Gln Thr Ser Gln Pro Asp Ser Ser Asn Ile Val
1685　　　　　　　　　1690　　　　　　　　　1695

Lys Val Ser Pro Arg Glu Ser Ser Ala Ser Leu Lys Ser Ser
1700　　　　　　　　　1705　　　　　　　　　1710

Pro Ile Ala Gln Pro Ala Ser Ser Phe Gln Val Glu Thr Ala Ser
1715　　　　　　　　　1720　　　　　　　　　1725

Gln Gly His Ser Ile Ser His His Lys Ser Thr Pro Ile Ser Ser
1730　　　　　　　　　1735　　　　　　　　　1740

Ser Arg Arg Lys Ser Arg Lys Leu Ala Val Asn Phe Gly Val Ser
1745　　　　　　　　　1750　　　　　　　　　1755

Lys Pro Ser Glu
1760

<210> SEQ ID NO 83
<211> LENGTH: 1060
<212> TYPE: PRT
<213> ORGANISM: Homo sapiens

<400> SEQUENCE: 83

Met Glu Gln Leu Asn Glu Leu Glu Leu Met Glu Lys Ser Phe Trp
1　　　　　　　　　5　　　　　　　　　10　　　　　　　　　15

Glu Glu Ala Glu Leu Pro Ala Glu Leu Phe Gln Lys Lys Val Val Ala
　　　　　　　　　20　　　　　　　　　25　　　　　　　　　30

Ser Phe Pro Arg Thr Val Leu Ser Thr Gly Met Asp Asn Arg Tyr Leu
　　　　　35　　　　　　　　　40　　　　　　　　　45

Val Leu Ala Val Asn Thr Val Gln Asn Lys Glu Gly Asn Cys Glu Lys
　　　50　　　　　　　　　55　　　　　　　　　60

Arg Leu Val Ile Thr Ala Ser Gln Ser Leu Glu Asn Lys Glu Leu Cys
65　　　　　　　　　70　　　　　　　　　75　　　　　　　　　80

Ile Leu Arg Asn Asp Trp Cys Ser Val Pro Val Glu Pro Gly Asp Ile
　　　　　　　　　85　　　　　　　　　90　　　　　　　　　95

Ile His Leu Glu Gly Asp Cys Thr Ser Asp Thr Trp Ile Ile Asp Lys
　　　　　　　　　100　　　　　　　　　105　　　　　　　　　110

-continued

```
Asp Phe Gly Tyr Leu Ile Leu Tyr Pro Asp Met Leu Ile Ser Gly Thr
            115                 120                 125

Ser Ile Ala Ser Ser Ile Arg Cys Met Arg Arg Ala Val Leu Ser Glu
130                 135                 140

Thr Phe Arg Ser Ser Asp Pro Ala Thr Arg Gln Met Leu Ile Gly Thr
145                 150                 155                 160

Val Leu His Glu Val Phe Gln Lys Ala Ile Asn Asn Ser Phe Ala Pro
                165                 170                 175

Glu Lys Leu Gln Glu Leu Ala Phe Gln Thr Ile Gln Glu Ile Arg His
            180                 185                 190

Leu Lys Glu Met Tyr Arg Leu Asn Leu Ser Gln Asp Glu Ile Lys Gln
        195                 200                 205

Glu Val Glu Asp Tyr Leu Pro Ser Phe Cys Lys Trp Ala Gly Asp Phe
210                 215                 220

Met His Lys Asn Thr Ser Thr Asp Phe Pro Gln Met Gln Leu Ser Leu
225                 230                 235                 240

Pro Ser Asp Asn Ser Lys Asp Asn Ser Thr Cys Asn Ile Glu Val Val
                245                 250                 255

Lys Pro Met Asp Ile Glu Glu Ser Ile Trp Ser Pro Arg Phe Gly Leu
            260                 265                 270

Lys Gly Lys Ile Asp Val Thr Val Gly Val Lys Ile His Arg Gly Tyr
        275                 280                 285

Lys Thr Lys Tyr Lys Ile Met Pro Leu Glu Leu Lys Thr Gly Lys Glu
    290                 295                 300

Ser Asn Ser Ile Glu His Arg Ser Gln Val Val Leu Tyr Thr Leu Leu
305                 310                 315                 320

Ser Gln Glu Arg Arg Ala Asp Pro Glu Ala Gly Leu Leu Leu Tyr Leu
                325                 330                 335

Lys Thr Gly Gln Met Tyr Pro Val Pro Ala Asn His Leu Asp Lys Arg
            340                 345                 350

Glu Leu Leu Lys Leu Arg Asn Gln Met Ala Phe Ser Leu Phe His Arg
        355                 360                 365

Ile Ser Lys Ser Ala Thr Arg Gln Lys Thr Gln Leu Ala Ser Leu Pro
    370                 375                 380

Gln Ile Ile Glu Glu Lys Thr Cys Lys Tyr Cys Ser Gln Ile Gly
385                 390                 395                 400

Asn Cys Ala Leu Tyr Ser Arg Ala Val Glu Gln Met Asp Cys Ser
                405                 410                 415

Ser Val Pro Ile Val Met Leu Pro Lys Ile Glu Glu Thr Gln His
            420                 425                 430

Leu Lys Gln Thr His Leu Glu Tyr Phe Ser Leu Trp Cys Leu Met Leu
        435                 440                 445

Thr Leu Glu Ser Gln Ser Lys Asp Asn Lys Lys Asn His Gln Asn Ile
450                 455                 460

Trp Leu Met Pro Ala Ser Glu Met Glu Lys Ser Gly Ser Cys Ile Gly
465                 470                 475                 480

Asn Leu Ile Arg Met Glu His Val Lys Ile Val Cys Asp Gly Gln Tyr
                485                 490                 495

Leu His Asn Phe Gln Cys Lys His Gly Ala Ile Pro Val Thr Asn Leu
            500                 505                 510

Met Ala Gly Asp Arg Val Ile Val Ser Gly Glu Glu Arg Ser Leu Phe
        515                 520                 525

Ala Leu Ser Arg Gly Tyr Val Lys Glu Ile Asn Met Thr Thr Val Thr
```

```
            530                 535                 540
Cys Leu Leu Asp Arg Asn Leu Ser Val Leu Pro Glu Ser Thr Leu Phe
545                 550                 555                 560

Arg Leu Asp Gln Glu Lys Asn Cys Asp Ile Asp Thr Pro Leu Gly
                565                 570                 575

Asn Leu Ser Lys Leu Met Glu Asn Thr Phe Val Ser Lys Lys Leu Arg
                580                 585                 590

Asp Leu Ile Ile Asp Phe Arg Glu Pro Gln Phe Ile Ser Tyr Leu Ser
                595                 600                 605

Ser Val Leu Pro His Asp Ala Lys Asp Thr Val Ala Cys Ile Leu Lys
                610                 615                 620

Gly Leu Asn Lys Pro Gln Arg Gln Ala Met Lys Lys Val Leu Leu Ser
625                 630                 635                 640

Lys Asp Tyr Thr Leu Ile Val Gly Met Pro Gly Thr Gly Lys Thr Thr
                645                 650                 655

Thr Ile Cys Thr Leu Val Arg Ile Leu Tyr Ala Cys Gly Phe Ser Val
                660                 665                 670

Leu Leu Thr Ser Tyr Thr His Ser Ala Val Asp Asn Ile Leu Leu Lys
                675                 680                 685

Leu Ala Lys Phe Lys Ile Gly Phe Leu Arg Leu Gly Gln Ile Gln Lys
690                 695                 700

Val His Pro Ala Ile Gln Gln Phe Thr Glu Gln Glu Ile Cys Arg Ser
705                 710                 715                 720

Lys Ser Ile Lys Ser Leu Ala Leu Leu Glu Glu Leu Tyr Asn Ser Gln
                725                 730                 735

Leu Ile Val Ala Thr Thr Cys Met Gly Ile Asn His Pro Ile Phe Ser
                740                 745                 750

Arg Lys Ile Phe Asp Phe Cys Ile Val Asp Glu Ala Ser Gln Ile Ser
                755                 760                 765

Gln Pro Ile Cys Leu Gly Pro Leu Phe Phe Ser Arg Arg Phe Val Leu
                770                 775                 780

Val Gly Asp His Gln Gln Leu Pro Pro Leu Val Leu Asn Arg Glu Ala
785                 790                 795                 800

Arg Ala Leu Gly Met Ser Glu Ser Leu Phe Lys Arg Leu Glu Gln Asn
                805                 810                 815

Lys Ser Ala Val Val Gln Leu Thr Val Gln Tyr Arg Met Asn Ser Lys
                820                 825                 830

Ile Met Ser Leu Ser Asn Lys Leu Thr Tyr Glu Gly Lys Leu Glu Cys
                835                 840                 845

Gly Ser Asp Lys Val Ala Asn Ala Val Ile Asn Leu Arg His Phe Lys
850                 855                 860

Asp Val Lys Leu Glu Leu Glu Phe Tyr Ala Asp Tyr Ser Asp Asn Pro
865                 870                 875                 880

Trp Leu Met Gly Val Phe Glu Pro Asn Asn Pro Val Cys Phe Leu Asn
                885                 890                 895

Thr Asp Lys Val Pro Ala Pro Glu Gln Val Glu Lys Gly Gly Val Ser
                900                 905                 910

Asn Val Thr Glu Ala Lys Leu Ile Val Phe Leu Thr Ser Ile Phe Val
                915                 920                 925

Lys Ala Gly Cys Ser Pro Ser Asp Ile Gly Ile Ile Ala Pro Tyr Arg
930                 935                 940

Gln Gln Leu Lys Ile Ile Asn Asp Leu Leu Ala Arg Ser Ile Gly Met
945                 950                 955                 960
```

```
Val Glu Val Asn Thr Val Asp Lys Tyr Gln Gly Arg Asp Lys Ser Ile
            965                 970                 975

Val Leu Val Ser Phe Val Arg Ser Asn Lys Asp Gly Thr Val Gly Glu
            980                 985                 990

Leu Leu Lys Asp Trp Arg Arg Leu Asn Val Ala Ile Thr Arg Ala Lys
            995                 1000                1005

His Lys Leu Ile Leu Leu Gly Cys Val Pro Ser Leu Asn Cys Tyr
        1010                1015                1020

Pro Pro Leu Glu Lys Leu Leu Asn His Leu Asn Ser Glu Lys Leu
        1025                1030                1035

Ile Ile Asp Leu Pro Ser Arg Glu His Glu Ser Leu Cys His Ile
        1040                1045                1050

Leu Gly Asp Phe Gln Arg Glu
        1055                1060

<210> SEQ ID NO 84
<211> LENGTH: 2618
<212> TYPE: PRT
<213> ORGANISM: Artificial Sequence
<220> FEATURE:
<223> OTHER INFORMATION: Fusion protein

<400> SEQUENCE: 84

Met Glu Gln Lys Leu Ile Ser Glu Glu Asp Leu Leu Arg Lys Arg Gly
1               5                   10                  15

Ile Leu Asn Leu Leu Arg Arg Ser Gly Lys Arg Arg Ser Glu Ser
            20                  25                  30

Gly Ser Asp Ser Phe Ser Gly Ser Gly Gly Asp Ser Ser Ala Ser Pro
        35                  40                  45

Gln Phe Leu Ser Gly Ser Val Leu Ser Pro Pro Gly Leu Gly Arg
    50                  55                  60

Cys Leu Lys Ala Ala Ala Gly Glu Cys Lys Pro Thr Val Pro Asp
65                  70                  75                  80

Tyr Glu Ile Asp Lys Leu Leu Leu Ala Asn Trp Gly Leu Pro Lys Ala
                85                  90                  95

Val Leu Glu Lys Tyr His Ser Phe Gly Val Lys Lys Met Phe Glu Trp
            100                 105                 110

Gln Ala Glu Cys Leu Leu Leu Gly Gln Val Leu Glu Gly Lys Asn Leu
        115                 120                 125

Val Tyr Ser Ala Pro Thr Ser Ala Gly Lys Thr Leu Val Ala Glu Leu
    130                 135                 140

Leu Ile Leu Lys Arg Val Leu Glu Met Arg Lys Lys Ala Leu Phe Ile
145                 150                 155                 160

Leu Pro Phe Val Ser Val Ala Lys Glu Lys Lys Tyr Tyr Leu Gln Ser
                165                 170                 175

Leu Phe Gln Glu Val Gly Ile Lys Val Asp Gly Tyr Met Gly Ser Thr
            180                 185                 190

Ser Pro Ser Arg His Phe Ser Ser Leu Asp Ile Ala Val Cys Thr Ile
        195                 200                 205

Glu Arg Ala Asn Gly Leu Ile Asn Arg Leu Ile Glu Glu Asn Lys Met
    210                 215                 220

Asp Leu Leu Gly Met Val Val Val Asp Glu Leu His Met Leu Gly Asp
225                 230                 235                 240

Ser His Arg Gly Tyr Leu Leu Glu Leu Leu Leu Thr Lys Ile Cys Tyr
                245                 250                 255
```

```
Ile Thr Arg Lys Ser Ala Ser Cys Gln Ala Asp Leu Ala Ser Ser Leu
            260                 265                 270

Ser Asn Ala Val Gln Ile Val Gly Met Ser Ala Thr Leu Pro Asn Leu
        275                 280                 285

Glu Leu Val Ala Ser Trp Leu Asn Ala Glu Leu Tyr His Thr Asp Phe
290                 295                 300

Arg Pro Val Pro Leu Leu Glu Ser Val Lys Val Gly Asn Ser Ile Tyr
305                 310                 315                 320

Asp Ser Ser Met Lys Leu Val Arg Glu Phe Glu Pro Met Leu Gln Val
                325                 330                 335

Lys Gly Asp Glu Asp His Val Val Ser Leu Cys Tyr Glu Thr Ile Cys
            340                 345                 350

Asp Asn His Ser Val Leu Leu Phe Cys Pro Ser Lys Lys Trp Cys Glu
        355                 360                 365

Lys Leu Ala Asp Ile Ile Ala Arg Glu Phe Tyr Asn Leu His His Gln
370                 375                 380

Ala Glu Gly Leu Val Lys Pro Ser Glu Cys Pro Pro Val Ile Leu Glu
385                 390                 395                 400

Gln Lys Glu Leu Leu Glu Val Met Asp Gln Leu Arg Arg Leu Pro Ser
                405                 410                 415

Gly Leu Asp Ser Val Leu Gln Lys Thr Val Pro Trp Gly Val Ala Phe
            420                 425                 430

His His Ala Gly Leu Thr Phe Glu Glu Arg Asp Ile Ile Glu Gly Ala
        435                 440                 445

Phe Arg Gln Gly Leu Ile Arg Val Leu Ala Ala Thr Ser Thr Leu Ser
450                 455                 460

Ser Gly Val Asn Leu Pro Ala Arg Arg Val Ile Ile Arg Thr Pro Ile
465                 470                 475                 480

Phe Gly Gly Arg Pro Leu Asp Ile Leu Thr Tyr Lys Gln Met Val Gly
                485                 490                 495

Arg Ala Gly Arg Lys Gly Val Asp Thr Val Gly Glu Ser Ile Leu Ile
            500                 505                 510

Cys Lys Asn Ser Glu Lys Ser Lys Gly Ile Ala Leu Leu Gln Gly Ser
        515                 520                 525

Leu Lys Pro Val Arg Ser Cys Leu Gln Arg Arg Glu Gly Glu Glu Val
530                 535                 540

Thr Gly Ser Met Ile Arg Ala Ile Leu Glu Ile Ile Val Gly Gly Val
545                 550                 555                 560

Ala Ser Thr Ser Gln Asp Met His Thr Tyr Ala Ala Cys Thr Phe Leu
                565                 570                 575

Ala Ala Ser Met Lys Glu Gly Lys Gln Gly Ile Gln Arg Asn Gln Glu
            580                 585                 590

Ser Val Gln Leu Gly Ala Ile Glu Ala Cys Val Met Trp Leu Leu Glu
        595                 600                 605

Asn Glu Phe Ile Gln Ser Thr Glu Ala Ser Asp Gly Thr Glu Gly Lys
610                 615                 620

Val Tyr His Pro Thr His Leu Gly Ser Ala Thr Leu Ser Ser Ser Leu
625                 630                 635                 640

Ser Pro Ala Asp Thr Leu Asp Ile Phe Ala Asp Leu Gln Arg Ala Met
                645                 650                 655

Lys Gly Phe Val Leu Glu Asn Asp Leu His Ile Leu Tyr Leu Val Thr
            660                 665                 670
```

```
Pro Met Phe Glu Asp Trp Thr Thr Ile Asp Trp Tyr Arg Phe Phe Cys
            675                 680                 685

Leu Trp Glu Lys Leu Pro Thr Ser Met Lys Arg Val Ala Glu Leu Val
690                 695                 700

Gly Val Glu Glu Gly Phe Leu Ala Arg Cys Val Lys Gly Lys Val Val
705                 710                 715                 720

Ala Arg Thr Glu Arg Gln His Arg Gln Met Ala Ile His Lys Arg Phe
                725                 730                 735

Phe Thr Ser Leu Val Leu Leu Asp Leu Ile Ser Glu Val Pro Leu Arg
            740                 745                 750

Glu Ile Asn Gln Lys Tyr Gly Cys Asn Arg Gly Gln Ile Gln Ser Leu
        755                 760                 765

Gln Gln Ser Ala Ala Val Tyr Ala Gly Met Ile Thr Val Phe Ser Asn
    770                 775                 780

Arg Leu Gly Trp His Asn Met Glu Leu Leu Leu Ser Gln Phe Gln Lys
785                 790                 795                 800

Arg Leu Thr Phe Gly Ile Gln Arg Glu Leu Cys Asp Leu Val Arg Val
                805                 810                 815

Ser Leu Leu Asn Ala Gln Arg Ala Arg Val Leu Tyr Ala Ser Gly Phe
            820                 825                 830

His Thr Val Ala Asp Leu Ala Arg Ala Asn Ile Val Glu Val Glu Val
        835                 840                 845

Ile Leu Lys Asn Ala Val Pro Phe Lys Ser Ala Arg Lys Ala Val Asp
    850                 855                 860

Glu Glu Glu Gly Ala Val Glu Glu Arg Arg Asn Met Arg Thr Ile Trp
865                 870                 875                 880

Val Thr Gly Arg Lys Gly Leu Thr Glu Arg Glu Ala Ala Ala Leu Ile
                885                 890                 895

Val Glu Glu Ala Arg Met Ile Leu Gln Gln Asp Leu Val Glu Met Gly
            900                 905                 910

Val Gln Trp Asn Pro Cys Ala Leu Leu His Ser Ser Thr Cys Ser Leu
        915                 920                 925

Thr His Ser Glu Ser Glu Val Lys Glu His Thr Phe Ile Ser Gln Thr
    930                 935                 940

Lys Ser Ser Tyr Lys Lys Leu Thr Ser Lys Asn Lys Ser Asn Thr Ile
945                 950                 955                 960

Phe Ser Asp Ser Tyr Ile Lys His Ser Pro Asn Ile Val Gln Asp Leu
                965                 970                 975

Asn Lys Ser Arg Glu His Thr Ser Ser Phe Asn Cys Asn Phe Gln Asn
            980                 985                 990

Gly Asn Gln Glu His Gln Arg Cys Ser Ile Phe Arg Ala Arg Lys Arg
        995                 1000                1005

Ala Ser Leu Asp Ile Asn Lys Glu Lys Pro Gly Ala Ser Gln Asn
    1010                1015                1020

Glu Gly Lys Thr Ser Asp Lys Lys Val Val Gln Thr Phe Ser Gln
    1025                1030                1035

Lys Thr Lys Lys Ala Pro Leu Asn Phe Asn Ser Glu Lys Met Ser
    1040                1045                1050

Arg Ser Phe Arg Ser Trp Lys Arg Arg Lys His Leu Lys Arg Ser
    1055                1060                1065

Arg Asp Ser Ser Pro Leu Lys Asp Ser Gly Ala Cys Arg Ile His
    1070                1075                1080

Leu Gln Gly Gln Thr Leu Ser Asn Pro Ser Leu Cys Glu Asp Pro
```

-continued

```
            1085                1090                1095
Phe Thr Leu Asp Glu Lys Lys Thr Glu Phe Arg Asn Ser Gly Pro
    1100                1105                1110
Phe Ala Lys Asn Val Ser Leu Ser Gly Lys Glu Lys Asp Asn Lys
    1115                1120                1125
Thr Ser Phe Pro Leu Gln Ile Lys Gln Asn Cys Ser Trp Asn Ile
    1130                1135                1140
Thr Leu Thr Asn Asp Asn Phe Val Glu His Ile Val Thr Gly Ser
    1145                1150                1155
Gln Ser Lys Asn Val Thr Cys Gln Ala Thr Ser Val Val Ser Glu
    1160                1165                1170
Lys Gly Arg Gly Val Ala Val Glu Ala Glu Lys Ile Asn Glu Val
    1175                1180                1185
Leu Ile Gln Asn Gly Ser Lys Asn Gln Asn Val Tyr Met Lys His
    1190                1195                1200
His Asp Ile His Pro Ile Asn Gln Tyr Leu Arg Lys Gln Ser His
    1205                1210                1215
Glu Gln Thr Ser Thr Ile Thr Lys Gln Lys Asn Ile Ile Glu Arg
    1220                1225                1230
Gln Met Pro Cys Glu Ala Val Ser Ser Tyr Ile Asn Arg Asp Ser
    1235                1240                1245
Asn Val Thr Ile Asn Cys Glu Arg Ile Lys Leu Asn Thr Glu Glu
    1250                1255                1260
Asn Lys Pro Ser His Phe Gln Ala Leu Gly Asp Asp Ile Ser Arg
    1265                1270                1275
Thr Val Ile Pro Ser Glu Val Leu Pro Ser Ala Gly Ala Phe Ser
    1280                1285                1290
Lys Ser Glu Gly Gln His Glu Asn Phe Leu Asn Ile Ser Arg Leu
    1295                1300                1305
Gln Glu Lys Thr Gly Thr Tyr Thr Thr Asn Lys Thr Lys Asn Asn
    1310                1315                1320
His Val Ser Asp Leu Gly Leu Val Leu Cys Asp Phe Glu Asp Ser
    1325                1330                1335
Phe Tyr Leu Asp Thr Gln Ser Glu Lys Ile Ile Gln Gln Met Ala
    1340                1345                1350
Thr Glu Asn Ala Lys Leu Gly Ala Lys Asp Thr Asn Leu Ala Ala
    1355                1360                1365
Gly Ile Met Gln Lys Ser Leu Val Gln Gln Asn Ser Met Asn Ser
    1370                1375                1380
Phe Gln Lys Glu Cys His Ile Pro Phe Pro Ala Glu Gln His Pro
    1385                1390                1395
Leu Gly Ala Thr Lys Ile Asp His Leu Asp Leu Lys Thr Val Gly
    1400                1405                1410
Thr Met Lys Gln Ser Ser Asp Ser His Gly Val Asp Ile Leu Thr
    1415                1420                1425
Pro Glu Ser Pro Ile Phe His Ser Pro Ile Leu Leu Glu Glu Asn
    1430                1435                1440
Gly Leu Phe Leu Lys Lys Asn Glu Val Ser Val Thr Asp Ser Gln
    1445                1450                1455
Leu Asn Ser Phe Leu Gln Gly Tyr Gln Thr Gln Glu Thr Val Lys
    1460                1465                1470
Pro Val Ile Leu Leu Ile Pro Gln Lys Arg Thr Pro Thr Gly Val
    1475                1480                1485
```

```
Glu Gly Glu Cys Leu Pro Val Pro Glu Thr Ser Leu Asn Met Ser
    1490            1495                1500

Asp Ser Leu Leu Phe Asp Ser Phe Ser Asp Tyr Leu Val Lys
    1505            1510                1515

Glu Gln Leu Pro Asp Met Gln Met Lys Glu Pro Leu Pro Ser Glu
    1520            1525                1530

Val Thr Ser Asn His Phe Ser Asp Ser Leu Cys Leu Gln Glu Asp
    1535            1540                1545

Leu Ile Lys Lys Ser Asn Val Asn Glu Asn Gln Asp Thr His Gln
    1550            1555                1560

Gln Leu Thr Cys Ser Asn Asp Glu Ser Ile Ile Phe Ser Glu Met
    1565            1570                1575

Asp Ser Val Gln Met Val Glu Ala Leu Asp Asn Val Asp Ile Phe
    1580            1585                1590

Pro Val Gln Glu Lys Asn His Thr Val Val Ser Pro Arg Ala Leu
    1595            1600                1605

Glu Leu Ser Asp Pro Val Leu Asp Glu His His Gln Gly Asp Gln
    1610            1615                1620

Asp Gly Gly Asp Gln Asp Glu Arg Ala Glu Lys Ser Lys Leu Thr
    1625            1630                1635

Gly Thr Arg Gln Asn His Ser Phe Ile Trp Ser Gly Ala Ser Phe
    1640            1645                1650

Asp Leu Ser Pro Gly Leu Gln Arg Ile Leu Asp Lys Val Ser Ser
    1655            1660                1665

Pro Leu Glu Asn Glu Lys Leu Lys Ser Met Thr Ile Asn Phe Ser
    1670            1675                1680

Ser Leu Asn Arg Lys Asn Thr Glu Leu Asn Glu Glu Gln Glu Val
    1685            1690                1695

Ile Ser Asn Leu Glu Thr Lys Gln Val Gln Gly Ile Ser Phe Ser
    1700            1705                1710

Ser Asn Asn Glu Val Lys Ser Lys Ile Glu Met Leu Glu Asn Asn
    1715            1720                1725

Ala Asn His Asp Glu Thr Ser Ser Leu Leu Pro Arg Lys Glu Ser
    1730            1735                1740

Asn Ile Val Asp Asp Asn Gly Leu Ile Pro Pro Thr Pro Ile Pro
    1745            1750                1755

Thr Ser Ala Ser Lys Leu Thr Phe Pro Gly Ile Leu Glu Thr Pro
    1760            1765                1770

Val Asn Pro Trp Lys Thr Asn Asn Val Leu Gln Pro Gly Glu Ser
    1775            1780                1785

Tyr Leu Phe Gly Ser Pro Ser Asp Ile Lys Asn His Asp Leu Ser
    1790            1795                1800

Pro Gly Ser Arg Asn Gly Phe Lys Asp Asn Ser Pro Ile Ser Asp
    1805            1810                1815

Thr Ser Phe Ser Leu Gln Leu Ser Gln Asp Gly Leu Gln Leu Thr
    1820            1825                1830

Pro Ala Ser Ser Ser Ser Glu Ser Leu Ser Ile Ile Asp Val Ala
    1835            1840                1845

Ser Asp Gln Asn Leu Phe Gln Thr Phe Ile Lys Glu Trp Arg Cys
    1850            1855                1860

Lys Lys Arg Phe Ser Ile Ser Leu Ala Cys Glu Lys Ile Arg Ser
    1865            1870                1875
```

```
Leu Thr Ser Ser Lys Thr Ala Thr Ile Gly Ser Arg Phe Lys Gln
    1880                1885                1890

Ala Ser Ser Pro Gln Glu Ile Pro Ile Arg Asp Asp Gly Phe Pro
    1895                1900                1905

Ile Lys Gly Cys Asp Asp Thr Leu Val Val Gly Leu Ala Val Cys
    1910                1915                1920

Trp Gly Gly Arg Asp Ala Tyr Tyr Phe Ser Leu Gln Lys Glu Gln
    1925                1930                1935

Lys His Ser Glu Ile Ser Ala Ser Leu Val Pro Pro Ser Leu Asp
    1940                1945                1950

Pro Ser Leu Thr Leu Lys Asp Arg Met Trp Tyr Leu Gln Ser Cys
    1955                1960                1965

Leu Arg Lys Glu Ser Asp Lys Glu Cys Ser Val Val Ile Tyr Asp
    1970                1975                1980

Phe Ile Gln Ser Tyr Lys Ile Leu Leu Leu Ser Cys Gly Ile Ser
    1985                1990                1995

Leu Glu Gln Ser Tyr Glu Asp Pro Lys Val Ala Cys Trp Leu Leu
    2000                2005                2010

Asp Pro Asp Ser Gln Glu Pro Thr Leu His Ser Ile Val Thr Ser
    2015                2020                2025

Phe Leu Pro His Glu Leu Pro Leu Leu Glu Gly Met Glu Thr Ser
    2030                2035                2040

Gln Gly Ile Gln Ser Leu Gly Leu Asn Ala Gly Ser Glu His Ser
    2045                2050                2055

Gly Arg Tyr Arg Ala Ser Val Glu Ser Ile Leu Ile Phe Asn Ser
    2060                2065                2070

Met Asn Gln Leu Asn Ser Leu Leu Gln Lys Glu Asn Leu Gln Asp
    2075                2080                2085

Val Phe Arg Lys Val Glu Met Pro Ser Gln Tyr Cys Leu Ala Leu
    2090                2095                2100

Leu Glu Leu Asn Gly Ile Gly Phe Ser Thr Ala Glu Cys Glu Ser
    2105                2110                2115

Gln Lys His Ile Met Gln Ala Lys Leu Asp Ala Ile Glu Thr Gln
    2120                2125                2130

Ala Tyr Gln Leu Ala Gly His Ser Phe Ser Phe Thr Ser Ser Asp
    2135                2140                2145

Asp Ile Ala Glu Val Leu Phe Leu Glu Leu Lys Leu Pro Pro Asn
    2150                2155                2160

Arg Glu Met Lys Asn Gln Gly Ser Lys Lys Thr Leu Gly Ser Thr
    2165                2170                2175

Arg Arg Gly Ile Asp Asn Gly Arg Lys Leu Arg Leu Gly Arg Gln
    2180                2185                2190

Phe Ser Thr Ser Lys Asp Val Leu Asn Lys Leu Lys Ala Leu His
    2195                2200                2205

Pro Leu Pro Gly Leu Ile Leu Glu Trp Arg Arg Ile Thr Asn Ala
    2210                2215                2220

Ile Thr Lys Val Val Phe Pro Leu Gln Arg Glu Lys Cys Leu Asn
    2225                2230                2235

Pro Phe Leu Gly Met Glu Arg Ile Tyr Pro Val Ser Gln Ser His
    2240                2245                2250

Thr Ala Thr Gly Arg Ile Thr Phe Thr Glu Pro Asn Ile Gln Asn
    2255                2260                2265

Val Pro Arg Asp Phe Glu Ile Lys Met Pro Thr Leu Val Gly Glu
```

```
                   2270                2275                2280

Ser  Pro  Pro  Ser  Gln  Ala  Val  Gly  Lys  Gly  Leu  Leu  Pro  Met  Gly
     2285                2290                2295

Arg  Gly  Lys  Tyr  Lys  Lys  Gly  Phe  Ser  Val  Asn  Pro  Arg  Cys  Gln
     2300                2305                2310

Ala  Gln  Met  Glu  Glu  Arg  Ala  Ala  Asp  Arg  Gly  Met  Pro  Phe  Ser
     2315                2320                2325

Ile  Ser  Met  Arg  His  Ala  Phe  Val  Pro  Phe  Pro  Gly  Gly  Ser  Ile
     2330                2335                2340

Leu  Ala  Ala  Asp  Tyr  Ser  Gln  Leu  Glu  Leu  Arg  Ile  Leu  Ala  His
     2345                2350                2355

Leu  Ser  His  Asp  Arg  Arg  Leu  Ile  Gln  Val  Leu  Asn  Thr  Gly  Ala
     2360                2365                2370

Asp  Val  Phe  Arg  Ser  Ile  Ala  Ala  Glu  Trp  Lys  Met  Ile  Glu  Pro
     2375                2380                2385

Glu  Ser  Val  Gly  Asp  Asp  Leu  Arg  Gln  Gln  Ala  Lys  Gln  Ile  Cys
     2390                2395                2400

Tyr  Gly  Ile  Ile  Tyr  Gly  Met  Gly  Ala  Lys  Ser  Leu  Gly  Glu  Gln
     2405                2410                2415

Met  Gly  Ile  Lys  Glu  Asn  Asp  Ala  Ala  Cys  Tyr  Ile  Asp  Ser  Phe
     2420                2425                2430

Lys  Ser  Arg  Tyr  Thr  Gly  Ile  Asn  Gln  Phe  Met  Thr  Glu  Thr  Val
     2435                2440                2445

Lys  Asn  Cys  Lys  Arg  Asp  Gly  Phe  Val  Gln  Thr  Ile  Leu  Gly  Arg
     2450                2455                2460

Arg  Arg  Tyr  Leu  Pro  Gly  Ile  Lys  Asp  Asn  Asn  Pro  Tyr  Arg  Lys
     2465                2470                2475

Ala  His  Ala  Glu  Arg  Gln  Ala  Ile  Asn  Thr  Ile  Val  Gln  Gly  Ser
     2480                2485                2490

Ala  Ala  Asp  Ile  Val  Lys  Ile  Ala  Thr  Val  Asn  Ile  Gln  Lys  Gln
     2495                2500                2505

Leu  Glu  Thr  Phe  His  Ser  Thr  Phe  Lys  Ser  His  Gly  His  Arg  Glu
     2510                2515                2520

Gly  Met  Leu  Gln  Ser  Asp  Arg  Thr  Gly  Leu  Ser  Arg  Lys  Arg  Lys
     2525                2530                2535

Leu  Gln  Gly  Met  Phe  Cys  Pro  Ile  Arg  Gly  Gly  Phe  Phe  Ile  Leu
     2540                2545                2550

Gln  Leu  His  Asp  Glu  Leu  Leu  Tyr  Glu  Val  Ala  Glu  Glu  Asp  Val
     2555                2560                2565

Val  Gln  Val  Ala  Gln  Ile  Val  Lys  Asn  Glu  Met  Glu  Ser  Ala  Val
     2570                2575                2580

Lys  Leu  Ser  Val  Lys  Leu  Lys  Val  Lys  Val  Lys  Ile  Gly  Ala  Ser
     2585                2590                2595

Trp  Gly  Glu  Leu  Lys  Asp  Phe  Asp  Val  Pro  Gly  Met  Asp  Tyr  Lys
     2600                2605                2610

Asp  Asp  Asp  Asp  Lys
     2615

<210> SEQ ID NO 85
<211> LENGTH: 375
<212> TYPE: PRT
<213> ORGANISM: Homo sapiens

<400> SEQUENCE: 85
```

| | | | | | | | | | | | | | | |
|---|---|---|---|---|---|---|---|---|---|---|---|---|---|---|
|Met|Asp|Tyr|Lys|Asp|His|Asp|Gly|Asp|Tyr|Lys|Asp|His|Ile|Asp|
|1| | | |5| | | |10| | | |15| | |
|Tyr|Lys|Asp|Asp|Asp|Lys|Met|Ala|Pro|Lys|Lys|Arg|Lys|Val| |
| | | |20| | | |25| | | |30| | | |
|Gly|Ile|His|Gly|Val|Pro|Ala|Ala|Ser|Lys|Arg|Lys|Ala|Pro|Gln|
| | |35| | | |40| | | |45| | | | |
|Glu|Thr|Leu|Asn|Gly|Gly|Ile|Thr|Asp|Met|Leu|Thr|Glu|Leu|Ala|Asn|
| |50| | | | |55| | | |60| | | | |
|Phe|Glu|Lys|Asn|Val|Ser|Gln|Ala|Ile|His|Lys|Tyr|Asn|Ala|Tyr|Arg|
|65| | | |70| | | |75| | | |80| | | |
|Lys|Ala|Ala|Ser|Val|Ile|Ala|Lys|Tyr|Pro|His|Lys|Ile|Lys|Ser|Gly|
| | | |85| | | |90| | | |95| | | | |
|Ala|Glu|Ala|Lys|Lys|Leu|Pro|Gly|Val|Gly|Thr|Lys|Ile|Ala|Glu|Lys|
| | |100| | | |105| | | |110| | | | |
|Ile|Asp|Glu|Phe|Leu|Ala|Thr|Gly|Lys|Leu|Arg|Lys|Leu|Glu|Lys|Ile|
| | |115| | | |120| | | |125| | | | |
|Arg|Gln|Asp|Asp|Thr|Ser|Ser|Ser|Ile|Asn|Phe|Leu|Thr|Arg|Val|Ser|
| |130| | | | |135| | | |140| | | | |
|Gly|Ile|Gly|Pro|Ser|Ala|Ala|Arg|Lys|Phe|Val|Asp|Glu|Gly|Ile|Lys|
|145| | | |150| | | |155| | | |160| | | |
|Thr|Leu|Glu|Asp|Leu|Arg|Lys|Asn|Glu|Asp|Lys|Leu|Asn|His|His|Gln|
| | | |165| | | |170| | | |175| | | | |
|Arg|Ile|Gly|Leu|Lys|Tyr|Phe|Gly|Asp|Phe|Glu|Lys|Arg|Ile|Pro|Arg|
| | |180| | | |185| | | |190| | | | |
|Glu|Glu|Met|Leu|Gln|Met|Gln|Asp|Ile|Val|Leu|Asn|Glu|Val|Lys|Lys|
| |195| | | | |200| | | |205| | | | |
|Val|Asp|Ser|Glu|Tyr|Ile|Ala|Thr|Val|Cys|Gly|Ser|Phe|Arg|Arg|Gly|
|210| | | |215| | | |220| | | | | | | |
|Ala|Glu|Ser|Ser|Gly|Asp|Met|Asp|Val|Leu|Leu|Thr|His|Pro|Ser|Phe|
|225| | | |230| | | |235| | | |240| | | |
|Thr|Ser|Glu|Ser|Thr|Lys|Gln|Pro|Lys|Leu|Leu|His|Gln|Val|Val|Glu|
| | | |245| | | |250| | | |255| | | | |
|Gln|Leu|Gln|Lys|Val|His|Phe|Ile|Thr|Asp|Thr|Leu|Ser|Lys|Gly|Glu|
| | |260| | | |265| | | |270| | | | |
|Thr|Lys|Phe|Met|Gly|Val|Cys|Gln|Leu|Pro|Ser|Lys|Asn|Asp|Glu|Lys|
| |275| | | | |280| | | |285| | | | |
|Glu|Tyr|Pro|His|Arg|Arg|Ile|Asp|Ile|Arg|Leu|Ile|Pro|Lys|Asp|Gln|
|290| | | | |295| | | |300| | | | | | |
|Tyr|Tyr|Cys|Gly|Val|Leu|Tyr|Phe|Thr|Gly|Ser|Asp|Ile|Phe|Asn|Lys|
|305| | | |310| | | |315| | | |320| | | |
|Asn|Met|Arg|Ala|His|Ala|Leu|Glu|Lys|Gly|Phe|Thr|Ile|Asn|Glu|Tyr|
| | | |325| | | |330| | | |335| | | | |
|Thr|Ile|Arg|Pro|Leu|Gly|Val|Thr|Gly|Val|Ala|Gly|Glu|Pro|Leu|Pro|
| | |340| | | |345| | | |350| | | | |
|Val|Asp|Ser|Glu|Lys|Asp|Ile|Phe|Asp|Tyr|Ile|Gln|Trp|Lys|Tyr|Arg|
| |355| | | | |360| | | |365| | | | |
|Glu|Pro|Lys|Asp|Arg|Ser|Glu| | | | | | | | | |
| |370| | | | |375| | | | | | | | | |

<210> SEQ ID NO 86
<211> LENGTH: 713
<212> TYPE: PRT
<213> ORGANISM: Homo sapiens

<400> SEQUENCE: 86

-continued

```
Met Ala Thr Gly Gln Asp Arg Val Val Ala Leu Val Asp Met Asp Cys
1               5                   10                  15

Phe Phe Val Gln Val Glu Gln Arg Gln Asn Pro His Leu Arg Asn Lys
                20                  25                  30

Pro Cys Ala Val Val Gln Tyr Lys Ser Trp Lys Gly Gly Ile Ile
            35                  40                  45

Ala Val Ser Tyr Glu Ala Arg Ala Phe Gly Val Thr Arg Ser Met Trp
    50                  55                  60

Ala Asp Asp Ala Lys Lys Leu Cys Pro Asp Leu Leu Ala Gln Val
65                  70                  75                  80

Arg Glu Ser Arg Gly Lys Ala Asn Leu Thr Lys Tyr Arg Glu Ala Ser
                85                  90                  95

Val Glu Val Met Glu Ile Met Ser Arg Phe Ala Val Ile Glu Arg Ala
                100                 105                 110

Ser Ile Asp Glu Ala Tyr Val Asp Leu Thr Ser Ala Val Gln Glu Arg
            115                 120                 125

Leu Gln Lys Leu Gln Gly Gln Pro Ile Ser Ala Asp Leu Leu Pro Ser
    130                 135                 140

Thr Tyr Ile Glu Gly Leu Pro Gln Gly Pro Thr Thr Ala Glu Glu Thr
145                 150                 155                 160

Val Gln Lys Glu Gly Met Arg Lys Gln Gly Leu Phe Gln Trp Leu Asp
                165                 170                 175

Ser Leu Gln Ile Asp Asn Leu Thr Ser Pro Asp Leu Gln Leu Thr Val
                180                 185                 190

Gly Ala Val Ile Val Glu Glu Met Arg Ala Ala Ile Glu Arg Glu Thr
            195                 200                 205

Gly Phe Gln Cys Ser Ala Gly Ile Ser His Asn Lys Val Leu Ala Lys
    210                 215                 220

Leu Ala Cys Gly Leu Asn Lys Pro Asn Arg Gln Thr Leu Val Ser His
225                 230                 235                 240

Gly Ser Val Pro Gln Leu Phe Ser Gln Met Pro Ile Arg Lys Ile Arg
                245                 250                 255

Ser Leu Gly Gly Lys Leu Gly Ala Ser Val Ile Glu Ile Leu Gly Ile
                260                 265                 270

Glu Tyr Met Gly Glu Leu Thr Gln Phe Thr Glu Ser Gln Leu Gln Ser
            275                 280                 285

His Phe Gly Glu Lys Asn Gly Ser Trp Leu Tyr Ala Met Cys Arg Gly
    290                 295                 300

Ile Glu His Asp Pro Val Lys Pro Arg Gln Leu Pro Lys Thr Ile Gly
305                 310                 315                 320

Cys Ser Lys Asn Phe Pro Gly Lys Thr Ala Leu Ala Thr Arg Glu Gln
                325                 330                 335

Val Gln Trp Trp Leu Leu Gln Leu Ala Gln Glu Leu Glu Glu Arg Leu
                340                 345                 350

Thr Lys Asp Arg Asn Asp Asn Asp Arg Val Ala Thr Gln Leu Val Val
            355                 360                 365

Ser Ile Arg Val Gln Gly Asp Lys Arg Leu Ser Ser Leu Arg Arg Cys
    370                 375                 380

Cys Ala Leu Thr Arg Tyr Asp Ala His Lys Met Ser His Asp Ala Phe
385                 390                 395                 400

Thr Val Ile Lys Asn Cys Asn Thr Ser Gly Ile Gln Thr Glu Trp Ser
                405                 410                 415
```

```
Pro Pro Leu Thr Met Leu Phe Leu Cys Ala Thr Lys Phe Ser Ala Ser
            420                 425                 430

Ala Pro Ser Ser Ser Thr Asp Ile Thr Ser Phe Leu Ser Ser Asp Pro
        435                 440                 445

Ser Ser Leu Pro Lys Val Pro Val Thr Ser Ser Glu Ala Lys Thr Gln
    450                 455                 460

Gly Ser Gly Pro Ala Val Thr Ala Thr Lys Lys Ala Thr Thr Ser Leu
465                 470                 475                 480

Glu Ser Phe Phe Gln Lys Ala Ala Glu Arg Gln Lys Val Lys Glu Ala
                485                 490                 495

Ser Leu Ser Ser Leu Thr Ala Pro Thr Gln Ala Pro Met Ser Asn Ser
            500                 505                 510

Pro Ser Lys Pro Ser Leu Pro Phe Gln Thr Ser Gln Ser Thr Gly Thr
        515                 520                 525

Glu Pro Phe Phe Lys Gln Lys Ser Leu Leu Leu Lys Gln Lys Gln Leu
530                 535                 540

Asn Asn Ser Ser Val Ser Ser Pro Gln Gln Asn Pro Trp Ser Asn Cys
545                 550                 555                 560

Lys Ala Leu Pro Asn Ser Leu Pro Thr Glu Tyr Pro Gly Cys Val Pro
                565                 570                 575

Val Cys Glu Gly Val Ser Lys Leu Glu Glu Ser Ser Lys Ala Thr Pro
            580                 585                 590

Ala Glu Met Asp Leu Ala His Asn Ser Gln Ser Met His Ala Ser Ser
                595                 600                 605

Ala Ser Lys Ser Val Leu Glu Val Thr Gln Lys Ala Thr Pro Asn Pro
        610                 615                 620

Ser Leu Leu Ala Ala Glu Asp Gln Val Pro Cys Glu Lys Cys Gly Ser
625                 630                 635                 640

Leu Val Pro Val Trp Asp Met Pro Glu His Met Asp Tyr His Phe Ala
                645                 650                 655

Leu Glu Leu Gln Lys Ser Phe Leu Gln Pro His Ser Ser Asn Pro Gln
            660                 665                 670

Val Val Ser Ala Val Ser His Gln Gly Lys Arg Asn Pro Lys Ser Pro
        675                 680                 685

Leu Ala Cys Thr Asn Lys Arg Pro Arg Pro Glu Gly Met Gln Thr Leu
    690                 695                 700

Glu Ser Phe Phe Lys Pro Leu Thr His
705                 710

<210> SEQ ID NO 87
<211> LENGTH: 1240
<212> TYPE: PRT
<213> ORGANISM: Homo sapiens

<400> SEQUENCE: 87

Met Ala Ser Arg Leu Leu Trp Arg Lys Val Ala Gly Ala Thr Val Gly
1               5                   10                  15

Pro Gly Pro Val Pro Ala Pro Gly Arg Trp Val Ser Ser Ser Val Pro
            20                  25                  30

Ala Ser Asp Pro Ser Asp Gly Gln Arg Arg Gln Gln Gln Gln Gln Gln
        35                  40                  45

Gln Gln Gln Gln Gln Gln Gln Pro Gln Gln Pro Gln Val Leu Ser
    50                  55                  60

Ser Glu Gly Gly Gln Leu Arg His Asn Pro Leu Asp Ile Gln Met Leu
65                  70                  75                  80
```

```
Ser Arg Gly Leu His Glu Gln Ile Phe Gly Gln Gly Glu Met Pro
             85                  90                  95

Gly Glu Ala Ala Val Arg Arg Ser Val Glu His Leu Gln Lys His Gly
            100                 105                 110

Leu Trp Gly Gln Pro Ala Val Pro Leu Pro Asp Val Glu Leu Arg Leu
            115                 120                 125

Pro Pro Leu Tyr Gly Asp Asn Leu Asp Gln His Phe Arg Leu Leu Ala
130                 135                 140

Gln Lys Gln Ser Leu Pro Tyr Leu Glu Ala Ala Asn Leu Leu Leu Gln
145                 150                 155                 160

Ala Gln Leu Pro Pro Lys Pro Pro Ala Trp Ala Trp Ala Glu Gly Trp
                165                 170                 175

Thr Arg Tyr Gly Pro Glu Gly Glu Ala Val Pro Val Ala Ile Pro Glu
            180                 185                 190

Glu Arg Ala Leu Val Phe Asp Val Glu Val Cys Leu Ala Glu Gly Thr
            195                 200                 205

Cys Pro Thr Leu Ala Val Ala Ile Ser Pro Ser Ala Trp Tyr Ser Trp
            210                 215                 220

Cys Ser Gln Arg Leu Val Glu Glu Arg Tyr Ser Trp Thr Ser Gln Leu
225                 230                 235                 240

Ser Pro Ala Asp Leu Ile Pro Leu Glu Val Pro Thr Gly Ala Ser Ser
                245                 250                 255

Pro Thr Gln Arg Asp Trp Gln Glu Gln Leu Val Val Gly His Asn Val
            260                 265                 270

Ser Phe Asp Arg Ala His Ile Arg Glu Gln Tyr Leu Ile Gln Gly Ser
            275                 280                 285

Arg Met Arg Phe Leu Asp Thr Met Ser Met His Met Ala Ile Ser Gly
290                 295                 300

Leu Ser Ser Phe Gln Arg Ser Leu Trp Ile Ala Ala Lys Gln Gly Lys
305                 310                 315                 320

His Lys Val Gln Pro Pro Thr Lys Gln Gly Gln Lys Ser Gln Arg Lys
                325                 330                 335

Ala Arg Arg Gly Pro Ala Ile Ser Ser Trp Asp Trp Leu Asp Ile Ser
            340                 345                 350

Ser Val Asn Ser Leu Ala Glu Val His Arg Leu Tyr Val Gly Gly Pro
            355                 360                 365

Pro Leu Glu Lys Glu Pro Arg Glu Leu Phe Val Lys Gly Thr Met Lys
370                 375                 380

Asp Ile Arg Glu Asn Phe Gln Asp Leu Met Gln Tyr Cys Ala Gln Asp
385                 390                 395                 400

Val Trp Ala Thr His Glu Val Phe Gln Gln Leu Pro Leu Phe Leu
                405                 410                 415

Glu Arg Cys Pro His Pro Val Thr Leu Ala Gly Met Leu Glu Met Gly
            420                 425                 430

Val Ser Tyr Leu Pro Val Asn Gln Asn Trp Glu Arg Tyr Leu Ala Glu
            435                 440                 445

Ala Gln Gly Thr Tyr Glu Glu Leu Gln Arg Glu Met Lys Lys Ser Leu
450                 455                 460

Met Asp Leu Ala Asn Asp Ala Cys Gln Leu Leu Ser Gly Glu Arg Tyr
465                 470                 475                 480

Lys Glu Asp Pro Trp Leu Trp Asp Leu Glu Trp Asp Leu Gln Glu Phe
                485                 490                 495
```

```
Lys Gln Lys Lys Ala Lys Val Lys Glu Pro Ala Thr Ala Ser
            500             505             510

Lys Leu Pro Ile Glu Gly Ala Gly Pro Gly Asp Pro Met Asp Gln
            515             520             525

Glu Asp Leu Gly Pro Cys Ser Glu Glu Glu Phe Gln Gln Asp Val
    530             535             540

Met Ala Arg Ala Cys Leu Gln Lys Leu Lys Gly Thr Thr Glu Leu Leu
545             550             555             560

Pro Lys Arg Pro Gln His Leu Pro Gly His Pro Gly Trp Tyr Arg Lys
            565             570             575

Leu Cys Pro Arg Leu Asp Asp Pro Ala Trp Thr Pro Gly Pro Ser Leu
            580             585             590

Leu Ser Leu Gln Met Arg Val Thr Pro Lys Leu Met Ala Leu Thr Trp
            595             600             605

Asp Gly Phe Pro Leu His Tyr Ser Glu Arg His Gly Trp Gly Tyr Leu
            610             615             620

Val Pro Gly Arg Arg Asp Asn Leu Ala Lys Leu Pro Thr Gly Thr Thr
625             630             635             640

Leu Glu Ser Ala Gly Val Val Cys Pro Tyr Arg Ala Ile Glu Ser Leu
            645             650             655

Tyr Arg Lys His Cys Leu Glu Gln Gly Lys Gln Gln Leu Met Pro Gln
            660             665             670

Glu Ala Gly Leu Ala Glu Glu Phe Leu Leu Thr Asp Asn Ser Ala Ile
            675             680             685

Trp Gln Thr Val Glu Glu Leu Asp Tyr Leu Glu Val Glu Ala Glu Ala
            690             695             700

Lys Met Glu Asn Leu Arg Ala Ala Val Pro Gly Gln Pro Leu Ala Leu
705             710             715             720

Thr Ala Arg Gly Gly Pro Lys Asp Thr Gln Pro Ser Tyr His His Gly
            725             730             735

Asn Gly Pro Tyr Asn Asp Val Asp Ile Pro Gly Cys Trp Phe Phe Lys
            740             745             750

Leu Pro His Lys Asp Gly Asn Ser Cys Asn Val Gly Ser Pro Phe Ala
            755             760             765

Lys Asp Phe Leu Pro Lys Met Glu Asp Gly Thr Leu Gln Ala Gly Pro
770             775             780

Gly Gly Ala Ser Gly Pro Arg Ala Leu Glu Ile Asn Lys Met Ile Ser
785             790             795             800

Phe Trp Arg Asn Ala His Lys Arg Ile Ser Ser Gln Met Val Val Trp
            805             810             815

Leu Pro Arg Ser Ala Leu Pro Arg Ala Val Ile Arg His Pro Asp Tyr
            820             825             830

Asp Glu Glu Gly Leu Tyr Gly Ala Ile Leu Pro Gln Val Val Thr Ala
            835             840             845

Gly Thr Ile Thr Arg Arg Ala Val Glu Pro Thr Trp Leu Thr Ala Ser
            850             855             860

Asn Ala Arg Pro Asp Arg Val Gly Ser Glu Leu Lys Ala Met Val Gln
865             870             875             880

Ala Pro Pro Gly Tyr Thr Leu Val Gly Ala Asp Val Asp Ser Gln Glu
            885             890             895

Leu Trp Ile Ala Ala Val Leu Gly Asp Ala His Phe Ala Gly Met His
            900             905             910

Gly Cys Thr Ala Phe Gly Trp Met Thr Leu Gln Gly Arg Lys Ser Arg
```

-continued

Gly Thr Asp Leu His Ser Lys Thr Ala Thr Val Gly Ile Ser Arg
    915                 920                 925

Glu His Ala Lys Ile Phe Asn Tyr Gly Arg Ile Tyr Gly Ala Gly Gln
930                 935                 940

Pro Phe Ala Glu Arg Leu Leu Met Gln Phe Asn His Arg Leu Thr Gln
945                 950                 955                 960

Gln Glu Ala Ala Glu Lys Ala Gln Gln Met Tyr Ala Ala Thr Lys Gly
            965                 970                 975

Leu Arg Trp Tyr Arg Leu Ser Asp Glu Gly Glu Trp Leu Val Arg Glu
        980                 985                 990

Leu Asn Leu Pro Val Asp Arg Thr Glu Gly Gly Trp Ile Ser Leu
    995                 1000                1005

Gln Asp Leu Arg Lys Val Gln Arg Glu Thr Ala Arg Lys Ser Gln
    1010            1015            1020

Trp Lys Lys Trp Glu Val Val Ala Glu Arg Ala Trp Lys Gly Gly
    1025            1030            1035

Thr Glu Ser Glu Met Phe Asn Lys Leu Glu Ser Ile Ala Thr Ser
    1040            1045            1050

Asp Ile Pro Arg Thr Pro Val Leu Gly Cys Cys Ile Ser Arg Ala
    1055            1060            1065

Leu Glu Pro Ser Ala Val Gln Glu Glu Phe Met Thr Ser Arg Val
    1070            1075            1080

Asn Trp Val Val Gln Ser Ser Ala Val Asp Tyr Leu His Leu Met
    1085            1090            1095

Leu Val Ala Met Lys Trp Leu Phe Glu Glu Phe Ala Ile Asp Gly
    1100            1105            1110

Arg Phe Cys Ile Ser Ile His Asp Glu Val Arg Tyr Leu Val Arg
    1115            1120            1125

Glu Glu Asp Arg Tyr Arg Ala Ala Leu Ala Leu Gln Ile Thr Asn
    1130            1135            1140

Leu Leu Thr Arg Cys Met Phe Ala Tyr Lys Leu Gly Leu Asn Asp
    1145            1150            1155

Leu Pro Gln Ser Val Ala Phe Phe Ser Ala Val Asp Ile Asp Arg
    1160            1165            1170

Cys Leu Arg Lys Glu Val Thr Met Asp Cys Lys Thr Pro Ser Asn
    1175            1180            1185

Pro Thr Gly Met Glu Arg Arg Tyr Gly Ile Pro Gln Gly Glu Ala
    1190            1195            1200

Leu Asp Ile Tyr Gln Ile Ile Glu Leu Thr Lys Gly Ser Leu Glu
    1205            1210            1215

Lys Arg Ser Gln Pro Gly Pro
    1220            1225

<210> SEQ ID NO 88
<211> LENGTH: 900
<212> TYPE: PRT
<213> ORGANISM: Homo sapiens

<400> SEQUENCE: 88

Met Glu Asn Tyr Glu Ala Leu Val Gly Phe Asp Leu Cys Asn Thr Pro
1               5                   10                  15

Leu Ser Ser Val Ala Gln Lys Ile Met Ser Ala Met His Ser Gly Asp
                20                  25                  30

-continued

Leu Val Asp Ser Lys Thr Trp Gly Lys Ser Thr Glu Thr Met Glu Val
                35                  40                  45

Ile Asn Lys Ser Ser Val Lys Tyr Ser Val Gln Leu Glu Asp Arg Lys
    50                  55                  60

Thr Gln Ser Pro Glu Lys Lys Asp Leu Lys Ser Leu Arg Ser Gln Thr
65                  70                  75                  80

Ser Arg Gly Ser Ala Lys Leu Ser Pro Gln Ser Phe Ser Val Arg Leu
                85                  90                  95

Thr Asp Gln Leu Ser Ala Asp Gln Lys Gln Lys Ser Ile Ser Ser Leu
                100                 105                 110

Thr Leu Ser Ser Cys Leu Ile Pro Gln Tyr Asn Gln Glu Ala Ser Val
            115                 120                 125

Leu Gln Lys Lys Gly His Lys Arg Lys His Phe Leu Met Glu Asn Ile
        130                 135                 140

Asn Asn Glu Asn Lys Gly Ser Ile Asn Leu Lys Arg Lys His Ile Thr
145                 150                 155                 160

Tyr Asn Asn Leu Ser Glu Lys Thr Ser Lys Gln Met Ala Leu Glu Glu
                165                 170                 175

Asp Thr Asp Asp Ala Glu Gly Tyr Leu Asn Ser Gly Asn Ser Gly Ala
                180                 185                 190

Leu Lys Lys His Phe Cys Asp Ile Arg His Leu Asp Asp Trp Ala Lys
            195                 200                 205

Ser Gln Leu Ile Glu Met Leu Lys Gln Ala Ala Ala Leu Val Ile Thr
        210                 215                 220

Val Met Tyr Thr Asp Gly Ser Thr Gln Leu Gly Ala Asp Gln Thr Pro
225                 230                 235                 240

Val Ser Ser Val Arg Gly Ile Val Val Leu Val Lys Arg Gln Ala Glu
                245                 250                 255

Gly Gly His Gly Cys Pro Asp Ala Pro Ala Cys Gly Pro Val Leu Glu
                260                 265                 270

Gly Phe Val Ser Asp Asp Pro Cys Ile Tyr Ile Gln Ile Glu His Ser
            275                 280                 285

Ala Ile Trp Asp Gln Glu Gln Glu Ala His Gln Gln Phe Ala Arg Asn
        290                 295                 300

Val Leu Phe Gln Thr Met Lys Cys Lys Cys Pro Val Ile Cys Phe Asn
305                 310                 315                 320

Ala Lys Asp Phe Val Arg Ile Val Leu Gln Phe Phe Gly Asn Asp Gly
                325                 330                 335

Ser Trp Lys His Val Ala Asp Phe Ile Gly Leu Asp Pro Arg Ile Ala
            340                 345                 350

Ala Trp Leu Ile Asp Pro Ser Asp Ala Thr Pro Ser Phe Glu Asp Leu
        355                 360                 365

Val Glu Lys Tyr Cys Glu Lys Ser Ile Thr Val Lys Val Asn Ser Thr
370                 375                 380

Tyr Gly Asn Ser Ser Arg Asn Ile Val Asn Gln Asn Val Arg Glu Asn
385                 390                 395                 400

Leu Lys Thr Leu Tyr Arg Leu Thr Met Asp Leu Cys Ser Lys Leu Lys
                405                 410                 415

Asp Tyr Gly Leu Trp Gln Leu Phe Arg Thr Leu Glu Leu Pro Leu Ile
            420                 425                 430

Pro Ile Leu Ala Val Met Glu Ser His Ala Ile Gln Val Asn Lys Glu
        435                 440                 445

Glu Met Glu Lys Thr Ser Ala Leu Leu Gly Ala Arg Leu Lys Glu Leu

```
              450                 455                 460
    Glu Gln Glu Ala His Phe Val Ala Gly Glu Arg Phe Leu Ile Thr Ser
    465                 470                 475                 480

Asn Asn Gln Leu Arg Glu Ile Leu Phe Gly Lys Leu Lys Leu His Leu
                        485                 490                 495

Leu Ser Gln Arg Asn Ser Leu Pro Arg Thr Gly Leu Gln Lys Tyr Pro
                    500                 505                 510

Ser Thr Ser Glu Ala Val Leu Asn Ala Leu Arg Asp Leu His Pro Leu
                515                 520                 525

Pro Lys Ile Ile Leu Glu Tyr Arg Gln Val His Lys Ile Lys Ser Thr
            530                 535                 540

Phe Val Asp Gly Leu Leu Ala Cys Met Lys Lys Gly Ser Ile Ser Ser
    545                 550                 555                 560

Thr Trp Asn Gln Thr Gly Thr Val Thr Gly Arg Leu Ser Ala Lys His
                        565                 570                 575

Pro Asn Ile Gln Gly Ile Ser Lys His Pro Ile Gln Ile Thr Thr Pro
                    580                 585                 590

Lys Asn Phe Lys Gly Lys Glu Asp Lys Ile Leu Thr Ile Ser Pro Arg
                595                 600                 605

Ala Met Phe Val Ser Ser Lys Gly His Thr Phe Leu Ala Ala Asp Phe
            610                 615                 620

Ser Gln Ile Glu Leu Arg Ile Leu Thr His Leu Ser Gly Asp Pro Glu
    625                 630                 635                 640

Leu Leu Lys Leu Phe Gln Glu Ser Glu Arg Asp Asp Val Phe Ser Thr
                        645                 650                 655

Leu Thr Ser Gln Trp Lys Asp Val Pro Val Glu Gln Val Thr His Ala
                    660                 665                 670

Asp Arg Glu Gln Thr Lys Lys Val Val Tyr Ala Val Val Tyr Gly Ala
                675                 680                 685

Gly Lys Glu Arg Leu Ala Ala Cys Leu Gly Val Pro Ile Gln Glu Ala
            690                 695                 700

Ala Gln Phe Leu Glu Ser Phe Leu Gln Lys Tyr Lys Lys Ile Lys Asp
    705                 710                 715                 720

Phe Ala Arg Ala Ala Ile Ala Gln Cys His Gln Thr Gly Cys Val Val
                        725                 730                 735

Ser Ile Met Gly Arg Arg Arg Pro Leu Pro Arg Ile His Ala His Asp
                    740                 745                 750

Gln Gln Leu Arg Ala Gln Ala Glu Arg Gln Ala Val Asn Phe Val Val
                755                 760                 765

Gln Gly Ser Ala Ala Asp Leu Cys Lys Leu Ala Met Ile His Val Phe
            770                 775                 780

Thr Ala Val Ala Ala Ser His Thr Leu Thr Arg Leu Val Ala Gln
    785                 790                 795                 800

Ile His Asp Glu Leu Leu Phe Glu Val Glu Asp Pro Gln Ile Pro Glu
                        805                 810                 815

Cys Ala Ala Leu Val Arg Arg Thr Met Glu Ser Leu Glu Gln Val Gln
                    820                 825                 830

Ala Leu Glu Leu Gln Leu Gln Val Pro Leu Lys Val Ser Leu Ser Ala
                835                 840                 845

Gly Arg Ser Trp Gly His Leu Val Pro Leu Gln Glu Ala Trp Gly Pro
            850                 855                 860

Pro Pro Gly Pro Cys Arg Thr Glu Ser Pro Ser Asn Ser Leu Ala Ala
    865                 870                 875                 880
```

```
Pro Gly Ser Pro Ala Ser Thr Gln Pro Pro Leu His Phe Ser Pro
                885                 890                 895

Ser Phe Cys Leu
            900

<210> SEQ ID NO 89
<211> LENGTH: 542
<212> TYPE: PRT
<213> ORGANISM: Homo sapiens

<400> SEQUENCE: 89

Met Ala Ser Pro Cys Pro Glu Glu Ala Met Arg Arg Glu Val Val
1               5                   10                  15

Lys Arg Ile Glu Thr Val Val Lys Asp Leu Trp Pro Thr Ala Asp Val
                20                  25                  30

Gln Ile Phe Gly Ser Phe Ser Thr Gly Leu Tyr Leu Pro Thr Ser Asp
                35                  40                  45

Ile Asp Leu Val Val Phe Gly Lys Trp Glu Arg Pro Pro Leu Gln Leu
50                  55                  60

Leu Glu Gln Ala Leu Arg Lys His Asn Val Ala Glu Pro Cys Ser Ile
65                  70                  75                  80

Lys Val Leu Asp Lys Ala Thr Val Pro Ile Ile Lys Leu Thr Asp Gln
                85                  90                  95

Glu Thr Glu Val Lys Val Asp Ile Ser Phe Asn Met Glu Thr Gly Val
                100                 105                 110

Arg Ala Ala Glu Phe Ile Lys Asn Tyr Met Lys Lys Tyr Ser Leu Leu
                115                 120                 125

Pro Tyr Leu Ile Leu Val Leu Lys Gln Phe Leu Leu Gln Arg Asp Leu
            130                 135                 140

Asn Glu Val Phe Thr Gly Gly Ile Ser Ser Tyr Ser Leu Ile Leu Met
145                 150                 155                 160

Ala Ile Ser Phe Leu Gln Leu His Pro Arg Ile Asp Ala Arg Arg Ala
                165                 170                 175

Asp Glu Asn Leu Gly Met Leu Leu Val Glu Phe Phe Glu Leu Tyr Gly
                180                 185                 190

Arg Asn Phe Asn Tyr Leu Lys Thr Gly Ile Arg Ile Lys Glu Gly Gly
            195                 200                 205

Ala Tyr Ile Ala Lys Glu Glu Ile Met Lys Ala Met Thr Ser Gly Tyr
            210                 215                 220

Arg Pro Ser Met Leu Cys Ile Glu Asp Pro Leu Leu Pro Gly Asn Asp
225                 230                 235                 240

Val Gly Arg Ser Ser Tyr Gly Ala Met Gln Val Lys Gln Val Phe Asp
                245                 250                 255

Tyr Ala Tyr Ile Val Leu Ser His Ala Val Ser Pro Leu Ala Arg Ser
                260                 265                 270

Tyr Pro Asn Arg Asp Ala Glu Ser Thr Leu Gly Arg Ile Ile Lys Val
            275                 280                 285

Thr Gln Glu Val Ile Asp Tyr Arg Arg Trp Ile Lys Glu Lys Trp Gly
            290                 295                 300

Ser Lys Ala His Pro Ser Pro Gly Met Asp Ser Arg Ile Lys Ile Lys
305                 310                 315                 320

Glu Arg Ile Ala Thr Cys Asn Gly Glu Gln Thr Gln Asn Arg Glu Pro
                325                 330                 335

Glu Ser Pro Tyr Gly Gln Arg Leu Thr Leu Ser Leu Ser Ser Pro Gln
```

```
            340                 345                 350
Leu Leu Ser Ser Gly Ser Ser Ala Ser Ser Val Ser Ser Leu Ser Gly
            355                 360                 365

Ser Asp Val Asp Ser Asp Thr Pro Pro Cys Thr Thr Pro Ser Val Tyr
    370                 375                 380

Gln Phe Ser Leu Gln Ala Pro Ala Pro Leu Met Ala Gly Leu Pro Thr
385                 390                 395                 400

Ala Leu Pro Met Pro Ser Gly Lys Pro Gln Pro Thr Thr Ser Arg Thr
                405                 410                 415

Leu Ile Met Thr Thr Asn Asn Gln Thr Arg Phe Thr Ile Pro Pro Pro
            420                 425                 430

Thr Leu Gly Val Ala Pro Val Pro Cys Arg Gln Ala Gly Val Glu Gly
        435                 440                 445

Thr Ala Ser Leu Lys Ala Val His His Met Ser Ser Pro Ala Ile Pro
        450                 455                 460

Ser Ala Ser Pro Asn Pro Leu Ser Ser Pro His Leu Tyr His Lys His
465                 470                 475                 480

Asn Gly Met Lys Leu Ser Met Lys Gly Ser His Gly His Thr Gln Gly
                485                 490                 495

Gly Gly Tyr Ser Ser Val Gly Ser Gly Val Arg Pro Pro Val Gly
            500                 505                 510

Asn Arg Gly His His Gln Tyr Asn Arg Thr Gly Trp Arg Arg Lys Lys
            515                 520                 525

His Thr His Thr Arg Asp Ser Leu Pro Val Ser Leu Ser Arg
        530                 535                 540

<210> SEQ ID NO 90
<211> LENGTH: 911
<212> TYPE: PRT
<213> ORGANISM: Homo sapiens

<400> SEQUENCE: 90

Met Ala Ala Ser Gln Thr Ser Gln Thr Val Ala Ser His Val Pro Phe
1               5                   10                  15

Ala Asp Leu Cys Ser Thr Leu Glu Arg Ile Gln Lys Ser Lys Gly Arg
                20                  25                  30

Ala Glu Lys Ile Arg His Phe Arg Glu Phe Leu Asp Ser Trp Arg Lys
            35                  40                  45

Phe His Asp Ala Leu His Lys Asn His Lys Asp Val Thr Asp Ser Phe
    50                  55                  60

Tyr Pro Ala Met Arg Leu Ile Leu Pro Gln Leu Glu Arg Glu Arg Met
65                  70                  75                  80

Ala Tyr Gly Ile Lys Glu Thr Met Leu Ala Lys Leu Tyr Ile Glu Leu
                85                  90                  95

Leu Asn Leu Pro Arg Asp Gly Lys Asp Ala Leu Lys Leu Leu Asn Tyr
                100                 105                 110

Arg Thr Pro Thr Gly Thr His Gly Asp Ala Gly Asp Phe Ala Met Ile
            115                 120                 125

Ala Tyr Phe Val Leu Lys Pro Arg Cys Leu Gln Lys Gly Ser Leu Thr
    130                 135                 140

Ile Gln Gln Val Asn Asp Leu Leu Asp Ser Ile Ala Ser Asn Asn Ser
145                 150                 155                 160

Ala Lys Arg Lys Asp Leu Ile Lys Lys Ser Leu Leu Gln Leu Ile Thr
                165                 170                 175
```

Gln Ser Ser Ala Leu Glu Gln Lys Trp Leu Ile Arg Met Ile Ile Lys
                180                 185                 190

Asp Leu Lys Leu Gly Val Ser Gln Gln Thr Ile Phe Ser Val Phe His
            195                 200                 205

Asn Asp Ala Ala Glu Leu His Asn Val Thr Thr Asp Leu Glu Lys Val
        210                 215                 220

Cys Arg Gln Leu His Asp Pro Ser Val Gly Leu Ser Asp Ile Ser Ile
225                 230                 235                 240

Thr Leu Phe Ser Ala Phe Lys Pro Met Leu Ala Ala Ile Ala Asp Ile
                245                 250                 255

Glu His Ile Glu Lys Asp Met Lys His Gln Ser Phe Tyr Ile Glu Thr
            260                 265                 270

Lys Leu Asp Gly Glu Arg Met Gln Met His Lys Asp Gly Asp Val Tyr
        275                 280                 285

Lys Tyr Phe Ser Arg Asn Gly Tyr Asn Tyr Thr Asp Gln Phe Gly Ala
290                 295                 300

Ser Pro Thr Glu Gly Ser Leu Thr Pro Phe Ile His Asn Ala Phe Lys
305                 310                 315                 320

Ala Asp Ile Gln Ile Cys Ile Leu Asp Gly Glu Met Met Ala Tyr Asn
                325                 330                 335

Pro Asn Thr Gln Thr Phe Met Gln Lys Gly Thr Lys Phe Asp Ile Lys
            340                 345                 350

Arg Met Val Glu Asp Ser Asp Leu Gln Thr Cys Tyr Cys Val Phe Asp
        355                 360                 365

Val Leu Met Val Asn Asn Lys Lys Leu Gly His Glu Thr Leu Arg Lys
370                 375                 380

Arg Tyr Glu Ile Leu Ser Ser Ile Phe Thr Pro Ile Pro Gly Arg Ile
385                 390                 395                 400

Glu Ile Val Gln Lys Thr Gln Ala His Thr Lys Asn Glu Val Ile Asp
                405                 410                 415

Ala Leu Asn Glu Ala Ile Asp Lys Arg Glu Glu Gly Ile Met Val Lys
            420                 425                 430

Gln Pro Leu Ser Ile Tyr Lys Pro Asp Lys Arg Gly Glu Gly Trp Leu
        435                 440                 445

Lys Ile Lys Pro Glu Tyr Val Ser Gly Leu Met Asp Glu Leu Asp Ile
450                 455                 460

Leu Ile Val Gly Gly Tyr Trp Gly Lys Gly Ser Arg Gly Gly Met Met
465                 470                 475                 480

Ser His Phe Leu Cys Ala Val Ala Glu Lys Pro Pro Gly Glu Lys
                485                 490                 495

Pro Ser Val Phe His Thr Leu Ser Arg Val Gly Ser Gly Cys Thr Met
            500                 505                 510

Lys Glu Leu Tyr Asp Leu Gly Leu Lys Leu Ala Lys Tyr Trp Lys Pro
        515                 520                 525

Phe His Arg Lys Ala Pro Pro Ser Ser Ile Leu Cys Gly Thr Glu Lys
530                 535                 540

Pro Glu Val Tyr Ile Glu Pro Cys Asn Ser Val Ile Val Gln Ile Lys
545                 550                 555                 560

Ala Ala Glu Ile Val Pro Ser Asp Met Tyr Lys Thr Gly Cys Thr Leu
                565                 570                 575

Arg Phe Pro Arg Ile Glu Lys Ile Arg Asp Asp Lys Glu Trp His Glu
            580                 585                 590

Cys Met Thr Leu Asp Asp Leu Glu Gln Leu Arg Gly Lys Ala Ser Gly

```
                595                 600                 605
Lys Leu Ala Ser Lys His Leu Tyr Ile Gly Gly Asp Asp Glu Pro Gln
610                 615                 620

Glu Lys Lys Arg Lys Ala Ala Pro Lys Met Lys Lys Val Ile Gly Ile
625                 630                 635                 640

Ile Glu His Leu Lys Ala Pro Asn Leu Thr Asn Val Asn Lys Ile Ser
                645                 650                 655

Asn Ile Phe Glu Asp Val Glu Phe Cys Val Met Ser Gly Thr Asp Ser
                660                 665                 670

Gln Pro Lys Pro Asp Leu Glu Asn Arg Ile Ala Glu Phe Gly Gly Tyr
            675                 680                 685

Ile Val Gln Asn Pro Gly Pro Asp Thr Tyr Cys Val Ile Ala Gly Ser
690                 695                 700

Glu Asn Ile Arg Val Lys Asn Ile Ile Leu Ser Asn Lys His Asp Val
705                 710                 715                 720

Val Lys Pro Ala Trp Leu Leu Glu Cys Phe Lys Thr Lys Ser Phe Val
                725                 730                 735

Pro Trp Gln Pro Arg Phe Met Ile His Met Cys Pro Ser Thr Lys Glu
            740                 745                 750

His Phe Ala Arg Glu Tyr Asp Cys Tyr Gly Asp Ser Tyr Phe Ile Asp
                755                 760                 765

Thr Asp Leu Asn Gln Leu Lys Glu Val Phe Ser Gly Ile Lys Asn Ser
770                 775                 780

Asn Glu Gln Thr Pro Glu Glu Met Ala Ser Leu Ile Ala Asp Leu Glu
785                 790                 795                 800

Tyr Arg Tyr Ser Trp Asp Cys Ser Pro Leu Ser Met Phe Arg Arg His
                805                 810                 815

Thr Val Tyr Leu Asp Ser Tyr Ala Val Ile Asn Asp Leu Ser Thr Lys
            820                 825                 830

Asn Glu Gly Thr Arg Leu Ala Ile Lys Ala Leu Glu Leu Arg Phe His
            835                 840                 845

Gly Ala Lys Val Val Ser Cys Leu Ala Glu Gly Val Ser His Val Ile
850                 855                 860

Ile Gly Glu Asp His Ser Arg Val Ala Asp Phe Lys Ala Phe Arg Arg
865                 870                 875                 880

Thr Phe Lys Arg Lys Phe Lys Ile Leu Lys Glu Ser Trp Val Thr Asp
                885                 890                 895

Ser Ile Asp Lys Cys Glu Leu Gln Glu Glu Asn Gln Tyr Leu Ile
            900                 905                 910

<210> SEQ ID NO 91
<211> LENGTH: 1028
<212> TYPE: PRT
<213> ORGANISM: Homo sapiens

<400> SEQUENCE: 91

Met Gly Ser Ala Ala Cys Pro Arg Gly Ala Leu Pro Glu Leu Ala Pro
1               5                   10                  15

Cys Cys Gln Pro Arg Glu Gln Ser Gln Pro His Thr Arg Trp Asp Ala
            20                  25                  30

Gly Cys Gly Ile Gln His Pro Gly Gly Glu Glu Phe Arg Thr Leu Gly
        35                  40                  45

Gly Ala Arg Ala Tyr Arg Val Pro Asn Ser Gln Glu Gly Arg Ser Ser
    50                  55                  60
```

```
Pro Thr Arg Phe Phe Pro Ala Pro Glu Gly Pro Ala His Cys Phe Val
 65                  70                  75                  80

Ser Ser Pro Asp Arg Ala Phe Trp Val Ser Glu Glu Val Gln Arg Leu
                 85                  90                  95

Leu Leu Ser Asn Ala Cys Gln Pro Lys Glu Cys Asn Gly Val Lys Ile
            100                 105                 110

Pro Val Asp Ala Ser Lys Pro Asn Pro Asn Asp Val Glu Phe Asp Asn
        115                 120                 125

Leu Tyr Leu Asp Met Asn Gly Ile Ile His Pro Cys Thr His Pro Glu
    130                 135                 140

Asp Lys Pro Ala Pro Lys Asn Glu Asp Glu Met Met Val Ala Ile Phe
145                 150                 155                 160

Glu Tyr Ile Asp Arg Leu Phe Ser Ile Val Arg Pro Arg Arg Leu Leu
                165                 170                 175

Tyr Met Ala Ile Asp Gly Val Ala Pro Arg Ala Lys Met Asn Gln Gln
            180                 185                 190

Arg Ser Arg Arg Phe Arg Ala Ser Lys Glu Gly Met Glu Ala Ala Val
        195                 200                 205

Glu Lys Gln Arg Val Arg Glu Glu Ile Leu Ala Lys Gly Gly Phe Leu
    210                 215                 220

Pro Pro Glu Glu Ile Lys Glu Arg Phe Asp Ser Asn Cys Ile Thr Pro
225                 230                 235                 240

Gly Thr Glu Phe Met Asp Asn Leu Ala Lys Cys Leu Arg Tyr Tyr Ile
                245                 250                 255

Ala Asp Arg Leu Asn Asn Asp Pro Gly Trp Lys Asn Leu Thr Val Ile
            260                 265                 270

Leu Ser Asp Ala Ser Ala Pro Gly Glu Gly Glu His Lys Ile Met Asp
        275                 280                 285

Tyr Ile Arg Arg Gln Arg Ala Gln Pro Asn His Asp Pro Asn Thr His
    290                 295                 300

His Cys Leu Cys Gly Ala Asp Ala Asp Leu Ile Met Leu Gly Leu Ala
305                 310                 315                 320

Thr His Glu Pro Asn Phe Thr Ile Ile Arg Glu Glu Phe Lys Pro Asn
                325                 330                 335

Lys Pro Lys Pro Cys Gly Leu Cys Asn Gln Phe Gly His Glu Val Lys
            340                 345                 350

Asp Cys Glu Gly Leu Pro Arg Glu Lys Lys Gly Lys His Asp Glu Leu
        355                 360                 365

Ala Asp Ser Leu Pro Cys Ala Glu Gly Glu Phe Ile Phe Leu Arg Leu
    370                 375                 380

Asn Val Leu Arg Glu Tyr Leu Glu Arg Glu Leu Thr Met Ala Ser Leu
385                 390                 395                 400

Pro Phe Thr Phe Asp Val Glu Arg Ser Ile Asp Asp Trp Val Phe Met
                405                 410                 415

Cys Phe Phe Val Gly Asn Asp Phe Leu Pro His Leu Pro Ser Leu Glu
            420                 425                 430

Ile Arg Glu Asn Ala Ile Asp Arg Leu Val Asn Ile Tyr Lys Asn Val
        435                 440                 445

Val His Lys Thr Gly Gly Tyr Leu Thr Glu Ser Gly Tyr Val Asn Leu
    450                 455                 460

Gln Arg Val Gln Met Ile Met Leu Ala Val Gly Glu Val Glu Asp Ser
465                 470                 475                 480

Ile Phe Lys Lys Arg Lys Asp Asp Glu Asp Ser Phe Arg Arg Arg Gln
```

-continued

```
              485                 490                 495
Lys Glu Lys Arg Lys Arg Met Lys Arg Asp Gln Pro Ala Phe Thr Pro
            500                 505                 510

Ser Gly Ile Leu Thr Pro His Ala Leu Gly Ser Arg Asn Ser Pro Gly
            515                 520                 525

Ser Gln Val Ala Ser Asn Pro Arg Gln Ala Ala Tyr Glu Met Arg Met
            530                 535                 540

Gln Asn Asn Ser Ser Pro Ser Ile Ser Pro Asn Thr Ser Phe Thr Ser
545                 550                 555                 560

Asp Gly Ser Pro Ser Pro Leu Gly Gly Ile Lys Arg Lys Ala Glu Asp
            565                 570                 575

Ser Asp Ser Glu Pro Glu Pro Glu Asp Asn Val Arg Leu Trp Glu Ala
            580                 585                 590

Gly Trp Lys Gln Arg Tyr Tyr Lys Asn Lys Phe Asp Val Asp Ala Ala
            595                 600                 605

Asp Glu Lys Phe Arg Arg Lys Val Val Gln Ser Tyr Val Glu Gly Leu
            610                 615                 620

Cys Trp Val Leu Arg Tyr Tyr Gln Gly Cys Ala Ser Trp Lys Trp
625                 630                 635                 640

Tyr Tyr Pro Phe His Tyr Ala Pro Phe Ala Ser Asp Phe Glu Gly Ile
                645                 650                 655

Ala Asp Met Pro Ser Asp Phe Glu Lys Gly Thr Lys Pro Phe Lys Pro
                660                 665                 670

Leu Glu Gln Leu Met Gly Val Phe Pro Ala Ala Ser Gly Asn Phe Leu
                675                 680                 685

Pro Pro Ser Trp Arg Lys Leu Met Ser Asp Pro Asp Ser Ser Ile Ile
            690                 695                 700

Asp Phe Tyr Pro Glu Asp Phe Ala Ile Asp Leu Asn Gly Lys Lys Tyr
705                 710                 715                 720

Ala Trp Gln Gly Val Ala Leu Leu Pro Phe Val Asp Glu Arg Arg Leu
                725                 730                 735

Arg Ala Ala Leu Glu Glu Val Tyr Pro Asp Leu Thr Pro Glu Glu Thr
                740                 745                 750

Arg Arg Asn Ser Leu Gly Gly Asp Val Leu Phe Val Gly Lys His His
            755                 760                 765

Pro Leu His Asp Phe Ile Leu Glu Leu Tyr Gln Thr Gly Ser Thr Glu
            770                 775                 780

Pro Val Glu Val Pro Pro Glu Leu Cys His Gly Ile Gln Gly Lys Phe
785                 790                 795                 800

Ser Leu Asp Glu Glu Ala Ile Leu Pro Asp Gln Ile Val Cys Ser Pro
                805                 810                 815

Val Pro Met Leu Arg Asp Leu Thr Gln Asn Thr Val Val Ser Ile Asn
                820                 825                 830

Phe Lys Asp Pro Gln Phe Ala Glu Asp Tyr Ile Phe Lys Ala Val Met
            835                 840                 845

Leu Pro Gly Ala Arg Lys Pro Ala Ala Val Leu Lys Pro Ser Asp Trp
            850                 855                 860

Glu Lys Ser Ser Asn Gly Arg Gln Trp Lys Pro Gln Leu Gly Phe Asn
865                 870                 875                 880

Arg Asp Arg Arg Pro Val His Leu Asp Gln Ala Ala Phe Arg Thr Leu
            885                 890                 895

Gly His Val Met Pro Arg Gly Ser Gly Thr Gly Ile Tyr Ser Asn Ala
            900                 905                 910
```

```
Ala Pro Pro Pro Val Thr Tyr Gln Gly Asn Leu Tyr Arg Pro Leu Leu
            915                 920                 925

Arg Gly Gln Ala Gln Ile Pro Lys Leu Met Ser Asn Met Arg Pro Gln
    930                 935                 940

Asp Ser Trp Arg Gly Pro Pro Leu Phe Gln Gln Gln Arg Phe Asp
945                 950                 955                 960

Arg Gly Val Gly Ala Glu Pro Leu Leu Pro Trp Asn Arg Met Leu Gln
                965                 970                 975

Thr Gln Asn Ala Ala Phe Gln Pro Asn Gln Tyr Gln Met Leu Ala Gly
            980                 985                 990

Pro Gly Gly Tyr Pro Pro Arg Arg Asp Asp Arg Gly Gly Arg Gln Gly
        995                 1000                1005

Tyr Pro Arg Glu Gly Arg Lys Tyr Pro Leu Pro Pro Pro Ser Gly
1010                1015                1020

Arg Tyr Asn Trp Asn
1025

<210> SEQ ID NO 92
<211> LENGTH: 620
<212> TYPE: PRT
<213> ORGANISM: Artificial Sequence
<220> FEATURE:
<223> OTHER INFORMATION: Fusion protein

<400> SEQUENCE: 92

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Ser Leu Lys Gly Lys Phe Phe Ala
        35                  40                  45

Phe Leu Pro Asn Pro Asn Thr Ser Ser Asn Lys Phe Phe Lys Ser Ile
    50                  55                  60

Leu Glu Lys Lys Gly Ala Thr Ile Val Ser Ser Ile Gln Asn Cys Leu
65                  70                  75                  80

Gln Ser Ser Arg Lys Glu Val Ile Ile Leu Ile Glu Asp Ser Phe Val
                85                  90                  95

Asp Ser Asp Met His Leu Thr Gln Lys Asp Ile Phe Gln Arg Glu Ala
            100                 105                 110

Gly Leu Asn Asp Val Asp Glu Phe Leu Gly Lys Ile Glu Gln Ser Gly
        115                 120                 125

Ile Gln Cys Val Lys Thr Ser Cys Ile Thr Lys Trp Val Gln Asn Asp
    130                 135                 140

Lys Phe Ala Phe Gln Lys Asp Asp Leu Ile Lys Phe Gln Pro Ser Ile
145                 150                 155                 160

Ile Val Ile Ser Asp Asn Ala Asp Gly Gln Ser Ser Thr Asp Lys
                165                 170                 175

Glu Ser Glu Ile Ser Thr Asp Val Glu Ser Glu Arg Asn Asp Asp Ser
            180                 185                 190

Asn Asn Lys Asp Met Ile Gln Ala Ser Lys Pro Leu Lys Arg Leu Leu
        195                 200                 205

Gln Glu Asp Lys Gly Arg Ala Ser Leu Val Thr Asp Lys Thr Lys Tyr
    210                 215                 220

Lys Asn Asn Glu Leu Ile Ile Gly Ala Leu Lys Arg Leu Thr Lys Lys
225                 230                 235                 240
```

Tyr Glu Ile Glu Gly Glu Lys Phe Arg Ala Arg Ser Tyr Arg Leu Ala
                245                 250                 255

Lys Gln Ser Met Glu Asn Cys Asp Phe Asn Val Arg Ser Gly Glu Glu
            260                 265                 270

Ala His Thr Lys Leu Arg Asn Ile Gly Pro Ser Ile Ala Lys Lys Ile
        275                 280                 285

Gln Val Ile Leu Asp Thr Gly Val Leu Pro Gly Leu Asn Asp Ser Val
    290                 295                 300

Gly Leu Glu Asp Lys Leu Lys Tyr Phe Lys Asn Cys Tyr Gly Ile Gly
305                 310                 315                 320

Ser Glu Ile Ala Lys Arg Trp Asn Leu Leu Asn Phe Glu Ser Phe Cys
                325                 330                 335

Val Ala Ala Lys Lys Asp Pro Glu Glu Phe Val Ser Asp Trp Thr Ile
            340                 345                 350

Leu Phe Gly Trp Ser Tyr Tyr Asp Asp Trp Leu Cys Lys Met Ser Arg
        355                 360                 365

Asn Glu Cys Phe Ala His Leu Lys Lys Val Gln Lys Ala Leu Arg Gly
    370                 375                 380

Ile Asp Pro Glu Cys Gln Val Glu Leu Gln Gly Ser Tyr Asn Arg Gly
385                 390                 395                 400

Tyr Ser Lys Cys Gly Asp Ile Asp Leu Leu Phe Phe Lys Pro Phe Cys
                405                 410                 415

Asn Asp Thr Thr Glu Leu Ala Lys Ile Met Glu Thr Leu Cys Ile Lys
            420                 425                 430

Leu Tyr Lys Asp Gly Tyr Ile His Cys Phe Leu Gln Leu Thr Pro Asn
        435                 440                 445

Leu Glu Lys Leu Phe Leu Lys Arg Ile Val Glu Arg Phe Arg Thr Ala
    450                 455                 460

Lys Ile Val Gly Tyr Gly Glu Arg Lys Arg Trp Tyr Ser Ser Glu Ile
465                 470                 475                 480

Ile Lys Lys Phe Phe Met Gly Val Lys Leu Ser Pro Arg Glu Leu Glu
                485                 490                 495

Glu Leu Lys Glu Met Lys Asn Asp Glu Gly Thr Leu Leu Ile Glu Glu
            500                 505                 510

Glu Glu Glu Glu Thr Lys Leu Lys Pro Ile Asp Gln Tyr Met Ser Leu
        515                 520                 525

Asn Ala Lys Asp Gly Asn Tyr Cys Arg Arg Leu Asp Phe Phe Cys Cys
    530                 535                 540

Lys Trp Asp Glu Leu Gly Ala Gly Arg Ile His Tyr Thr Gly Ser Lys
545                 550                 555                 560

Glu Tyr Asn Arg Trp Ile Arg Ile Leu Ala Ala Gln Lys Gly Phe Lys
                565                 570                 575

Leu Thr Gln His Gly Leu Phe Arg Asn Asn Ile Leu Leu Glu Ser Phe
            580                 585                 590

Asn Glu Arg Arg Ile Phe Glu Leu Leu Asn Leu Lys Tyr Ala Glu Pro
        595                 600                 605

Glu His Arg Asn Ile Glu Trp Glu Lys Lys Thr Gly
    610                 615                 620

<210> SEQ ID NO 93
<211> LENGTH: 495
<212> TYPE: PRT
<213> ORGANISM: Artificial Sequence
<220> FEATURE:

-continued

<223> OTHER INFORMATION: Fusion protein

<400> SEQUENCE: 93

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Leu Pro Ser Gln Ser Pro Ala Ile
            35                  40                  45

Phe Thr Val Ser Arg Leu Asn Gln Thr Val Arg Leu Leu Glu His
        50                  55                  60

Glu Met Gly Gln Val Trp Ile Ser Gly Glu Ile Ser Asn Phe Thr Gln
65                  70                  75                  80

Pro Ala Ser Gly His Trp Tyr Phe Thr Leu Lys Asp Asp Thr Ala Gln
                85                  90                  95

Val Arg Cys Ala Met Phe Arg Asn Ser Asn Arg Arg Val Thr Phe Arg
            100                 105                 110

Pro Gln His Gly Gln Gln Val Leu Val Arg Ala Asn Ile Thr Leu Tyr
        115                 120                 125

Glu Pro Arg Gly Asp Tyr Gln Ile Ile Val Glu Ser Met Gln Pro Ala
130                 135                 140

Gly Glu Gly Leu Leu Gln Gln Lys Tyr Glu Gln Leu Lys Ala Lys Leu
145                 150                 155                 160

Gln Ala Glu Gly Leu Phe Asp Gln Gln Tyr Lys Lys Pro Leu Pro Ser
                165                 170                 175

Pro Ala His Cys Val Gly Val Ile Thr Ser Lys Thr Gly Ala Ala Leu
            180                 185                 190

His Asp Ile Leu His Val Leu Lys Arg Arg Asp Pro Ser Leu Pro Val
        195                 200                 205

Ile Ile Tyr Pro Ala Ala Val Gln Gly Asp Asp Ala Pro Gly Gln Ile
210                 215                 220

Val Arg Ala Ile Glu Leu Ala Asn Gln Arg Asn Glu Cys Asp Val Leu
225                 230                 235                 240

Ile Val Gly Arg Gly Gly Ser Leu Glu Asp Leu Trp Ser Phe Asn
                245                 250                 255

Asp Glu Arg Val Ala Arg Ala Ile Phe Thr Ser Arg Ile Pro Val Val
            260                 265                 270

Ser Ala Val Gly His Glu Thr Asp Val Thr Ile Ala Asp Phe Val Ala
        275                 280                 285

Asp Leu Arg Ala Pro Thr Pro Ser Ala Ala Ala Glu Val Val Ser Arg
290                 295                 300

Asn Gln Gln Glu Leu Leu Arg Gln Val Gln Ser Thr Arg Gln Arg Leu
305                 310                 315                 320

Glu Met Ala Met Asp Tyr Tyr Leu Ala Asn Arg Thr Arg Arg Phe Thr
                325                 330                 335

Gln Ile His His Arg Leu Gln Gln His Pro Gln Leu Arg Leu Ala
            340                 345                 350

Arg Gln Gln Thr Met Leu Glu Arg Leu Gln Lys Arg Met Ser Phe Ala
        355                 360                 365

Leu Glu Asn Gln Leu Lys Arg Thr Gly Gln Gln Gln Arg Leu Thr
370                 375                 380

Gln Arg Leu Asn Gln Gln Asn Pro Gln Pro Lys Ile His Arg Ala Gln
385                 390                 395                 400
```

Thr Arg Ile Gln Gln Leu Glu Tyr Arg Leu Ala Glu Thr Leu Arg Ala
                405                 410                 415

Gln Leu Ser Ala Thr Arg Glu Arg Phe Gly Asn Ala Val Thr His Leu
            420                 425                 430

Glu Ala Val Ser Pro Leu Ser Thr Leu Ala Arg Gly Tyr Ser Val Thr
        435                 440                 445

Thr Ala Thr Asp Gly Asn Val Leu Lys Lys Val Lys Gln Val Lys Ala
    450                 455                 460

Gly Glu Met Leu Thr Thr Arg Leu Glu Asp Gly Trp Ile Glu Ser Glu
465                 470                 475                 480

Val Lys Asn Ile Gln Pro Val Lys Lys Ser Arg Lys Lys Val His
                485                 490                 495

<210> SEQ ID NO 94
<211> LENGTH: 119
<212> TYPE: PRT
<213> ORGANISM: Artificial Sequence
<220> FEATURE:
<223> OTHER INFORMATION: Fusion protein

<400> SEQUENCE: 94

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Pro Lys Lys Asn Glu Ala Pro Ala
        35                  40                  45

Ser Phe Glu Lys Ala Leu Ser Glu Leu Glu Gln Ile Val Thr Arg Leu
    50                  55                  60

Glu Ser Gly Asp Leu Pro Leu Glu Glu Ala Leu Asn Glu Phe Glu Arg
65                  70                  75                  80

Gly Val Gln Leu Ala Arg Gln Gly Gln Ala Lys Leu Gln Gln Ala Glu
                85                  90                  95

Gln Arg Val Gln Ile Leu Leu Ser Asp Asn Glu Asp Ala Ser Leu Thr
            100                 105                 110

Pro Phe Thr Pro Asp Asn Glu
        115

<210> SEQ ID NO 95
<211> LENGTH: 1423
<212> TYPE: PRT
<213> ORGANISM: Artificial Sequence
<220> FEATURE:
<223> OTHER INFORMATION: Fusion protein

<400> SEQUENCE: 95

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

```
Thr Ala Glu Ala Thr Arg Leu Lys Arg Thr Ala Arg Arg Tyr Thr
                100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510
```

```
Thr Pro Trp Asn Phe Glu Glu Val Asp Lys Gly Ala Ser Ala Gln
            515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
            610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
675                 680                 685

Gln Leu Lys Arg Arg Arg Tyr Thr Gly Trp Gly Arg Leu Ser Arg Lys
    690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
```

-continued

```
                930            935              940
Gly Gly Leu Ser Glu Leu Asp Lys Ala Gly Phe Ile Lys Arg Gln Leu
945                 950              955                 960

Val Glu Thr Arg Gln Ile Thr Lys His Val Ala Gln Ile Leu Asp Ser
            965              970              975

Arg Met Asn Thr Lys Tyr Asp Glu Asn Asp Lys Leu Ile Arg Glu Val
            980              985              990

Lys Val Ile Thr Leu Lys Ser Lys Leu Val Ser Asp Phe Arg Lys Asp
        995             1000             1005

Phe Gln Phe Tyr Lys Val Arg Glu Ile Asn Asn Tyr His His Ala
    1010            1015            1020

His Asp Ala Tyr Leu Asn Ala Val Val Gly Thr Ala Leu Ile Lys
    1025            1030            1035

Lys Tyr Pro Lys Leu Glu Ser Glu Phe Val Tyr Gly Asp Tyr Lys
    1040            1045            1050

Val Tyr Asp Val Arg Lys Met Ile Ala Lys Ser Glu Gln Glu Ile
    1055            1060            1065

Gly Lys Ala Thr Ala Lys Tyr Phe Phe Tyr Ser Asn Ile Met Asn
    1070            1075            1080

Phe Phe Lys Thr Glu Ile Thr Leu Ala Asn Gly Glu Ile Arg Lys
    1085            1090            1095

Arg Pro Leu Ile Glu Thr Asn Gly Glu Thr Gly Glu Ile Val Trp
    1100            1105            1110

Asp Lys Gly Arg Asp Phe Ala Thr Val Arg Lys Val Leu Ser Met
    1115            1120            1125

Pro Gln Val Asn Ile Val Lys Lys Thr Glu Val Gln Thr Gly Gly
    1130            1135            1140

Phe Ser Lys Glu Ser Ile Leu Pro Lys Arg Asn Ser Asp Lys Leu
    1145            1150            1155

Ile Ala Arg Lys Lys Asp Trp Asp Pro Lys Lys Tyr Gly Gly Phe
    1160            1165            1170

Asp Ser Pro Thr Val Ala Tyr Ser Val Leu Val Val Ala Lys Val
    1175            1180            1185

Glu Lys Gly Lys Ser Lys Lys Leu Lys Ser Val Lys Glu Leu Leu
    1190            1195            1200

Gly Ile Thr Ile Met Glu Arg Ser Ser Phe Glu Lys Asn Pro Ile
    1205            1210            1215

Asp Phe Leu Glu Ala Lys Gly Tyr Lys Glu Val Lys Lys Asp Leu
    1220            1225            1230

Ile Ile Lys Leu Pro Lys Tyr Ser Leu Phe Glu Leu Glu Asn Gly
    1235            1240            1245

Arg Lys Arg Met Leu Ala Ser Ala Gly Glu Leu Gln Lys Gly Asn
    1250            1255            1260

Glu Leu Ala Leu Pro Ser Lys Tyr Val Asn Phe Leu Tyr Leu Ala
    1265            1270            1275

Ser His Tyr Glu Lys Leu Lys Gly Ser Pro Glu Asp Asn Glu Gln
    1280            1285            1290

Lys Gln Leu Phe Val Glu Gln His Lys His Tyr Leu Asp Glu Ile
    1295            1300            1305

Ile Glu Gln Ile Ser Glu Phe Ser Lys Arg Val Ile Leu Ala Asp
    1310            1315            1320

Ala Asn Leu Asp Lys Val Leu Ser Ala Tyr Asn Lys His Arg Asp
    1325            1330            1335
```

```
Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 96
<211> LENGTH: 1422
<212> TYPE: PRT
<213> ORGANISM: Artificial Sequence
<220> FEATURE:
<223> OTHER INFORMATION: Fusion protein

<400> SEQUENCE: 96

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Asp Lys Lys Tyr Ser Ile Gly Leu
                35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270
```

```
Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
290                 295                 300

Leu Ser Lys Asp Thr Tyr Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
                340                 345                 350

Lys Ala Pro Leu Ser Ala Ser Met Ile Lys Arg Tyr Asp Glu His His
                355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
                435                 440                 445

Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
                500                 505                 510

Thr Pro Trp Asn Phe Glu Glu Val Val Asp Lys Gly Ala Ser Ala Gln
                515                 520                 525

Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
                595                 600                 605

Lys Lys Ile Glu Cys Phe Asp Ser Val Glu Ile Ser Gly Val Glu Asp
                610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
                675                 680                 685
```

Gln Leu Lys Arg Arg Tyr Thr Gly Trp Gly Arg Leu Ser Arg Lys
690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
            725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
            835                 840                 845

Lys Leu Tyr Leu Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Ile Lys Arg Gln Leu Val
945                 950                 955                 960

Glu Thr Arg Gln Ile Thr Lys His Val Ala Gln Ile Leu Asp Ser Arg
            965                 970                 975

Met Asn Thr Lys Tyr Asp Glu Asn Asp Lys Leu Ile Arg Glu Val Lys
            980                 985                 990

Val Ile Thr Leu Lys Ser Lys Leu Val Ser Asp Phe Arg Lys Asp Phe
            995                 1000                1005

Gln Phe Tyr Lys Val Arg Glu Ile Asn Asn Tyr His His Ala His
    1010                1015                1020

Asp Ala Tyr Leu Asn Ala Val Val Gly Thr Ala Leu Ile Lys Lys
    1025                1030                1035

Tyr Pro Lys Leu Glu Ser Glu Phe Val Tyr Gly Asp Tyr Lys Val
    1040                1045                1050

Tyr Asp Val Arg Lys Met Ile Ala Lys Ser Glu Gln Glu Ile Gly
    1055                1060                1065

Lys Ala Thr Ala Lys Tyr Phe Phe Tyr Ser Asn Ile Met Asn Phe
    1070                1075                1080

Phe Lys Thr Glu Ile Thr Leu Ala Asn Gly Glu Ile Arg Lys Arg
    1085                1090                1095

Pro Leu Ile Glu Thr Asn Gly Glu Thr Gly Glu Ile Val Trp Asp

```
            1100                1105                1110

Lys Gly Arg Asp Phe Ala Thr Val Arg Lys Val Leu Ser Met Pro
    1115                1120                1125

Gln Val Asn Ile Val Lys Lys Thr Glu Val Gln Thr Gly Gly Phe
    1130                1135                1140

Ser Lys Glu Ser Ile Leu Pro Lys Arg Asn Ser Asp Lys Leu Ile
    1145                1150                1155

Ala Arg Lys Lys Asp Trp Asp Pro Lys Lys Tyr Gly Gly Phe Asp
    1160                1165                1170

Ser Pro Thr Val Ala Tyr Ser Val Leu Val Val Ala Lys Val Glu
    1175                1180                1185

Lys Gly Lys Ser Lys Lys Leu Lys Ser Val Lys Glu Leu Leu Gly
    1190                1195                1200

Ile Thr Ile Met Glu Arg Ser Ser Phe Glu Lys Asn Pro Ile Asp
    1205                1210                1215

Phe Leu Glu Ala Lys Gly Tyr Lys Glu Val Lys Lys Asp Leu Ile
    1220                1225                1230

Ile Lys Leu Pro Lys Tyr Ser Leu Phe Glu Leu Glu Asn Gly Arg
    1235                1240                1245

Lys Arg Met Leu Ala Ser Ala Gly Glu Leu Gln Lys Gly Asn Glu
    1250                1255                1260

Leu Ala Leu Pro Ser Lys Tyr Val Asn Phe Leu Tyr Leu Ala Ser
    1265                1270                1275

His Tyr Glu Lys Leu Lys Gly Ser Pro Glu Asp Asn Glu Gln Lys
    1280                1285                1290

Gln Leu Phe Val Glu Gln His Lys His Tyr Leu Asp Glu Ile Ile
    1295                1300                1305

Glu Gln Ile Ser Glu Phe Ser Lys Arg Val Ile Leu Ala Asp Ala
    1310                1315                1320

Asn Leu Asp Lys Val Leu Ser Ala Tyr Asn Lys His Arg Asp Lys
    1325                1330                1335

Pro Ile Arg Glu Gln Ala Glu Asn Ile Ile His Leu Phe Thr Leu
    1340                1345                1350

Thr Asn Leu Gly Ala Pro Ala Ala Phe Lys Tyr Phe Asp Thr Thr
    1355                1360                1365

Ile Asp Arg Lys Arg Tyr Thr Ser Thr Lys Glu Val Leu Asp Ala
    1370                1375                1380

Thr Leu Ile His Gln Ser Ile Thr Gly Leu Tyr Glu Thr Arg Ile
    1385                1390                1395

Asp Leu Ser Gln Leu Gly Gly Asp Lys Arg Pro Ala Ala Thr Lys
    1400                1405                1410

Lys Ala Gly Gln Ala Lys Lys Lys Lys
    1415                1420

<210> SEQ ID NO 97
<211> LENGTH: 1423
<212> TYPE: PRT
<213> ORGANISM: Artificial Sequence
<220> FEATURE:
<223> OTHER INFORMATION: Fusion protein

<400> SEQUENCE: 97

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
```

```
            20                  25                  30
Gly Ile His Gly Val Pro Ala Ala Asp Lys Lys Tyr Ser Ile Gly Leu
            35                  40                  45
Asp Ile Gly Thr Asn Ser Val Gly Trp Ala Val Ile Thr Asp Glu Tyr
50                  55                  60
Lys Val Pro Ser Lys Lys Phe Lys Val Leu Gly Asn Thr Asp Arg His
65                  70                  75                  80
Ser Ile Lys Lys Asn Leu Ile Gly Ala Leu Leu Phe Asp Ser Gly Glu
            85                  90                  95
Thr Ala Glu Ala Thr Arg Leu Lys Arg Thr Ala Arg Arg Arg Tyr Thr
            100                 105                 110
Arg Arg Lys Asn Arg Ile Cys Tyr Leu Gln Glu Ile Phe Ser Asn Glu
            115                 120                 125
Met Ala Lys Val Asp Asp Ser Phe Phe His Arg Leu Glu Glu Ser Phe
            130                 135                 140
Leu Val Glu Glu Asp Lys Lys His Glu Arg His Pro Ile Phe Gly Asn
145                 150                 155                 160
Ile Val Asp Glu Val Ala Tyr His Glu Lys Tyr Pro Thr Ile Tyr His
                165                 170                 175
Leu Arg Lys Lys Leu Val Asp Ser Thr Asp Lys Ala Asp Leu Arg Leu
                180                 185                 190
Ile Tyr Leu Ala Leu Ala His Met Ile Lys Phe Arg Gly His Phe Leu
                195                 200                 205
Ile Glu Gly Asp Leu Asn Pro Asp Asn Ser Asp Val Asp Lys Leu Phe
            210                 215                 220
Ile Gln Leu Val Gln Thr Tyr Asn Gln Leu Phe Glu Glu Asn Pro Ile
225                 230                 235                 240
Asn Ala Ser Gly Val Asp Ala Lys Ala Ile Leu Ser Ala Arg Leu Ser
                245                 250                 255
Lys Ser Arg Arg Leu Glu Asn Leu Ile Ala Gln Leu Pro Gly Glu Lys
                260                 265                 270
Lys Asn Gly Leu Phe Gly Asn Leu Ile Ala Leu Ser Leu Gly Leu Thr
            275                 280                 285
Pro Asn Phe Lys Ser Asn Phe Asp Leu Ala Glu Asp Ala Lys Leu Gln
            290                 295                 300
Leu Ser Lys Asp Thr Tyr Asp Asp Asp Leu Asp Asn Leu Leu Ala Gln
305                 310                 315                 320
Ile Gly Asp Gln Tyr Ala Asp Leu Phe Leu Ala Ala Lys Asn Leu Ser
                325                 330                 335
Asp Ala Ile Leu Leu Ser Asp Ile Leu Arg Val Asn Thr Glu Ile Thr
            340                 345                 350
Lys Ala Pro Leu Ser Ala Ser Met Ile Lys Arg Tyr Asp Glu His His
            355                 360                 365
Gln Asp Leu Thr Leu Leu Lys Ala Leu Val Arg Gln Gln Leu Pro Glu
            370                 375                 380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
            420                 425                 430
Asn Arg Glu Asp Leu Leu Arg Lys Gln Arg Thr Phe Asp Asn Gly Ser
            435                 440                 445
```

```
Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
            530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
            610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
            690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
            770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
            850                 855                 860
```

```
Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
        900                 905                 910

Glu Val Val Lys Lys Met Lys Asn Tyr Trp Arg Gln Leu Leu Asn Ala
        915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Phe Phe Ile Lys Arg Gln Leu
945                 950                 955                 960

Val Glu Thr Arg Gln Ile Thr Lys His Val Ala Gln Ile Leu Asp Ser
            965                 970                 975

Arg Met Asn Thr Lys Tyr Asp Glu Asn Asp Lys Leu Ile Arg Glu Val
        980                 985                 990

Lys Val Ile Thr Leu Lys Ser Lys Leu Val Ser Asp Phe Arg Lys Asp
    995                 1000                1005

Phe Gln Phe Tyr Lys Val Arg Glu Ile Asn Asn Tyr His His Ala
    1010                1015                1020

His Asp Ala Tyr Leu Asn Ala Val Val Gly Thr Ala Leu Ile Lys
    1025                1030                1035

Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
```

```
                  1265                1270                1275

Ser His Tyr Glu Lys Leu Lys Gly Ser Pro Glu Asp Asn Glu Gln
            1280                1285                1290

Lys Gln Leu Phe Val Glu Gln His Lys His Tyr Leu Asp Glu Ile
        1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 98
<211> LENGTH: 1423
<212> TYPE: PRT
<213> ORGANISM: Artificial Sequence
<220> FEATURE:
<223> OTHER INFORMATION: Fusion protein

<400> SEQUENCE: 98

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
```

```
                195                 200                 205
Ile Glu Gly Asp Leu Asn Pro Asp Asn Ser Asp Val Asp Lys Leu Phe
210                     215                 220
Ile Gln Leu Val Gln Thr Tyr Asn Gln Leu Phe Glu Glu Asn Pro Ile
225                 230                  235                 240
Asn Ala Ser Gly Val Asp Ala Lys Ala Ile Leu Ser Ala Arg Leu Ser
                245                  250                 255
Lys Ser Arg Arg Leu Glu Asn Leu Ile Ala Gln Leu Pro Gly Glu Lys
            260                  265                 270
Lys Asn Gly Leu Phe Gly Asn Leu Ile Ala Leu Ser Leu Gly Leu Thr
            275                 280                 285
Pro Asn Phe Lys Ser Asn Phe Asp Leu Ala Glu Asp Ala Lys Leu Gln
            290                 295                 300
Leu Ser Lys Asp Thr Tyr Asp Asp Leu Asp Asn Leu Leu Ala Gln
305                 310                 315                 320
Ile Gly Asp Gln Tyr Ala Asp Leu Phe Leu Ala Ala Lys Asn Leu Ser
                325                 330                 335
Asp Ala Ile Leu Leu Ser Asp Ile Leu Arg Val Asn Thr Glu Ile Thr
                340                 345                 350
Lys Ala Pro Leu Ser Ala Ser Met Ile Lys Arg Tyr Asp Glu His His
            355                 360                 365
Gln Asp Leu Thr Leu Leu Lys Ala Leu Val Arg Gln Gln Leu Pro Glu
370                 375                 380
Lys Tyr Lys Glu Ile Phe Phe Asp Gln Ser Lys Asn Gly Tyr Ala Gly
385                 390                 395                 400
Tyr Ile Asp Gly Gly Ala Ser Gln Glu Glu Phe Tyr Lys Phe Ile Lys
                405                 410                 415
Pro Ile Leu Glu Lys Met Asp Gly Thr Glu Glu Leu Leu Val Lys Leu
                420                 425                 430
Asn Arg Glu Asp Leu Leu Arg Lys Gln Arg Thr Phe Asp Asn Gly Ser
            435                 440                 445
Ile Pro His Gln Ile His Leu Gly Glu Leu His Ala Ile Leu Arg Arg
            450                 455                 460
Gln Glu Asp Phe Tyr Pro Phe Leu Lys Asp Asn Arg Glu Lys Ile Glu
465                 470                 475                 480
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
            500                 505                 510
Thr Pro Trp Asn Phe Glu Glu Val Val Asp Lys Gly Ala Ser Ala Gln
            515                 520                 525
Ser Phe Ile Glu Arg Met Thr Asn Phe Asp Lys Asn Leu Pro Asn Glu
530                 535                 540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
            580                 585                 590
Lys Thr Asn Arg Lys Val Thr Val Lys Gln Leu Lys Glu Asp Tyr Phe
            595                 600                 605
Lys Lys Ile Glu Cys Phe Asp Ser Val Glu Ile Ser Gly Val Glu Asp
            610                 615                 620
```

-continued

```
Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
            645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
                675                 680                 685

Gln Leu Lys Arg Arg Arg Tyr Thr Gly Trp Gly Arg Leu Ser Arg Lys
            690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
                820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
                885                 890                 895

Thr Arg Ser Asp Lys Asn Arg Gly Lys Ser Asp Asn Val Pro Ser Glu
                900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Phe Ile Lys Arg Pro Leu
945                 950                 955                 960

Val Glu Thr Arg Gln Ile Thr Lys His Val Ala Gln Ile Leu Asp Ser
                965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
            995                 1000                1005

Phe Gln Phe Tyr Lys Val Arg Glu Ile Asn Asn Tyr His His Ala
        1010                1015                1020

His Asp Ala Tyr Leu Asn Ala Val Val Gly Thr Ala Leu Ile Lys
        1025                1030                1035
```

```
Lys Tyr Pro Lys Leu Glu Ser Glu Phe Val Tyr Gly Asp Tyr Lys
    1040                1045                1050

Val Tyr Asp Val Arg Lys Met Ile Ala Lys Ser Glu Gln Glu Ile
    1055                1060                1065

Gly Lys Ala Thr Ala Lys Tyr Phe Phe Tyr Ser Asn Ile Met Asn
    1070                1075                1080

Phe Phe Lys Thr Glu Ile Thr Leu Ala Asn Gly Glu Ile Arg Lys
    1085                1090                1095

Arg Pro Leu Ile Glu Thr Asn Gly Glu Thr Gly Glu Ile Val Trp
    1100                1105                1110

Asp Lys Gly Arg Asp Phe Ala Thr Val Arg Lys Val Leu Ser Met
    1115                1120                1125

Pro Gln Val Asn Ile Val Lys Lys Thr Glu Val Gln Thr Gly Gly
    1130                1135                1140

Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420
```

```
<210> SEQ ID NO 99
<211> LENGTH: 1423
<212> TYPE: PRT
<213> ORGANISM: Artificial Sequence
<220> FEATURE:
<223> OTHER INFORMATION: Fusion protein

<400> SEQUENCE: 99
```

| | | | | | | | | | | | | | | | |
|---|---|---|---|---|---|---|---|---|---|---|---|---|---|---|---|
| Met | Asp | Tyr | Lys | Asp | His | Asp | Gly | Asp | Tyr | Lys | Asp | His | Asp | Ile | Asp |
| 1 | | | | 5 | | | | | 10 | | | | | 15 | |
| Tyr | Lys | Asp | Asp | Asp | Asp | Lys | Met | Ala | Pro | Lys | Lys | Lys | Arg | Lys | Val |
| | | | 20 | | | | | 25 | | | | | 30 | | |
| Gly | Ile | His | Gly | Val | Pro | Ala | Ala | Asp | Lys | Lys | Tyr | Ser | Ile | Gly | Leu |
| | | 35 | | | | | 40 | | | | | 45 | | | |
| Asp | Ile | Gly | Thr | Asn | Ser | Val | Gly | Trp | Ala | Val | Ile | Thr | Asp | Glu | Tyr |
| | 50 | | | | | 55 | | | | | 60 | | | | |
| Lys | Val | Pro | Ser | Lys | Lys | Phe | Lys | Val | Leu | Gly | Asn | Thr | Asp | Arg | His |
| 65 | | | | | 70 | | | | | 75 | | | | | 80 |
| Ser | Ile | Lys | Lys | Asn | Leu | Ile | Gly | Ala | Leu | Leu | Phe | Asp | Ser | Gly | Glu |
| | | | | 85 | | | | | 90 | | | | | 95 | |
| Thr | Ala | Glu | Ala | Thr | Arg | Leu | Lys | Arg | Thr | Ala | Arg | Arg | Arg | Tyr | Thr |
| | | | 100 | | | | | 105 | | | | | 110 | | |
| Arg | Arg | Lys | Asn | Arg | Ile | Cys | Tyr | Leu | Gln | Glu | Ile | Phe | Ser | Asn | Glu |
| | | 115 | | | | | 120 | | | | | 125 | | | |
| Met | Ala | Lys | Val | Asp | Asp | Ser | Phe | Phe | His | Arg | Leu | Glu | Glu | Ser | Phe |
| | 130 | | | | | 135 | | | | | 140 | | | | |
| Leu | Val | Glu | Glu | Asp | Lys | Lys | His | Glu | Arg | His | Pro | Ile | Phe | Gly | Asn |
| 145 | | | | | 150 | | | | | 155 | | | | | 160 |
| Ile | Val | Asp | Glu | Val | Ala | Tyr | His | Glu | Lys | Tyr | Pro | Thr | Ile | Tyr | His |
| | | | | 165 | | | | | 170 | | | | | 175 | |
| Leu | Arg | Lys | Lys | Leu | Val | Asp | Ser | Thr | Asp | Lys | Ala | Asp | Leu | Arg | Leu |
| | | | 180 | | | | | 185 | | | | | 190 | | |
| Ile | Tyr | Leu | Ala | Leu | Ala | His | Met | Ile | Lys | Phe | Arg | Gly | His | Phe | Leu |
| | | 195 | | | | | 200 | | | | | 205 | | | |
| Ile | Glu | Gly | Asp | Leu | Asn | Pro | Asp | Asn | Ser | Asp | Val | Asp | Lys | Leu | Phe |
| | 210 | | | | | 215 | | | | | 220 | | | | |
| Ile | Gln | Leu | Val | Gln | Thr | Tyr | Asn | Gln | Leu | Phe | Glu | Glu | Asn | Pro | Ile |
| 225 | | | | | 230 | | | | | 235 | | | | | 240 |
| Asn | Ala | Ser | Gly | Val | Asp | Ala | Lys | Ala | Ile | Leu | Ser | Ala | Arg | Leu | Ser |
| | | | | 245 | | | | | 250 | | | | | 255 | |
| Lys | Ser | Arg | Arg | Leu | Glu | Asn | Leu | Ile | Ala | Gln | Leu | Pro | Gly | Glu | Lys |
| | | | 260 | | | | | 265 | | | | | 270 | | |
| Lys | Asn | Gly | Leu | Phe | Gly | Asn | Leu | Ile | Ala | Leu | Ser | Leu | Gly | Leu | Thr |
| | | 275 | | | | | 280 | | | | | 285 | | | |
| Pro | Asn | Phe | Lys | Ser | Asn | Phe | Asp | Leu | Ala | Glu | Asp | Ala | Lys | Leu | Gln |
| | 290 | | | | | 295 | | | | | 300 | | | | |
| Leu | Ser | Lys | Asp | Thr | Tyr | Asp | Asp | Asp | Leu | Asp | Asn | Leu | Leu | Ala | Gln |
| 305 | | | | | 310 | | | | | 315 | | | | | 320 |
| Ile | Gly | Asp | Gln | Tyr | Ala | Asp | Leu | Phe | Leu | Ala | Ala | Lys | Asn | Leu | Ser |
| | | | | 325 | | | | | 330 | | | | | 335 | |
| Asp | Ala | Ile | Leu | Leu | Ser | Asp | Ile | Leu | Arg | Val | Asn | Thr | Glu | Ile | Thr |
| | | | 340 | | | | | 345 | | | | | 350 | | |
| Lys | Ala | Pro | Leu | Ser | Ala | Ser | Met | Ile | Lys | Arg | Tyr | Asp | Glu | His | His |
| | | 355 | | | | | 360 | | | | | 365 | | | |
| Gln | Asp | Leu | Thr | Leu | Leu | Lys | Ala | Leu | Val | Arg | Gln | Gln | Leu | Pro | Glu |

```
            370                 375                 380
Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
                435                 440                 445

Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
                500                 505                 510

Thr Pro Trp Asn Phe Glu Glu Val Val Asp Lys Gly Ala Ser Ala Gln
                515                 520                 525

Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
                580                 585                 590

Lys Thr Asn Arg Lys Val Thr Val Lys Gln Leu Lys Glu Asp Tyr Phe
                595                 600                 605

Lys Lys Ile Glu Cys Phe Asp Ser Val Glu Ile Ser Gly Val Glu Asp
                610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
                675                 680                 685

Gln Leu Lys Arg Arg Arg Tyr Thr Gly Trp Gly Arg Leu Ser Arg Lys
                690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
                740                 745                 750

Ser Gly Gln Gly Asp Ser Leu His Glu His Ile Ala Asn Leu Ala Gly
                755                 760                 765

Ser Pro Ala Ile Lys Lys Gly Ile Leu Gln Thr Val Lys Val Val Asp
                770                 775                 780

Glu Leu Val Lys Val Met Gly Arg His Lys Pro Glu Asn Ile Val Ile
785                 790                 795                 800
```

-continued

Glu Met Ala Arg Glu Asn Gln Thr Thr Gln Lys Gly Gln Lys Asn Ser
            805                 810                 815

Arg Glu Arg Met Lys Arg Ile Glu Glu Gly Ile Lys Glu Leu Gly Ser
        820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
850                 855                 860

Gln Glu Leu Asp Ile Asn Arg Leu Ser Asp Tyr Asp Val Asp His Ile
865                 870                 875                 880

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
930                 935                 940

Gly Gly Leu Ser Glu Leu Asp Lys Ala Gly Pro Ile Lys Arg Gln Leu
945                 950                 955                 960

Val Glu Thr Arg Gln Ile Thr Lys His Val Ala Gln Ile Leu Asp Ser
            965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
            995                 1000                1005

Phe Gln Phe Tyr Lys Val Arg Glu Ile Asn Asn Tyr His His Ala
            1010                1015                1020

His Asp Ala Tyr Leu Asn Ala Val Val Gly Thr Ala Leu Ile Lys
            1025                1030                1035

Lys Tyr Pro Lys Leu Glu Ser Glu Phe Val Tyr Gly Asp Tyr Lys
            1040                1045                1050

Val Tyr Asp Val Arg Lys Met Ile Ala Lys Ser Glu Gln Glu Ile
            1055                1060                1065

Gly Lys Ala Thr Ala Lys Tyr Phe Phe Tyr Ser Asn Ile Met Asn
            1070                1075                1080

Phe Phe Lys Thr Glu Ile Thr Leu Ala Asn Gly Glu Ile Arg Lys
            1085                1090                1095

Arg Pro Leu Ile Glu Thr Asn Gly Glu Thr Gly Glu Ile Val Trp
            1100                1105                1110

Asp Lys Gly Arg Asp Phe Ala Thr Val Arg Lys Val Leu Ser Met
            1115                1120                1125

Pro Gln Val Asn Ile Val Lys Lys Thr Glu Val Gln Thr Gly Gly
            1130                1135                1140

Phe Ser Lys Glu Ser Ile Leu Pro Lys Arg Asn Ser Asp Lys Leu
            1145                1150                1155

Ile Ala Arg Lys Lys Asp Trp Asp Pro Lys Lys Tyr Gly Gly Phe
            1160                1165                1170

Asp Ser Pro Thr Val Ala Tyr Ser Val Leu Val Val Ala Lys Val
            1175                1180                1185

Glu Lys Gly Lys Ser Lys Lys Leu Lys Ser Val Lys Glu Leu Leu
            1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 100
<211> LENGTH: 1423
<212> TYPE: PRT
<213> ORGANISM: Artificial Sequence
<220> FEATURE:
<223> OTHER INFORMATION: Fusion protein

<400> SEQUENCE: 100

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

```
Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
        355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
        435                 440                 445

Ile Pro His Gln Ile His Leu Gly Glu Leu His Ala Ile Leu Arg Arg
    450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
        515                 520                 525

Ser Phe Ile Glu Arg Met Thr Asn Phe Asp Lys Asn Leu Pro Asn Glu
    530                 535                 540

Lys Val Leu Pro Lys His Ser Leu Leu Tyr Glu Tyr Phe Thr Val Tyr
```

-continued

```
         545                 550                 555                 560
Asn Glu Leu Thr Lys Val Lys Tyr Val Thr Glu Gly Met Arg Lys Pro
                 565                 570                 575

Ala Phe Leu Ser Gly Glu Gln Lys Lys Ala Ile Val Asp Leu Leu Phe
                 580                 585                 590

Lys Thr Asn Arg Lys Val Thr Val Lys Gln Leu Lys Glu Asp Tyr Phe
                 595                 600                 605

Lys Lys Ile Glu Cys Phe Asp Ser Val Glu Ile Ser Gly Val Glu Asp
                 610                 615                 620

Arg Phe Asn Ala Ser Leu Gly Thr Tyr His Asp Leu Leu Lys Ile Ile
625                              630                 635             640

Lys Asp Lys Asp Phe Leu Asp Asn Glu Glu Asn Glu Asp Ile Leu Glu
                 645                 650                 655

Asp Ile Val Leu Thr Leu Thr Leu Phe Glu Asp Arg Glu Met Ile Glu
                 660                 665                 670

Glu Arg Leu Lys Thr Tyr Ala His Leu Phe Asp Asp Lys Val Met Lys
                 675                 680                 685

Gln Leu Lys Arg Arg Arg Tyr Thr Gly Trp Gly Arg Leu Ser Arg Lys
                 690                 695                 700

Leu Ile Asn Gly Ile Arg Asp Lys Gln Ser Gly Lys Thr Ile Leu Asp
705                              710                 715             720

Phe Leu Lys Ser Asp Gly Phe Ala Asn Arg Asn Phe Met Gln Leu Ile
                 725                 730                 735

His Asp Asp Ser Leu Thr Phe Lys Glu Asp Ile Gln Lys Ala Gln Val
                 740                 745                 750

Ser Gly Gln Gly Asp Ser Leu His Glu His Ile Ala Asn Leu Ala Gly
                 755                 760                 765

Ser Pro Ala Ile Lys Lys Gly Ile Leu Gln Thr Val Lys Val Val Asp
                 770                 775                 780

Glu Leu Val Lys Val Met Gly Arg His Lys Pro Glu Asn Ile Val Ile
785                              790                 795             800

Glu Met Ala Arg Glu Asn Gln Thr Thr Gln Lys Gly Gln Lys Asn Ser
                 805                 810                 815

Arg Glu Arg Met Lys Arg Ile Glu Glu Gly Ile Lys Glu Leu Gly Ser
                 820                 825                 830

Gln Ile Leu Lys Glu His Pro Val Glu Asn Thr Gln Leu Gln Asn Glu
                 835                 840                 845

Lys Leu Tyr Leu Tyr Tyr Leu Gln Asn Gly Arg Asp Met Tyr Val Asp
                 850                 855                 860

Gln Glu Leu Asp Ile Asn Arg Leu Ser Asp Tyr Asp Val Asp His Ile
865                              870                 875             880

Val Pro Gln Ser Phe Leu Lys Asp Asp Ser Ile Asp Asn Lys Val Leu
                 885                 890                 895

Thr Arg Ser Asp Lys Asn Arg Gly Lys Ser Asp Asn Val Pro Ser Glu
                 900                 905                 910

Glu Val Val Lys Lys Met Lys Asn Tyr Trp Arg Gln Leu Leu Asn Ala
                 915                 920                 925

Lys Leu Ile Thr Gln Arg Lys Phe Asp Asn Leu Thr Lys Ala Glu Arg
                 930                 935                 940

Gly Gly Leu Ser Glu Leu Asp Lys Ala Gly Phe Ile Ala Arg Gln Leu
945                              950                 955             960

Val Glu Thr Arg Gln Ile Thr Lys His Val Ala Gln Ile Leu Asp Ser
                 965                 970                 975
```

```
Arg Met Asn Thr Lys Tyr Asp Glu Asn Asp Lys Leu Ile Arg Glu Val
            980                 985                 990

Lys Val Ile Thr Leu Lys Ser Lys   Leu Val Ser Asp Phe  Arg Lys Asp
            995                 1000                1005

Phe Gln Phe Tyr Lys Val Arg  Glu Ile Asn Asn Tyr  His His Ala
    1010                1015                1020

His Asp Ala Tyr Leu Asn Ala  Val Val Gly Thr Ala  Leu Ile Lys
    1025                1030                1035

Lys Tyr Pro Lys Leu Glu Ser  Glu Phe Val Tyr Gly  Asp Tyr Lys
    1040                1045                1050

Val Tyr Asp Val Arg Lys Met  Ile Ala Lys Ser Glu  Gln Glu Ile
    1055                1060                1065

Gly Lys Ala Thr Ala Lys Tyr  Phe Phe Tyr Ser Asn  Ile Met Asn
    1070                1075                1080

Phe Phe Lys Thr Glu Ile Thr  Leu Ala Asn Gly Glu  Ile Arg Lys
    1085                1090                1095

Arg Pro Leu Ile Glu Thr Asn  Gly Glu Thr Gly Glu  Ile Val Trp
    1100                1105                1110

Asp Lys Gly Arg Asp Phe Ala  Thr Val Arg Lys Val  Leu Ser Met
    1115                1120                1125

Pro Gln Val Asn Ile Val Lys  Lys Thr Glu Val Gln  Thr Gly Gly
    1130                1135                1140

Phe Ser Lys Glu Ser Ile Leu  Pro Lys Arg Asn Ser  Asp Lys Leu
    1145                1150                1155

Ile Ala Arg Lys Lys Asp Trp  Asp Pro Lys Lys Tyr  Gly Gly Phe
    1160                1165                1170

Asp Ser Pro Thr Val Ala Tyr  Ser Val Leu Val Val  Ala Lys Val
    1175                1180                1185

Glu Lys Gly Lys Ser Lys Lys  Leu Lys Ser Val Lys  Glu Leu Leu
    1190                1195                1200

Gly Ile Thr Ile Met Glu Arg  Ser Ser Phe Glu Lys  Asn Pro Ile
    1205                1210                1215

Asp Phe Leu Glu Ala Lys Gly  Tyr Lys Glu Val Lys  Lys Asp Leu
    1220                1225                1230

Ile Ile Lys Leu Pro Lys Tyr  Ser Leu Phe Glu Leu  Glu Asn Gly
    1235                1240                1245

Arg Lys Arg Met Leu Ala Ser  Ala Gly Glu Leu Gln  Lys Gly Asn
    1250                1255                1260

Glu Leu Ala Leu Pro Ser Lys  Tyr Val Asn Phe Leu  Tyr Leu Ala
    1265                1270                1275

Ser His Tyr Glu Lys Leu Lys  Gly Ser Pro Glu Asp  Asn Glu Gln
    1280                1285                1290

Lys Gln Leu Phe Val Glu Gln  His Lys His Tyr Leu  Asp Glu Ile
    1295                1300                1305

Ile Glu Gln Ile Ser Glu Phe  Ser Lys Arg Val Ile  Leu Ala Asp
    1310                1315                1320

Ala Asn Leu Asp Lys Val Leu  Ser Ala Tyr Asn Lys  His Arg Asp
    1325                1330                1335

Lys Pro Ile Arg Glu Gln Ala  Glu Asn Ile Ile His  Leu Phe Thr
    1340                1345                1350

Leu Thr Asn Leu Gly Ala Pro  Ala Ala Phe Lys Tyr  Phe Asp Thr
    1355                1360                1365
```

-continued

```
Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
1385                1390                1395

Ile Asp Leu Ser Gln Leu Gly Gly Asp Lys Arg Pro Ala Ala Thr
1400                1405                1410

Lys Lys Ala Gly Gln Ala Lys Lys Lys Lys
    1415                1420

<210> SEQ ID NO 101
<211> LENGTH: 1423
<212> TYPE: PRT
<213> ORGANISM: Artificial Sequence
<220> FEATURE:
<223> OTHER INFORMATION: Fusion protein

<400> SEQUENCE: 101

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Lys Arg Lys Val
            20                  25                  30

Gly Ile His Gly Val Pro Ala Ala Asp Lys Lys Tyr Ser Ile Gly Leu
        35                  40                  45

Asp Ile Gly Thr Asn Ser Val Gly Trp Ala Val Ile Thr Asp Glu Tyr
    50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
        115                 120                 125

Met Ala Lys Val Asp Asp Ser Phe Phe His Arg Leu Glu Glu Ser Phe
    130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
        195                 200                 205

Ile Glu Gly Asp Leu Asn Pro Asp Asn Ser Asp Val Asp Lys Leu Phe
    210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
        275                 280                 285

Pro Asn Phe Lys Ser Asn Phe Asp Leu Ala Glu Asp Ala Lys Leu Gln
    290                 295                 300
```

```
Leu Ser Lys Asp Thr Tyr Asp Asp Leu Asp Asn Leu Leu Ala Gln
305                 310                 315                 320

Ile Gly Asp Gln Tyr Ala Asp Leu Phe Leu Ala Ala Lys Asn Leu Ser
            325                 330                 335

Asp Ala Ile Leu Leu Ser Asp Ile Leu Arg Val Asn Thr Glu Ile Thr
                340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
    370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
                420                 425                 430

Asn Arg Glu Asp Leu Leu Arg Lys Gln Arg Thr Phe Asp Asn Gly Ser
            435                 440                 445

Ile Pro His Gln Ile His Leu Gly Glu Leu His Ala Ile Leu Arg Arg
450                 455                 460

Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
            515                 520                 525

Ser Phe Ile Glu Arg Met Thr Asn Phe Asp Lys Asn Leu Pro Asn Glu
530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
            595                 600                 605

Lys Lys Ile Glu Cys Phe Asp Ser Val Glu Ile Ser Gly Val Glu Asp
610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
                660                 665                 670

Glu Arg Leu Lys Thr Tyr Ala His Leu Phe Asp Asp Lys Val Met Lys
            675                 680                 685

Gln Leu Lys Arg Arg Arg Tyr Thr Gly Trp Gly Arg Leu Ser Arg Lys
            690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
```

-continued

His Asp Asp Ser Leu Thr Phe Lys Glu Asp Ile Gln Lys Ala Gln Val
725                     730                     735

Ser Gly Gln Gly Asp Ser Leu His Glu His Ile Ala Asn Leu Ala Gly
        740                     745                     750

Ser Pro Ala Ile Lys Lys Gly Ile Leu Gln Thr Val Lys Val Val Asp
        755                     760                     765

Glu Leu Val Lys Val Met Gly Arg His Lys Pro Glu Asn Ile Val Ile
770                     775                     780

Glu Met Ala Arg Glu Asn Gln Thr Thr Gln Lys Gly Gln Lys Asn Ser
785                     790                     795                     800

Arg Glu Arg Met Lys Arg Ile Glu Glu Gly Ile Lys Glu Leu Gly Ser
        805                     810                     815

Gln Ile Leu Lys Glu His Pro Val Glu Asn Thr Gln Leu Gln Asn Glu
        820                     825                     830

Lys Leu Tyr Leu Tyr Tyr Leu Gln Asn Gly Arg Asp Met Tyr Val Asp
        835                     840                     845

Gln Glu Leu Asp Ile Asn Arg Leu Ser Asp Tyr Asp Val Asp His Ile
        850                     855                     860

Val Pro Gln Ser Phe Leu Lys Asp Asp Ser Ile Asp Asn Lys Val Leu
865                     870                     875                     880

Thr Arg Ser Asp Lys Asn Arg Gly Lys Ser Asp Asn Val Pro Ser Glu
        885                     890                     895

Glu Val Val Lys Lys Met Lys Asn Tyr Trp Arg Gln Leu Leu Asn Ala
        900                     905                     910

Lys Leu Ile Thr Gln Arg Lys Phe Asp Asn Leu Thr Lys Ala Glu Arg
        915                     920                     925

Gly Gly Leu Ser Glu Leu Asp Lys Ala Gly Phe Ile Lys Pro Gln Leu
930                     935                     940

Val Glu Thr Arg Gln Ile Thr Lys His Val Ala Gln Ile Leu Asp Ser
        945                     950                     955

Arg Met Asn Thr Lys Tyr Asp Glu Asn Asp Lys Leu Ile Arg Glu Val
        960                     965                     970                     975

Lys Val Ile Thr Leu Lys Ser Lys Leu Val Ser Asp Phe Arg Lys Asp
        980                     985                     990

Phe Gln Phe Tyr Lys Val Arg Glu Ile Asn Asn Tyr His His Ala
        995                     1000                    1005

His Asp Ala Tyr Leu Asn Ala Val Val Gly Thr Ala Leu Ile Lys
        1010                    1015                    1020

Lys Tyr Pro Lys Leu Glu Ser Glu Phe Val Tyr Gly Asp Tyr Lys
        1025                    1030                    1035

Val Tyr Asp Val Arg Lys Met Ile Ala Lys Ser Glu Gln Glu Ile
        1040                    1045                    1050

Gly Lys Ala Thr Ala Lys Tyr Phe Phe Tyr Ser Asn Ile Met Asn
        1055                    1060                    1065

Phe Phe Lys Thr Glu Ile Thr Leu Ala Asn Gly Glu Ile Arg Lys
        1070                    1075                    1080

Arg Pro Leu Ile Glu Thr Asn Gly Glu Thr Gly Glu Ile Val Trp
        1085                    1090                    1095

Asp Lys Gly Arg Asp Phe Ala Thr Val Arg Lys Val Leu Ser Met
        1100                    1105                    1110

Pro Gln Val Asn Ile Val Lys Lys Thr Glu Val Gln Thr Gly Gly
        1115                    1120                    1125

-continued

```
Phe Ser Lys Glu Ser Ile Leu Pro Lys Arg Asn Ser Asp Lys Leu
    1145                1150                1155

Ile Ala Arg Lys Lys Asp Trp Asp Pro Lys Lys Tyr Gly Gly Phe
    1160                1165                1170

Asp Ser Pro Thr Val Ala Tyr Ser Val Leu Val Val Ala Lys Val
    1175                1180                1185

Glu Lys Gly Lys Ser Lys Lys Leu Lys Ser Val Lys Glu Leu Leu
    1190                1195                1200

Gly Ile Thr Ile Met Glu Arg Ser Ser Phe Glu Lys Asn Pro Ile
    1205                1210                1215

Asp Phe Leu Glu Ala Lys Gly Tyr Lys Glu Val Lys Lys Asp Leu
    1220                1225                1230

Ile Ile Lys Leu Pro Lys Tyr Ser Leu Phe Glu Leu Glu Asn Gly
    1235                1240                1245

Arg Lys Arg Met Leu Ala Ser Ala Gly Glu Leu Gln Lys Gly Asn
    1250                1255                1260

Glu Leu Ala Leu Pro Ser Lys Tyr Val Asn Phe Leu Tyr Leu Ala
    1265                1270                1275

Ser His Tyr Glu Lys Leu Lys Gly Ser Pro Glu Asp Asn Glu Gln
    1280                1285                1290

Lys Gln Leu Phe Val Glu Gln His Lys His Tyr Leu Asp Glu Ile
    1295                1300                1305

Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 102
<211> LENGTH: 1423
<212> TYPE: PRT
<213> ORGANISM: Artificial Sequence
<220> FEATURE:
<223> OTHER INFORMATION: Fusion protein

<400> SEQUENCE: 102

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
        50                  55                  60
```

```
Lys Val Pro Ser Lys Lys Phe Lys Val Leu Gly Asn Thr Asp Arg His
 65                  70                  75                  80

Ser Ile Lys Lys Asn Leu Ile Gly Ala Leu Phe Asp Ser Gly Glu
             85                  90                  95

Thr Ala Glu Ala Thr Arg Leu Lys Arg Thr Ala Arg Arg Tyr Thr
            100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
            130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
            195                 200                 205

Ile Glu Gly Asp Leu Asn Pro Asp Asn Ser Asp Val Asp Lys Leu Phe
210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
            290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
            370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
            435                 440                 445

Ile Pro His Gln Ile His Leu Gly Glu Leu His Ala Ile Leu Arg Arg
            450                 455                 460

Gln Glu Asp Phe Tyr Pro Phe Leu Lys Asp Asn Arg Glu Lys Ile Glu
465                 470                 475                 480
```

```
Lys Ile Leu Thr Phe Arg Ile Pro Tyr Tyr Val Gly Pro Leu Ala Arg
                485                 490                 495
Gly Asn Ser Arg Phe Ala Trp Met Thr Arg Lys Ser Glu Glu Thr Ile
            500                 505                 510
Thr Pro Trp Asn Phe Glu Glu Val Val Asp Lys Gly Ala Ser Ala Gln
        515                 520                 525
Ser Phe Ile Glu Arg Met Thr Asn Phe Asp Lys Asn Leu Pro Asn Glu
    530                 535                 540
Lys Val Leu Pro Lys His Ser Leu Leu Tyr Glu Tyr Phe Thr Val Tyr
545                 550                 555                 560
Asn Glu Leu Thr Lys Val Lys Tyr Val Thr Glu Gly Met Arg Lys Pro
                565                 570                 575
Ala Phe Leu Ser Gly Glu Gln Lys Lys Ala Ile Val Asp Leu Leu Phe
            580                 585                 590
Lys Thr Asn Arg Lys Val Thr Val Lys Gln Leu Lys Glu Asp Tyr Phe
        595                 600                 605
Lys Lys Ile Glu Cys Phe Asp Ser Val Glu Ile Ser Gly Val Glu Asp
    610                 615                 620
Arg Phe Asn Ala Ser Leu Gly Thr Tyr His Asp Leu Leu Lys Ile Ile
625                 630                 635                 640
Lys Asp Lys Asp Phe Leu Asp Asn Glu Glu Asn Glu Asp Ile Leu Glu
                645                 650                 655
Asp Ile Val Leu Thr Leu Thr Leu Phe Glu Asp Arg Glu Met Ile Glu
            660                 665                 670
Glu Arg Leu Lys Thr Tyr Ala His Leu Phe Asp Asp Lys Val Met Lys
        675                 680                 685
Gln Leu Lys Arg Arg Arg Tyr Thr Gly Trp Gly Arg Leu Ser Arg Lys
    690                 695                 700
Leu Ile Asn Gly Ile Arg Asp Lys Gln Ser Gly Lys Thr Ile Leu Asp
705                 710                 715                 720
Phe Leu Lys Ser Asp Gly Phe Ala Cys Arg Asn Phe Met Gln Leu Ile
                725                 730                 735
His Asp Asp Ser Leu Thr Phe Lys Glu Asp Ile Gln Lys Ala Gln Val
            740                 745                 750
Ser Gly Gln Gly Asp Ser Leu His Glu His Ile Ala Asn Leu Ala Gly
        755                 760                 765
Ser Pro Ala Ile Lys Lys Gly Ile Leu Gln Thr Val Lys Val Val Asp
    770                 775                 780
Glu Leu Val Lys Val Met Gly Arg His Lys Pro Glu Asn Ile Val Ile
785                 790                 795                 800
Glu Met Ala Arg Glu Asn Gln Ile Thr Gln Lys Gly Gln Lys Asn Ser
                805                 810                 815
Arg Glu Arg Met Lys Arg Ile Glu Glu Gly Ile Lys Glu Leu Gly Ser
            820                 825                 830
Gln Ile Leu Lys Glu His Pro Val Glu Asn Thr Gln Leu Gln Asn Glu
        835                 840                 845
Lys Leu Tyr Leu Tyr Tyr Leu Gln Asn Gly Arg Asp Met Tyr Val Asp
    850                 855                 860
Gln Glu Leu Asp Ile Asn Arg Leu Ser Asp Tyr Asp Val Asp His Ile
865                 870                 875                 880
Val Pro Gln Ser Phe Leu Lys Asp Asp Ser Ile Asp Asn Lys Val Leu
                885                 890                 895
Thr Arg Ser Asp Lys Asn Arg Gly Lys Ser Asp Asn Val Pro Ser Glu
```

```
            900             905             910
Glu Val Val Lys Lys Met Lys Asn Tyr Trp Arg Gln Leu Leu Asn Ala
        915             920             925
Lys Leu Ile Thr Gln Arg Lys Phe Asp Asn Leu Thr Lys Ala Glu Arg
        930             935             940
Gly Gly Leu Ser Glu Leu Asp Lys Ala Met Phe Ile Lys Arg Gln Leu
945             950             955             960
Val Glu Thr Arg Gln Ile Thr Lys His Val Ala Gln Ile Leu Asp Ser
                965             970             975
Arg Met Asn Thr Lys Tyr Asp Glu Asn Asp Lys Leu Ile Arg Glu Val
            980             985             990
Lys Val Ile Thr Leu Lys Ser Lys Leu Val Ser Asp Phe Arg Lys Asp
        995             1000            1005
Phe Gln Phe Tyr Lys Val Arg Glu Ile Asn Lys Tyr His His Ala
    1010            1015            1020
His Asp Ala Tyr Leu Asn Ala Val Val Gly Thr Ala Leu Ile Lys
    1025            1030            1035
Lys Tyr Pro Lys Leu Glu Ser Glu Phe Val Tyr Gly Asp Tyr Lys
    1040            1045            1050
Val Tyr Asp Val Arg Lys Met Ile Ala Lys Ser Glu Gln Glu Ile
    1055            1060            1065
Gly Lys Ala Thr Ala Lys Tyr Phe Phe Tyr Ser Asn Ile Met Asn
    1070            1075            1080
Phe Phe Lys Thr Glu Ile Thr Leu Ala Asn Gly Glu Ile Arg Lys
    1085            1090            1095
Arg Pro Leu Ile Glu Thr Asn Gly Glu Thr Gly Glu Ile Val Trp
    1100            1105            1110
Asp Lys Gly Arg Asp Phe Ala Thr Val Arg Lys Val Leu Ser Met
    1115            1120            1125
Pro Gln Val Asn Ile Val Lys Lys Thr Glu Val Gln Thr Gly Gly
    1130            1135            1140
Phe Ser Lys Glu Ser Ile Leu Pro Lys Arg Asn Ser Asp Lys Leu
    1145            1150            1155
Ile Ala Arg Lys Lys Asp Trp Asp Pro Lys Lys Tyr Gly Gly Phe
    1160            1165            1170
Asp Ser Pro Thr Val Ala Tyr Ser Val Leu Val Val Ala Lys Val
    1175            1180            1185
Glu Lys Gly Lys Ser Lys Lys Leu Lys Ser Val Lys Glu Leu Leu
    1190            1195            1200
Gly Ile Thr Ile Met Glu Arg Ser Ser Phe Glu Lys Asn Pro Ile
    1205            1210            1215
Asp Phe Leu Glu Ala Lys Gly Tyr Lys Glu Val Lys Lys Asp Leu
    1220            1225            1230
Ile Ile Lys Leu Pro Lys Tyr Ser Leu Phe Glu Leu Glu Asn Gly
    1235            1240            1245
Arg Lys Arg Met Leu Ala Ser Ala Gly Glu Leu Gln Lys Gly Asn
    1250            1255            1260
Glu Leu Ala Leu Pro Ser Lys Tyr Val Asn Phe Leu Tyr Leu Ala
    1265            1270            1275
Ser His Tyr Glu Lys Leu Lys Gly Ser Pro Glu Asp Asn Glu Gln
    1280            1285            1290
Lys Gln Leu Phe Val Glu Gln His Lys His Tyr Leu Asp Glu Ile
    1295            1300            1305
```

```
Ile Glu Gln Ile Ser Glu Phe Ser Lys Arg Val Ile Leu Ala Asp
    1310                1315                1320

Ala Asn Leu Asp Lys Val Leu Ser Ala Tyr Asn Lys His Arg Asp
    1325                1330                1335

Lys Pro Ile Arg Glu Gln Ala Glu Asn Ile Ile His Leu Phe Thr
    1340                1345                1350

Leu Thr Asn Leu Gly Ala Pro Ala Ala Phe Lys Tyr Phe Asp Thr
    1355                1360                1365

Thr Ile Asp Arg Lys Arg Tyr Thr Ser Thr Lys Glu Val Leu Asp
    1370                1375                1380

Ala Thr Leu Ile His Gln Ser Ile Thr Gly Leu Tyr Glu Thr Arg
    1385                1390                1395

Ile Asp Leu Ser Gln Leu Gly Gly Asp Lys Arg Pro Ala Ala Thr
    1400                1405                1410

Lys Lys Ala Gly Gln Ala Lys Lys Lys Lys
    1415                1420

<210> SEQ ID NO 103
<211> LENGTH: 1350
<212> TYPE: PRT
<213> ORGANISM: Artificial Sequence
<220> FEATURE:
<223> OTHER INFORMATION: Fusion protein

<400> SEQUENCE: 103

Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Glu Ala Ser Met Lys Arg Asn Tyr Ile Leu Gly Leu Asp Ile Gly Ile
            35                  40                  45

Thr Ser Val Gly Tyr Gly Ile Ile Asp Tyr Glu Thr Arg Asp Val Ile
        50                  55                  60

Asp Ala Gly Val Arg Leu Phe Lys Glu Ala Asn Val Glu Asn Asn Glu
65                  70                  75                  80

Gly Arg Arg Ser Lys Arg Gly Ala Arg Arg Leu Lys Arg Arg Arg Arg
                85                  90                  95

His Arg Ile Gln Arg Val Lys Lys Leu Leu Phe Asp Tyr Asn Leu Leu
                100                 105                 110

Thr Asp His Ser Glu Leu Ser Gly Ile Asn Pro Tyr Glu Ala Arg Val
            115                 120                 125

Lys Gly Leu Ser Gln Lys Leu Ser Glu Glu Glu Phe Ser Ala Ala Leu
        130                 135                 140

Leu His Leu Ala Lys Arg Arg Gly Val His Asn Val Asn Glu Val Glu
145                 150                 155                 160

Glu Asp Thr Gly Asn Glu Leu Ser Thr Lys Glu Gln Ile Ser Arg Asn
                165                 170                 175

Ser Lys Ala Leu Glu Glu Lys Tyr Val Ala Glu Leu Gln Leu Glu Arg
            180                 185                 190

Leu Lys Lys Asp Gly Glu Val Arg Gly Ser Ile Asn Arg Phe Lys Thr
        195                 200                 205

Ser Asp Tyr Val Lys Glu Ala Lys Gln Leu Leu Lys Val Gln Lys Ala
    210                 215                 220

Tyr His Gln Leu Asp Gln Ser Phe Ile Asp Thr Tyr Ile Asp Leu Leu
225                 230                 235                 240
```

-continued

Glu Thr Arg Arg Thr Tyr Tyr Glu Gly Pro Gly Gly Ser Pro Phe
            245                 250                 255

Gly Trp Lys Asp Ile Lys Glu Trp Tyr Glu Met Leu Met Gly His Cys
            260                 265                 270

Thr Tyr Phe Pro Glu Glu Leu Arg Ser Val Lys Tyr Ala Tyr Asn Ala
            275                 280                 285

Asp Leu Tyr Asn Ala Leu Asn Asp Leu Asn Asn Leu Val Ile Thr Arg
            290                 295                 300

Asp Glu Asn Glu Lys Leu Glu Tyr Tyr Glu Lys Phe Gln Ile Ile Glu
305                 310                 315                 320

Asn Val Phe Lys Gln Lys Lys Pro Thr Leu Lys Gln Ile Ala Lys
                    325                 330                 335

Glu Ile Leu Val Asn Glu Glu Asp Ile Lys Gly Tyr Arg Val Thr Ser
            340                 345                 350

Thr Gly Lys Pro Glu Phe Thr Asn Leu Lys Val Tyr His Asp Ile Lys
            355                 360                 365

Asp Ile Thr Ala Arg Lys Glu Ile Ile Glu Asn Ala Glu Leu Leu Asp
            370                 375                 380

Gln Ile Ala Lys Ile Leu Thr Ile Tyr Gln Ser Ser Glu Asp Ile Gln
385                 390                 395                 400

Glu Glu Leu Thr Asn Leu Asn Ser Glu Leu Thr Gln Glu Glu Ile Glu
            405                 410                 415

Gln Ile Ser Asn Leu Lys Gly Tyr Thr Gly Thr His Asn Leu Ser Leu
            420                 425                 430

Lys Ala Ile Asn Leu Ile Leu Asp Glu Leu Trp His Thr Asn Asp Asn
            435                 440                 445

Gln Ile Ala Ile Phe Asn Arg Leu Lys Leu Val Pro Lys Lys Val Asp
            450                 455                 460

Leu Ser Gln Gln Lys Glu Ile Pro Thr Thr Leu Val Asp Asp Phe Ile
465                 470                 475                 480

Leu Ser Pro Val Val Lys Arg Ser Phe Ile Gln Ser Ile Lys Val Ile
            485                 490                 495

Asn Ala Ile Ile Lys Lys Tyr Gly Leu Pro Asn Asp Ile Ile Glu
            500                 505                 510

Leu Ala Arg Glu Lys Asn Ser Lys Asp Ala Gln Lys Met Ile Asn Glu
            515                 520                 525

Met Gln Lys Arg Asn Arg Gln Thr Asn Glu Arg Ile Glu Glu Ile Ile
            530                 535                 540

Arg Thr Thr Gly Lys Glu Asn Ala Lys Tyr Leu Ile Glu Lys Ile Lys
545                 550                 555                 560

Leu His Asp Met Gln Glu Gly Lys Cys Leu Tyr Ser Leu Glu Ala Ile
            565                 570                 575

Pro Leu Glu Asp Leu Leu Asn Asn Pro Phe Asn Tyr Glu Val Asp His
            580                 585                 590

Ile Ile Pro Arg Ser Val Ser Phe Asp Asn Ser Phe Asn Asn Lys Val
            595                 600                 605

Leu Val Lys Gln Glu Glu Asn Ser Lys Lys Gly Asn Arg Thr Pro Phe
            610                 615                 620

Gln Tyr Leu Ser Ser Ser Asp Ser Lys Ile Ser Tyr Glu Thr Phe Lys
625                 630                 635                 640

Lys His Ile Leu Asn Leu Ala Lys Gly Lys Gly Arg Ile Ser Lys Thr
            645                 650                 655

```
Lys Lys Glu Tyr Leu Leu Glu Glu Arg Asp Ile Asn Arg Phe Ser Val
            660                 665                 670

Gln Lys Asp Phe Ile Asn Arg Asn Leu Val Asp Thr Arg Tyr Ala Thr
            675                 680                 685

Arg Gly Leu Met Asn Leu Leu Arg Ser Tyr Phe Arg Val Asn Asn Leu
            690                 695                 700

Asp Val Lys Val Lys Ser Ile Asn Gly Gly Phe Thr Ser Phe Leu Arg
705                 710                 715                 720

Arg Lys Trp Lys Phe Lys Lys Glu Arg Asn Lys Gly Tyr Lys His His
                    725                 730                 735

Ala Glu Asp Ala Leu Ile Ile Ala Asn Ala Asp Phe Ile Phe Lys Glu
            740                 745                 750

Trp Lys Lys Leu Asp Lys Ala Lys Lys Val Met Glu Asn Gln Met Phe
            755                 760                 765

Glu Glu Lys Gln Ala Glu Ser Met Pro Glu Ile Glu Thr Glu Gln Glu
            770                 775                 780

Tyr Lys Glu Ile Phe Ile Thr Pro His Gln Ile Lys His Ile Lys Asp
785                 790                 795                 800

Phe Lys Asp Tyr Lys Tyr Ser His Arg Val Asp Lys Lys Pro Asn Arg
                    805                 810                 815

Glu Leu Ile Asn Asp Thr Leu Tyr Ser Thr Arg Lys Asp Asp Lys Gly
            820                 825                 830

Asn Thr Leu Ile Val Asn Asn Leu Asn Gly Leu Tyr Asp Lys Asp Asn
            835                 840                 845

Asp Lys Leu Lys Lys Leu Ile Asn Lys Ser Pro Glu Lys Leu Leu Met
850                 855                 860

Tyr His His Asp Pro Gln Thr Tyr Gln Lys Leu Lys Leu Ile Met Glu
865                 870                 875                 880

Gln Tyr Gly Asp Glu Lys Asn Pro Leu Tyr Lys Tyr Tyr Glu Glu Thr
            885                 890                 895

Gly Asn Tyr Leu Thr Lys Tyr Ser Lys Lys Asp Asn Gly Pro Val Ile
            900                 905                 910

Lys Lys Ile Lys Tyr Tyr Gly Asn Lys Leu Asn Ala His Leu Asp Ile
            915                 920                 925

Thr Asp Asp Tyr Pro Asn Ser Arg Asn Lys Val Val Lys Leu Ser Leu
930                 935                 940

Lys Pro Tyr Arg Phe Asp Val Tyr Leu Asp Asn Gly Val Tyr Lys Phe
945                 950                 955                 960

Val Thr Val Lys Asn Leu Asp Val Ile Lys Lys Glu Asn Tyr Tyr Glu
            965                 970                 975

Val Asn Ser Lys Cys Tyr Glu Glu Ala Lys Lys Leu Lys Lys Ile Ser
            980                 985                 990

Asn Gln Ala Glu Phe Ile Ala Ser Phe Tyr Asn Asn Asp Leu Ile Lys
            995                 1000                1005

Ile Asn Gly Glu Leu Tyr Arg Val Ile Gly Val Asn Asn Asp Leu
            1010                1015                1020

Leu Asn Arg Ile Glu Val Asn Met Ile Asp Ile Thr Tyr Arg Glu
            1025                1030                1035

Tyr Leu Glu Asn Met Asn Asp Lys Arg Pro Pro Arg Ile Ile Lys
            1040                1045                1050

Thr Ile Ala Ser Lys Thr Gln Ser Ile Lys Lys Tyr Ser Thr Asp
            1055                1060                1065

Ile Leu Gly Asn Leu Tyr Glu Val Lys Ser Lys Lys His Pro Gln
```

```
                 1070                1075                1080

Ile Ile Lys Lys Gly Arg Ser Gly Gly Gly Glu Gly Arg Gly Ser
         1085                1090                1095

Leu Leu Thr Cys Gly Asp Val Glu Glu Asn Pro Gly Pro Met Val
         1100                1105                1110

Ser Lys Gly Glu Glu Leu Phe Thr Gly Val Val Pro Ile Leu Val
         1115                1120                1125

Glu Leu Asp Gly Asp Val Asn Gly His Lys Phe Ser Val Ser Gly
         1130                1135                1140

Glu Gly Glu Gly Asp Ala Thr Tyr Gly Lys Leu Thr Leu Lys Phe
         1145                1150                1155

Ile Cys Thr Thr Gly Lys Leu Pro Val Pro Trp Pro Thr Leu Val
         1160                1165                1170

Thr Thr Leu Thr Tyr Gly Val Gln Cys Phe Ser Arg Tyr Pro Asp
         1175                1180                1185

His Met Lys Gln His Asp Phe Phe Lys Ser Ala Met Pro Glu Gly
         1190                1195                1200

Tyr Val Gln Glu Arg Thr Ile Phe Phe Lys Asp Asp Gly Asn Tyr
         1205                1210                1215

Lys Thr Arg Ala Glu Val Lys Phe Glu Gly Asp Thr Leu Val Asn
         1220                1225                1230

Arg Ile Glu Leu Lys Gly Ile Asp Phe Lys Glu Asp Gly Asn Ile
         1235                1240                1245

Leu Gly His Lys Leu Glu Tyr Asn Tyr Asn Ser His Asn Val Tyr
         1250                1255                1260

Ile Met Ala Asp Lys Gln Lys Asn Gly Ile Lys Val Asn Phe Lys
         1265                1270                1275

Ile Arg His Asn Ile Glu Asp Gly Ser Val Gln Leu Ala Asp His
         1280                1285                1290

Tyr Gln Gln Asn Thr Pro Ile Gly Asp Gly Pro Val Leu Leu Pro
         1295                1300                1305

Asp Asn His Tyr Leu Ser Thr Gln Ser Ala Leu Ser Lys Asp Pro
         1310                1315                1320

Asn Glu Lys Arg Asp His Met Val Leu Leu Glu Phe Val Thr Ala
         1325                1330                1335

Ala Gly Ile Thr Leu Gly Met Asp Glu Leu Tyr Lys
         1340                1345

<210> SEQ ID NO 104
<211> LENGTH: 1345
<212> TYPE: PRT
<213> ORGANISM: Artificial Sequence
<220> FEATURE:
<223> OTHER INFORMATION: Fusion protein

<400> SEQUENCE: 104

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
            20                  25                  30

Ala Arg Gly Leu Ile Leu Asp Asp Glu Lys Arg Ala Lys Asp Tyr Lys
        35                  40                  45

Lys Ala Lys Gln Ile Ile Asp Lys Tyr His Gln Phe Phe Ile Glu Glu
    50                  55                  60

Ile Leu Ser Ser Val Cys Ile Ser Glu Asp Leu Leu Gln Asn Tyr Ser
```

```
                65                  70                  75                  80
Asp Val Tyr Phe Lys Leu Lys Lys Ser Asp Asp Asn Leu Gln Lys
                        85                  90                  95
Asp Phe Lys Ser Ala Lys Asp Thr Ile Lys Lys Gln Ile Ser Glu Tyr
                100                 105                 110
Ile Lys Asp Ser Glu Lys Phe Lys Asn Leu Phe Asn Gln Asn Leu Ile
                115                 120                 125
Asp Ala Lys Lys Gly Gln Glu Ser Asp Leu Ile Leu Trp Leu Lys Gln
        130                 135                 140
Ser Lys Asp Asn Gly Ile Glu Leu Phe Lys Ala Asn Ser Asp Ile Thr
145                 150                 155                 160
Asp Ile Asp Glu Ala Leu Glu Ile Ile Lys Ser Phe Lys Gly Trp Thr
                165                 170                 175
Thr Tyr Phe Lys Gly Phe His Glu Asn Arg Lys Asn Val Tyr Ser Ser
                180                 185                 190
Asn Asp Ile Pro Thr Ser Ile Ile Tyr Arg Ile Val Asp Asp Asn Leu
        195                 200                 205
Pro Lys Phe Leu Glu Asn Lys Ala Lys Tyr Glu Ser Leu Lys Asp Lys
        210                 215                 220
Ala Pro Glu Ala Ile Asn Tyr Glu Gln Ile Lys Lys Asp Leu Ala Glu
225                 230                 235                 240
Glu Leu Thr Phe Asp Ile Asp Tyr Lys Thr Ser Glu Val Asn Gln Arg
                245                 250                 255
Val Phe Ser Leu Asp Glu Val Phe Glu Ile Ala Asn Phe Asn Asn Tyr
                260                 265                 270
Leu Asn Gln Ser Gly Ile Thr Lys Phe Asn Thr Ile Ile Gly Gly Lys
        275                 280                 285
Phe Val Asn Gly Glu Asn Thr Lys Arg Lys Gly Ile Asn Glu Tyr Ile
        290                 295                 300
Asn Leu Tyr Ser Gln Gln Ile Asn Asp Lys Thr Leu Lys Lys Tyr Lys
305                 310                 315                 320
Met Ser Val Leu Phe Lys Gln Ile Leu Ser Asp Thr Glu Ser Lys Ser
                325                 330                 335
Phe Val Ile Asp Lys Leu Glu Asp Asp Ser Asp Val Val Thr Thr Met
                340                 345                 350
Gln Ser Phe Tyr Glu Gln Ile Ala Ala Phe Lys Thr Val Glu Glu Lys
                355                 360                 365
Ser Ile Lys Glu Thr Leu Ser Leu Leu Phe Asp Asp Leu Lys Ala Gln
        370                 375                 380
Lys Leu Asp Leu Ser Lys Ile Tyr Phe Lys Asn Asp Lys Ser Leu Thr
385                 390                 395                 400
Asp Leu Ser Gln Gln Val Phe Asp Tyr Ser Val Ile Gly Thr Ala
                405                 410                 415
Val Leu Glu Tyr Ile Thr Gln Gln Ile Ala Pro Lys Asn Leu Asp Asn
                420                 425                 430
Pro Ser Lys Lys Glu Gln Glu Leu Ile Ala Lys Lys Thr Glu Lys Ala
        435                 440                 445
Lys Tyr Leu Ser Leu Glu Thr Ile Lys Leu Ala Leu Glu Glu Phe Asn
        450                 455                 460
Lys His Arg Asp Ile Asp Lys Gln Cys Arg Phe Glu Glu Ile Leu Ala
465                 470                 475                 480
Asn Phe Ala Ala Ile Pro Met Ile Phe Asp Glu Ile Ala Gln Asn Lys
                485                 490                 495
```

-continued

Asp Asn Leu Ala Gln Ile Ser Ile Lys Tyr Gln Asn Gln Gly Lys Lys
            500                 505                 510

Asp Leu Leu Gln Ala Ser Ala Glu Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
        675                 680                 685

Leu Arg Ile Arg Asn His Ser Thr His Thr Lys Asn Gly Ser Pro Gln
    690                 695                 700

Lys Gly Tyr Glu Lys Phe Glu Phe Asn Ile Glu Asp Cys Arg Lys Phe
705                 710                 715                 720

Ile Asp Phe Tyr Lys Gln Ser Ile Ser Lys His Pro Glu Trp Lys Asp
                725                 730                 735

Phe Gly Phe Arg Phe Ser Asp Thr Gln Arg Tyr Asn Ser Ile Asp Glu
            740                 745                 750

Phe Tyr Arg Glu Val Glu Asn Gln Gly Tyr Lys Leu Thr Phe Glu Asn
        755                 760                 765

Ile Ser Glu Ser Tyr Ile Asp Ser Val Val Asn Gln Gly Lys Leu Tyr
    770                 775                 780

Leu Phe Gln Ile Tyr Asn Lys Asp Phe Ser Ala Tyr Ser Lys Gly Arg
785                 790                 795                 800

Pro Asn Leu His Thr Leu Tyr Trp Lys Ala Leu Phe Asp Glu Arg Asn
                805                 810                 815

Leu Gln Asp Val Val Tyr Lys Leu Asn Gly Glu Ala Glu Leu Phe Tyr
            820                 825                 830

Arg Lys Gln Ser Ile Pro Lys Lys Ile Thr His Pro Ala Lys Glu Ala
        835                 840                 845

Ile Ala Asn Lys Asn Lys Asp Asn Pro Lys Lys Glu Ser Val Phe Glu
    850                 855                 860

Tyr Asp Leu Ile Lys Asp Lys Arg Phe Thr Glu Asp Lys Phe Phe Phe
865                 870                 875                 880

His Cys Pro Ile Thr Ile Asn Phe Lys Ser Ser Gly Ala Asn Lys Phe
                885                 890                 895

Asn Asp Glu Ile Asn Leu Leu Leu Lys Glu Lys Ala Asn Asp Val His
            900                 905                 910

```
Ile Leu Ser Ile Asp Arg Gly Glu Arg His Leu Ala Tyr Tyr Thr Leu
            915                 920                 925

Val Asp Gly Lys Gly Asn Ile Ile Lys Gln Asp Thr Phe Asn Ile Ile
930                 935                 940

Gly Asn Asp Arg Met Lys Thr Asn Tyr His Asp Lys Leu Ala Ala Ile
945                 950                 955                 960

Glu Lys Asp Arg Asp Ser Ala Arg Lys Asp Trp Lys Lys Ile Asn Asn
            965                 970                 975

Ile Lys Glu Met Lys Glu Gly Tyr Leu Ser Gln Val Val His Glu Ile
            980                 985                 990

Ala Lys Leu Val Ile Glu Tyr Asn Ala Ile Val Val Phe Glu Asp Leu
            995                 1000                1005

Asn Phe Gly Phe Lys Arg Gly Arg Phe Lys Val Glu Lys Gln Val
    1010                1015                1020

Tyr Gln Lys Leu Glu Lys Met Leu Ile Glu Lys Leu Asn Tyr Leu
    1025                1030                1035

Val Phe Lys Asp Asn Glu Phe Asp Lys Thr Gly Gly Val Leu Arg
    1040                1045                1050

Ala Tyr Gln Leu Thr Ala Pro Phe Glu Thr Phe Lys Lys Met Gly
    1055                1060                1065

Lys Gln Thr Gly Ile Ile Tyr Tyr Val Pro Ala Gly Phe Thr Ser
    1070                1075                1080

Lys Ile Cys Pro Val Thr Gly Phe Val Asn Gln Leu Tyr Pro Lys
    1085                1090                1095

Tyr Glu Ser Val Ser Lys Ser Gln Glu Phe Phe Ser Lys Phe Asp
    1100                1105                1110

Lys Ile Cys Tyr Asn Leu Asp Lys Gly Tyr Phe Glu Phe Ser Phe
    1115                1120                1125

Asp Tyr Lys Asn Phe Gly Asp Lys Ala Ala Lys Gly Lys Trp Thr
    1130                1135                1140

Ile Ala Ser Phe Gly Ser Arg Leu Ile Asn Phe Arg Asn Ser Asp
    1145                1150                1155

Lys Asn His Asn Trp Asp Thr Arg Glu Val Tyr Pro Thr Lys Glu
    1160                1165                1170

Leu Glu Lys Leu Leu Lys Asp Tyr Ser Ile Glu Tyr Gly His Gly
    1175                1180                1185

Glu Cys Ile Lys Ala Ala Ile Cys Gly Glu Ser Asp Lys Lys Phe
    1190                1195                1200

Phe Ala Lys Leu Thr Ser Val Leu Asn Thr Ile Leu Gln Met Arg
    1205                1210                1215

Asn Ser Lys Thr Gly Thr Glu Leu Asp Tyr Leu Ile Ser Pro Val
    1220                1225                1230

Ala Asp Val Asn Gly Asn Phe Phe Asp Ser Arg Gln Ala Pro Lys
    1235                1240                1245

Asn Met Pro Gln Asp Ala Asp Ala Asn Gly Ala Tyr His Ile Gly
    1250                1255                1260

Leu Lys Gly Leu Met Leu Leu Gly Arg Ile Lys Asn Asn Gln Glu
    1265                1270                1275

Gly Lys Lys Leu Asn Leu Val Ile Lys Asn Glu Glu Tyr Phe Glu
    1280                1285                1290

Phe Val Gln Asn Arg Asn Asn Lys Arg Pro Ala Ala Thr Lys Lys
    1295                1300                1305

Ala Gly Gln Ala Lys Lys Lys Lys Gly Ser Tyr Pro Tyr Asp Val
```

-continued

```
            1310                1315                1320

Pro Asp Tyr Ala Tyr Pro Tyr Asp Val Pro Asp Tyr Ala Tyr Pro
    1325                1330                1335

Tyr Asp Val Pro Asp Tyr Ala
    1340            1345

<210> SEQ ID NO 105
<211> LENGTH: 1352
<212> TYPE: PRT
<213> ORGANISM: Artificial Sequence
<220> FEATURE:
<223> OTHER INFORMATION: Fusion protein

<400> SEQUENCE: 105

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
```

-continued

```
                325                 330                 335
Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
                450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
                580                 585                 590

Met Tyr Tyr Asp Tyr Phe Pro Asp Ala Ala Lys Met Ile Pro Lys Cys
                595                 600                 605

Ser Thr Gln Leu Lys Ala Val Thr Ala His Phe Gln Thr His Thr Thr
                610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
                660                 665                 670

Leu Cys Lys Trp Ile Asp Phe Thr Arg Asp Phe Leu Ser Lys Tyr Thr
                675                 680                 685

Lys Thr Thr Ser Ile Asp Leu Ser Ser Leu Arg Pro Ser Ser Gln Tyr
                690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
                740                 745                 750
```

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
        770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Leu Lys Asp Gln Lys Thr
                    805                 810                 815

Pro Ile Pro Asp Thr Leu Tyr Gln Glu Leu Tyr Asp Tyr Val Asn His
                    820                 825                 830

Arg Leu Ser His Asp Leu Ser Asp Glu Ala Arg Ala Leu Leu Pro Asn
                    835                 840                 845

Val Ile Thr Lys Glu Val Ser His Glu Ile Ile Lys Asp Arg Arg Phe
850                 855                 860

Thr Ser Asp Lys Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                    885                 890                 895

Lys Glu His Pro Glu Thr Pro Ile Ile Gly Ile Asp Arg Gly Glu Arg
                    900                 905                 910

Asn Leu Ile Tyr Ile Thr Val Ile Asp Ser Thr Gly Lys Ile Leu Glu
                    915                 920                 925

Gln Arg Ser Leu Asn Thr Ile Gln Gln Phe Asp Tyr Gln Lys Lys Leu
                    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                    965                 970                 975

His Glu Ile Val Asp Leu Met Ile His Tyr Gln Ala Val Val Val Leu
                    980                 985                 990

Glu Asn Leu Asn Phe Gly Phe Lys Ser Lys Arg Thr Gly Ile Ala Glu
                    995                 1000                1005

Lys Ala Val Tyr Gln Gln Phe Glu Lys Met Leu Ile Asp Lys Leu
        1010                1015                1020

Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
        1040                1045                1050

Lys Met Gly Thr Gln Ser Gly Phe Leu Phe Tyr Val Pro Ala Pro
        1055                1060                1065

Tyr Thr Ser Lys Ile Asp Pro Leu Thr Gly Phe Val Asp Pro Phe
        1070                1075                1080

Val Trp Lys Thr Ile Lys Asn His Glu Ser Arg Lys His Phe Leu
        1085                1090                1095

Glu Gly Phe Asp Phe Leu His Tyr Asp Val Lys Thr Gly Asp Phe
        1100                1105                1110

Ile Leu His Phe Lys Met Asn Arg Asn Leu Ser Phe Gln Arg Gly
        1115                1120                1125

Leu Pro Gly Phe Met Pro Ala Trp Asp Ile Val Phe Glu Lys Asn
        1130                1135                1140

Glu Thr Gln Phe Asp Ala Lys Gly Thr Pro Phe Ile Ala Gly Lys
        1145                1150                1155

```
Arg Ile Val Pro Val Ile Glu Asn His Arg Phe Thr Gly Arg Tyr
            1160                1165                1170

Arg Asp Leu Tyr Pro Ala Asn Glu Leu Ile Ala Leu Leu Glu Glu
1175                1180                1185

Lys Gly Ile Val Phe Arg Asp Gly Ser Asn Ile Leu Pro Lys Leu
        1190                1195                1200

Leu Glu Asn Asp Asp Ser His Ala Ile Asp Thr Met Val Ala Leu
    1205                1210                1215

Ile Arg Ser Val Leu Gln Met Arg Asn Ser Asn Ala Ala Thr Gly
1220                1225                1230

Glu Asp Tyr Ile Asn Ser Pro Val Arg Asp Leu Asn Gly Val Cys
        1235                1240                1245

Phe Asp Ser Arg Phe Gln Asn Pro Glu Trp Pro Met Asp Ala Asp
    1250                1255                1260

Ala Asn Gly Ala Tyr His Ile Ala Leu Lys Gly Gln Leu Leu Leu
1265                1270                1275

Asn His Leu Lys Glu Ser Lys Asp Leu Lys Leu Gln Asn Gly Ile
        1280                1285                1290

Ser Asn Gln Asp Trp Leu Ala Tyr Ile Gln Glu Leu Arg Asn Lys
    1295                1300                1305

Arg Pro Ala Ala Thr Lys Lys Ala Gly Gln Ala Lys Lys Lys Lys
1310                1315                1320

Gly Ser Tyr Pro Tyr Asp Val Pro Asp Tyr Ala Tyr Pro Tyr Asp
        1325                1330                1335

Val Pro Asp Tyr Ala Tyr Pro Tyr Asp Val Pro Asp Tyr Ala
    1340                1345                1350
```

<210> SEQ ID NO 106
<211> LENGTH: 1273
<212> TYPE: PRT
<213> ORGANISM: Artificial Sequence
<220> FEATURE:
<223> OTHER INFORMATION: Fusion protein

<400> SEQUENCE: 106

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160
```

```
Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
```

-continued

```
                580             585             590
Leu Pro Lys Val Phe Ser Lys Lys Trp Met Ala Tyr Tyr Asn Pro
            595                 600                 605
Ser Glu Asp Ile Gln Lys Ile Tyr Lys Asn Gly Thr Phe Lys Lys Gly
    610                 615                 620
Asp Met Phe Asn Leu Asn Asp Cys His Lys Leu Ile Asp Phe Phe Lys
625                 630                 635                 640
Asp Ser Ile Ser Arg Tyr Pro Lys Trp Ser Asn Ala Tyr Asp Phe Asn
                645                 650                 655
Phe Ser Glu Thr Glu Lys Tyr Lys Asp Ile Ala Gly Phe Tyr Arg Glu
            660                 665                 670
Val Glu Glu Gln Gly Tyr Lys Val Ser Phe Glu Ser Ala Ser Lys Lys
        675                 680                 685
Glu Val Asp Lys Leu Val Glu Glu Gly Lys Leu Tyr Met Phe Gln Ile
    690                 695                 700
Tyr Asn Lys Asp Phe Ser Asp Lys Ser His Gly Thr Pro Asn Leu His
705                 710                 715                 720
Thr Met Tyr Phe Lys Leu Leu Phe Asp Glu Asn Asn His Gly Gln Ile
                725                 730                 735
Arg Leu Ser Gly Gly Ala Glu Leu Phe Met Arg Arg Ala Ser Leu Lys
            740                 745                 750
Lys Glu Glu Leu Val Val His Pro Ala Asn Ser Pro Ile Ala Asn Lys
        755                 760                 765
Asn Pro Asp Asn Pro Lys Lys Thr Thr Thr Leu Ser Tyr Asp Val Tyr
    770                 775                 780
Lys Asp Lys Arg Phe Ser Glu Asp Gln Tyr Glu Leu His Ile Pro Ile
785                 790                 795                 800
Ala Ile Asn Lys Cys Pro Lys Asn Ile Phe Lys Ile Asn Thr Glu Val
                805                 810                 815
Arg Val Leu Leu Lys His Asp Asp Asn Pro Tyr Val Ile Gly Ile Asp
            820                 825                 830
Arg Gly Glu Arg Asn Leu Leu Tyr Ile Val Val Asp Gly Lys Gly
        835                 840                 845
Asn Ile Val Glu Gln Tyr Ser Leu Asn Glu Ile Ile Asn Asn Phe Asn
    850                 855                 860
Gly Ile Arg Ile Lys Thr Asp Tyr His Ser Leu Leu Asp Lys Lys Glu
865                 870                 875                 880
Lys Glu Arg Phe Glu Ala Arg Gln Asn Trp Thr Ser Ile Glu Asn Ile
                885                 890                 895
Lys Glu Leu Lys Ala Gly Tyr Ile Ser Gln Val Val His Lys Ile Cys
            900                 905                 910
Glu Leu Val Glu Lys Tyr Asp Ala Val Ile Ala Leu Glu Asp Leu Asn
        915                 920                 925
Ser Gly Phe Lys Asn Ser Arg Val Lys Val Glu Lys Gln Val Tyr Gln
    930                 935                 940
Lys Phe Glu Lys Met Leu Ile Asp Lys Leu Asn Tyr Met Val Asp Lys
945                 950                 955                 960
Lys Ser Asn Pro Cys Ala Thr Gly Gly Ala Leu Lys Gly Tyr Gln Ile
                965                 970                 975
Thr Asn Lys Phe Glu Ser Phe Lys Ser Met Ser Thr Gln Asn Gly Phe
            980                 985                 990
Ile Phe Tyr Ile Pro Ala Trp Leu Thr Ser Lys Ile Asp Pro Ser Thr
        995                 1000                1005
```

Gly Phe Val Asn Leu Leu Lys Thr Lys Tyr Thr Ser Ile Ala Asp
            1010                1015                1020

Ser Lys Lys Phe Ile Ser Ser Phe Asp Arg Ile Met Tyr Val Pro
            1025                1030                1035

Glu Glu Asp Leu Phe Glu Phe Ala Leu Asp Tyr Lys Asn Phe Ser
            1040                1045                1050

Arg Thr Asp Ala Asp Tyr Ile Lys Lys Trp Lys Leu Tyr Ser Tyr
            1055                1060                1065

Gly Asn Arg Ile Arg Ile Phe Arg Asn Pro Lys Lys Asn Asn Val
            1070                1075                1080

Phe Asp Trp Glu Glu Val Cys Leu Thr Ser Ala Tyr Lys Glu Leu
            1085                1090                1095

Phe Asn Lys Tyr Gly Ile Asn Tyr Gln Gln Gly Asp Ile Arg Ala
            1100                1105                1110

Leu Leu Cys Glu Gln Ser Asp Lys Ala Phe Tyr Ser Ser Phe Met
            1115                1120                1125

Ala Leu Met Ser Leu Met Leu Gln Met Arg Asn Ser Ile Thr Gly
            1130                1135                1140

Arg Thr Asp Val Asp Phe Leu Ile Ser Pro Val Lys Asn Ser Asp
            1145                1150                1155

Gly Ile Phe Tyr Asp Ser Arg Asn Tyr Glu Ala Gln Glu Asn Ala
            1160                1165                1170

Ile Leu Pro Lys Asn Ala Asp Ala Asn Gly Ala Tyr Asn Ile Ala
            1175                1180                1185

Arg Lys Val Leu Trp Ala Ile Gly Gln Phe Lys Lys Ala Glu Asp
            1190                1195                1200

Glu Lys Leu Asp Lys Val Lys Ile Ala Ile Ser Asn Lys Glu Trp
            1205                1210                1215

Leu Glu Tyr Ala Gln Thr Ser Val Lys His Lys Arg Pro Ala Ala
            1220                1225                1230

Thr Lys Lys Ala Gly Gln Ala Lys Lys Lys Lys Gly Ser Tyr Pro
            1235                1240                1245

Tyr Asp Val Pro Asp Tyr Ala Tyr Pro Tyr Asp Val Pro Asp Tyr
            1250                1255                1260

Ala Tyr Pro Tyr Asp Val Pro Asp Tyr Ala
            1265                1270

<210> SEQ ID NO 107
<211> LENGTH: 12
<212> TYPE: PRT
<213> ORGANISM: Artificial Sequence
<220> FEATURE:
<223> OTHER INFORMATION: Linker

<400> SEQUENCE: 107

Gly Gly Gly Ser Gly Gly Gly Ser Gly Gly Gly Ser
1               5                   10

<210> SEQ ID NO 108
<211> LENGTH: 32
<212> TYPE: PRT
<213> ORGANISM: Artificial Sequence
<220> FEATURE:
<223> OTHER INFORMATION: Linker

<400> SEQUENCE: 108

Ser Gly Gly Ser Ser Gly Gly Ser Ser Gly Ser Glu Thr Pro Gly Thr

```
                 1               5                  10                  15
               Ser Glu Ser Ala Thr Pro Glu Ser Ser Gly Gly Ser Ser Gly Gly Ser
                                20                  25                  30

<210> SEQ ID NO 109
<211> LENGTH: 46
<212> TYPE: PRT
<213> ORGANISM: Artificial Sequence
<220> FEATURE:
<223> OTHER INFORMATION: Linker

<400> SEQUENCE: 109

Ala Glu Ala Ala Ala Lys Glu Ala Ala Ala Lys Glu Ala Ala Ala Lys
1               5                   10                  15

Glu Ala Ala Ala Lys Ala Leu Glu Ala Glu Ala Ala Ala Lys Glu Ala
                20                  25                  30

Ala Ala Lys Glu Ala Ala Ala Lys Glu Ala Ala Ala Lys Ala
            35                  40                  45

<210> SEQ ID NO 110
<211> LENGTH: 41
<212> TYPE: PRT
<213> ORGANISM: Artificial Sequence
<220> FEATURE:
<223> OTHER INFORMATION: Linker

<400> SEQUENCE: 110

Gly Ser Asp Tyr Lys Asp His Asp Gly Asp Tyr Lys Asp His Asp Ile
1               5                   10                  15

Asp Tyr Lys Asp Asp Asp Asp Lys Met Ala Pro Lys Lys Lys Arg Lys
                20                  25                  30

Val Gly Ile His Gly Val Pro Ala Ala
            35                  40

<210> SEQ ID NO 111
<211> LENGTH: 32
<212> TYPE: PRT
<213> ORGANISM: Artificial Sequence
<220> FEATURE:
<223> OTHER INFORMATION: Linker

<400> SEQUENCE: 111

Gly Ser Asp Tyr Lys Asp His Asp Gly Asp Tyr Lys Asp His Asp Ile
1               5                   10                  15

Asp Tyr Lys Asp Asp Asp Asp Lys Gly Ile His Gly Val Pro Ala Ala
                20                  25                  30

<210> SEQ ID NO 112
<211> LENGTH: 74
<212> TYPE: PRT
<213> ORGANISM: Artificial Sequence
<220> FEATURE:
<223> OTHER INFORMATION: Linker

<400> SEQUENCE: 112

Gly Ser Gly Ser Glu Ala Ala Ala Lys Glu Ala Ala Ala Lys Glu Ala
1               5                   10                  15

Ala Ala Lys Glu Ala Ala Ala Lys Leu Glu Ala Ala Ala Ala Lys
                20                  25                  30

Glu Ala Ala Ala Lys Glu Ala Ala Ala Lys Glu Ala Ala Ala Lys Gly
            35                  40                  45

Ser Gly Ser Ala Ala Ala Lys Glu Ala Ala Ala Lys Glu Ala Ala Ala
```

```
                 50                  55                  60

Lys Glu Ala Ala Ala Lys Gly Ser Gly Ser
 65                  70

<210> SEQ ID NO 113
<211> LENGTH: 74
<212> TYPE: PRT
<213> ORGANISM: Artificial Sequence
<220> FEATURE:
<223> OTHER INFORMATION: Linker

<400> SEQUENCE: 113

Ala Gly Ser Gly Gly Ser Gly Gly Ser Gly Gly Ser Pro Val Pro Ser
 1               5                  10                  15

Thr Pro Pro Thr Asn Ser Ser Ser Thr Pro Pro Thr Pro Ser Pro Ser
                20                  25                  30

Pro Val Pro Ser Thr Pro Pro Thr Asn Ser Ser Ser Thr Pro Pro Thr
                35                  40                  45

Pro Ser Pro Ser Pro Val Pro Ser Thr Pro Pro Thr Asn Ser Ser Ser
                50                  55                  60

Thr Pro Pro Thr Pro Ser Pro Ser Ala Ser
 65                  70

<210> SEQ ID NO 114
<211> LENGTH: 66
<212> TYPE: PRT
<213> ORGANISM: Artificial Sequence
<220> FEATURE:
<223> OTHER INFORMATION: Linker

<400> SEQUENCE: 114

Ala Gly Ser Gly Gly Ser Gly Gly Ser Gly Gly Ser Pro Val Pro Ser
 1               5                  10                  15

Thr Pro Pro Thr Pro Ser Pro Ser Thr Pro Pro Thr Pro Ser Pro Ser
                20                  25                  30

Gly Gly Ser Gly Asn Ser Ser Gly Gly Gly Ser Pro Val Pro Ser
                35                  40                  45

Thr Pro Pro Thr Pro Ser Pro Ser Thr Pro Pro Thr Pro Ser Pro Ser
                50                  55                  60

Ala Ser
 65

<210> SEQ ID NO 115
<211> LENGTH: 262
<212> TYPE: PRT
<213> ORGANISM: Artificial Sequence
<220> FEATURE:
<223> OTHER INFORMATION: Artificial sequence

<400> SEQUENCE: 115

Ala Gly Ser Gly Gly Ser Gly Gly Ser Gly Gly Ser Pro Val Pro Ser
 1               5                  10                  15

Thr Pro Pro Thr Pro Ser Pro Ser Thr Pro Pro Thr Pro Ser Pro Ser
                20                  25                  30

Ile Gln Arg Thr Pro Lys Ile Gln Val Tyr Ser Arg His Pro Ala Glu
                35                  40                  45

Asn Gly Lys Ser Asn Phe Leu Asn Cys Tyr Val Ser Gly Phe His Pro
                50                  55                  60

Ser Asp Ile Glu Val Asp Leu Leu Lys Asn Gly Glu Arg Ile Glu Lys
 65                  70                  75                  80
```

Val Glu His Ser Asp Leu Ser Phe Ser Lys Asp Trp Ser Phe Tyr Leu
            85                  90                  95

Leu Tyr Tyr Thr Glu Phe Thr Pro Thr Glu Lys Asp Glu Tyr Ala Cys
        100                 105                 110

Arg Val Asn His Val Thr Leu Ser Gln Pro Lys Ile Val Lys Trp Asp
        115                 120                 125

Arg Asp Gly Ser Gly Gly Ser Gly Gly Ser Gly Gly Ser Ile Gln
    130                 135                 140

Arg Thr Pro Lys Ile Gln Val Tyr Ser Arg His Pro Ala Glu Asn Gly
145                 150                 155                 160

Lys Ser Asn Phe Leu Asn Cys Tyr Val Ser Gly Phe His Pro Ser Asp
            165                 170                 175

Ile Glu Val Asp Leu Leu Lys Asn Gly Glu Arg Ile Glu Lys Val Glu
        180                 185                 190

His Ser Asp Leu Ser Phe Ser Lys Asp Trp Ser Phe Tyr Leu Leu Tyr
        195                 200                 205

Tyr Thr Glu Phe Thr Pro Thr Glu Lys Asp Glu Tyr Ala Cys Arg Val
    210                 215                 220

Asn His Val Thr Leu Ser Gln Pro Lys Ile Val Lys Trp Asp Arg Asp
225                 230                 235                 240

Pro Val Pro Ser Thr Pro Pro Thr Pro Ser Pro Ser Thr Pro Pro Thr
            245                 250                 255

Pro Ser Pro Ser Ala Ser
            260

<210> SEQ ID NO 116
<211> LENGTH: 326
<212> TYPE: PRT
<213> ORGANISM: Artificial Sequence
<220> FEATURE:
<223> OTHER INFORMATION: Artificial sequence

<400> SEQUENCE: 116

Ala Gly Ser Gly Gly Ser Gly Gly Ser Gly Gly Ser Pro Val Pro Ser
1               5                   10                  15

Thr Pro Pro Thr Pro Ser Pro Ser Thr Pro Pro Thr Pro Ser Pro Ser
            20                  25                  30

Asp Gly Arg Tyr Ser Leu Thr Tyr Ile Tyr Thr Gly Leu Ser Lys His
        35                  40                  45

Val Glu Asp Val Pro Ala Phe Gln Ala Leu Gly Ser Leu Asn Asp Leu
    50                  55                  60

Gln Phe Phe Arg Tyr Asn Ser Lys Asp Arg Lys Ser Gln Pro Met Gly
65                  70                  75                  80

Leu Trp Arg Gln Val Glu Gly Met Glu Asp Trp Lys Gln Asp Ser Gln
            85                  90                  95

Leu Gln Lys Ala Arg Glu Asp Ile Phe Met Glu Thr Leu Lys Asp Ile
        100                 105                 110

Val Glu Tyr Tyr Asn Asp Ser Asn Gly Ser His Val Leu Gln Gly Arg
        115                 120                 125

Phe Gly Cys Glu Ile Glu Asn Asn Arg Ser Ser Gly Ala Phe Trp Lys
    130                 135                 140

Tyr Tyr Tyr Asp Gly Lys Asp Tyr Ile Glu Phe Asn Lys Glu Ile Pro
145                 150                 155                 160

Ala Trp Val Pro Phe Asp Pro Ala Ala Gln Ile Thr Lys Gln Lys Trp
            165                 170                 175

```
Glu Ala Glu Pro Val Tyr Val Gln Arg Ala Lys Ala Tyr Leu Glu Glu
            180                 185                 190

Glu Cys Pro Ala Thr Leu Arg Lys Tyr Leu Lys Tyr Ser Lys Asn Ile
            195                 200                 205

Leu Asp Arg Gln Asp Pro Pro Ser Val Val Thr Ser His Gln Ala
210                 215                 220

Pro Gly Glu Lys Lys Leu Lys Cys Leu Ala Tyr Asp Phe Tyr Pro
225                 230                 235                 240

Gly Lys Ile Asp Val His Trp Thr Arg Ala Gly Glu Val Gln Glu Pro
            245                 250                 255

Glu Leu Arg Gly Asp Val Leu His Asn Gly Asn Gly Thr Tyr Gln Ser
            260                 265                 270

Trp Val Val Val Ala Val Pro Pro Gln Asp Thr Ala Pro Tyr Ser Cys
            275                 280                 285

His Val Gln His Ser Ser Leu Ala Gln Pro Leu Val Val Pro Trp Glu
            290                 295                 300

Ala Ser Pro Val Pro Ser Thr Pro Pro Thr Pro Ser Pro Ser Thr Pro
305                 310                 315                 320

Pro Thr Pro Ser Ala Ser
                325

<210> SEQ ID NO 117
<211> LENGTH: 606
<212> TYPE: PRT
<213> ORGANISM: Artificial Sequence
<220> FEATURE:
<223> OTHER INFORMATION: Artificial sequence

<400> SEQUENCE: 117

Ala Gly Ser Gly Gly Ser Gly Gly Ser Gly Gly Ser Gly Gly Ser Gly
1               5                   10                  15

Gly Ser Gly Gly Ser Gly Gly Ser Asp Gly Arg Tyr Ser Leu Thr Tyr
            20                  25                  30

Ile Tyr Thr Gly Leu Ser Lys His Val Glu Asp Val Pro Ala Phe Gln
            35                  40                  45

Ala Leu Gly Ser Leu Asn Asp Leu Gln Phe Phe Arg Tyr Asn Ser Lys
50                  55                  60

Asp Arg Lys Ser Gln Pro Met Gly Leu Trp Arg Gln Val Glu Gly Met
65                  70                  75                  80

Glu Asp Trp Lys Gln Asp Ser Gln Leu Gln Lys Ala Arg Glu Asp Ile
            85                  90                  95

Phe Met Glu Thr Leu Lys Asp Ile Val Glu Tyr Tyr Asn Asp Ser Asn
            100                 105                 110

Gly Ser His Val Leu Gln Gly Arg Phe Gly Cys Glu Ile Glu Asn Asn
            115                 120                 125

Arg Ser Ser Gly Ala Phe Trp Lys Tyr Tyr Asp Gly Lys Asp Tyr
130                 135                 140

Ile Glu Phe Asn Lys Glu Ile Pro Ala Trp Val Pro Phe Asp Pro Ala
145                 150                 155                 160

Ala Gln Ile Thr Lys Gln Lys Trp Glu Ala Glu Pro Val Tyr Val Gln
            165                 170                 175

Arg Ala Lys Ala Tyr Leu Glu Glu Glu Cys Pro Ala Thr Leu Arg Lys
            180                 185                 190

Tyr Leu Lys Tyr Ser Lys Asn Ile Leu Asp Arg Gln Asp Pro Pro Ser
            195                 200                 205
```

```
Val Val Val Thr Ser His Gln Ala Pro Gly Glu Lys Lys Leu Lys
    210                 215                 220

Cys Leu Ala Tyr Asp Phe Tyr Pro Gly Lys Ile Asp Val His Trp Thr
225                 230                 235                 240

Arg Ala Gly Glu Val Gln Glu Pro Glu Leu Arg Gly Asp Val Leu His
                245                 250                 255

Asn Gly Asn Gly Thr Tyr Gln Ser Trp Val Val Ala Val Pro Pro
                260                 265                 270

Gln Asp Thr Ala Pro Tyr Ser Cys His Val Gln His Ser Ser Leu Ala
                275                 280                 285

Gln Pro Leu Val Val Pro Trp Glu Ala Ser Gly Ser Gly Gly Ser
290                 295                 300

Gly Gly Ser Gly Gly Ser Asp Gly Arg Tyr Ser Leu Thr Tyr Ile Tyr
305                 310                 315                 320

Thr Gly Leu Ser Lys His Val Glu Asp Val Pro Ala Phe Gln Ala Leu
                325                 330                 335

Gly Ser Leu Asn Asp Leu Gln Phe Phe Arg Tyr Asn Ser Lys Asp Arg
                340                 345                 350

Lys Ser Gln Pro Met Gly Leu Trp Arg Gln Val Glu Gly Met Glu Asp
                355                 360                 365

Trp Lys Gln Asp Ser Gln Leu Gln Lys Ala Arg Glu Asp Ile Phe Met
                370                 375                 380

Glu Thr Leu Lys Asp Ile Val Glu Tyr Tyr Asn Asp Ser Asn Gly Ser
385                 390                 395                 400

His Val Leu Gln Gly Arg Phe Gly Cys Glu Ile Glu Asn Asn Arg Ser
                405                 410                 415

Ser Gly Ala Phe Trp Lys Tyr Tyr Tyr Asp Gly Lys Asp Tyr Ile Glu
                420                 425                 430

Phe Asn Lys Glu Ile Pro Ala Trp Val Pro Phe Asp Pro Ala Ala Gln
                435                 440                 445

Ile Thr Lys Gln Lys Trp Glu Ala Glu Pro Val Tyr Val Gln Arg Ala
    450                 455                 460

Lys Ala Tyr Leu Glu Glu Glu Cys Pro Ala Thr Leu Arg Lys Tyr Leu
465                 470                 475                 480

Lys Tyr Ser Lys Asn Ile Leu Asp Arg Gln Asp Pro Pro Ser Val Val
                485                 490                 495

Val Thr Ser His Gln Ala Pro Gly Glu Lys Lys Leu Lys Cys Leu
                500                 505                 510

Ala Tyr Asp Phe Tyr Pro Gly Lys Ile Asp Val His Trp Thr Arg Ala
                515                 520                 525

Gly Glu Val Gln Glu Pro Glu Leu Arg Gly Asp Val Leu His Asn Gly
                530                 535                 540

Asn Gly Thr Tyr Gln Ser Trp Val Val Ala Val Pro Pro Gln Asp
545                 550                 555                 560

Thr Ala Pro Tyr Ser Cys His Val Gln His Ser Ser Leu Ala Gln Pro
                565                 570                 575

Leu Val Val Pro Trp Glu Ala Ser Pro Val Pro Ser Thr Pro Pro Thr
                580                 585                 590

Pro Ser Pro Ser Thr Pro Pro Thr Pro Ser Pro Ser Ala Ser
                595                 600                 605

<210> SEQ ID NO 118
<211> LENGTH: 31
```

```
<212> TYPE: DNA
<213> ORGANISM: Artificial Sequence
<220> FEATURE:
<223> OTHER INFORMATION: Artificial Sequence

<400> SEQUENCE: 118
acattgtagc cctctgtgtg ctcaaggggg g                               31

<210> SEQ ID NO 119
<211> LENGTH: 31
<212> TYPE: DNA
<213> ORGANISM: Artificial Sequence
<220> FEATURE:
<223> OTHER INFORMATION: Artificial Sequence

<400> SEQUENCE: 119
ccccccttga gcacacagag ggctacaatg t                               31

<210> SEQ ID NO 120
<211> LENGTH: 22
<212> TYPE: DNA
<213> ORGANISM: Artificial Sequence
<220> FEATURE:
<223> OTHER INFORMATION: Artificial Sequence

<400> SEQUENCE: 120
acattgtagc cctctgtgtg ct                                         22

<210> SEQ ID NO 121
<211> LENGTH: 23
<212> TYPE: DNA
<213> ORGANISM: Artificial Sequence
<220> FEATURE:
<223> OTHER INFORMATION: Artificial Sequence

<400> SEQUENCE: 121
gagcacacag agggctacaa tgt                                        23

<210> SEQ ID NO 122
<211> LENGTH: 9
<212> TYPE: DNA
<213> ORGANISM: Artificial Sequence
<220> FEATURE:
<223> OTHER INFORMATION: Artificial Sequence

<400> SEQUENCE: 122 caagggggg                                                         9

<210> SEQ ID NO 123
<211> LENGTH: 8
<212> TYPE: DNA
<213> ORGANISM: Artificial Sequence
<220> FEATURE:
<223> OTHER INFORMATION: Artificial Sequence

<400> SEQUENCE: 123 cccccctt                                                          8

<210> SEQ ID NO 124
<211> LENGTH: 22
<212> TYPE: DNA
<213> ORGANISM: Artificial Sequence
<220> FEATURE:
<223> OTHER INFORMATION: Artificial Sequence

<400> SEQUENCE: 124
```

```
acattgtagc cctctgtgtg ct                                              22

<210> SEQ ID NO 125
<211> LENGTH: 22
<212> TYPE: DNA
<213> ORGANISM: Artificial Sequence
<220> FEATURE:
<223> OTHER INFORMATION: Artificial Sequence

<400> SEQUENCE: 125
agcacacaga gggctacaat gt                                              22

<210> SEQ ID NO 126
<211> LENGTH: 9
<212> TYPE: DNA
<213> ORGANISM: Artificial Sequence
<220> FEATURE:
<223> OTHER INFORMATION: Artificial Sequence

<400> SEQUENCE: 126 caagggggg                                                              9

<210> SEQ ID NO 127
<211> LENGTH: 9
<212> TYPE: DNA
<213> ORGANISM: Artificial Sequence
<220> FEATURE:
<223> OTHER INFORMATION: Artificial Sequence

<400> SEQUENCE: 127 cccccctgg                                                              9

<210> SEQ ID NO 128
<211> LENGTH: 23
<212> TYPE: DNA
<213> ORGANISM: Artificial Sequence
<220> FEATURE:
<223> OTHER INFORMATION: Artificial Sequence

<400> SEQUENCE: 128
acattgtagc cctctgtgtg ctc                                             23

<210> SEQ ID NO 129
<211> LENGTH: 23
<212> TYPE: DNA
<213> ORGANISM: Artificial Sequence
<220> FEATURE:
<223> OTHER INFORMATION: Artificial Sequence

<400> SEQUENCE: 129
gagcacacag agggctacaa tgt                                             23

<210> SEQ ID NO 130
<211> LENGTH: 9
<212> TYPE: DNA
<213> ORGANISM: Artificial Sequence
<220> FEATURE:
<223> OTHER INFORMATION: Artificial Sequence

<400> SEQUENCE: 130 caagggggg                                                              9

<210> SEQ ID NO 131
<211> LENGTH: 9
<212> TYPE: DNA
<213> ORGANISM: Artificial Sequence
```

-continued

<220> FEATURE:
<223> OTHER INFORMATION: Artificial Sequence

<400> SEQUENCE: 131 cccccttg                                                                        9

<210> SEQ ID NO 132
<211> LENGTH: 22
<212> TYPE: DNA
<213> ORGANISM: Artificial Sequence
<220> FEATURE:
<223> OTHER INFORMATION: Artificial Sequence

<400> SEQUENCE: 132
acattgtagc cctctgtgtg ct                                                        22

<210> SEQ ID NO 133
<211> LENGTH: 22
<212> TYPE: DNA
<213> ORGANISM: Artificial Sequence
<220> FEATURE:
<223> OTHER INFORMATION: Artificial Sequence

<400> SEQUENCE: 133
agcacacaga gggctacaat gt                                                        22

<210> SEQ ID NO 134
<211> LENGTH: 8
<212> TYPE: DNA
<213> ORGANISM: Artificial Sequence
<220> FEATURE:
<223> OTHER INFORMATION: Artificial Sequence

<400> SEQUENCE: 134 aagggggg                                                                        8

<210> SEQ ID NO 135
<211> LENGTH: 8
<212> TYPE: DNA
<213> ORGANISM: Artificial Sequence
<220> FEATURE:
<223> OTHER INFORMATION: Artificial Sequence

<400> SEQUENCE: 135 ccccectt                                                                        8

<210> SEQ ID NO 136
<211> LENGTH: 32
<212> TYPE: DNA
<213> ORGANISM: Artificial Sequence
<220> FEATURE:
<223> OTHER INFORMATION: Artificial Sequence

<400> SEQUENCE: 136
acattgtagc cctctgtgtg ctccaagggg gg                                             32

<210> SEQ ID NO 137
<211> LENGTH: 30
<212> TYPE: DNA
<213> ORGANISM: Artificial Sequence
<220> FEATURE:
<223> OTHER INFORMATION: Artificial Sequence

<400> SEQUENCE: 137
acattgtagc cctctgtgtg ctaaggggggg                                               30

```
<210> SEQ ID NO 138
<211> LENGTH: 27
<212> TYPE: DNA
<213> ORGANISM: Artificial Sequence
<220> FEATURE:
<223> OTHER INFORMATION: Artificial Sequence

<400> SEQUENCE: 138
aatccttatg cagaatcaga gctcaaa                                        27

<210> SEQ ID NO 139
<211> LENGTH: 27
<212> TYPE: DNA
<213> ORGANISM: Artificial Sequence
<220> FEATURE:
<223> OTHER INFORMATION: Artificial Sequence

<400> SEQUENCE: 139
aatccttatg cagacagaat cagagct                                        27

<210> SEQ ID NO 140
<211> LENGTH: 27
<212> TYPE: DNA
<213> ORGANISM: Artificial Sequence
<220> FEATURE:
<223> OTHER INFORMATION: Artificial Sequence

<400> SEQUENCE: 140
agatcggcta taaaaagat aatggaa                                         27

<210> SEQ ID NO 141
<211> LENGTH: 27
<212> TYPE: DNA
<213> ORGANISM: Artificial Sequence
<220> FEATURE:
<223> OTHER INFORMATION: Artificial Sequence

<400> SEQUENCE: 141
agatcggcta taaaaaaga taatgga                                         27

<210> SEQ ID NO 142
<211> LENGTH: 27
<212> TYPE: DNA
<213> ORGANISM: Artificial Sequence
<220> FEATURE:
<223> OTHER INFORMATION: Artificial Sequence

<400> SEQUENCE: 142
agatcggcta taaaaaagt aatggaa                                         27

<210> SEQ ID NO 143
<211> LENGTH: 27
<212> TYPE: DNA
<213> ORGANISM: Artificial Sequence
<220> FEATURE:
<223> OTHER INFORMATION: Artificial Sequence

<400> SEQUENCE: 143 ggaaccccc cgatttgccg acaagcc                                         27

<210> SEQ ID NO 144
<211> LENGTH: 27
<212> TYPE: DNA
<213> ORGANISM: Artificial Sequence
<220> FEATURE:
<223> OTHER INFORMATION: Artificial Sequence
```

```
<400> SEQUENCE: 144
ggaacccccc gatttgccga caagccc                                              27

<210> SEQ ID NO 145
<211> LENGTH: 27
<212> TYPE: DNA
<213> ORGANISM: Artificial Sequence
<220> FEATURE:
<223> OTHER INFORMATION: Artificial Sequence

<400> SEQUENCE: 145
ggaacccccc cgatttgccg acaagcc                                              27

<210> SEQ ID NO 146
<211> LENGTH: 24
<212> TYPE: DNA
<213> ORGANISM: Artificial Sequence
<220> FEATURE:
<223> OTHER INFORMATION: Artificial Sequence

<400> SEQUENCE: 146
ccgactttgt ccctctctca gccc                                                 24

<210> SEQ ID NO 147
<211> LENGTH: 24
<212> TYPE: DNA
<213> ORGANISM: Artificial Sequence
<220> FEATURE:
<223> OTHER INFORMATION: Artificial Sequence

<400> SEQUENCE: 147
gggctgagag agggacaaag tcgg                                                 24

<210> SEQ ID NO 148
<211> LENGTH: 24
<212> TYPE: DNA
<213> ORGANISM: Artificial Sequence
<220> FEATURE:
<223> OTHER INFORMATION: Artificial Sequence

<400> SEQUENCE: 148
ccgactttgt ccctctctca gccc                                                 24

<210> SEQ ID NO 149
<211> LENGTH: 24
<212> TYPE: DNA
<213> ORGANISM: Artificial Sequence
<220> FEATURE:
<223> OTHER INFORMATION: Artificial Sequence

<400> SEQUENCE: 149
gggctgagag agggacaaag tcgg                                                 24
```